(12) United States Patent
Sirbasku

(10) Patent No.: US 7,947,463 B2
(45) Date of Patent: *May 24, 2011

(54) COMPOSITIONS AND METHODS FOR THE DIAGNOSIS, TREATMENT AND PREVENTION OF STEROID HORMONE RESPONSIVE CANCERS

(75) Inventor: David A. Sirbasku, Houston, TX (US)

(73) Assignee: Signe Biopharma, Inc., Irving, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/852,547

(22) Filed: May 10, 2001

(65) Prior Publication Data

US 2002/0006630 A1    Jan. 17, 2002

Related U.S. Application Data

(60) Provisional application No. 60/208,348, filed on May 31, 2000, provisional application No. 60/208,111, filed on May 31, 2000, provisional application No. 60/229,071, filed on Aug. 30, 2000, provisional application No. 60/231,273, filed on Sep. 8, 2000.

(51) Int. Cl.
*G01N 33/567* (2006.01)
*G01N 33/574* (2006.01)
*C12N 5/071* (2010.01)
*C12N 5/09* (2010.01)

(52) U.S. Cl. ...... 435/7.21; 435/7.23; 435/325; 435/375; 435/405

(58) Field of Classification Search ............... 435/4, 7.1, 435/7.23, 7.8, 6, 375; 436/64
See application file for complete search history.

(56) References Cited

U.S. PATENT DOCUMENTS

| | | | |
|---|---|---|---|
| 4,849,508 A | 7/1989 | Magnin et al. | 530/387 |
| 4,859,585 A | 8/1989 | Sonnenschein et al. | 435/29 |
| 5,075,425 A | 12/1991 | Kotitschke et al. | 530/387 |
| 5,135,849 A | 8/1992 | Soto et al. | 435/29 |
| 5,405,772 A | 4/1995 | Ponting | |
| 5,866,323 A * | 2/1999 | Markowitz et al. | |
| 5,877,147 A * | 3/1999 | Pinegin | 514/8 |
| 6,200,547 B1 | 3/2001 | Volkonsky et al. | |

FOREIGN PATENT DOCUMENTS

| | | |
|---|---|---|
| EP | 0702960 A | 3/1996 |
| WO | WO 91/16061 | 10/1991 |
| WO | WO 92/13563 | 8/1992 |
| WO | WO 95/09011 | 6/1995 |
| WO | WO 97/46715 * | 12/1997 |
| WO | WO98/04681 | 2/1998 |
| WO | WO98/08934 | 3/1998 |
| WO | WO 99/05171 * | 2/1999 |
| WO | WO 00/05403 * | 2/2000 |
| WO | WO 00/06723 | 10/2000 |

OTHER PUBLICATIONS

Ghosh et al (Indian Journal of Experimental Biology, Apr. 2000, vol. 38, pp. 313-322).*
Abstract of Das et al (Endocrinologia Japonica, 1976, vol. 23, pp. 275-279).*
Sonnenchein et al (J Steroid Biochemistry, 1996, vol. 59, pp. 147-154.*
Tanji et al (Anticancer Research, Jul.-Aug. 2000, vol. 20, pp. 2785-2790).*
Garde et al, Clinical Chemistry, 2000, vol. 46, pp. 551-559.*
Gomez et al, Amer J Reproduc Immunol, 1993, vol. 29, pp. 219-223.*
Krishnan et al (Prevention and Detection of Cancer, 1977, Nieburgs, Ed., pp. 449-453.*
Becchis et al (Breast Cancer Research and Treatment, 1999, vol. 54, pp. 101-107.*
Sullivan et al (Immunology, 1983, vol. 49, pp. 379-386).*
Hurlimann et al (Virchows Arch A Path Anat and Histol, 1978, vol. 377, pp. 211-223).*
Fudenberg et al (Basic and Clinical Immunology, 1978, p. 326, pp. 324-328).*
Richarson et al (Journal of Steroid Biochemistry and Molecular Biology, 1993, vol. 47, pp. 143-149).*
Brandtzaeg et al (In: Developments in Biological Standarization, Brown and Haaheim, Ed.s, Mar. 1998, vol. 92, pp. 93-108).*
Verrijdt et al (Biochem Soc Transactions, May 1997, vol. 25, p. 186S).*
Tamiolakis et al (European Journal of Gynaecological Oncology, 2002, vol. 23, pp. 453-456).*
Klein et al (Journal of the National Cancer Institute, 1978, vol. 61, pp. 57-60).*
Garcia et al (American Journal of Obstetrics and Gynecology, 1977, vol. 129, pp. 281-284).*
Thalman et al (American Journal of Obstetrics and Gynecology, 1979, vol. 134, pp. 899-903).*
Abstract of Ohwada et al (Nippon Sanka Fujinka Gakkai Zasshi, 1986, vol. 38, pp. 1707-1712).*
Abstract of Cassamassima et al (Minerva Ginecol, 1997, vol. 1-2, pp. 7-12).*
Abstract of Barton et al (Gut, 1990, vol. 31, pp. 378-382).*
Tomasi et al (Journal of Experimental Medicine, 1965, vol. 121, pp. 101-125).*
Furuya et al (Cancer Research, Dec. 1989, vol. 49, pp. 6670-6674).*
Hoffman ('The Biochemistry of Clinical Medicine', 1970, pp. 48 and 55).*
Sirbasku, Cancer Research, 1978, vol. 38, pp. 1154-1165.*
Sirbasku et al, Endocrinology, 1976, vol. 98, pp. 1260-1272.*
Partial International Search in PCT/US 01/15183, Applicant David A. Sirbasku, International Filing Date Oct. 5, 2001, Date of Mailing Aug. 27, 2002, pp. 4.

(Continued)

*Primary Examiner* — Karen A Canella
(74) *Attorney, Agent, or Firm* — Woodard, Emhardt, Moriarty, McNett & Henry LLP

(57) ABSTRACT

Compositions and methods that use the body's natural secretory immune system in a new way against steroid hormone responsive tumors of the breast and prostate, as well as other glandular/mucus epithelial tissues such as colon, ovary, endometrium, kidney, bladder, stomach, pancreas and secretory pituitary gland are provided. Also provided are new ways of identifying carcinogenic, or potentially carcinogenic, bacteria in a tissue or body fluid to provide better anti-cancer therapies and preventatives than have been available previously.

14 Claims, 133 Drawing Sheets

OTHER PUBLICATIONS

Partial International Search in PCT/US 01/15171, Applicant David A. Sirbasku, International Filing Date Oct. 5, 2001, Date of Mailing Aug. 29, 2002, pp. 3.

JP Parisot et al., "Altered Expression of the IGF-1 Receptor in a Tamoxifen-Resistant Human Breast Cancer Cell Line," British Journal of Cancer, vol. 79, No. 5-6, pp. 693-700, 1999.

David Danielpour et al., "Growth of MTW9/PL2 Estrogen-Responsive Rat Mammary Tumor Cells in Hormonally Defined Serum-Free Media," In Vitro Cell. Dev. Biol., vol. 24, No. 1, pp. 42-52, Jan. 1988.

Research Diagnostics Inc., 'Online! Jan. 10, 2000, XP002207863, Retrieved from the Internet: <URL:http://www.researchd.com/rdiabs/igref.ser.htm> 'retrieved on Jul. 29, 2002! The whole document, p. 1.

Jorge E. Moreno-Cuevas et al., "Estrogen Mitogenic Action. I. Demonstration of Estrogen-Dependent MTW9/PL2 Carcinogen-Induced Rat Mammary Tumor Cell Growth in Serum-Supplemented Culture and Technical Implications," In Vitro Cell. Dev. Biol.—Animal, vol. 36, No. 7, pp. 410-427, Jul.-Aug. 2000.

David A. Sirbasku et al., "Estrogen Mitogenic Action. II. Negative Regulation of the Steroid Hormone-Responsive Growth of Cell Lines Derived From Human and Rodent Target Tissue Tumors and Conceptual Implications," In Vitro Cell. Dev. Biol.—Animal, vol. 36, No. 7, pp. 428-446, Jul.-Aug. 2000.

Helenice Gobbi et al., "Transforming Growth Factor-β and Breast Cancer Risk in Women With Mammary Epithelial Hyperplasia," Journal of the National Cancer Institute, vol. 91, No. 24, pp. 2096-2101, Dec. 15, 1999.

Ruth Sager, "Expression Genetics in Cancer: Shifting the Focus from DNA to RNA," Proc. Natl. Acad. Sci. USA, vol. 94, No. 3, pp. 952-955, Feb. 1997.

Sanford D. Markowitz et al., "Tumor Suppressor Activity of the TGF-β Pathway in Human Cancers," Cytokine & Growth Factor Reviews, vol. 7, No. 1, pp. 99-102, 1996.

A.J. Alberg et al., *Epidemiology, prevention, and early detection of breast cancer [Breast]*, Current Opinion in Oncology (Nov. 1997) vol. 9, 6, pp. 505-511, PMID: 9370070 [PubMed—indexed for Medline); Abstract http://www.ncbi.nlm.nih.gov/entrez/query.fcgi?cmd=Retrieve&db=PubMed&list_uids=9370070&d... printed on Feb. 15, 2003 (1 page).

T. Anttila et al., *Serotypes of Chlamydia Trachomatis and Risk for Development of Cervical Squamous Cell Carcinoma*, JAMA (Jan. 2001) vol. 285, No. 1, pp. 47-51, PMID: 11150108 [PubMed—indexed for Medline]; Abstract http://www.ncbi.nlm.nih.gov/entrez/query.fcgi?cmd=Retrieve&db=PubMed&list_uids=11150108&d... printed on Feb. 15, 2003 (2 pages).

B.A. Arrick, *Therapeutic implications of the TGF-beta system*, J. Mammary Gland Biol. Neoplasia. (Oct. 1996) 1(4):391-7, PMID: 10887513 [PubMed—indexed for Medline); Abstract http://www.ncbi.nlm.nih.gov/entrez/query.fcgi?cmd=Retrieve&db=PubMed&list_uids=10887513&d... printed on Feb. 21, 2003 (1 page).

C.L. Arteaga et al., *The multifunctional role of transforming growth factor (TGF)-beta s on mammary epithelial cell biology*, Breast Cancer Res. Treat. 1996; 38(1):49-56, PMID: 8825122 [PubMed—indexed for Medline]; Abstract; http://www.ncbi.nlm.nih.gov/entrez/query.fcgi?cmd=Retrieve&db=PubMed&list_uids=8825122&d... printed on Feb. 21, 2003 (1 page).

C.L. Arteaga et al., *Transforming Growth factor beta: potential autocrine growth inhibitor of estrogen receptor-negative human breast cancer cells*, Breast Cancer Res Treat. (Jul. 1998) 48(14):3898-904, PMID: 3164252 [PubMed—indexed for Medline]; Abstract; http://www.ncbi.nlm.nih.gov/entrez/query.fcgi?cmd= Retrieve&db=PubMed&list_uids=3164252&d... printed on Feb. 21, 2003 (2 pages).

M.A. Bakos et al., *Expression and purification of biologically active domain I of the human polymeric immunoglobulin receptor*, Mol. Immunol. (Feb. 1994) 31(2):165-8, PMID: 8309479 [PubMed—indexed for Medline]; Abstract; http://www.ncbi.nlm.nih.gov/entrez/query.fcgi?cmd=Retrieve&db= PubMed&list_uids=8309479&d... printed on Feb. 22, 2003, 1 page.

M.A. Bakos et al., *Characterization of a critical binding site for human polymeric Ig on secretory component*, J. Immunol. (Nov. 1991) 147(10):3419-26, PMID: 1940346 [PubMed—indexed for Medline]; Abstract Http://www.ncbi.nlm.nih.gov/entrez/query.fcgi?cmd=Retrieve&db=PubMed&list_uids=1940346&d... printed on Feb. 20, 2003, 1 page.

J. Baselga et al., *Phase II study of weekly intravenous recombinant humanized anti-p185HER2 monoclonal antibody in patients with HER2/neu-overexpressing metastatic breast cancer*, Comment in J. Clin. Oncol. (Mar. 1996) vol. 14, No. 3, pp. 697-699, PMID: 8622019 [PubMed—indexed for Medline]; Abstract, http://www.ncbi.nlm.nih.gov/entrez/query.fcgi?cmd=Retrieve&db=PubMed&list_uids=8622019&dc printed on Feb. 22, 2003, 2 pages.

I. Bieche et al., *Loss and gain of distinct regions of chromosome 1q in primary breast cancer*, Clin. Cancer Res. (Jan. 1995) vol. 1, No. 1, pp. 123-127, PMID: 9815894 [PubMed—indexed for Medline], Abstract, http://www.ncbi.nlm.nih.gov/entrez/query.fcgi?cmd=Retrieve&db=PubMed&list_uids=9815894&dc..., printed on Feb. 21, 2003, 1 page.

W.P. Bocchinfuso et al., *Mammary gland development and tumorigenesis in estrogen receptor knockout mice*, J. Mammary Gland Biol. Neoplasia (Oct. 1977) vol. 2, No. 4, pp. 323-334, PMID: 10935020 [PubMed—indexed for Medline], Abstract, http://www.ncbi.nlm.nih.gov/enrez/query.fcgi?cmd=Retrieve&db=PubMed&list_uids=109335020&... printed on Feb. 21, 2003, 1 page.

E. Boder, *Ataxia-telangiectasia: some historic, clinical and athologic observations*, Birth Defects Orig. Artic. Ser. 1975;11(1):255-70, PMID: 1096982 [PubMed—indexed for Medline], Abstract, http://www.ncbi.nlm.nih.gov/enrez/query.fcgi?cmd-Retrieve&db=PubMed&list_uids=1096982&... printed on Feb. 12, 2003, 1 page.

P. Bordigoni et al., *Improvement of cellular immunity and IgA production in immunodeficient children after treatment with synthetic serum thymic factor (FTS)*, Lancet (Aug. 1982) vol. 2, No. 8293, pp. 293-297, PMID: 6124716 [PubMed—indexed for Medline], Abstract, http://www.ncbi.nlm.nih.gov/entrez/query.fcgi?cmd=Retrieve?db=PubMed&list_uids=6124716?... printed on Feb. 12, 2003, 1 page.

P.N. Boyaka et al., *Strategies for mucosal vaccine development* Am. J. Trop. Med. Hyg (Apr. 1999) vol. 4 Supple., pp. 35-45, PMID: 10344675 [PubMed—indexed for Medline], Abstract, http://www.ncbi.nlm.nih.gov/enrez/query.fcgi?cmd =Retrieve&db=PubMed&list_uids=10344675&... printed on Feb. 21, 2003, 1 page.

P. Brandtzaeg, *Immunoglobulin M: local synthesis and selective secretion in patients with immunoglobulin A deficiency*, Science (May 1968) vol. 160, No. 829, pp. 789-791, PMID 4171541 [PubMed—indexed for Medline], Abstract, http://www.ncbi.nlm.nih.gov/enrez/query.fcgi?cmd=Retrieve&db=PubMed&list_uids=417541&... printed on Feb. 12, 2003, 1 page.

P. Brandtzaeg, *The secretory immune system on lactating human mammary glands compared with other exocrine organs*, Annals N.Y. Acad. Sciences (Jun. 1983) vol. 409, pp. 353-382, PMID 6408971 [PubMed—indexed for Medline], Abstract, http://www.ncbi.nlm.nih.gov/enrez/query.fcgi?cmd=Retrieve&db=PubMed&list_uids=6408971&... printed on Feb. 20, 2003, 1 page.

P. Brandtzaeg, *Molecular and cellular aspects of the secretory immunoglobulin system*, APMIS (Jan. 1995) vol. 103, No. 1, pp. 1-19, PMID 7695886 [PubMed—indexed for Medline], Abstract, http://www.ncbi.nlm.nih.gov/enrez/query.fcgi?cmd=Retrieve&db=PubMed&list_uids=7695886&... printed on Feb. 22, 2003, 1 page.

D.A. Bronzert et al., *Transforming growth factor-beta induces platelet-derived growth factor (PDGF) messenger RNA and PDGF secretion while inhibiting growth in normal human mammary epithelial cells*, Mol. Endocrinol (Jul. 1990) vol. 4, No. 7, pp. 981-989, PMID 2178225 [PubMed—indexed for Medline], Abstract, http://www.ncbi.nlm.nih.gov/enrez/query.fcgi?cmd=Retrieve&db=PubMed&list_uids=2178225&... printed on Feb. 19, 2003, 1 page.

M.G. Brattain et al., *Defects of TGF-beta receptor signaling in mammary cell tumorigenesis*, J. Mammary Gland Biol. Neoplasia (Oct. 1996) vol. 1, No. 4, pp. 365-372, PMID 10887510 [PubMed—indexed for Medline], Abstract, http://www.ncbi.nlm.nih.gov/enrez/query.fcgi?cmd=Retrieve&db=PubMed&list_uids=10887510&..., printed on Feb. 21, 2003, 1 page.

J. Brolin et al., *Immunohistory and biochemistry in detection of androgen, progesterone, and estrogen receptors in benign and malignant human prostatic tissue, Prostate (1992) vol. 20, No. 4, pp. 281-295, PMID 1376911 [PubMed—indexed for Medline], Abstrast, http://www.ncbi.nlm.nih.gov/enrez/query.fcgi?cmd= Retrieve&db=PubMed&list_iuds=1376911&... printed on Feb. 20, 2003, 1 page.

L.A. Castagnetta et al., *Human prostate cancer: a direct role for oestrogens*, Ciba Found Symp (1995) vol. 191, pp. 269-286; discussion pp. 286-289, PMID 8582203 [PubMed—indexed for Medline], Abstract, http://www.ncbi.nlm.nih.gov/enrez/query.fcgi?cmd=Retrieve&db=PubMed&list_uids=8582203&... printed on Feb. 20, 2003, 1 page.

D. Chakravarthy et al., *Expression and secretion of TGF-beta isoforms and expression of TGF-beta-receptors I, II and III in normal and neoplastic human breast*, Int. J. Oncol. (Jul. 1999) vol. 15, No. 1, pp. 187-194, PMID 10375614 [PubMed—indexed for Medline], Abstract, http://www.ncbi.nlm.nih.gov/enrez/query.fcgi?cmd=Retrieve&db=PubMed&list_unids=10375614&... printed on Feb. 22, 2003, 1 page.

T.R. Chen et al., *WiDr is a derivative of another colon adenocarcinoma cell line, HT-29*, Cancer Genet Cytogenet (Jul. 1987) vol. 1, pp. 125-134, PMID 3472642 [PubMed—indexed for Medline], Abstract, http://www.ncbi.nlm.nih.gov/enrez/query.fcgi?cmd=Retrieve&db=PubMed&list_uids=3472642 &... printed on Feb. 19, 2003, 1 page.

M.E. Conley et al., *Intravascular and mucosal immunoglobulin A: two separate but related systems of immune defense?* Ann Intern Med. (Jun. 1987) vol. 106, No. 6, pp. 892-899, PMID 3579073 [PubMed—indexed for Medline], Abstract, http://www.ncbi.nlm.nih.gov/enrez/query.fcgi?cmd=Retrieve&db=PubMed&list_uids=3579073&... printed on Feb. 22, 2003, 1 page.

C.W. Daniel et al., *The role of TGF-beta in patterning and growth of the mammary ductal tree*, J. Mammary Gland Biol. Neoplasia (Oct. 1996) vol. 1, No. 4, pp. 331-341, PMID 10887507 [PubMed—indexed for Medline], Abstract, http://www.ncbi.nlm.nih.gov/enrez/query.fcgu?cmd=Retrieve&db=PubMed&list_uids=10887507&... printed on Feb. 21, 2003, 1 page.

R.B. Dickson et al., *Induction of epidermal growth factor-related polypeptides by 17 beta-estradiol in MCF-7 human breast cancer cells*, Endocrinology (Jan. 1986) vol. 118, No. 1, pp. 138-142, PMID 3000728 [PubMed—indexed for Medline], Abstract, http://www.ncbi.nlm.nih.gov/enrez/query.fcgi?cmd=Retrieve&db=PubMed&list_uids=3000728&... printed on Feb. 19, 2003, 1 page.

R.H. Evans, *The Steroid and Thyroid Hormone Receptor Superfamily*, Science (May 1988) vol. 240, No. 4854, pp. 889-895, PMID 3283939 [PubMed—indexed for Medline], Abstract, http://www.ncbi.nlm.nih.gov/enrez/query.fcgi? cmd=Retrieve&db=PubMed&list_uids=3283939&... printed on Feb. 20, 2003, 1 page.

W.H. Fridman, *Fc receptors and immunoglobulin binding factors*, FSAEB J. (Sep. 1991) vol. 5, No. 12, pp. 2684-2690, PMID 1916092 [PubMed—indexed for Medline], Abstract, http://www.ncbi.nlm.nih.gov/enrez/query.fcgi?cmd=Retrieve&db=PubMed&list_uids=1916092&... printed on Feb. 15, 2003, 1 page.

S.A. Fuqua et al., *Variant human breast tumor estrogen receptor with constitutive transcriptional activity*, Cancer Res. (Jan. 1991) vol. 51, No. 1, pp. 105-109, PMID 1988075 [PubMed—indexed for Medline], Abstract, http://www.ncbi.nlm.nih.gov/enrez/query.fcgi?cmd=Retrieve&db=PubMed&list_uids=1988075&... printed on Feb. 20, 2003, 1 page.

S.A. Fuqua et al., *Inhibition of estrogen receptor action by a naturally occurring variant in human breast tumors*, Cancer Res. (Jan. 1992) vol. 52, No. 2, pp. 483-486, PMID 1728420 [PubMed—indexed for Medline], http://www.ncbi.nlm.nih.gov/enrez/query.fcgi?cmd=Retrieve&db=PubMed&list_uids=1988075&... printed on Feb. 20, 2003, 1 page.

V. Giguere et al., *Identification of a new class of steroid hormone receptors*, Nature (Jan. 1988) vol. 331, No. 6151, pp. 91-94, PMID 3267207 [PubMed—indexed for Medline], Abstract, http://www.ncbi.nlm.nih.gov/enrez/query.fcgi?cmd=Retrieve&db=PubMed&list_uids=3267207&... printed on Feb. 21, 2003, 1 page.

D. Gospodarowicz et al., *Heparin protects basic and acidic FGF from inactivation*, J. Cell Physiol. (Sep. 1986) vol. 128, No. 3, pp. 475-484, PMID 3528177 [PubMed—indexed for Medline], Abstract, http://www.ncbi.nlm.nih.gov/enrez/query.fcgi?cmd=Retrieve&db=PubMed&list_uids=3528177&... printed on Feb. 20, 2003, 1 page.

M.L. Graham et al., *T47DCO cells, genetically unstable and containing estrogen receptor mutations, are a model for the progression of breast cancers to hormone resistance*, Cancer Res. (Oct. 1990) vol. 50, No. 19, pp. 6208-6217, PMID 2400987 [PubMed—indexed for Medline], Abstract, http://www.ncbi.nlm.nih.gov/enrez/query.fcgi?cmd=Retrieve&db=PubMed&list_uids=2400987&... printed on Feb. 20, 2003, 1 page.

E. Haug et al., *Receptors for 17beta-estradiol in prolactin-secreting rat pituitary cells*, Mol. Cell Endocrinol (Oct. 1978) vol. 12, No. 1, pp. 81-95, PMID 569089 [PubMed—indexed for Medline], Abstract, http://www.ncbi.nlm.nih.gov/enrez/query.fcgi?cmd=Retrieve&db=PubMed&list_uids=569089&... printed on Feb. 19, 2003, 1 page.

I.C. Henderson et al., *The relationship between prognostic and predictive factors in the management of breast cancer*, Breast Cancer Res. Treat (1998) vol. 52, No. 1-3, pp. 261-288, PMID 10066087 [PubMed—indexed for Medline], Abstract, http://www.ncbi.nlm.nih.gov/enrez/query.fcgi?cmd=Retrieve&db=PubMed&list_uids=10066087&... printed on Feb. 21, 2003, 1 page.

M. Hosobuchi, *Effects of transforming growth factor beata on growth of human mammary epithelial cells in culture*, In Vitro Cell Dev. Biol (Aug. 1998) vol. 24, No. 8, pp. 705-713, [PubMed—indexed for Medline], Abstract, http://www.ncbi.nlm.nih.gov/enrez/query.fcgi?cmd=Retrieve&db=PubMed&list_uids=2548988&... printed on Feb. 21, 2003, 1 page.

S. Jackson et al., *Normal human sera contain antibodies directed at Fab of IgA*, J Immunol (Apr. 1987) vol. 138, No. 7, pp. 2244-2248, PMID 3494062 [PubMed—indexed for Medline], Abstract, http://www.ncbi.nlm.nih.gov/enrez/query.fcgi?cmd=Retrieve&db=PubMed&list_uids=3494062&... printed on Feb. 21, 2003, 1 page.

N. Janin et al., *Breast cancer risk in ataxia telangiectasia (AT) heterozygotes: haplotype study in French AT families*, Br J Cancer (Jun. 1999) vol. 80, No. 7, pp. 1042-1045, PMID 10362113 [PubMed—indexed for Medline], Abstract, http://www.ncbi.nlm.nih.gov/enrez/query.fcgi?cmd=Retrieve&db=PubMed&list_uids=10362113&... printed on Feb. 21, 2003, 1 page.

E. Haug, *Progesterone suppression of estrogen-stimulated prolactin secretion and estrogen receptor levels in rat pituitary cells*, Endocrinology (Feb. 1979) vol. 104, No. 2, pp. 429-437, PMID 109280 [PubMed—indexed for Medline], Abstract, http://www.ncbi.nlm.nih.gov/enrez/query.fcgi?cmd=Retrieve&db=PubMed&list_uids=109280&... printed on Feb. 19, 2003, 1 page.

J. Gorski et al., *Hormone receptors: studies on the interaction of estrogen with the uterus*, Recent Prog Horm Res. (1968) vol. 24, pp. 45-80, PMID 4885833 [PubMed—indexed for Medline], Abstract, http://www.ncbi.nlm.nih.gov/enrez/query.fcgi?cmd=Retrieve&db=PubMed&list_uids=4885833&... printed on Feb. 20, 2003, 1 page.

K. el-Bayoumy, *Environmental carcinogens that may be involved in human breast cancer etiology*, Chem Res. Toxicol (Sep.-Oct. 1992) vol. 5, No. 5, pp. 585-590, PMID 1445997 [PubMed—indexed for Medline], Abstract, http://www.ncbi.nlm.nih.gov/enrez/query.fcgi?cmd=Retrieve&db=PubMed&list_uids=1445997&... printed on Feb. 21, 2003, 1 page.

D.F. Easton et al., *The genetic epidemiology of BRCAI. Breast Cancer Linkage Consortium*, Lancet (Sep. 1994) vol. 344, No. 8924, pp. 761, PMID 7915813 [PubMed—indexed for Medline], Abstract, http://www.ncbi.nlm.nih.gov/enrez/query.fcgi?cmd=Retrieve&db=PubMed&list_uids=7915813&... printed on Feb. 15, 2003, 1 page.

S.C. Brooks et al., *Estrogen receptor in a human cell line (MCF-7) from breast carcinoma*, J Biol Chem (Sep. 1973) vol. 248, No. 17, pp. 6251-6253, PMID 4353636 [PubMed—indexed for Medline], Abstract, http://www.ncbi.nlm.nih.gov/enrez/query.fcgi?cmd=Retrieve&db=PubMed&list_uids=4353636&... printed on Feb. 19, 2003, 1 page.

W.S. Bullough, *Chalone control mechanisms*, Life Sci (Feb. 1975) vol. 16, No. 3, pp. 323-330, PMID 123999 [PubMed—indexed for Medline], Abstract, http://www.ncbi.nlm.nih.gov/enrez/query.fcgi?cmd=Retrive&db=PubMed&list_uids=123999&... printed on Feb. 12, 2003, 1 page.

E.V. Jensen et al., *A two-step mechanism for the interaction of estradiol with rat uterus*, Proc Natl. Acad. Sci USA (Feb. 1968) vol. 59, No. 2, pp. 632-638, PMID 5238991 [PubMed—indexed for Medline], Abstract, http://www.ncbi.nlm.nih.gov/enrez/query.fcgi?cmd=Retrieve&db=PubMed&list_uids=5238991&... printed on Feb. 20, 2003, 1 page.

E.V. Jensen et al., *Estrogen-receptor interaction*Science (Oct. 1973) vol. 182, No. 108, pp. 126-134, PMID 4354173 [PubMed—indexed for Medline], Abstract, http://www.ncbi.nlm.nih.gov/enrez/query.fcgi?cmd=Retrieve&db=PubMed&list_uids=4354173&... printed on Feb. 20, 2003, 1 page.

M.E. Kaighn et al., *Establishment and characterization of a human prostatic carcinoma cell line (PC-3)*, Invest. Urol. (Jul. 1979) No. 1, pp. 16-23, PMID 447482 [PubMed—indexed for Medline], Abstract, http://www.ncbi.nlm.nih.gov/enrez/query.fcgi?cmd=Retrieve&db=PubMed&list_uids=447482&... printed on Feb. 19, 2003, 1 page.

M. Kaufmann, *Review of known prognostic variables*, Recent Results Cancer Res. (1996) vol. 140, pp. 77-78, PMID 8787079 [PubMed—indexed for Medline], Abstract, http://www.ncbi.nlm.nih.gov/enrez/query.fcgi?cmd=Retrieve&db=PubMed&list_uids=8787079&... printed on Feb. 21, 2003, 1 page.

R. Kemler et al., In vitro *studies on the selective binding of IgG from different species to tissue section s of the bovine mammary glands*, Eur. J. Immunol (Sep. 1975) vol. 5, No. 9, pp. 603-608, PMID 11993319 [PubMed—indexed for Medline], Abstract, http://www.ncbi.nlm.nih.gov/enrez/query.fcgi?cmd=Retrieve&db=PubMed&list_uids=11993319&... printed on Feb. 15, 2003, 1 page.

R.S. Kerbel et al., *Analysis of established human carcinoma cell lines for lynmphoreticular-associated membrane receptors*, Int. J. Cancer (Nov. 1977) vol. 20, No. 5, pp. 673-679, PMID 924690 [PubMed—indexed for Medline], Abstract, http://www.ncbi.nlm.nih.gov/enrez/query.fcgi?cmd=Retrieve&db=PubMed&list_uids=924690&... printed on Feb. 21, 2003, 1 page.

M.S. Khan et al., *Size isomers of testosterone-estradiol-binding globulin exist in the plasma of individual men and women*, Steroids *(May 1985), vol. 45, No. 5, pp. 463-472, PMID 3834662 [PubMed—indexed for Medline], Abstract, http://www.ncbi.nlm.nih.gov/enrez/query.fcgi?cmd=Retrieve&db=PubMed&list_uids=3834662&...* printed on Feb. 21, 2003, 1 page.

K. Kim et al., *Immunoglobulin G Subclasses in Human Colostrum, Milk and Saliva*Acta Paediatr (Feb. 1992) vol. 81, No. 2, pp. 113-118, PMID 1515753 [PubMed—indexed for Medline], Abstract, http://www.ncbi.nlm.nih.gov/enrez/query.fcgi?cmd=Retrieve&db=PubMed&list_uids=15157532&... printed on Feb. 21, 2003, 1 page.

C. Knabbe et al., *Evidence that transforming growth factor-beta is a hormonally regulated negative growth factor in human breast cancer cells*, Cell *(Feb. 1987) vol. 48, No. 3, pp. 417-428, PMID 2879636 [PubMed—indexed for Medline], Abstract, http://www.ncbi.nlm.nih.gov/enrez/query.fcgi?cmd=Retrieve&db=PubMed&list_uids=28796362&...* printed on Feb. 19, 2003, 1 page.

H. Kondoh et al., *Jacalin, a jackfruit lectin, precipitates IgA1 but not IgA2 subclass on gel diffusion reaction*, J. Immunol Methods (Apr. 1986) vol. 88, No. 2, pp. 171-173, PMID 3082992 [PubMed—indexed for Medline], Abstract, http://www.ncbi.nlm.nih.gov/enrez/query.fcgi?cmd=Retrieve&db=PubMed&list_uids=3082992&... printed on Feb. 21, 2003, 1 page.

P. Krajci et al., *The gene encoding human transmembrane secretory component (locus P1GR) is linked to DiS58 on chromosome 1*, Hum Genet (Nov. 1992) vol. 90, No. 3, pp. 215-219, PMID 1487233 [PubMed—indexed for Medline], Abstract, http://www.ncbi.nlm.nih.gov/enrez/query.fcgi?cmd=Retrieve&db=PubMed&list_uids=14872332&... printed on Feb. 21, 2003, 1 page.

P. Krajci et al., *Cloning, chromosomal localization, and linkage analysis of the gene encoding human transmembrane secretory component (the poly-Ig receptor)*, Adv Exp. Med Biol (1995) No. 371A, pp. 617-623, PMID 8526003 [PubMed—indexed for Medline], Abstract, http://www.ncbi.nlm.nih.gov/enrez/query.fcgi?cmd=Retrieve&db=PubMed&list_uids=8526003&... printed on Feb. 21, 2003, 1 page.

I. Laursen et al., *Serum albumin as a modulator on growth of the human breast cancer cell line, MCF-7*, Anticancer Res. (Mar.-Apr. 1990) vol. 10, No. 2A, pp. 343-351, PMID 2346307 [PubMed—indexed for Medline], Abstract, http://www.ncbi.nlm.nih.gov/enrez/query.fcgi?cmd=Retrieve&db=PubMed&list_uids=2346307&... printed on Feb. 21, 2003, 1 page.

L.M. Loomes et al., *Purification and characterization of human immunoglobulin IgA1 and IgA2 isotypes from serum*, J Immunol Methods (Aug. 1991) vol. 141, No. 2, pp. 209-218, PMID 1880427 [PubMed—indexed for Medline], Abstract, http://www.ncbi.nlm.nih.gov/enrez/query.fcgi?cmd=Retrieve&db=PubMed&list_uids=1880427&... printed on Feb. 21, 2003, 1 page.

M.L. Loupart et al., *Allelic imbalance on chromosome I in human breast cancer. I. Minisatellite and RFLP analysis*, Genes Chromosomes Cancer (Jan. 1995) vol. 12, No. 1, pp. 16-23, PMID 7534106 [PubMed—indexed for Medline], Abstract, http://www.ncbi.nlm.nih.gov/enrez/query.fcgi?cmd=Retrieve&db=PubMed&list_uids=7534106&... printed on Feb. 21, 2003, 1 page.

S. Mathew et al., *Transforming growth factor receptor gene TGFBR2 maps to human chromosome band 3p22*, Genomics (Mar. 1994) vol. 20, No. 1, pp. 114-115, PMID 8020936 [PubMed—indexed for Medline], Abstract, http://www.ncbi.nlm.nih.gov/enrez/query.fcgi?cmd=Retrieve&db=PubMed&list_uids=8020936&... printed on Feb. 21, 2003, 1 page.

M.I. McBurney et al., *Colonic carcinogenesis: the microbial feast or famine mechanism*, Nutr Cancer (1987) vol. 10, No. 1-2, pp. 23-28, PMID 3039469 [PubMed—indexed for Medline], Abstract, http://www.ncbi.nlm.nih.gov/enrez/query.fcgi?cmd=Retrieve&db=PubMed&list_uids=3039469&... printed on Feb. 15, 2003, 1 page.

S. Mosselman et al., *ER beta: identification and characterization of a novel human estrogen receptor*, FEBS Lett (Aug. 1996) vol. 392, No. 1, pp. 49-53, PMID 8769313 [PubMed—indexed for Medline], Abstract, http://www.ncbi.nlm.nih.gov/enrez/query.fcgi?cmd=Retrieve&db=PubMed&list_uids=8769313&... printed on Feb. 20, 2003, 1 page.

L.C. Murphy et al., *Variant estrogen receptor mRNA species detected in human breast cancer biopsy sample*, Mol Endocrinol (Apr. 1989) vol. 3, No. 4, pp. 687-693, PMID 2725532 [PubMed—indexed for Medline], Abstract, http://www.ncbi.nlm.nih.gov/enrez/query.fcgi?cmd=Retrieve&db=PubMed&list_uids=2725532&... printed on Feb. 20, 2003, 1 page.

A.M. Nakhla et al., *Induction of adenylate cyclase in a mammary carcinoma cell line by human corticosteroid-binding globulin*, Biochem Biophys Res. Commun (Jun. 1988) vol. 153, No. 3, pp. 1012-1018, PMID 2839166 [PubMed—indexed for Medline], Abstract, http://www.ncbi.nlm.nih.gov/enrez/query.fcgi?cmd=Retrieve&db=PubMed&list_uids=2839166&... printed on Feb. 19, 2003, 1 page.

F.R. Ochsendorf, *Infections in the male genital tract and reactive oxygen species*, Hum Reprod Update (Sep.-Oct. 1999) vol. 5, No. 5, pp. 399-420, PMID 10582780 [PubMed—indexed for Medline], Abstract, http://www.ncbi.nlm.nih.gov/enrez/query.fcgi?cmd=Retrieve&db=PubMed&list_uids=10582780&... printed on Feb. 22, 2003, 1 page.

B.W. O'Malley et al., *Female steroid hormones and target cell nuclei*, Science (Feb. 1974) vol. 183, No. 125, pp. 610-620, PMID 4359082 [PubMed—indexed for Medline], Abstract, http://www.ncbi.nlm.nih.gov/enrez/query.fcgi?cmd=Retrieve&db=PubMed&list_uids=4359082&... printed on Feb. 20, 2003, 1 page.

C.K. Osborne, *Steroid hormone receptors in breast cancer management*, Breast Cancer Res. Treat (1998) vol. 51, No. 3, pp. 227-238, PMID 10068081 [PubMed—indexed for Medline], Abstract, http://www.ncbi.nlm.nih.gov/enrez/query.fcgi?cmd=Retrieve&db=PubMed&list_uids=10068081&... printed on Feb. 21, 2003, 1 page.

M.A. Palladino et al., *The transforming growth factor-betas. A new family of immunoregulatory molecules*, Ann NY Acad. Sci (1990) vol. 593, pp. 181-187, PMID 2197960 [PubMed—indexed for Medline], Abstract, http://www.ncbi.nlm.nih.gov/enrez/query.fcgi?cmd=Retrieve&db=PubMed&list_uids=2197960&... printed on Feb. 12, 2003, 1 page.

U. Pfeffer et al., *Estrogen receptor variant messenger RNA lacking exon 4 in estrogen-responsive human breast cancer cell lines*, Cancer Res. (Feb. 1993) vol. 53, No. 4, pp. 741-743, PMID 7916651 [PubMed—indexed for Medline], Abstract, http://www.ncbi.nlm.nih.gov/enrez/query.fcgi?cmd=Retrieve&db=PubMed&list_uids=7916651&... printed on Feb. 20, 2003, 1 page.

C.C. Reese et al., *Alternative models for estrogen and androgen regulation of human breast cancer cell (T47D) growth* Ann NY Acad. Sci (1988) vol. 538, pp. 112-121, PMID 3190080 [PubMed—indexed for Medline], Abstract, http://www.ncbi.nlm.nih.gov/enrez/query.fcgi?cmd=Retrieve&db=PubMed&list_uids=3190080&... printed on Feb. 21, 2003, 1 page.

C.B. Reimer et al., *Specificity and association constants of 33 monoclonal antibodies to human IgA epitopes*, Immunol Lett (Jun. 1989) vol. 21, No. 3, pp. 209-215, PMID 2475439 [PubMed—indexed for Medline], Abstract, http://www.ncbi.nlm.nih.gov/enrez/query.fcgi?cmd=Retrieve&db=PubMed&list_uids=2475439&... printed on Feb. 22, 2003, 1 page.

M. Reiss et al., *Transforming growth factor-beta in breast cancer: a working hypothesis*, Breast Cancer Res. Treat (Aug. 1997) vol. 45, No. 1, pp. 81-95, PMID 9285120 [PubMed—indexed for Medline], Abstract, http://www.ncbi.nlm.nih.gov/enrez/query.fcgi?cmd=Retrieve&db=PubMed&list_uids=9285120&... printed on Feb. 21, 2003, 1 page.

S.F. Retta et al., *Purification of fibronectin from human plasma*, Methods Mol Biol (1999) vol. 96,pp. 119-124, PMID 10098128 [PubMed—indexed for Medline], Abstract, http://www.ncbi.nlm.nih.gov/enrez/query.fcgi?cmd=Retrieve&db=PubMed&list_uids=10098128&... printed on Mar. 12, 2003, 1 page.

A. Richardson, *Is breast cancer caused by late exposure to a common virus?* Med Hypothesis (Jun. 1997) vol. 48, No. 6, pp. 491-497, PMID 9247892 [PubMed—indexed for Medline], Abstract, http://www.ncbi.nlm.nih.gov/enrez/query.fcgi?cmd=Retrieve&db=PubMed&list_uids=9247892&... printed on Feb. 22, 2003, 1 page.

M.C. Roque-Barreira et al., *Jacalin: an IgA-binding lectin*, J. Immunol (Mar. 1985) vol. 134, No. 3, pp. 1740-1743, PMID 3871459 [PubMed—indexed for Medline], Abstract, http://www.ncbi.nlm.nih.gov/enrez/query.fcgi?cmd=Retrieve&db=PubMed&list_uids=3871459&... printed on Feb. 21, 2003, 1 page.

M. Sabel et al., *Recent developments in breast imaging*, Phys Med Biol (Mar. 1996), vol. 41, No. 3, pp. 315-368, PMID 8778818 [PubMed—indexed for Medline], Abstract, http://www.ncbi.nlm.nih.gov/enrez/query.fcgi?cmd=Retrieve&db=PubMed&list_uids=8778818&... printed on Feb. 21, 2003, 1 page.

R.L. Smith et al., *Separation of plasma fibronectin from associated hemagglutinating acivity by elution from gelatin-agarose at pH 5.5*, Thromb Res. (Jan. 1985), vol. 37, No. 1, pp. 91-101, PMID 3983905 [PubMed—indexed for Medline], Abstract, http://www.ncbi.nlm.nih.gov/enrez/query.fcgi?cmd=Retrieve&db=PubMed&list_uids=3983905&... printed on Feb. 20, 2003, 1 page.

A.M. Soto et al., *The role of estrogen on the proliferation of human breast tumor cells*, J. Steroid Biochem (Jul. 1985) vol. 23, No. 1, pp. 87-94, PMID 4021494 [PubMed—indexed for Medline], Abstract, http://www.ncbi.nlm.nih.gov/enrez/query.fcgi?cmd=Retrieve&db=PubMed&list_uids=4021494&... printed on Feb. 20, 2003, 1 page.

A.M. Soto et al., *Estrogen-Sensitive Proliferation pattern of Cloned Syrian Hamster Kidney Tumor Cells*, Cancer Res. (Jul. 1988), vol. 48, No. 13, pp. 3676-3680, PMID 3288322 [PubMed—indexed for Medline], Abstract, http://www.ncbi.nlm.nih.gov/enrez/query.fcgi?cmd=Retrieve&db=PubMed&list_uids=3288332&... printed on Feb. 20, 2003, 1 page.

H.D. Soule et al., *A human cell line from apleural effusion derived from a breast carcinoma*, J Natl. Cancer Inst. (Nov. 1973) vol. 51, No. 5, pp. 409-416, PMID 4357757 [PubMed—indexed for Medline], Abstract, http://www.ncbi.nlm.nih.gov/enrez/query.fcgi?cmd=Retrieve&db=PubMed&list_uids=4357757&... printed on Feb. 19, 2003, 1 page.

H.L. Spiegelberg, *Biological activities of immunoglobulins of different classes and subclasses*, Adv Immunol (1974) vol. 19, pp. 259-294, PMID 4611172 [PubMed—indexed for Medline], Abstract, http://www.ncbi.nlm.nih.gov/enrez/query.fcgi?cmd=Retrieve&db=PubMed&list_uids=4611172&... printed on Feb. 15, 2003, 1 page.

J.E. Stern et al., *Secretory immune system of the male reproductive tract: effects of dihydrotestosterone and estradiol on IgA and secretory component levels*, J Reprod Immunol (Jun. 1992) vol. 22, No. 1, pp. 73-85, PMID 1522564 [PubMed—indexed for Medline], Abstract, http://www.ncbi.nlm.nih.gov/enrez/query.fcgi?cmd=Retrieve&db=PubMed&list_uids=1522564&... printed on Feb. 22, 2003, 1 page.

J.E. Stern et al., *Sectetory component in breast cancer, Analysis of the levels in primary and metastatic disease*, Cancer Immunol. Immunother. (1985) vol. 19, No. 2, pp. 226-230, PMID 3847292 [PubMed—indexed for Medline], Abstract, http://www.ncbi.nlm.nih.gov/enrez/query.fcgi?cmd=Retrieve&db=PubMed&list_uids=3847292&... printed on Feb. 21, 2003, 1 page.

R.L. Sutherland et al., *High-Affinity Anti-Oestrogen Binding Site Distinct From The Oestrogen Receptor*, Nature (Nov. 1980) vol. 288, No. 5788, pp. 273-275, PMID 7432524 [PubMed—indexed for Medline], Abstract, http://www.ncbi.nlm.nih.gov/enrez/query.fcgi?cmd=Retrieve&db= PubMed&list_uids=7432524&... printed on Feb. 20, 2003, 1 page.

S.V. Tavtigian et al., *The Complete BRCA2 Gene and Mutations in Chromosome 13q-Linked Kindreds*, Nat. Genet (Mar. 1996) vol. 12, No. 3, pp. 333-337, PMID 8589730 [PubMed—indexed for Medline], Abstract, http://www.ncbi.nlm.nih.gov/enrez/query.fcgi?cmd=Retrieve&db= PubMed&list_uids=8589730&... printed on Feb. 15, 2003, 1 page.

M.J. Tsai et al., *Molecular mechanisms of action of steroid/thyroid receptor superfamily members*, Annu. Rev. Biochem (1994) vol. 63, pp. 451-486, PMID 7979245 [PubMed—indexed for Medline], Abstract, http://www.ncbi.nlm.nih.gov/enrez/query.fcgi?cmd=Retrieve&db= PubMed&list_uids=7979245&... printed on Feb. 21, 2003, 1 page.

F. Vignon et al., *Antiestrogens inhibit the mitogenic effect of growth factors on breast cancer cells in the total absence of estrogens*, Biochem Biophys Res. Commun (Aug. 1987) vol. 146, No. 3, pp. 1502-1508, PMID 3304294 [PubMed—indexed for Medline], Abstract, http://www.ncbi.nlm.nih.gov/enrez/query.fcgi?cmd=Retrieve&db=PubMed&list_uids=3304294&... printed on Feb. 20, 2003, 1 page.

I Vorechovsky et al., *the ATM gene and susceptibility to breast cancer: analysis of 38 breast tumors reveals no evidence for mutation*, Cancer Res. (Jun. 1996) vol. 56, No. 12, pp. 2726-2732, PMID 8665503 [PubMed—indexed for Medline], Abstract, http://www.ncbi.nlm.nih.gov/enrez/query.fcgi?cmd=Retrieve&db=PubMed&list_uids=8665503&... printed on Feb. 21, 2003, 1 page.

Y. Wang et al., *Identification of a dominant negative form of the human estrogen receptor*, Mol. Endocrinol (Nov. 1991) vol. 5, No. 11, pp. 1707-1715, PMID 1779972 [PubMed—indexed for Medline], Abstract, http://www.ncbi.nlm.nih.gov/enrez/query.fcgi?cmd=Retrieve&db=PubMed&list_uids=1779972&... printed on Feb. 20, 2003, 1 page.

R. Wooster et al., *Identification of the breast cancer susceptibility gene BRCA2*, Nature (Dec. 1995) vol. 378, No. 6559, pp. 789-792, PMID 8524414 [PubMed—indexed for Medline], Abstract, http://www.ncbi.nlm.nih.gov/enrez/query.fcgi?cmd=Retrieve&db= PubMed&list_uids=8524414&... printed on Feb. 15, 2003, 1 page.

J. Yang et al., *Estrogen receptor variants in epithelial compartment of normal human breast*, Endocrine (Jun. 2000), vol. 12, No. 3, pp. 243-247, PMID 10963044 [PubMed—indexed for Medline], Abstract, http://www.ncbi.nlm.nih.gov/enrez/query.fcgi?cmd=Retrieve&db=PubMed&list_uids=10963044&... printed on Feb. 12, 2003, 1 page.

K.R. Yamamoto, *Steroid receptor regulated transcription of specific genes and gene networks*, Annu Rev Genet (1985) vol. 19, pp. 209-252, PMID 3909942 [PubMed—indexed for Medline], Abstract, http://www.ncbi.nlm.nih.gov/enrez/query.fcgi?cmd=Retrieve&db=PubMed&list_uids=3909942&... printed on Feb. 21, 2003, 1 page.

D.A. Zajchowski et al., *Estrogen inhibits the growth of estrogen receptor-negative, but not estrogen receptor-positive, human mammary epithelial cells expressing a recombination estrogen receptor*, Cancer Res. (Oct. 1993) vol. 53, No. 20, pp. 5004-5011, PMID 8402691 [PubMed—indexed for Medline], Abstract, http://www.ncbi.nlm.nih.gov/enrez/query.fcgi?cmd=Retrieve&db=PubMed&list_uids=8402691&... printed on Feb. 21, 2003, 1 page.

International Search Report, PCT/US02/36632 dated Jul. 28, 2003 (1 p.).

Iype LE, Michael M, Verna M & Iype PT (1998) *Development and characterization of new immortalized human breast cancer cell lines.* Cytotechnology 26:207-218.

Ogmundsdottir HM, Petursdottir I, Gudmundsdottir I, Arnundadottir L, Ronnov-Jessen L & Petersen OW (Dec. 1993) *Effects of lympho-* cytes and fibroblasts on the growth of human mammary carcinoma cells studied in short-term primary cultures. In Vitro Cell Dev Biol Anim. 29A(12):936-42. (abstract).

Ethier SP, Summerfelt RM, Cundiff KC & Asch BB (Jan.-Feb. 1991) *The influence of growth factors on the proliferative potential of normal and primary breast cancer-derived human breast epithelial cells.* Breast Cancer Res Treat. 17(3):221-30. (abstract).

Emennan JT & Wilkinson DA (Dec. 1990) *Routine culturing of normal, dysplastic and malignant human mammary epithelial cells from small tissue samples.* In Vitro Cell Dev Biol. 26(12):1186-94. (abstract).

Medina D & Obom CJ (Nov. 1980) *Growth of preneoplastic mammary epithelial cells in serum-free medium.* Cancer Res 40(II)3982-3987. (abstract).

Peterson OW, van Deurs B, Nielsen KV, Madsen MW, Laursen I, Balslev I & Briand P (Feb. 1990) *Differential tumorigenicity of two autologous human breast carcinoma cell lines, HMT-3909S1 and HMT-3909S8, established in serum-free medium.* Cancer Res 50(4)1257-1270. (abstract).

Biran S, Vlodaysky I, Fuks Z, Lijovetzky G, Horowitz AT (Sep. 1986) *Growth of human carcinoma cells from biopsy specimens in serum-free medium on extracellular matrix.* Int J Cancer 38(3):345-354. (abstract).

Yasunaga Y, Nakamura K, Ewing CM, Isaacs WB, Hukku B & Rhim JS (Aug. 15, 2001) *A Novel Cell Culture Model for the Study of Familial Prostate Cancer.* Cancer Res 61, 5969-5973.

Xu Y, Iyengar S, Roberts RL, Shappell SB & Peehl DM (2003) *Primary Culture Model of Peroxisome Proliferator-Activated Receptor γ Activity in Prostate Cancer Cells.* J Cell Physiol 196:131-143.

Krill D, Shuman M, Thompson MT, Becich MJ & Strom SC (1997) *A Simple Method for the Isolation and Culture of Epithelial and Stromal Cells From Benign and Neoplastic Prostates.* Urology 49:981-988.

Chopra DP, Sakar FH, Grignon DJ, Sakr WA, Mohamed A, Waghray A (Sep. 1997) *Growth of human nondiploid primary prostate tumor epithelial cells in vitro.* Cancer Res 57(17)3688-3692. (abstract).

Chopra DP, Grignon DJ, Joiakim A, Mathieu PA, Mohamed A, Sakr WA, Powell IJ & Sakar FH (Nov. 1996) *Differential growth factor responses of epithelial cell cultures derived from normal human prostate, benign prostatic hyperplasia and primary prostate carcinoma.* J Cell Physiol 169(2)269-80. (abstract).

Peehl DM & Stamey TA (Feb. 1986) *Serum free growth of adult human prostatic epithelial cells.* In Vitro Cell Dev Biol 22(2)82-90. (abstract).

Wang J, Torbenson M, Wang Q, Ro JY & Becich M (2003) *Expression of inducible nitric oxide synthase in paired neoplastic and non-neoplastic primary prostate cell cultures and prostatectomy specimen.* Urologic Oncology: Seminars and Original Investigations. 21:117-122.

Thodou E, Ramyar L, Cohen AI, Singer W & Asa SL (Winter 1995) *A Serum-Free System for Primary Cultures of Human Pituitary Adenomas.* Endocr Pathol 6(4)289-299. (abstract).

Reynolds RK, Owens CA & Roberts JA (1996) *Cultured endometrial cancer cells exhibit autocrine growth factor stimulation that is not observed in culture normal endometrial cells.* Gynecologic Oncology 60, 380-386, Article No. 0058.

Miyazaki K, Masui H & Sato GH (1984) *Growth and Differentiation of Human Bronchogenic Epidermoid Carcinoma Cells in Serum-Free Media.* Methods for Serum Free Culture of Epithelial and Fibroblastic Cells, vol. 3, pp. 83-94, Alan R Liss, New York.

Carney DN, Brower M, Bertness V & Oie HK (1984) *Selective Growth of Human Small Cell Lung Cancer Cell Lines and Clinical Specimens in Serum-Free Medium.* Methods for Serum Free Culture of Epithelial and Fibroblastic Cells, vol. 3, pp. 57-71, Alan R Liss, New York.

Masuda N, Fukuoka M, Takada M, Kudoh S & Kusunoki Y (Aug. 1991) *Establishment and characterization of 20 human non-small cell lung cancer cell lines in serum free defined medium (ACL-4).* Chest 100:429-438. (abstract).

van der Bosch J (1984) *Primary Tissue Cultures of Human Colon Carcinomas in Serum-Free Medium: An in Vitro System for Tumor Analysis and Therapy Experiments.* Methods for Serum Free Culture of Epithelial and Fibroblastic Cells, vol. 3, pp. 73-81, Alan R Liss, New York.

Peretz T, Antebi SU, Beller U, Horowitz AT, Fuks Z & Vlodaysky I (Jun. 1990) *Maintenance on extracellular matrix and expression of heparinase activity by human ovarian carcinoma cells from biopsy specimens.* Int J Cancer 45(6)1054-1060. (abstract).

Golombick T, Dansey R, Bezwoda WR & Rosendorff J (May 1990) *Establishment and characterization of two new human ovarian cancer cell lines UWOV1 and UWOV2 and a subline UWOV2 (Sf) growing in serum-free conditions: growth characteristics, biochemical, and cytogenetic studies.* In Vitro Cell Dev Biol 26(5)447-454. (abstract).

Hirte HW, Kaiser JS & Bacchetti S (Aug. 1994) *Establishment and characterization of four human epithelial ovarian carcinoma cell lines.* Cancer 74(3)900-906. (abstract).

Emoto M, Oshima K, Ishiguro M, Iwasaki H, Hawarabayashi T & Kikuchi M (1999) *Establishment and characterization of a serous papillary adenocarcinoma cell line of the human ovary in a serum free culture.* Pathol Res Pract 1995(4)237-42. (abstract).

Ito H, Yamaguchi K, Kotake T & Matsuzaki O (Dec. 1989) *Development of a serum free medium and primary culture of human renal cell carcinomas by serum-free culture.* Nippon Hinyokika Gakkai Zasshi 80(12)1741-8. (abstract).

Yanagihara K, Kamada N. Tsumuraya M & Amano F (May 1993) *Establishment and characxterization of a huan gastric scirrhous carcinoma cell line in serum free chemically defined medium.* In J Cancer 54(2)200-207. (abstract).

Messing EM, Fahey JL, deKernion JB, Bhuta SM & Bubbers JE (Jun. 1982) *Serum free medium for the in vitro growth of normal and malignant urinary bladder epithelial cells.* Cancer Res 42(6)2392-2397. (abstract).

Ito H, Yamaguchi K, Kotake T & Matsuzaki O (Dec. 1989) *Primary culture of human bladder carcinomas and establishment of human bladder carcinoma cell line by serum free culture.* Nippon Hinyolalca Gakkai Zasshi 80:1749-1754. (abstract).

P. Brandtzaeg & FR Korsrud (Dec. 1984) *Significance of different J chain profiles in human tissues: generation of IgA and IgM with binding site for secretory component is related to the J chain expressing capacity of the total local immuniocyte population, including IgG and IgD producing cells, and depends on the clinical state of the tissue.* Clin Exp Immunol 58(3)709-18. (abstract).

O'Shaughnessy JA, et al., (Jan. 15, 2002) *Ductal Lavage and the Clinical Management of Women at High Risk for Breast Cancer.* Cancer 94(2)292-298.

Wrensch MR et al. (1992) *Breast Cancer Incidence in Women With Abnormal Cytology in Nipple Aspirates of Breast Fluid.* Am J Epidemiol 135(2)130-141.

Devlin TM (2002) *Biochemistry of Hormones I. Polypeptide Hormones.* Textbook of Biochemistry With Cortical Correlations, Fifth Edition, John Wiley & Sons, Inc., New York, NY 936-939.

Feng et al. (Journal Diary Science 78:2352-2357 (1995)).

Hallaway et al. (Proc. Nat'l. Acad. Sci. 85:10108-10112 (1989)).

Jiang et al. (Anticancer Research 22:2685-2692 (2002)).

Kresse et al (Magnetic Resonance in Medicine 10(2):236-242 (1998)).

Larson et al. (J. Nat'l. Cancer Inst. 64(1):41-53 (1980)).

Mathias et al. (J. Nuclear Medicine 37(6): 1003-1008 (1996)).

Murphy (The Oncologist 3: 129-130 (1998)).

Patel et al. (Proc. Nat'l. Acad. Sci. 80:6518-6522 (1983)).

Reddell et al (Exp. Cell Research 161:277-284 (1985)).

Sato (Nippon Gan Chiryo Gakkaisi 28(10): 1716-1723 (1993)).

Wang et a.. (Anticancer Research 19:445-450 (1999)).

\* cited by examiner

FIGURE 1

MTW9/PL2 CELL GROWTH IN 50% CDE - HORSE SERUM

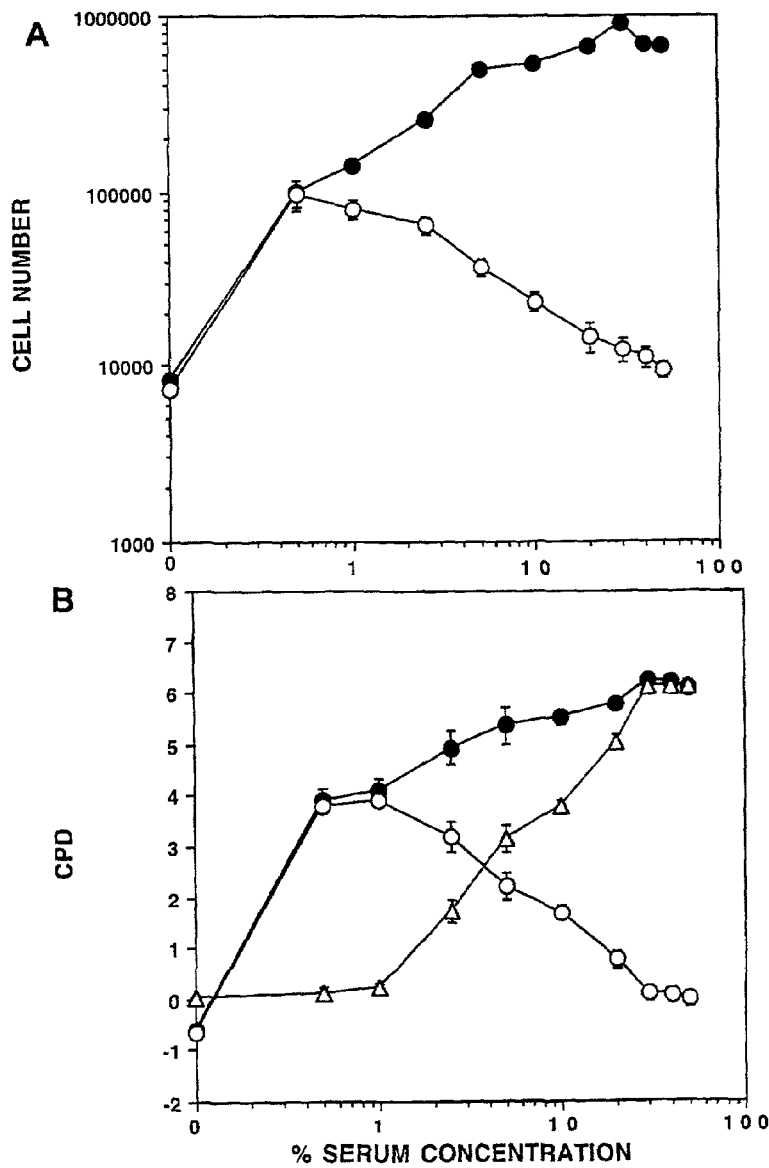

A: DATA EXPRESSED AS CELL NUMBER AFTER 7 DAYS
Growth with $1.0 \times 10^{-8}$ M $E_2$ (closed circles) and without hormone (open circles) in medium containing the designated concentrations of serum.

B. DATA IN (A) EXPRESSED AS CPD
The symbols indicate the same conditions as (A) except the open triangles show CPD differences between growth in dishes with and without the hormone (Difference = estrogenic effect on growth).

MTW9/PL2 CELL GROWTH IN 50% CDE - HORSE SERUM WITH ESTROGENS ADDED AT VARIOUS TIMES AFTER SEEDING

LEGEND:

Control growth in the absence of exogenous estrogen is shown by (triangles). In other dishes, $1.0 \times 10^{-8}$ M $E_2$ was added at the beginning of the experiment (closed circles), after 48 h (open circles), after 96 h (closed squares), or after 144 h (open squares).

STEROID HORMONE DOSE RESPONSE EFFECTS WITH
MTW9/PL2 CELLS IN 50% CDE - HORSE SERUM

STEROID HORMONE (M)

LEGEND:

Closed circles = $E_2$
Open circles = $E_1$
Closed squares = $E_3$
Open squares = Progesterone
Closed triangles = DHT
Open triangles = T

MTW9PL2 CELL GROWTH IN CDE SERUM FROM DIFFERENT SPECIES

LEGEND: Open circles = $-E_2$
Closed circles = $+E_2$
Open triangles = Estrogenic effect

ZR-75-1 CELLS IN CDE - HORSE SERUM ± 10 nM $E_2$

% SERUM CONCENTRATION

LEGEND:

Closed circles = $+E_2$
Open circles = $-E_2$
Closed triangles = Estrogenic effect MCF7A CELL GROWTH IN CDE - HORSE SERUM $\pm E_2$

% SERUM CONCENTRATION

LEGEND:

Closed circles = $+E_2$
Open circles = $-E_2$
Closed triangles = Estrogenic effect

FIGURE 8

GROWTH KINETICS OF T47D HUMAN BREAST CANCER CELLS IN CDE - HORSE SERUM ±10 nM E$_2$

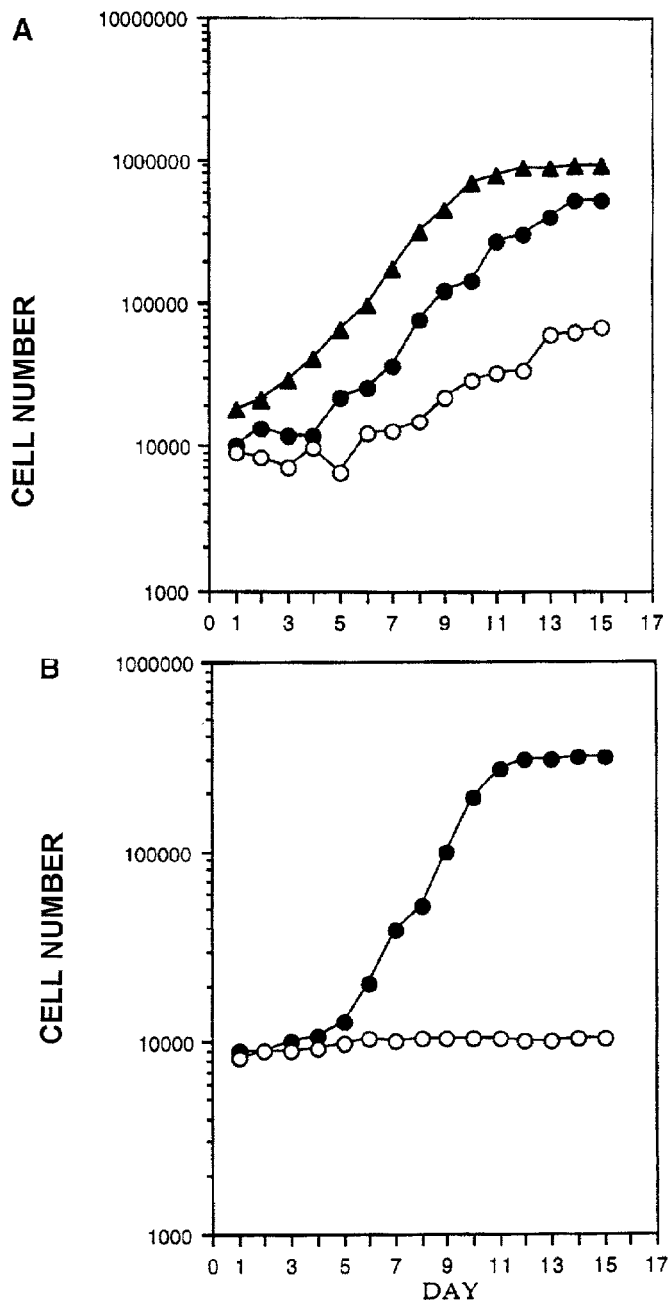

(A) The growth of the cells in medium with 20% (v/v) serum with 10 nM E$_2$ (closed circles) and without the steroid (open circles). As comparison, growth is shown in medium containing 10% (v/v) FBS (triangles).

(B) T47D cell growth kinetics in medium with 50% (v/v) serum with E$_2$ (closed circles) and without the steroid (open circles).

GROWTH OF HUMAN & RODENT CELL LINES IN 50% CDE - HORSE SERUM ±E$_2$ (10 nM)

LEGEND: Closed circles = Medium with 10 nM E$_2$
Open circles = Medium without E$_2$
Triangles = Estrogenic effect

DOSE RESPONSE OF STEROID HORMONES
WITH T47D CELLS IN 50% CDE - HORSE SERUM

LEGEND:
Growth after 14 days is shown in response to:
Closed circles = $E_2$
Open circles = $E_1$
Closed triangles = $E_3$
Open triangles = DHT
Closed squares = Testosterone
Open squares = Progesterone
Crosses = Cortisol

DOSE RESPONSE OF STEROID HORMONES
WITH H-301 CELLS IN 50% CDE - HORSE SERUM

LEGEND:
  Growth after 9 days is shown in response to:
    Closed circles = $E_2$
    Open circles = $E_1$
    Closed triangles = $E_3$
    Open triangles = DHT
    Closed squares = Testosterone
    Open squares = Progesterone
    Crosses = Cortisol

DOSE RESPONSE OF STEROID HORMONES
WITH H-301 CELLS IN 50% CDE - HORSE SERUM

LEGEND:

Growth after 9 days is shown in response to:
  Closed circles = $E_2$
  Open circles = $E_1$
  Closed triangles = $E_3$
  Open triangles = DHT
  Closed squares = Testosterone
  Open squares = Progesterone
  Crosses = Cortisol DOSE RESPONSE OF STEROID HORMONES WITH LNCaP CELLS IN 50% CDE - HORSE SERUM

LEGEND:

Growth after 14 days is shown in response to:
Closed circles = $E_2$
Open triangles = $E_1$
Open squares = $E_3$
Open circles = DHT
Closed triangles = Testosterone
Closed squares = Progesterone
Crosses = Cortisol $T_3$ TITRATION OF $GH_3$ CELLS GROWN IN SERUM - FREE MEDIUM (PCM)

$E_2$ TITRATION OF $GH_3$ CELLS GROWN IN SERUM-FREE MEDIUM MINUS $T_3$

EFFECT OF $T_3$ ON GH CELL LINES:
GROWTH IN 2.5% CDE - HORSE SERUM WITH NO $E_2$

EFFECT OF XAD-4 RESIN TREATED HORSE SERUM ON MTW9/PL2 CELL GROWTH $\pm E_2$

% SERUM CONCENTRATION

LEGEND:

Open squares = + $E_2$

Closed squares = - $E_2$

EFFECT OF XAD-4 RESIN TREATED HORSE SERUM ON T47D CELL GROWTH $\pm E_2$

% SERUM CONCENTRATION

LEGEND:

Open squares = + $E_2$

XXX = - $E_2$

Closed squares = Estrogenic effect

FIGURE 20

MCF-7 CELL GROWTH IN CDE - HORSE SERUM ± PHENOL RED AND ± E$_2$

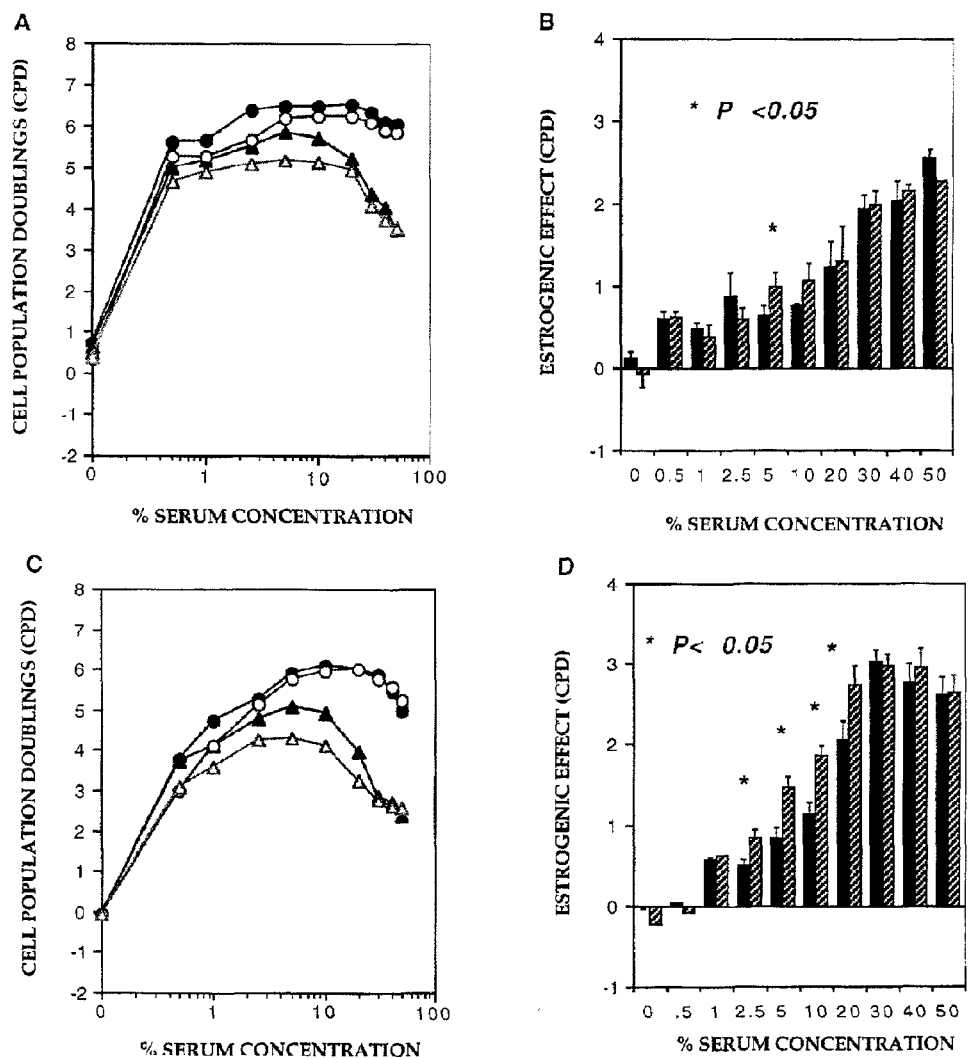

LEGEND:

(A) MCF-7A cell growth in phenol red containing medium with E$_2$ (closed circles) and without E$_2$ (closed triangles), and in phenol red-free medium with E$_2$ (open circles) and without E$_2$ (open triangles).

(B) Estrogenic effects with MCF-7A cells in medium with phenol red (solid bars) and without phenol red (shaded bars) were calculated from (A) and defined as the CPD in medium containing E$_2$ minus the CPD in medium without added E$_2$.

(C) MCF-7K cell growth in phenol red medium with E$_2$ (closed circles) and without E$_2$ (closed triangles), and in phenol red-free medium with E$_2$ (open circles) and without E$_2$ (open triangles).

(D) Estrogenic effects with MCF-7K cells in medium with phenol red (solid bars) and without phenol red (shaded bars), calculated from (C).

FIGURE 21

T47D AND ZR-75-1 CELL GROWTH IN CDE-HS ± PHENOL RED AND ± $E_2$

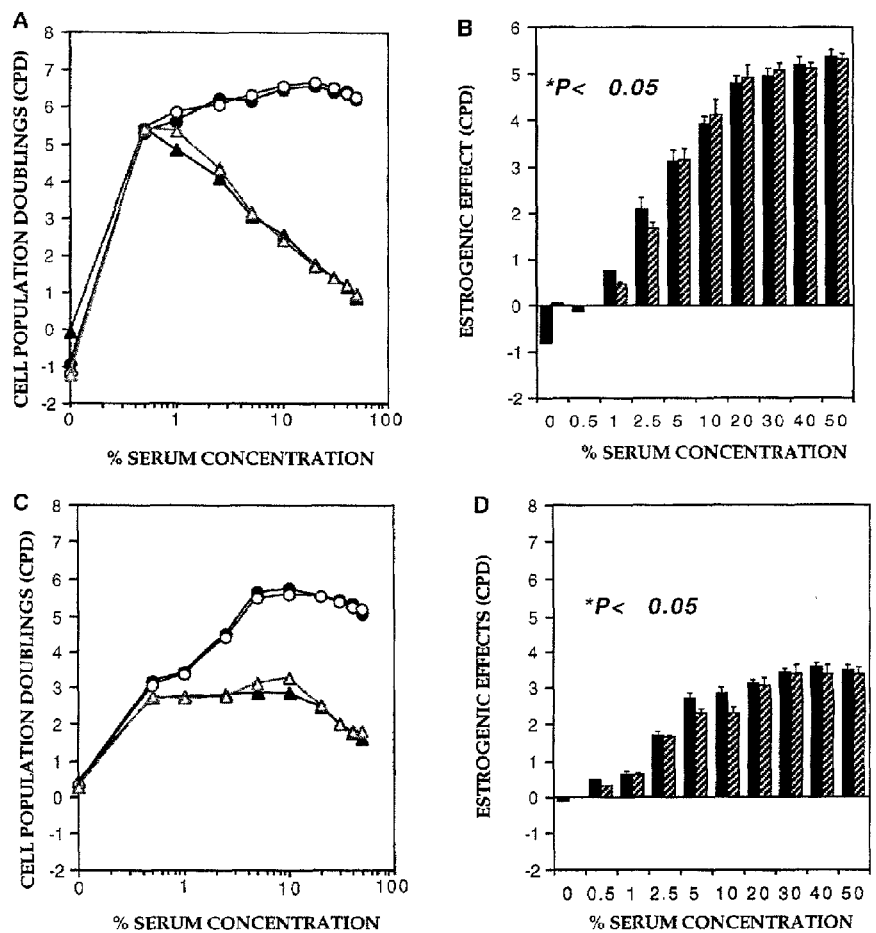

LEGEND:

(A) T47D cell growth in phenol red containing medium with $E_2$ (closed circles) and without $E_2$ (closed triangles), and in phenol red-free medium with $E_2$ (open circles) and without $E_2$ (open triangles).
(B) Estrogenic effects with T47D cells in medium with phenol red (solid bars) and without phenol red (shaded bars) were calculated from (A) and defined as the CPD in medium containing $E_2$ minus the CPD in medium without added $E_2$.
(C) ZR-75-1 cell growth in phenol red medium with $E_2$ (closed circles) and without $E_2$ (closed triangles), and in phenol red-free medium with $E_2$ (open circles) and without $E_2$ (open triangles).
(D) Estrogenic effects with ZR-75-1 cells in medium with phenol red (solid bars) and without phenol red (shaded bars), calculated from (C).

FIGURE 22

MTW9/PL2 CELL GROWTH IN CDE - HORSE SERUM
± PHENOL RED AND ±E$_2$

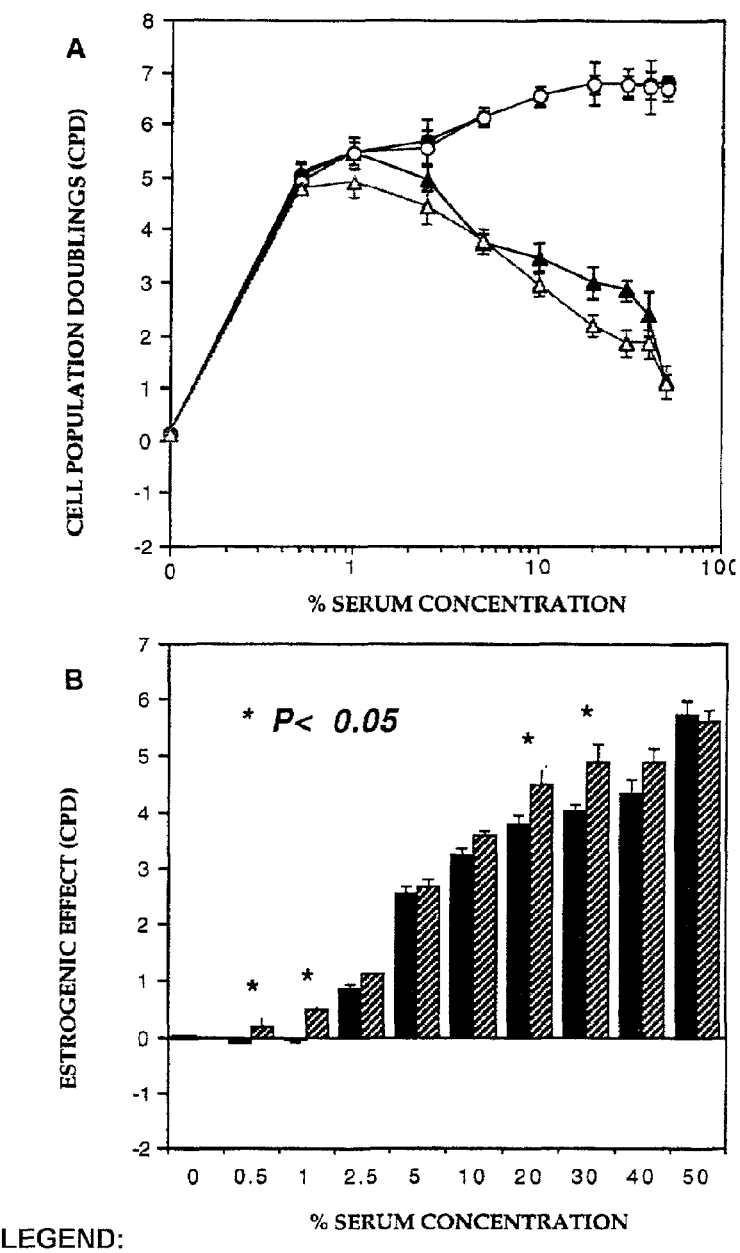

LEGEND:

(A) MTW9/PL2 growth in phenol red medium with E$_2$ (closed circles) and without E$_2$ (closed triangles), and in phenol red-free medium with E$_2$ (open circles) and without E$_2$ (open triangles).

(B) Estrogenic effects with MTW9/PL2 cells in medium with phenol red (solid bars) and without (shaded bars) were calculated from (A).

DOSE RESPONSE TO PHENOL RED AND $E_2$ IN THREE CELL LINES

LEGEND: The growth of the MCF-7A (closed circles), MTW9/PL2 (open circles) and T47D (closed triangles) cell lines was assessed at 14, 7, and 12 days.

FIGURE 24

PROGESTERONE RECEPTOR INDUCTION IN
T47D CELLS BY PHENOL RED AND $E_2$

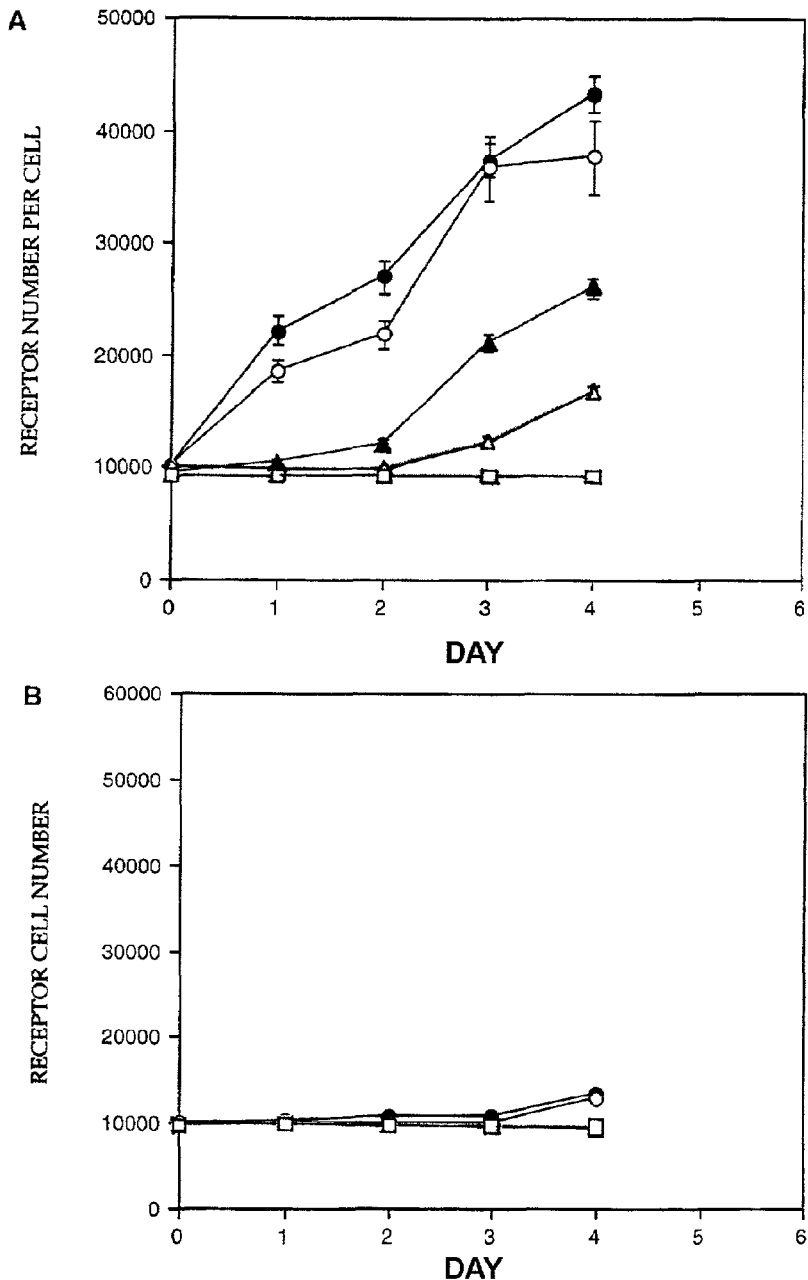

LEGEND:
(A) The effects of $E_2$ at $1.0 \times 10^{-8}$ M (closed circles), $1.0 \times 10^{-10}$ M (open circles), $1.0 \times 10^{-12}$ M (closed triangles), $1.0 \times 10^{-14}$ M (open triangles) and the control without added $E_2$ (open squares).

(B) The effects of phenol red at 16 mg/L (closed circles), 8mg/L (open circles), 4 mg/L (closed triangles), 2 mg/L (open triangles), and the control without phenol red (open squares).

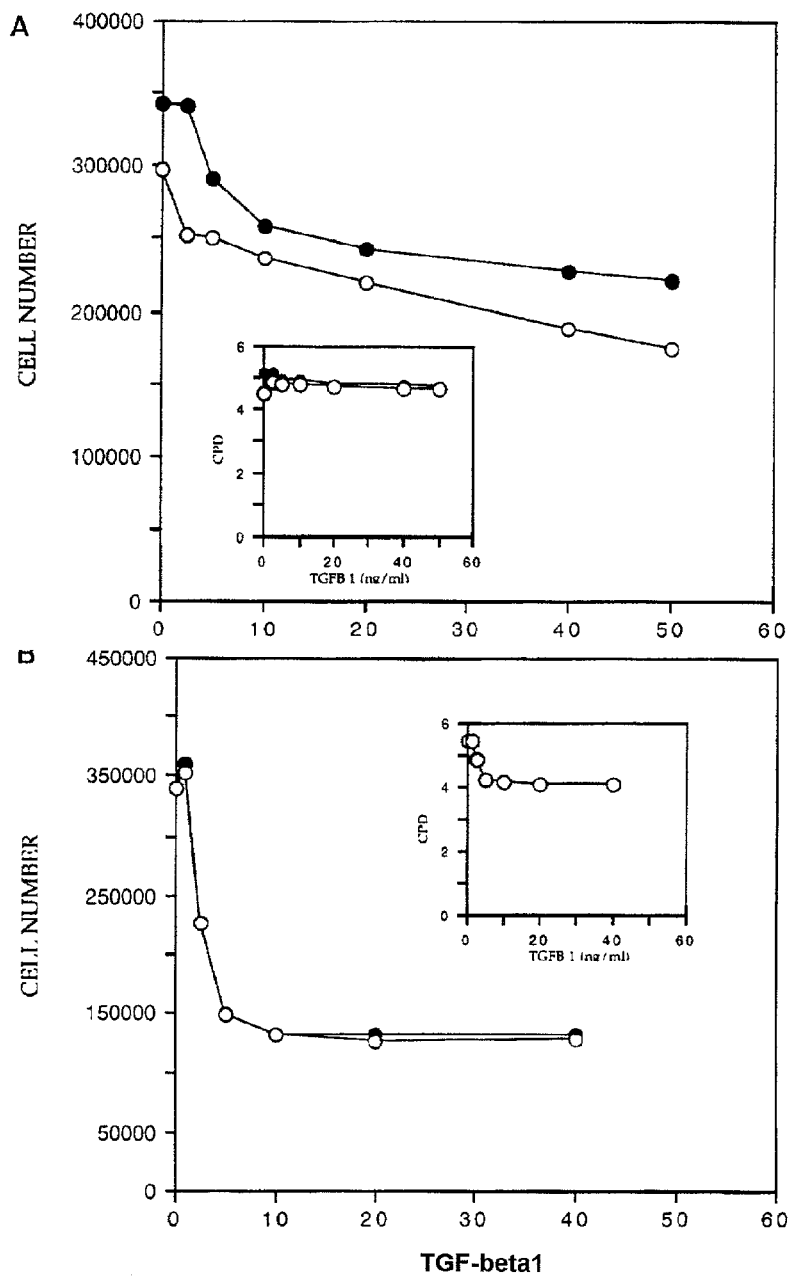

FIGURE 25

EFFECT OF TGF-beta1 ON THE GROWTH OF BREAST/MAMMARY ORIGIN CELL LINES

LEGEND:

(A) The effect of the transforming growth inhibitor on human breast MCF-7K cell growth as measured after 12 d either with 10 nM $E_2$ (closed circles) or without the hormone (open circles). The insert shows conversion of the cell number results to CPD.

(B) The same experiment with rat mammary MTW9/PL2 cells after 9 d growth.

FIGURE 26

EFFECT OF TGF-beta1 ON THE GROWTH OF CELL LINES FROM BOTH HUMAN AND RODENT TUMORS

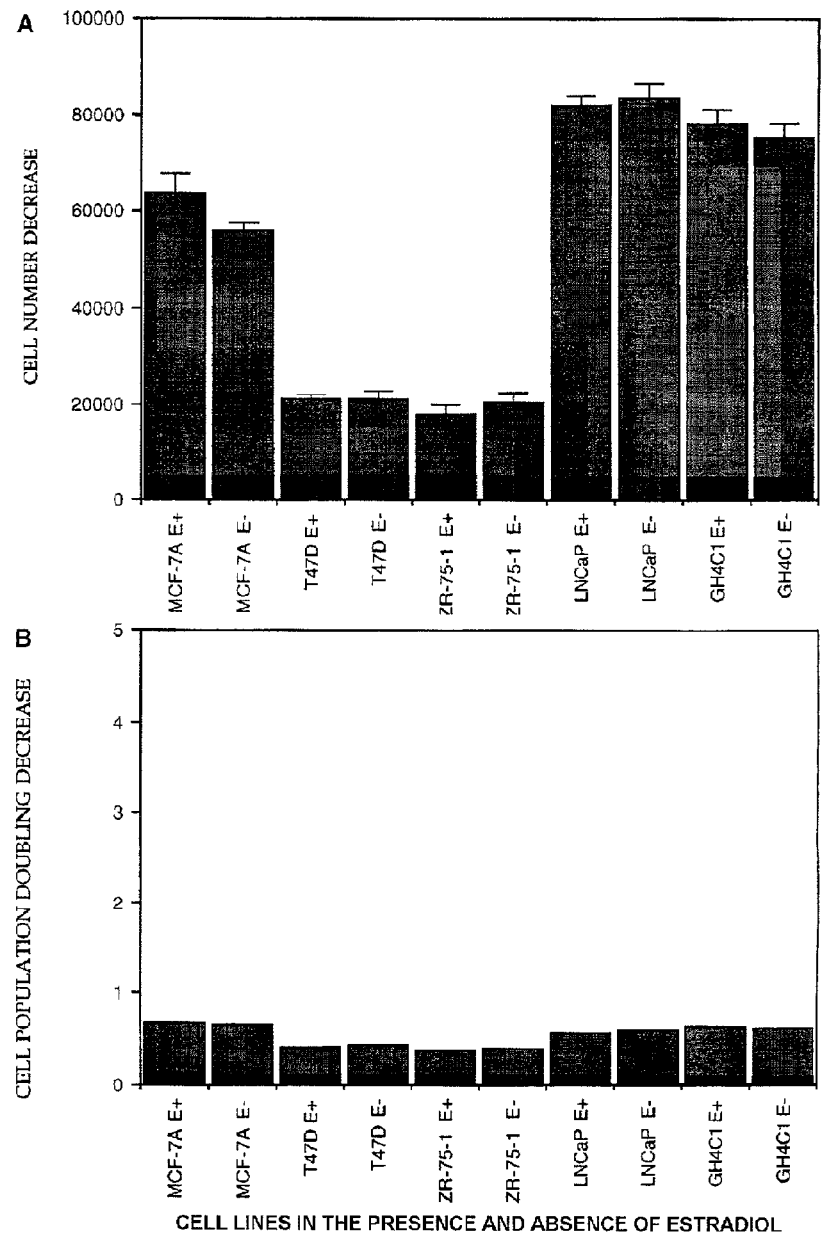

CELL LINES IN THE PRESENCE AND ABSENCE OF ESTRADIOL

In these studies, TGF-beta1 was added at 40 ng/ml. Estradiol (± E) indicates either no added $E_2$ or the steroid at 10 nM.

(A) The effect of TGF-beta1 on five cell lines after 10-14 d growth in medium ± $E_2$. The results are expressed as cell number decreases caused by TGF-beta1.
(B) The CPD decreases caused by TGF-beta1 ± $E_2$ with each of the cell lines shown in (A).

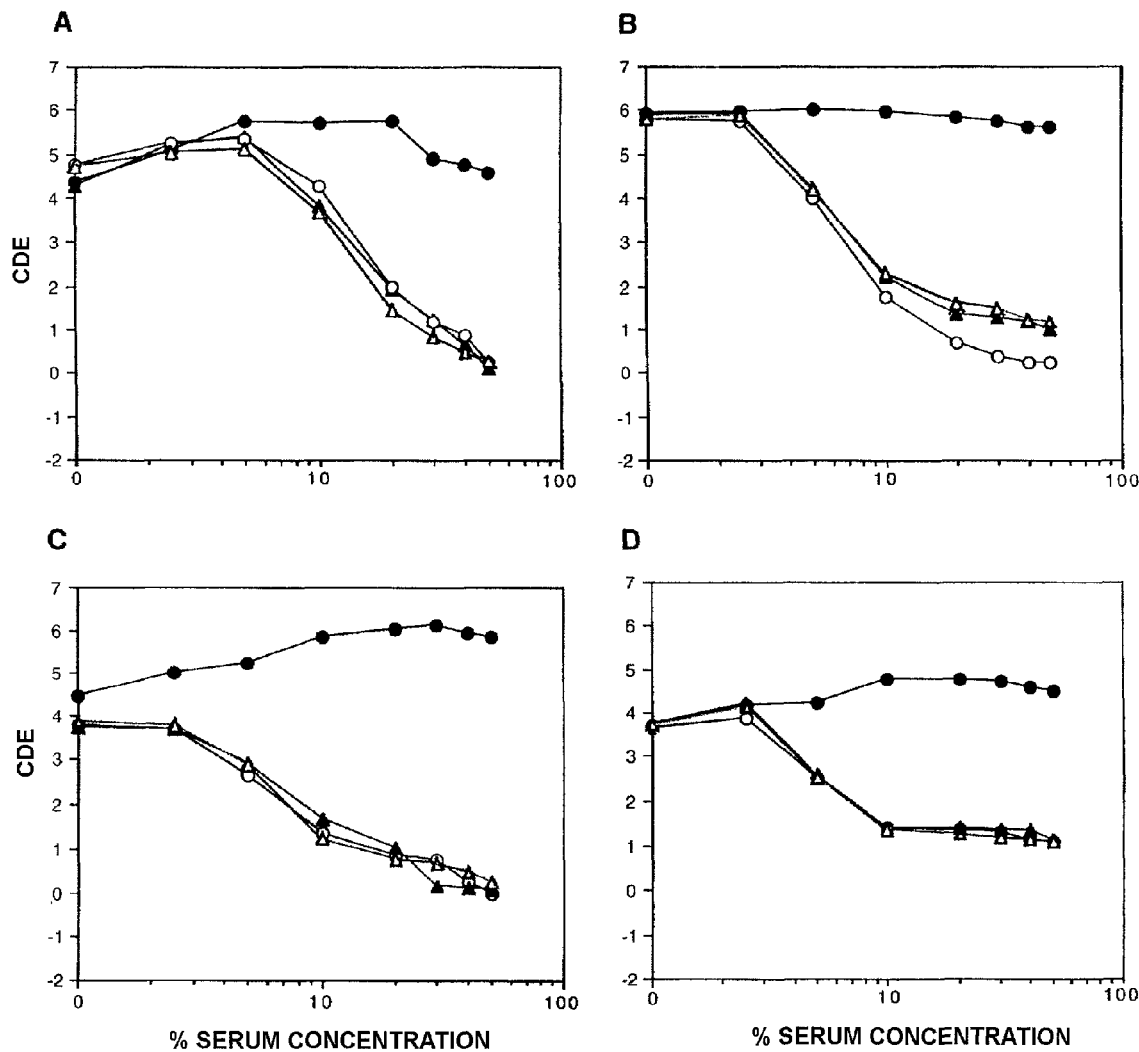

FIGURE 27

EFFECT OF EGF AND TGF-alpha ON THE GROWTH OF HUMAN BREAST CANCER CELLS

The cells were grown in D-MEM/F-12 supplemented with increasing concentrations of CDE horse serum. Each line tested was grown in serum alone (open circles) and in serum plus 50 ng/ml EGF (open triangles), 50 ng/ml TGF-alpha (closed triangles), or 10 nM $E_2$ without exogenous growth factors (closed circles). (A) - (D) show the results with the MCF-7A, MCF-7K, T47D, and ZR-75-1 cell lines, respectively.

FIGURE 28

EFFECT OF IGF-I ON THE GROWTH OF HUMAN BREAST CANCER CELLS

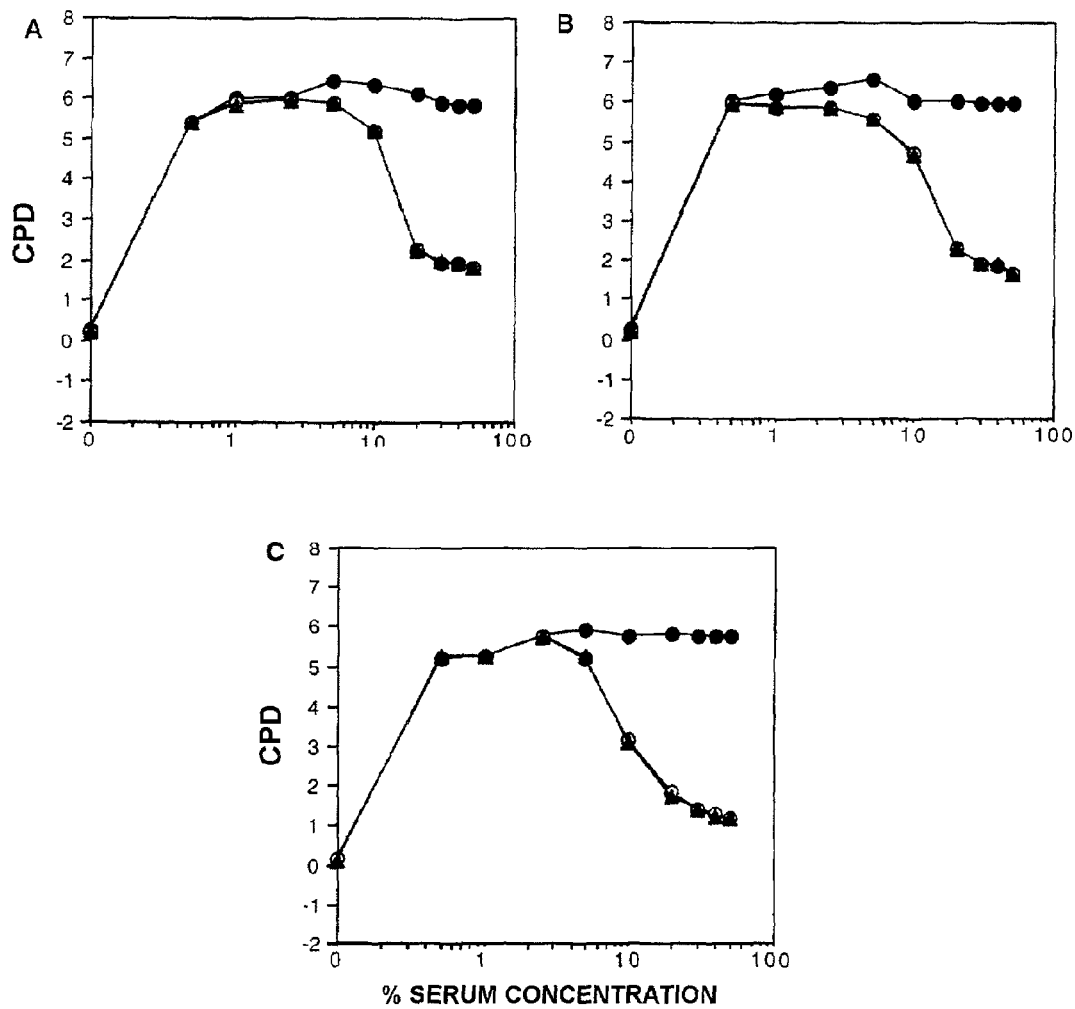

% SERUM CONCENTRATION

Breast cancer cells were grown in D-MEM/F-12 supplemented with increasing concentrations of CDE horse serum. Each cell line tested was grown in serum alone (open circles) and in serum plus 1.0 ug/ml IGF-I (triangles), or in serum with 10 nM $E_2$ without exogenous growth factors (closed circles). (A) - (C) show the results with the MCF-7K, MCF-7A and T47D cells, respectively. Assays were conducted for 12-14 d.

T47D CELLS IN STANDARD D-MEM/F-12 MEDIUM
VS "LOW FE" SERUM-FREE SERUM

LEGEND:

■ "STANDARD" MEDIUM

▲ "LOW-FE" MEDIUM

LNCaP CELLS IN STANDARD D-MEM/F-12 MEDIUM
VS "LOW-FE" SERUM-FREE MEDIUM

LEGEND:

—○— "STANDARD" MEDIUM

—●— "LOW-FE" MEDIUM

MDCK CELLS IN STANDARD D-MEM/F-12 MEDIUM VS "LOW FE" SERUM-FREE MEDIUM

LEGEND:

—○— "STANDARD" MEDIUM

—●— "LOW-FE" MEDIUM

PC3 AND DU145 GROWTH IN SERUM - FREE MEDIUM VS MEDIUM WITH 10% FETAL CALF SERUM

LEGEND:

— ▫ — PC3 IN SERUM-FREE MEDIUM

— ♦ — DU145 IN SERUM-FREE MEDIUM

— ■ — PC3 IN 10% FETAL CALF SERUM

— ◊ — DU145 IN 10% FETAL CALF SERUM

FIGURE 34
DOSE-RESPONSE EFFECTS OF INDIVIDUAL COMPONENTS
OF CAPM SERUM-FREE MEDIUM ON LNCAP CELL GROWTH
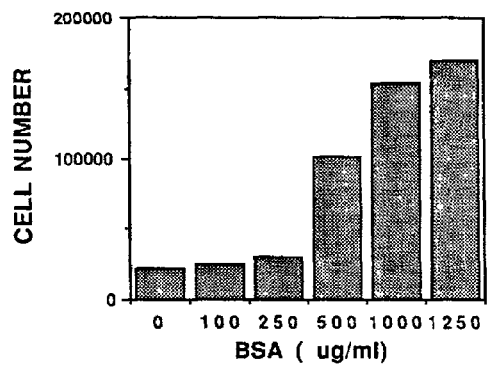
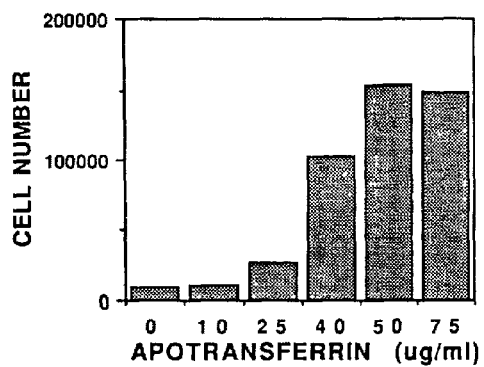
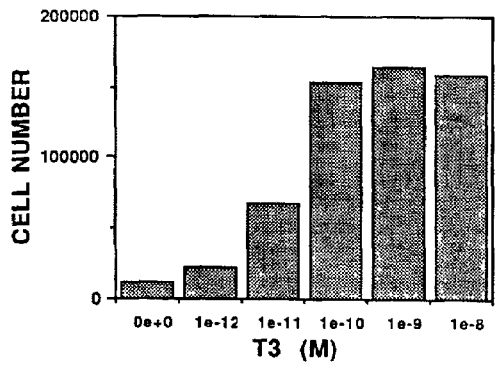
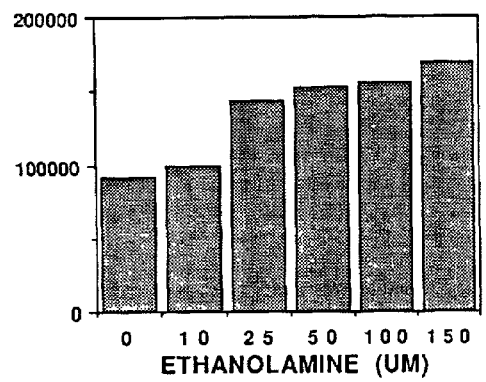
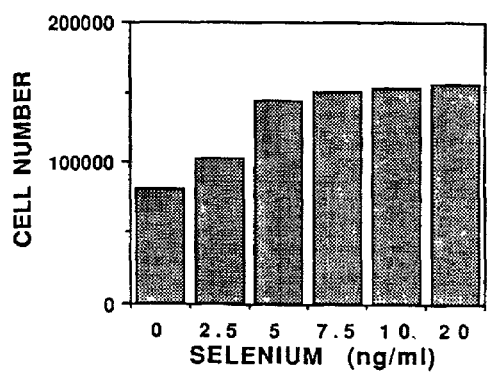
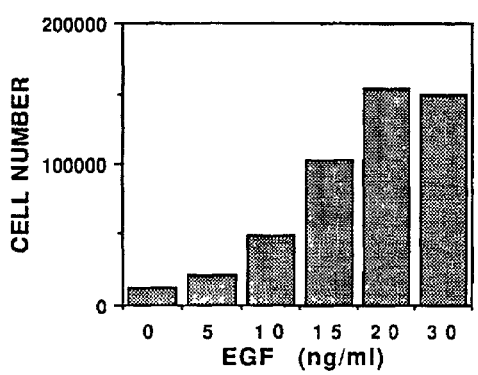

EFFECT OF FE (III) IN MCF-7A CELL GROWTH IN DDM-2MF DEFINED MEDIUM

LEGEND:

—■— plus $E_2$

—▲— minus $E_2$

EFFECT OF FE (III) IN T47D CELL GROWTH IN DDM-2MF DEFINED MEDIUM

LEGEND:

—■— plus $E_2$

—▲— minus $E_2$

EFFECTS OF INCREASING CONCENTRATIONS OF IRON ON LNCaP CELLS GROWN IN SERUM-FREE MEDIUM WITH APOTRANSFERRIN

EFFECTS OF IRON AND $T_3$ ON THREE PROSTATIC
CELL LINES IN SERUM-FREE MEDIUM

INSERT:

DARK BARS = GROWTH IN CAPM PLUS $T_3$

LIGHT (HATCHED) BARS = GROWTH IN CAPM MINUS $T_3$

NOTE THE STRIKING DEPENDENCE OF LNCaP CELLS ON $T_3$

EFFECT OF CHELATORS ON SERUM-FREE T47D GROWTH UNDER HIGH IRON CONDITIONS

LEGEND:
- □ DEFEROXAMINE
- ♦ EDTA
- ■ CITRATE

EFFECT OF CHELATORS ON SERUM-FREE LNCaP GROWTH UNDER HIGH IRON CONDITIONS

LEGEND:

Closed circles = Deferoxamine

Open circles = Citrate

Closed triangles = EDTA

DU145 GROWTH IN SERUM-FREE MEDIUM BASED ON "LOW FE" OR "STANDARD" MEDIUM

LEGEND:

Open circles = "Low Fe" medium

Closed circles = "Standard" medium

PC3 GROWTH IN SERUM-FREE MEDIUM BASED ON "LOW FE" OR "STANDARD" MEDIUM

LEGEND:

Open circles = "Low Fe" medium

Closed triangles = "Standard" medium

CDE HORSE SERUM TITRATION ON ALVA-41 CELLS

% SERUM CONCENTRATION

LEGEND:

●  = + 10 nM DHT
○  = STEROID FREE
▲  = ANDROGENIC EFFECT

FIGURE 47

EFFECTS OF ESTROGEN ON STEROID HORMONE-RESPONSIVE HUMAN TUMOR CELL GROWTH

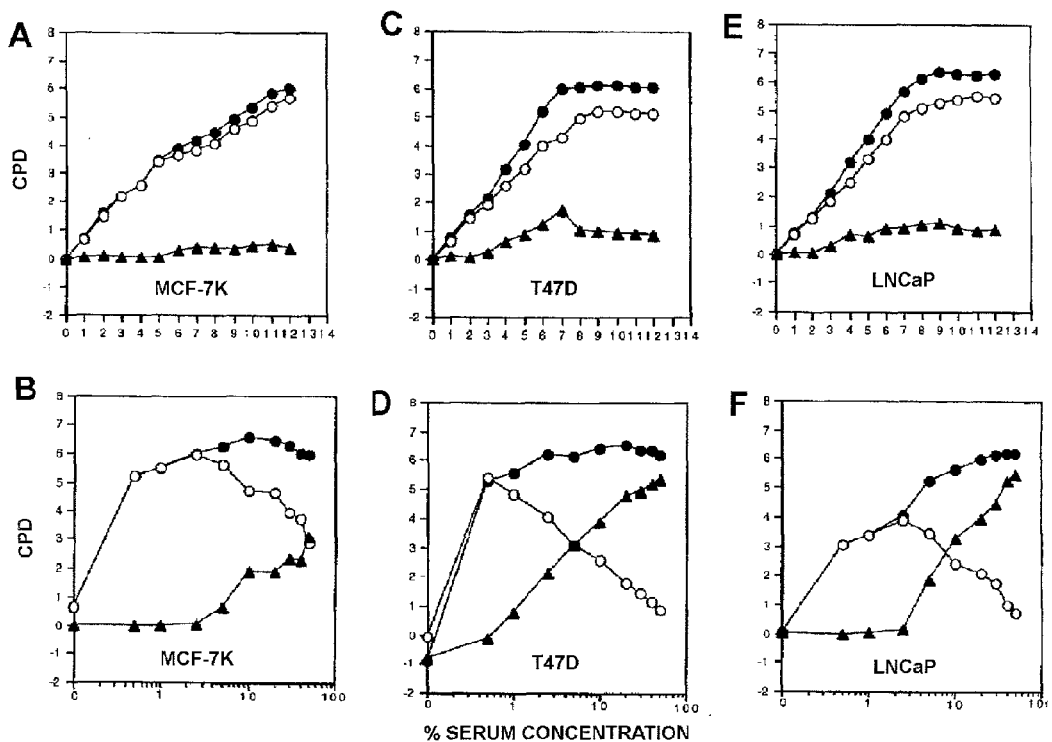

The cells were grown in serum-free defined medium and in D-MEM/F-12 supplemented with increasing concentrations of CDE horse serum.

(A) MCF-7K cell growth was measured daily in serum-free defined DDM-2MF with 10 nM $E_2$ (closed circles) and without steroid (open circles) $E_2$. Triangles = estrogenic effect.
(B) MCF-7K cell growth measured after 12 d in D-MEM-F-12 supplemented with the designated concentrations of serum with $E_2$ (closed circles) and without steroid (open circles). The estrogenic effect is shown by triangles.
(C) and (D) show the same experiments as in (A) and (B), respectively, except with T47D cells.
(E) and (F) show the same experiments as in (A) and (B), respectively, except with LNCaP cells. In (E) the serum-free medium was CAPM.

CDE HORSE SERUM TITRATION ON LNCaP GROWTH IN SERUM FREE CONDITIONS

LEGEND:

—○— NO STEROID

—●— + $E_2$

—□— + DHT

FIGURE 49

EFFECTS OF ESTROGEN ON STEROID HORMONE-RESPONSIVE RODENT TUMOR CELL GROWTH

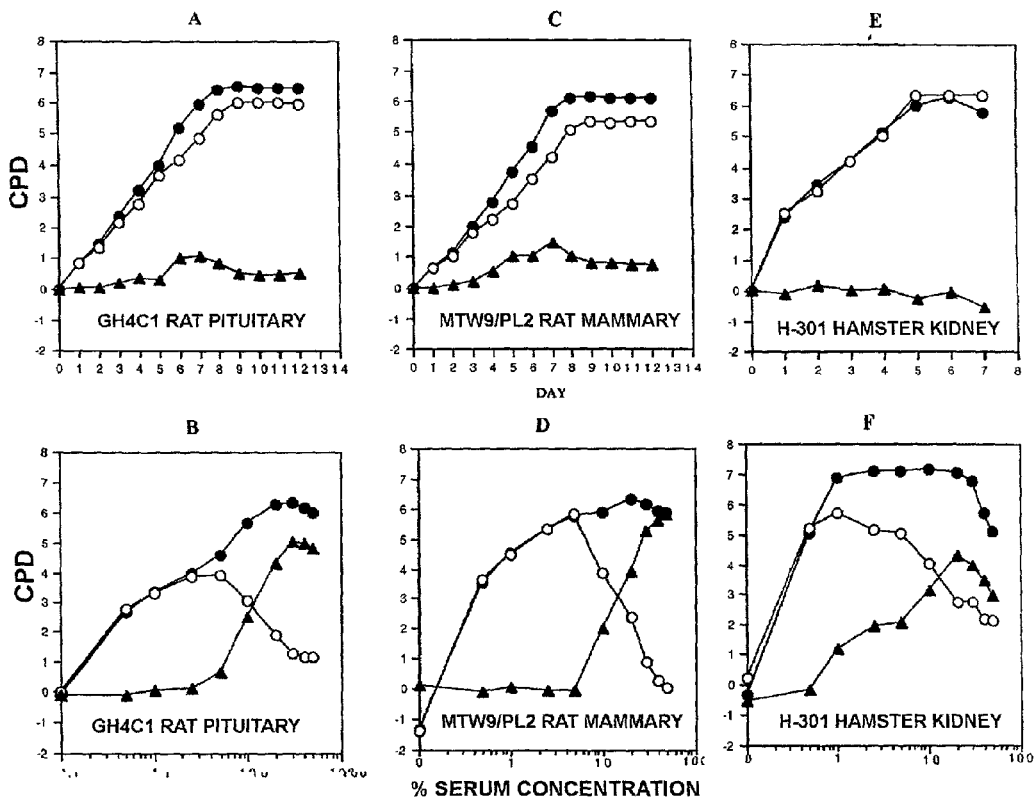

Comparison of the effects of estrogen on steroid hormone-responsive rodent tumor cell growth in serum-free defined medium and in D-MEM/F-12 supplemented with increasing concentrations of CDE horse serum.

(A) $GH_4C_1$ rat pituitary tumor cell growth measured daily in serum-free PCM-9 with $E_2$ (closed circles) and without $E_2$ (open circles). The estrogenic effect is shown by triangles.
(B) $GH_4 C_1$ cell growth measured after 9 d in D-MEM-F-12 supplemented with the designated concentrations of CDE horse serum with $E_2$ (closed circles) and without $E_2$ (open circles). The estrogenic effect is shown by triangles.
(C) and (D) show the same experiments as in (A) and (B) respectively, but with the MTW9/PL2 rat mammary tumor cells. The serum-free medium in (D) was DDM-2A.
(E) and (F) show the same experiments as in (A) and (B), respectively, except with the H-301 hamster kidney tumor cells. In (E) the serum-free medium was CAPM.

FIGURE 50

THE EFFECT OF DHT, E$_2$, AND DES ON LNCaP CELLS GROWN IN CDE HORSE SERUM

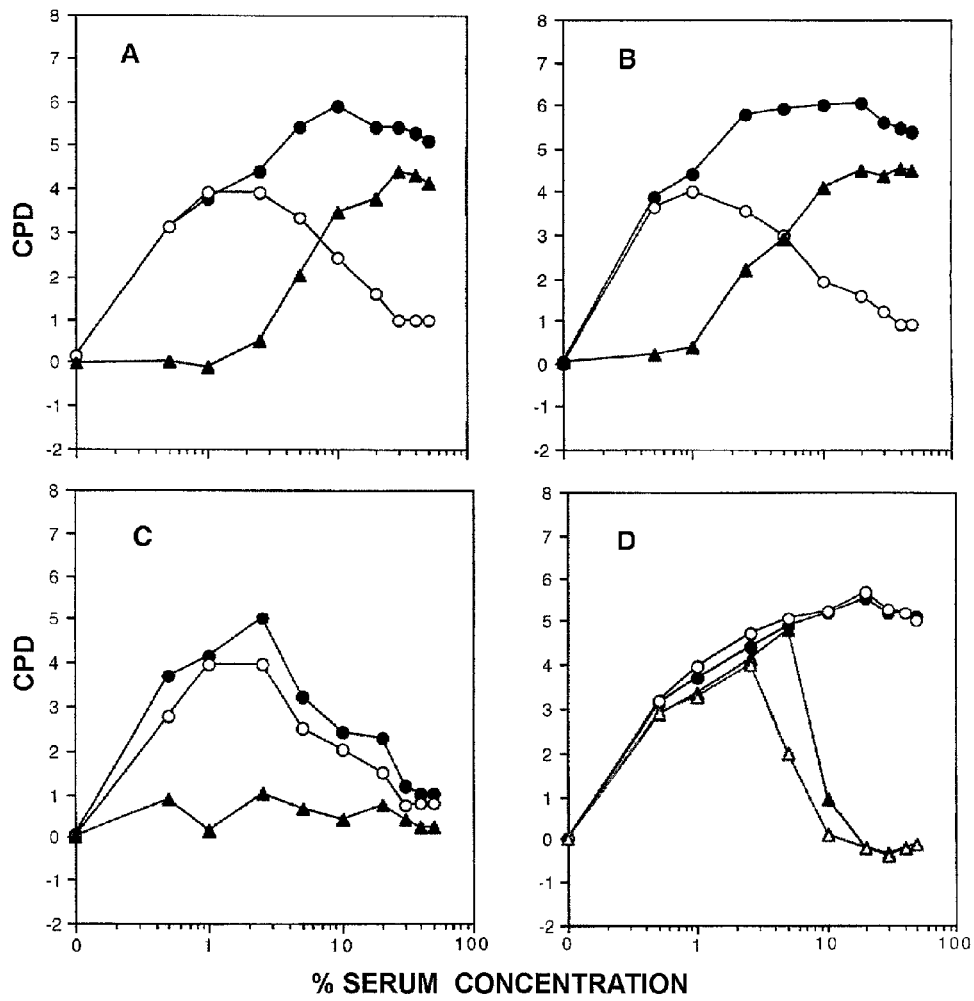

LEGEND:

(A) Open circles = - DHT
Closed circles = + DHT
Closed trianges = Androgenic effect (B) Open circles = - E$_2$
Closed circles = + E$_2$
Closed triangles = Estrogenic effect (C) Open circles = - DES
Closed circles = + DES
Closed triangles = Estrogenic effect (D) Open circles = DHT & DES
Closed circles = E$_2$ & DES
Open triangles = No additions
Closed triangles = DES only

PHENYL SEPHAROSE ELUTION OF
CBG (CA-PS-POOL 1) AND SHBG-LIKE (CA-PS-POOL 11)

ARROW = ELUTION WITH 40% ETHYLENE GLYCOL

INSERT: CORTISOL AFFINITY COLUMN ELUTION

BARS = POOLED ACTIVE FRACTION

SDS PAGE (A) AND WESTERN ANALYSIS (B) OF THREE

PREPARATIONS OF CA-PS-POOL II VS HUMAN SHBG

LANES 1, 2, AND 3 = 10 ug each of CA-PS-POOL II

LANE "SHBG" = 10 mg of purified protein

ASSAY OF CA-PS-POOL II ESTROGEN REVERSIBLE INHIBITORY ACTIVITY WITH SEVERAL ER+CELL LINES

LEGEND:
Open circles = $-E_2$
Closed circles = $+E_2$
Closed triangles = Estrogenic effect

CORTISOL-AGAROSE AFFINITY REMOVAL OF THE INHIBITOR FROM CDE-SERUM

LEGEND: Open circles = $-E_2$
Closed circles = $+E_2$
Closed triangles = Estrogenic effect

GROWTH OF ER+ CELL LINES IN SERUM-FREE MEDIUM ± $E_2$

LEGEND:

Closed circles = + $E_2$

Open circles = − $E_2$

FIGURE 56
EFFECT OF CDE-SERUM ON ESTROGEN RESPONSIVE
GROWTH OF THREE ER+ CANCER CELL LINES IN SFM
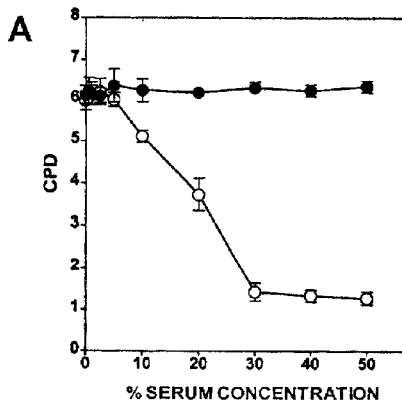
A =
T47D IN DDM-2MF
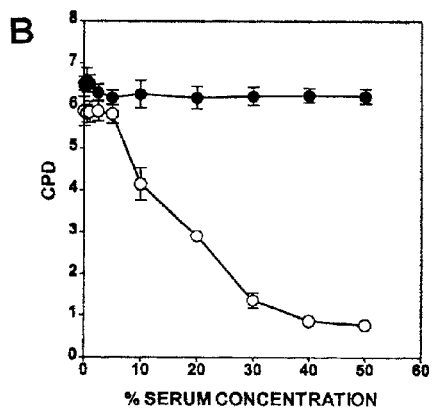
B =
MTW9/PL2 IN DDM-2A
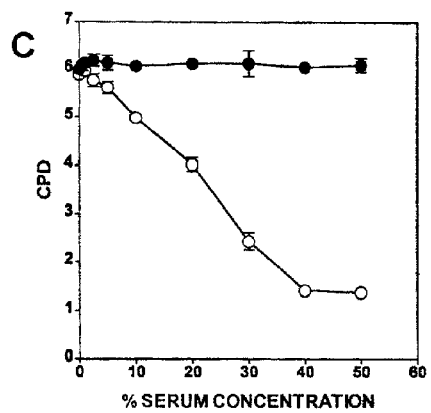
C =
$GH_4C_1$ IN PCM 9

EFFECT OF CA-PS-POOL II ON ESTROGEN
RESPONSIVE GROWTH IN SERUM FREE MEDIUM

LEGEND: Open circles = $-E_2$
Closed circles = $+E_2$

WESTERN ANALYSIS OF CBG (POOL I) AND SHBG (POOL II) PREPARATION WITH ANTI-54 kDa

----- 67 kDa
----- 58 kDa
----- 54 kDa

LANES:  1   2   3   4   5   6

1 = CBG PREPARATION #5
2 = CBG PREPARATION #6
3 = SHBG PREPARATION #5.1
4 = SHBG PREPARATION #5.2
5 = SHBG PREPARATION #6.1
6 = SHBG PREPARATION #6.2
ANTIBODY = RABBIT ANTI-54 kDa 1:5000 DILUTION

EFFECT OF ANTI-54kDa ANTISERUM ON MTW9/PL2
CELLS GROWN IN THE PRESENCE OF CA-PS-POOL II

LEGEND:
—●— No antibody
—○— Antibody 1:5000
—▼— Antibody 1:1000
—▽— Antibody 1:500
—■— Antibody 1:100
—□— Antibody 1:50

WESTERN BLOT OF COMMERCIAL PREPARATIONS
OF HORSE IgA, IgG AND IgM WITH THE
ANTI-54 kDa ANTIBODY

EFFECT OF COMMERCIALLY PURIFIED HORSE IgG

ON MTW9/PL2 CELL GROWTH IN 2.5% CDE-HORSE SERUM

LEGEND: ■ plus $E_2$
▲ minus $E_2$

EFFECT OF HORSE IgM ON GROWTH OF THE
MTW9/PL2 CELLS IN 2.5% CDE HORSE SERUM $\pm E_2$

LEGEND:

—●— = + $E_2$

—○— = − $E_2$

—▼— = Estrogenic effect

EFFECT OF HORSE IgA ON GROWTH OF THE MTW9/PL2 CELLS IN 2.5% CDE HORSE SERUM $\pm E_2$

LEGEND:

—●— = + $E_2$

—○— = − $E_2$

—▼— = Estrogenic effect

FIGURE 64
SDS PAGE AND WESTERN ANALYSIS OF RAT "SHBG-LIKE" PREPARATIONS
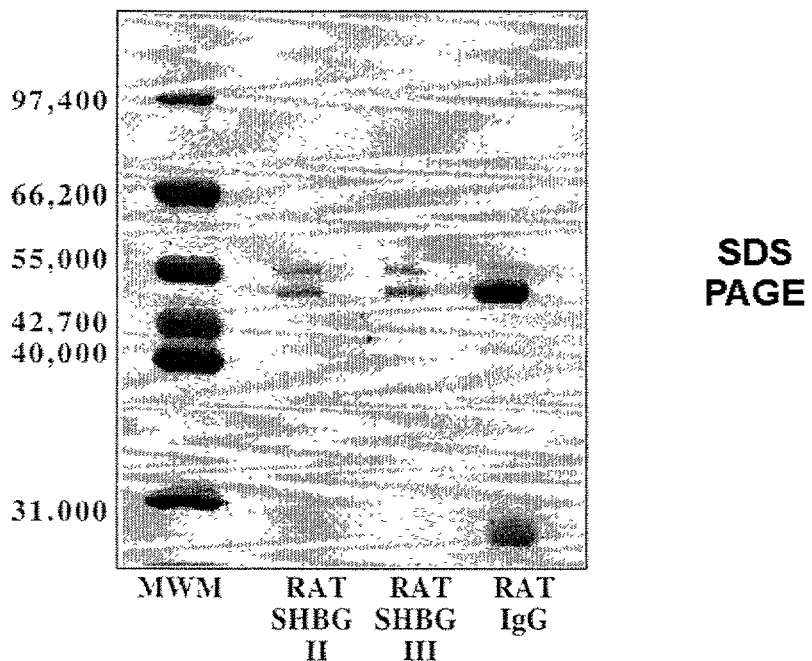
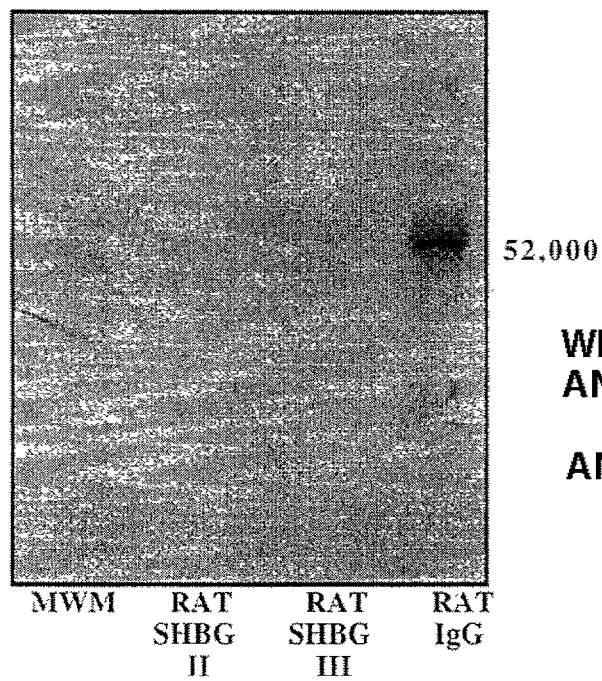

CROSSREACTION OF THE PURIFIED RAT "SHBG-LIKE" PROTEINS
WITH ANTI- IgA, IgG1 AND IgM MONOCLONAL ANTIBODIES

EFFECT OF RAT IgG ON MTW9/PL2 CELL GROWTH IN 2.5% CDE RAT SERUM

LEGEND:

Closed circles = + $E_2$

Open circles = − $E_2$

Closed triangles = Estrogenic effect

EFFECT OF RAT IgA ON MTW9/PL2 CELL
GROWTH IN 2.5% CDE RAT SERUM

CONCENTRATION OF RAT IgA (ug/mL)

LEGEND:

Closed circles = + $E_2$

Closed squares = − $E_2$

Closed triangles = Estrogenic effect

EFFECT OF RAT IgM ON MTW9/PL2 CELL GROWTH IN 2.5% CDE RAT SERUM

LEGEND:

Closed squares = − $E_2$

Closed circles = + $E_2$

Closed triangles = Estrogenic effect

ELUTION OF IgM FROM MANNAN BINDING PROTEIN COLUMN

IgM PURIFICATION FROM

PLASMA BY JACALIN

MW    HUMAN    PURIFIED
      IgA      IgA

EFFECT OF IgM ISOLATED FROM HUMAN PLASMA
ON MTW9/PL2 GROWTH IN SERUM-FREE CONDITIONS

LEGEND:

●— = + $E_2$

—— = – $E_2$

▼— = Estrogenic effect

THE EFFECT OF VARIOUS IgA AND IgM PREPARATIONS
ON MTW9/PL2 CELLS GROWN IN SERUM-FREE MEDIUM

RAT MYELOMA IgA TITRATION ON GH$_1$ CELLS GROWN IN SERUM-FREE CONDITIONS

LEGEND:

Closed circles = + E$_2$

Open circles = − E$_2$

Closed triangles = Estrogenic effect

HUMAN PLASMA IgA TITRATION ON $GH_1$ CELLS GROWN IN SERUM-FREE CONDITIONS

LEGEND:

Closed circles = + $E_2$

Open circles = − $E_2$

Closed triangles = Estrogenic effect

HUMAN PLASMA IgM TITRATION ON $GH_1$ CELLS GROWN IN SERUM-FREE CONDITIONS

LEGEND:
- ● = + $E_2$
- ■ = − $E_2$
- ▲ = Estrogenic effect

EFFECT OF HUMAN SECRETORY IgA ON GH$_1$ CELLS GROWN IN SERUM-FREE CONDITIONS

LEGEND:

Closed circles = + E$_2$

Open circles = − E$_2$

Closed triangles = Estrogenic effect

MECHANISM OF TRANSCYTOSIS OF IgA AND IgM
BY MUCOSAL EPITHELIAL CELLS

FIGURE 79
ESSENTIAL STRUCTURES OF HUMAN
PLASMA AND SECRETORY IgA
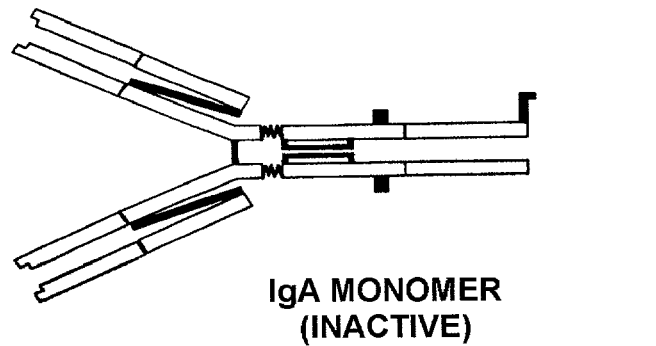 
IgA MONOMER    J CHAIN
(INACTIVE)
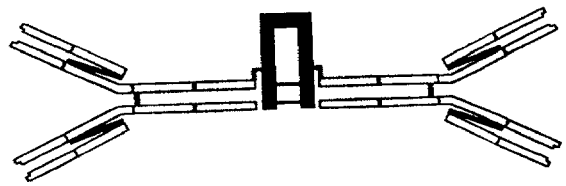 
IgA DIMER WITH    SECRETORY PIECE OR
ATTACHED J CHAIN (ACTIVE)    SECRETORY COMPONENT
    (80% POLY-IgR)
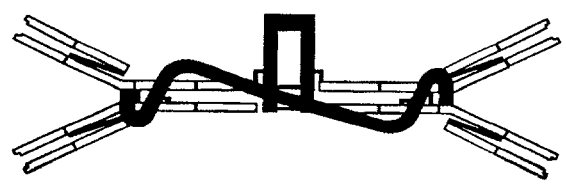
SECRETORY IgA SHOWING J CHAIN
AND SECRETORY COMPONENT (INACTIVE)

EFFECT OF RAT MYELOMA IgA ON GH$_3$ CELLS GROWN IN SERUM-FREE MEDIUM

LEGEND:

Closed circles = + E$_2$

Open circles = − E$_2$

Closed triangles = Estrogenic effect

EFFECT OF RAT IgM ON $GH_3$ CELL
GROWTH IN SERUM-FREE MEDIUM

LEGEND:

—●— = + $E_2$

—○— = − $E_2$

—▲— = Estrogenic effect

EFFECT OF HUMAN PLASMA IgA ON GH$_3$ CELL GROWTH IN SERUM-FREE MEDIUM

LEGEND:

Closed circles = + E$_2$

Open circles = − E$_2$

Closed triangles = Estrogenic effect

EFFECT OF HUMAN PLASMA IgM ON GH$_3$ CELL GROWTH IN SERUM-FREE MEDIUM

LEGEND:

— ● — = + E$_2$

— ■ — = − E$_2$

— ▼ — = Estrogenic effect

EFFECT OF HUMAN MILK SECRETORY IgA ON GH$_3$ CELL GROWTH IN SERUM-FREE MEDIUM

LEGEND:

Closed circles = + E$_2$

Open circles = − E$_2$

Closed triangles = Estrogenic effect

EFFECT OF RAT MYELOMA IgA ON $GH_4$ CELL GROWTH IN SERUM-FREE MEDIUM

CONCENTRATION OF RAT MYELOMA IgA (ug/mL)

LEGEND:

Closed circles = $+ E_2$

Open circles = $- E_2$

Closed triangles = Estrogenic effect

EFFECT OF RAT PLASMA IgM ON GH$_4$ CELL GROWTH IN SERUM-FREE MEDIUM

LEGEND:

─○─ = + E$_2$

─●─ = − E$_2$

─▲─ = Estrogenic effect

EFFECT OF HUMAN PLASMA IgA ON $GH_4C_1$ CELL GROWTH IN SERUM-FREE MEDIUM

LEGEND:

Closed circles = + $E_2$

Open circles = − $E_2$

Closed triangles = Estrogenic effect

EFFECT OF HUMAN PLASMA IgM ON $GH_4C_1$
CELL GROWTH IN SERUM-FREE MEDIUM

CONCENTRATION OF HUMAN PLASMA IgM (ug/mL)

LEGEND:

—●— = + $E_2$

—X— = − $E_2$

—▲— = Estrogenic effect

EFFECT OF HUMAN MILK SECRETORY IgA ON
$GH_4C_1$ CELL GROWTH IN SERUM-FREE MEDIUM

LEGEND:

Closed circles = + $E_2$

Open circles = – $E_2$

Closed triangles = Estrogenic effect

EFFECT OF MOUSE IgA ON H301 CELL GROWTH IN SERUM-FREE MEDIUM

LEGEND:

Closed circles = + $E_2$

Open circles = − $E_2$

Closed triangles = Estrogenic effect

EFFECT OF HUMAN PLASMA IgA (A) AND SECRETORY IgA (B) ON H301 CELL GROWTH IN SERUM-FREE MEDIUM

LEGEND: Closed circles = + $E_2$
Open circles = − $E_2$
Closed triangles = Estrogenic effect EFFECT OF ESTRADIOL ON H301 CELL GROWTH IN SERUM-FREE MEDIUM AND 40 ug/mL OF HUMAN IgM EFFECT OF HUMAN PLASMA IgA (A) AND SECRETORY IgA (B) ON MCF-7K CELL GROWTH IN SERUM-FREE MEDIUM LEGEND: Closed circles = + $E_2$
Open circles = − $E_2$
Closed triangles = Estrogenic effect EFFECT OF HUMAN PLASMA IgA (A) AND SECRETORY IgA (B) ON MCF-7K CELL GROWTH IN SERUM-FREE MEDIUM LEGEND: Closed circles = + $E_2$
Open circles = − $E_2$
Closed triangles = Estrogenic effect EFFECT OF HUMAN IgM ON MCF-7A CELL GROWTH IN SERUM-FREE MEDIUM

LEGEND:

—●— = + $E_2$

—○— = − $E_2$

—▼— = Estrogenic effect

EFFECT OF HUMAN IgM ON MCF-7K
CELL GROWTH IN SERUM-FREE MEDIUM

LEGEND:

—●— = + $E_2$

—○— = − $E_2$

—▼— = Estrogenic effect

EFFECT OF ESTRADIOL ON MCF-7K CELL GROWTH IN SERUM-FREE MEDIUM WITH 40 ug/mL HUMAN IgM

EFFECT OF HUMAN PLASMA IgA (A) AND SECRETORY IgA (B) ON T47D CELL GROWTH IN SERUM-FREE MEDIUM

LEGEND: Closed circles = + $E_2$
Open circles = − $E_2$
Closed triangles = Estrogenic effect

EFFECT OF HUMAN IgM ON T47D CELL GROWTH IN SERUM-FREE MEDIUM

LEGEND: Closed circles = + $E_2$

Open circles = – $E_2$

Closed triangles = Estrogenic effect

EFFECT OF ESTRADIOL ON T47D CELL GROWTH IN SERUM-FREE MEDIUM WITH 40 ug/mL HUMAN IgM

EFFECT OF HUMAN PLASMA IgA (A) AND SECRETORY IgA (B) ON ZR-75-1 CELL GROWTH IN SERUM-FREE MEDIUM

LEGEND: Closed circles = + $E_2$
Open circles = − $E_2$
Closed triangles = Estrogenic effect EFFECT OF HUMAN PLASMA IgM ON
ZR-75-1 CELL GROWTH IN SERUM-FREE MEDIUM

LEGEND:

—●— = − $E_2$

−○− = + $E_2$

EFFECT OF HUMAN IgM ON HT-29 CELL GROWTH IN THE PRESENCE OF INCREASING CONCENTRATIONS OF $T_3$

LEGEND:

☐ = $T_3$ Titration

■ = $T_3$ Titration + 40 ug/mL IgM

EFFECT OF HUMAN PLASMA IgA (A) AND SECRETORY IgA (B) ON LNCaP CELL GROWTH IN SERUM-FREE MEDIUM

LEGEND:  Closed circles = + $E_2$
Open circles = – $E_2$
Closed triangles = Estrogenic effect

FIGURE 106

ESTROGENIC EFFECT OF 50 ug/mL OF VARIOUS IgM'S ON SEVERAL DIFFERENT CELL LINES

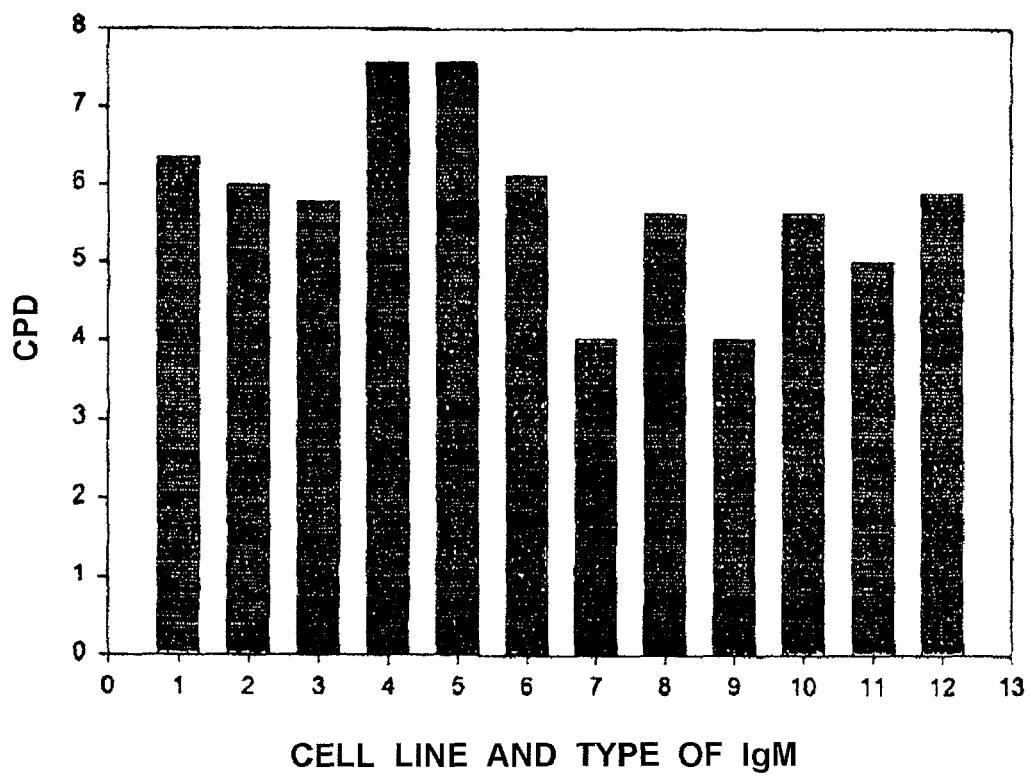

CELL LINE AND TYPE OF IgM

LEGEND:

1. Human IgM on MTW9/PL2 Cells = 6.36 cpd
2. Mouse IgM on MTW9/PL2 Cells = 6.00 cpd
3. Rat IgM on MTW9/PL2 Cells = 5.77 cpd
4. Human IgM on H301 Cells = 7.57 cpd
5. Mouse IgM on H301 Cells = 7.56 cpd
6. Rat IgM on H301 Cells = 6.11 cpd
7. Human IgM on GH1 Cells = 4.12 cpd
8. Rat IgM on GH1 Cells = 5.83 cpd
9. Human IgM on GH3 Cells = 4.09 cpd
10. Human IgM on GH4 Cells = 5.41 cpd
11. Human IgM on MCF-7A Cells = 5.01 cpd
12. Human IgM on MCF-7K Cells = 5.89 cpd

EFFECT OF TAMOXIFEN ON T47D CELL GROWTH
IN DDM-2MF DEFINED MEDIUM

LEGEND:
- SFM + $E_2$
- SFM - $E_2$
- SFM + $10^{-9}$ M TAM
- SFM + $10^{-8}$ M TAM
- SFM + $10^{-7}$ M TAM
- SFM + $10^{-6}$ M TAM
- SFM + $10^{-5}$ M TAM

EFFECT OF INCREASING ESTRADIOL CONCENTRATIONS
ON T47D CELL GROWTH IN SERUM-FREE AND
PHENOL-RED FREE MEDIUM WITH $10^{-7}$ TAMOXIFEN

NOTE:

DATA ARE EXPRESSED AS BOTH CELL NUMBER AND CPD $E_2$ RESCUE OF MTW9/PL2 CELL GROWTH IN SERUM-FREE MEDIUM WITH 40 ug/mL HORSE IgM

SUMMARY OF $E_2$ RESCUE OF MTW9/PL2 CELL GROWTH
IN SERUM-FREE MEDIUM WITH 40 ug/mL HORSE IgM

$E_2$ RESCUE OF T47D CELL GROWTH IN SERUM-FREE MEDIUM WITH 40 ug/mL HORSE IgM $E_2$ ADDITION (DAY)

LEGEND:

■ = + $E_2$

▨ = − $E_2$

ESTROGEN RESCUE OF MCF-7A CELL GROWTH IN SERUM-FREE MEDIUM WITH 40 ug/mL OF HUMAN SERUM IgM

DETECTION OF SECRETORY COMPONENT
IN SECRETORY IgA WITH ANTI-SC ANTIBODY 20 ug/mL APPLIED IN ALL LINES

IgA = Human Plasma

IgG = Human Plasma

Secretory IgA = IgA from Milk

Albumin = Human

HUMAN IgM TITRATION ON T47D CELLS GROWN IN SERUM-FREE MEDIUM WITH DIFFERENT DILUTIONS OF ANTI-SC ANTIBODY

LEGEND:   ●  = + $E_2$
          ○  = − $E_2$
          ▲  = 1:5000 Dilution of Anti-SC Antibody
          △  = 1:1000 Dilution of Anti-SC Antibody
          ■  = 1:500 Dilution of Anti-SC Antibody INSERT:   EFFECT OF RABBIT SERUM ON T47D CELLS INCUBATED WITH 40 ug/mL HUMAN IgM EFFECT OF IgA ON LNCaP GROWTH IN THE PRESENCE OF ANTI-SECRETORY COMPONENT ANTIBODY AT DIFFERENT DILUTIONS

WESTERN BLOT: ANTI-SECRETORY COMPONENT

LEGEND:

1. MW
2. ALVA 41: 40 ug
3. ALVA 41: 20 ug
4. DU 145: 40 ug
5. DU 145: 20 ug
6. HUMAN FIBROBLAST: 40 ug
7. HUMAN FIBROBLAST: 20 ug
8. LNCaP: 40 ug
9. LNCaP: 20 ug
10. MDCK1: 20 ug
11. MDCK1: 10 ug
12. PC3: 40 ug

EFFECT OF HUMAN PLASMA IgA ON DU145
CELL GROWTH WITH AND WITHOUT DHT

LEGEND:
─◆─ = + DHT
─■─ = − DHT

EFFECT OF HUMAN PLASMA IgA ON PC3 CELL GROWTH WITH AND WITHOUT DHT

EFFECT OF RAT IMMUNOGLOBULINS ON MTW9/PL2 CELL GROWTH IN SERUM-FREE MEDIUM

CONCENTRATION OF RAT IMMUNOGLOBULINS (15 ug/mL)

LEGEND:

■ = + $E_2$

▨ = − $E_2$

▦ = Estrogenic effect

CONTROL IS SERUM-FREE MEDIUM ALONE ± $E_2$

ESTROGENIC EFFECT GENERATED BY IMMUNOGLOBULINS
WITH T47D CELLS IN SERUM-FREE MEDIUM

EFFECT OF IgG ISOTYPES (40 ug/mL) ON LNCaP CELL GROWTH IN SERUM-FREE MEDIUM

LEGEND: + = DHT Added
— = No DHT Added

IgG ISOTYPE ASSAYS WITH LNCaP CELLS IN SERUM-FREE DEFINED MEDIUM ± DHT

FIGURE 123

MODEL OF EARLY ONSET BREAST CANCER
INCLUDING TGF-BETA

ER⁺ BREAST CANCERS (i) Inhibitory receptor(s) for IgA & IgM & IgG1

(ii) Growth inhibition by IgA & IgM (iii) Little or no TGFβ growth inhibition (iv) No TGFβ receptors

NORMAL EPITHELIAL CELLS

I. Inhibitory receptor(s) for IgA & IgM & IgG1 & TGFβ

II. Growth inhibition by IgA & IgM & TGFβ

ER⁻ BREAST CANCERS (i) No functional receptors for IgA or IgM & IgG1

(ii) No growth inhibition by IgA & IgM (iii) High sensitivity TGFβ growth inhibition (iv) TGFβ receptors present FIGURE 124
EFFECT OF CARCINOGENS ON MAMMARY TUMOR
INDUCTION IN RATS OF VARIOUS AGES
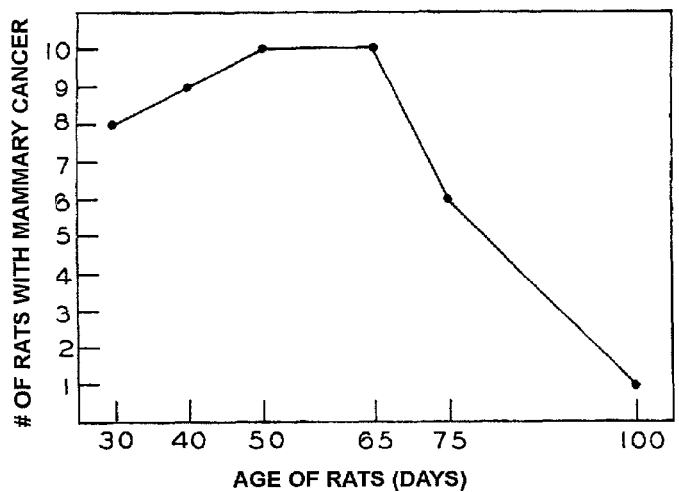
INCIDENCE OF MAMMARY CANCER IN GROUPS OF 10
FEMALE RATS OF VARIOUS AGES FED 3-MC, 100 MG
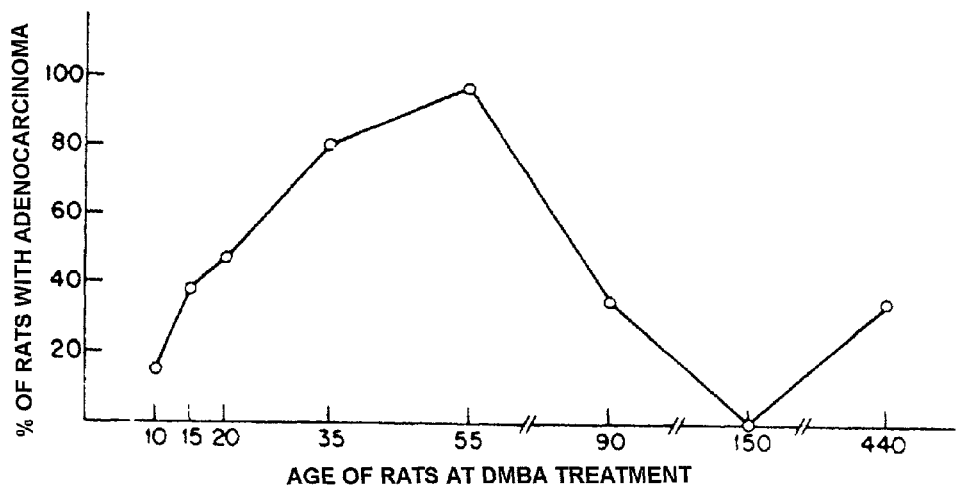
INCIDENCE OF MAMMARY ADENOCARCINOMA IN
RATS GIVEN DMBA AT DIFFERENT AGES

FIGURE 125
ANTI-HUMAN SHBG ANTIBODY IMMUNOPRECIPITATION OF THE ESTROGENIC ACTIVITY PRESENT IN CDE-HORSE SERUM WITH MTW9/PL2 CELLS
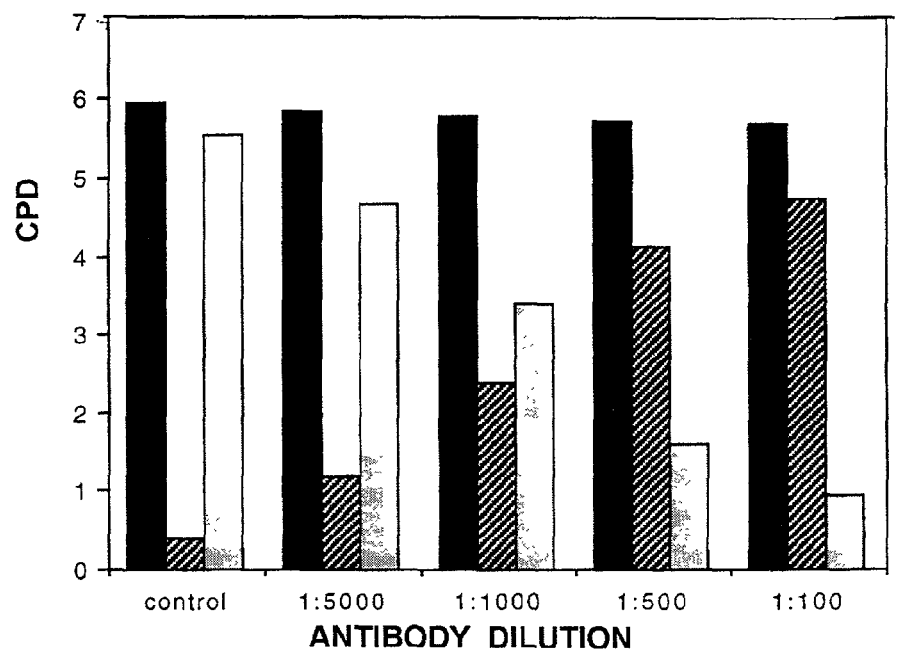
LEGEND: ■ = GROWTH IN 50% CDE WITH $E_2$
▨ = GROWTH IN 50% WITHOUT $E_2$
▦ = $E_2$ EFFECT
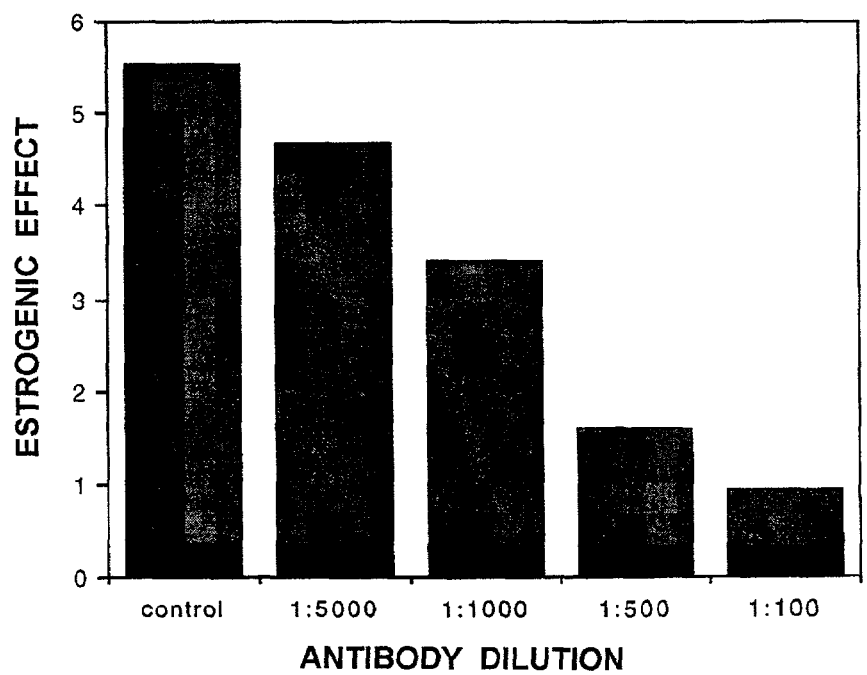

ANTI-HUMAN SHBG ANTIBODY IMMUNOPRECIPITATION OF THE ESTROGENIC ACTIVITY PRESENT IN CDE-RAT SERUM ASSAYED WITH MTW9/PL2 CELLS

ANTI-HUMAN SHBG ANTIBODY IMMUNOPRECIPITATION OF THE LABELED STEROID HORMONE BINDING ACTIVITY PRESENT IN CDE-RAT SERUM

FIGURE 128
WESTERN ANALYSIS AND DENSITOMETRY OF THE
IMMUNOGLOBULIN LEVELS IN THE SERUM OF
FEMALE RATS OF SPECIFIED AGE GROUPS
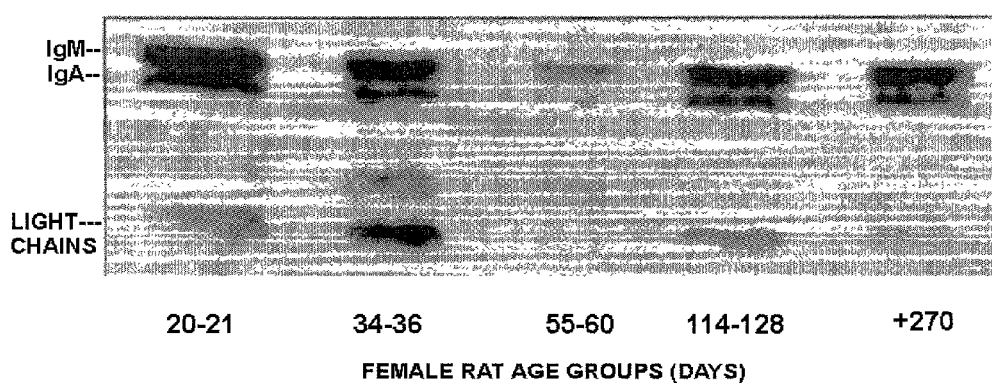
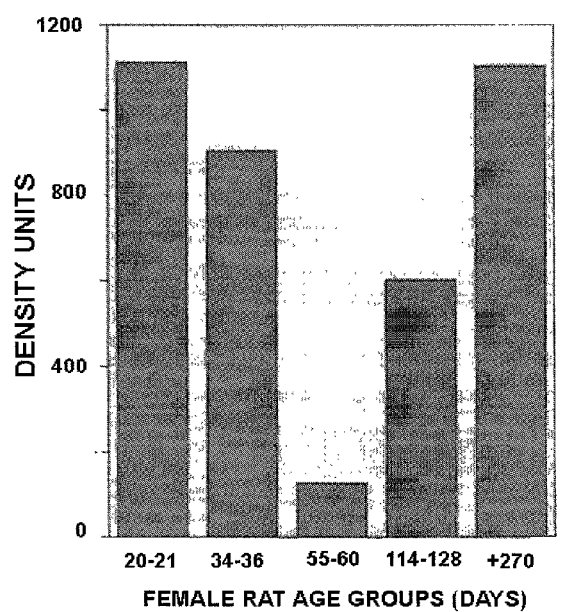

STRUCTURAL AND FUNCTIONAL ORGANIZATION

OF THE HUMAN ESTROGEN RECEPTOR-alpha

FIGURE 130
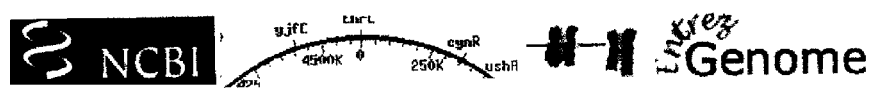
"BREAST CANCER" SEARCH - 31 "HITS"
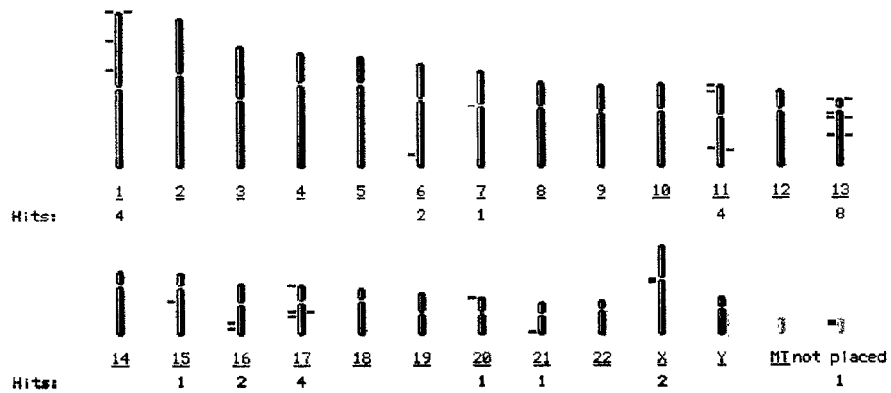
"PIGR" (POLY-Ig RECEPTOR) SEARCH - 1 "HIT"
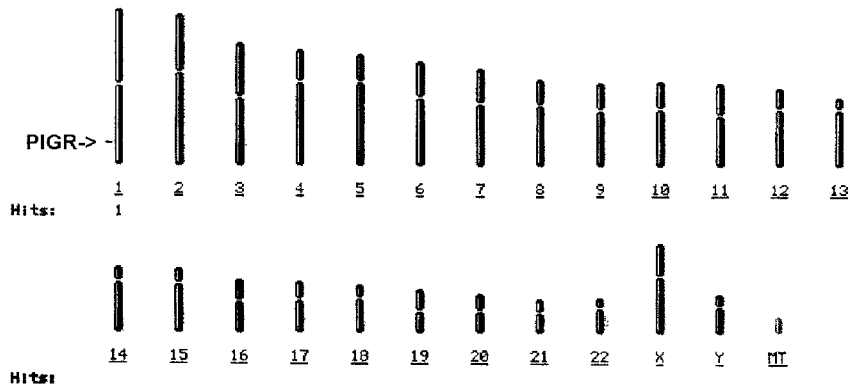
NOTE: THERE ARE NO BREAST CANCER "HITS" IN THE AREA OF THE POLY-Ig RECEPTOR ON CHROMOSOME 1

CHROMOSOME 1

FIGURE 132

CANCER AROUND THE WORLD, 1994-1997
DEATH RATES PER 100,000 (45 COUNTRIES)

| Country | Colon & Rectum Male | Colon & Rectum Female | Breast Female | Prostate Male |
|---|---|---|---|---|
| United States† | 15.2 (27) | 10.4 (23) | 20.0 (14) | 15.9 (20) |
| Australia‡ | 20.2 (10) | 13.3 (10) | 19.9 (15) | 19.0 (9) |
| Austria† | 21.7 (8) | 12.2 (14) | 20.9 (13) | 16.9 (14) |
| Azerbaijan§ | 6.0 (41) | 4.2 (43) | 8.6 (42) | 5.1 (41) |
| Bulgaria^ | 17.2 (20) | 11.4 (19) | 15.9 (31) | 8.5 (34) |
| Canada‡ | 16.1 (26) | 10.3 (25) | 21.5 (10) | 16.4 (17) |
| Chile^ | 7.0 (38) | 6.7 (36) | 12.1 (35) | 16.0 (19) |
| China¶^ | 7.9 (36) | 6.4 (37) | 5.0 (44) | — |
| Colombia^ | 4.8 (44) | 5.1 (40) | 9.1 (40) | 12.6 (28) |
| Croatia# | 22.5 (6) | 11.5 (18) | 18.5 (20) | 13.0 (25) |
| Cuba‡ | 9.4 (34) | 11.3 (20) | 14.9 (33) | 20.8 (4) |
| Czech Republic§ | 34.3 (1) | 17.3 (3) | 21.1 (12) | 16.0 (18) |
| Denmark§ | 22.7 (5) | 15.6 (4) | 27.6 (1) | 19.9 (6) |
| Estonia§ | 18.1 (16) | 12.2 (13) | 18.5 (19) | 12.8 (27) |
| Finland‡ | 12.1 (31) | 8.5 (31) | 16.8 (25) | 17.6 (12) |
| France‡ | 16.6 (22) | 9.6 (29) | 19.6 (16) | 15.8 (21) |
| Germany† | 20.8 (9) | 14.0 (7) | 21.7 (8) | 16.6 (16) |
| Greece§ | 8.0 (35) | 6.2 (38) | 16.2 (27) | 9.3 (33) |
| Hungary^^ | 34.3 (2) | 18.7 (2) | 23.7 (6) | 18.7 (11) |
| Ireland‡ | 22.5 (7) | 13.3 (9) | 26.1 (2) | 18.8 (10) |
| Israel§ | 17.9 (18) | 13.8 (8) | 25.1 (4) | 12.0 (30) |
| Japan** | 17.1 (21) | 9.9 (28) | 7.7 (43) | 5.1 (42) |
| Kazakhstan§ | 12.6 (30) | 8.6 (30) | 13.2 (34) | 5.7 (39) |
| Kyrgyzstan§ | 6.9 (39) | 4.5 (41) | 10.6 (37) | 4.3 (43) |
| Latvia‡ | 18.3 (12) | 11.8 (15) | 17.3 (24) | 11.5 (31) |
| Lithuania§ | 18.2 (13) | 11.7 (16) | 18.7 (18) | 15.2 (22) |
| Macedonia§ | 10.8 (33) | 7.1 (34) | 16.1 (30) | 6.2 (38) |
| Mauritius§ | 6.0 (42) | 3.8 (44) | 9.0 (41) | 7.7 (36) |
| Mexico‡ | 3.6 (45) | 3.3 (45) | 9.3 (39) | 12.8 (26) |
| Netherlands‡ | 17.7 (19) | 12.7 (11) | 26.0 (3) | 19.4 (8) |
| New Zealand^ | 26.4 (3) | 19.1 (1) | 22.9 (7) | 19.8 (7) |
| Norway‡ | 20.0 (11) | 14.7 (5) | 19.4 (17) | 23.2 (2) |
| Poland§ | 16.4 (23) | 11.0 (22) | 16.1 (29) | 11.1 (32) |
| Portugal§ | 18.1 (15) | 10.4 (24) | 17.6 (22) | 17.2 (13) |
| Rep. of Moldova‡ | 16.2 (25) | 11.1 (21) | 18.2 (21) | 5.7 (40) |
| Romania§ | 11.3 (32) | 7.9 (33) | 15.7 (32) | 8.3 (35) |
| Russian Fed.‡ | 18.2 (14) | 12.6 (12) | 16.1 (28) | 7.2 (37) |
| Slovakia‡ | 14.6 (28) | 6.8 (35) | — | 12.2 (29) |
| Slovenia§ | 23.9 (4) | 14.0 (6) | 21.2 (11) | 14.7 (23) |
| Spain‡ | 16.4 (24) | 10.0 (27) | 17.5 (23) | 13.9 (24) |
| Sweden§ | 13.8 (29) | 10.2 (26) | 16.8 (26) | 21.4 (3) |
| Trinidad & Tobago^ | 7.8 (37) | 8.3 (32) | 21.5 (9) | 35.5 (1) |
| Turkmenistan^ | 6.2 (40) | 4.4 (42) | 9.5 (38) | 1.4 (44) |
| United Kingdom† | 18.0 (17) | 11.6 (17) | 24.5 (5) | 16.6 (15) |
| Venezuela^ | 5.9 (43) | 6.2 (39) | 11.8 (36) | 20.3 (5) |

FIGURES IN PARENTHESES ARE ORDER OF RANK WITHIN SITE AND SEX GROUP

SOURCE: MORTALITY DATABASE 1994-97 WORLD HEALTH ORGANIZATION, 1999

FIGURE 133
A: TYPICAL CONCENTRATIONS OF IgG SUBCLASSES DURING CHILDHOOD
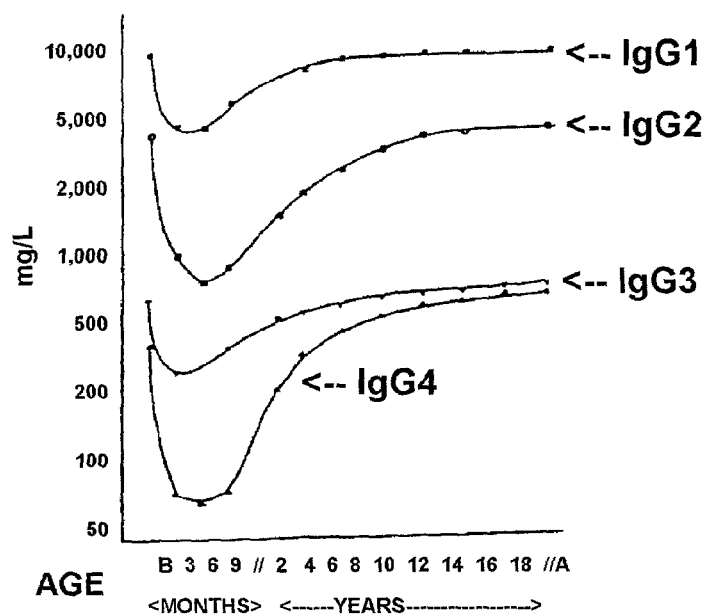
B: IMMUNOGLOBULIN CHANGES WITH AGE
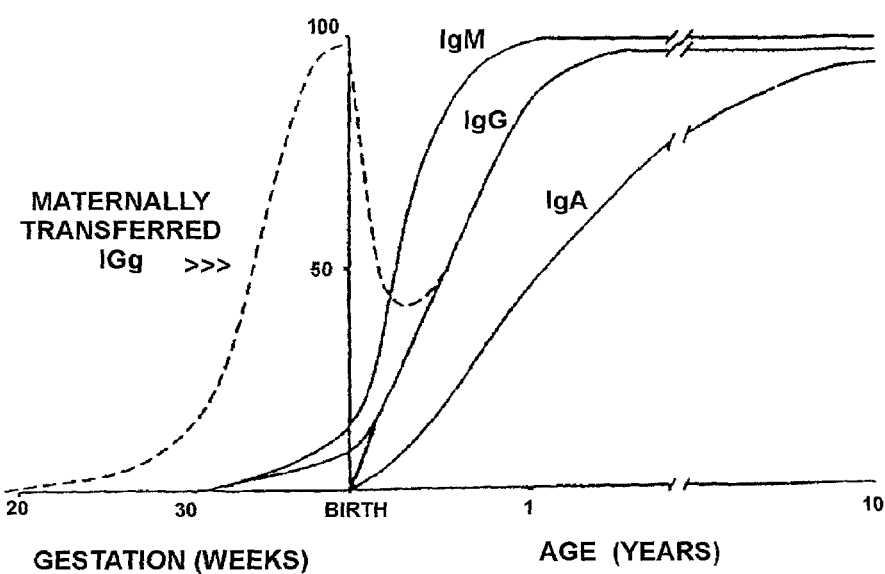

COMPOSITIONS AND METHODS FOR THE DIAGNOSIS, TREATMENT AND PREVENTION OF STEROID HORMONE RESPONSIVE CANCERS

CROSS-REFERENCE TO RELATED APPLICATIONS

This application claims the benefit under 35 U.S.C. §119 (e) of U.S. Provisional Patent Application Nos. 60/208,348 filed May 31, 2000; 60/208,111 filed May 31, 2000; 60/229,071 filed Aug. 30, 2000; and 60/231,273 filed Sep. 8, 2000.

STATEMENT REGARDING FEDERALLY SPONSORED RESEARCH OR DEVELOPMENT

Research leading to the present invention was supported in part by the federal government under Grant Nos. DAMD17-94-J-4473, DAMD17-98-8337 and DAMD17-99-1-9405 awarded by the Defense Department through the US Army Medical Research and Materiel Command, Breast Cancer Research Program. The United States government may have certain rights in the invention.

BACKGROUND OF THE INVENTION

1. Field of the Invention

The present invention generally relates to risk assessment, detection, diagnosis, prognosis, treatment and prevention of steroid hormone responsive cancers of mucosal epithelial tissues (i.e., glands and tissues that secrete or are bathed by secretory immunoglobulins). More particularly, the invention relates to negative (inhibitory) regulation of steroid hormone responsive cancer cell proliferation, and to the immunoglobulin inhibitors and the receptors that mediate such regulation.

2. Description of Related Art

Finding a naturally occurring biochemical defense mechanism capable of controlling neoplastic growth has been the goal of a number of researchers for many years. Use of the immune system against malignant tumors forms the basis for many anti-cancer strategies. For example, U.S. Pat. No. 5,980,896 describes certain antibodies, antibody fragments and antibody conjugates and single-chain immunotoxins directed against human carcinoma cells. Conventional anti-tumor immunotherapies rely on antibody-antigen recognition chemistry, and on targeting of antibodies against various antigenic features of tumor cells in order to trigger destruction of the tumor cells by the body's immune system or to target the tumor cells with antibody conjugates of various cytotoxic or chemotherapeutic agents. In practice, however, tumors in vivo have generally not been found to be very immunogenic and in many instances appear to be capable of evading the body's immune response. Today a great deal of anti-cancer work is directed at finding ways of increasing the immunogenicity of a tumor cell in vivo. For example, U.S. Pat. No. 6,120,763 (Fakhrai et al.) describes a method of preventing or reducing the severity of a cancer in a subject by stimulating the subject's immune response against the cancer. Many studies have attempted use of IgG as passive immunity or stimulation of natural IgG production to restrict tumor growth. As of today, there are no known vaccines for breast cancer, prostate cancer, or any other forms of mucosal cancers (Smyth M J et al. (2001) *Nature Immunol* 2, 293-299).

There is a second type of immune system that is very important to the function and protection of the body. The immunological function and physiological properties of the body's secretory immune system has been recognized for many years (Tomasi T B et al. (1965) *J Exp Med* 121, 101-124; Brandtzaeg P and Baklien K (1977) *Ciba Foundation Symposium* 46, 77-113; Tomasi T B (1970) *Ann Rev Med* 21, 281-298; Spiegelberg H L (1974) *Adv Immunol* 19, 259-294; Tomasi T B (1976) *The Immune System of Secretions*, Prentice-Hall, Englewood Clifts, N.J.; Mestecky J and McGhee J R (1987) *Adv Immunol* 40, 153-245). It was established that immunoglobulin A (IgA) represents 5 to 15% of the total plasma immunoglobulins in humans (Spiegelberg H L (1974) *Adv Immunol* 19, 259-294). IgA has a typical immunoglobulin four-chain structure ($M_r$ 160,000) made up of two heavy chains ($M_r$ 55,000) and two light chains ($M_r$ 23,000) (Fallgreen-Gebauer E et al (1993) *Biol Chem Hoppe-Seyler* 374, 1023-1028; Kratzin H et al. (1978) *Hoppe-Seylers Z Physiol Chem* 359, 1717-1745; Yang C et al. (1979) *Hoppe-Seylers Z Physiol Chem* 360, 1919-1940; Eiffert H et al. (1984) *Hoppe-Seylers Z Physiol Chem* 365, 1489-1495). In humans, there are two subclasses of IgA. These are IgA1 and IgA2 that have 1 and 2 heavy chains, respectively. The IgA2 subclass has been further subdivided into $A_2m(1)$ and $A_2m(2)$ allotypes (Mestecky J and Russell M W (1986) *Monogr Allergy* 19, 277-301; Morel A et al. (1973) *Clin Exp Immunol* 13, 521-528). IgA can occur as monomers, dimers, trimers or multimers (Lüllau E et al. (1996) *J Biol Chem* 271, 16300-16309). In plasma, 10% of the total IgA is polymeric while the remaining 90% is monomeric. Formation of dimeric or multimeric IgA requires the participation of an elongated glycoprotein of approximately $M_r$ 15,000 designated the "J" chain (Mestecky J et al. (1990) *Am J Med* 88, 411-416; Mestecky J and McGhee J R (1987) *Adv Immunol* 40, 153-245; Cann G M et al. (1982) *Proc Natl Acad Sci USA* 79, 6656-6660). Structurally, the J chain is disulfide linked to the penultimate cysteine residue of heavy chains of two IgA monomers to form a dimeric complex of approximately $M_r$ 420,000. The general structure of the dimer has been well described in the literature (Fallgreen-Gebauer E et al (1993) *Biol Chem Hoppe-Seyler* 374, 1023-1028). Multimeric forms of IgA and IgM require only a single J chain to form (Mestecky J and McGhee J R (1987) *Adv Immunol* 40, 153-245; Chapus R M and Koshland M E (1974) *Proc Natl Acad Sci USA* 71, 657-661; Brewer J W et al. (1994) *J Biol Chem* 269, 17338-17348). The structures and chemical properties of IgA and IgM have been described in detail (Janeway C A Jr et al. (1996) *Immunobiology, The Immune System in Health and Disease*, Second edition, Garland Publishing, New York, pp 3-32 and pp 8-19).

Dimeric and multimeric IgA and IgM are secreted by a number of exocrine tissues. IgA is the predominant secretory immunoglobulin present in colostrum, saliva, tears, bronchial secretions, nasal mucosa, prostatic fluid, vaginal secretions, and mucous secretions from the small intestine (Mestecky J et al. (1987) *Adv Immunol* 40, 153-245; Goldblum R M, et al. (1996) In: Stiehm E R, ed, *Immunological Disorders in Infants and Children*, 4th edition, Saunders, Philadelphia, pp 159-199; Heremans J F (1970) In: *Immunoglobulins, Biological Aspects and Clinical Uses*, Merler E, ed, National Academy of Sciences, Wash D.C. pp 52-73; Tomasi T B Jr (1971) In: *Immunology, Current Knowledge of Basic Concepts in Immunology and their Clinical Applications*, Good R A and Fisher D W, eds, Sinauer Associates, Stanford, Conn., p 76; Brandtzaeg P (1971) *Acta Path Microbiol Scand* 79, 189-203). IgA output exceeds that of all other immunoglobulins, making it the major antibody produced by the body daily (Heremans J F (1974) In: *The Antigens*, Vol 2, Sela M, ed, Academic Press, New York, pp 365-522; Conley M E et al. (1987) *Ann Intern Med* 106, 892-899. IgA is the major immunoglobulin found in human milk/whey/colostrum (Ammann A J et al. (1966) *Soc Exp Biol Med* 122, 1098-1113; Peitersen B et al. (1975) *Acta Paediatr Scand* 64, 709-717); Woodhouse L et al. (1988) *Nutr Res* 8, 853-864). IgM secretion is less abundant but can increase to compensate for deficiencies in IgA secretion. J chain containing IgA is produced and secreted by plasma B immunocytes located in the lamina propria just beneath the basement membrane of exocrine cells (Brandtzaeg P (1985) *Scan J Immunol* 22, 111-146). The secreted IgA binds to a $M_r$ 100,000 poly-Ig receptor positioned in the basolateral surface of most mucosal cells (Heremans J F (1970) In: *Immunoglobulins, Biological Aspects and Clinical Uses*, Merler E, ed, National Academy of Sciences, Wash D.C., pp 52-73; Brandtzaeg P (1985) *Clin Exp Immunol* 44, 221-232; Goodman J W (1987) In: *Basic and Clinical Immunology*, Stites D P, Stobo J D and Wells J V, eds, Appleton and Lange, Norwalk, Conn., Chapter 4). The receptor-IgA complex is next translocated to the apical surface where IgA is secreted. The binding of dimeric IgA to the poly-Ig receptor is completely dependent upon the presence of a J chain (Brandtzaeg P (1985) *Scan J Immunol* 22, 111-146; Brandtzaeg P and Prydz H (1984) *Nature* 311:71-73; Vaerman J-P et al. (1998) *Eur J Immunol* 28, 171-182). Monomeric IgA will not bind to the receptor. The J chain requirement for IgM binding to the poly-Ig receptor is also true for this immunoglobulin (Brandtzaeg P (1985) *Scan J Immunol* 22, 111-146; Brandtzaeg P (1975) *Immunology* 29, 559-570; Norderhaug I N et al. (1999) *Crit Rev Immunol* 19, 481-508). Because IgA and IgM bind to the poly-Ig receptor via their Fc domains, and because of a repeating Ig-like structure in the extracellular domains, the poly-Ig receptor classifies as a member of the Fc superfamily of immungobulin receptors (Krajči P et al. (1992) *Eur J Immunol* 22, 2309-2315; Daëron M (1997) *Annu Rev Immunol* 15, 203-234). During passage of IgA through the cell, its structure is modified. A $M_r$ 80,000 fragment of the receptor containing all five of the extracellular domains becomes covalently attached to dimeric IgA to form secretory IgA (sIgA) (Fallgreen-Gebauer E et al (1993) *Biol Chem Hoppe-Seyler* 374, 1023-1028). The receptor that mediates the translocation has been interchangeably called the "poly-Ig receptor" (poly-Ig receptor) or the "secretory component" (Krajči P et al. (1992) *Eur J Immunol* 22, 2309-2315). Except where noted otherwise, for the purposes of the present disclosure, the term "poly-Ig receptor" refers to the full length $M_r$ 100,000 transmembrane protein and the term "secretory component" denotes only the $M_r$ 80,000 extracellular five domains of the receptor that become covalently attached to IgA in forming the sIgA structure (Fallgreen-Gebauer E et al (1993) *Biol Chem Hoppe-Seyler* 374, 1023-1028; Krajči P et al. (1992) *Eur J Immunol* 22, 2309-2315). Because of the unique structure of sIgA, it is highly resistant to acid and proteolysis (Lindh E (1975) *J Immunol* 114, 284-286) and therefore remains intact in secretions to perform extracellular immunological functions. IgM also binds secretory component, but not covalently (Lindh E and Bjork I (1976) *Eur J Biochem* 62, 271-278). However, IgM is less stabilized because of its different association with the secretory component, and therefore has a shorter functional survival time in acidic secretions (Haneberg B (1974) *Scand J Immunol* 3, 71-76; Haneberg B (1974) *Scand J Immunol* 3, 191-197). IgA and IgM are known to bind to bacterial, parasite and viral surface antigens. These complexes bind to receptors on inflammatory cells leading to destruction of the pathogen by antibody-dependent cell-mediated cytotoxicity (Hamilton R G (1997) "Human immunoglobulins" In: *Handbook of Human Immunology*, Leffell M S et al., eds, CRC Press, Boca Raton, Chapter 3).

The major immunoglobulins secreted as mucosal immune protectors include IgA, IgM and IgG. In human serum, the percent content of IgG, IgA and IgM are 80, 6 and 13%, respectively. In humans, the major subclasses of IgG are IgG1, IgG2, IgG3 and IgG4. These are 66, 23, 7 and 4% of the total IgG, respectively. The relative content of human immunoglobulin classes/subclasses in adult serum follow the order IgG1>IgG2>IgA1>IgM>IgG3>IgA2>IgD>IgE (Spiegelberg H L (1974) *Adv Immunol* 19, 259-294). When the serum concentrations of immunoglobulins are compared to those in exocrine secretion fluids, the relative contents change dramatically (Brandtzaeg P (1983) *Ann NY Acad Sci* 409, 353-382; Brandtzaeg P (1985) *Scand J Immunol* 22, 111-146). For example in colostrum (a breast fluid secretion), IgA is $\geq$80% of the total immunoglobulins. IgM is $\leq$10% of the total. IgG represents a few percent. In human colostrum and milk, IgG1 and IgG2 are the major subclasses of IgG (Kim K et al. (1992) *Acta Paediatr* 81, 113-118). Clearly, comparison of serum and mucosal fluid concentrations indicate selective immunoglobulin secretion. The secretion mechanism for IgA and IgM are well described. Conversely, there is a fundamental question surrounding IgG secretion. There is no "J" chain present in IgG1 and IgG2. From the known facts of transcytosis/secretion of immunoglobulins (Johansen F E et al. (2000) *Scand J Immunol* 52, 240-248), it is unlikely that IgG secretion is mediated by the poly-Ig receptor. An epithelial receptor specific for IgG1 has been reported in bovine mammary gland (Kemler R et al. (1975) *Eur J Immunol* 5, 603-608). Apparently, it preferentially transports this class of immunoglobulins from serum into colostrum. Despite this 1975 report however, the receptor has not been chemically or structurally identified nor has the mechanism of transport of IgG monomers been satisfactorily defined. Certainly no growth function was ascribed to this "IgG1 receptor" in the 1975 Kemler et al. report. It is possible that this receptor is a member of a large group now designated as Fc receptors (Fridman W H (1991) *FASEB J* 5, 2684-2690), but there is one study with IgG showing that of 31 different long-term human carcinoma cell lines including breast "all lines were found to be consistently Fc receptor negative" (Kerbel R S et al. (1997) *Int J Cancer* 20, 673-679). One possible candidate for the epithelial transport of IgG1 is the neonatal Fc receptor (Raghavan M and Bjorkman P J (1996) *Annu Rev Cell Dev Biol* 12, 181-220). However, there is no indication yet of the presence of this receptor in adult mucosal tissues.

All human mucus membranes are protected by the secretory immune system (Hanson L Å and Brandtzaeg P (1989) In: *Immunological Disorders in Infants and Children*, 3$^{rd}$ edition, Stiehm E R, ed, Saunders, Philadelphia, pp 169-172). The primary protector is sIgA that is produced as dimers and larger polymers. A single joining "J" chain connects IgA monomers to form the dimers and polymers (Garcia-Pardo A et al. (1981) *J Biol Chem* 256, 11734-11738), and connects monomers of IgM to give pentamers (Niles M J et al. (1995) *Proc Natl Acad Sci USA* 92, 2884-2888). This critical joining endows these structures with a very important immunological property. Dimeric and polymeric sIgA have a high antigen binding valence that effectively agglutinates/neutralizes bacteria and virus (Janeway C A Jr et al. (1999) *Immunobiology, The Immune System in Health and Disease*, 4$^{th}$ edition, Garland Publishing, New York, pp 326-327). Also, sIgA shows little or no complement activation. This means that it does not cause inflammatory responses (Johansen F E et al. (2000) *Scand J Immunol* 52, 240-248). In addition, the fact that IgA exists as two separate forms is significant (Loomes L M et al (1991) *J Immunol Methods* 141, 209-218). The IgA1 predominates in the general circulation. In contrast, IgA2 is often higher in mucosal secretions such as those from breast, gut, and respiratory epithelium, salivary and tear glands, the male and female reproductive tracts, and the urinary tracts of both males and females. This difference in proportions is important to immune protection of mucosal surfaces. Although the secretory form of IgA1 is by and large resistant to proteolysis (Lindh E (1975) *J Immunol* 114, 284-286), a number of different bacteria secrete proteolytic enzymes that cleave it into Fab and Fc fragments (Wann J H et al. (1996) *Infect Immun* 64, 3967-3974; Poulsen K et al. (1989) *Infect Immun* 57, 3097-3105; Gilbert J V et al. (1988) *Infect Immun* 56, 1961-1966; Reinholdt J et al (1993) *Infect Immun* 61, 3998-4000; Blake M S and Eastby C (1991) *J Immunol Methods* 144, 215-221; Burton J et al. (1988) *J Med Chem* 31, 1647-1651; Mortensen S B and Kilian M (1984) *Infect Immun* 45, 550-557; Simpson D A et al. (1988) *J Bacteriol* 170, 1866-1873; Blake M S and Swanson J et al. (1978) *Infect Immun* 22, 350-358; Labib R S et al. (1978) *Biochim Biophys Acta* 526, 547-559). In effect, the bacterial proteinases negate the neutralizing effects of multivalent sIgA1. In contrast, because of structural differences (Chintalacharuvu K R and Morrison S L (1996) *J Immunol* 157, 3443-3449), IgA2 lacks sites required for proteolysis. This makes IgA2 more resistant to bacterial digest than IgA1 (Hamilton R G (1997) "Human immunoglobulins" In: *Handbook of Human Immunology*, Leffell M S et al., eds, CRC Press, Boca Raton, Chapter 3). With regard to IgM, its function is somewhat different. IgM antibodies serve primarily as efficient agglutinating and cytolytic agents. They appear early in the response to infection and are largely confined to the bloodstream. Whether secreted or plasma-borne, IgM is a highly effective activator of the classical complement cascade. It is less effective as a neutralizing agent or an effector of opsinization (i.e. facilitation of phagocytosis of microorganisms). Nonetheless, IgM complement activation causes lysis of some bacteria. The effects of the IgG class are more encompassing. All four subclasses cause neutralization, opsinization and complement activation to defend against mucosal microorganisms. IgG1 is an active subclass in this regard (Janeway C A Jr et al. (1999) *Immunobiology, The Immune System in Health and Disease*, 4$^{th}$ edition, Garland Publishing, New York pp 326-327).

With regard to breast cancer and prostate cancer etiology, there has been only limited attention given to the role of the immune system. Other issues have been considered more important for placing individuals in the at-risk groups for developing cancer in general and breast cancer specifically. This has led to searches for risk factors. Advances certainly have been made. We now have the benefit of the investment of scientific effort and volume of new information that was obtained. Breast cancer is one useful example of our advances. There have been several reviews of this topic published since 1979 (Kelsey J L (1979) *Epidemiol Rev* 1, 74-109; Kelsey J L and Berkowitz G S (1988) *Cancer Res* 48, 5615-5623; Kelsey J L and Gammon M D (1990) *Epidemiol Rev* 12, 228-240; Colditz G A (1993) *Cancer* 71, 1480-1489; Alberg A J and Helzlsouer K J (1997) *Current Opinion Oncology* 9, 505-5111). Although reproductive factors, body build, oral contraceptives, estrogen replacement therapy, diethylstilbestrol, hormonal imbalances, diet (particularly high fat consumption), alcohol consumption, radiation, familial aggregation and heredity have been studied, and some of these identified as risk factors, there remains no known cause of the 70% or more of breast cancers now known as "sporadic" because they appear to occur randomly in the population and certainly without any known genetic pattern. Plainly stated, for the vast majority of women who develop breast cancer, there is no known genetic cause. Even with the best applications of the epidemiology cited above, the answer has not been forthcoming for this majority.

The only cases where there is a defined genetic origin of breast cancer involve the BRCA1 and BRCA2 genes. The BRCA1 gene has been cloned, sequenced and localized to chromosome 17 (Hall J M et al. (1990) *Science* (Wash D.C.) 250, 1684-1689; Bowcock A M (1993) *Breast Cancer Res Treat* 28, 121-135; Miki Y et al. (1994) *Science* (Wash D.C.) 266, 66-71). Another gene, BRCA2, has also been identified and linked to chromosome 13q (Wooster R et al. (1995) *Nature* (Lond) 378, 789-792; Tavigian S V et al. (1996) *Nature Genet* 12, 333-337). BRCA1 gene lesions are linked to breast and ovarian cancer. BRCA2 is more associated with ovarian cancer than breast cancer. Together, these two genes are thought to account for most of the inheritable/familial breast cancer in the United States (Krainer M et al. (1997) *New Eng J Med* 336, 1416-1421). However, one important fact that must be recognized is that these genes are probably carried by fewer than 400 women in the United States and therefore are responsible for a relatively small number of human breast cancers (King M-C et al (1993) *JAMA* 269, 1975-1980; Biesecker B B et al. (1993) JAMA 269, 1970-1974). Although these genes continue to be studied intensively, it is far from clear that they have a significant causative role in the 70% or more of "sporadic" non-inherited breast cancers. In fact, the essential point is that the origin of the vast majority of breast cancers remains unknown.

Currently these two genes, BRCA1 (Lynch H et al. (1978) *Cancer* 41, 1543-1549; Hall J M et al. (1990) *Science* (Wash D.C.) 250, 1684-1689; Narod S A et al. (1991) *Lancet* 338, 82-83; Steichen-Gersdorf E et al. (1994) *Am J Hum Genet* 55, 870-875; Miki Y et al. (1994) *Science* (Wash D.C.) 266, 66-71; Smith S et al. (1992) *Nature Genet* 2, 128-131) and BRCA2 (Wooster R et al. (1994) *Science* (Wash D.C.) 265, 2088-2090; Wooster R et al. (1995) *Nature* 378, 789-792), have been related to early onset of familial (autosomal dominant) breast and ovarian cancer. In contrast to BRCA1, which is linked predominantly to female cancers, BRCA2 is also linked to male breast cancer. As pointed out above, about 1% of the breast cancers occurring in the United States are related to those genes (Easton F D et al. (1994) *Lancet* 344, 761). Their gene sequences have been fully characterized and in the case of BRCA1, many mutations have been identified (Shattuck-Eidens D et al. (1995) *JAMA* 273, 535-552; Simard J et al. (1994) *Nature Genet* 8, 392-398; Castilla L H et al. (1994) *Nature Genet* 8, 387-391). Mutations in these genes were initially considered to confer more than 80% lifetime risk for developing breast and/or ovarian cancer (Easton D F et al. (1993) *Am J Hum Genet* 52, 678-701). More recent results have reduced the roles of BRCA1 and BRCA2 in breast cancers (Struewing J P et al. (1997) *New Eng J Med* 336, 1401-1408; Couch F J et al. (1997) *New Eng J Med* 336, 1409-1415; Krainer M et al. (1997) *New Eng J Med* 336, 1416-1421). BRCA1 and BRCA2 may have roles in sporadic breast and ovarian cancers, but to what extent is open to question (Futreal P A et al. (1994) *Science* (Wash D.C.) 266, 120-122; Merajver S D et al. (1995) *Nature Genet* 9, 439-443). In addition to BRCA1 and BRCA2, the tumor suppressor gene p53 has been implicated in both familial (germ line) and sporadic breast cancers (Malkin D et al. (1990) *Science* (Wash D.C.) 250, 1233-1238; Coles C et al. (1992) *Cancer Res* 52, 5291-5298; Elledge R M and Allred D C (1994) *Breast Cancer Res Treat* 32, 39-47). However, this genetic link accounts for at most 25% of breast cancers. It is possible that germ line mutations in p53 also are related to a fraction of prostate cancers (Malkin D et al. (1990) *Science* (Wash D.C.)

250, 1233-1238). One area of active investigation focuses on the 70% of breast cancers termed "sporadic," because they are not familial and not related to any currently known epidemiological risk factor. An effective means of assessing genetic risk for sporadic breast cancers, prostate cancers, and other cancers of glandular/mucosal epithelial tissues, simply does not exist today in the conventional medical arsenal against cancer.

The genetic origin of prostate cancers has been even more elusive than that of breast cancers. Although a gene for prostate cancer susceptibility has been localized to chromosome 17q, it does not appear to be related to BRCA1 (PCT Pub. App. No. WO0027864). Other prostate cancer susceptibility genes have been localized to chromosomes 13q (Cooney K A et al. (1996) Cancer Res 56, 1142-1145) and to chromosomes 8p, 10q and 16q (Veronese M L et al. (1996) Cancer Res 56, 728-732). From the data available, it is clear that the genetic origin of prostate cancer has not been identified. This fact alone opens the issue of cause. While genetic analysis will continue to be important, it will not provide the essential information about what is causing breast and prostate cancer.

In a conceptually different approach to identifying cancer-related genes, Dr. Ruth Sager has suggested a departure from the conventional avenues of identifying cancer-related genes by searching for mutations (Class I genes), and instead or additionally focusing on the role of expression genetics in cancer (Class II genes) (Sager R (1997) Proc Natl Acad Sci 94, 952-955). Dr. Sager has proposed that far more genes are down regulated at the transcriptional level in cancer cells than are mutated and that crucial "oncogenic" molecules may not be mutated. Consistent with that proposition others have reported (Thompson M F et al. (1995) Nature Genet 9, 444-450) that reduced amounts of BRCA1 mRNA, representing down-regulation of the wild-type gene, were found in primary tumors of the nonfamilial disease. Characterization of other genes whose expression is altered in cancer cells, and understanding their functions, will provide penetrating insight into the regulatory interactions that have been upset in cancer.

With regard to the origins of mucosal cancer, and especially breast and prostate, there has been little advance. In general, it is thought that environmental carcinogens are the origin. However, this has yet to be proven. Another familiar concept is the idea that bacteria may be involved in carcinogenesis (oncogenesis). For example, see Parsonnet J (1995) Environ Health Perspect 103 (Suppl), 263-268; Mackowiak P A (1987) Am J Med 82, 79-97; Cassell G H (1998) Emerg Infect Dis 4, 475-487; Nauts H C (1989) Cancer Surv 8, 713-723; Venitt S (1996) Environ Health Perspect 104 (Suppl), 633-637; Miller J H (1996) Cancer Surv 28, 141-153; Buiuc D and Dorneanu O (1989) Rev Med Chir Soc Med Nat Iasi 93, 223-227).

Involvement of bacteria, or other infectious agents, in some types of lymphoid cancers such as Hodgkin's disease and leukemia has been suggested (Comment of Editor: Infective cause of childhood leukaemia (1989) Lancet 1 (1829), 94-95; Serraino D et al. (1991) Int J Cancer 47, 352-357; Glaser S L and Jarrett R F Baillieres (1996) Clin Haematol 9401-416; Wolf J and Diehl V (1994) Ann Oncol 5 (Suppl 1), 105-111).

Studies suggesting that Helicobacter pylori is directly causative in gastric cancer have recently been described. H. pylori is the only bacterium known to date to have been classified as a Class I carcinogen by the International Agency for Research on Cancer (IARC). This classification indicates that by generally accepted scientific standards (Nyren O (1998) Semin Cancer Biol 8, 275-283) this microorganism is now generally considered to be a causative factor in development of gastric cancers in infected humans. Recently it has been reported that Chlamydia trachomatis infection is strongly associated with subsequent development of invasive cervical squamous cell carcinoma (Anttila T et al. (2001) JAMA 283, 47-51). The possibility that bacteria are involved in large bowel/colon cancer has also been mentioned (McBurney M I et al. (1987) Nutr Cancer 10, 23-28), however no firm conclusions have been reached as yet.

Finally, the issue of prevention deserves special comment. There are no known methods of preventing cancer other than observing life style changes and environmental changes that place individuals in the low risk groups. Tamoxifen has been considered as a potential "prevention" for breast cancer in high risk women, but as yet has not been widely accepted because of the physiologic and endocrine aberrations caused by this agent when used long term. In short, even though prevention is remarkably pressing, there has been a dearth of studies of new methods that do not disrupt the normal lifestyles and reproductive capacity of women.

Conventional immunological approaches to treating malignant tumors have generally proven inadequate. In addition, except for recent advances with respect to Helicobacter pylori and Chlamydia trachomatis (Anttila T et al. (2001) JAMA 283:47-51), anti-bacterial approaches for combating the cause(s) of malignant transformation do not appear promising. Relying only on the existing technologies, effective diagnostic and therapeutic agents, treatments and preventatives for widespread use in breast and prostate cancers, and cancers of other glandular/mucosal epithelial tissues, do not appear to be on the near horizon.

SUMMARY OF THE INVENTION

New methods and compositions for use against steroid hormone responsive tumors of the breast and prostate, as well as against tumors of other glandular/mucus epithelial tissues such as colon, ovary, endometrium, kidney, bladder, stomach, pancreas and secretory pituitary gland are provided which are based on previously unrecognized activities of certain components of the body's natural immune system. References in this disclosure to the "new natural immune mechanism" or the "new immunotherapies," refer to the previously unrecognized cell growth inhibitory function of certain constituent parts of the secretory immune system, particularly dimeric/polymeric IgA, polymeric IgM and IgG1, as distinguished from the well known functions of those immunoglobulins based on antigen-antibody recognition. For the purposes of this disclosure, the term "cell growth" refers to cell proliferation or an increase in the size of a population of cells rather than merely to an increase in cytoplasmic volume of an individual cell. The term "steroid hormone responsive" cell refers to a cell that requires the binding of a steroid hormone to a steroid hormone binding receptor in the cell in order for that cell to be stimulated to grow (i.e., proliferate). For example, normal ductile cells in the pubescent breast are estrogen responsive or stimulated by estrogen to proliferate. $ER^+$ breast cancer cells also possess a functional estrogen binding receptor and are also estrogen responsive. By contrast, $ER^-$ breast cancer cells do not have a functional estrogen receptor and demonstrate autonomous cell growth, i.e., they are stimulated to proliferate without the influence of a steroid hormone. New ways of identifying carcinogenic, or potentially carcinogenic, bacteria in a tissue or body fluid are also provided, and, individually or together with the above-described new immunotechnologies, are expected to provide or aid in widespread implementation of better anti-cancer therapies and preventatives than have been available previously.

In accordance with certain embodiments of the present invention, methods of assessing risk or susceptibility of an individual to developing a neoplastic lesion or cancerous tumor of a mucosal epithelial tissue are provided. In some embodiments the method includes detecting, and in some cases also quantitating, a steroid hormone reversible immunoglobulin inhibitor of steroid hormone responsive cell growth in a body fluid or secretion obtained from said subject, such as serum, plasma, colostrum, breast aspirates, saliva, tears, bronchial secretions, nasal mucosa, prostatic fluid, urine, semen or seminal fluid, vaginal secretions, ovarian aspirates, stool, and mucous secretions from the small intestine or stomach. The absence or deficiency of the immunoglobulin inhibitor compared to a predetermined standard material indicates or suggests that a steroid hormone responsive mucosal epithelial tissue in the body of the individual is secreting or bathed by less than a cell growth inhibitory amount of the immunoglobulin inhibitor. For the purposes of this disclosure, the term "immunoglobulin inhibitor" refers to a secretory immunoglobulin, preferably one or more of the secretory immunoglobulins IgA, IgM and IgG1, that is active for inhibiting proliferation of a steroid hormone responsive cancer cell maintained in a suitable nutrient medium under cell growth promoting conditions, in the absence of an inhibition-reversing amount of the steroid hormone or other substance that mimics this steroid hormone effect. The immunoglobulin inhibitory activity, also referred to as immunoglobulin inhibition, is distinct from any additional antigen-antibody recognition based immunological functions of the immunoglobulin inhibitors. The term "steroid hormone reversible immunoglobulin inhibitor" refers to the characteristic of the preferred immunoglobulin inhibitors that their cell growth inhibitory activity is steroid hormone reversible. "Cell growth promoting conditions" refer to favorable environmental conditions, other than defined medium components, and include such things as gaseous environment, humidity, temperature, pH, and the like. For example, cell growth promoting conditions could include incubation at 37° C. in a humid atmosphere of 5% (v/v) $CO_2$ and 95% (v/v) air in a defined nutrient medium at pH 7.4.

In certain embodiments the risk assessment method includes measuring the amount and/or activity of an immunoglobulin inhibitor in a specimen comprising a defined amount of body fluid or secretion from the individual. In certain preferred embodiments the method includes substantially depleting steroid hormone from the fluid specimen to yield a steroid hormone depleted specimen, and then assaying an aliquot of that hormone depleted specimen for detecting or measuring steroid hormone reversible inhibition of steroid hormone responsive cancer cell proliferation.

Some embodiments of the risk assessment method include the following assay protocol: (a) maintaining a predetermined population of steroid hormone-responsive cells in a ferric ion-free, calcium ion-containing, serum-free nutrient medium, the cells being serum free and obtained from a steroid hormone-responsive cell line; (b) adding a predetermined amount of the steroid hormone to the medium, the amount being sufficient to stimulate cell growth under cell growth promoting conditions; (c) adding a predetermined amount of a steroid hormone depleted specimen of a body fluid or secretion to the medium, to yield a test mixture; (d) incubating the test mixture for a predetermined period of time under cell growth promoting conditions; (e) measuring the cell population in the test mixture after the predetermined period of time; (f) measuring the cell population in a control incubation mixture like the test mixture, except lacking an amount of the specimen. Preferably any cytotoxic effects of the specimen are also measured. The difference between the cell populations before and after the incubation period is determined, a significant increase in the population indicating the absence of inhibition of cell growth by that amount of specimen in the presence of the selected amount of steroid hormone. A significant lack of increase in the cell population, which is not attributable to cytotoxic effects of the specimen, is an indicator of inhibition of cell growth by the inhibitors contained in the specimen when tested in the presence of a given concentration of steroid hormone. In preferred embodiments the assay also includes detecting or determining steroid hormone reversibility of the specimen's inhibitory activity in the presence of a predetermined increased amount of steroid hormone.

Also provided in accordance with certain embodiments of the present invention are an in vitro method of detecting loss of immunoglobulin regulation of steroid hormone responsive cell growth. In certain embodiments the method comprises assaying for inability of a mucosal epithelial cell to bind at least one of the immunoglobulins IgA, IgM and IgG1.

Certain other embodiments of the invention provide a method of detecting a mediator of immunoglobulin inhibition of steroid hormone responsive cell growth that includes detecting a poly-Ig receptor in a mucosal epithelial cell.

Certain other embodiments of the invention provide a method of detecting a gene coding for a mediator of immunoglobulin inhibition of steroid hormone responsive cell growth that includes detecting the presence of a poly-Ig receptor gene in a mucosal epithelial cell.

Still other embodiments of the invention provide a method of detecting a genetic defect in a gene coding for a mediator of immunoglobulin inhibition of steroid hormone responsive cell growth comprising screening a genomic or cDNA library of a mucosal epithelial cell for a defect in a poly-Ig receptor gene.

Some embodiments of the present invention provide a method of detecting expression of a defective mediator of immunoglobulin inhibition of steroid hormone responsive cell growth in a specimen of mucosal epithelial tissue, the method including detecting a defective poly-Ig receptor or Fcγ receptor protein in said specimen. The term "defective" means that the detected protein is physically similar to the native receptor protein, but is incapable or less capable of mediating the immunoglobulin cell growth inhibitory effects, compared to the native receptor protein. Preferably the ability to mediate cell growth inhibitory effects is measured in a cell growth assay as described elsewhere herein.

In accordance with certain other embodiments of the present invention, methods to aid in predicting increased susceptibility of a mammalian subject to development or growth of a steroid hormone responsive cancer in a mucosal epithelial tissue is provided. In some embodiments, the method comprises detecting the loss or impairment of negative regulation of breast tissue proliferation by the secretory immune system. In some embodiments, the method includes assaying a specimen of mucosal epithelial tissue obtained from the subject for the presence of a poly-Ig receptor capable of mediating immunoglobulin inhibition of steroid hormone responsive cell growth in a suitable in vitro cell culture assay. An absence of the receptor or absence of its activity for mediating the immunoglobulin inhibition is suggestive that the tissue lacks functional mediators of immunoglobulin inhibition sufficient to deter development or growth of a steroid hormone responsive cancer of the mucosal epithelial tissue.

Also provided by certain embodiments of the invention is a method to aid in detecting transformation of a mucosal epithelial cell from normally steroid hormone responsive to a steroid hormone responsive neoplastic, precancerous or cancerous condition, the method including assaying a population of the cells for loss or inactivity of receptors that mediate IgG1 inhibition of cell growth.

Further provided by certain embodiments of the invention are methods to aid in detecting progression of a steroid hormone responsive malignant mucosal epithelial cell to an autonomous cancer cell. In some embodiments, the method includes assaying for loss or inactivity of a receptor that mediates IgA and/or IgM inhibition of cell growth.

According to certain other embodiments of the invention, methods of imaging a steroid hormone responsive mucosal epithelial tumor in vivo is provided. In certain embodiments, the method includes contacting the tumor with at least one tagged or labeled monoclonal antibody raised against a poly-Ig receptor, Fcγ receptor, IgA, IgM and IgG1, and then imaging the tag.

In some embodiments of the present invention a method to aid in detecting or diagnosing cancer in a mammalian subject is provided. The method comprises determining in a population of neoplastic cells in a mucosal epithelial tissue specimen obtained from the subject at least one of the following conditions: (a) absence or diminution of immunoglobulin inhibition of steroid hormone responsive cell growth; (b) absence or diminution of at least one immunoglobulin inhibitor of steroid hormone responsive cell growth from a body fluid or secretion secreted by or bathing said tissue; (c) absence or diminution of a poly-Ig receptor in said cells; (d) absence of a poly-Ig receptor gene from said cells; (e) absence of heterozygosity for said poly-Ig receptor gene in said cells; (f) absence or diminution of a Fcγ receptor in said cells; (g) absence of a Fcγ receptor gene from said cells; (h) absence of heterozygosity for said Fcγ receptor gene in said cells; (i) absence or diminution of TGFβ regulation of cell growth; (j) absence or diminution of a TGFβ receptor in said cells; (k) absence of a TGFβ receptor gene from said cells; and (l) absence of heterozygosity for said TGFβ receptor gene in said cells. The absence or diminution is preferably measured by comparison to similar determinations in non-neoplastic cells from the same patient or by comparison to predetermined standard values. The presence of at least one of those conditions is suggestive or indicative of the presence of a cancerous or precancerous lesion, and an absence of one or more of the conditions suggests or indicates absence of a cancerous or precancerous lesion in the patient.

In accordance with certain additional embodiments of the invention, a method to aid in staging a cancer of a mucosal epithelial tissue is provided. The method includes testing or determining, in a specimen of neoplastic cells obtained from the cancer, if the cells are stimulated by a preselected steroid hormone proliferate in a suitable cell growth nutrient medium, and also determining at least one of the following conditions: (a) in a specimen of body fluid or secretion secreted by or bathing said mucosal epithelial tissue, the lack of a cell growth inhibitory amount of at least one immunoglobulin inhibitor of steroid hormone responsive cell growth, (b) loss or diminution of a TGFβ receptor in said cells, (c) loss of a TGFβ receptor gene in said cells in said cells, (d) loss of heterozygosity for said TGFβ receptor gene in said cells, (e) loss or diminution of a poly-Ig receptor in said cells, (f) loss of a poly-Ig receptor gene in said cells, (g) loss of heterozygosity for said poly-Ig receptor gene in said cells, (h) loss or diminution of a Fcγ receptor in said cells, (i) loss of a Fcγ receptor gene in said cells, and (j) loss of heterozygosity for said Fcy receptor gene in said cells. The loss or diminution in each case is measured by comparison to similar determinations in non-neoplastic cells from the same patient, or by previous values obtained from a previous test, or by comparison to predetermined standard values. The presence of one or more of the conditions suggests or indicates advancement of the stage of the cancer.

According to some embodiments of the present invention a method to aid in prognosis of a mammalian cancer patient is provided. This method comprises determining at least one of the following conditions: (a) in a specimen of body fluid or secretion secreted by or bathing a mucosal epithelial tissue obtained from said patient, the lack of a cell growth inhibitory amount of at least one immunoglobulin inhibitor of steroid hormone responsive cell growth, (b) in a specimen of neoplastic cells from said tissue, the loss or diminution of a TGFβ receptor, (c) in a specimen of neoplastic cells from said tissue, the loss of a TGFβ receptor gene, (d) in a specimen of neoplastic cells from said tissue, the loss of heterozygosity for said TGFβ receptor gene, (e) in a specimen of neoplastic cells from said tissue, the loss or diminution of a poly-Ig receptor, (f) in a specimen of neoplastic cells from said tissue, the loss of a poly-Ig receptor gene, (g) in a specimen of neoplastic cells from said tissue, the loss of heterozygosity for said poly-Ig receptor gene, (h) in a specimen of neoplastic cells from said tissue, the loss or diminution of a Fcγ receptor, (i) in a specimen of neoplastic cells from said tissue, loss of a Fcγ receptor gene, and (j) in a specimen of neoplastic cells from said tissue, loss of heterozygosity for said Fcγ receptor gene. The loss or diminution in each instance is measured by comparison to similar determinations in non-neoplastic cells from the patient, and/or to the patient's previous test results, and/or by comparison to predetermined standard values. The presence of one or more of the conditions is suggestive or indicative of at least some degree of reduced prognosis of the patient, and an absence of one or more of said conditions being suggestive or indicative of at least some degree of favorable prognosis.

In accordance with certain other embodiments of the present invention, a method to aid in suppressing or inhibiting malignant transformation or progression in a steroid hormone responsive mucosal epithelial cell is provided. The method comprises ensuring expression of a TGFβ receptor in the cell sufficient to mediate TGFβ inhibition of neoplastic cell growth, and also ensuring expression of a poly-Ig receptor and/or a Fcγ receptor. In preferred embodiments, the method ensures that poly-Ig receptor is expressed in the cell sufficient to mediate IgA and/or IgM inhibition of steroid hormone responsive growth of the cell in the absence of an inhibition reversing amount of the steroid hormone or steroid hormone mimicking substance; and the Fcγ receptor is expressed sufficiently to mediate IgG1 inhibition of steroid hormone responsive growth of the cell in the absence of an inhibition reversing amount of the steroid hormone or steroid hormone mimicking substance. If expression of one of those native receptors is lacking, it may be necessary to introduce an exogenous receptor gene using known gene transfer techniques.

In accordance with certain other embodiments of the invention, a method of inhibiting or arresting in vivo cancer cell growth is provided. The method comprises contacting a steroid hormone responsive mucosal epithelial tissue with a pharmaceutical composition comprising a pharmacologically acceptable carrier and at least one immunoglobulin inhibitor of steroid hormone responsive cell growth chosen from the group consisting of IgA, IgM and IgG1, preferably dimeric or polymeric IgA, polymeric IgM and IgG1. In some embodiments, the treatment method also includes administering an immunoglobulin inhibitor-mimicking substance such as tamoxifen or a metabolite thereof.

Certain other embodiments of the present invention provide a method of treating cancer of a glandular or tissue that secretes or is bathed by an immunoglobulin, the method comprising enhancing the amount of at least one immunoglobulin inhibitor of steroid hormone responsive cancer cell growth secreted by or contacting the tissue. The inhibitor is preferably IgA, IgM and IgG1.

According to certain embodiments of the present invention, a method of treating cancer of a steroid hormone responsive mucosal/epithelial tissue is provided. In some embodiments, the method comprises detecting in a population of cancer calls obtained from the tissue the presence of a poly-Ig receptor or a portion thereof. In some embodiments, the method also includes detecting in the population of cancer cells the presence of ERγ. In still other embodiments, the method also includes administering to an individual in need thereof, an effective amount of an immunoglobulin mimicking substance (e.g., tamoxifen or a tamoxifen metabolite) sufficient to inhibit cancer cell growth.

Although the cell growth inhibitory activity of the immunoglobulin inhibitors is a function that is distinct from any additional antibody-antigen recognition type immune activities, in some instances conventional immunological techniques can be advantageously employed to produce the desired inhibitors. Accordingly, in certain embodiments of the invention a method of inhibiting or arresting growth of a steroid hormone responsive tumor in a mammal is provided which includes administering an immunogen to the mammal in an amount sufficient to induce plasma and/or mucosal production of at least one secretory immunoglobulin inhibitor of steroid hormone responsive cell growth sufficient to inhibit steroid hormone responsive proliferation of a plurality of steroid hormone responsive cancer cells in the mammal. In some embodiments the mode of administration is oral. In certain embodiments, the method also includes determining an age range of the mammal during which the native production of the inhibitor(s) in the mammal is less than a predetermined value. An age range in which there are low concentrations of natural immunoglobulin inhibitors may present a window of increased susceptibility to mutagenic or other carcinogenic events. Some embodiments provide for administering the immunogen at a predetermined time such that production of the inhibitor(s) by the mammal during that window of susceptibility is enhanced.

In certain other embodiments of the invention a method of inducing natural mucosal production of cancer deterring factors is provided. The method comprises parenteral administration to a mammal of an amount of secretory immunoglobulin-stimulating antigen sufficient to induce plasma and/or mucosal production of a predetermined steroid hormone responsive cancer cell growth inhibiting amount of at least one secretory immunoglobulin IgA, IgM and IgG1.

In still other embodiments of the invention a method of enhancing levels of cancer deterring factors in a body fluid bathing a gland or mucosal tissue is provided. The method includes introducing into the body of an individual in need thereof at least one exogenous steroid hormone responsive cell growth immunoglobulin inhibitor. In preferred embodiments the inhibitor(s) is/are IgA, IgM and IgG1. In some embodiments, the method also includes qualitatively and/or quantitatively testing a body fluid or secretion, such as saliva, for said at least one inhibitor to confirm immunization.

In accordance with still other embodiments of the invention, a method of restoring or enhancing immunoglobulin regulation of steroid hormone responsive cell growth in a mucosal epithelial cell is provided. The method comprises restoring or enhancing expression in the cell of a mediator of immunoglobulin regulation chosen from the group consisting of a poly-Ig receptor and a Fcγ receptor. In some embodiments the method comprises inserting a gene for a poly-Ig receptor into said cell and expressing said gene.

Also provided in accordance with certain embodiments of the present invention is a method of identifying carcinogenic bacteria. In certain embodiments the method includes: (a) obtaining a bacteria-containing specimen of glandular/mucosal epithelial tissue or body fluid secreted by or bathing a gland or mucosal epithelial tissue; (b) taking precautions in obtaining and handling said specimen such that contamination by extraneous microorganisms is avoided; (c) culturing the bacteria in said specimen such that at least one isolated bacterial colony is obtained; (d) selecting at least one of said bacterial colonies for further examination; and (e) conducting an Ames Test on each selected colony such that mutagen-producing bacterial isolates are identifiable. In certain embodiments the method also contains one or more of the following steps: (f) determining the gram stain negative or gram stain positive classification of said bacterial colonies; (g) testing the bacterial isolates for production of defined metabolites known to or suspected of being mutagenic; (h) testing the bacterial isolates for induction of an oxidative burst when incubated with a neutrophil or macrophage; and (i) testing the bacterial isolates for immunoglobulin protease activity. In some embodiments the method also contains one or more of the following steps: (j) when the fluid comprises a breast secretion, determining whether a bacterial isolate survives and grows in the presence of a normal bacterial cell inhibiting amount of lactoferrin; (k) growing a bacterial isolate in a medium and, after growing the bacterial isolate, testing the medium with a non-tumorigenic human mucosal epithelial cell line such that cells that are altered to a malignant phenotype by a component of the medium are detectable; and (l) identifying a bacterial isolate using a polymerase chain reaction (PCR) technique.

In accordance with certain additional embodiments of the invention, a method of conferring or enhancing resistance by a mucosal epithelial cell to malignant transformation is provided. The method comprises inducing immunity in a host to at least one bacteria known to or suspected of being oncogenic, as identified by the above-described method.

In some embodiments of the invention a method of deterring malignant transformation of a mucosal epithelial cell is provided that includes administering an effective amount of an antibiotic to a host infected by an oncogenic bacteria, as identified by the above-described method.

In certain other embodiments, a method of suppressing an effect of malignant transformation of a mucosal epithelial cell is provided in which a cell growth arresting amount of at least one immunoglobulin chosen from the group consisting of dimeric or polymeric IgA, polymeric IgM and IgG1 is administered to an individual in need thereof.

Still other embodiments of the present invention provide a method of preparing an anti-cancer antibody comprising selecting at least one bacteria known to, or suspected of, inducing malignant transformation in mucosal epithelial cells, according to the above-described method, and inducing immunity to the bacteria in an individual considered to be at risk of developing cancer in a tissue comprising the cells.

Also provided in accordance with certain embodiments of the invention is a method of preventing or reducing the risk of developing cancer in a mucosal epithelial tissue comprising immunizing an individual against at least one bacteria known to or suspected of inducing malignant transformation in that tissue. Preferably the bacteria is identified as previously described. In certain embodiments, the immunization comprises orally, nasally or rectally administering an inactivated or attenuated form of the bacteria to the individual such that mucosal immunity against the bacteria is conferred.

In certain embodiments of the invention, a method of suppressing an effect of malignant transformation of a steroid hormone responsive epithelial cell is provided. Representative steroid hormone responsive epithelial cells are breast, prostate, oral cavity mucosa, salivary/parotid glands, esophagus, stomach, small intestine, colon, tear ducts, nasal passages, liver and bile ducts, bladder, secretory/exocrine pancreas, adrenals, kidney tubules, glomeruli, lungs, ovaries, fallopian tube, uterus, cervix, vagina, and secretory anterior pituitary gland cells. The method comprises enhancing the amount of IgA and/or IgM and/or IgG1 secreted by or contacting the cell such that steroid responsive growth stimulation of the cell is inhibited in the absence of a inhibition reversing amount of the steroid hormone or a steroid hormone mimicking substance.

In accordance with certain additional embodiments of the present invention, a method of detecting previous or active infection by a bacteria known to or suspected of being oncogenic in mucosal epithelial tissue is provided which includes detecting in plasma or a body fluid or secretion an antibody against the bacteria. In preferred embodiments the bacteria known to or suspected of being oncogenic is identified in accordance with the above-described screening method.

In certain embodiments of the present invention, a method of preventing or reducing the risk of occurrence of cancer of a mucosal epithelial tissue, such as breast, prostate, colon, kidney and ovary, is provided. The method includes administering to a mammalian subject in need thereof at least one of the following treatments: (a) administering an antibiotic active against at least one bacteria known to or suspected of inducing malignant transformation in mucosal epithelial cells; and (b) administering an immunogen to said subject in an amount sufficient to induce plasma and/or mucosal production of at least one secretory immunoglobulin inhibitor of steroid hormone responsive cell growth sufficient to inhibit steroid hormone responsive proliferation of a plurality of steroid hormone responsive cancer cells in said mammal; administering at least one immunoglobulin inhibitor of steroid hormone responsive cell growth in an amount sufficient to inhibit or arrest steroid hormone responsive growth of said cells.

In accordance with certain other embodiments of the present invention, a pharmaceutical composition is provided that comprises at least one immunoglobulin inhibitor of steroid hormone responsive cell growth and a pharmacologically acceptable carrier. The cell is preferably a cancerous mucosal epithelial cell. In certain embodiments at least one immunoglobulin inhibitor is IgA, IgM or IgG1, preferably dimeric IgA, polymeric IgA, polymeric IgM or IgG1κ. In some embodiments the composition also contains one or more immunoglobulin inhibitor-mimicking substances, such as tamoxifen or a metabolite of tamoxifen.

Also provided in accordance with certain embodiments of the present invention is an anti-cancer composition comprising a pharmacologically acceptable carrier and a cytotoxic agent or a chemotherapeutic agent conjugated to an immunoglobulin inhibitor of steroid hormone responsive cancer cell growth. In preferred embodiments the inhibitor is IgA, IgM, IgG1, or any combination of those.

In accordance with certain other embodiments of the present invention a mediator of steroid hormone reversible IgA and/or IgM inhibition of steroid hormone responsive cell growth is provided that comprises a poly-Ig receptor. In certain embodiments a mediator of steroid hormone reversible IgG1 inhibition of steroid hormone responsive cell growth is provided which comprises a Fcγ receptor.

Also provided in certain embodiments of the present invention is an expression vector for gene replacement therapy in a mammalian cell to restore or enhance expression of a poly-IgR. In some embodiments the vector comprises a preselected deoxyribonucleic acid (DNA) sequence encoding a poly-Ig receptor, or a biologically active subunit or variant thereof, operably linked to a promoter capable of functioning in a preselected mammalian target cell. In some embodiments, an expression vector for gene replacement therapy in a mammalian cell to restore or enhance expression of a Fcγ receptor is provided which comprises a preselected DNA sequence encoding a Fcγ receptor, or a biologically active subunit or variant thereof, which is operably linked to a promoter functional in a preselected mammalian target cell.

Still other embodiments of the present invention provide an expression vector for gene replacement therapy in a mammalian cell to restore or enhance expression of a TGFβ receptor. This vector comprises a preselected DNA sequence encoding a TGFβ receptor, or a biologically active subunit or variant thereof, which is operably linked to a promoter functional in a preselected mammalian target cell.

Also provided in accordance with certain embodiments of the present invention is a method of expressing a DNA sequence encoding a mediator of immunoglobulin inhibition of cell growth, the mediator being chosen from among a poly-Ig receptor, a Fcγ receptor, and biologically active subunits and variants thereof operably linked to a promoter that is capable of functioning in a preselected mammalian target cell. The method includes introducing the DNA sequence and the linked promoter into the mammalian cell and allowing the cell to express the DNA sequence. In certain embodiments the also includes expressing a DNA sequence encoding a TGFβ receptor, or a biologically active subunit or variant thereof, which is operably linked to a promoter that is capable of functioning in a preselected mammalian target cell. In this embodiment the TGFβ receptor DNA sequence and its linked promoter are introduced into the mammalian cell and the cell is allowed to express the DNA sequence.

These and other embodiments, features and advantages of the present invention will become apparent with reference to the following description and drawings.

BRIEF DESCRIPTION OF THE DRAWINGS

For the detailed descriptions of the preferred embodiments, reference will now be made to the accompanying figures which include graphs, charts, and test results:

FIG. 1. CDE-horse Serum Effect on MTW9/PL2 Cell Growth ±10 nM $E_2$ for 7 days. (A) Dose-response data expressed as cell numbers; (B) Dose-response data expressed as cell population doublings (CPD) per 7 days.

FIG. 8. Kinetics of T47D Cell Growth in CDE-horse Serum ±10 nM $E_2$. (A) Growth Kinetics in 20% CDE-horse ±$E_2$ versus 10% Fetal Bovine Serum; (B) Growth Kinetics in 50% CDE-horse Serum ±$E_2$.

FIG. 20. Effect of Phenol Red on Estrogen Responsive MCF-7 Cell Growth. (A) MCF-7A Cell Growth in CDE-horse Serum ±Phenol Red and ±$E_2$; (B) Estrogenic Effects with MCF-7A Cells ±Phenol Red; (C) MCF-7K Cell Growth in CDE-horse Serum ±Phenol Red and ±$E_2$; (D) Estrogenic Effects with MCF-7K Cells ±Phenol Red.

FIG. 21. Effect of Phenol Red on Estrogen Responsive T47D and ZR-75-1 Cell Growth; (A) T47D Cell Growth in CDE-horse Serum ±Phenol Red and ±$E_2$; (B) Estrogenic Effects with T47D Cells ±Phenol Red; (C) ZR-75-1 Cell Growth in CDE-horse Serum ±Phenol Red and ±$E_2$; (D) Estrogenic Effects with ZR-75-1 Cells ±Phenol Red.

FIG. 22. Effect of Phenol Red on Estrogen Responsive MTW9/PL2 Cell Growth; (A) MTW9/PL2 Cell Growth in CDE-horse Serum ±Phenol Red and ±$E_2$; (B) Estrogenic Effects with MTW9/PL2 Cells ±Phenol Red.

FIG. 24. Estrogen Induction of Progesterone Receptors by Phenol Red versus $E_2$. (A) Induction by $E_2$ with T47D Cells; (B) Induction by Phenol Red with T47D Cells.

FIG. 25. Effects of TGFβ1 on Cell Growth in 2.5% CDE-horse Serum ±$E_2$. (A) MCF-7K Cell Growth; (B) MTW9/PL2 Cell Growth.

FIG. 26. TGFβ1 Inhibition of ER$^+$ Rodent and Human Cell Line Growth ±$E_2$. (A) Inhibition Data ±$E_2$ Presented in Cell Number; (B) Inhibition Data ±$E_2$ Presented in CPD.

FIG. 27. EGF and TGFα as Substitutes for the Effects of $E_2$ in CDE-horse Serum. (A) MCF-7A Cell Growth; (B) MCF-7K Cell Growth; (C) T47D Cell Growth; (D) ZR-75-1 Cell Growth.

FIG. 28. IGF-I as a Substitute for the Effects of $E_2$ in CDE-horse Serum. (A) MCF-7K Cell Growth; (B) MCF-7A Cell Growth; (C) T47D Cell Growth.

FIG. 34. Dose-Response Effects of Individual Components of CAPM Serum-free Defined Medium on LNCaP Cell Growth.

FIG. 47. Comparison of Estrogenic Effects in Serum-free Defined Medium and in D-MEM/F-12 Medium Supplemented with CDE-Horse Serum; (A) MCF-7K Cell Growth in Serum-free Defined Medium ±$E_2$; (B) MCF-7K Cell Growth in D-MEM/F-12 with CDE-horse Serum ±$E_2$; (C) T47D Cell Growth in Serum-free Defined Medium ±$E_2$; (D) T47D Cell Growth in D-MEM/F-12 with CDE-horse Serum ±$E_2$; (E) LNCaP Cell Growth in Serum-free Defined Medium ±$E_2$; (F) LNCaP Cell Growth in D-MEM/F-12 with CDE-horse Serum ±$E_2$.

FIG. 49. Comparison of Estrogenic Effects in Serum-free Defined Medium.

and in D-MEM/F-12 Medium Supplemented with CDE-Horse Serum.

$GH_4C_1$ Cell Growth in Serum-free Defined Medium ±$E_2$.

$GH_4C_1$ Cell Growth in D-MEM/F-12 with CDE-horse Serum ±$E_2$.

MTW9/PL2 Cell Growth in Serum-free Defined Medium ±$E_2$.

MTW9/PL2 Cell Growth in D-MEM/F-12 with CDE-horse Serum ±$E_2$.

H301 Cell Growth in Serum-free Defined Medium ±$E_2$.

H301 Cell Growth in D-MEM/F-12 with CDE-horse Serum ±$E_2$.

FIG. 50. Comparison of the Inhibitor Reversing Effects of DHT, $E_2$, and DES on LNCaP Cell Growth in CDE-horse Serum Containing Medium; (A) Effect of DHT as an Inhibitor Reversing Steroid; (B) Effect of $E_2$ as an Inhibitor Reversing Steroid; (C) Effect of DES as an Inhibitor Reversing Steroid; (D) Effect of Combinations of DHT, $E_2$, and DES as Inhibitor Reversing Steroids.

Figure 51:
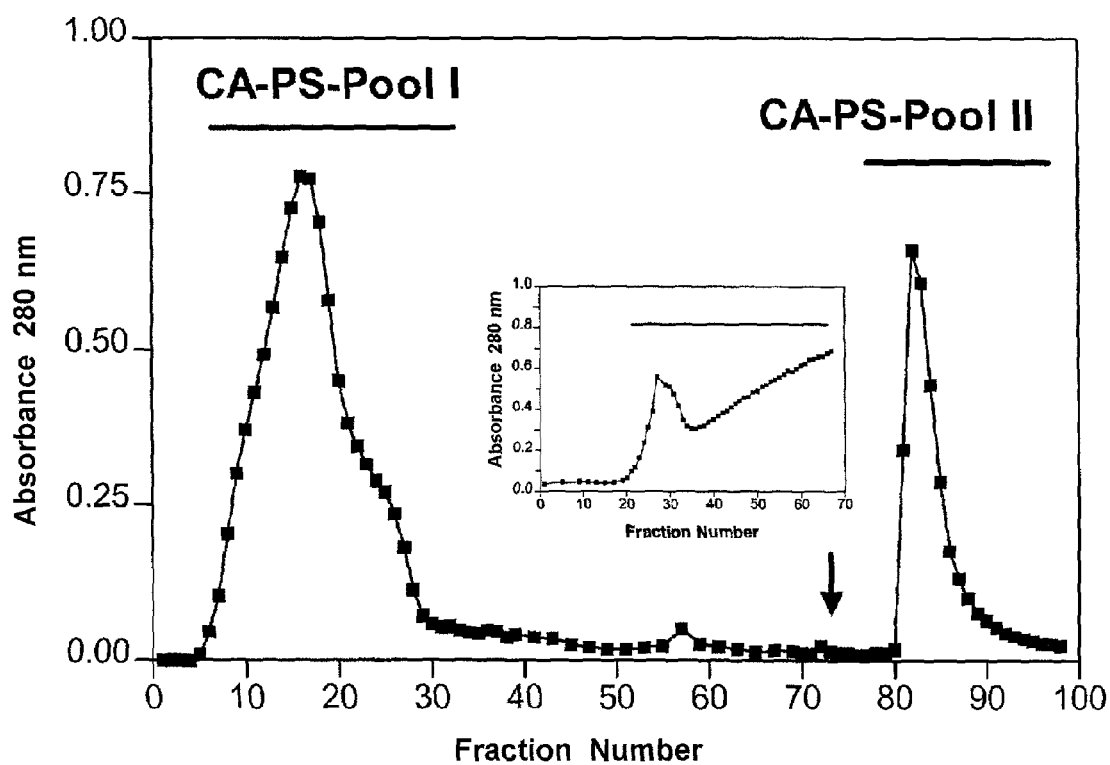

FIG. 51. Column Elution Profiles of the Two-step Cortisol Affinity and phenyl Sepharose Elution of CA-PA-pool I and CA-PS-pool II.

Figure 52:
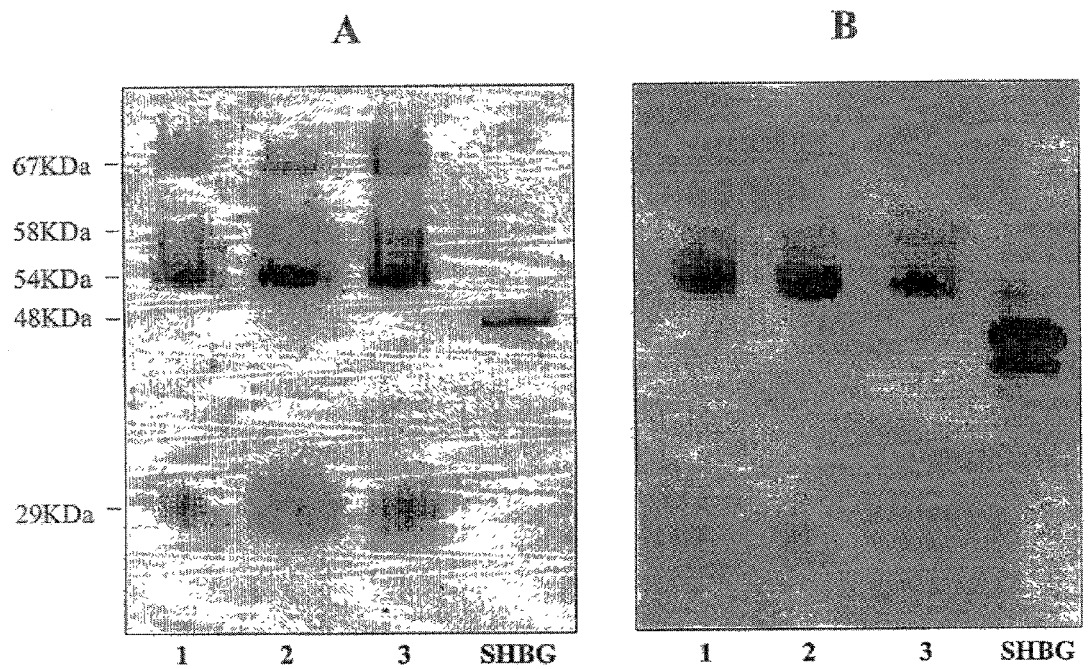

FIG. 52. Identification of the Molecular Forms Present in Active CA-PS-pool II. (A) SDS-PAGE with Coomassie Blue Staining; (B) Western Analysis with Anti-human SHBG.

Figure 53:
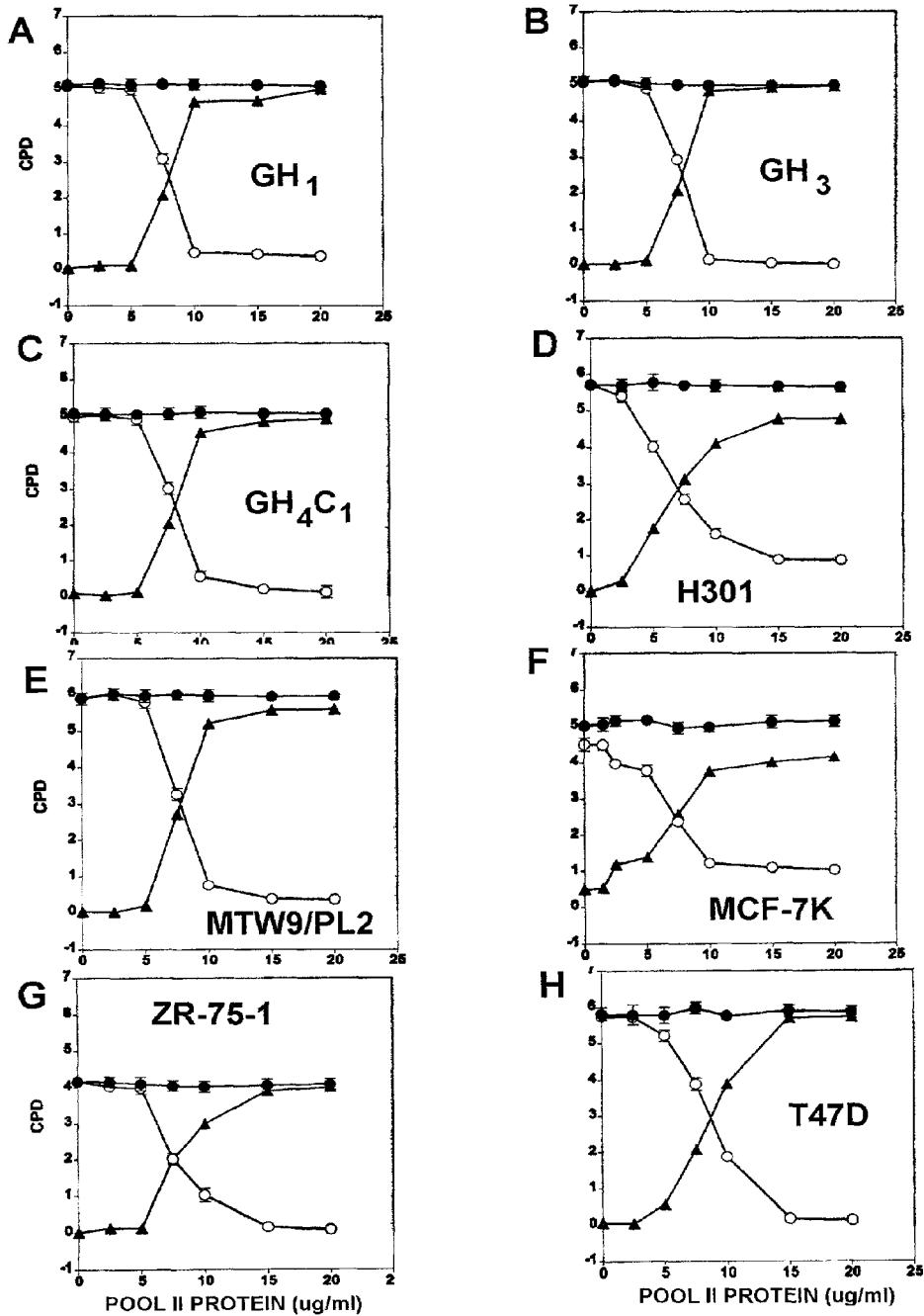

FIG. 53. CA-PS-pool II Effect on $ER^+$ Cell Growth in 2.5% CDE-horse Serum ±$E_2$. (A) $GH_1$ Cells; (B) $GH_3$ Cells; (C) $GH_4C_1$ Cells; (D) H301 Cells; (E) MTW9/PL2 Cells; (F) MCF-7K Cells; (G) ZR-75-1 Cells (H) T47D Cells.

Figure 54:
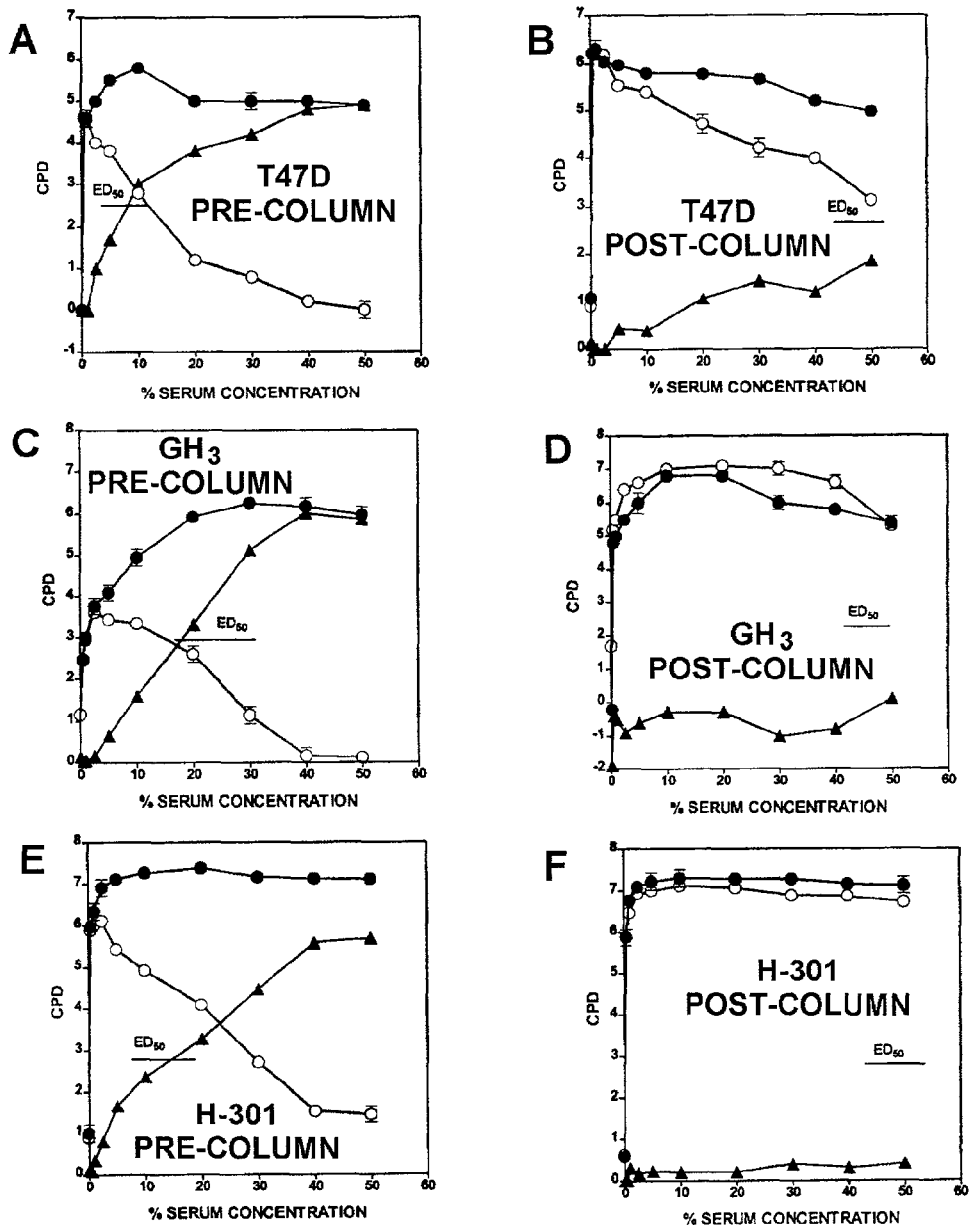

FIG. 54. Cortisol Affinity Column Depletion of the Estrogenic Activity in CDE-horse Serum Assayed with $ER^+$ Cell Lines ±$E_2$. (A) T47D Cells Pre-Column; (B) T47D Cells Post-Column; (C) $GH_3$ Cells Pre-Column; (D) $GH_3$ Cells Pre-Column; (E) H301 Cells Pre-Column; (F) H301 Cells Post-Column.

Figure 55:
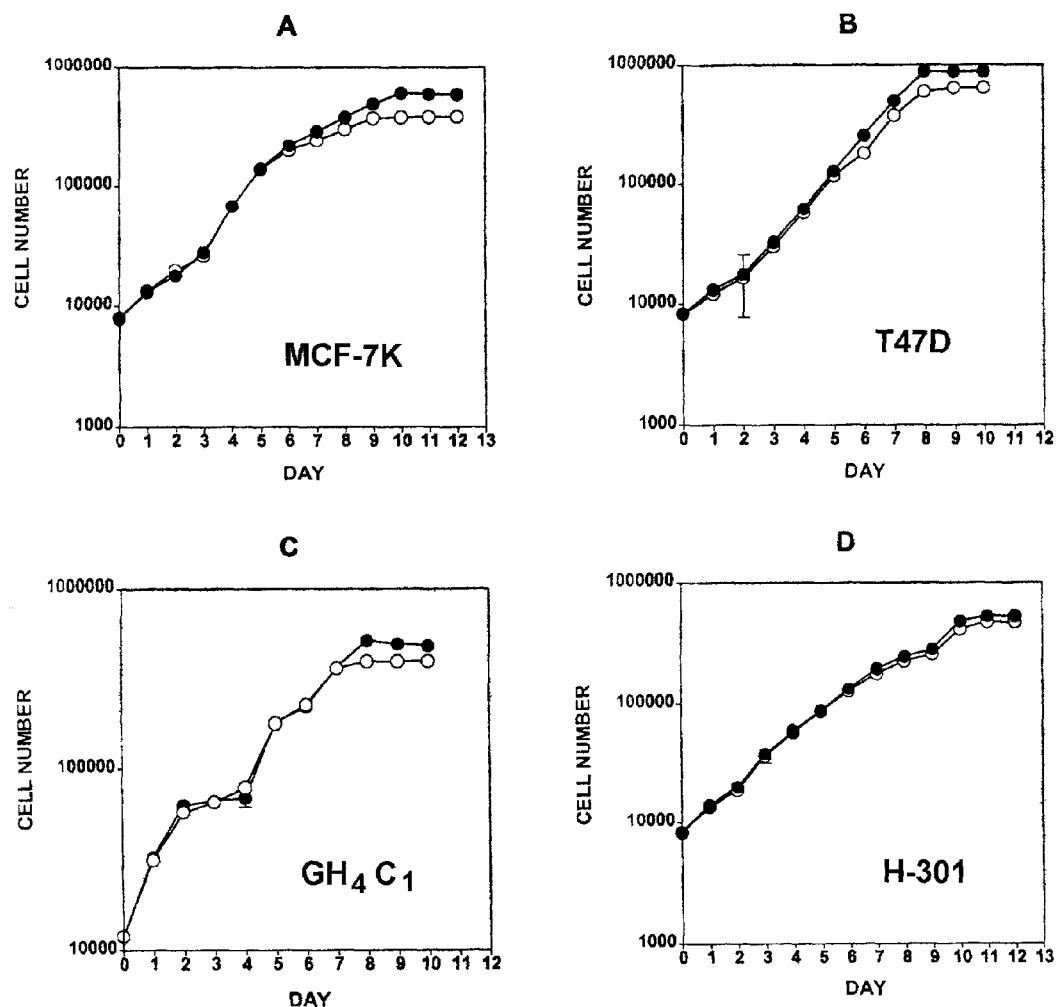

FIG. 55. Serum-free Growth of Cells in Four Different Defined Media ±$E_2$. (A) MTW9/PL2 Cells in DDM-2A; (B) T47D Cells in DDM-2MF; (C) $GH_4C_1$ Cells in PCM-9; and (D) H301 Cells in CAPM.

FIG. 56. Effects of CDE-horse Serum on Estrogen Responsiveness of Three ER ±Cell Lines Growing in Serum-free Defined Media. (A) T47D Cells in DDM-2MF; (13) MTW9/PL2 Cells in DDM-2A; (C) $GH_4C_1$ Cells in PCM-9.

Figure 57:
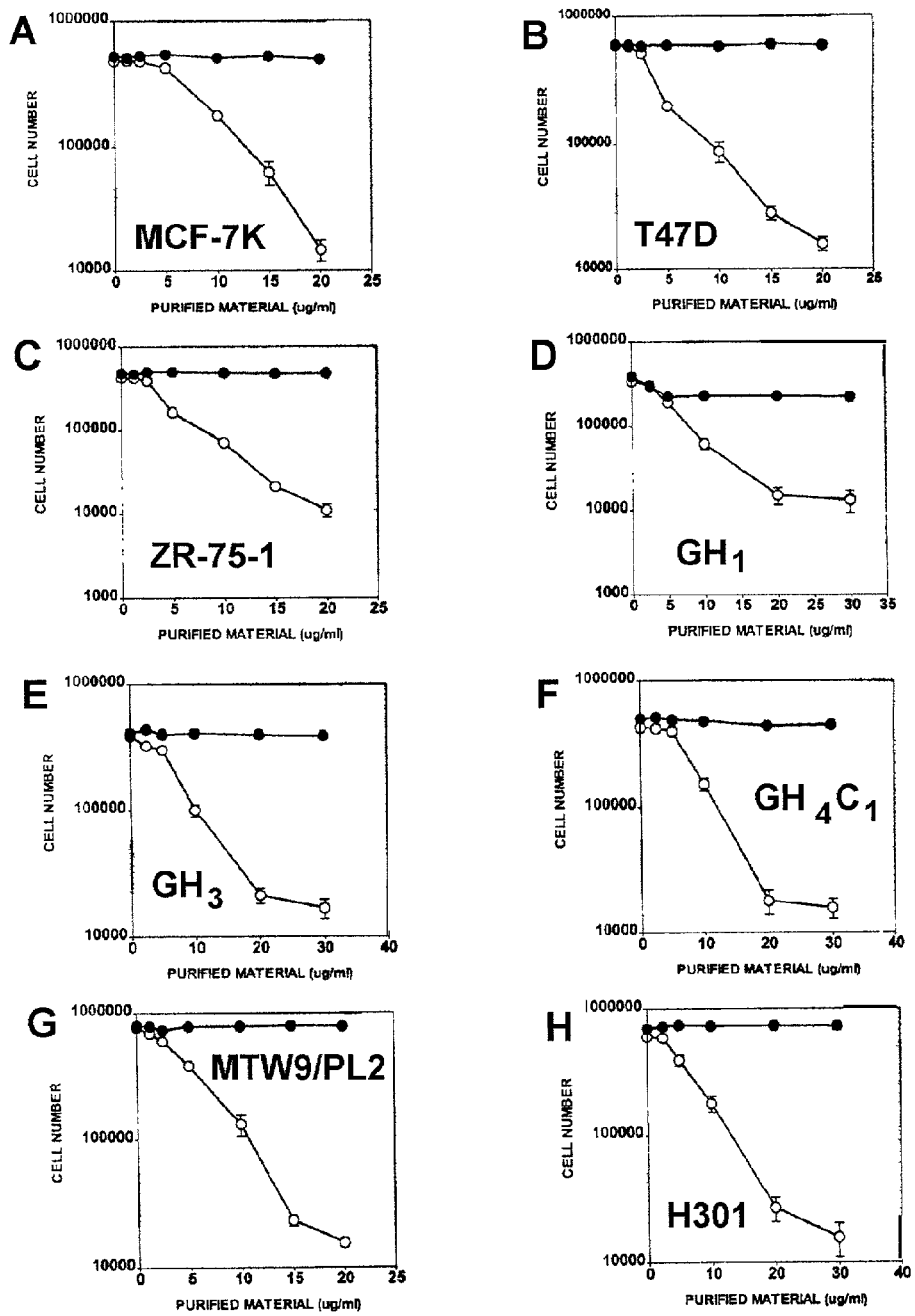

FIG. 57. Effects of CA-PS-pool II on the Growth of Eight $ER^+$ Cell Lines in Serum-free Defined Medium ±$E_2$.

Figure 58:
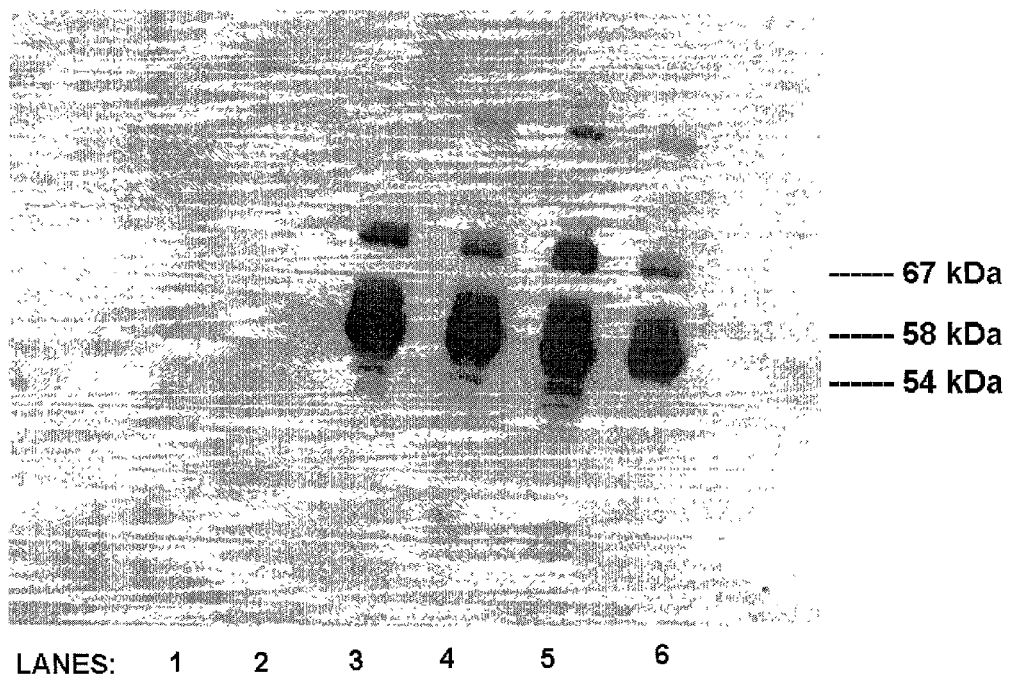

FIG. 58. Western Analysis of CA-PS-pool I and CA-PS-pool II with the Antibody Raised to the 54 kDa Band.

Figure 59:
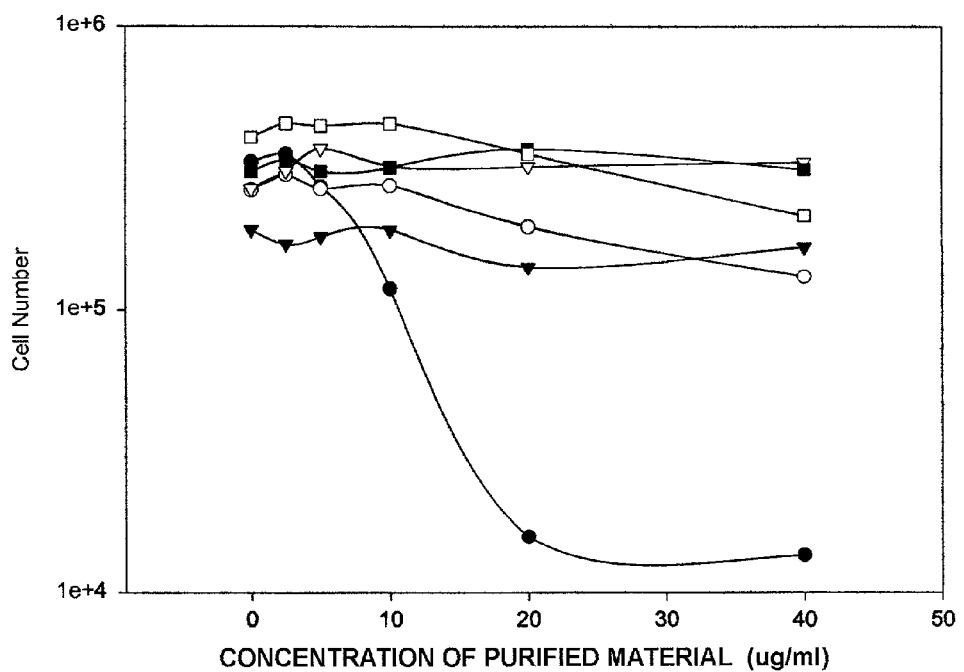

FIG. 59. Effect of the Anit-54 kDa Antiserum on the Inhibition of MWT9/PL2 Cell Growth by the Isolated Fraction CS-PS-Pool II.

Figure 60:
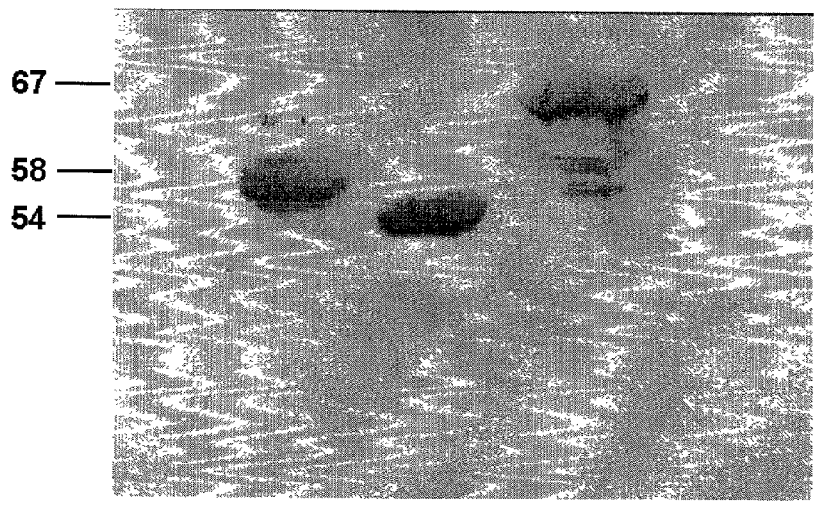

FIG. 60. Western Immunoblotting of Commercially Prepared Horse IgG, IgA and IgM with anti-54 kDa Antiserum.

Figure 61:
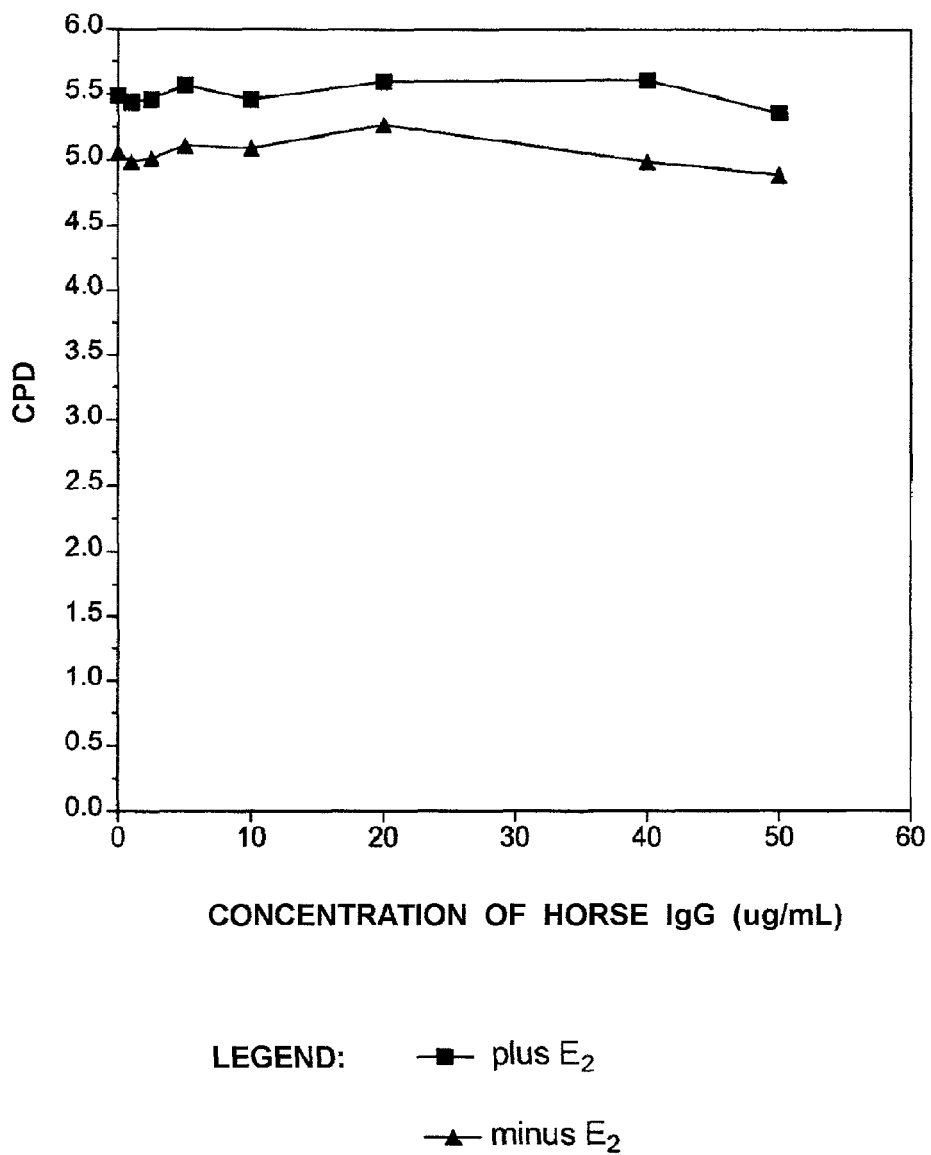

FIG. 61. Effect of Horse IgG on MTW9/PL2 Cell Growth in 2.5% CDE-horse Serum ±$E_2$.

Figure 62:
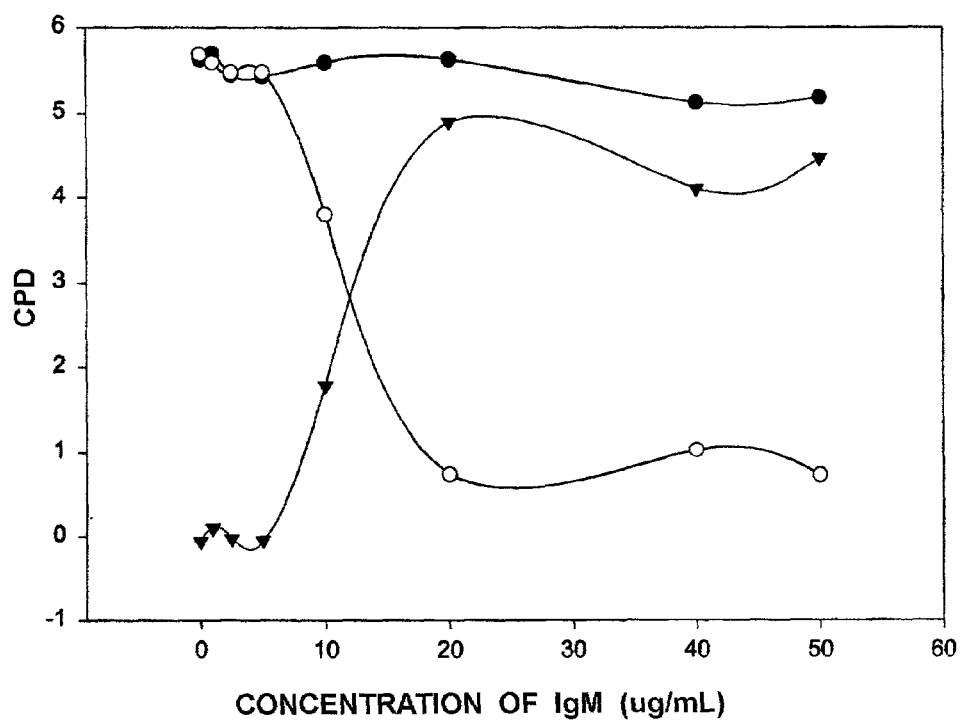

FIG. 62. Effect of Horse IgM on MTW9/PL2 Cell Growth in 2.5% CDE-horse Serum ±$E_2$.

Figure 63:
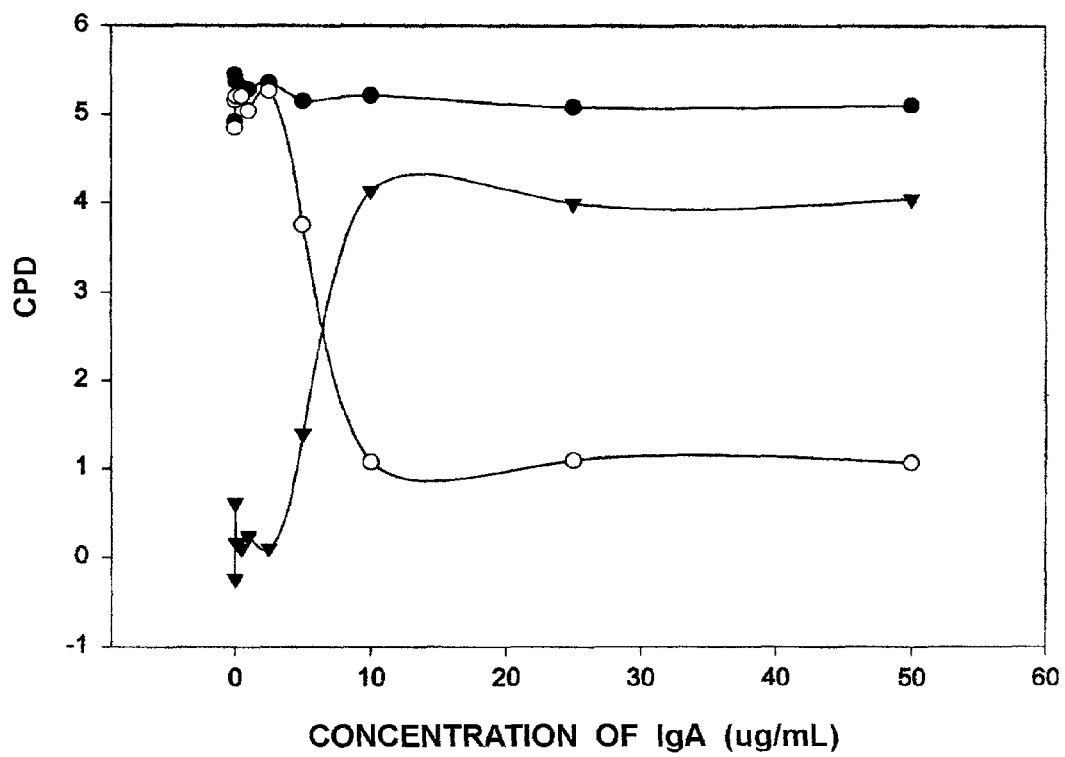

FIG. 63. Effect of Horse IgA on MTW9/PL2 Cell Growth in 2.5% CDE-horse Serum ±$E_2$.

FIG. 64. SDS-PAGE with Coomassie Staining and Western Analysis of Rat Purified "SHBG-like" Proteins. (A) SDS-PAGE of Purified Rat Preparations; (B) Western Analysis with Anti-rat IgG.

Figure 65:
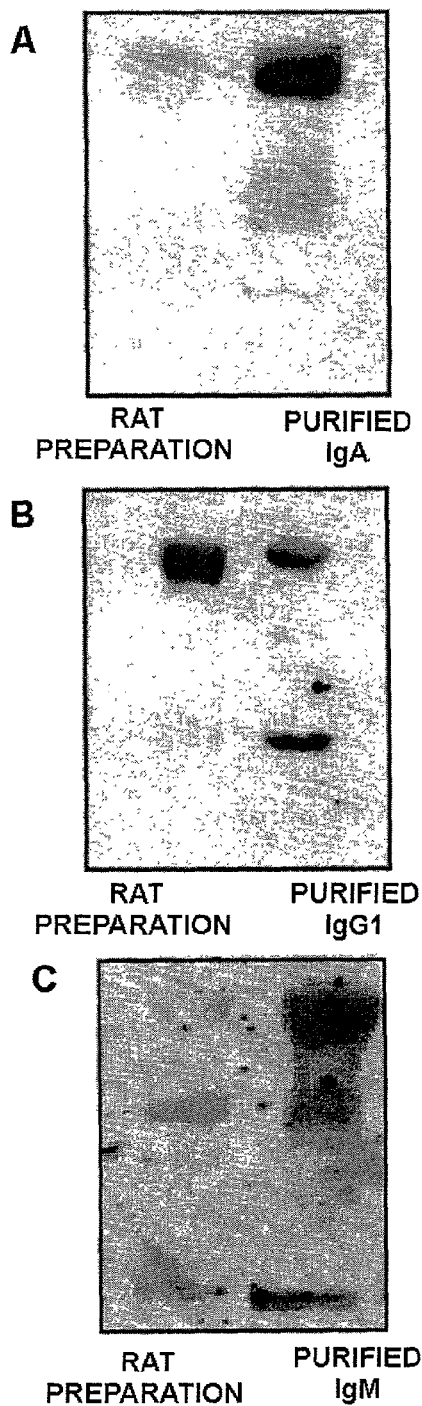

FIG. 65. Western Analysis of a Rat Purified "SHBG-like" Preparation. (A) Western with Anti-rat IgA with Purified IgA Control; (B) Western with Anti-rat IgG1 with Purified IgG1 Control; (C) Western with Anti-rat IgM with Purified IgM Control.

Figure 66:
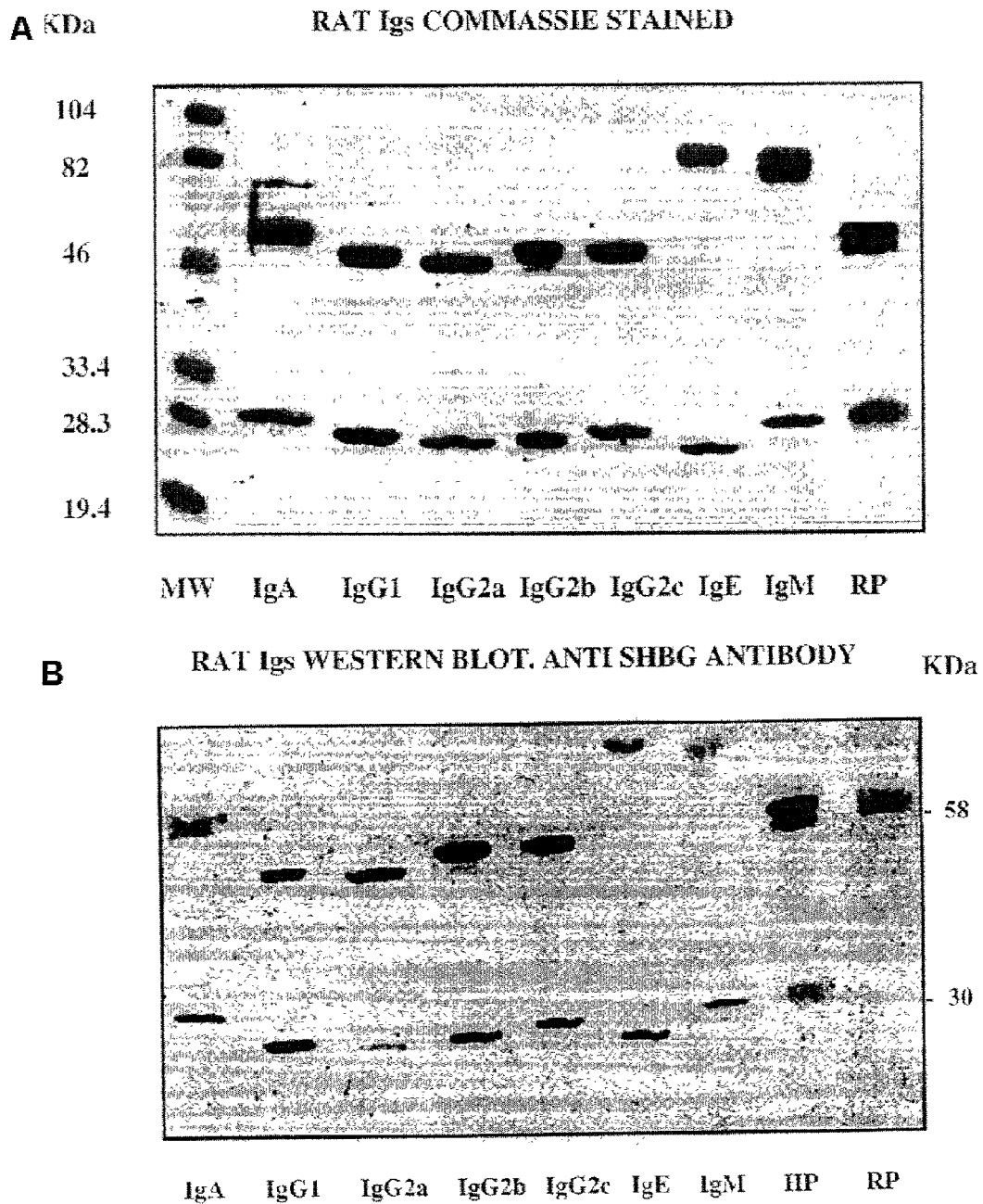

FIG. 66. Comparison of Rat IgG Subclasses for Antibody Cross-Reaction. (A) SDS-PAGE with Coomassie Blue Staining; (B) Western Analysis with Rabbit Anti-Human SHBG.

Figure 67:
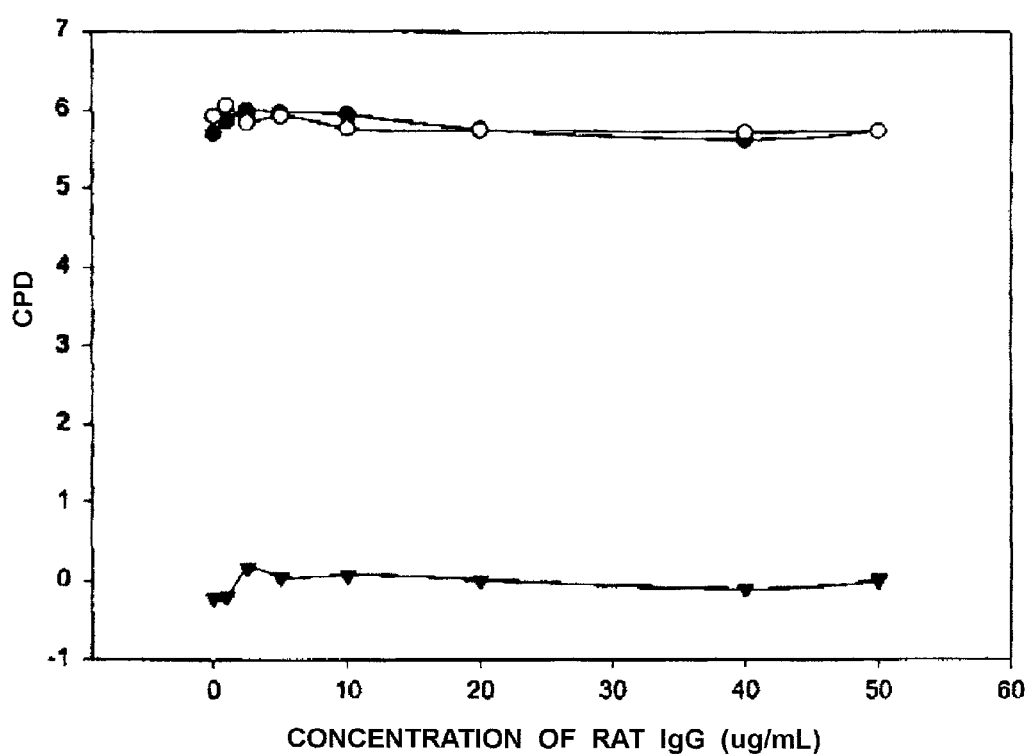

FIG. 67. Effect of Rat IgG on MTW9/PL2 Cell Growth in Medium with 2.5% CDE-rat Serum ±$E_2$.

Figure 68:
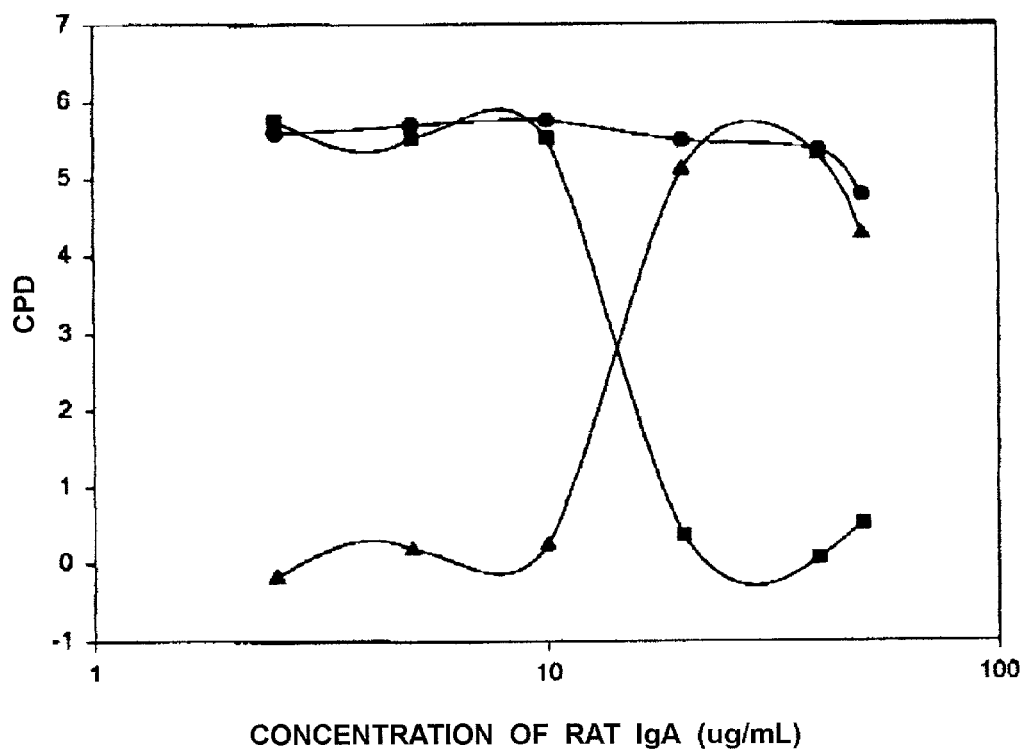

FIG. 68. Effect of Rat IgA on MTW9/PL2 Cell Growth in Medium with 2.5% CDE-rat Serum ±$E_2$.

Figure 69:
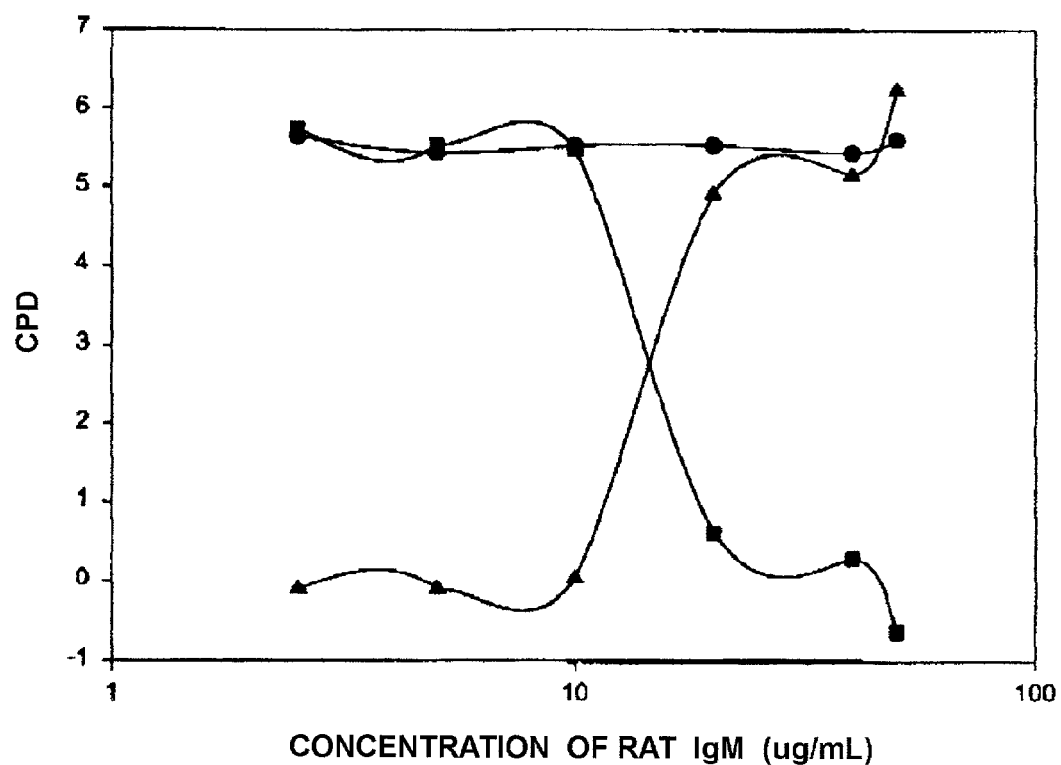

FIG. 69. Effect of Rat IgM on MTW9/PL2 Cell Growth in Medium with 2.5% CDE-rat Serum ±$E_2$.

Figure 70:
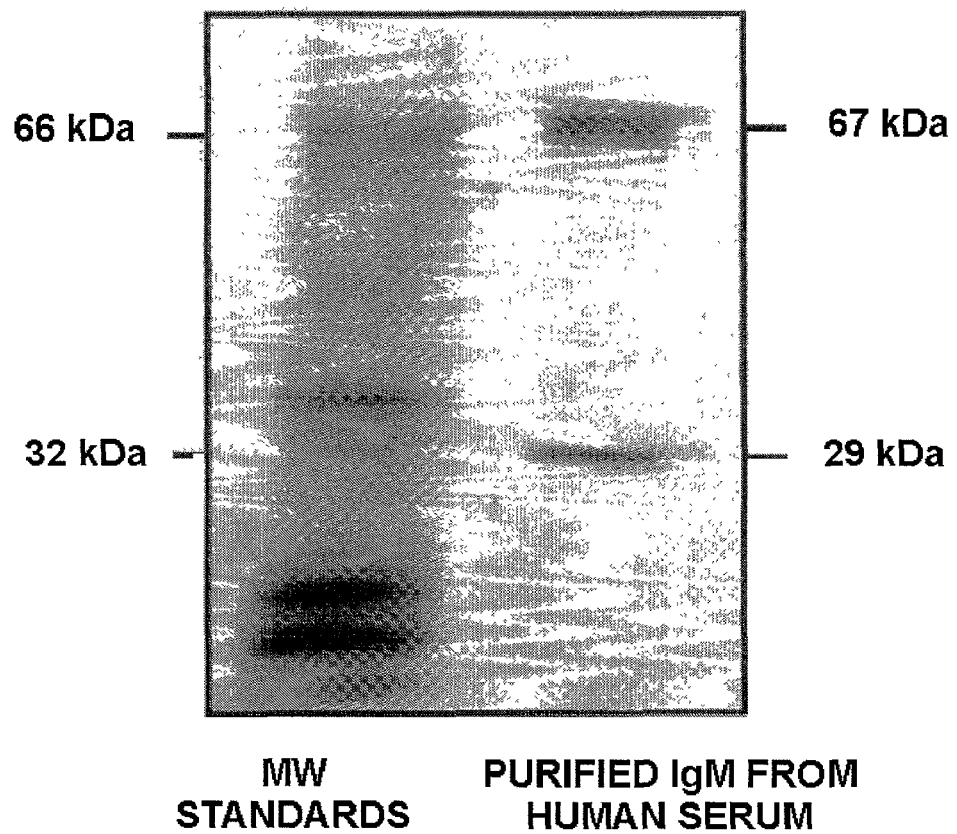

FIG. 70. Mannan Binding Protein Isolation of Human Plasma/Serum IgM.

Figure 71:
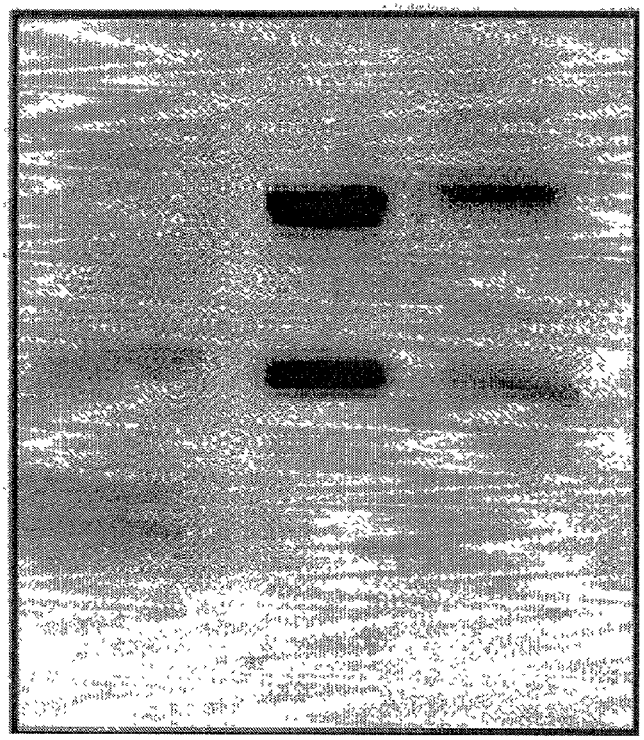

FIG. 71. Jacalin Lectin Purification of Human Plasma/Serum IgA.

Figure 72:
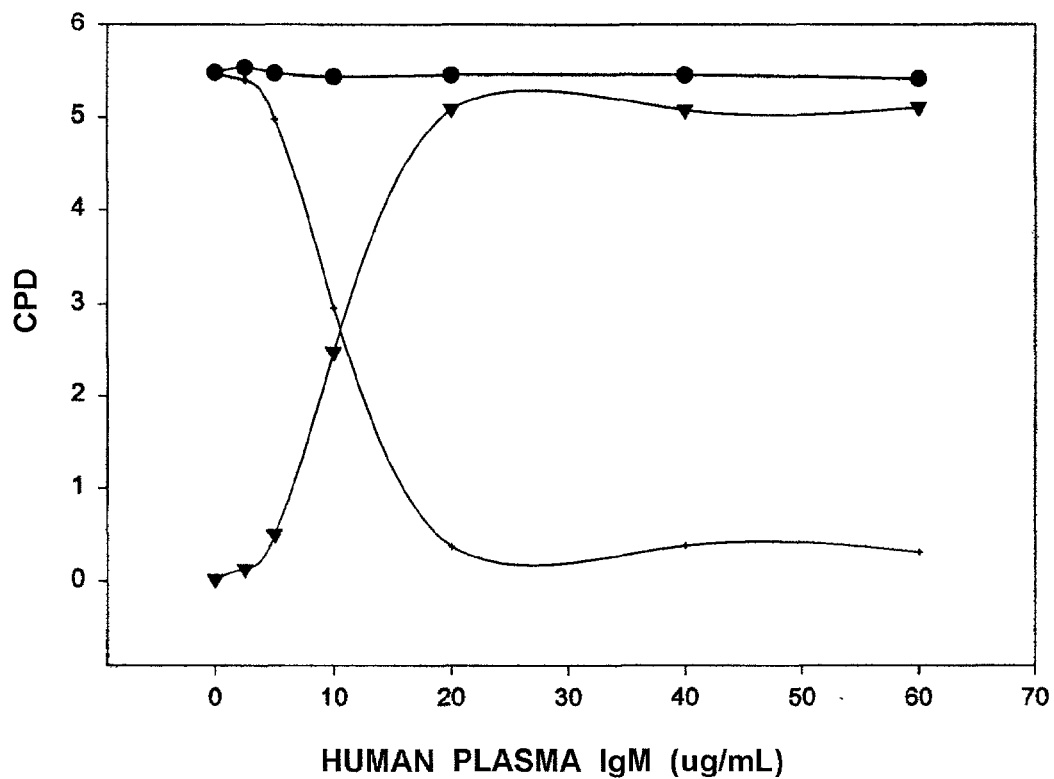

FIG. 72. Effect of Human IgM on MTW9/PL2 Cell Growth ±$E_2$ in Serum-free Defined Medium.

Figure 73:
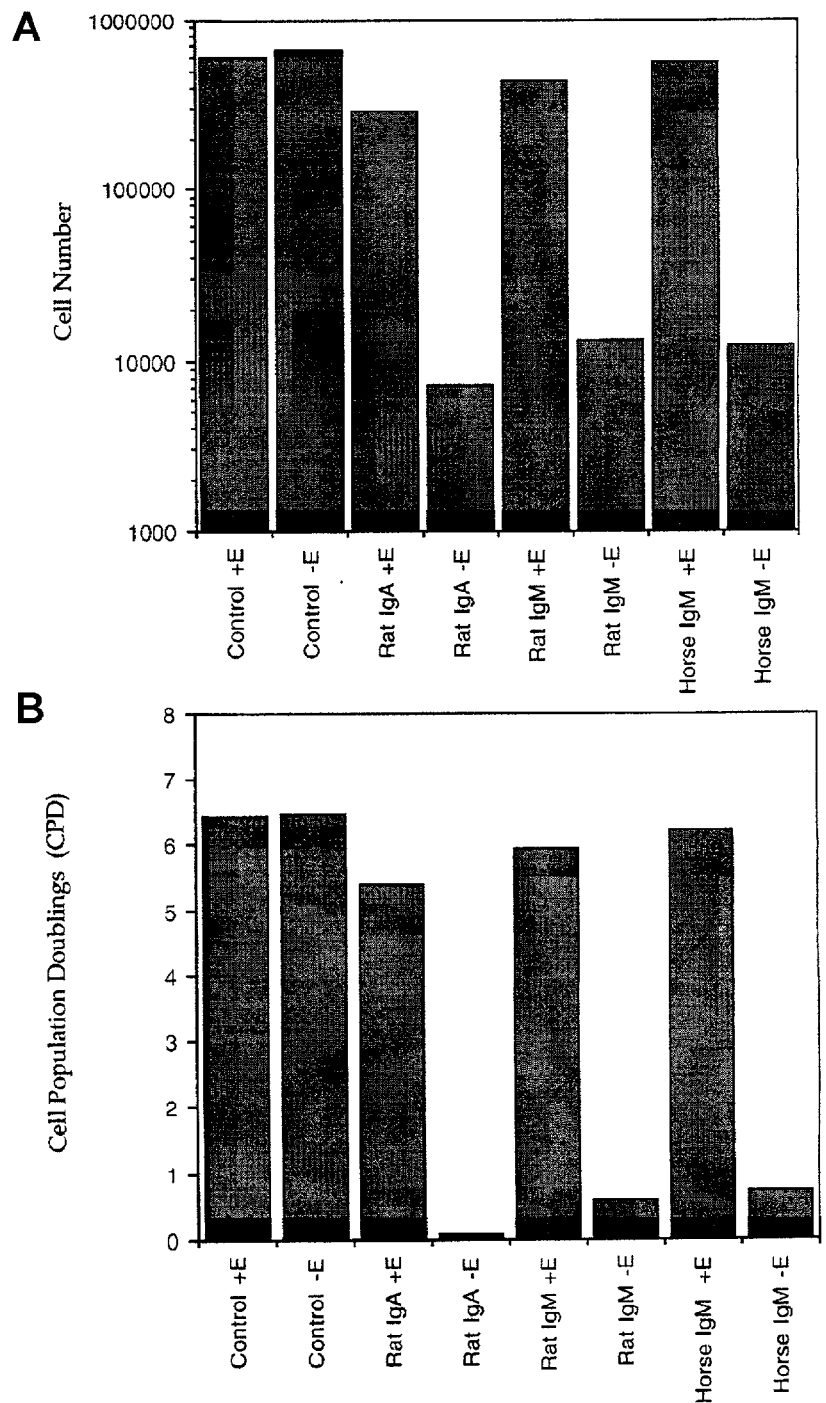

FIG. 73. Comparison of the Effects of Rat and Horse IgA and IgM on MTW9/PL2 Cell Growth ±$E_2$ in Serum-free Defined Medium Expressed in Cell Number and CPD.

Figure 74:
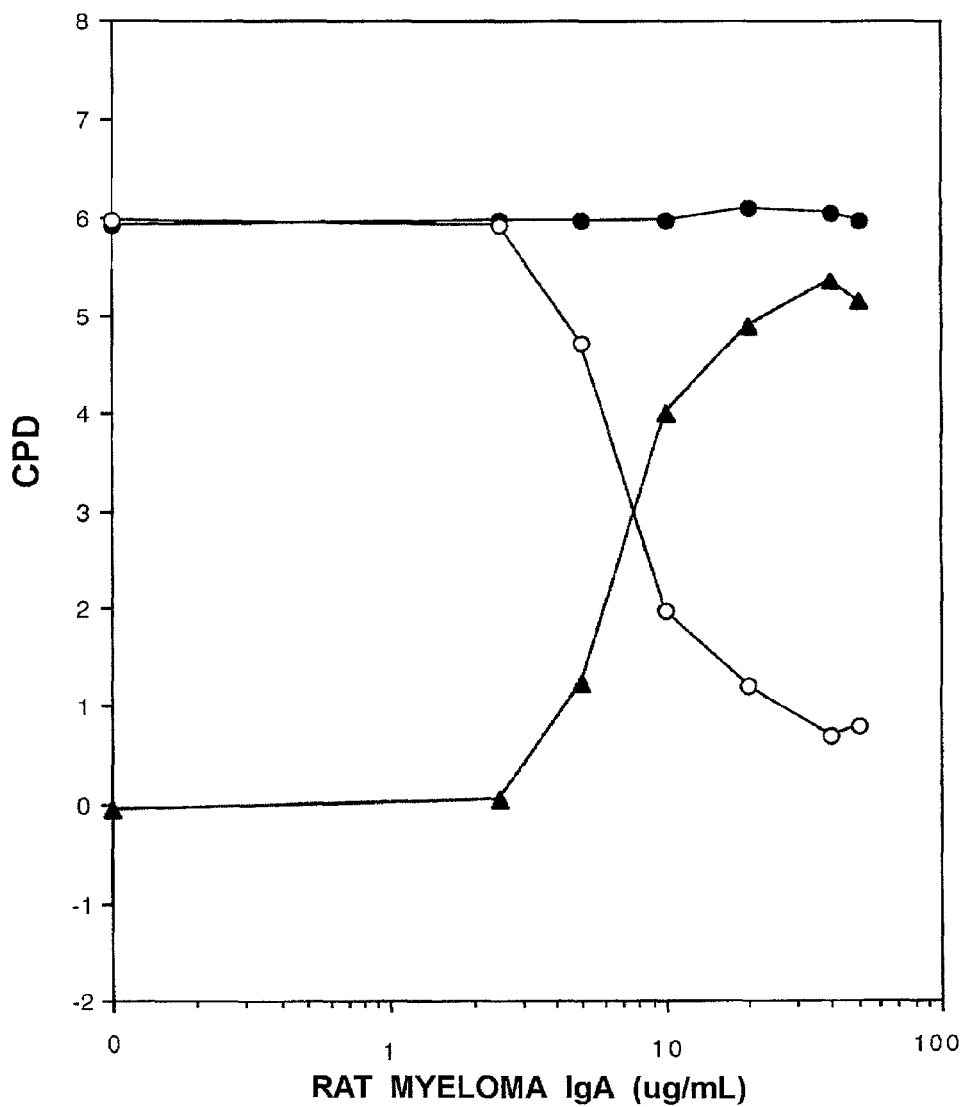

FIG. 74. Effect of Rat Myeloma IgA on $GH_1$ Cell Growth in Serum-free Defined Medium ±$E_2$.

Figure 75:
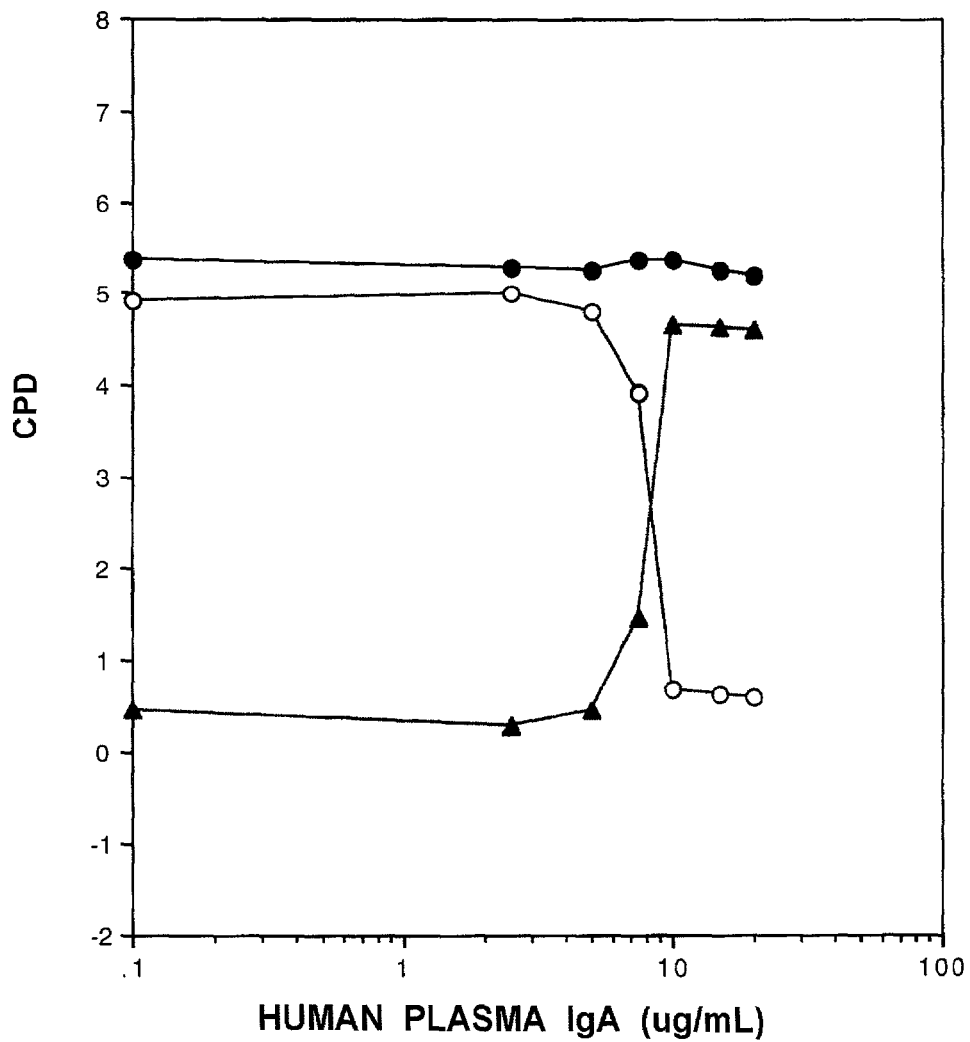

FIG. 75. Effect of Human Plasma IgA on $GH_1$ Cell Growth in Serum-free Defined Medium ±$E_2$.

Figure 76:
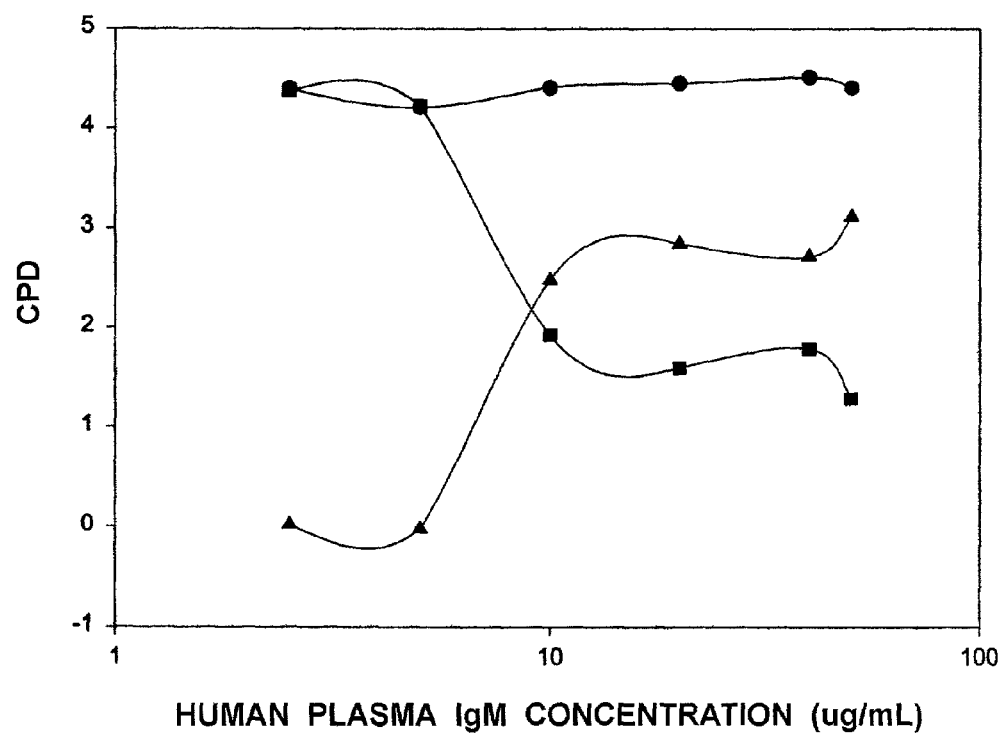

FIG. 76. Effect of Human Plasma IgA on $GH_1$ Cell Growth in Serum-free Defined Medium ±$E_2$.

Figure 77:
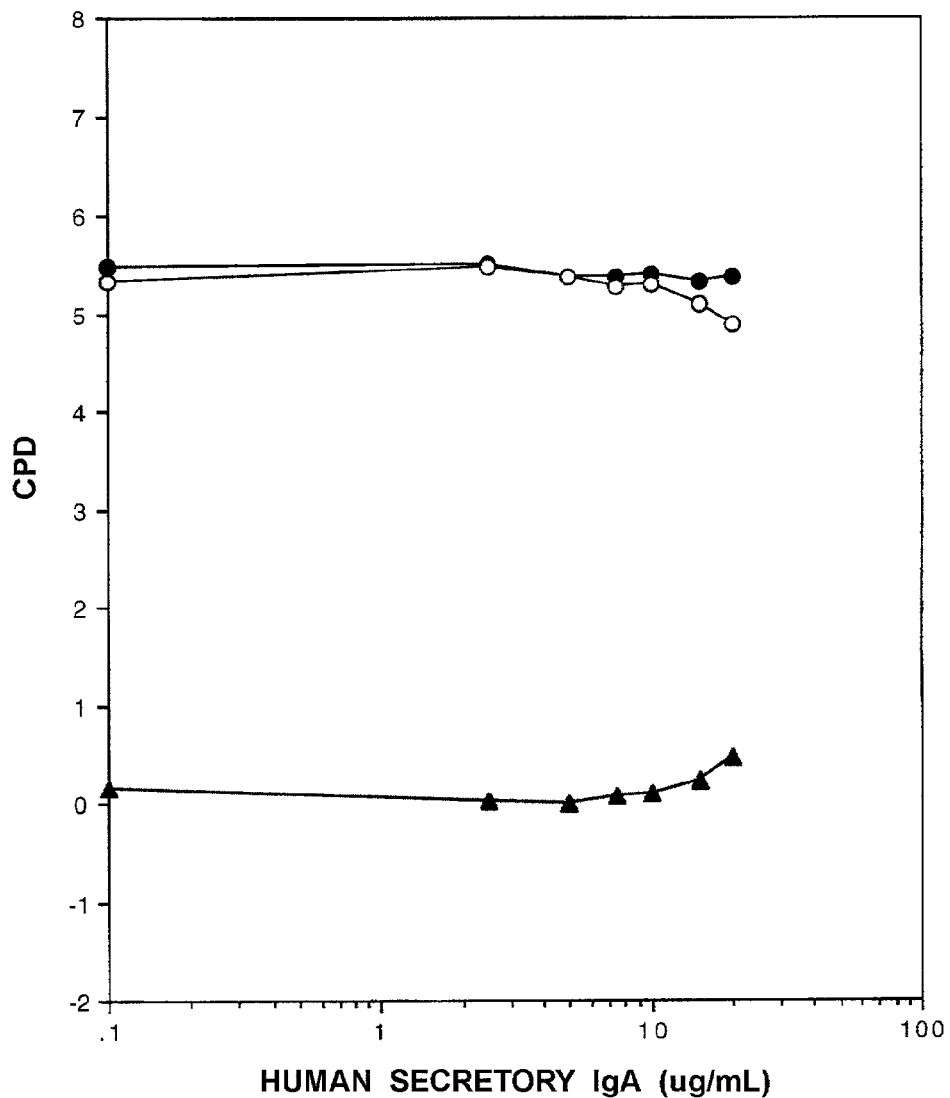

FIG. 77. Effects of sIgA on $GH_1$ Cell Growth in Serum-free Defined Medium ±$E_2$.

Figure 78:
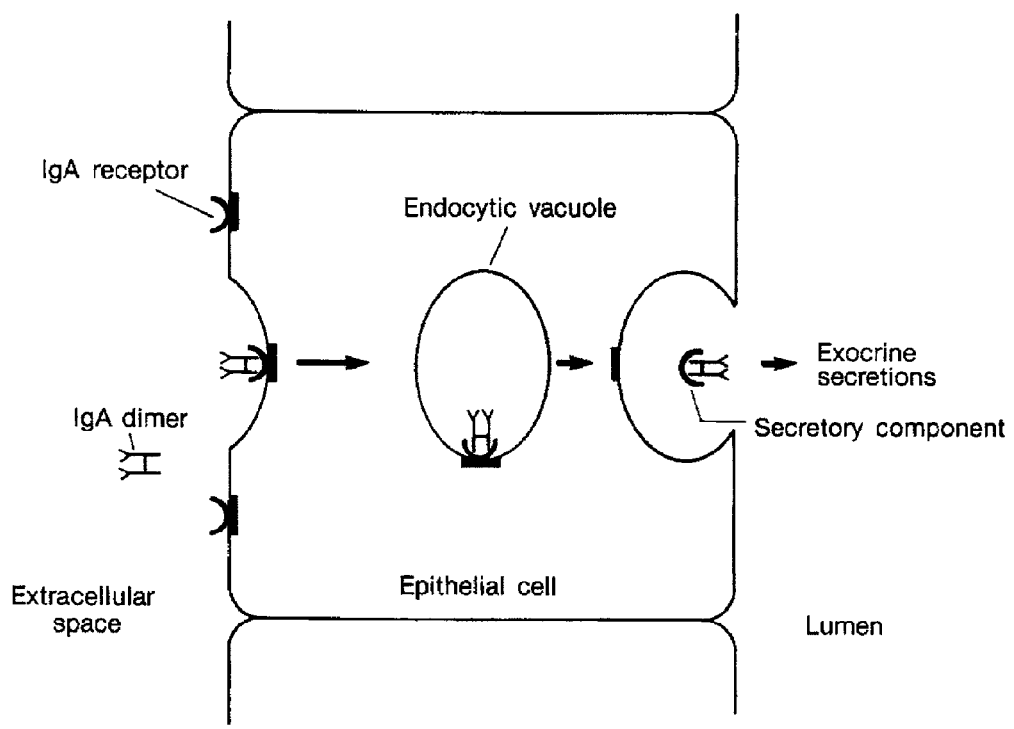

FIG. 78. Model of Mucosal Epithelial Cell Transport of IgA/IgM.

FIG. 79. Essential Structures of Human Plasma and Secretory IgA.

Figure 80:
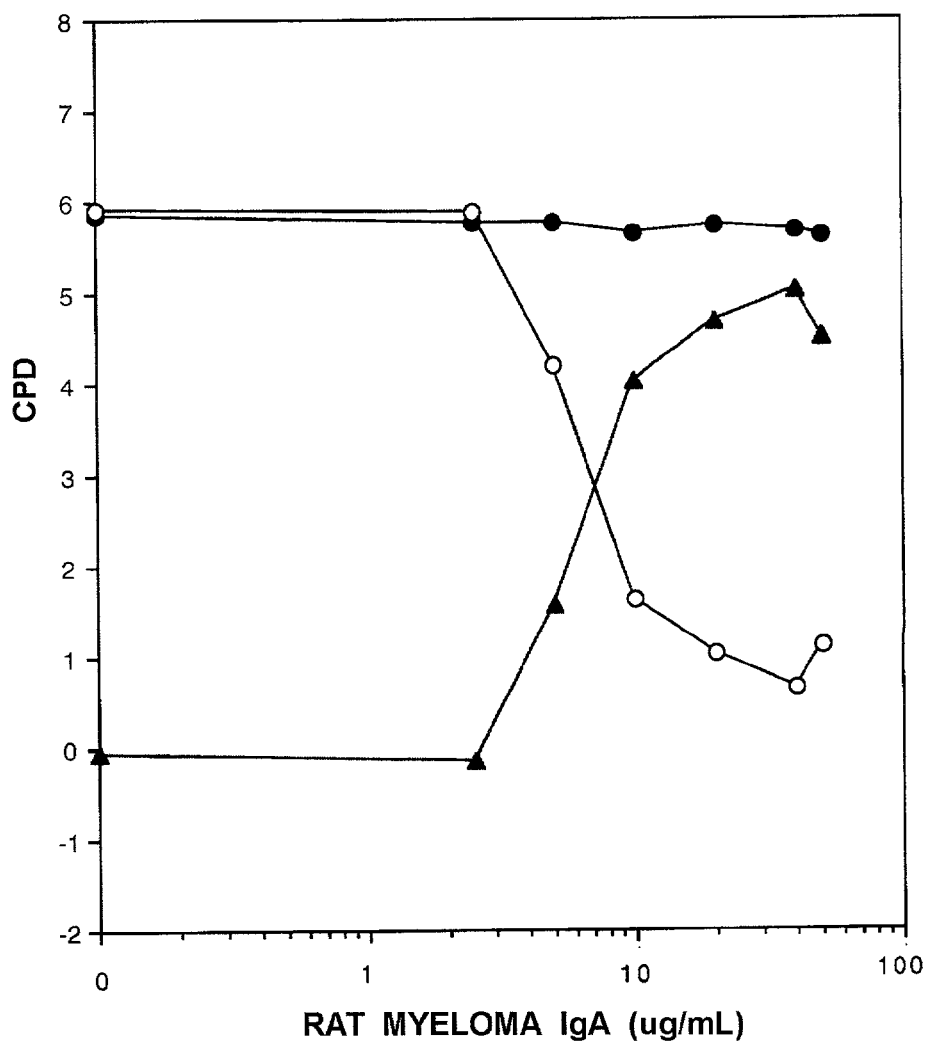

FIG. 80. Effect of Rat Myeloma IgA on $GH_3$ Cell Growth in Serum-free Defined Medium ±$E_2$.

Figure 81:
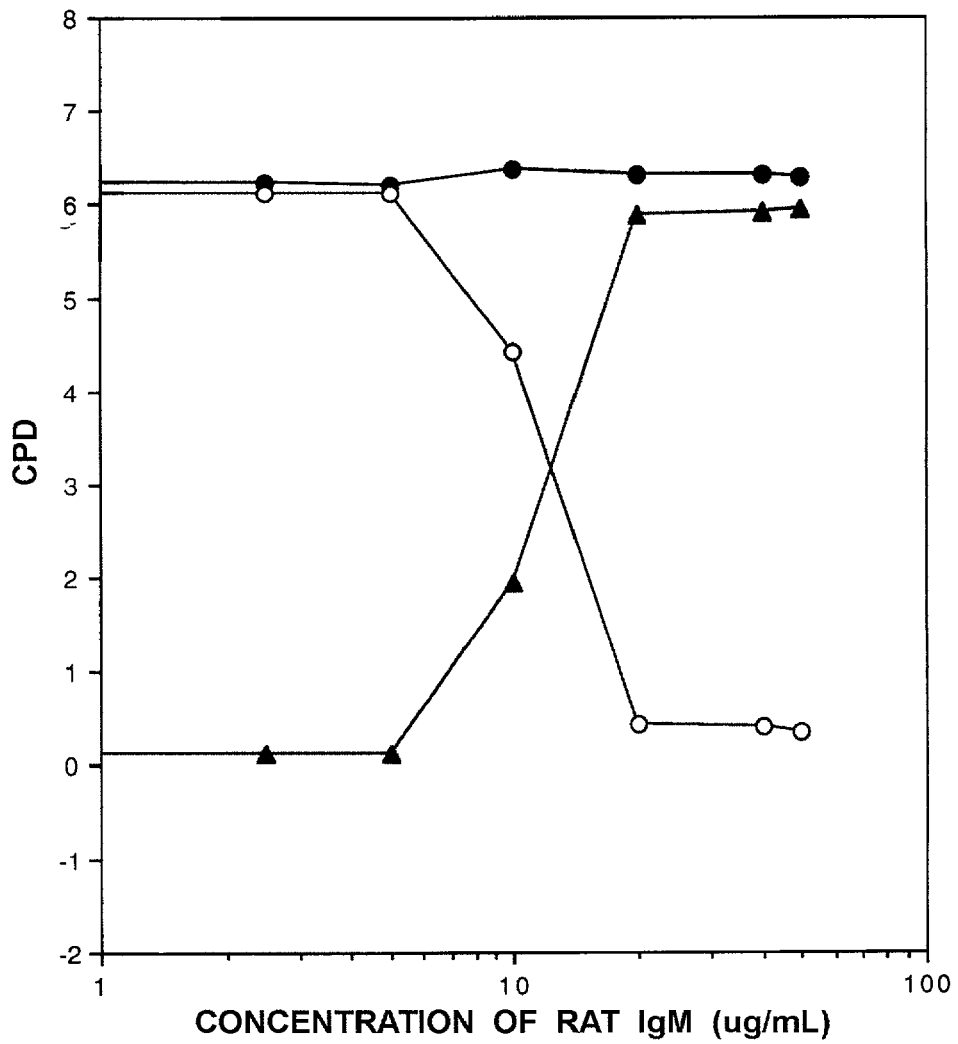

FIG. 81. Effect of Rat IgM on $GH_3$ Cell Growth in Serum-free Defined Medium ±$E_2$.

Figure 82:
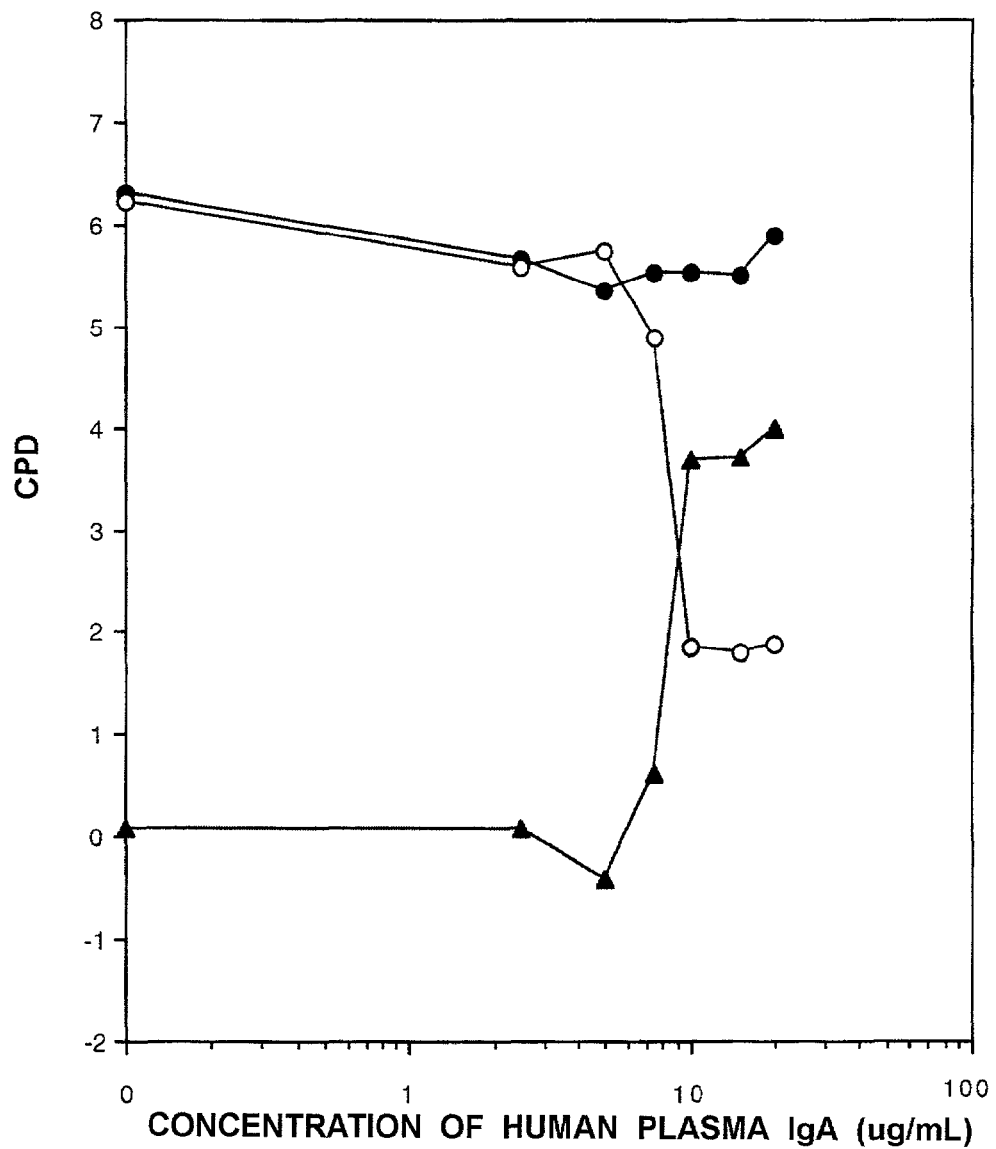

FIG. 82. Effect of Human Plasma IgA on $GH_3$ Cell Growth in Serum-free Defined Medium ±$E_2$.

Figure 83:
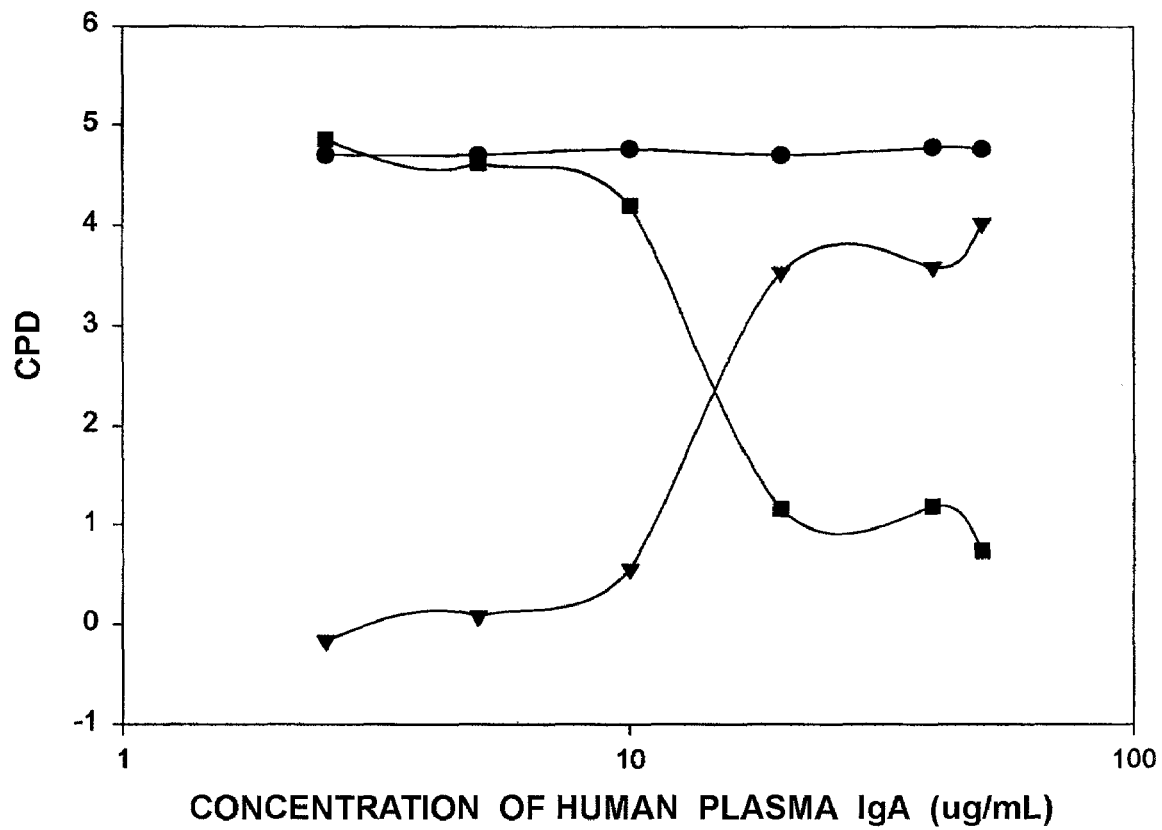

FIG. 83. Effect of Human Plasma IgM on $GH_3$ Cell Growth in Serum-free Defined Medium ±$E_2$.

Figure 84:
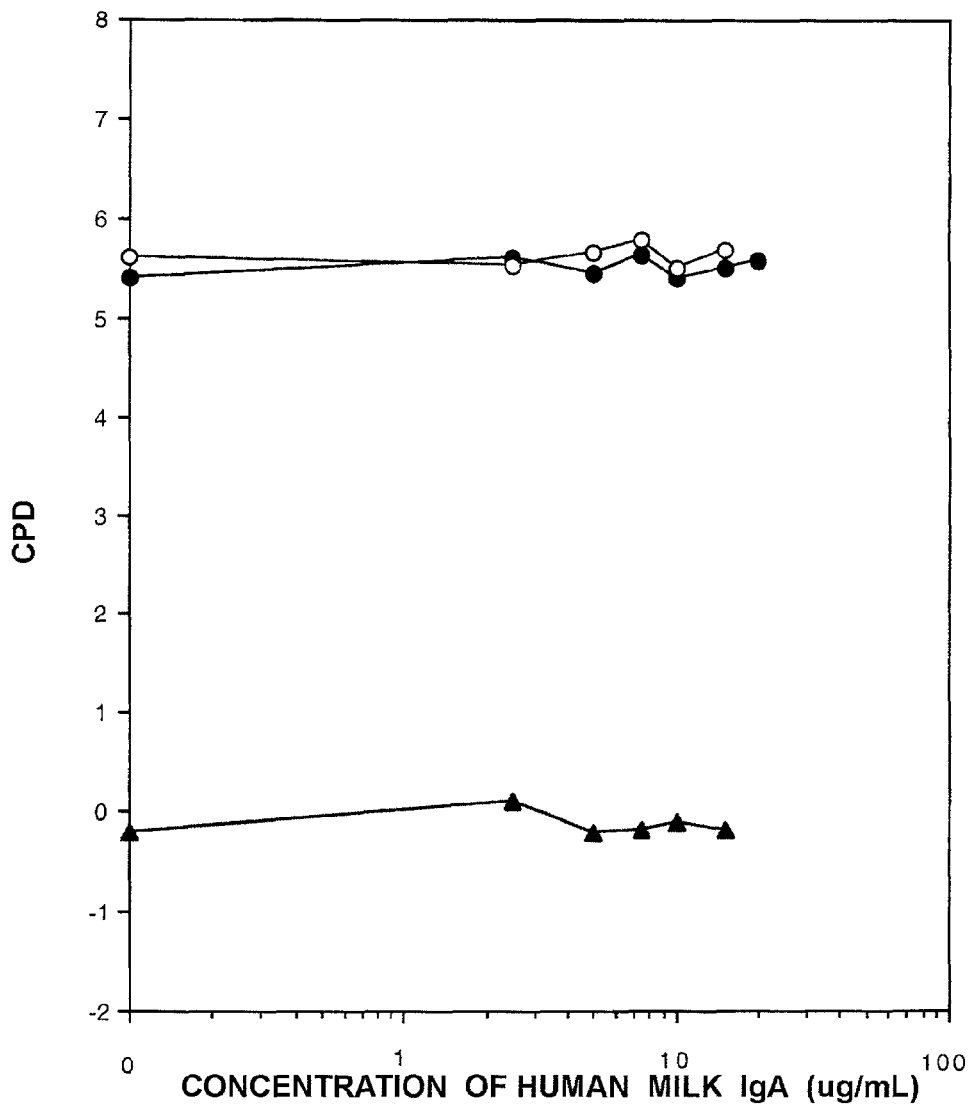

FIG. 84. Effect of Human Secretory IgA on $GH_3$ Cell Growth in Serum-free Defined Medium ±$E_2$.

Figure 85:
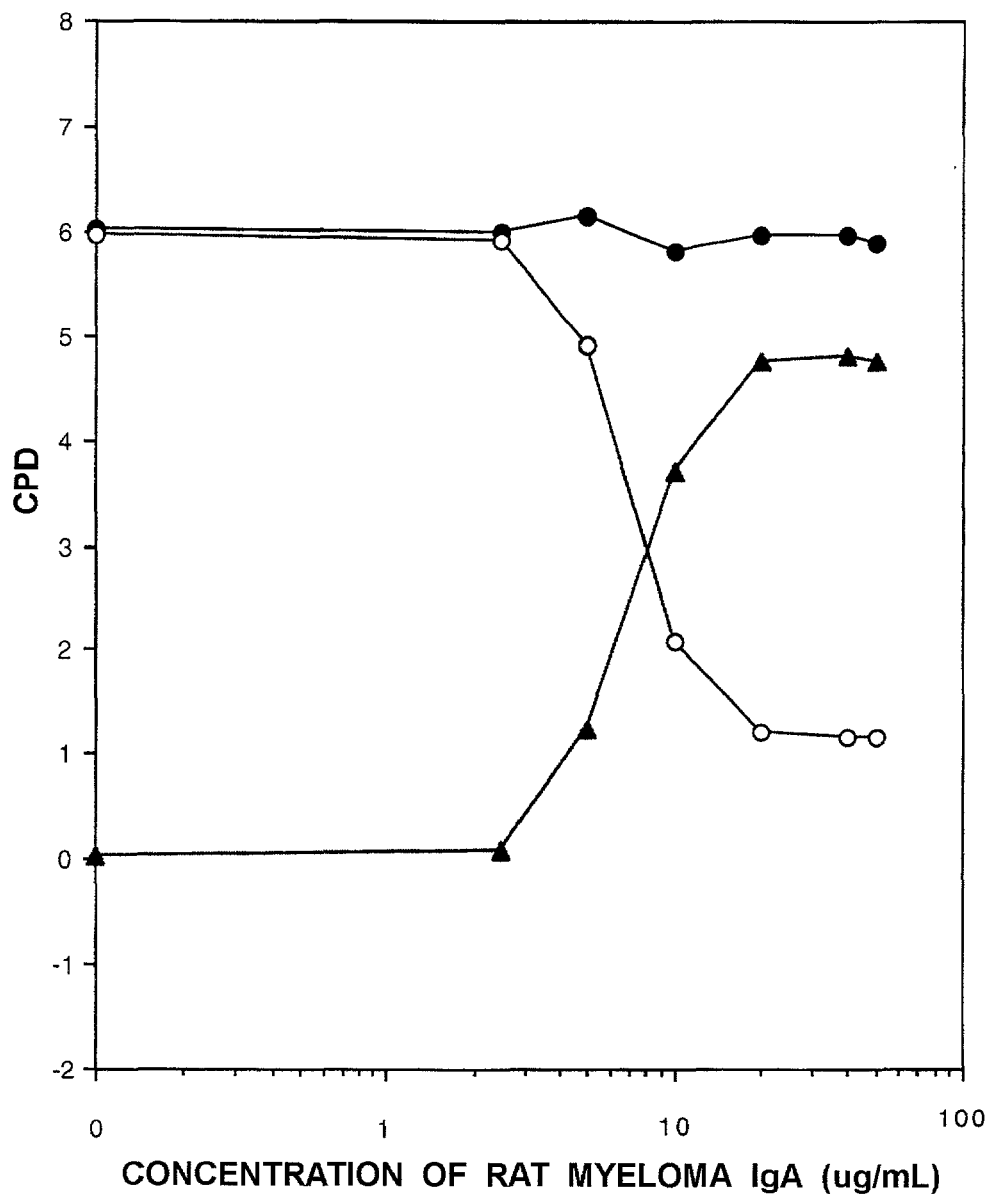

FIG. 85. Effect of Rat Myeloma IgA on $GH_4C_1$ Cell Growth in Serum-free Defined Medium ±$E_2$.

Figure 86:
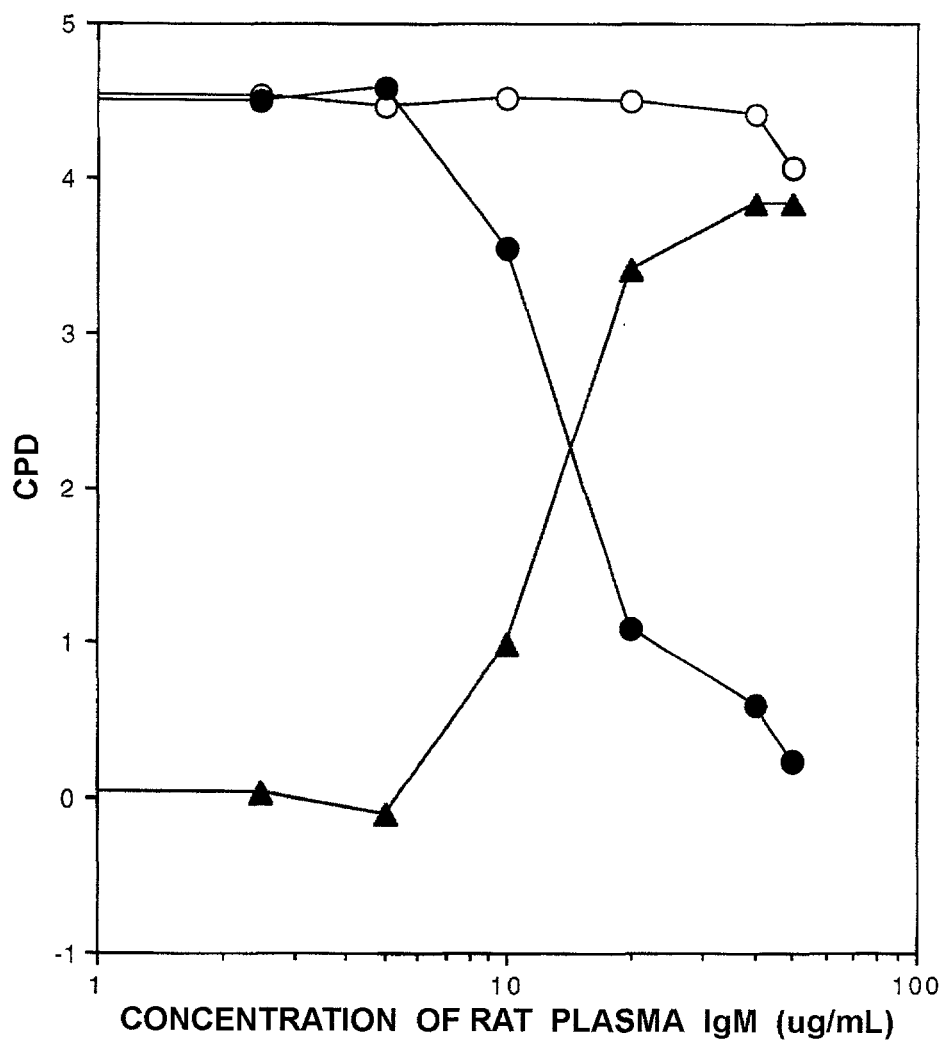

FIG. 86. Effect of Rat Plasma IgM on $GH_4C_1$ Cell Growth in Serum-free Defined Medium ±$E_2$.

Figure 87:
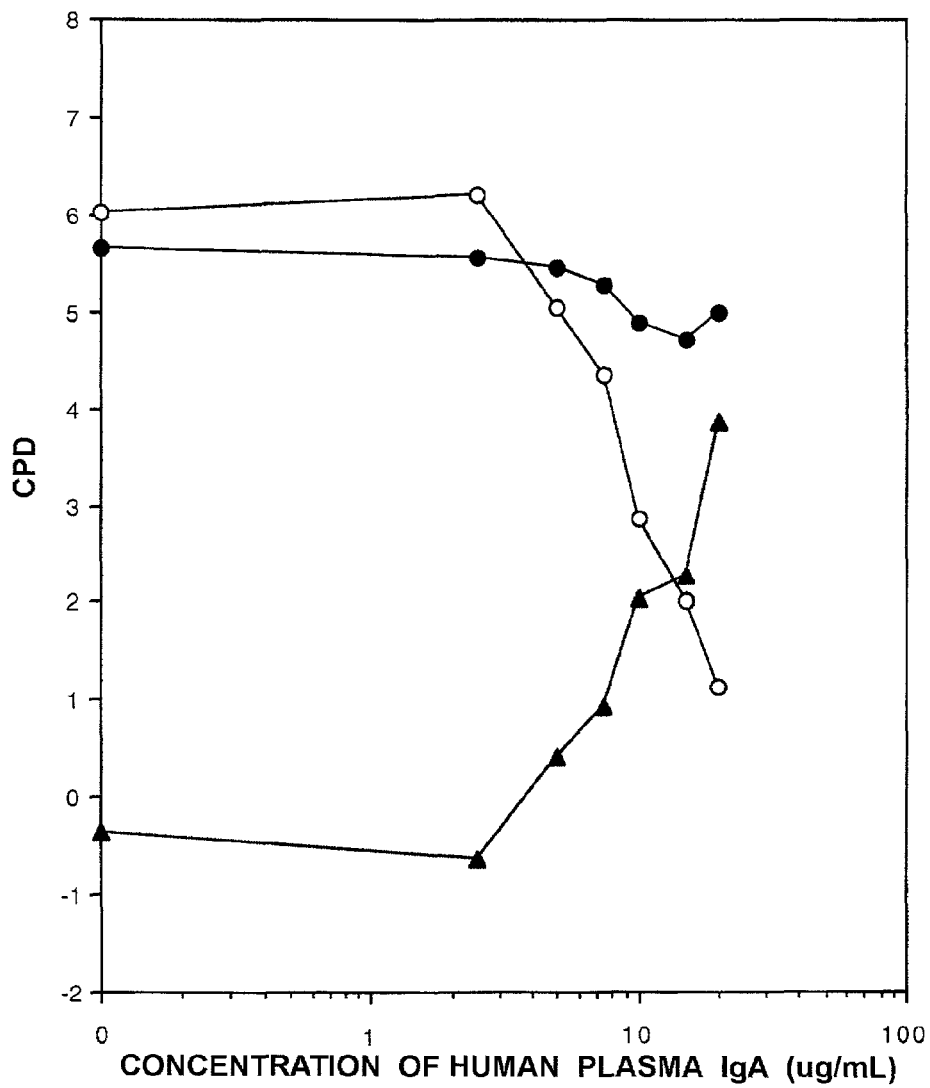

FIG. 87. Effect of Human Plasma IgA on $GH_4C_1$ Cell Growth in Serum-free Defined Medium ±$E_2$.

Figure 88:
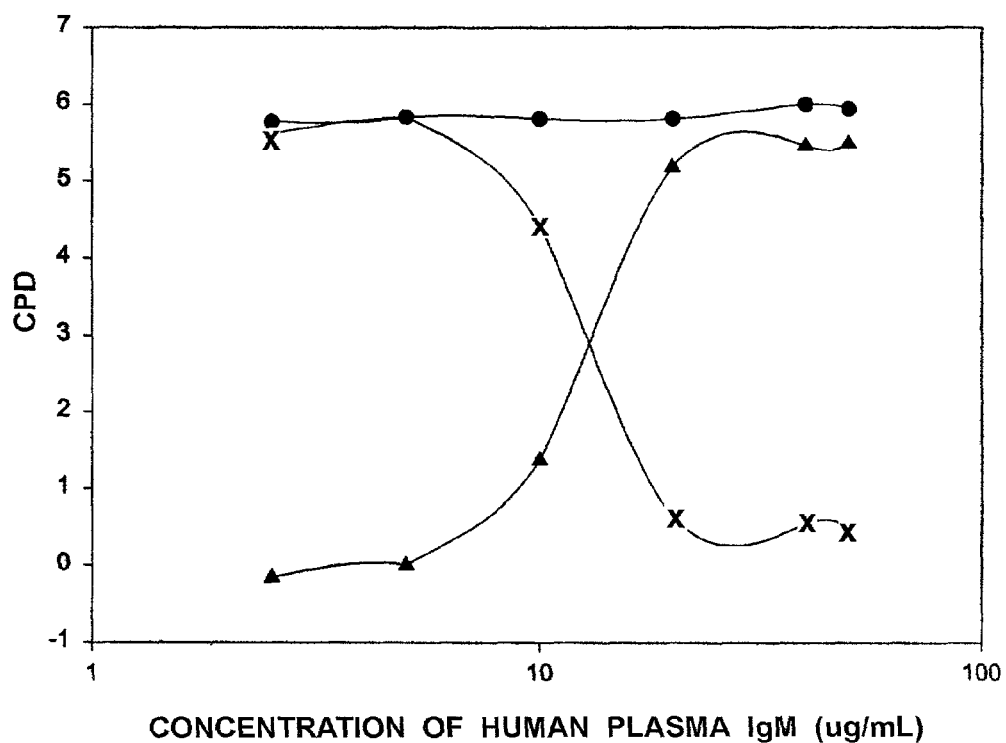

FIG. 88. Effect of Human Plasma IgM on $GH_4C_1$ Cell Growth in Serum-free Defined Medium ±$E_2$.

Figure 89:
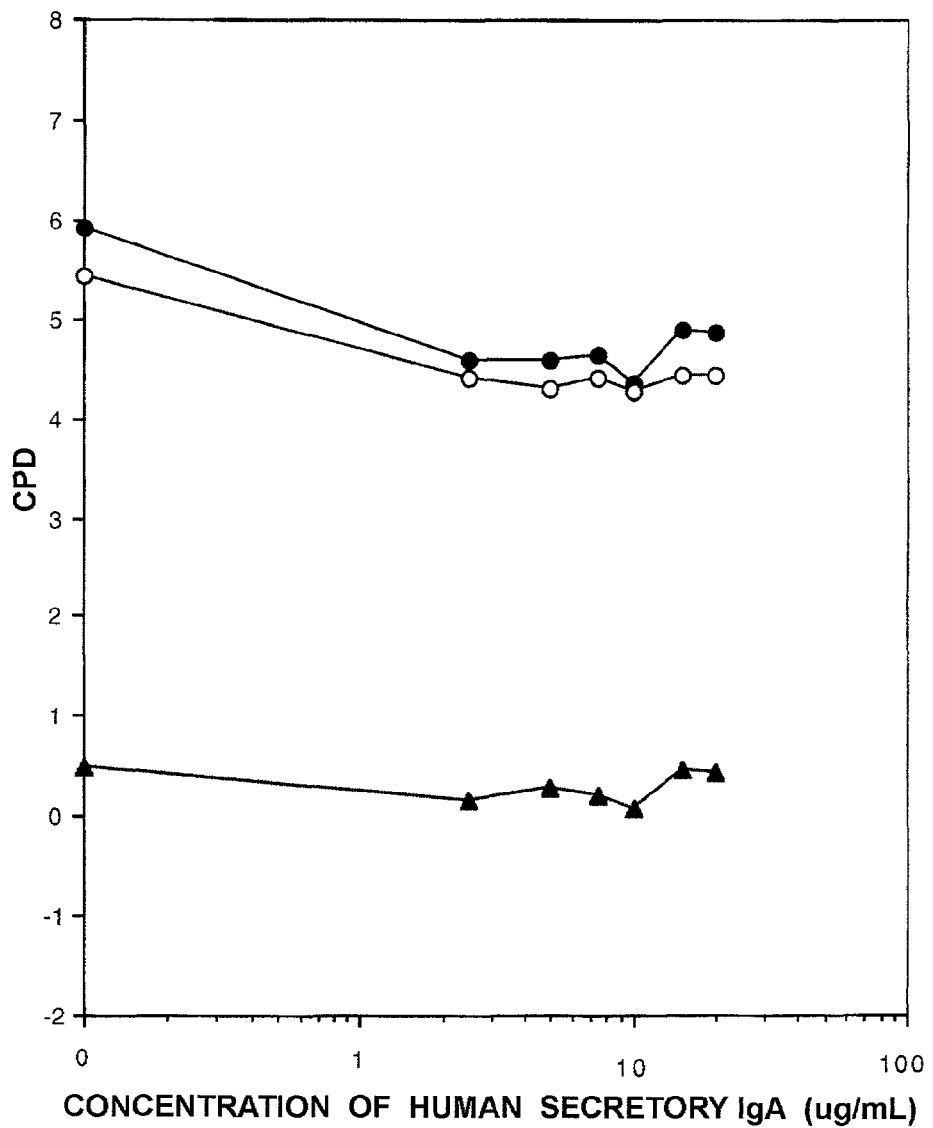

FIG. 89. Effect of Human Secretory IgA on $GH_4C_1$ Cell Growth in Serum-free Defined Medium ±$E_2$.

Figure 90:
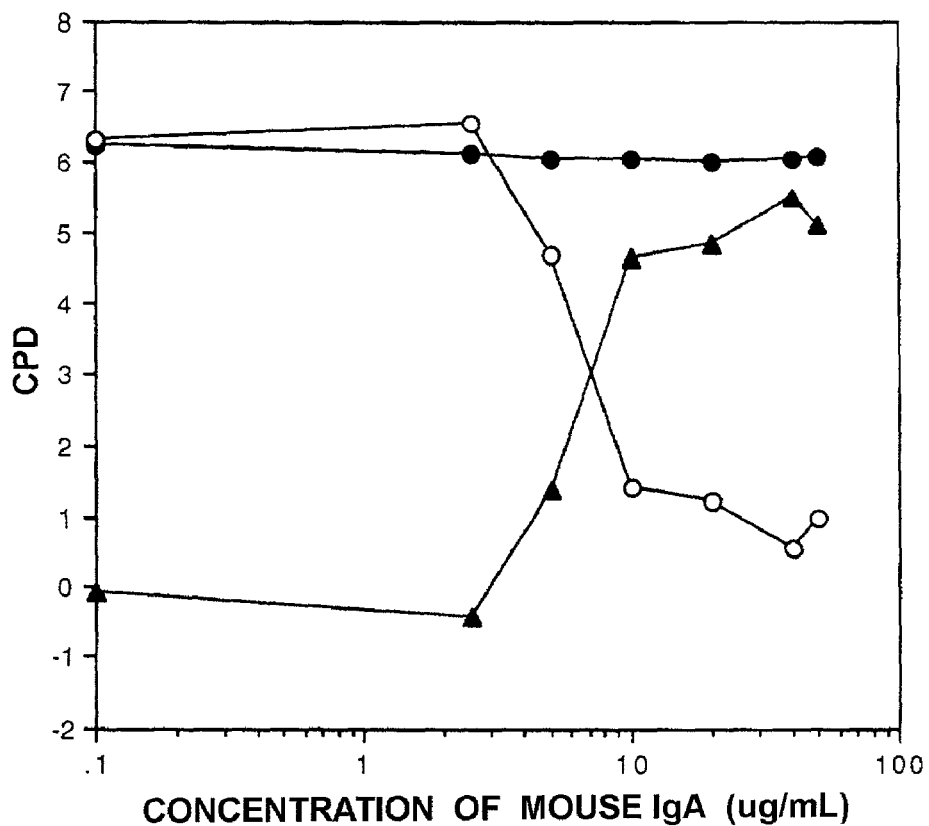

FIG. 90. Effect of Mouse IgA on H301 Cell Growth in Serum-free Defined Medium ±$E_2$.

Figure 91:
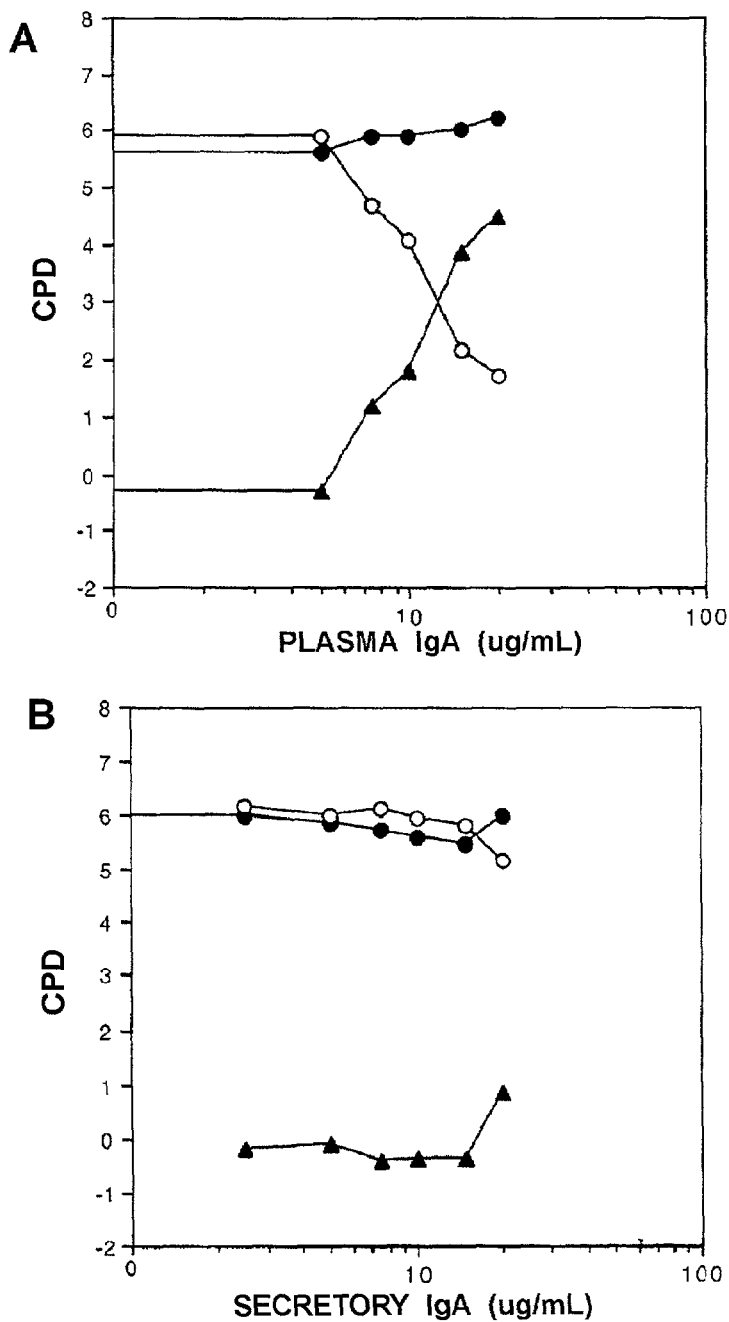

FIG. 91. Effect of Human IgA on H301 Cell Growth in Serum-free Defined Medium ±$E_2$. (A) Plasma IgA Effects; (B) Secretory sIgA Effects.

Figure 92:
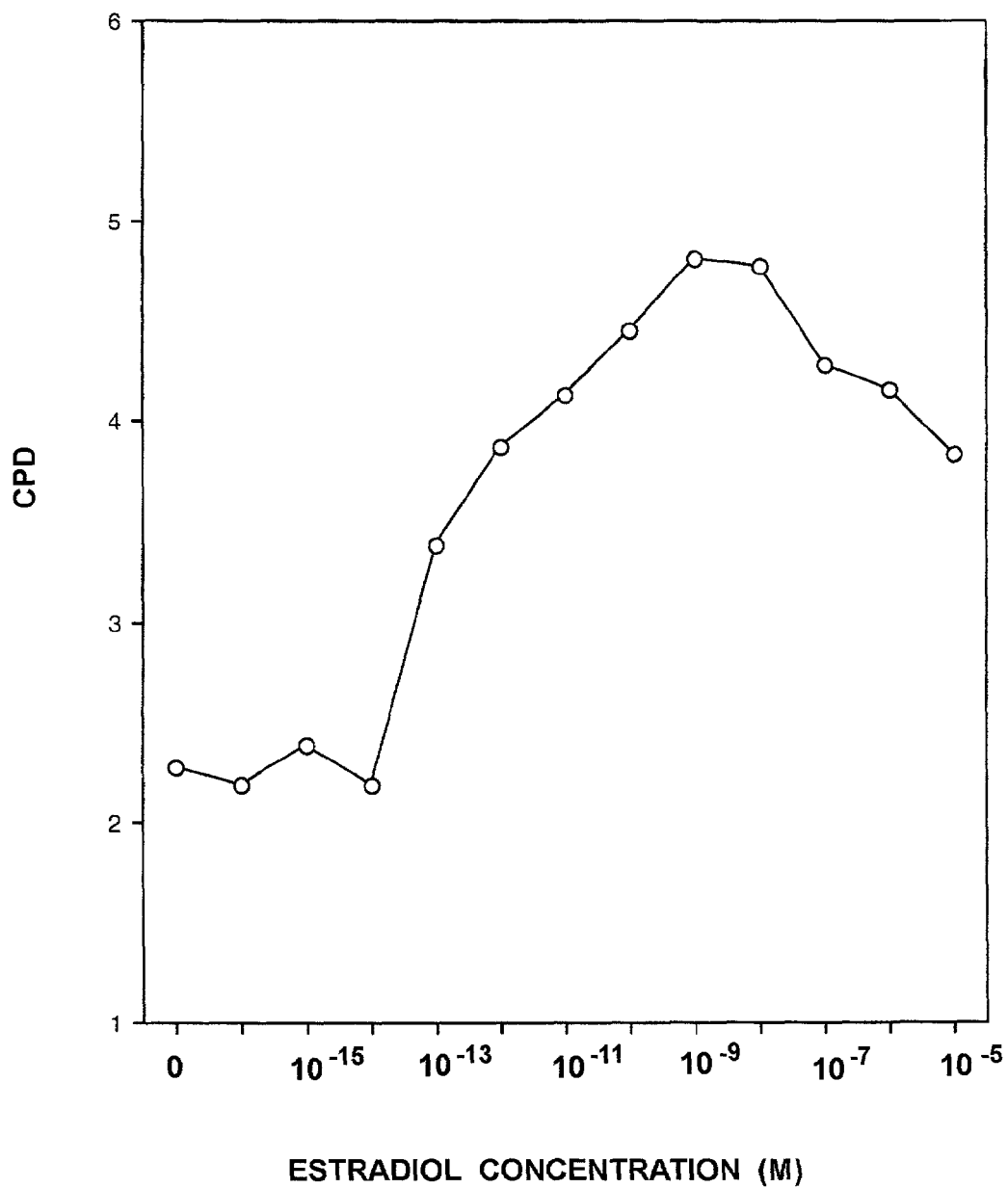

FIG. 92. Dose-Response Effects of $E_2$ on H301 Cell Growth in Serum-free Defined Medium Containing 40 µg/mL Human Plasma IgM.

Figure 93:
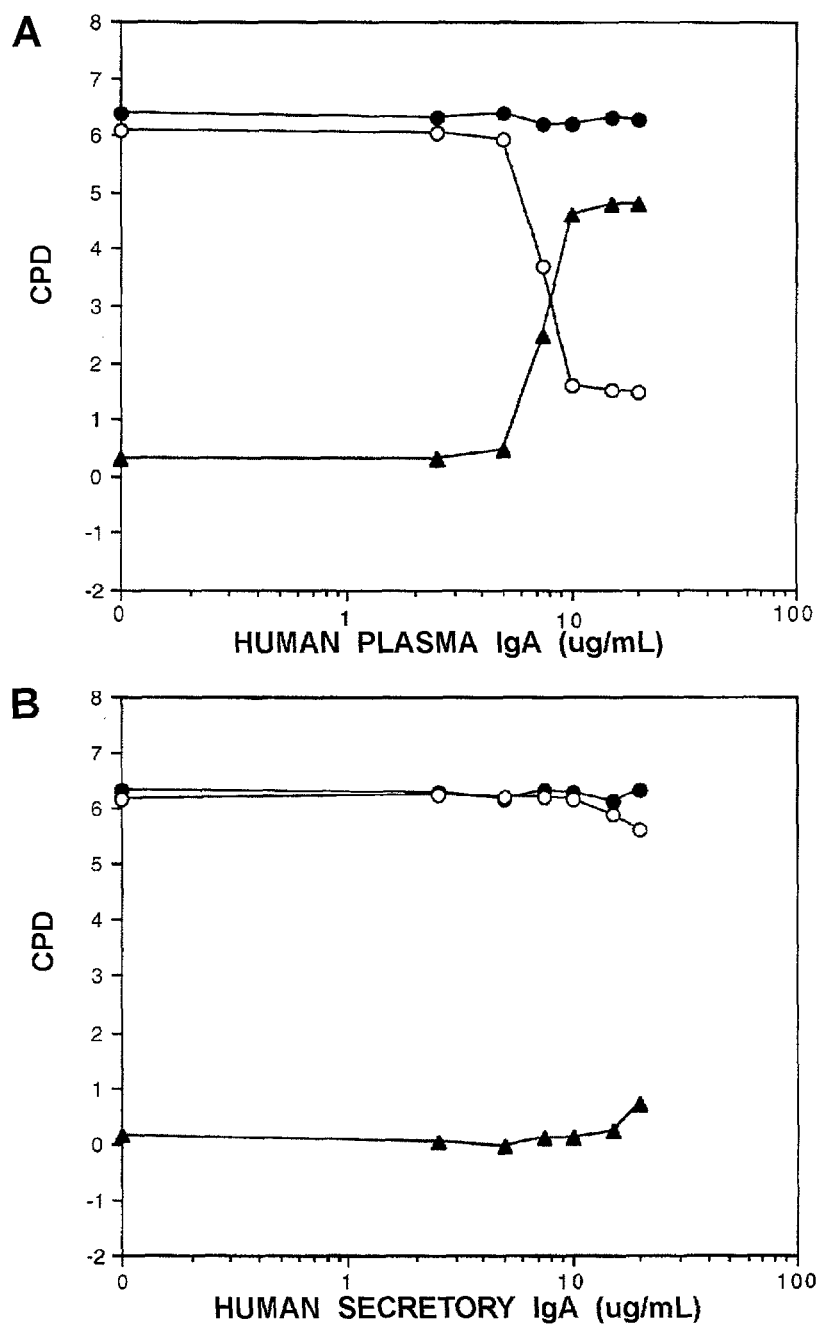

FIG. 93. Effect of Human IgA on MCF-7A Cell Growth in Serum-free Defined Medium ±$E_2$. (A) Plasma IgA Effects; (B) Secretory sIgA Effects.

Figure 94:
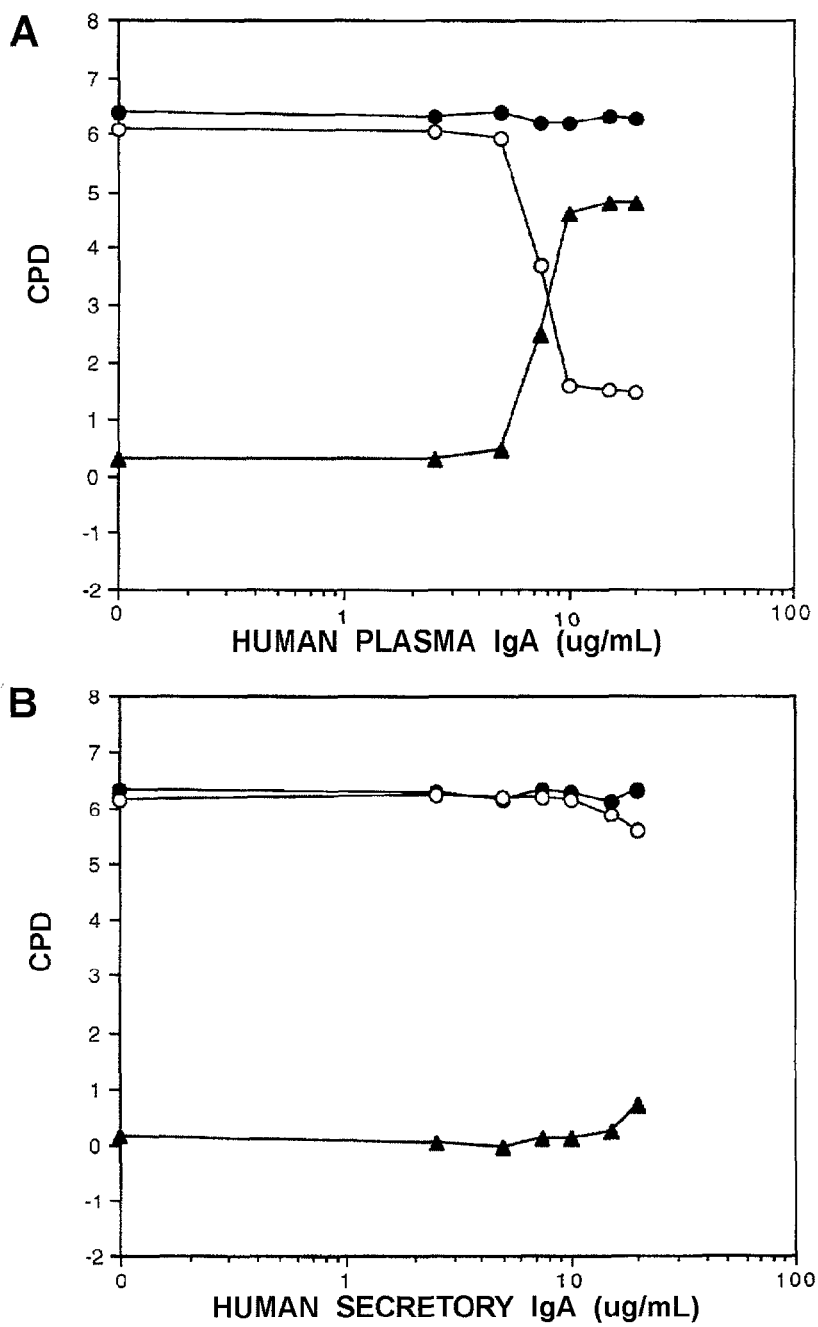

FIG. 94. Effect of Human IgA on MCF-7K Cell Growth in Serum-free Defined Medium ±$E_2$. (A) Plasma IgA Effects; (B) Secretory sIgA Effects.

Figure 95:
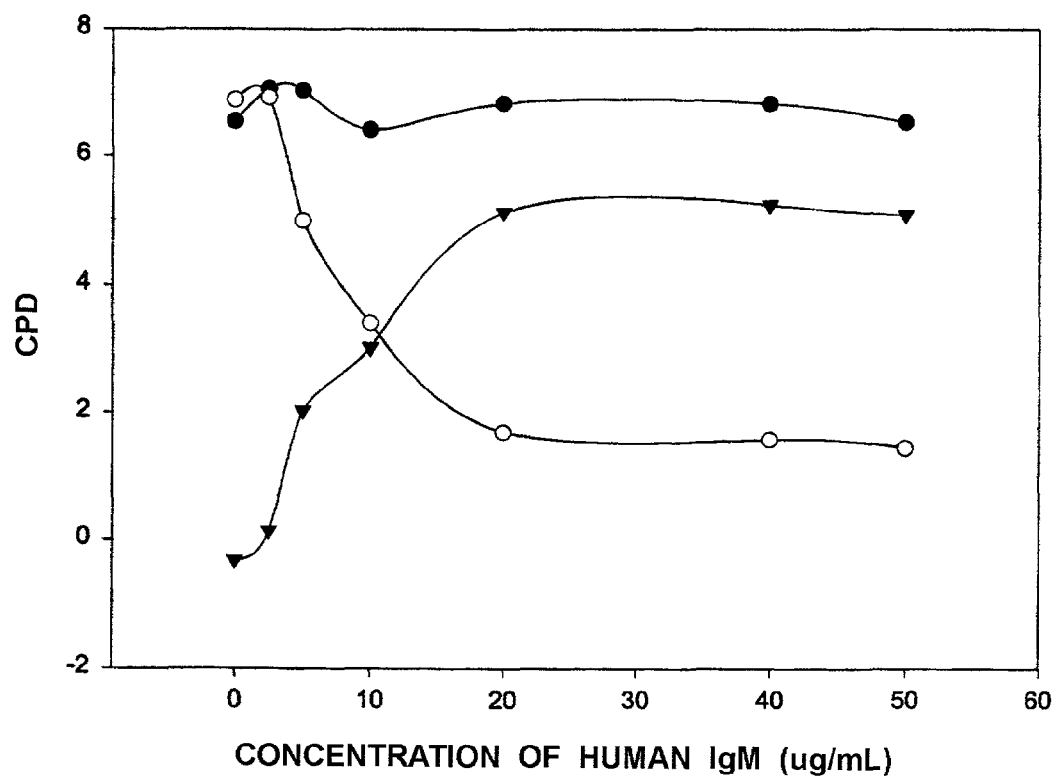

FIG. 95. Effect of Human IgM on MCF-7A Cell Growth in Serum-free Defined Medium ±$E_2$.

Figure 96:
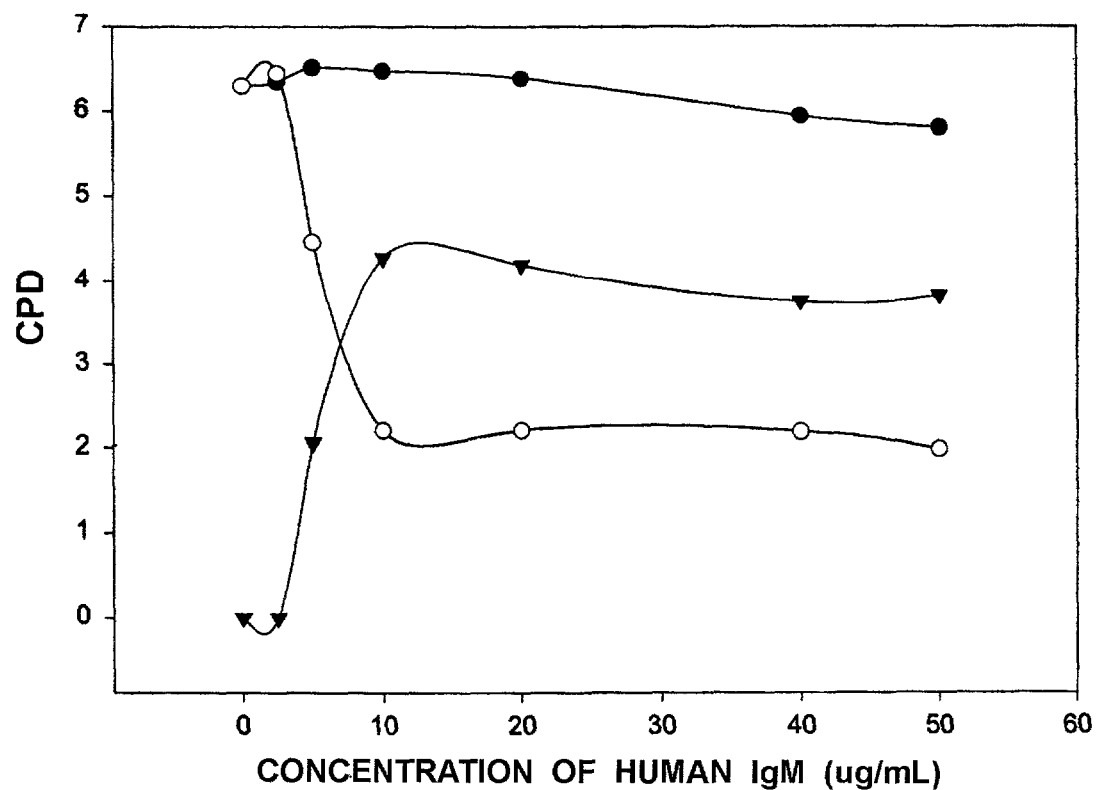

FIG. 96. Effect of Human IgM on MCF-7K Cell Growth in Serum-free Defined Medium ±$E_2$.

Figure 97:
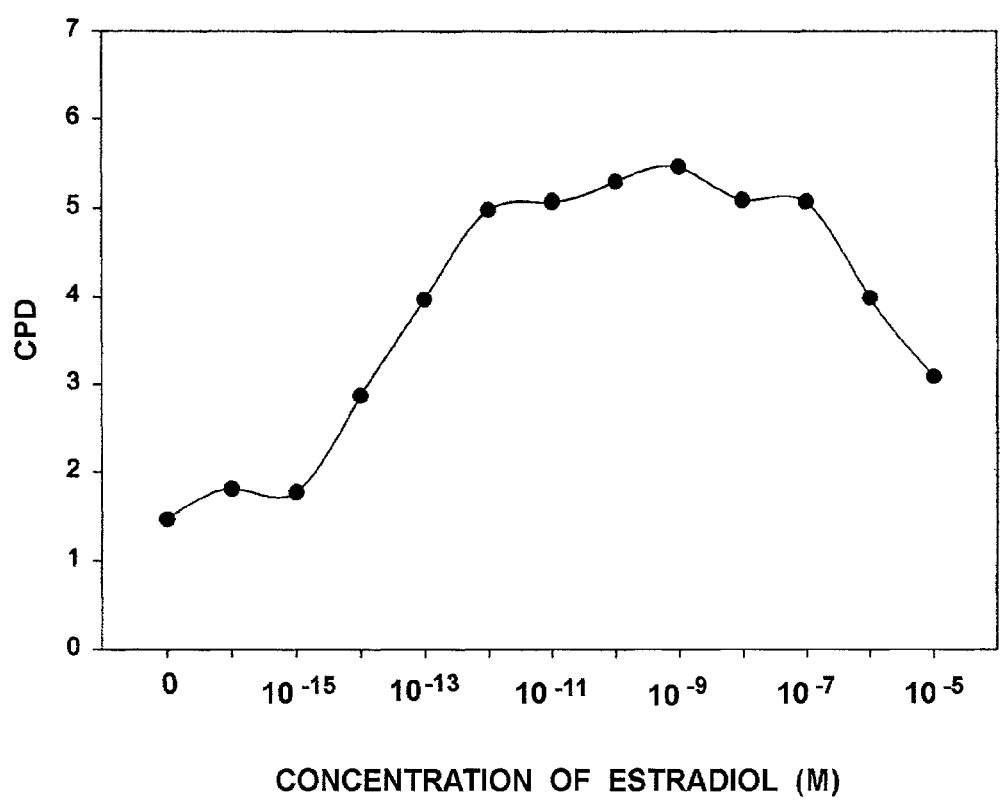

FIG. 97. Dose-Response Effects of $E_2$ on MCF-7K Cell Growth in Serum-free Defined Medium Containing 40 µg/mL Human Plasma Ig.

Figure 98:
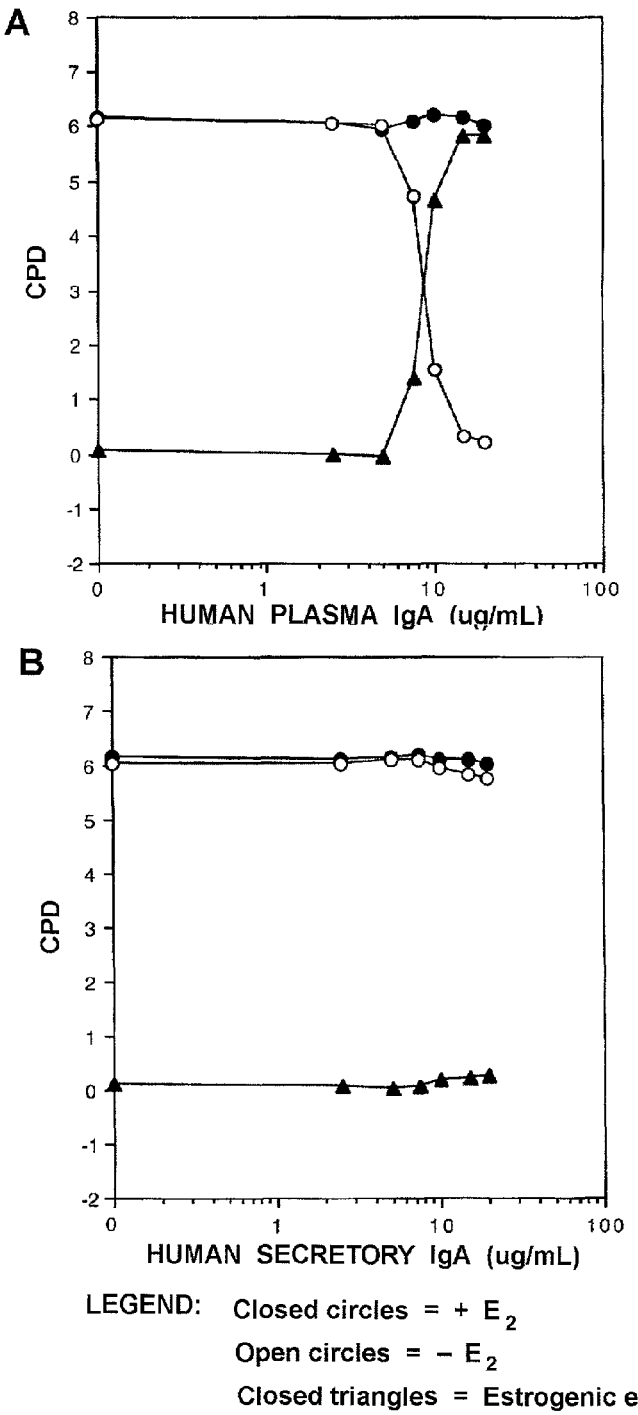

FIG. 98. Effect of Human IgA on T47D Cell Growth in Serum-free Defined Medium ±$E_2$. (A) Plasma IgA Effects; (B) Secretory sIgA Effects.

Figure 99:
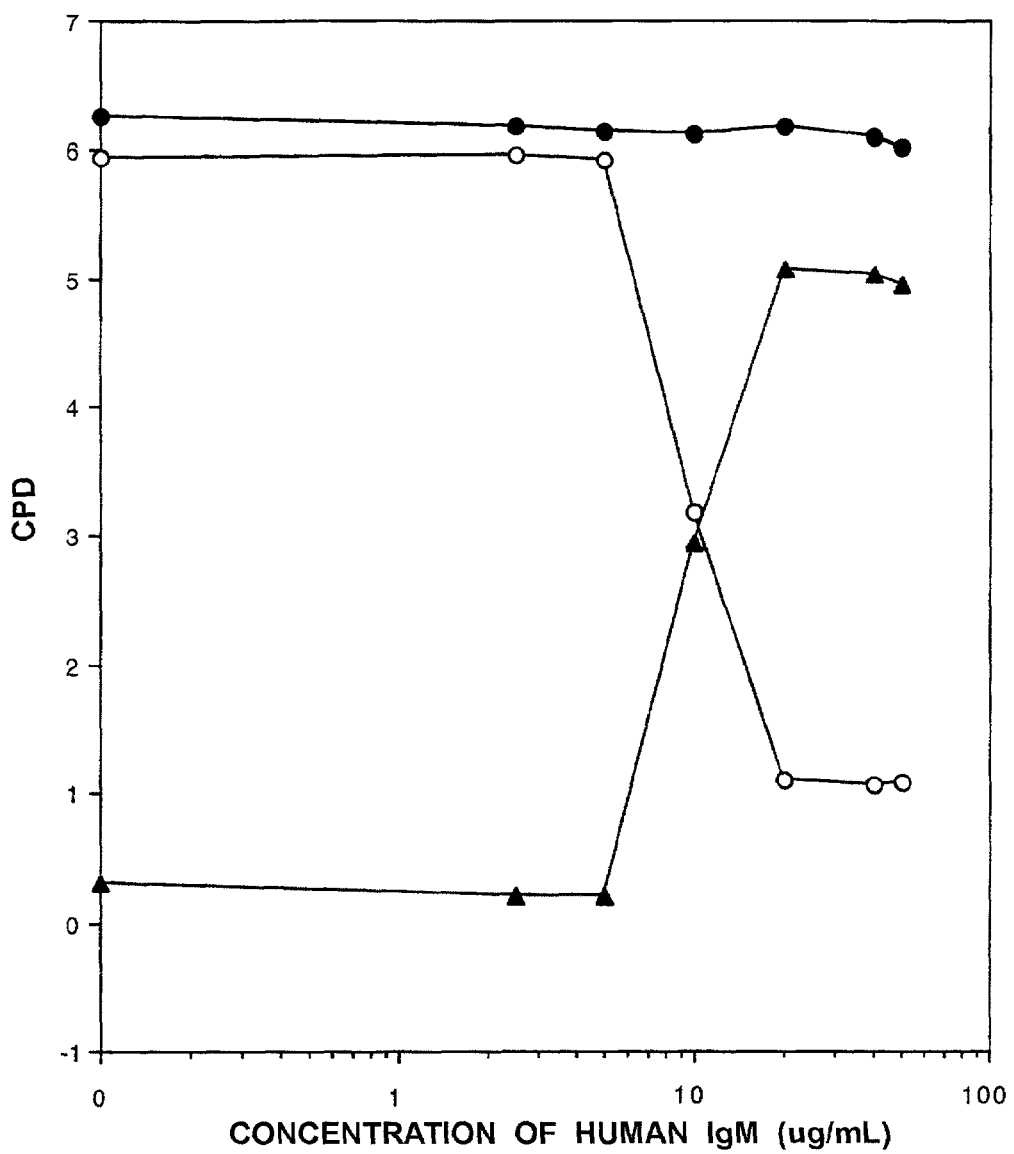

FIG. 99. Effect of Human IgM on T47D Cell Growth in Serum-free Defined Medium ±$E_2$.

Figure 100:
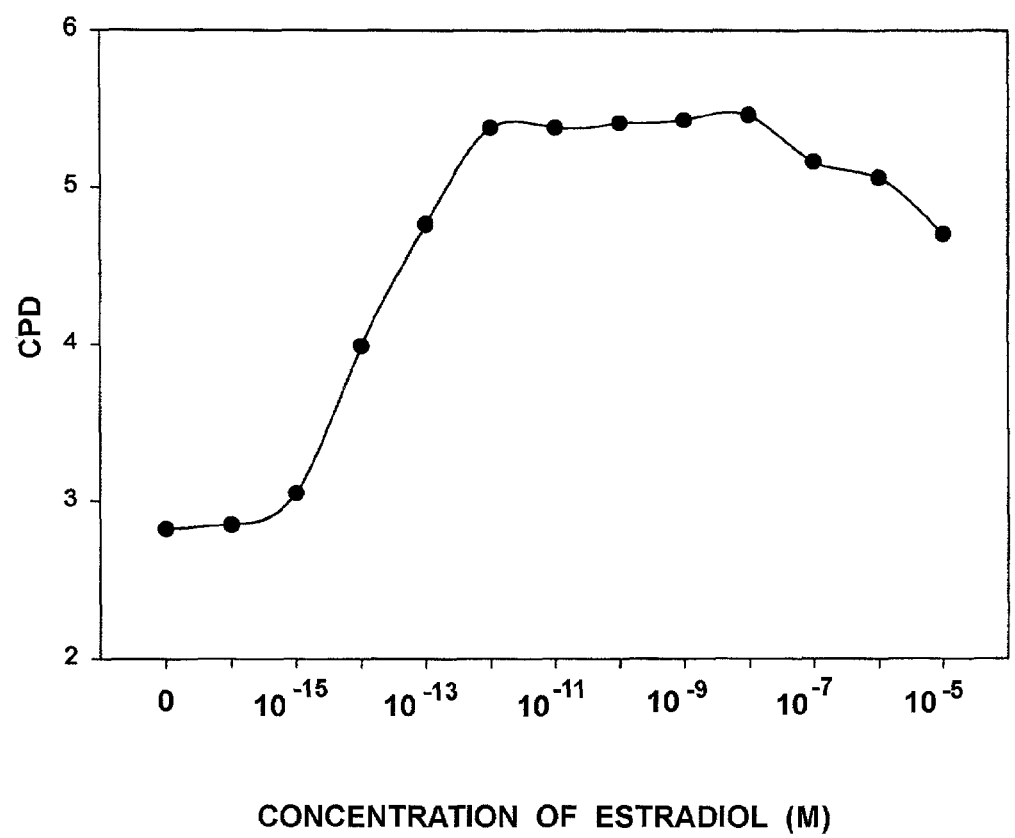

FIG. 100. Dose-Response Effects of $E_2$ on T47D Cell Growth in Serum-free Defined Medium Containing 40 μg/mL Human Plasma IgM.

Figure 101:
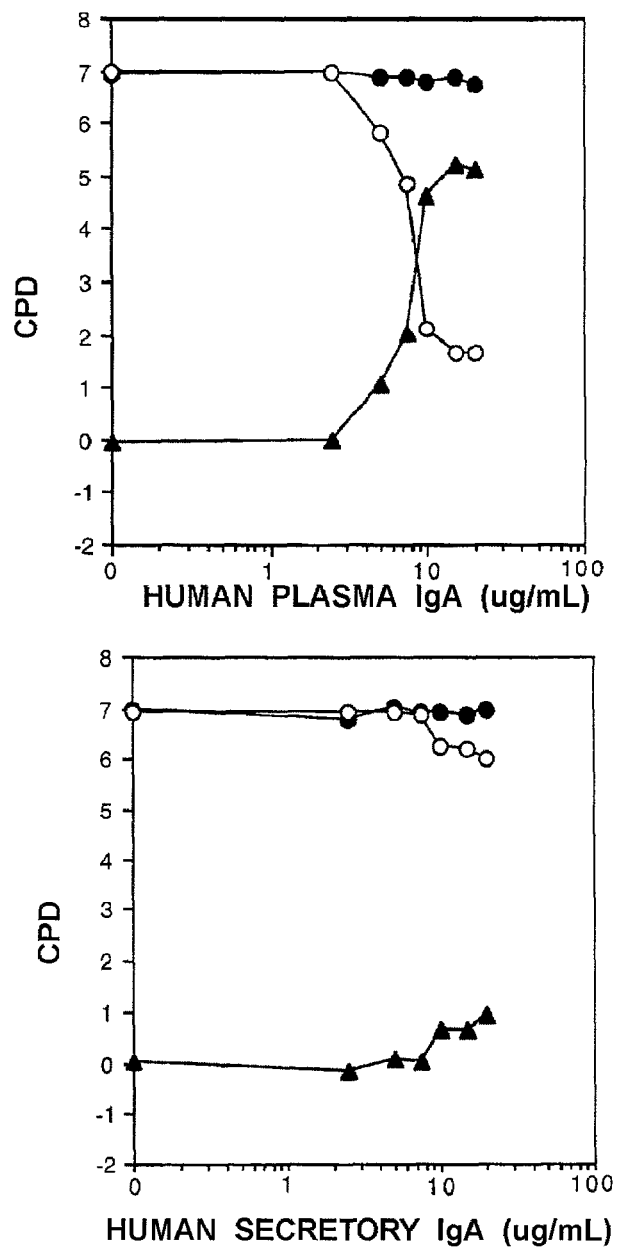

FIG. 101. Effect of Human IgA on ZR-75-1 Cell Growth in Serum-free Defined Medium ±$E_2$. (A) Plasma IgA Effects; (B) Secretory sIgA Effects.

Figure 102:
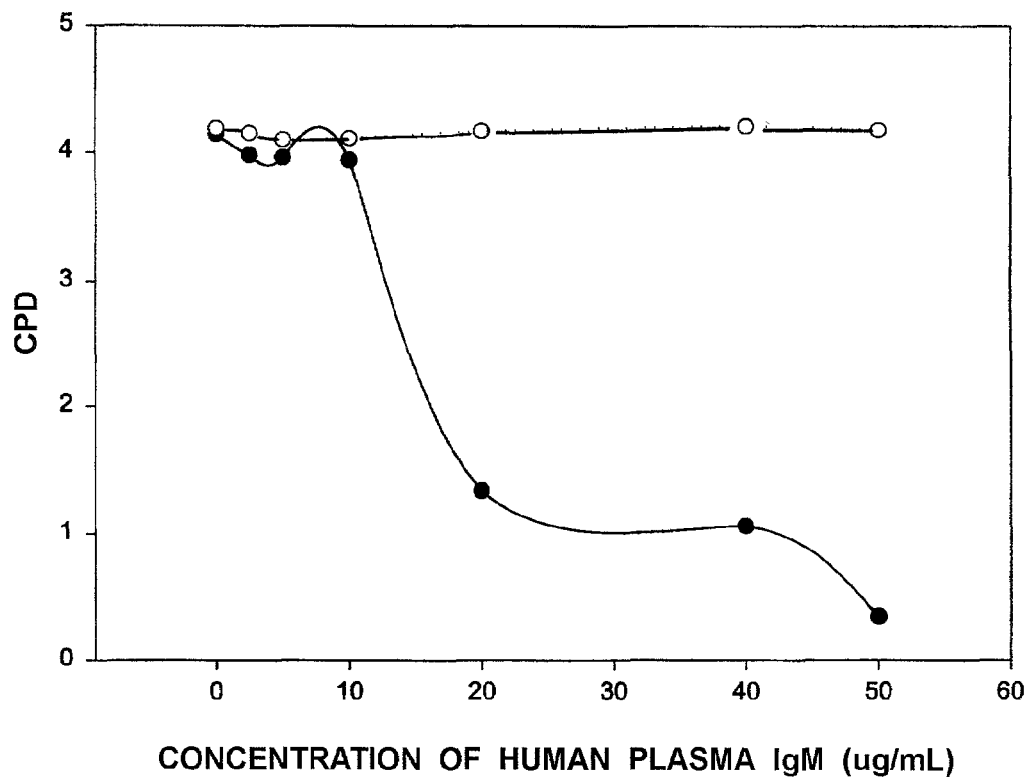

FIG. 102. Effect of Human IgM on ZR-75-1 Cell Growth in Serum-free Defined Medium ±$E_2$.

Figure 103:
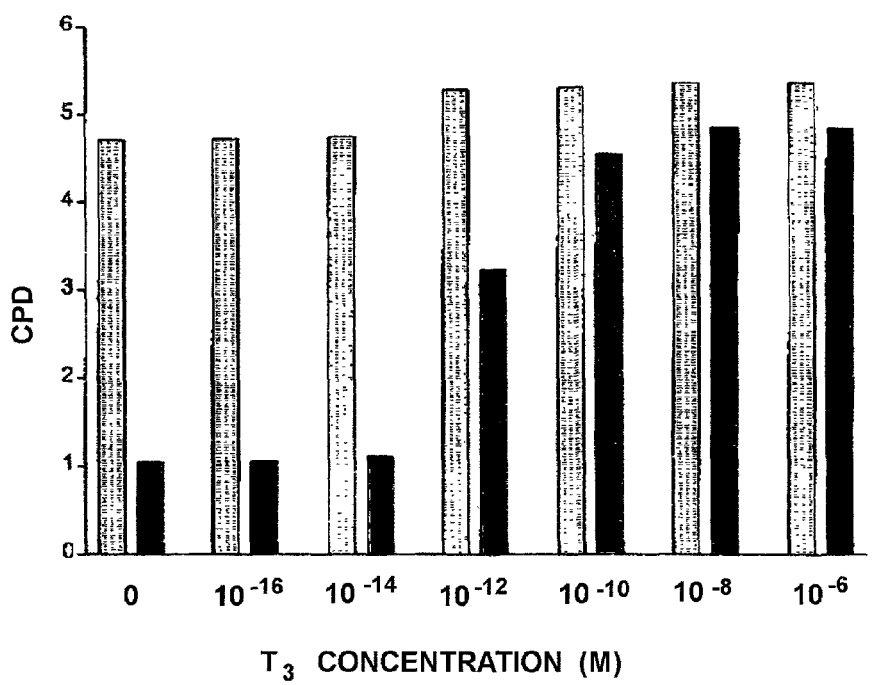

FIG. 103. Effect of Human IgM on HT-29 Cell Growth in Serum-free Defined Medium ±$T_3$.

Figure 104:
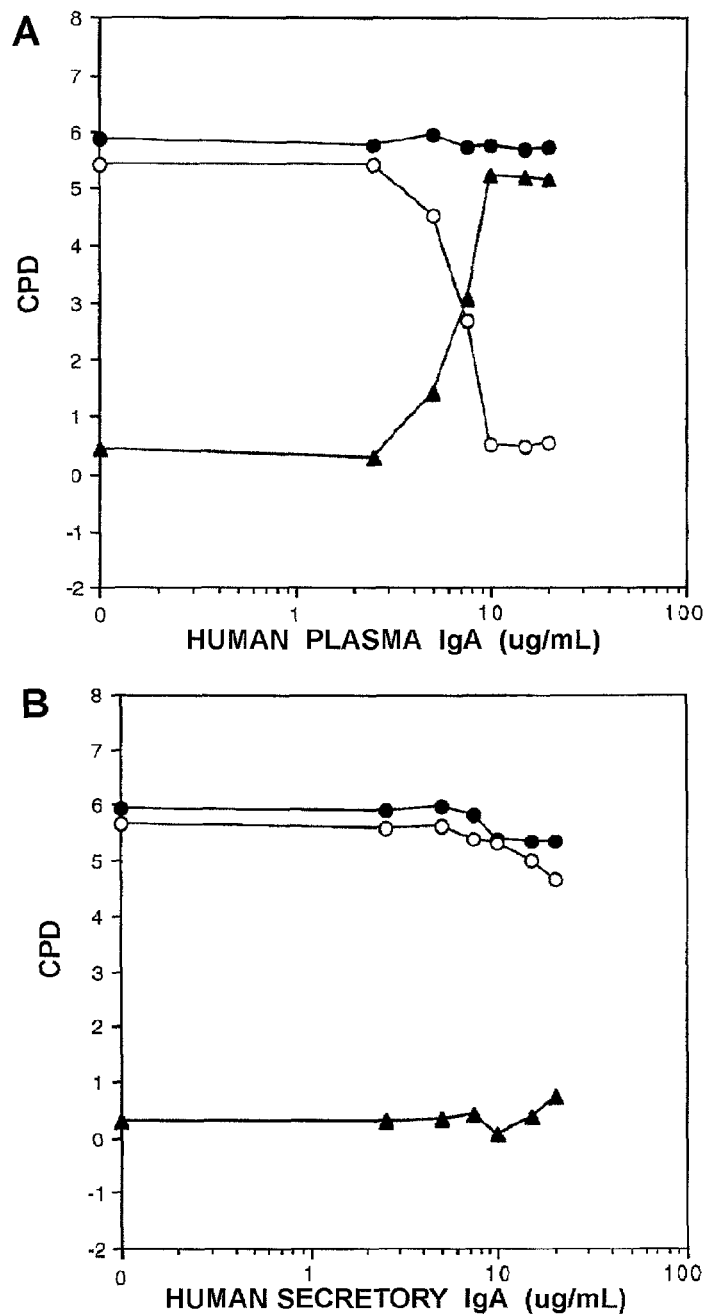

FIG. 104. Effect of Human IgA on LNCaP Cell Growth in Serum-free Defined Medium ±$E_2$. (A) Plasma IgA Effects; (B) Secretory sIgA Effects.

Figure 105:
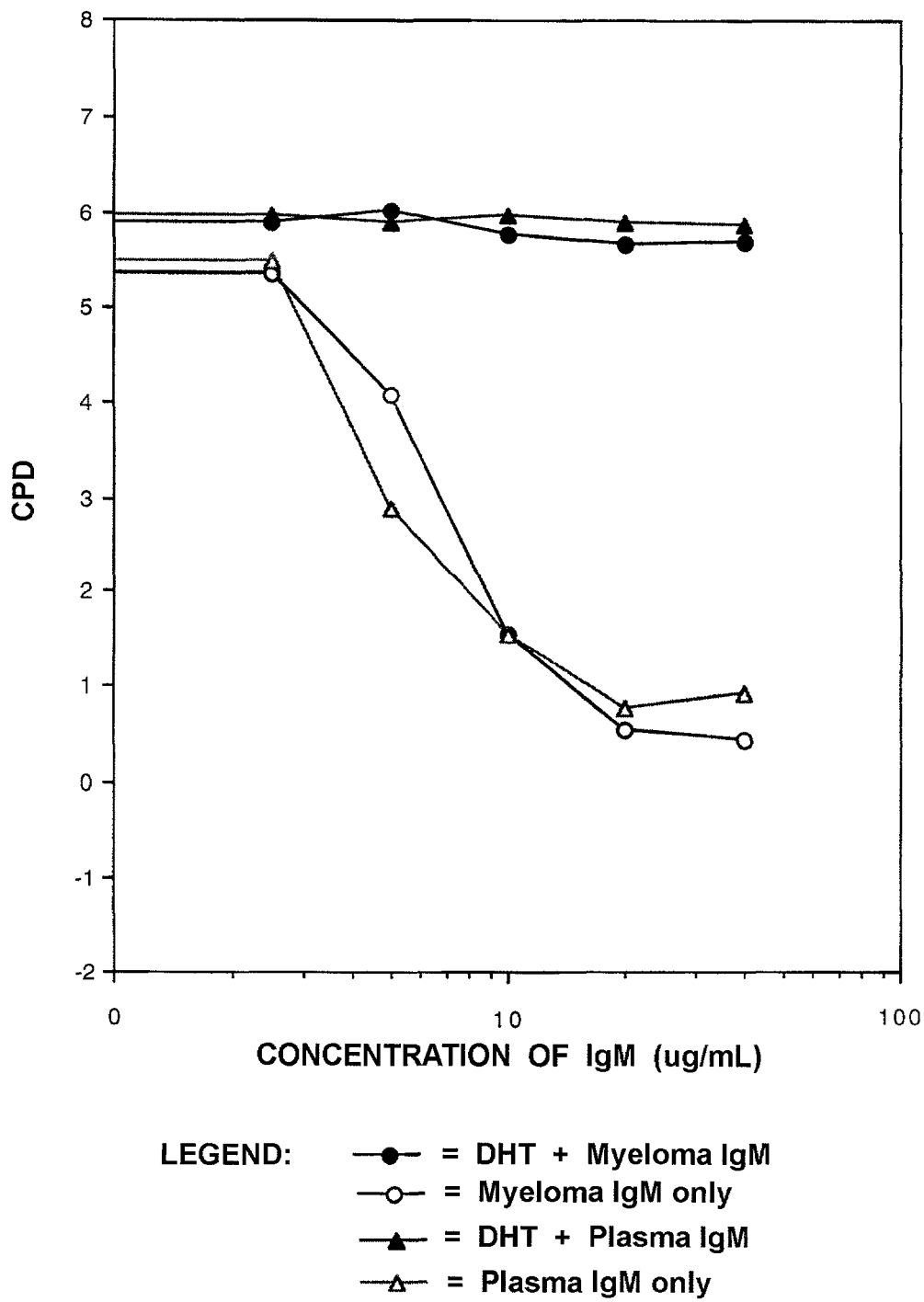

FIG. 105. Effects of Human Plasma versus Human Myeloma IgM on LNCaP Cell Growth in Serum-free Defined Medium ±DHT.

FIG. 106. Summary of Estrogenic Effects with Various $ER^+$ Cell lines and Different Ig Sources.

Figure 107:
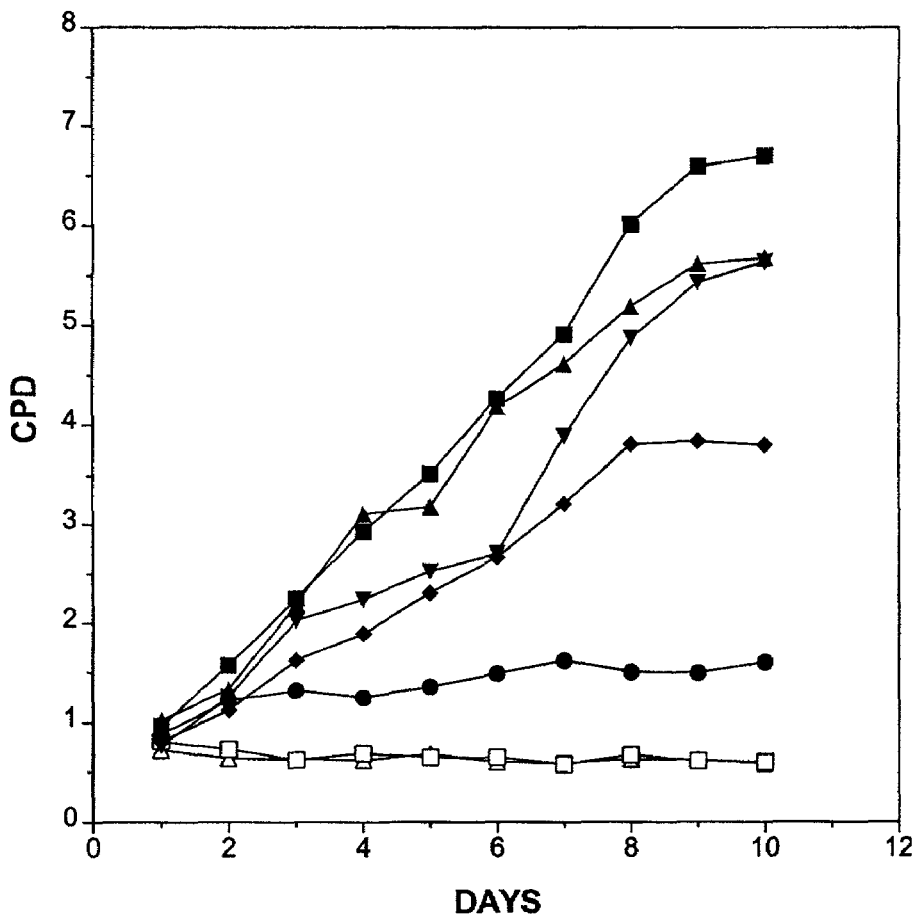

FIG. 107. Effect of Tamoxifen on T47D Cell Growth in Serum-free Defined Medium.

Figure 108:
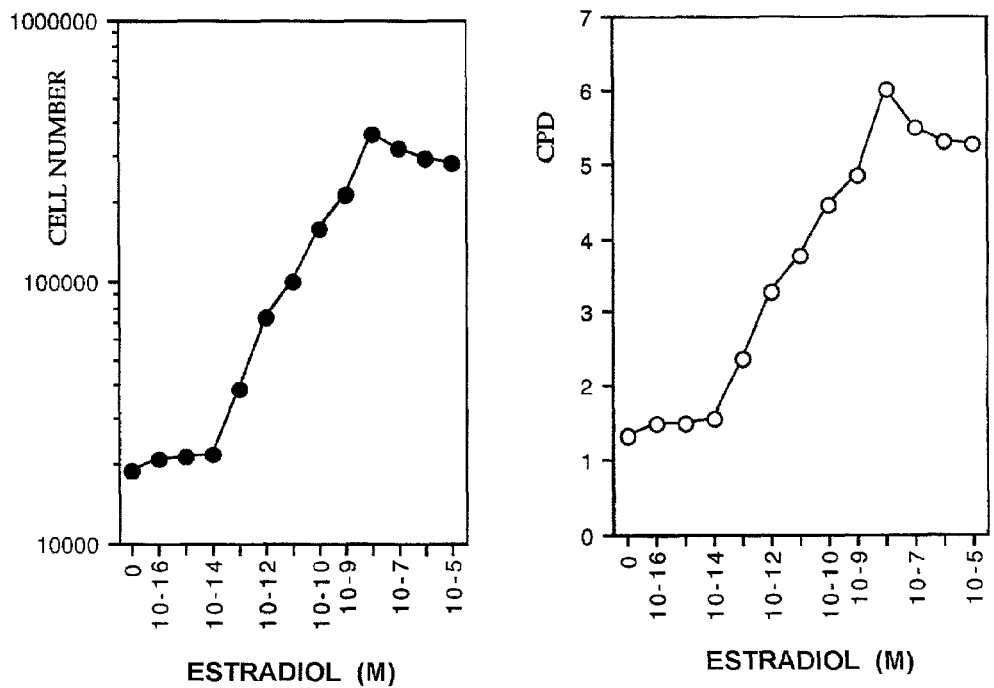

FIG. 108. Estrogen Reversal of Tamoxifen Inhibition of T47D cells in Serum-free Defined Medium.

Figure 109:
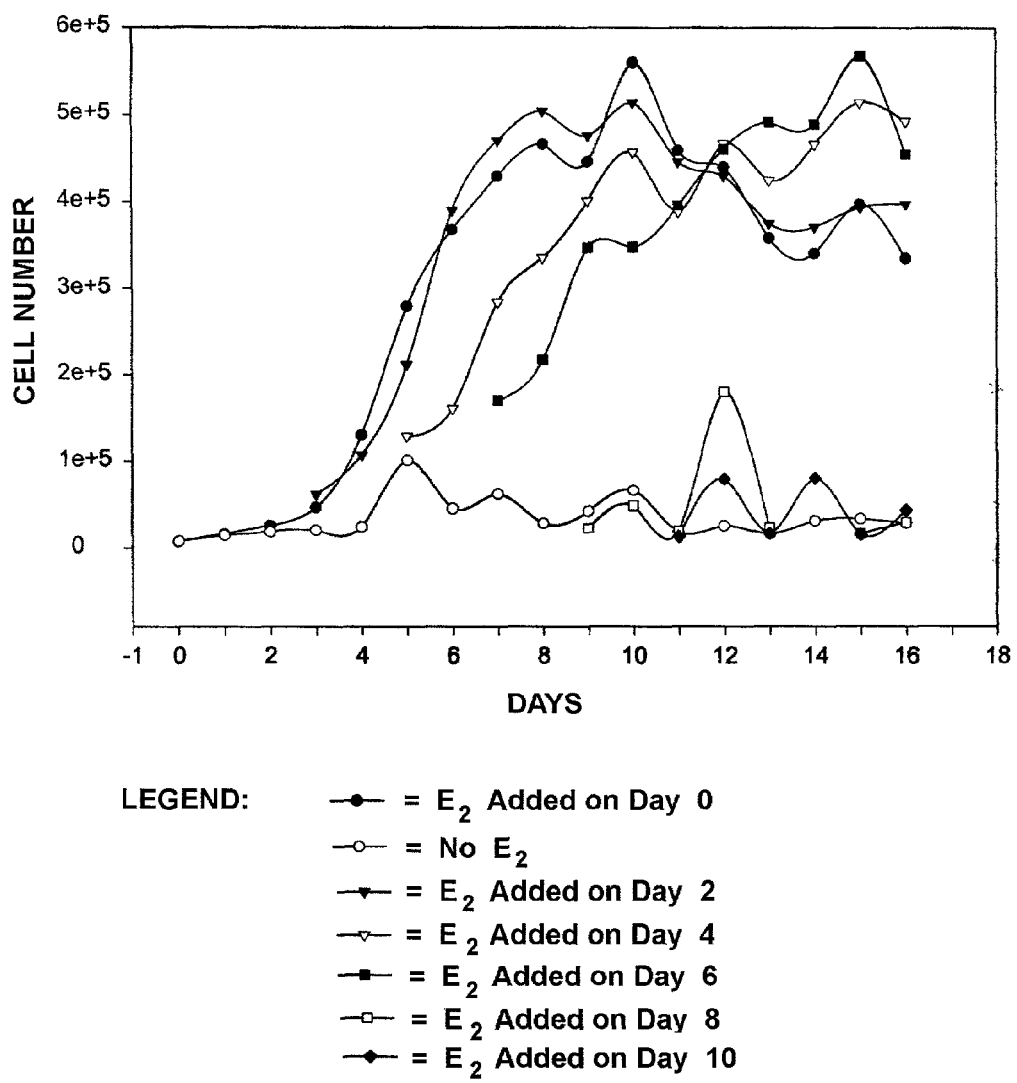

FIG. 109. Estrogen Rescue of MTW9/PL2 Cell Growth in Serum-free Medium Containing 40 μg/mL of Horse Serum IgM.

Figure 110:
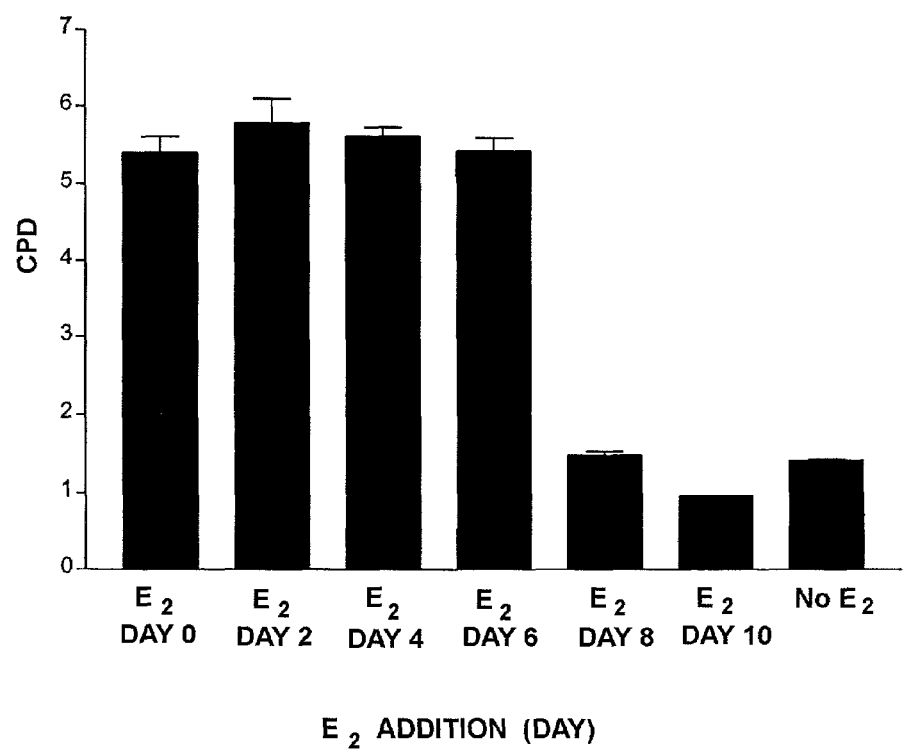

FIG. 110. Summary of Estrogen Rescue of MTW9/PL2 Cell Growth in Serum-free Medium Containing 40 μg/mL of Horse Serum IgM.

Figure 111:
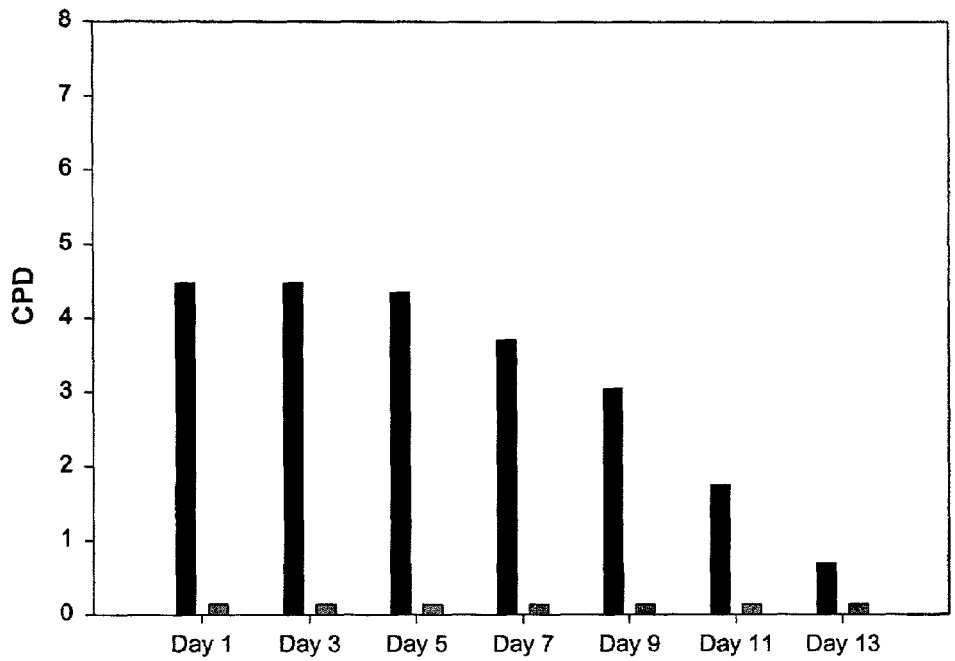

FIG. 111. Estrogen Rescue of T47D Cell Growth in Serum-free Medium Containing 40 μg/mL of Human Serum IgM.

Figure 112:
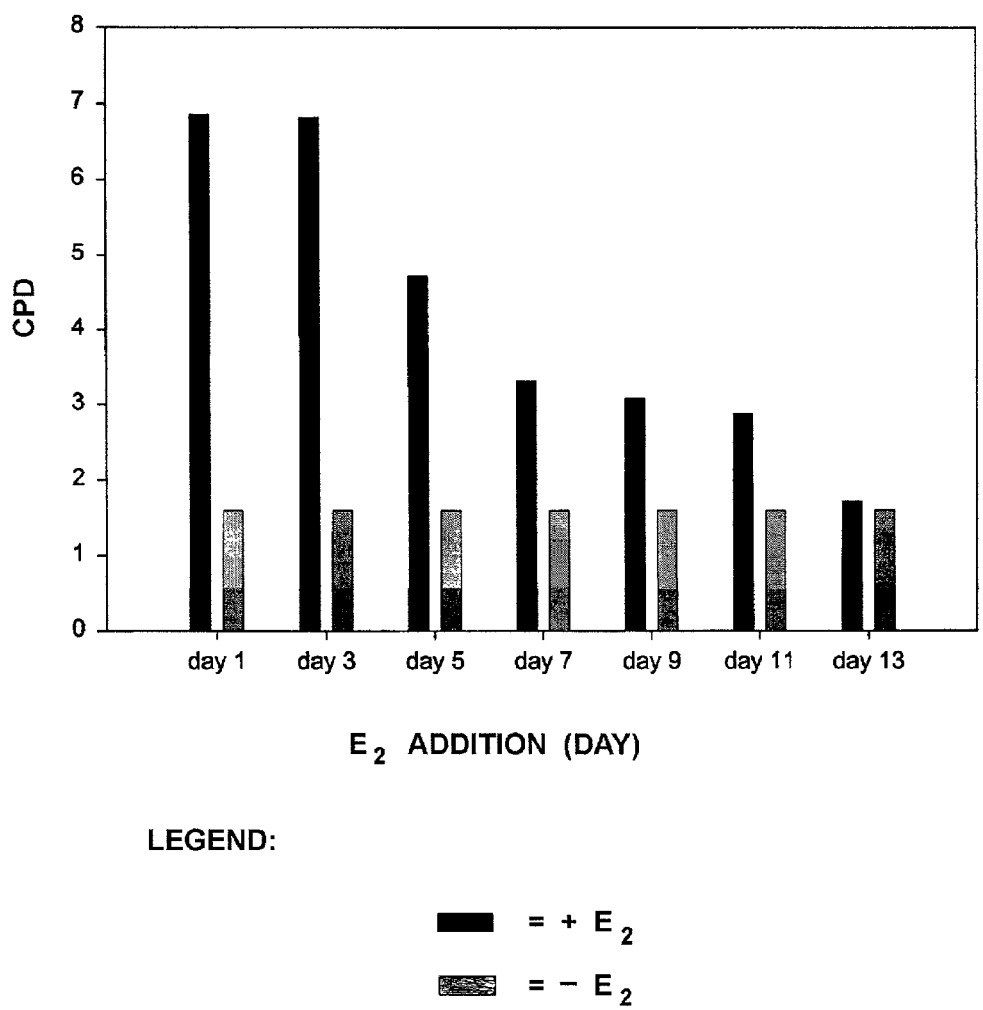

FIG. 112. Estrogen Rescue of MCF-7A Cell Growth in Serum-free Medium Containing 40 μg/mL of Human Serum IgM.

Figure 113:
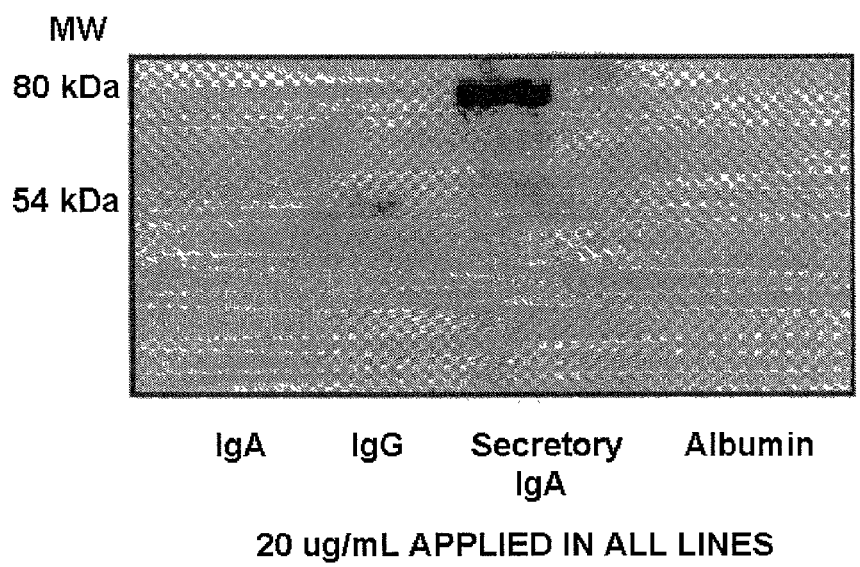

FIG. 113. Western Detection of the Secretory Component of Human Milk sIgA.

Figure 114:
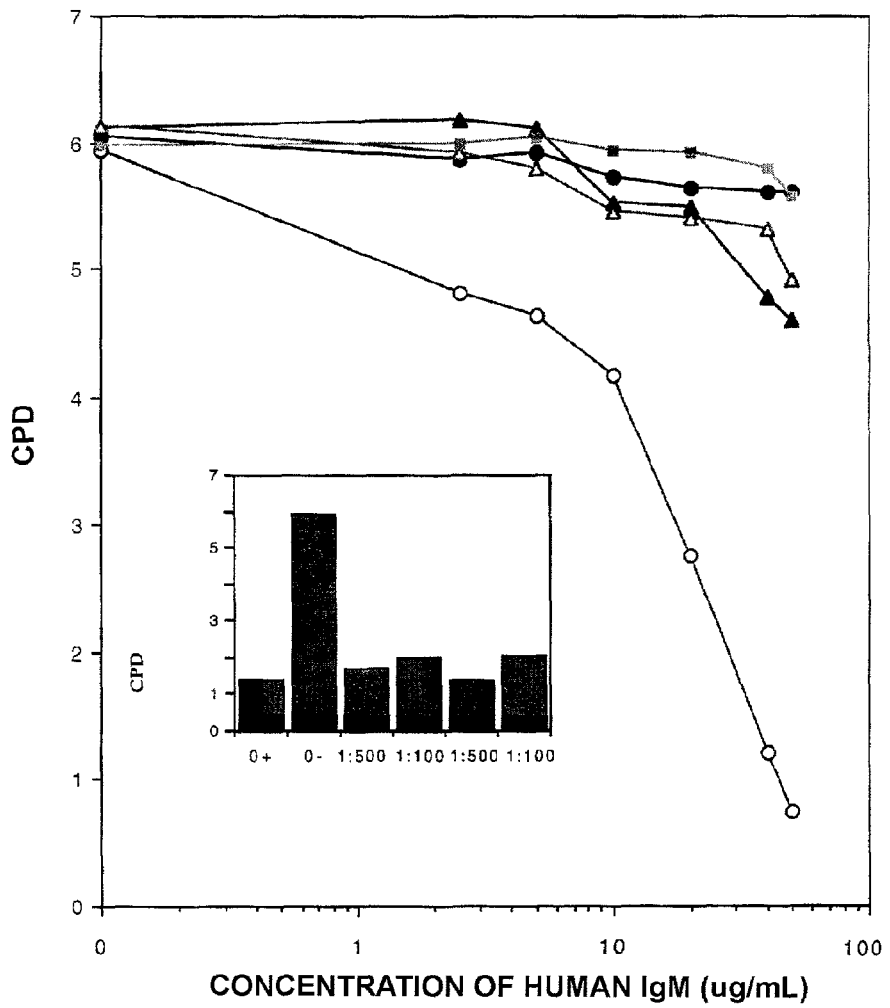

FIG. 114. Effect of Anti-Secretory Component on IgM Inhibition of T47D Cell Growth in Serum-free Defined Medium.

Figure 115:
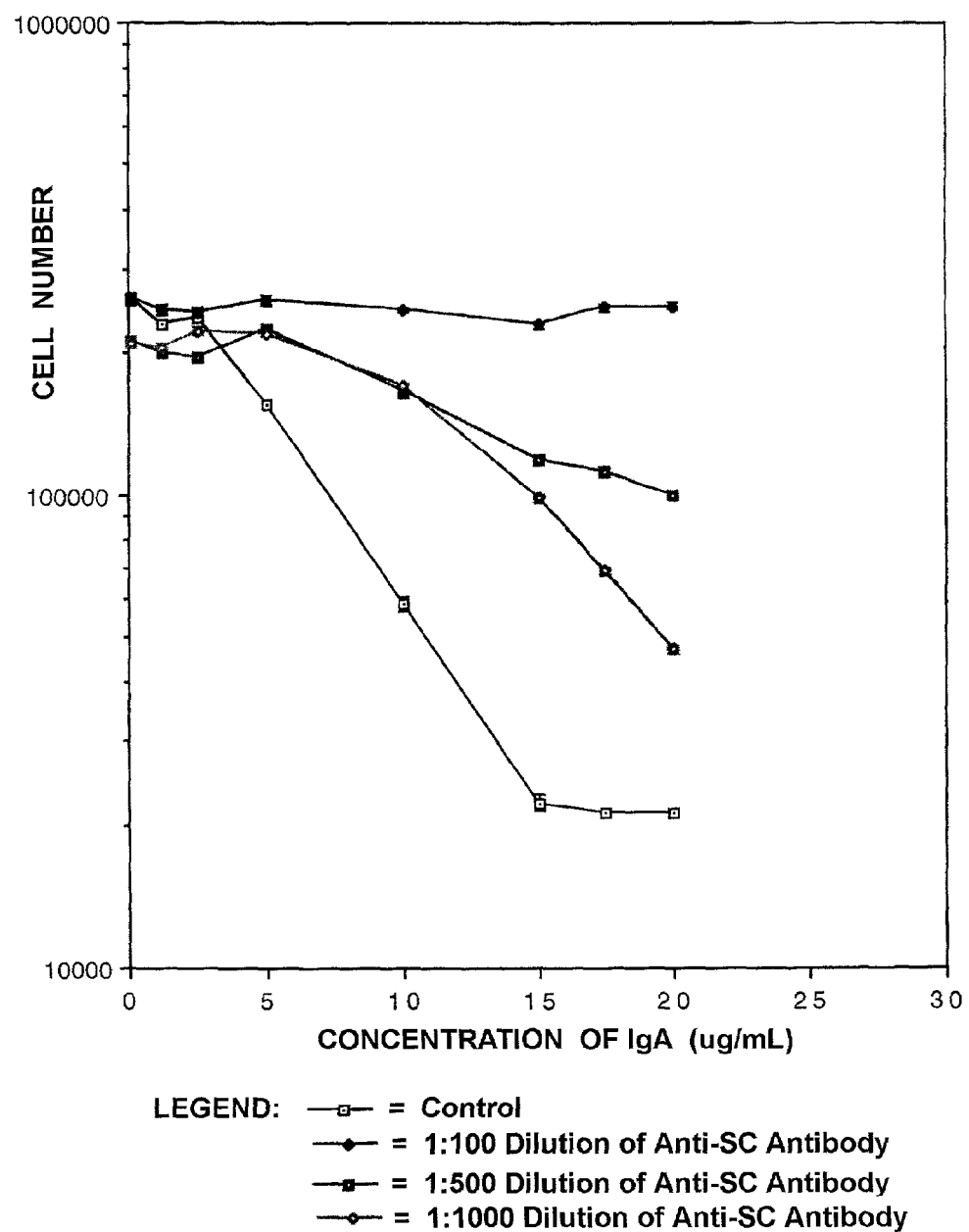

FIG. 115. Effect of Anti-Secretory Component on pIgA Inhibition of LNCaP Cell Growth in Serum-free Defined Medium.

Figure 116:
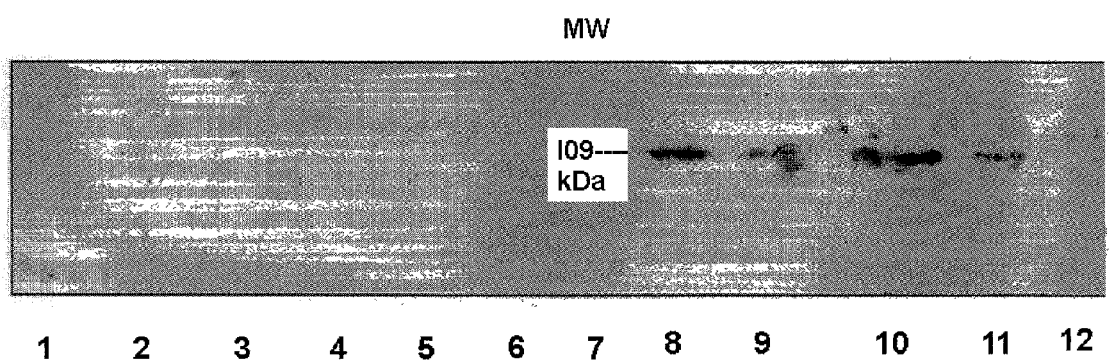

FIG. 116. Western Analysis with Anti-Secretory Component to Detect the Poly-Ig Receptor in $AR^+$ and $AR^-$ Prostate Cancer Cells plus Control Cell Lines.

Figure 117:
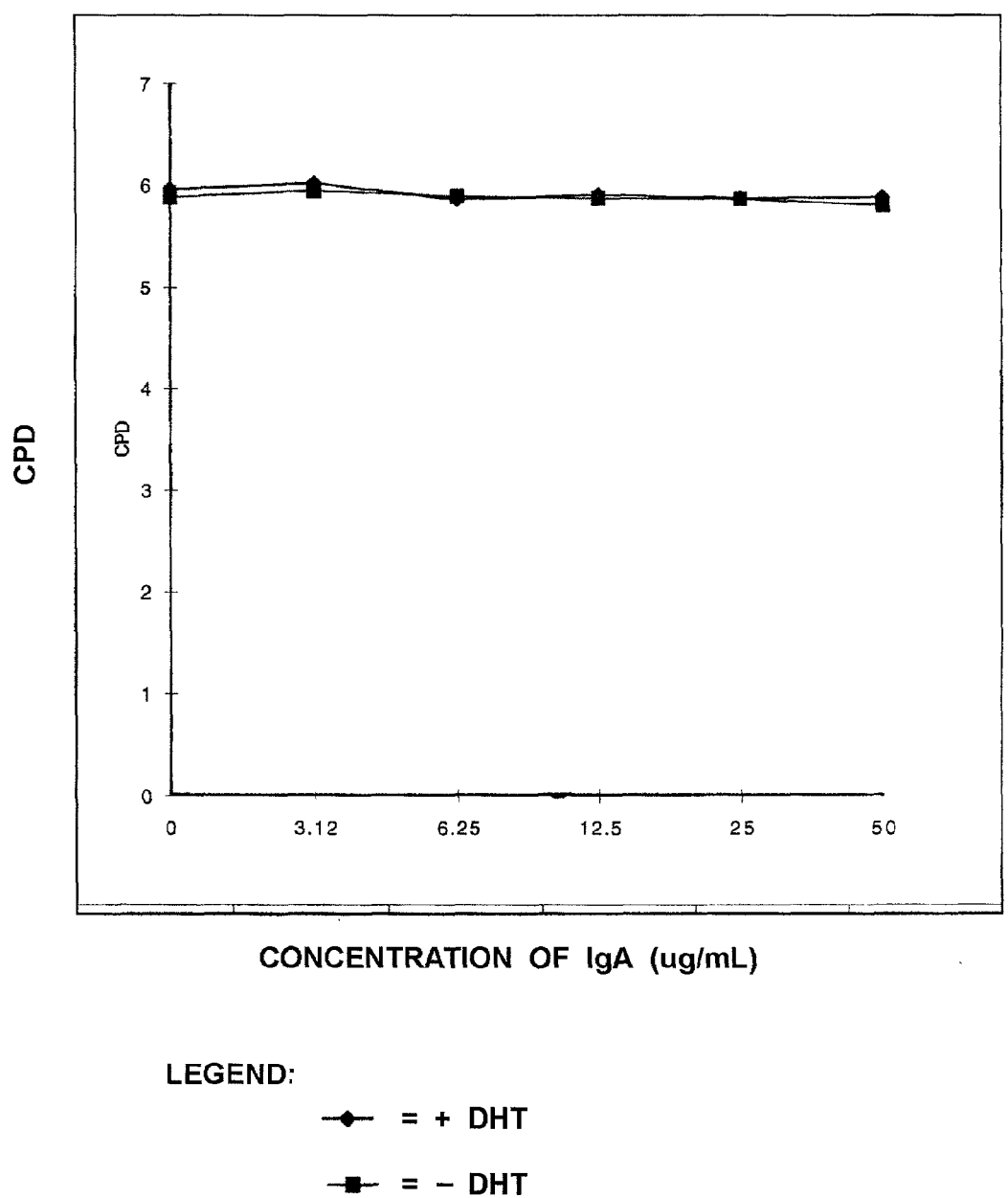

FIG. 117. Effect of Human pIgA on DU145 Cell Growth in Serum-free Defined Medium DHT.

Figure 118:
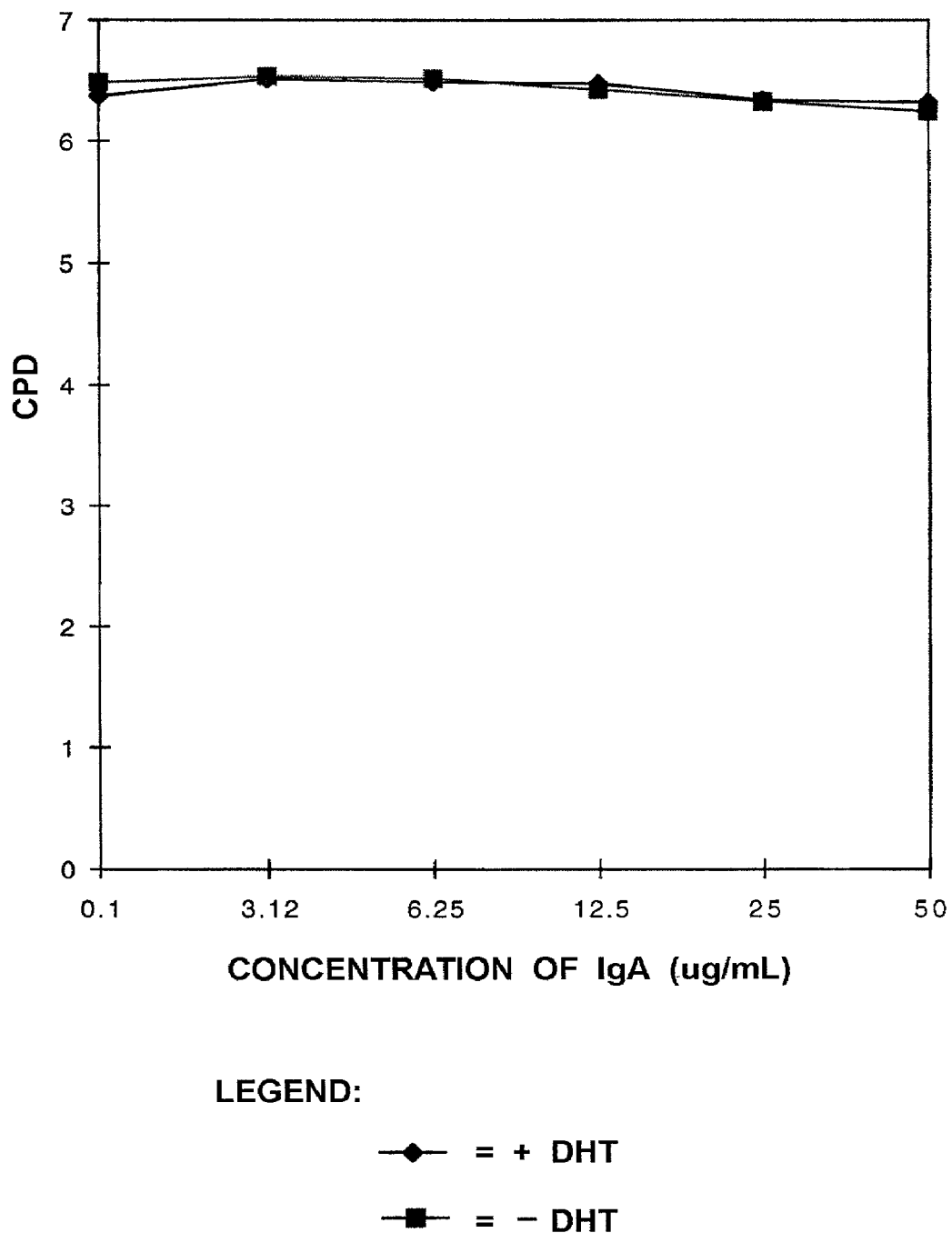

FIG. 118. Effect of Human pIgA on PC3 Cell Growth in Serum-free Defined Medium ±DHT.

Figure 119:
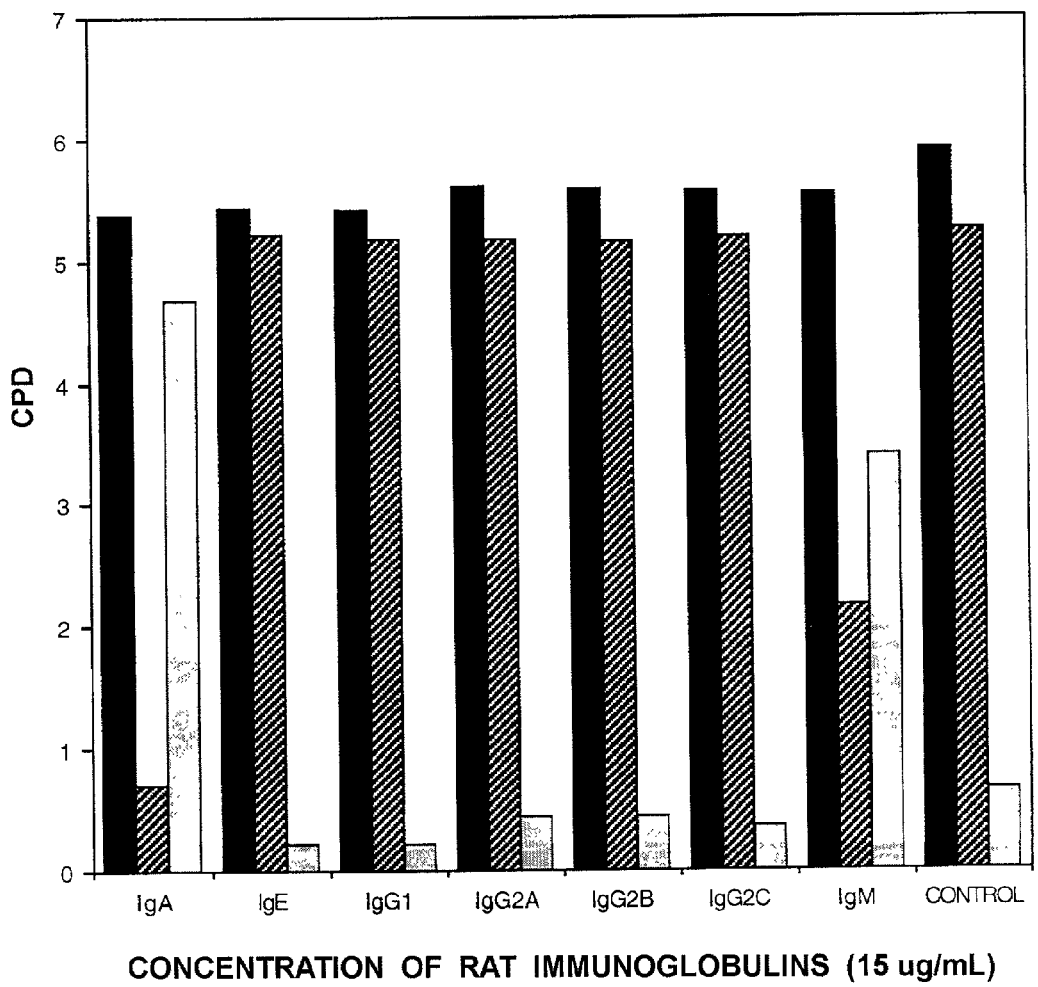

FIG. 119. Effect of Rat Immunoglobulins on Estrogen Responsive Growth of MTW9/PL2 Cells In Serum-free Defined Medium.

Figure 120:
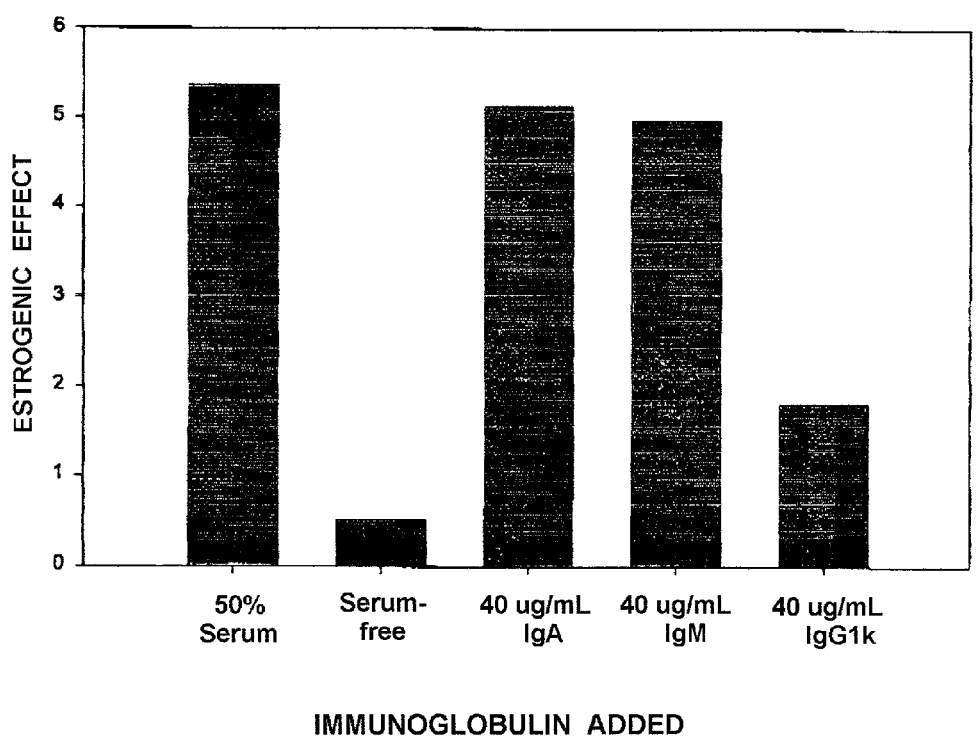

FIG. 120. Comparison of the Estrogenic Effects of Human Immungobulin with T47D Cells in Serum-free Defined Medium.

Figure 121:
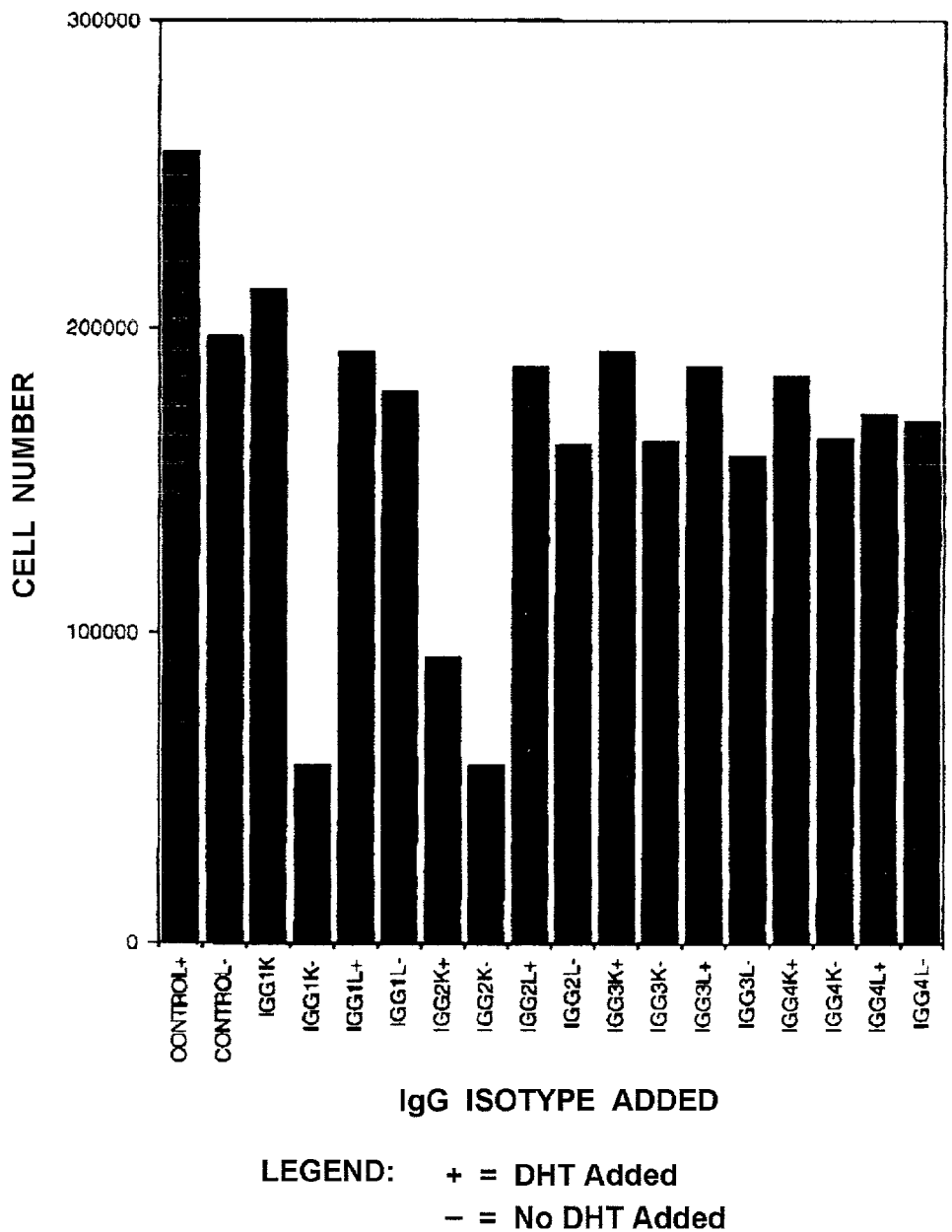

FIG. 121. Effect of Human IgG Isotypes on LNCaP Cell Growth in Serum-free Defined Medium ±DHT.

Figure 122:
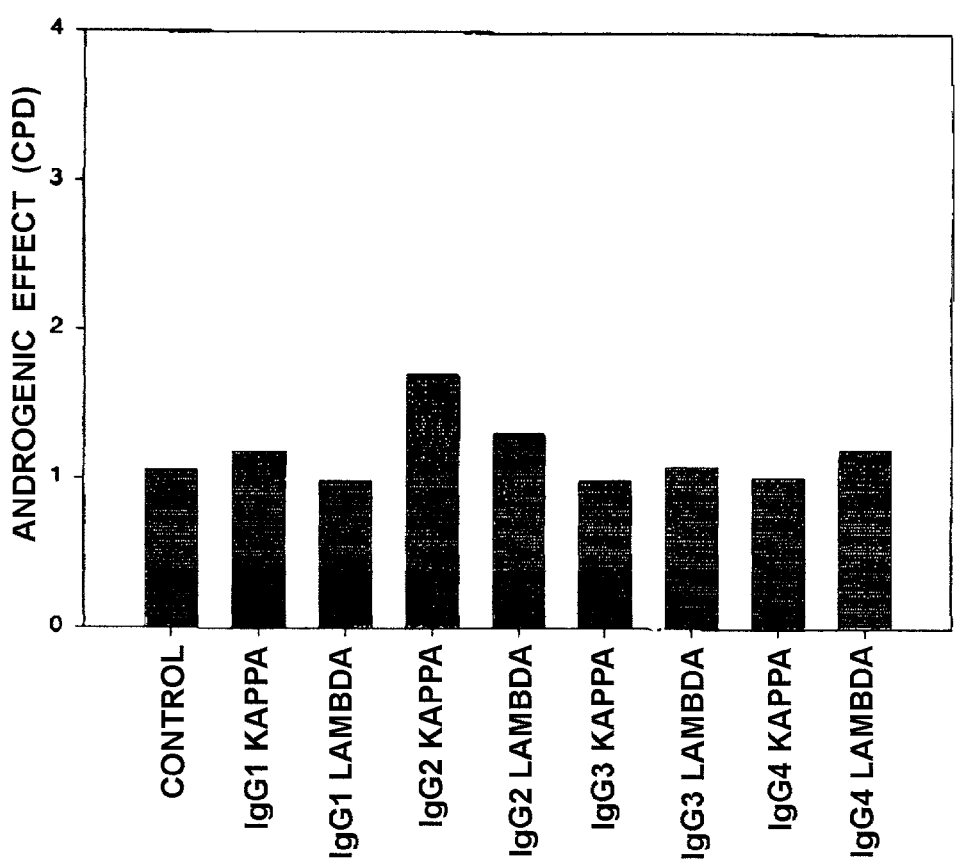

FIG. 122. IgG Isotype Assays with LNCaP Cells in Serum-free Defined Medium ±DHT.

FIG. 123. Model of Early Onset Breast Cancer Including TGFβ.

FIG. 124. Effect of Carcinogens on Mammary Tumor Induction in Rats of Various Ages.

FIG. 125. Anti-human SHBG Antibody Immunoprecipitation of the Estrogenic Activity Present in CDE-horse Serum Assayed with MTW9/PL2 Cells.

Figure 126:
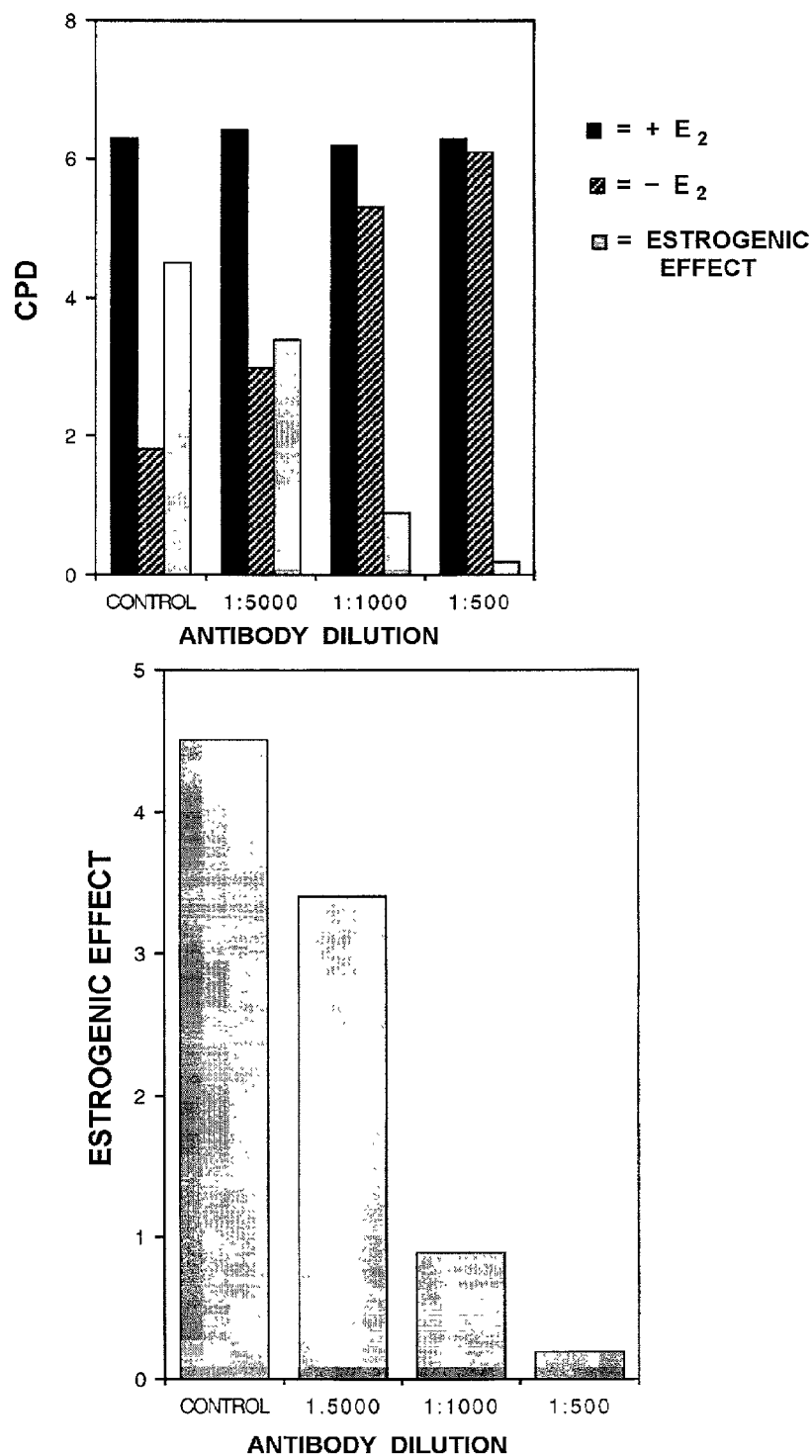

FIG. 126. Anti-human SHBG Antibody Immunoprecipitation of the Estrogenic Activity Present in CDE-rat Serum Assayed with MTW9/PL2 Cells.

Figure 127:
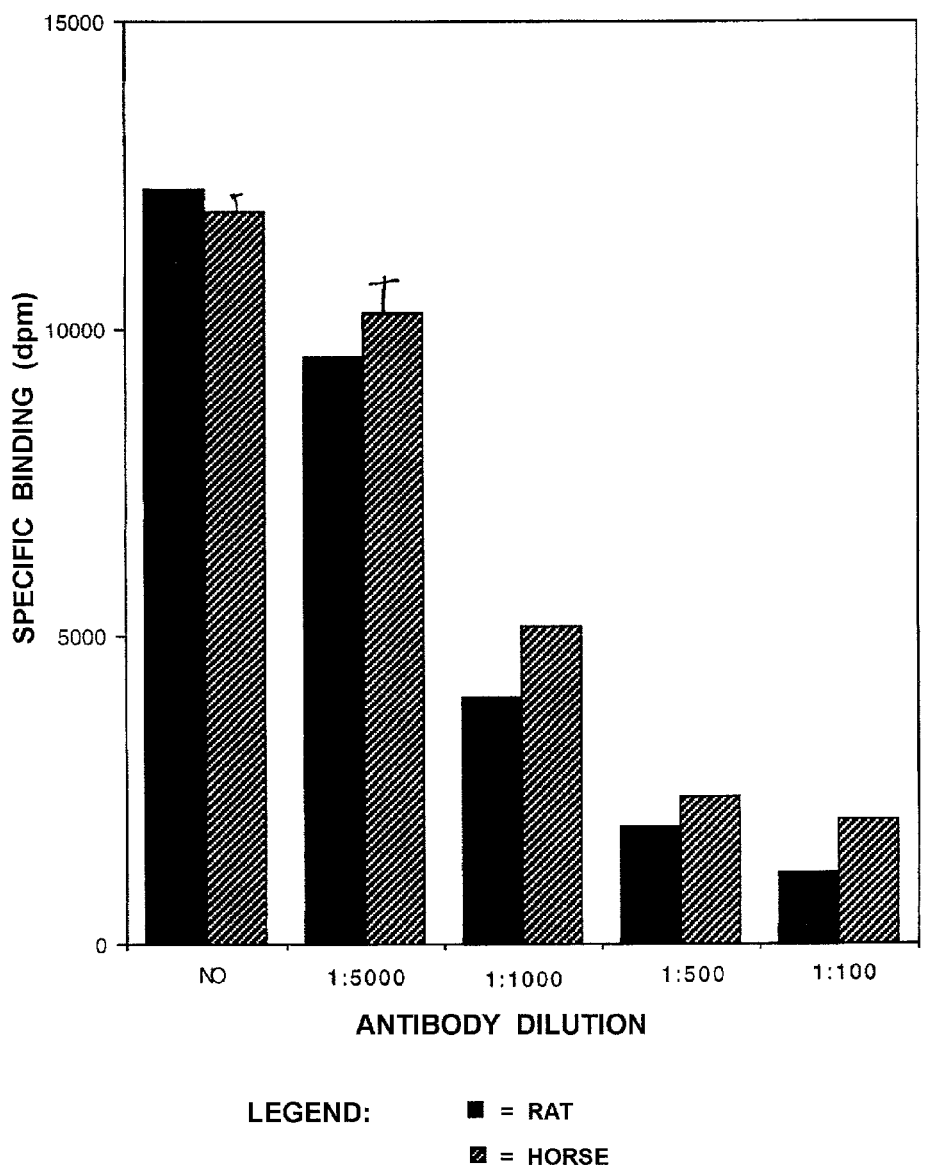

FIG. 127. Anti-human SHBG Antibody Immunoprecipitation of the Labeled Steroid Hormone Binding Activity Present in CDE-rat Serum.

FIG. 128. Western Analysis and Densitometry of the Immunoglobulin Levels in the Serum of Female Rats of Specified Age Groups.

Figure 129:
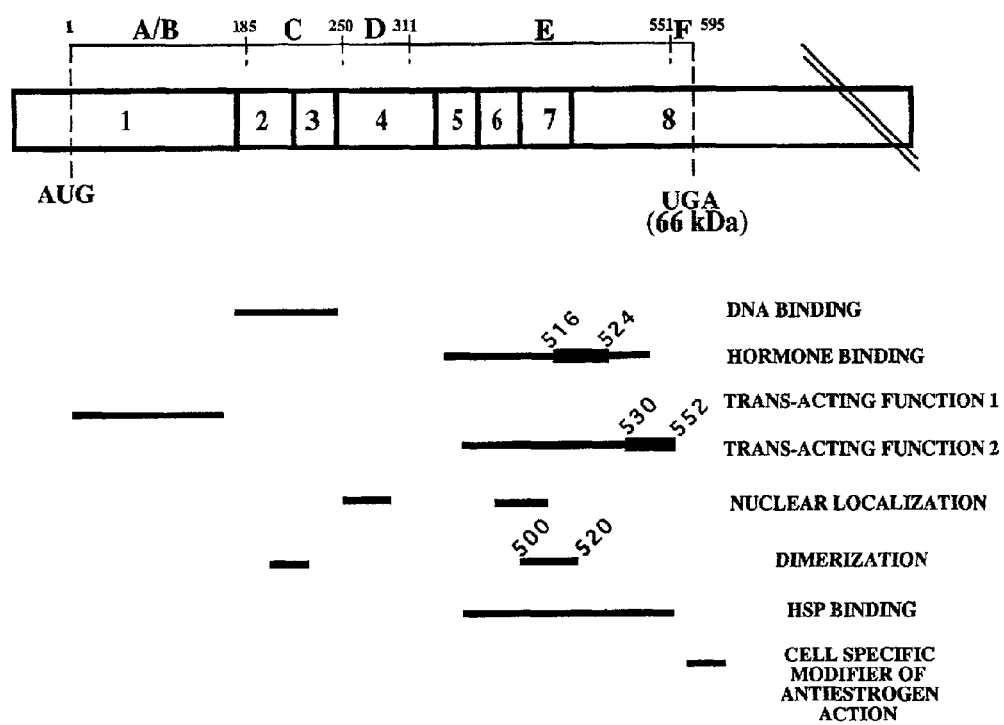

FIG. 129. Structural and Functional Organization of the Human Estrogen Receptor α.

FIG. 130. Entre Genome NCBI Search of "Breast Cancer Mutations" and Chromosomes.

Figure 131:
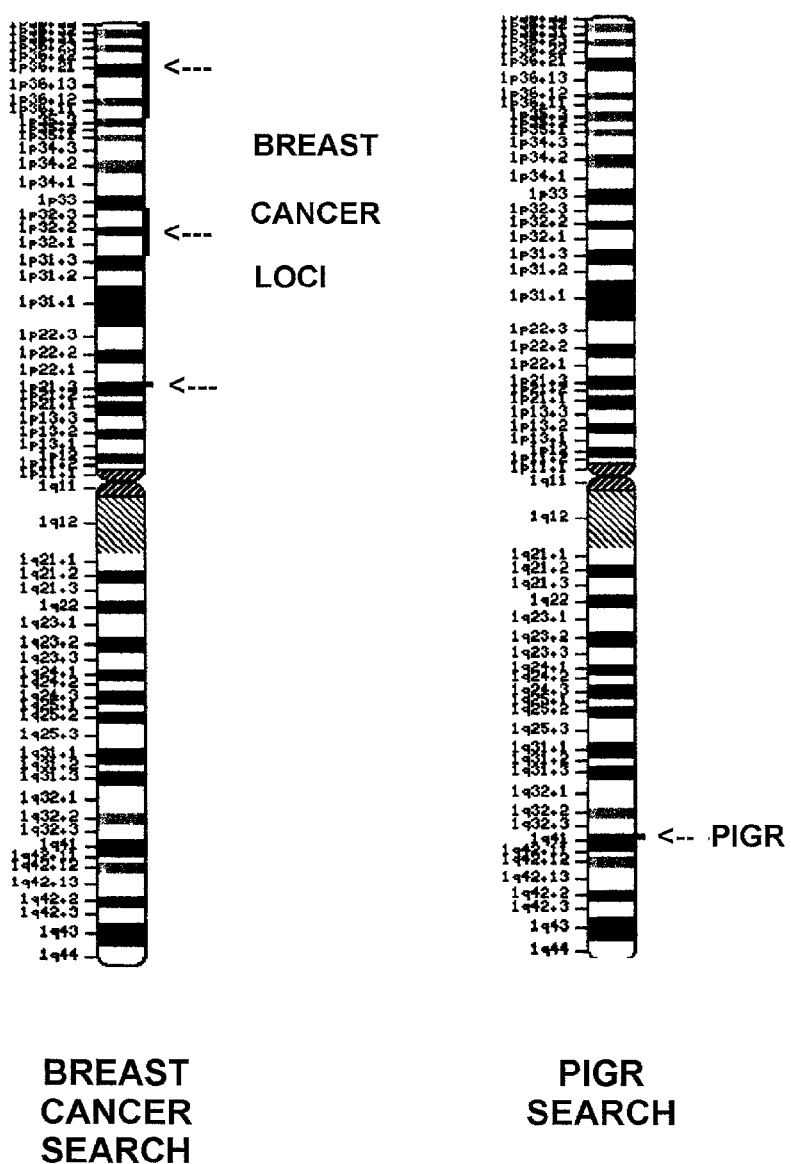

FIG. 131. Chromosome 1 Map of Breast Cancer Loci versus the Poly-Ig Receptor Locus.

FIG. 132. Colon, Breast and Prostate Cancer Death Rates Around the World.

FIG. 133. Immunoglobulin IgG, IgA and IgM Concentrations in Plasma versus Human Age.

DETAILED DESCRIPTION OF PREFERRED EMBODIMENTS

To facilitate review of the detailed description of preferred embodiments, a Table of Contents is provided. The titles used for the various subsections and examples are not intended to be limiting and are only an aid to locating certain subject matter. In addition, some of the Examples that follow begin with a short introduction and/or summary, which is intended merely to facilitate review and is not limiting on the disclosure contained in the full Example, and end with a Discussion, which may include some conclusions that may be drawn from that Example.

| Table of Contents | | |
|---|---|---|
| Subsection | | Paragraph No. |
| Introduction | | 199 |
| Example 1: | Methods and Compositions For Demonstration of Steroid Hormone Responsive Cancer Cell Growth in Culture | 206 |
| Example 2: | Preparations of Steroid Hormone Depleted Serum | 224 |
| Example 3: | MTW9/PL2 Rat Mammary Tumor Cell Estrogen Responsive Growth in 34° C. Charcoal-dextran Extracted Serum | 230 |
| Example 4: | Estrogen Responsive Growth of Additional Rodent and Human Cell Lines In 34° C. Charcoal-dextran Extracted Horse and Human Serum | 245 |
| Example 5: | Thyroid Hormone Growth Effects in CDE-Horse Serum Prepared at 34° C. | 257 |
| Example 6: | Estrogenic Effects in XAD-4 ™ Resin Treated Horse Serum | 259 |
| Example 7: | Testing of Substances for Estrogenic Activity | 261 |
| Example 8: | Roles of TGFβ and Growth Factors: Conceptual Implications | 275 |
| Example 9: | Serum-free Defined Culture Medium Compositions | 293 |

-continued

Table of Contents

| Subsection | | Paragraph No. |
|---|---|---|
| Example 10: | Serum-free Defined Medium Supports Both Hormone Sensitive and Autonomous Cancer Cells | 316 |
| Example 11: | Differential Effects of Fe (III) on the Growth of Hormone Responsive and Autonomous Human Breast and Human Prostate Cancer Cells | 322 |
| Example 12: | Growth in Serum-free Defined Medium versus Growth in CDE-Serum ± $E_2$ | 332 |
| Example 13: | Action of DES on Human AR $^+$LNCaP Prostate Cancer Cells | 341 |
| Example 14: | Properties and Rationale For Serum Purification Source | 343 |
| Example 15: | Cortisol Affinity and Phenyl Sepharose Isolation of the "SHBG-like" Estrogen Reversible Inhibitor from CDE-Horse Serum | 347 |
| Example 16: | Serum-free Assay Systems for Measuring Large Magnitude Steroid Hormone Mitogenic Responses with the Two-Step Purified Inhibitor | 366 |
| Example 17: | Chemical and Immunological Properties of the Partially Purified CA-PS-Pool II Inhibitors and Identification as IgA and IgM | 370 |
| Example 18: | Regulation of Steroid Hormone-responsive and Thyroid Hormone-responsive Cancer Cell Growth in Serum-free Defined Medium by Secretory and Plasma Forms of IgA and Plasma and Cell Culture Derived IgM | 391 |
| Example 19: | A New High Estrogen Affinity Growth Regulating Estrogen Receptor (ERγ) | 407 |
| Example 20: | Effect of Tamoxifen Antiestrogen in Serum-free Defined Medium | 419 |
| Example 21: | Effect of Long-Term Exposure of Breast Cancer Cells to IgM Under Serum-free Defined Conditions | 428 |
| Example 22: | The Role of the Poly-Ig Receptor in Hormone Responsive and Autonomous Breast and Prostate Cell Growth Regulation | 433 |
| Example 23: | IgG1 and IgG2 as Immunoglobulin Regulators of Estrogen and Androgen Responsive Cancer Cell Growth | 445 |
| Example 24: | Mediation of IgG1κ Effects by a Fc-like Receptor | 452 |
| Example 25: | Immunoglobulin Inhibitors as Tools for Identifying the Receptors that Mediate the IgA/IgM/IgG Cell Growth Regulating Effects | 455 |
| Example 26: | Conceptual Model for Cascading Loss of Immunoglobulin Control in Progression from Normal Cells to Steroid Hormone Responsive and Autonomous Cancers | 466 |
| Example 27: | Role of TGFβ in Breast Cancer Predicts the Cellular Progression in Early Onset Breast Cancer | 475 |
| Example 28: | Windows of Breast Susceptibility to Carcinogenesis and Mutation and the Levels of Immunoglobulin Inhibitors | 480 |
| Example 29: | Risk Factors: IgA/IgM Based Test to Detect Lowered Levels of Steroid Hormone Reversible Cell Growth Inhibitors in Plasma or Body Secretions | 492 |
| Example 30: | Risk Factors: IgA Deficiencies and Malignancies | 498 |
| Example 31: | Risk Factors: Autoimmunity Test for Anti-IgA and IgM In Plasma | 500 |
| Example 32: | Diagnostic and Prognostic Tools: Estrogen Receptor γ (ERγ) | 505 |
| Example 33: | Diagnostic, Prognostic and Treatment Decision Tools: Poly-Ig Receptor (or Poly-Ig like Receptor) | 511 |
| Example 34: | Diagnostic Tools: Monoclonal Antibodies to the Poly-Ig Receptor and Breast Cancer Imaging | 517 |
| Example 35: | Diagnostic, Prognostic and Treatment Decision Tools: Fc-like Receptor for IgG1/IgG2 | 520 |
| Example 36: | Diagnostic, Prognostic and Treatment Decision Tools: TGFβ Receptors | 524 |
| Example 37: | Ataxia Telangiectasia as an Example of a Human Genetic Disorder with High Rates of Breast Cancer Coupled with an IgA Deficiency | 529 |
| Example 38: | Diagnostic and Predictive: Poly-Ig Receptor Based Genetic Screening for Breast, Prostate and other Mucosal Cancer Susceptibility | 531 |
| Example 39: | Treatment: Breast Cancer Prevention with Applications to Prostate Cancer and other Mucosal Cancers | 543 |
| Example 40: | Treatment: Rat Model for Testing Oral Immunization Effects on Mammary Gland Carcinogenesis | 558 |
| Example 41: | Treatment: Bacterial Oncogenesis and Prevention by Oral Immunization | 573 |
| Example 42: | Treatment: Treatment of Steroid Hormone Responsive Breast or Prostate Cancer by Administration of IgA/IgM/IgG1 | 601 |
| Example 43: | Treatment: Monoclonal Antibodies that Mimic or block IgA or IgM Binding to the Poly-Ig Receptor | 609 |
| Example 44: | Treatment: Delivery of Chemotherapeutic Agents and Cytotoxins to Cancer Cells via IgA/IgM/IgG1 or Monoclonal Antibodies to Poly-Ig Receptor | 616 |

Introduction

In the course of searching for what causes the growth of estrogen responsive breast and androgen responsive prostate cancers, it was discovered that the secretory immune system plays a major role in those diseases. More specifically, it was discovered that the secretory immune system (i.e., the immunoglobulins IgA, IgM and IgG1) provide negative (inhibitory) regulation of steroid hormone responsive mucosal epithelial cancer cell growth in serum-free model cell culture systems, including breast, prostate, pituitary, kidney, colon, and other glandular cancer cells. Prior to that discovery, which is described in co-owned concurrently filed U.S. patent application Ser. No. 09/852,958/PCT/US2001/15183 entitled "Compositions and Methods for Demonstrating Secretory Immune System Regulation of Steroid Hormone Responsive Cancer Cell Growth," hereby incorporated herein by reference, no cell growth regulating role was known for the secretory immune system. The secretory immune system produces predominantly dimeric/polymeric IgA, secretory IgA (sIgA), polymeric IgM, and IgG1. The discovery of immunoglobulin inhibitors of cell growth is a major breakthrough in the understanding of cancers of breast and prostate, as well as other glandular/mucosal tissues that secrete or are bathed by the secretory immunoglobulins.

For the first time, a direct link is established between the secretory immune system and the most prevalent types of cancer that occur throughout the world. Binding of IgA and IgM to the polyimmunoglobulin receptor (poly-Ig receptor) is an important step in carrying out the regulatory function of IgA and IgM, and it is probable that the known poly-Ig receptor, or a closely related poly-Ig like receptor, mediates the negative regulation of steroid hormone dependent cell growth. Similarly, it is believed that the binding of IgG1 to the Fcλ receptor is a mediating step in carrying out the regulatory function of IgG1. The application of this new understanding of immune system regulation of cancer cell growth to the risk assessment, detection, diagnosis, prognosis, treatment and deterrence or prevention of a host of mucosal epithelial cell cancers is described in the following examples.

A new conceptual model described herein, offers an explanation of how normal breast tissue may give rise to highly malignant, and dangerous, hormone autonomous forms. This model is contrary in some respects to the well-established "linear progression" model, in which breast cancers pass through a characteristic natural history that involves a gradual evolution from near normal growth patterns into cancers that are completely steroid hormone autonomous (i.e., they are no longer stimulated by steroid hormones), and describes cell growth regulatory roles for TGFβ, IgA, IgM and IgG1.

The secretory immune system was not previously known to have any cell growth regulatory role in breast or prostate cancer, or in other cancers of the mucus epithelial tissues. As set forth in various of the following examples, new compositions and "immunotherapy" protocols based on production or administration of IgA, IgM and IgG1, as well as new methods of immune-related diagnosis and assessment of susceptibility are provided. Also, effective new gene expression and gene transfection therapies by which malignant breast cells may be returned to natural immune control are described. Such strategies will be far less toxic than those now employing chemotherapeutic agents. A significant feature of the discovery is that a new natural "immune" mechanism exists that is distinct from the anti-tumor immunological approaches of the past, and which can be exploited to control breast cancer.

It should be readily appreciated that this discovery has implications well beyond cancers of the breast and prostate. The secretory immune system is an integral part of the physiology of all mucosal epithelial tissues. Most, if not all, mucosal tissues secrete IgA, IgM and IgG1 directly into the lumen of biological passageways. This includes salivary glands, oral and nasal cavities, stomach, small and large bowel, lung passageways, the kidney tubule, liver and bile ducts, prostate, bladder, the anterior pituitary, and the secretory/exocrine pancreas. Secretory immune system control of cell proliferation is also relevant to cancers of the female reproductive tract. The entire female reproductive tract including ovaries, uterus, cervix and vagina either secretes IgA and IgM or is a target for these immunoglobulins. In fact, malignancies of all secretory epithelial tissues represent 80% or more of the cancers in human females.

The compositions and methods, and the biochemical, genetic and immunological tools described herein, and those described in U.S. patent application Ser. No. 09/852,958/ PCT/US2001/15183 entitled "Compositions and Methods for Demonstrating Secretory Immune System Regulation of Steroid Hormone Responsive Cancer Cell Growth" (hereby incorporated herein by reference), are employed in the present investigations to further elucidate the cascade of cellular changes that lead to malignancy in glandular/mucosal tissues and to provide, among other things, ways of testing cancer cells for loss of IgA/IgM/IgG1 regulation, ways to detect genetic changes in the poly-Ig receptor, biochemical and genetic screening procedures to identify individuals at high risk for developing breast or prostate cancer, and ways of deterring or reducing the risk of development of such cancers. Additionally, in light of the discovery that the secretory immune system immunoglobulins IgA, IgM and IgG1 are potent inhibitors of steroid hormone responsive cancer cell growth, it is now proposed that the steroid hormone responsive tissues in the body can be protected from the cancer causing actions of certain environmental carcinogens, especially during age related "windows" of increased susceptibility, by enhancement of the IgA/IgM/IgG1 secreted by or coming in contact with those tissues. In this way, DNA synthesis dependent mutations can be prevented or substantially reduced in those tissues. Likewise, deleterious down-modulation or inactivation of critical gene expression (e.g., the poly-Ig receptor) due to environmental carcinogens may also be remediable by restoration of IgA, IgM and/or IgG1 control of cell growth.

Also described in examples that follow is the use of cell growth inhibitory amounts iron, in the form of Fe (III), to treat malignancies and/or surgical sites. Still other Examples which follow describe screening procedures for detecting potentially cancer-inducing bacteria, and offer preventative measures for decreasing the effects of bacterial carcinogenesis.

EXAMPLES

Example 1

Methods and Compositions for Demonstration of Steroid Hormone Dependent Cancer Cell Growth in Culture In the following Examples, which describe representative, preferred embodiments of the present invention, the following general materials and methods are employed, except as otherwise noted therein.

Cell Culture Medium. The water used to prepare culture media and all other solutions was purified first by reverse osmosis followed by passage through a U.S. Filter Corporation system with a charcoal filter and two mixed bed ion exchangers. The effluent was distilled using a Bellco glass apparatus with quartz heating elements. The distilled water was stored in airflow restricted glass containers. No metal fittings are allowed in contact with the final purified water. This necessary precaution minimizes recontamination with metal ions. Standard phenol red containing Ham's F12-Dulbecco's modified Eagle's medium (D-MEM/F-12), phenol red-free standard D-MEM/F-12 and a custom-prepared "low-Fe" D-MEM/F-12 medium were supplied by Gibco-BRL (Catalog No. 11330-032) or Bio◆Whittacker (Catalog No. 12-719, liquid). The "low-Fe" medium was standard phenol red containing D-MEM/F-12 from which the usual additions of ferric nitrate and ferrous sulfate had been omitted (Eby J E et al. (1992) *Anal Biochem* 203, 317-325; Eby J E et al. (1993) *J Cell Physiol* 156, 588-600). This medium was a special formulation purchased from Gibco-BRL as a powder and prepared in the highly purified water before 0.2 μm pore filter membrane sterilization. A number of other stock solutions are required for cell culture in either serum containing or serum-free defined medium. Descriptions of each preparation are provided along with specific instructions for their use. The solutions used were designed to minimize the exogenous content of steroid hormone and to minimize the Fe (III) content of the water. Steps are taken for the exclusion of all extraneous sources of steroid hormones and Fe (III). Exclusion of Fe (III) is highly preferred, and in most of the totally serum-free applications, it is considered essential. Wherever possible, disposable plastic ware or glassware is used to minimize potential contamination. It is important to note that excess solutions are preferably discarded after use with each individual cell line to avoid cross-contamination of cell types (Nelson-Rees W A and Fladermeyer R R (1977) *Science* (Wash D.C.) 195, 134-136).

General Cell Culture—Serum. Adult and fetal horse, adult pig, adult sheep and adult and fetal bovine serum were obtained from Gibco-BRL. A mixture of adult male and female rat serum was purchased from Pel-Freez, Rodgers, A R. Human serum was purchased from Bio♦Whittacker. Human plasma was a pool of samples collected from pregnant females during routine visits to a local clinic. All serum was stored frozen at −20° C. until used. Repeated freeze-thaw of serum or plasma is avoided. Before charcoal extraction, the EDTA was removed by dialysis at 7° C. for 24 hours against forty volumes of 0.05 M Tris-HCl, pH 7.4, containing 50 mM $CaCl_2$. Dialysis was done with Spectropor 1 membranes (Spectrum Medical Industries, molecular weight cut-off 6,000 to 8,000). The clotted material was removed by centrifugation. This preparation is termed plasma-derived serum. The serum or plasma was not heat pre-treated, or heat inactivated prior to use in the methods described below.

General Cell Culture—Normal Saline. Sterile normal saline (0.15 M NaCl) was prepared in 10 mL aliquots and stored at room temperature. Unused portions are discarded at the end of each experiment. A large supply is sterilized by autoclaving and used to prepare the solutions described below.

General Cell Culture—Trypsin/EDTA for Subculture. Sterile preparations were purchased from Irvine Scientific (Catalog No. 9341) or Bio♦Whittacker (Trypsin-Versene EDTA Mixture) (Catalog No. 17-161F). This preparation contained 0.5 g/L trypsin and 0.2 g/L EDTA in Hank's balanced salts solutions with 10 mg/L phenol red. This preparation does not contain Ca or Mg salts nor does it have $NaHCO_3$. To trypsinize cells, 1.5 mL of this preparation was typically used. Aliquots (2 mL) were stored frozen until used and residual solution discarded at the end of each experiment or application to a cell line.

General Cell Culture—Soybean Trypsin Inhibitor (STI). STI was purchased from Sigma (Catalog No. T9128, Type II-2). An amount of 1.0 mg of this preparation will inactivate 1.0 mg of trypsin activity. The solution is prepared as 0.2% (w/v) in normal saline and sterilized using a 0.2 µm pore diameter filter membranes. Aliquots of 3.0 mL are stored at −20° C. until used. This preparation is used to stop the action of trypsin during harvest of stock cultures for growth assays. STI ensures that all trypsin used to harvest cells for growth assays is inactivated and therefore will not damage the protein additions to serum-free defined medium. Also, use of STI ensures that no extraneous steroid hormones are introduced after harvest of cells from the stock culture dishes.

General Cell Culture—Crude Pancreatic Trypsin for Cell Counting. This trypsin preparation was used to harvest the cells for determining cell numbers. The cells are typically grown in 35-mm diameter dishes. This enzyme was purchased from ICN Biochemicals as the 1-300 porcine pancreatic trypsin preparation (Catalog No. 103140). A stock solution is typically prepared by adding the contents of a preweighed bottle of 1× Dulbecco's modified PBS medium without calcium or magnesium to 800 mL of water. This solution dissolves very gradually with adjustment to pH 7.3 using NaOH. After the solution was clear, 20 g of crude trypsin was added and this mixture stirred for 30 minutes at room temperature. The somewhat cloudy solution was diluted to 1000 mL with water and this volume was stored frozen in bulk overnight at −20° C. to induce cold related precipitation that typically occurs when this preparation was frozen and thawed. After thawing at 37° C. in a water bath, the preparation was filtered through 0.45 µm pore membranes. This preparation was stored at −20° C. in useable portions.

General Cell Culture—EDTA for Cell Counting. The EDTA used is the disodium and dihydrate salt (Sigma Catalog No. E1644). A 0.29 M solution is prepared by adding 107.9 g to 800 mL of water with stirring and adjustment to pH 7.2 with NaOH. The volume is brought to one liter with water and the solution stored at room temperature. Because this solution is used only at the end of the experiments, it does not require sterilization.

General Cell Culture. In Table 1 the cell lines used in the described Examples are listed. The abbreviation "KCC" is the Karmanos Cancer Center, Cell Line Repository, Detroit, Mich. The abbreviation "ATCC" is the American Type Culture Collection, Cell Line Repository, Manassas, Va. Professor Armen Tashjian's address is Harvard University, Boston, Mass. Dr. William Rosner's address is Columbia University, New York. Dr. Sirbasku's address is The University of Texas, Houston, Tex. The superscript designations in Table 1 for each of the cell lines indicate references that verify that the estrogen and androgen responsive cell lines used in this study are bona fide hormone responsive based on their tumor forming characteristics in host animals. Those reports are clear demonstrations of the reliability of the models used in the present investigations to study sex hormone dependence in culture.

TABLE 1

Cell Lines Employed in the Examples. $ER^+$ indicates receptor containing/$E_2$ sensitive

| CELL LINES | SOURCES | REFERENCES/CELL LINE ORIGIN |
|---|---|---|
| MCF-7K[1] | KCC | Soule HD et al. (1973) J Natl Cancer Inst 51, 1409–1416<br>$ER^+$ human breast cancer |
| MCF-7A[1] | ATCC | Soule HD et al. (1973) J Natl Cancer Inst 51, 1409–1416<br>$ER^+$ human breast cancer |
| T47D[2] | ATCC | Keydar I et al. (1979) Eur J Cancer 15, 659–670<br>$ER^+$ human breast cancer |
| ZR-75-1[3] | ATCC | Engle LW et al. (1978) Cancer Res 38, 3352–3364.<br>$ER^+$ human breast cancer |
| $GH_4C_1$[4] | Dr. A. Tashjian | Tashjian AH Jr (1979) Methods Enzymol 58, 527–535<br>$ER^+$ rat pituitary tumor |
| $GH_3$[5] | ATCC | Tashjian AH Jr (1979) Methods Enzymol 58, 527–535.<br>$ER^+$ rat pituitary tumor |
| GH[1] | ATCC | Tashjian AH Jr (1979) Methods Enzymol 58, 527–535<br>$ER^+$ rat pituitary tumor |
| MTW9/PL2[6] | Dr. D. Sirbasku | Danielpour D et al. (1988) In Vitro Cell Dev Biol 24, 42–52<br>$ER^+$ rat mammary tumor |
| H301[7] | Dr. D. Sirbasku | Sirbasku DA and Kirkland WL (1976) Endocrinology 98, 1260–1272<br>$ER^+$ Syrian hamster kidney tumor |
| LNCaP[8] | ATCC | Horoszewicz JS et al. (1983) Cancer Res 43, 1809–1818<br>$AR^+$ human prostatic carcinoma |

TABLE 1-continued

Cell Lines Employed in the Examples. ER+ indicates receptor containing/E$_2$ sensitive

| CELL LINES | SOURCES | REFERENCES/CELL LINE ORIGIN |
|---|---|---|
| Fibroblasts | Dr. D. Sirbasku | Primary cultures of human foreskin and rat ear cartilage; Eastment CT and Sirbasku DA (1980) In Vitro 16, 694–705 |
| ALVA-41 | Dr. W. Rosner | Nakhla AM and Rosner W (1994) Steroids 59, 586–589 AR− human prostate cancer; androgen growth insensitive |
| DU145 | ATCC | Stone KR et al. (1978) Int J Cancer 21, 274–281 AR− human prostate cancer; androgen growth insensitive |
| PC3 | ATCC | Kaighn ME et al. (1979) Invest Urol 17, 16–23 AR− human prostate cancer; androgen growth insensitive |
| HT-29 | ATCC | Chen TR et al. (1987) Cancer Genet Cytogenet 27, 125–134 Thyroid hormone responsive human colon cancer |

ER+ indicates estrogen receptor containing. AR+ indicates androgen receptor containing. Unless otherwise noted, these designations indicate sex steroid hormone growth responsive in culture.
In vivo Tumor Forming Properties. The references below refer to the superscript designations in Table 1 for the cell lines. The references verify that the estrogen and androgen responsive cell lines used in this disclosure are hormone responsive based on their tumor forming characteristics in host animals. These reports are demonstration the reliability of the models used in this disclosure to study sex hormone dependence in culture.
[1] The use of two strains of MCF-7 cells has been described (Sirbasku DA and Moreno-Cuevas (2000) In Vitro Cell Dev Biol 36, 428–446). Clonal variations of this line are known (Seibert K et al. (1983) Cancer Res 43, 2223–2239). Demonstration of estrogen responsive MCF-7 tumor formation in vivo (Huseby RA et al. (1984) Cancer Res 44, 2654–2659; Soule HD and McGrath CM (1980) Cancer Lett 10, 177–189; Welsch CW et al. (1981) Cancer Lett 14, 309–316).
[2] Estrogen responsive T47D tumors in vivo (Leung CKH and Shiu RPC (1981) Cancer Res 41, 546–551).
[3] Estrogen responsive ZR-75-1 tumors in vivo (Osborne CK et al. (1985) Cancer Res 45, 584–589).
[4] Estrogen responsive GH$_4$C$_1$ tumors in vivo (Riss TL and Sirbasku DA (1989) In Vitro Cell Dev Biol 25, 136–142).
[5] Estrogen responsive GH$_3$ tumors in vivo (Sorrentino JM et al. (1976) J Natl Cancer Inst 56, 1149–1154).
[6] Estrogen responsive MTW9/PL2 tumors in vivo (Sirbasku DA (1978) Cancer Res 38, 1154–1165; Danielpour D and Sirbasku DA (1984) In Vitro 20, 975–980).
[7] Estrogen responsive H301 tumors in vivo (Sirbasku DA and Kirkland WL (1976) Endocrinology 98, 1260–1272; Liehr JG et al. (1986) J Steroid Biochem 24, 353–356).
[8] Androgen responsive LNCaP tumors in vivo (Sato N et al. (1997) Cancer Res 57, 1584–1589; Gleave M et al (1991) Cancer Res 51, 3753–3761; Horoszewicz JS et al. (1983) Cancer Res 43, 1809–1818; Pretlow TG et al. (1991) Cancer Res 51, 3814–3817; Passaniti A et al. (1992) Int J Cancer 51, 318–324).

General Cell Culture—Cell Passage Method. All stock cultures were grown in medium containing phenol red. Stocks of the cells were maintained at 37° C. in a humid atmosphere of 5% (v/v) CO$_2$ and 95% (v/v) air in 17 to 20 mL of standard D-MEM/F-12 with 2.2 g per liter sodium bicarbonate, 15 mM HEPES (pH 7.4), and serum. With all cell lines except the rat pituitary cells, the serum used for stock culture was 10% (v/v) fetal bovine serum (FBS). For the three rat pituitary tumor cell lines GH$_4$C$_1$, GH$_1$ and GH$_3$, the medium contained 12.5% (v/v) horse serum and 2.5% (v/v) FBS. To passage the cells, the medium was removed and the dishes washed with 10 mL of saline. Next, the cells were dissociated by incubation at room temperature or at 37° C. for 3 to 10 minutes with 1.5 mL of trypsin/EDTA. The action of the trypsin was stopped by addition of 8 mL of D-MEM/F-12 containing 10% (v/v) FBS or 8 mL of the horse serum or FBS. The cells were collected by centrifugation at 1000×g for 5 minutes and suspended in 10 mL of fresh serum containing medium. Aliquots were diluted into Isoton II (Coulter Diagnostics) and cell numbers determined with a Model ZBI or ZI Coulter Particle Counter. The new dishes (100-mm diameter with 15 to 20 mL of fresh medium) were seeded with 2.0×10$^5$ to 1.0×10$^6$ cells on an alternating three-four day schedule or weekly as dictated by cell line growth rate. Cultures were used for growth assays between three and six days after passage. Acidic (yellow medium indicator color) cultures are not used for growth assays.

General Cell Culture—Media Types Used. The assays done in the presence of serum were initially in "low-Fe" D-MEM/F-12 containing phenol red (Moreno-Cuevas J E and Sirbasku D A (2000) In Vitro Cell Dev Biol 36, 410-427). The issue of the significance of the presence or absence of phenol red, a potential estrogen (Berthois Y et al. (1986) Proc Natl Acad Sci USA 83, 2496-2500), has been dealt with in considerable detail (Moreno-Cuevas J E and Sirbasku D A (2000) In Vitro Cell Dev Biol 36, 447-464). The Fe (III) content of this medium was $\leq 0.2$ μM (Eby J E et al. (1992) Anal Biochem 203, 317-325). Fe (III) levels of $\geq 1.0$ μM interfere with thyroid hormone and estrogen responsive rat pituitary tumor cell growth in culture (Eby J E et al. (1992) Anal Biochem 203, 317-325; Eby J E et al. (1993) J Cell Physiol 156, 588-600; Sato H et al. (1991) In Vitro Cell Dev Biol 27A, 599-602; Sato H et al (1992) Mol Cell Endocrinol 83, 239-251). Although Fe (III) might prevent estrogen responsiveness from being identified in culture with MTW9/PL2 cells, as shown herein and reported (Sirbasku D A and Moreno-Cuevas J E (2000) In Vitro Cell Dev Biol 36, 428-446; Moreno-Cuevas J E and Sirbasku D A (2000) In Vitro Cell Dev Biol 36, 447-464), this is not the case when serum is present. Standard Fe (III)/Fe (III) containing D-MEM/F-12 was as effective as the low-Fe medium. It is clear that the apotransferrin in the serum effectively reduced the free Fe (III) in the medium to less than cytotoxic levels. As stated above, apotransferrin binds Fe (III) with very high affinity at pH 7.4 in plasma. The total concentration of transferrin in serum is about 3 mg/mL. Usually, two-thirds of the total is apotransferrin. This amount is more than adequate to chelate Fe (III) in culture medium (Eby J E et al. (1992) Anal Biochem 203, 317-325). However, in assays in serum-free defined medium, as described below, a Fe (III) chelator (e.g. apotransferrin or DFX) is present in the serum-free defined medium at sufficient levels to neutralize the toxic iron.

General Cell Culture—Growth Assay Methods. Cell growth assays were initiated with stock cultures that were harvested by trypsin/EDTA treatment as described above with one exception. It was highly preferred to stop the action of trypsin with 3 mL of soybean trypsin inhibitor (0.5% w/v in saline) instead of medium containing serum. The use of trypsin inhibitor reduced the possibility of contamination of the subsequent assay media by serum-derived steroid hormones. The dissociated cells were collected by centrifugation as described above and washed three times with 10 mL volumes of serum-free standard D-MEM/F-12. After each wash, care was taken to aspirate all medium from the cell pellet and the walls of the centrifuge tubes. This minimized the carryover of steroid hormones into the experimental test dishes. By taking steps to avoid carryover of serum, steroid hormones are prevented from being retained by the cells in culture. It is highly preferred to wash the cells in this way before assaying to measure various steroid hormone effects in culture. It has been reported that steroid hormones are retained long term by breast cancer cells in culture (Strobl J S and Lippman M E (1979) Cancer Res 39, 3319-3327). The above-described wash procedure negates this problem. After the final wash, the cells were suspended in 10 mL of serum-free D-MEM/F-12 and cell numbers determined. When cells were to be assayed in medium without phenol red discussed elsewhere herein and reported (Moreno-Cuevas J E and Sirbasku D A (2000) In Vitro Cell Dev Biol 36, 447-464), the cells were washed and resuspended in phenol red free D-MEM/F-12 purchased from Gibco-BRL. The growth assays were initiated in 35-mm dishes containing a total of 2.0 mL of medium and the final concentration of all components except steroid hormones. The steroid hormone stocks were diluted to appropriate concentrations in serum-free D-MEM/F-12 and 20 μL aliquots added to each dish. For all growth assays, the medium was not changed after the initial inoculation. Because several of the cell lines described in Table 2 grow in serum containing medium and serum-free defined medium as mixtures of suspension and attached cells, removal or changing of the medium during the course of the assays causes substantial cell losses. For all cell growth assays, the initial seed densities ranged from 5,000 to 12,000 cells per 35-mm diameter dish.

General Cell Culture—Steroid Hormone Preparations. A number of hormone preparations are used to supplement the cell cultures. Unlabeled steroid hormones were obtained from Sigma or Steraloids. Stock solutions were prepared in sterile glass containers. The powder (non-sterile) steroid is added to the bottle along with 200 ml of 70% aqueous ethanol (ready as sterile). The steroids dissolve within an hour at room temperature, or when required were dissolved by gentle heating on a hot plate (hand temperature test—no boiling—no open flames). The stock solutions were stored at 4° C. and renewed at six-month intervals. It is not necessary or desirable to filter sterilize these solutions because of steroid hormone loss on filter membranes. Stocks of 1.0 mM steroid hormones were prepared. To prepare diluted stocks for direct use in culture, 10 μL of 1.0 mM steroid hormone is diluted into 10 mL of D-MEM/F-12. This gives a stock of 1.0 μM. It is used in the assay dishes or diluted further in D-MEM/F-12 as needed. The diluted steroids are discarded after each use because they bind to the plastic with storage. The formula weight (FW) of each of the common natural and synthetic hormones used is listed below in Table 2 along the abbreviation used for each and the amounts required to prepare 200 mL of stock.

TABLE 2

Preparation of Steroid Hormone Stocks for Cell Culture and Hormone Binding Assays

| STEROID HORMONES | FORMULA WEIGHT (FW) | MIILLIGRAMS/200 mL |
|---|---|---|
| 17β-estradiol (E$_2$) | 272.4 | 54.4 |
| Estrone (E$_1$) | 270.4 | 54.1 |
| Estriol (E$_3$) | 288.4 | 57.7 |
| Diethylstilbestrol (DES) | 268.4 | 53.7 |
| Tamoxifen Citrate (TAM) | 563.6 | 112.7 |
| Progesterone (PROG) | 314.5 | 62.9 |
| Hydrocortisone/Cortisol (C) | 362.5 | 72.5 |
| Dexamethasone (DEX) | 392.5 | 78.5 |
| Testosterone (T) | 288.4 | 57.7 |
| Dihydrotestosterone (DHT) | 290.4 | 58.1 |

General Cell Culture—Harvest and Counting Cells. At the termination of the experiments, each plate received 0.4 mL of crude pancreatic trypsin dissolved in phosphate buffered saline was added along with 0.3 mL of 0.29 M EDTA. After 4 to 40 minutes incubation at room temperature or at 37° C., the action of the trypsin was stopped by addition of 0.6 mL of horse serum. The cell clumps were dissociated further by one passage through a 20½ or 23-gauge needle and syringe. This suspension was then diluted to 10 mL with Isoton II and cell numbers determined with a Coulter Counter. The results are presented as the average of triplicate dishes for each test medium. To determine day zero cell numbers, at least triplicate 1.0 mL aliquots of the inoculum were collected for counting during the seeding of the test dishes. Coulter Counter standardization and monitoring were performed by the manufacturer.

General Cell Culture—Quantification of Growth. The cell number results are converted to cell population doublings (CPD) by the following calculation:

$$CPD = \frac{\text{Log}_{10} \text{ Average Cell Number on Collection Day} - \text{Log}_{10} \text{ Average Cell Number on Day Zero}}{\text{Log}_{10} 2}$$

For the purposes of this Disclosure, the mitogenic response to sex steroid hormones is designated the "steroidogenic effect." For example, the "estrogenic effect" is calculated as the difference between CPD measured in the presence of an estrogen minus CPD in the absence of the steroid. These values equal cell number increases of $2^{CPD}$. The term "androgenic effect" has the same meaning except that it describes growth caused by androgens such as DHT and T. CPD is used herein as a measure of growth because it is a direct calculation of the number of times a cell population undergoes cell division. Furthermore, CPD use permits a direct measure of $ED_{50}$ and $ED_{100}$ Concentrations in different and in replicate assays. The significance of differences between test dishes and controls was evaluated by the student's t test. Values of p<0.05 were accepted as significant. Standard deviations (±SD) are included when appropriate.

Discussion of Example 1. The cell culture methods outlined above are highly preferred as procedures to obtain cells sufficiently washed of steroid hormone to measure low concentration effects in medium with hormone depleted serum prepared as described in the next Example. The use of STI to stop the action of the trypsin is highly preferred. Application of serum to stop the action of the trypsin causes a substantial loss of hormone responsiveness.

Example 2

Methods of Preparing Steroid Hormone Depleted Serum

In this example, two methods for preparing steroid hormone depleted serum are described. The primary purpose was to prepare serum that supported large magnitude sex steroid growth effects in culture and to identify the dose-response concentrations that cause the effects, as demonstrated in Examples that follow. This meant preparing serum with ≦5 pg/mL estrogen (and other steroid hormones). This concentration corresponds approximately to the lower limit of detection of steroids by radio immunoassay. The methods tested included (A) a two-step charcoal/dextran extraction of serum at 34° C., and (B) a one step treatment with Amberlite™ XAD™-4 resin at 37° C.

A. Charcoal-Dextran Extraction at 34° C.

Preparation of the charcoal/dextran mixture. Activated charcoal, untreated powder (100 to 400 mesh), was obtained from Sigma (Catalog No. C5260). This preparation was done at room temperature. The powder (30 g) was suspended in 600 mL of water and stirred for 20-30 minutes at room temperature. The water used to wash and suspend the charcoal was a purified source made by reverse osmosis/ion exchange treatment/charcoal filtration/0.2 μm pore diameter filtration/distillation into glass (only) containers. Next, 3.0 g of Dextran T70 (Pharmacia) was dissolved in 300 mL of water, added to the charcoal suspension with stirring, and the mixture stirred for 30-60 minutes at room temperature, preferably 60 minutes. The mixture was then washed with about 6-8 liters of distilled water in a sintered glass funnel (2000 mL, ASTM 40-60, C#36060). This wash removes impurities as well as fine particles of charcoal that cannot be separated from serum by centrifugation. The charcoal-dextran retentate was suspended in a final volume of 300 mL of distilled water to yield a suspension of 100 mg/mL charcoal and 10 mg/mL dextran. Preferably the mixture is stirred vigorously for about an hour, and then stored at room temperature for no more than about 2-3 weeks prior to use.

Charcoal-dextran extraction at 34° C. of horse serum (CDE-horse serum). This serum in 500 mL sterile bottles was removed from the freezer (−17° C.) and thawed at 4° C. for 24 to 48 hours. Alternatively, fresh serum could be used. The thawed serum (still in the 500 mL sterile bottles) was placed in an orbital shaker water bath (Lab-Line Orbit Shaker Water Bath) equilibrated at 34° C. The serum was incubated at 140 RPM for 45-60 minutes to reach 34° C. Approximately 250 mL portions of the 34° C. serum (total volume about 1 liter) were transferred to one liter Erlenmeyer flasks and tightly capped with aluminum foil. These were incubated for 20-30 minutes (preferably 30 minutes) in the 34° C. orbital shaker water bath at a medium-high rotation speed. Thereafter, 25 mL of the charcoal/dextran suspension was added to each flask. The charcoal-dextran suspension was stirred at room temperature while removing the 25 mL aliquot. The final charcoal concentration in each flask was 10 mg/mL, and the final concentration of dextran was 1 mg/mL. After addition of the charcoal-dextran mixture to each flask, the extraction mixtures were shaken at 140-160 RPM at 34° C. for two hours. After this, the mixture was cooled on ice and the charcoal removed by centrifugation at 10,000×g for about 60 minutes at room temperature. In some preparations the temperature of the mixture gradually warmed to about 40° C. during centrifugation. The supernatants were pooled in a two-liter beaker and 275 mL portions of the supernatant (serum) transferred to fresh one-liter Erlenmeyer flasks. These were then incubated in the orbital shaker water bath at 34° C. for 20-30 minutes (preferably 30 minutes) to re-equilibrate the temperature. A second extraction was done by addition of a fresh aliquot (about 14 mL) of the charcoal-dextran suspension. This re-extraction mixture was incubated with shaking for another 2 hours at 34° C. The final charcoal concentration during this extraction was about 5 mg/mL. Afterward the bulk of the charcoal was removed by centrifugation, as before. In some preparations the temperature of the mixture reached about 41° C., without harming the quality of the serum. The supernatants were collected into a two-liter beaker and filtered through 5 μm pore diameter filters to remove residual charcoal. If it was considered necessary for particular preparations that still contained residual charcoal, (for example, due to charcoal darkening serum) the serum was also filtered with 0.45 μm pore diameterMillipore filters. These filtrations were done with plastic reusable filter holders and light vacuum. The steroid hormone depleted serum was then sterilized using 0.2 μm pore diameter filters. After sterilization, aliquots of about 26 mL were dispensed into sterile glass (50 mL) bottles or sterile 50 mL polypropylene tubes and stored frozen at −17° C. Although 34° C. is preferred in the above-described regime, and provides the best results, satisfactory depletion of steroid hormones can be obtained over the temperature range of about 30 to 37° C. The 2 hour incubation times for the extraction and re-extraction mixture (at 34° C.) are preferred, but a time range of 30 minute to 3 hours could also be used with success, employing longer incubation times for the lower temperatures within the 30-37° C. range. A ±25% variation in the charcoal concentration used for each extraction had no detrimental effects on the final product.

B. Amberlite™ XAD™-4 Resin Treatment. In a different procedure carried out to free corticosteroids binding globulin (CBG) of storage cortisol, XAD resin has been used to remove the steroid by incubation for 5 hrs at room temperature (A. M. Nakhla, et al. (1988) *Biochem. Biophys. Res. Commun.* 153, 1012-1018). Described as such, this method removed only about 80% of cortisol from the purified protein. Careful application of that method failed to yield serum suitable for the purpose of this study. As an alternative to preparing steroid hormone depleted serum by charcoal-dextran extraction, horse serum was treated by incubation with Amberlite™ XAD™-4 nonionic polymeric absorbent (Aldrich, Catalog. No. 21,648-8; or Sigma Catalog No. XAD-4 3738042-0). Specifically, a 500 nL bottle of horse serum was thawed at 37° C. and divided into 250 mL portions that were each in a one-liter Erlenmeyer flask. To each flask was added 25 grams of moist XAD-4™ resin. The mixtures of serum and resin were then incubated with shaking in a rotary Labline Orbital Shaker water bath at 34° C. at about two-thirds of the maximum rate for 24 hours (speed adjusted to control foaming). This extraction can be done at temperatures from 30° C. to 37° C. At 30° C., the extraction requires 24 to 36 hours. At 37° C., it requires 18-24 hours to be complete. The 34° C. and 37° C. procedures are preferred. Each flask was tightly capped with aluminum foil and taped. After 24 hrs, the resin is allowed to settle by gravity, the supernatant decanted, and then vacuum filtered using a glass fiber filter in a Buchner funnel. The resulting serum was filter sterilized using 0.2 μm pore filter units. Aliquots of about 26 mL were frozen at −17° C. in 50 mL sterile bottles or 50 mL polypropylene tubes.

Discussion of Example 2. Each of the methods presented have advantages, depending on the particular needs and desires of the user. The scale procedures described are useful to prepared sufficient serum for testing of plasma or bodily fluids samples for inhibitors and for hormone activities or anti-hormone activities or evaluation of toxicity of compounds in cell culture assays. To ensure uniformity, large batches of the serum can be prepared, if desired. The charcoal method described above is readily applicable to one to five liter volumes of serum per preparation. With use of moderate numbers of test samples or ≦50 mL per test substance, this is an adequate supply. To prepare larger volumes of serum (i.e. ≧20 liters) for extensive testing programs or commercial applications, the charcoal-dextran methods will preferably employ industrial filtration or other separation equipment to remove the carbon after each extraction. The XAD-4™ resin method as presented is adaptable to one to five liters for testing purposes. For industrial applications, where ≧20 to 100 liter batches are customarily required, the resin method is preferred because of the need for only one separation after extraction. However, where "foaming" of the serum protein is to be avoided completely, charcoal extraction is superior. The materials cost for charcoal-dextran has an advantage when economy is a major consideration. It is less expensive than XAD-4™ resin on a per liter basis, although the resin is commercially available at low cost when purchased in large amounts (i.e. ≧50-100 kilograms). XAD-4™ resin method is highly adaptable to small clinically derived samples of plasma or other bodily fluids.

This 34° C. method has been used to prepare CDE human serum, porcine serum, rat serum, hamster serum, ovine serum, fetal bovine serum, new born bovine serum (0 to 10 days old), young donor bovine serum (10 days to 6 moths old) young adult bovine serum (300 to 900 lbs), fetal horse serum, chicken serum, turkey serum, dog serum, goat serum, rabbit serum and monkey serum. Subsequent Examples demonstrate how these stripped sera are preferably employed. The results demonstrate the broad utility of the method of preparing charcoal-dextran extracted serum for testing of cell lines from many species using homologous serum assays. From these results it can also be readily appreciated that these methods are applicable not only to testing of human plasma/serum, but also to veterinary medicine samples or compounds of significance to domestic animals, as well as any application where a steroid hormone stripped serum is used. For example, in the diagnosis, prevention/risk management or therapy of mucosal origin cancers.

Example 3

MTW9/PL2 Rat Mammary Tumor Cells

This Example describes a sensitive in vitro model assay system for detecting and measuring steroid hormone responsive cell growth.

The MTW9/PL2 Rat Mammary Tumor Cell Line. The properties of the MTW9/PL2 have been summarized (Moreno-Cuevas J E and Sirbasku D A *In Vitro Cell Dev Biol* 36, 410-427). The MTW9/PL cell line was established by our laboratory in culture from the carcinogen-induced hormone-responsive MT-W9A rat mammary tumor of a W/Fu rat. This tumor formed estrogen, androgen and progesterone responsive tumors in W/Fu rats (Sirbasku D A (1978) *Cancer Res* 38, 1154-1165). It was later used to derive the MTW9/PL2 cell population that was also estrogen-responsive in vivo (Danielpour D et al. (1988) *In Vitro Cell Dev Biol* 24, 42-52). In serum supplemented culture conditions the MTW9/PL2 cells demonstrate 80-fold steroid hormone growth responses. All sera used were steroid hormone-depleted by charcoal-dextran treatment at 34° C. The studies were done with horse serum as well as serum from other mammalian species. The growth of the MTW9/PL2 cells was biphasic in response to hormone-depleted serum. Concentrations of $\leq 5\%$ (v/v) promoted optimum growth. Above this concentration, serum was inhibitory. Concentrations $\geq 40\%$ (v/v) inhibited growth altogether. Addition of $1.0 \times 10^{-13}$ to $1.0 \times 10^8$ M 17-estradiol ($E_2$) reversed the inhibition completely. At $1.0 \times 10^{-8}$ M, $E_1$, $E_3$ and DES promoted growth as well as $E_2$. Testosterone and DHT promoted growth only at $10^{-7}$ M. Progesterone was effective at $10^{-6}$ M. Cortisol was ineffective. Labeled hormone binding analysis and Western immunoblotting documented that MTW9/PL2 cells had estrogen and progesterone receptors but not androgen or cortisol receptors. Estrogen treatment of MTW9/PL2 cells induced a concentration and time dependent increase in progesterone receptors. It was concluded that (1) the MTW9/PL2 population is the first highly steroid hormone responsive rat mammary tumor cell line to be established in culture from a carcinogen induced tumor and (2) sera from a number of species including horse, rat and human contain an inhibitor which mediates estrogen sensitive MTW9/PL2 cell growth in culture.

Estrogenic Effects with MTW9/PL2 Rat Mammary Tumor Cells in Cultures Supplemented with CDE-horse Serum. Unless otherwise stated, references in this and the following Examples to "CDE-horse serum" refer to the 34° C. charcoal-dextran extraction process described in above. The MTW9/PL2 cells were assayed for $E_2$ responsiveness in cultures supplemented with increasing concentrations of CDE-horse serum (FIG. 1A). Concentrations $\leq 5\%$ (v/v) promoted growth. Typically within seven days cell numbers increased from 6,000 per dish to more than 200,000 in 2 to 5% serum. This most likely resulted from stimulation by serum-borne growth factors as well as the mitogenic effect of transferrin (Danielpour D et al (1988) *In Vitro Cell Dev Biol* 24, 42-52; Riss T L and Sirbasku D A (1987) *In Vitro Cell Dev Biol* 23, 841-849; Riss T L et al. (1986) *J Tissue Culture Methods* 10, 133-150). As serum concentrations exceeded 5% (v/v), the effects of the growth promoters were counteracted by a serum-borne inhibitor(s). At serum concentrations of 30 to 50% (v/v), growth was completely inhibited. Usually only seed density cell numbers were found after seven days in cultures containing 50% (v/v) CDE-horse serum. In contrast, the presence of $1.0 \times 10^{-8}$ M $E_2$ completely reversed the serum dependent inhibition. In cultures supplemented with 20 to 50% (v/v) CDE-serum plus $1.0 \times 10^{-8}$ M $E_2$, cell numbers were $\geq 400,000$ per dish. Logarithmic quantifying of cell growth was done by converting the cell number data in FIG. 1A into CPD. A plot of these values is shown in FIG. 1B. The estrogenic effect is also presented. In FIG. 1B, the difference was maximum at 30% (v/v) CDE-horse serum. It was a 6.14 CPD or a 70-fold (i.e. $2^{CPD}$ or $2^{6.14}$) increase in cell numbers in response to $E_2$. In randomly selected replicate experiments (N=9) done over a two-year period with different preparations of CDE-horse serum, the average maximum estrogen effect ±SEM was 6.43 CPD±0.49 (range 5.63 to 7.22). This was an 86-fold ($2^{6.43}$) estrogenic effect. The modal concentration of serum that promoted maximum $E_2$ effects was 40% (range 20 to 50%).

Figure 2:
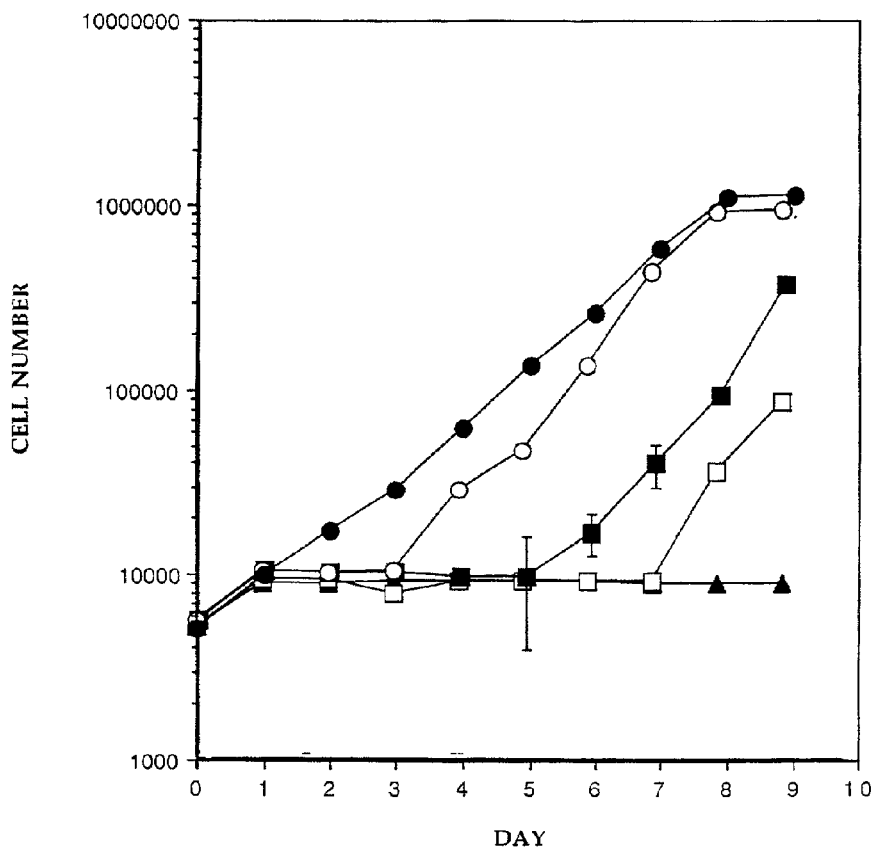
FIG. 2. Restoration of Growth by Addition of 10 nM $E_2$ on days 0, 2, 4 and 6 After Seeding the MTW9/PL2 cells into Inhibitory Medium Containing 50% (v/v) of CDE-horse serum.

Estrogen Reversibility of the Growth Inhibition Caused by CDE-horse Serum. It was examined whether inhibition caused by CDE-horse serum was reversible even after several days in culture (FIG. 2). The MTW9/PL2 cells were seeded into medium containing 50% (v/v) CDE-horse without $E_2$ and cell numbers monitored daily. Growth ceased within 48 hours; thereafter cell numbers remained static. In parallel cultures, addition of $E_2$ on days two, four, and six after seeding caused resumption of growth (after a lag period) at nearly the same rate as cultures that received hormone at the time of inoculation. These results show that the cells survived in the presence of the inhibitor without $E_2$ for at least six days. As described in a later Example, longer exposure to the purified inhibitors was cytotoxic and suggested therapeutic value.

Storage Stability of CDE-horse Serum. In Table 3, the effect of storage temperature on the estrogen mediating activity of CDE-horse serum is shown. The assays were done with MTW9/PL2 cells as shown in FIGS. 1A and 1B. Stability was assessed by four criteria: (i) the concentration of serum needed to give an estrogenic effect of 2.5 CPD (i.e. $ED_{2.5}$), (ii) the percent serum needed for the maximum estrogenic effect, and the magnitude of the estrogenic effects (CPD) at (iii) 20% and (iv) 30% serum. CDE-horse serum was stable at 23° C. for three weeks without loss of activity as assessed by all four criteria. Storage at 4° C. was detrimental within 24 days as measured by the CPD at 20% and 30% (v/v) serum concentrations. Longer storage at 4° C. was not advisable. Storage at −17° C. was most effective; the activity was unchanged even after 90 days. In experiments not shown, repeated freeze-thaw cycles caused an appreciable loss of inhibitor activity. The results in Table 3 show that serum stored frozen has utility for long periods and therefore provides a stable supply for testing of clinically relevant samples. Also, it is clear that clinical samples to be assayed for inhibitor can be stored for a few days at room temperature without damage.

TABLE 3

Summary of the Effects of Serum Storage Temperature on Activity.

| Days of Storage | % Serum needed for 2.5 CPD ($ED_{2.5}$) of $E_2$ Induced growth | Maximum $E_2$ Induced CPDs (% serum, v/v, for the maximum) | CPD at 20% (v/v) serum | CPD at 30% (v/v) serum |
|---|---|---|---|---|
| Storage at 23° C. | | | | |
| 1 | 2.1 | 4.9 (10%) | 5.0 | 3.2 |
| 3 | 5.2 | 5.4 (20%) | 6.2 | 5.2 |
| 6 | 5.0 | 4.2 (10%) | 3.5 | 0.9 |
| 14 | 2.9 | 6.0 (10%) | 4.3 | 2.6 |
| 23 | 4.0 | 6.3 (10%) | 3.9 | 2.5 |
| Storage at 4° C. | | | | |
| 1 | 1.8 | 5.9 (10%) | 4.9 | 4.0 |
| 7 | 6.8 | 5.7 (20%) | 6.4 | 5.4 |
| 15 | 3.8 | 4.1 (30%) | 5.5 | 4.2 |
| 24 | 5.3 | 5.3 (10%) | 1.0 | 2.8 |
| 44 | 3.0 | 4.8 (5%) | 0.04 | 0.26 |
| 55 | 2.2 | 5.0 (5%) | 0.00 | 0.24 |
| 90 | >50 | 2.1 (5%) | 0.30 | 0.40 |
| Storage at −17° C. | | | | |
| 1 | 2.6 | 5.2 (10%) | 5.0 | 3.1 |
| 7 | 4.0 | 5.8 (30%) | 6.8 | 5.8 |
| 44 | 3.3 | 5.8 (20%) | 6.0 | 5.4 |
| 90 | 6.1 | 5.2 (30%) | 6.2 | 5.9 |

Dose-Response Effects of Steroid Hormones in CDE-horse Serum. The dose effects of a number of steroid hormones were evaluated with MTW9/PL2 cells in medium containing 50% (v/v) CDE-horse serum. The results of one of these studies (N=3) are presented in FIG. 3. Estrogens were the most effective mitogens. Their order of potency was $E_2 > E_1 > E_3$. This relative potency was expected based on the affinities of these steroids for the estrogen receptors of other target tissues (Clark J H and Markaverich B M (1983) *Pharmacol Ther* 21, 429-453). The cell numbers in dishes containing $1.0 \times 10^{-13}$ M $E_2$ were 32-fold (p<0.01) higher than in dishes without the hormone. Concentrations of $1.0 \times 10^{-12}$ to $1.0 \times 10^{-11}$ M $E_2$ promoted 6.73 CPD that was a 110-fold estrogenic effect in seven days. The $ED_{50}$ of $E_2$ was about 0.5 to $1.0 \times 10^{-12}$ M. Using $E_1$ and $E_3$, optimum growth was achieved at $1.0 \times 10^{-9}$ and $1.0 \times 10^{-8}$ M, respectively. In experiments not shown, the mitogenic potency of the synthetic estrogen DES was assessed. At $1.0 \times 10^{-8}$ M, it caused the same growth as saturating concentrations of the natural estrogens. The DES effect was 6.98 CPD in seven days that was a 126-fold ($2^{6.98}$) increase in cell number. The next most potent hormone was DHT. It caused significant (p<0.05) growth at supraphysiologic concentrations $\geq 1.0 \times 10^{-8}$ M. Progesterone also caused significant growth, but only at supraphysiological concentrations $\geq 1.0 \times 10^{-7}$ M. Cortisol was ineffective at concentrations up to $1.0 \times 10^{-5}$ M.

Figure 4:
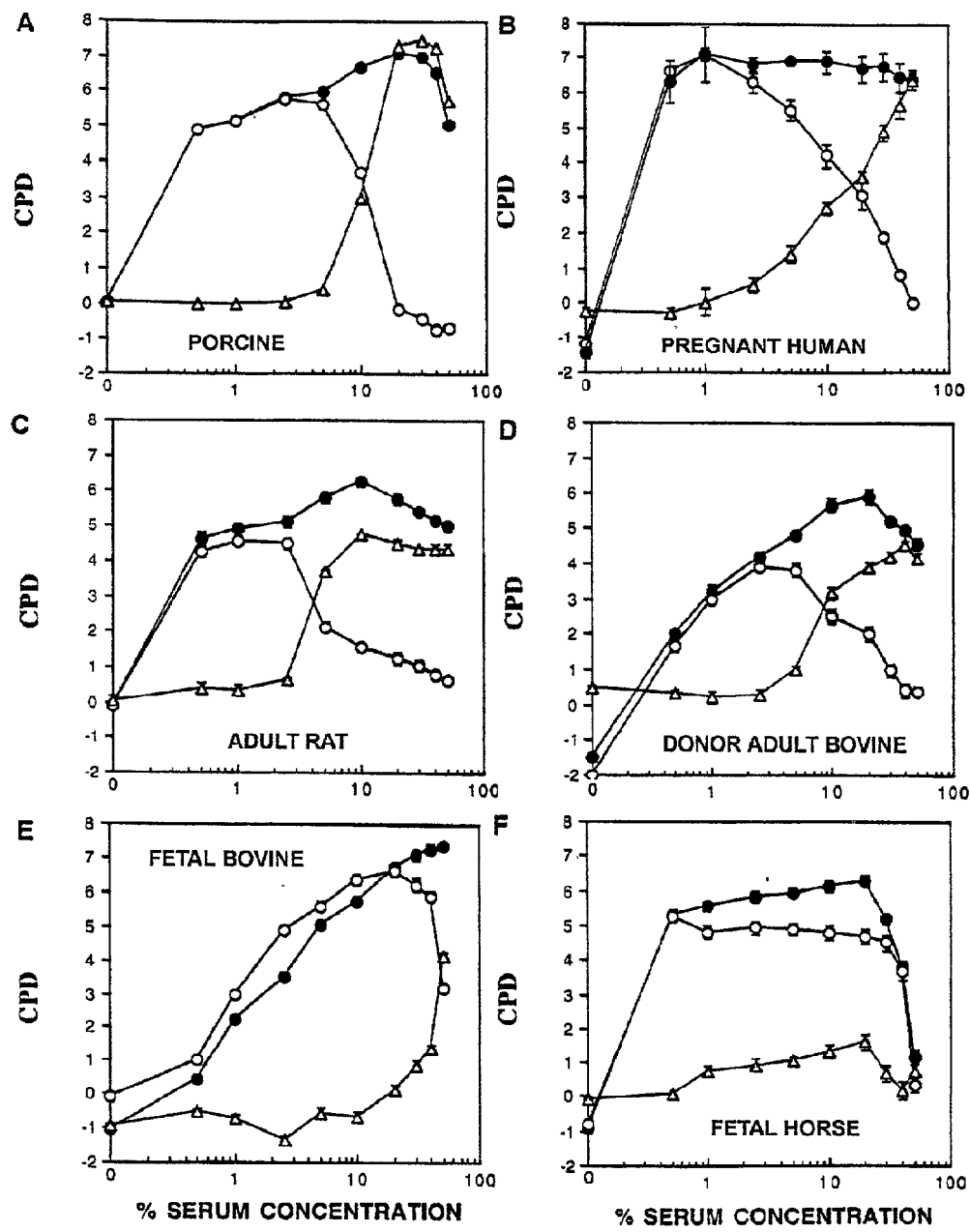
FIG. 4. MTW9/PL2 Cell Growth ±$E_2$ in Medium with CDE Sera from Several Species. (A) CDE-porcine Serum; (B) CDE-pregnant Human Serum; (C) CDE-adult Rat Serum; (D) CDE-adult Bovine Serum; (E) CDE-fetal Bovine Serum; (F) CDE-fetal Horse Serum.

Estrogen Mitogenic Effects with MTW9/PL2 Cells in CDE-serum from Several Species. Serum from species other than horse were examined to determine they also possessed estrogen reversible inhibitory activity with rat MTW9/PL2 cells. These experiments are shown in FIG. 4. All of the sera tested were charcoal dextran extracted at 34° C. CDE-porcine (FIG. 4A), and CDE-human serum (FIG. 4B) showed patterns nearly identical to that of CDE-horse serum. The maximum estrogenic effects with both sera were six to seven CPD (N=3). CDE-rat serum also showed the same pattern of estrogen reversible growth inhibition (FIG. 4C). CDE-ovine serum showed estrogen reversible inhibition equivalent to CDE rat serum (data not shown). With serum from rats, the maximum estrogenic effect was four to five CPD (N=4). CDE-bovine serum (adult donor herd) displayed the same pattern of activity as other sera (FIG. 4D). CDE-fetal bovine serum showed a different pattern (FIG. 4E). Even at 40% (v/v), there was no inhibition. With some batches of this serum, there was no inhibition even at 50% (N=2). With others (N=2), inhibition was found. In these experiments, the estrogenic effects reached three to four CPD in 50% (v/v) CDE-serum. Even with this variability, fetal bovine serum has less activity than the serum from the adults of this species. The assays with CDE-fetal horse serum (N=3) showed inhibition at 50% (v/v) that was not reversible by 10 nM $E_2$ (FIG. 4F).

Discussion of Example 3.

The MTW9/PL2 Cell Line as a Unique Rodent Test System. The present study shows very clearly that ($ER^+$) MTW9/PL2 cells are estrogen growth sensitive in culture and applicable to testing of serum or bodily fluid inhibitors or sex steroids in such preparations. The estrogen receptor content and estrogen affinity characteristics of the MTW9/PL2 cells indicate appropriate stability for commercial applications. The MTW9/PL2 population is the first highly steroid hormone-responsive rat mammary tumor cell line to be established in culture from a carcinogen-induced tumor". As a direct consequence of the information provided above, this cell line is a unique and valuable asset for combination in vitro and in vivo modalities to be applied to clinically and commercially significant compounds or preparations and for the assay of the inhibitor content or hormone or anti-hormone activities.

Technical Conditions for Demonstrating Estrogen Responsiveness in Culture and Evidence for a Serum-borne Inhibitor. Conditions that permit the observation of very large magnitude estrogen mitogenic effects with the permanent MTW9/PL2 cell line in culture are defined herein. As mentioned in the Background of the Invention, most existing rat mammary tumor cell lines are not suitable for use in evaluating hormone responsiveness in vivo because they are derived from outbred animals. This problem was overcome by developing the MTW9/PL2 rat mammary tumor cell line from a carcinogen-induced hormone responsive tumor (i.e. the MT-W9A tumor), first induced and transplanted in an inbred W/Fu rat as described (MacLeod R M et al. (1964) *Cancer Res* 75, 249-258). The MTW9/PL2 cells form hormone responsive tumors when implanted in these rats (Sirbasku D A (1978) *Cancer Res* 38, 1154-1165; Danielpour D and Sirbasku D A (1984) *In Vitro* 20, 975-980; Riss T L et al. (1986) *J Tissue Culture Methods* 10, 133-150). In culture, the MTW9/PL2 cells showed the same hormone responsiveness expected of rat and human breast epithelial cells, as shown herein and subsequently reported (Moreno-Cuevas J E and Sirbasku D A (2000) *In Vitro Cell Dev Biol* 36, 410-427; Sirbasku D A and Moreno-Cuevas J E (2000) *In Vitro Cell Dev Biol* 36, 428-446; Moreno-Cuevas J E and Sirbasku D A (2000) *In Vitro Cell Dev Biol* 36, 447-464).

The effects of the steroid hormones in culture were the same as described for the growth of the original MT-W9A tumor in W/Fu rats (MacLeod et al. (1964) *Endocrinology* 75, 249-258) and tumor formation by the parental MTW9/PL cell line in this same strain of rats (Sirbasku D A (1978) *Cancer Res* 38, 1154-1165). The present embodiment is the first established cell line derived from a carcinogen induced rat mammary tumor that continues to show large magnitude growth responses to estrogens, progesterone and androgens even after extended periods in culture, preferably when cultured under the conditions disclosed herein. Thyroid hormone responsiveness has also been demonstrated for MTW9/PL cells (Leland F E et al. (1981) In: *Functionally Differentiated Cell Lines*, Sato G, ed, Alan Liss, New York, pp 1-46). Of the other important hormones known to influence the growth of the original MT-W9A tumor, only prolactin remains to be investigated. Prolactin is not mitogenic for the parental MTW9/PL cells under serum-free defined conditions (Danielpour D et al. (1988) *In Vitro Cell Dev Biol* 24, 42-52). Continuing investigations are directed toward evaluating the possibility that prolactin also reverses the effects of the serum-borne inhibitor or otherwise acts as a cytokine to influence the production of immunoglobulins in breast and other mucosal tissues. The development of this cell line now permits not only sensitive steroid hormone growth analysis in culture, but also direct comparisons to the effectiveness of the same test substances in animals. No other such rat mammary system is currently available.

MTW9/PL2 Receptor Not Lost in Culture. The present results showing an average 86-fold MTW9/PL2 cell number increase in seven days in response to physiological concentrations of $E_2$ have several important technical implications. Most notably, they contradict many earlier explanations for why estrogen stimulated cell growth has been difficult to demonstrate in culture. Originally, the lack of estrogenic effects in culture was thought to be due to a dedifferentiation of cells that resulted in a loss of functional receptors or some other aberration that disrupted the growth response. In light of the present Disclosure, this explanation now seems very unlikely. The present results show the presence of similar levels of estrogen receptors in both the original MTW9/PL cell line reported in 1982 and the current MTW9/PL2 cells. Analyses made by others showing estrogen receptors in established cell lines in culture (Horwitz K B et al. (1978) *Cancer Res* 38, 2434-2437; Haug E (1976) *Endocrinology* 104, 429-437; Soto A M et al. (1988) *Cancer Res* 48, 3676-3680; Keydar I et al. (1979) *Eur J Cancer* 15, 659-670; Engel L W et al. (1978) *Cancer Res* 38, 3352-3364) also mitigate against this explanation. Furthermore, the estrogen receptors of the MCF-7 cells were functional based on the demonstration of estrogen inducibility of the progesterone receptor (Horwitz K B and McGuire W L (1978) *J Biol Chem* 253, 2223-2228). As with the human breast cancer cells, the MTW9/PL2 line was also significantly estrogen responsive by this criterion. When all of the available data is considered in light of the presently disclosed observations, the notion that long-term culture necessarily leads to loss of functional estrogen receptors is laid to rest. A major advantage of the MTW9/PL2 line is its long-term stability permitting series analyses over long periods of time without concern for cell property changes.

Figure 3:
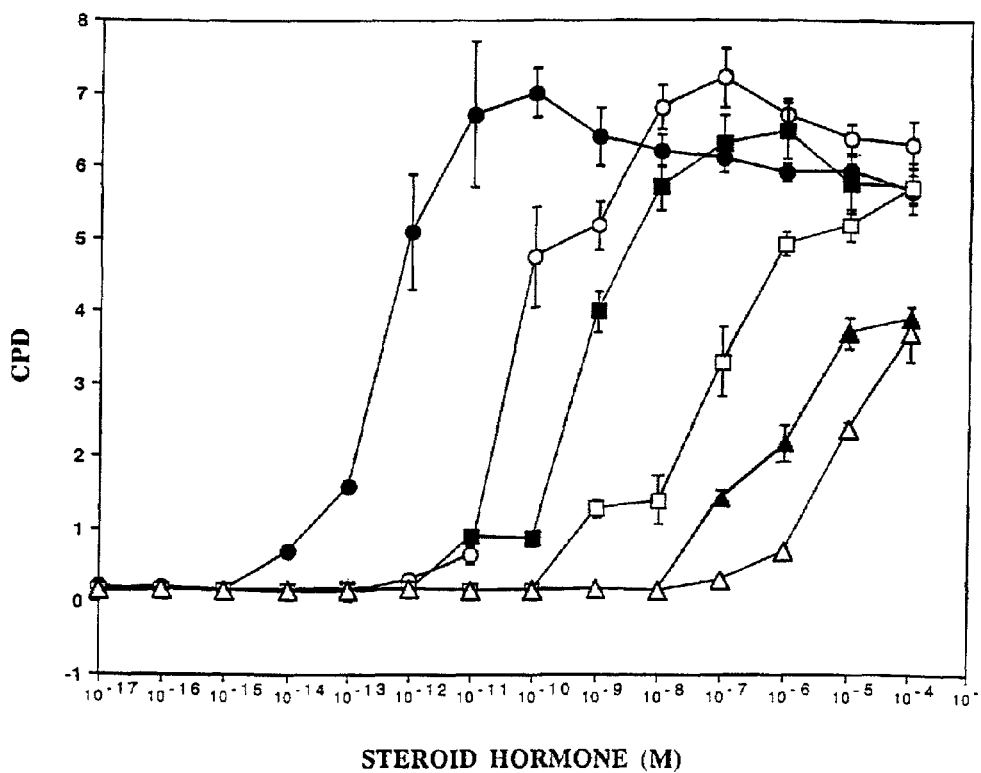
FIG. 3. Dose-Response Effects of Steroid Hormones on Growth of the MTW9/PL2 Cells in Medium Containing 50% (v/v) CDE-horse Serum.

Prolonged Steroid Hormone Retention by Culture Cells. It has been suggested that prolonged retention of estrogens might be the reason for a lack of responsiveness of target cells in culture (Strobl J S and Lippman M E (1979) *Cancer Res* 39, 3319-3327). Investigators have reported that the half-life of loss of specifically bound $^3H$-$E_2$ from MCF-7 cells was about 24 hours at 37° C. (Strobl J S and Lippman M E (1979) *Cancer Res* 39, 3319-3327). Cells from stock cultures grown in untreated/steroid hormone containing serum were proposed to retain stimulating levels of estrogens. Even several washes over 78 hours did not attenuate the problem (Strobl J S and Lippman M E (1979) *Cancer Res* 39, 3319-3327). Conversely, the studies herein did not identify this problem. All the assays reported here were done with cells taken directly from cultures grown in steroid hormone containing serum (e.g. fetal bovine serum). After trypsinization of the MTW9/PL2 cells from stock culture, only three careful washes with serum-free D-MEM/F-12 were performed before initiating the growth assays. The results in FIG. 3 show clearly that $1.0 \times 10^{-12}$ M $E_2$ caused significant MTW9/PL2 cell growth. Also, the results in FIG. 2 show that MTW9/PL2 cells cease proliferation within 48 hours of starting a growth assay. These observations either support the conclusion that prolonged steroid hormone retention by cells is not as serious an issue as first proposed or are evidence that the technical processes described herein to prepare cells for assays have eliminated this problem. With regard to the present investigation, all cell lines studied showed this same property when prepared by the same technical process for growth assays.

Merits of Charcoal Extraction. Other investigators have challenged the use of charcoal extraction to deplete serum of steroid hormones. It has been stated that this procedure absorbs or otherwise alters serum to make it ineffective (Amara J F and Dannies P S (1983) *Endocrinology* 112, 1141-1143; Wiese T E et al. (1992) *In Vitro Cell Dev Biol* 28A, 595-602). To counter this problem, either individual lots of untreated serum were used to seek estrogenic effects (Wiese T E et al. (1992) *In Vitro Cell Dev Biol* 28A, 595-602), or serum was prepared from animals after endocrine ablation surgery (Amara J F and Dannies P S (1983) *Endocrinology* 112, 1141-1143). One of the best examples of use of surgically depleted serum came from the study of the $GH_4C_1$ rat pituitary cells (Amara J F and Dannies P S (1983) *Endocrinology* 112, 1141-1143). They were highly $E_2$ responsive in medium supplemented with the serum from a gelded horse (Amara J F and Dannies P S (1983) *Endocrinology* 112, 1141-1143). However, experience with serum derived by these methods has not been as positive. For example, this issue was investigated in 1976 with the related $GH_3C_{14}$ rat pituitary tumor cell line (Kirkland W L et al. (1976) *J Natl Cancer Inst* 56, 1159-1164), and found that serum from ovariectomized sheep or adrenalectomized and ovariectomized sheep did not support estrogen effects. Furthermore, unextracted sera from different species can at times support limited estrogenic effects. However, the estrogenic effects are of lower magnitude than those in the CDE-serum described herein. The results are so variable that they typically exclude use as a clinical testing assay. Based on the observation that CDE-serum from a number of species was very effective, it seems highly unlikely that the now-disclosed preferred 34° C. procedure is deleterious. However, it is clear from other studies that the 56° C. charcoal method caused a temperature dependent loss of the inhibitor (data not shown). The presently described CDE-serum provides greater consistency and reproducibility than the other proposed approaches (Amara J F and Dannies P S (1983) *Endocrinology* 112, 1141-1143; Wiese T E et al. (1992) *In Vitro Cell Dev Biol* 28A, 595-602). Another advantage is that these results do not dependent significantly on the lot of serum purchased. Furthermore, CDE-serum consistently provides larger magnitude estrogenic effects than serum obtained by either of the other approaches discussed above.

Steroid Hormone Conjugates are Non-problematic. While charcoal treatment can be expected to remove the major classes of steroid hormones from serum, there is a question about its effect on the more soluble and potentially active conjugates. It has been reported that hydrolysis of estrogen sulfates provided free estrogens in human breast cancer cell cultures (Vignon F et al. (1980) *Endocrinology* 106, 1079-1086). This abrogated the effects of exogenous $E_2$. Although the previous investigations did not address estradiol sulfate, it was shown that more than 95% of estrone sulfate and estradiol glucuronide were removed from serum by a single 56° C.

charcoal extraction (Sirbasku D A and Kirkland W L (1976) *Endocrinology* 98, 1260-1272). Additionally, in previous studies MTW9/PL cells were incubated with tritium labeled estradiol glucuronide for up to 24 hours under cell culture conditions and found no organic solvent extractable free steroid. Both past and current results indicate that the impact of the estrogen conjugates has been overestimated. In the present study, no precautions were taken to remove the conjugated forms of estrogens from any of the sera tested. Despite this, it was found that many different types of serum were effective after charcoal extraction at 34° C. Thus, it is concluded that removal of steroid conjugates by digestion or any procedure beyond charcoal treatment is unnecessary. This is a further advantage of the new 34° C. method because the additional treatment to remove the steroid conjugates could be prohibitively expensive for larger scale production than a few liters, and could potentially introduce undesirable effects in the serum.

Plastic Product Use for Cell Culture. The present studies were done with plastic ware made of polystyrene. Plastic is manufactured using alkylphenols (Platt A E (1978) In: *Encyclopedia of Chemical Technology*, Kirk R E, Othmer D F, eds, 3$^{rd}$ Edition, Volume 26, Wiley, New York, pp 801-847). One of these compounds, p-nonyl-phenol, has been reported to be estrogenic for MCF-7 cells in culture (Soto A M et al. (1991) *Environ Health Perspect* 92, 167-173). This xenobiotic most likely is present in the cultures used in these studies. No precautions were taken to exclude compounds leaching from plastic. In fact, the bioassay procedures herein are done with polystyrene plastic ware and culture dishes almost exclusively. If there had been a significant contamination of the medium by such compounds, the estrogenic effects reported in this study should not have been seen or should have been markedly attenuated. An advantage of the assay systems described herein is that they have no need for expensive and or exotic substitutes for the common plastic ware used in cell culture laboratories to conduct bioassays. Also, the CDE-serum can be stored and shipped for commercial use in conventional plastic containers without concern for creation of plastic-induced artifacts. Clinical samples for assay can also be stored and shipped in common plastic ware.

Example 4

Estrogen Responsive Growth of Additional Rodent and Human Cell Lines in 34° C. Charcoal-Dextran Extracted Horse and Human Serum In addition to the above-described studies using the MTW9/PL2 rat mammary tumor cell line, several other cell lines were employed to define the conditions for demonstrating estrogen and androgen responsive cell growth. Established cell lines from a number of different steroid hormone target tissues were selected for growth regulation analysis under those defined conditions. Additional model cell growth assays for measuring steroid hormone responsive cell growth are described.

Figure 5:
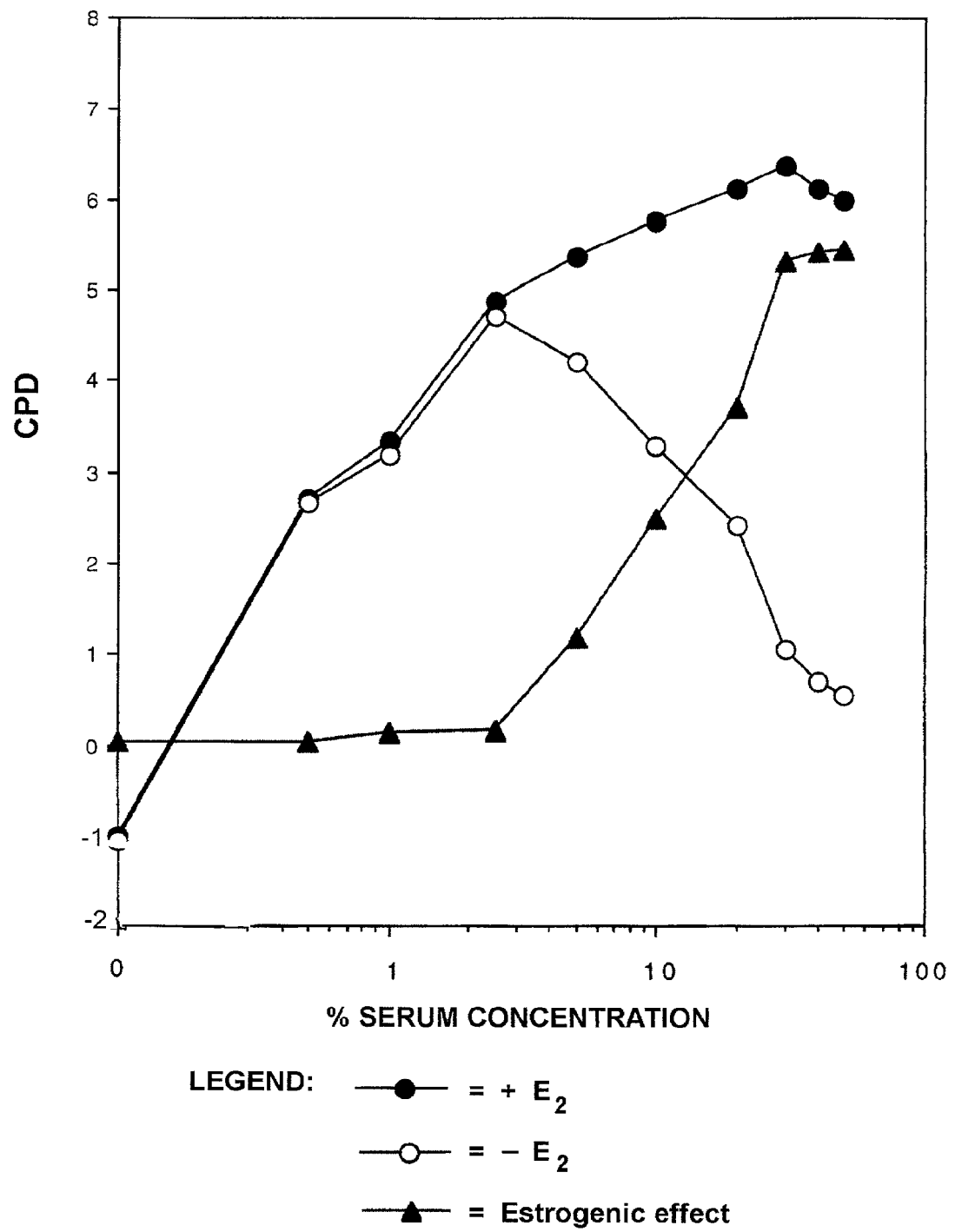
FIG. 5. CDE-horse Serum Effect on $GH_4C_1$ Cell Growth ±10 nM $E_2$ for 10 days.
Figure 6:
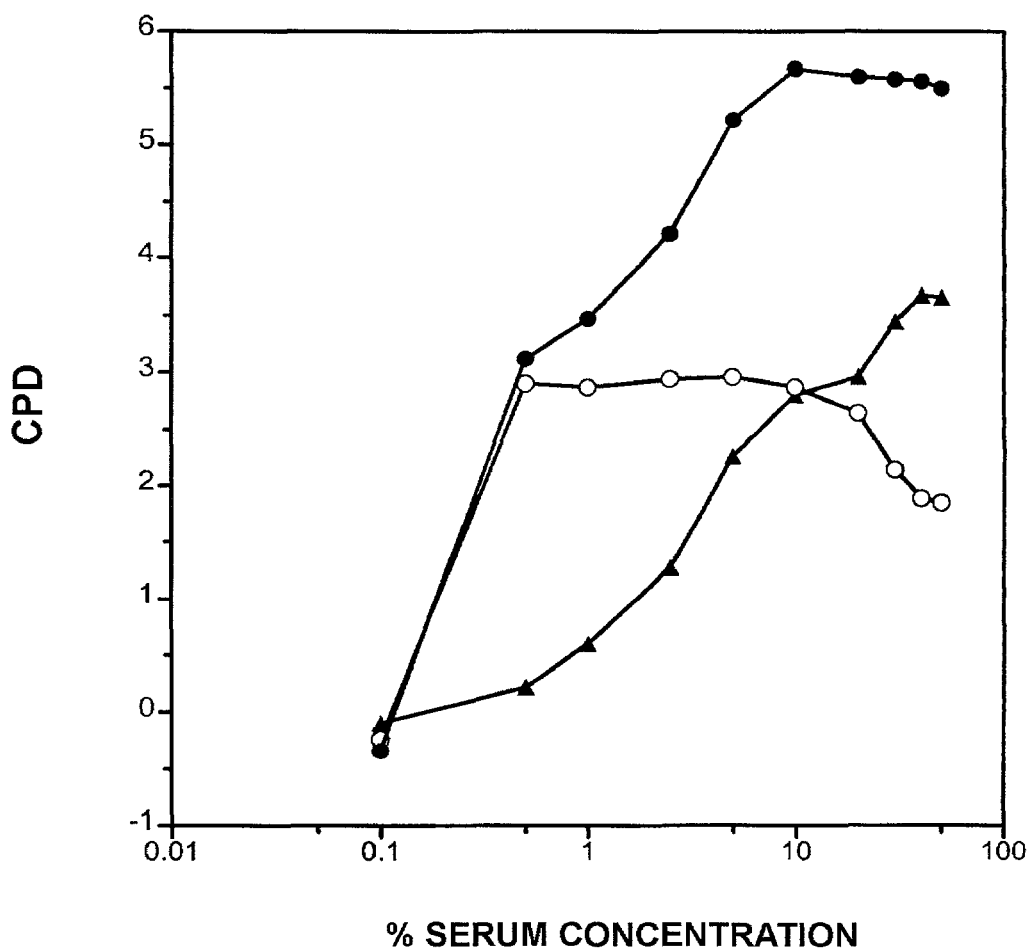
FIG. 6. CDE-horse Serum Effect on ZR-75-1 Cell Growth ±10 nM $E_2$ for 14 days.
Figure 7:
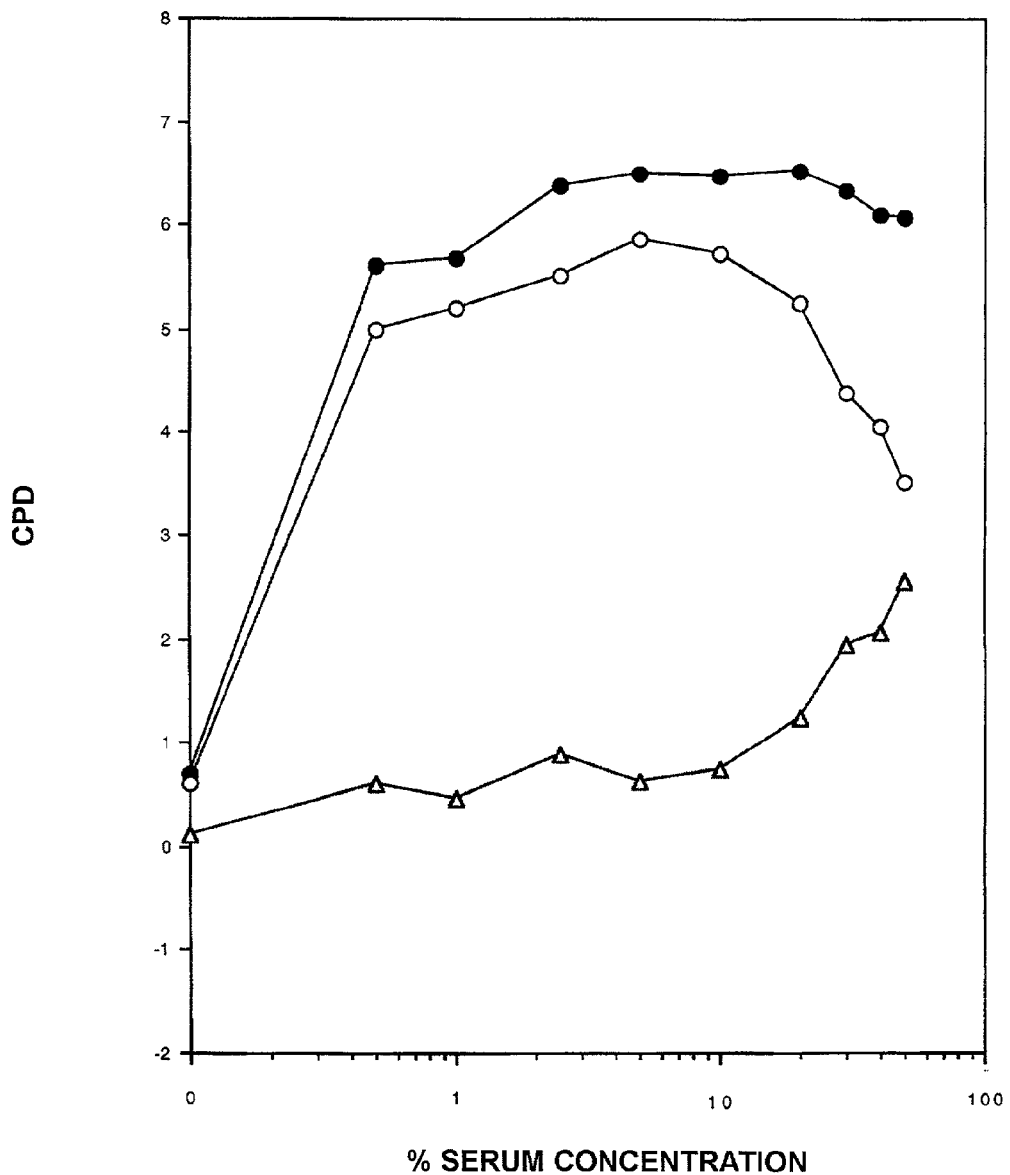
FIG. 7. CDE-horse Serum Effect on MCF-7A Cell Growth ±10 nM $E_2$ for 10 days.

Estrogen Mitogenic Effects with Established ER$^+$ Rodent Tumor and Human Carcinoma Cells in CDE-horse Serum. In the first study of this series, the three GH rat pituitary tumor cell lines were examined for estrogenic effects in CDE-horse serum. This was considered important in light of their clear responsiveness to many hormones (Tashjian A H Jr (1979) *Methods Enzymol* 58, 527-535). Furthermore, these cells are from a tissue that grows coordinately with mammary tissue in castrated rats administered exogenous estrogens. As described above, this suggested a common regulation mechanism. FIG. 5 shows an estrogenic effect $\geqq 5$ CPD with GH$_4$C$_1$ cells in 10 days. The results with GH$_3$ and GH$_1$ cells ranged between 4.0 and 5.2 CPD in 10 to 14 day assays (data not shown). The same progressive estrogen reversible CDE-serum inhibition was demonstrable with both rat mammary and rat pituitary tumor cells in CDE-horse serum. To confirm the effectiveness CDE-horse serum with human cells, the ZR-75-1 breast cancer line was selected because of previous attempts to demonstrate its estrogen responsiveness in culture (Allegra J C and Lippman M E (1978) *Cancer Res* 38, 3823-3829; Darbre P D et al. (1984) *Cancer Res* 44, 2790-2793; Darbre P et al. (1983) *Cancer Res* 43, 349-355). The ZR-75-1 cells showed the same CDE-serum caused estrogen reversible inhibition as seen with rodent cell lines in this serum. In 14 days, there was a 3.65 CPD (i.e. 12.5-fold) estrogenic effect (FIG. 6). This was a greater response than recorded in the ZR-75-1 cell studies cited above. Of all of the cell lines studied, the MCF-7A was the least estrogen responsive even in 50% CDE-horse (FIG. 7). The estrogenic effect was 2.65 CPD in 10-12 days. This was still significant ($p<0.01$) as a $2^{2.65}$ or 6.3-fold increase in cell number caused by estrogen. The present serum-derived inhibitor exhibited biological activity exactly opposite the estrogen reversible inhibitors described by M Tanji et al. (Tanji M et al. (2000) *Anticancer Res.* 20, 2779-2783; Tanji M et al. (2000) *Anticancer Res.* 20, 2785-2789).

Additional Cell Lines Evaluated. Evidence is presented herein that the MCF-7K, T47D, LNCaP, and H301cells are highly sex steroid hormone responsive in CDE-horse serum.

Kinetics of Estrogen Responsive Growth in CDE Serum Containing Medium. In the experiments presented in FIGS. 8A and 8B, ER$^+$ cell growth was measured daily for 15 days to determine cell growth kinetics $\pm$E$_2$. The results with the T47D line are presented as characteristic of human cells. When evaluated in medium with partially inhibitory 20% (v/v) CDE horse serum, the effect of E$_2$ on cell number increase was not apparent until after 4 days (FIG. 8A). Increasing the concentration of CDE serum to 50% (v/v) further delayed the effect of E$_2$ (FIG. 8B). Clearly, whatever mechanism is proposed for the action of the steroid hormone, it takes a significant period to reverse the effects of the inhibitor. This process cannot be simply due to a rapid effect on transcription caused by steroid hormones. The interaction of $^3$H-E$_2$ with intracellular estrogen receptors saturates in $\leqq 1$ hour at 37° C. (Horwitz K B and McGuire W L (1978) *J Biol Chem* 253, 8185-8191; MacIndoe J H et al. (1982) *Steroids* 39, 245-258; Moreno-Cuevas J E and Sirbasku D A (2000) *In Vitro Cell Dev Biol* 36, 410-427), while de novo hormone induced protein synthesis requires only a few hours (Beato M (1989) *Cell* 56, 335-344). Based on a growth lag of $\geqq 4$ days, it is likely that steroid hormones initiate a cascade of signaling events that are more complex than recognized today. To demonstrate that the lag period was related to the inhibitor, T47D growth was monitored daily in D-MEM/F-12 supplemented with 10% (v/v) fetal bovine serum (FIG. 8A). This concentration of fetal bovine serum shows no inhibitor (Moreno-Cuevas J E and Sirbasku D A (2000) *In Vitro Cell Dev Biol* 36, 410-427). Cell growth in medium with fetal bovine serum showed at most a one or two day lag period.

Figure 9:
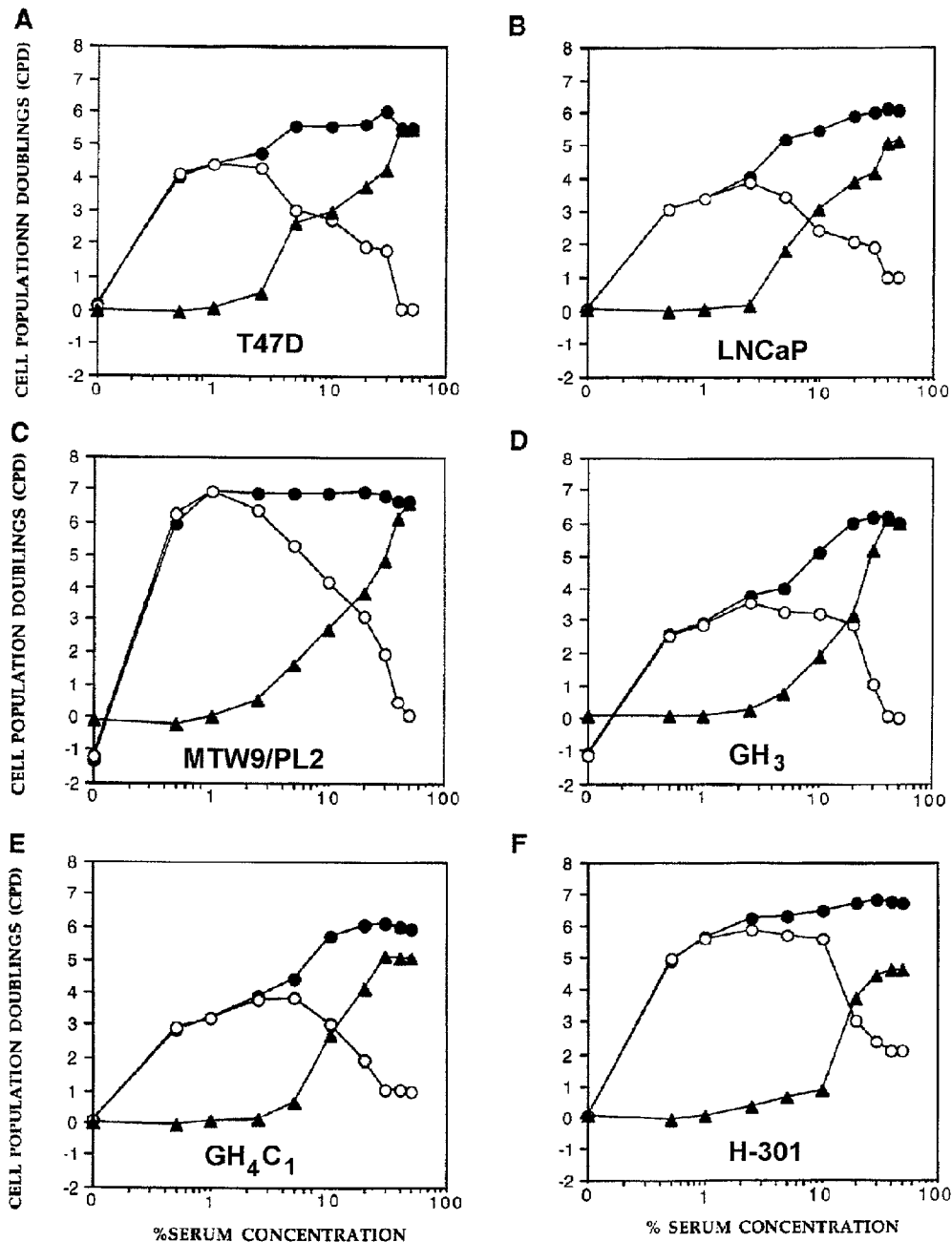
FIG. 9. Rodent and Human ER$^+$ Cell Line Growth in 50% CDE-human Serum ±$E_2$. (A) T47D Human Breast Cancer Cells; (B) LNCaP Human Prostate Cancer Cells; (C) MTW9/PL2 Rat Mammary Tumor Cells; (D) $GH_3$ Rat Pituitary Tumor Cells; (E) $GH_4C_1$ Rat Pituitary Tumor Cells (F) H301 Syrian Hamster Kidney Tumor Cells.

Effect of CDE-human Serum on Estrogen Responsive Cell Growth. The next study examined whether human serum was a source of inhibitor for steroid hormone sensitive cell lines from different species and tissues. The results confirm that CDE-human serum contains approximately the same level of inhibitor as CDE-horse serum. Results are shown with T47D human breast cancer cells (FIG. 9A), LNCaP human prostatic carcinoma cells (FIG. 9B), MTW9/PL2 rat mammary tumor cells (FIG. 9C), two GH rat pituitary tumor cell lines (FIGS. 9D and 9E), and the Syrian hamster H301 kidney tumor cells (FIG. 9F). All lines showed the same biphasic response to CDE-human serum. Low concentrations (i.e. ≦10%) promoted growth whereas higher concentrations (i.e. ≧20%) progressively inhibited growth. Only the absolute magnitudes of the estrogenic effects varied. Replicate assays with MCF-7A, MCF-7K and ZR-75-1 cells gave the same outcomes (data not shown). The experiments reported thus far herein support the conclusion that the inhibitor is ubiquitous in mammals and is not species specific, also subsequently reported (Sirbasku D A and Moreno-Cuevas (2000) *In Vitro Cell Dev Biol* 36, 428-446).

Figure 10:
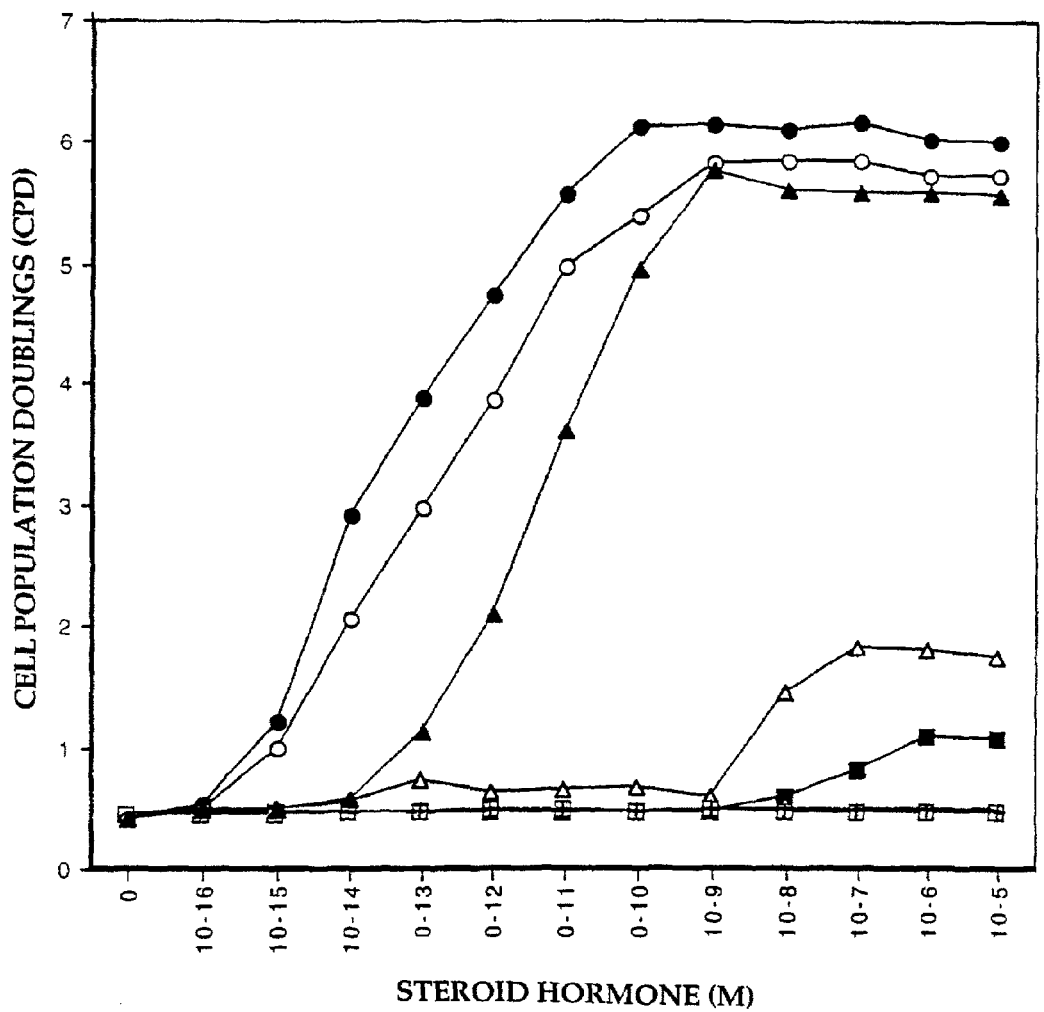
FIG. 10. Dose-Response of Steroid Hormones with T47D Cells in 50% CDE-horse Serum.

Dose-response Effects of Steroid Hormones with Human Breast Cancer Cells in CDE Serum. The studies presented thus far have assessed estrogen effects using 10 nM $E_2$. Although 10 nM saturates growth, it is decidedly at the high boundary of physiological. It is important to note that circulating estrogens in non-pregnant females are generally thought to be in the range of $10^{-8}$ to $10^{-10}$ M (Clark J H et al. In: *Williams Textbook of Endocrinology* (1992), Saunders, Philadelphia, pp 35-90). Tissue concentrations are generally conceded to be lower due to SHBG that reduces the "free" or "active" form of sex steroid hormones (Rosner W (1990) *Endocr Rev* 11, 80-91). The next studies with T47D cells determined the effective concentration ranges for the three most common estrogens and compared these to non-estrogen steroid hormones. FIG. 10 shows an analysis with T47D cells in D-MEM/F-12 containing 50% (v/v) CDE horse serum for 14 days. Estrogens were the only physiologically relevant activators of T47D growth. As expected from previous studies with breast cancer cells (Lippman M E et al. (1977) *Cancer Res* 37, 1901-1907; Jozan S et al. (1979) *J Steroid Biochem* 10, 341-342; Katenellenbogen B S (1980) *Annu Rev Physiol* 42, 17-35) and other estrogen target tissues (Clark J H and Markaverich B M (1983) *Pharmacol Ther* 21, 429-453), their order of effectiveness was $E_2 > E_1 > E_3$. $E_2$ caused significant (p<0.05) growth when present at $1.0 \times 10^{-14}$ M and optimum growth at $1.0 \times 10^{-10}$ M. Higher concentrations were not inhibitory. The $ED_{50}$ concentration of $E_2$ was $\leq 1.0 \times 10^{-13}$ M. It is noteworthy that even $E_3$ was remarkably potent. Others also had commented that $E_3$ was more potent than expected (Lippman M E et al. (1977) *Cancer Res* 37, 1901-1907). This observation may have special significance because breast cancers that appear during pregnancy can be particularly life threatening. Human maternal plasma has greatly elevated levels of $E_3$ during the last trimester of pregnancy. Testosterone and DHT promoted growth but only at supraphysiological concentrations (FIG. 10). Other investigators have suggested that supraphysiological concentrations of androgens act through the ER of human breast cancer cells (Zava D T and McGuire W L (1978) *Science* (Wash D.C.) 199, 787-788). However, another group has reported no effect of androgens on human breast cancer cell proliferation (Soto A M and Sonnenschein C (1985) *J Steroid Biochem* 23, 87-94). In the present study, progesterone and cortisol were completely ineffective with T47D cells (FIG. 10). Others have also reported negative results with these hormones and human breast cancer cells (Schatz R W (1985) *J Cell Physiol* 124, 386-390; Soto A M and Sonnenschein C (1985) *J Steroid Biochem* 23, 87-94). The data presented in this Disclosure support the conclusion that the new CDE serum culture conditions yield physiologically relevant information.

Figure 11:
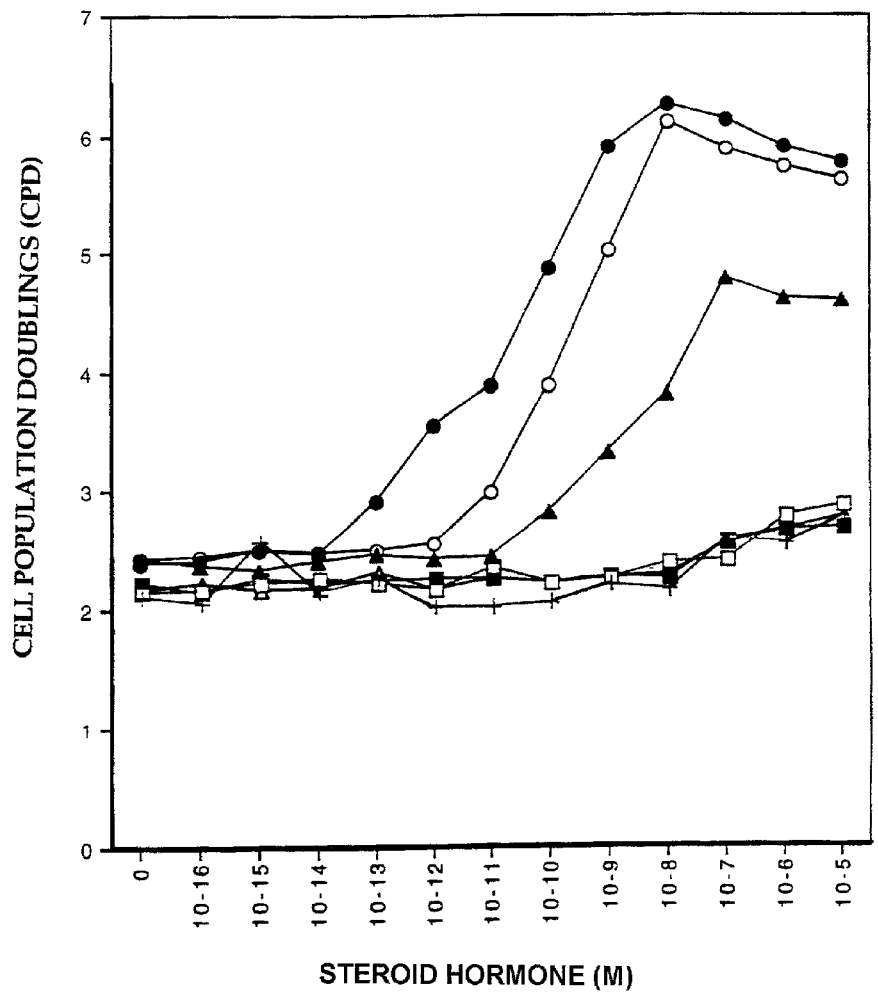
FIG. 11. Dose-Response of Steroid Hormones with $GH_4C_1$ Cells in 50% CDE-horse Serum.

Dose-response Effects of Steroid Hormones with Rat Pituitary Tumor Cells in CDE Serum. The GH family of related cell lines responds to a number of different classes of hormones (Amara J F and Dannies P S (1983) *Endocrinology* 112, 1141-1143; Tashjian A H Jr et al. (1970) *J Cell Biol* 47, 61-70; Tashjian A H Jr (1979) *Methods Enzymol* 58, 527-535; Haug E (1979) *Endocrinology* 104, 429-437; Schonbrunn A et al. (1980) *J Cell Biol* 85, 786-797; Sorrentino J M et al. (1976) *J Natl Cancer Inst* 56, 1159-1164; Ramsdell J S (1991) *Endocrinology* 128, 1981-1990; Hayashi I et al. (1978) *In Vitro* 14, 23-30; Faivre-Bauman A et al. (1975) *Biochem Biophys Res Commun* 67, 50-57). These cells also form steroid hormone responsive tumors in W/Fu rats (Sorrentino J M et al. (1976) *J Natl Cancer Inst* 56, 1149-1154). The $GH_4C_1$ strain was selected as an example for this next study because of its marked $E_2$ responsiveness in culture (Amara J F and Dannies P S (1983) *Endocrinology* 112, 1141-1143; Sirbasku D A and Moreno-Cuevas J E (2000) *In Vitro Cell Dev Biol* 36, 428-446; Sato H et al. (1991) *In Vitro Cell Dev Biol* 27A, 599-602) and estrogen requirement for tumor formation in rats (Riss T L and Sirbasku D A (1989) *In Vitro Cell Dev Biol* 25, 136-142). The dose-response effect of steroid hormones with $GH_4C_1$ rat pituitary tumor cells in 50% CDE-horse serum was analyzed next. FIG. 11 shows the results of these experiments. All three major estrogens promoted growth. The potencies of $E_2$ and $E_1$ were equivalent whereas $E_3$ was substantially less effective. Even at supraphysiologic concentrations, $E_3$ did not promote the saturation densities seen with $E_2$ and $E_1$. The lowest concentration of $E_2$ and $E_1$ that gave significant (p<0.05) growth was $1.0 \times 10^{-12}$ M. The $ED_{50}$ of $E_2$ was $\leq 1.0 \times 10^{-11}$ M. Optimum growth required supraphysiological concentrations (i.e. $1.0 \times 10^{-8}$ M) of $E_2$ and $E_1$. In the present studies, the biphasic effect of $E_2$ reported by Amara and Dannies (Amara J F and Dannies P S (1983) *Endocrinology* 112, 1141-1143) was not found. This may be explained by the different conditions used to conduct the assays. The matter of assay culture conditions with $ER^+$ cells has been discussed (Zugmaier G et al. (1991) *J Steroid Biochem Mol Biol* 39, 681-685). Certainly however, the low $E_2$ concentration for $ED_{50}$ still speaks to a problem with ERα as the mediating receptor. Furthermore, the pattern reported in this Example is consistent with physiological facts. Tumor formation by GH cells was greater in W/Fu rats treated with 25 mg estrogen pellets than in untreated intact sexually mature females (Sorrentino J M et al. (1976) *J Natl Cancer Inst* 56, 1149-1154). Without a doubt, supraphysiological levels of estrogens were most effective in vivo. In contrast to estrogens, progesterone and cortisol had no effect on $GH_4C_1$ growth in culture FIG. 11. These steroids also did not promote GH cell tumor growth in vivo (Sorrentino J M et al. (1976) *J Natl Cancer Inst* 56, 1149-1154). The findings with androgens and $GH_4C_1$ cell growth shown in FIG. 11 revealed another important contribution made by the work in CDE serum supplemented cultures described herein. The Inventor had shown before that T promoted GH tumor growth in vivo (Sorrentino J M et al. (1976) *J Natl Cancer Inst* 56, 1149-1154). It was proposed at that time that T was effective because it was metabolized to estrogens in the rat. Therefore, it was expected that T would be ineffective in culture. The results in FIG. 11 confirm this expectation. In this case, the new culture methods permitted resolution of an issue arising from previous in vivo observations. The dose-response results in FIG. 11 fortify a conclusion arrived at earlier that cell culture can be used to uncover physiologically important new information not accessible by in vitro methods (McKeehan W L et al. (1990) *In Vitro Cell Dev Biol* 26, 9-23).

Dose-response Effects of Steroid Hormones with Hamster Kidney Tumor Cells in CDE Serum. To explore the utility of the new culture conditions further, steroid hormone effects on the H301 Syrian hamster kidney tumor cells in D-MEM/F-12 containing 50% (v/v) CDE-horse serum were investigated.

Figure 12:
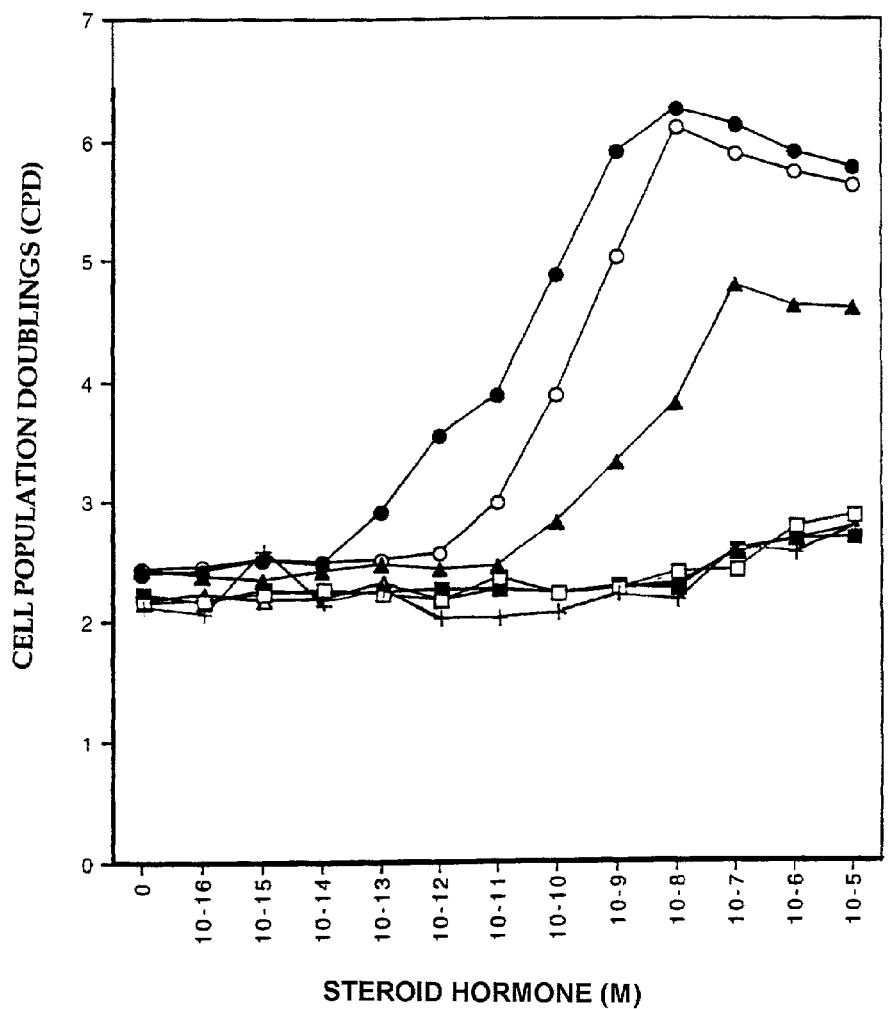
FIG. 12. Dose-Response of Steroid Hormones with H301 Cells in 50% CDE-horse Serum.

This cell line has two unique characteristics. First, tumors form from H301 cells in Syrian hamsters only in response to exogenous estrogens (Sirbasku D A and Kirkland W L (1976) *Endocrinology* 98, 1260-1272). It is very important to note that normal physiologic levels in intact adult female hamsters do not support tumor formation (Sirbasku D A and Kirkland W L (1976) *Endocrinology* 98, 1260-1272). It is thought that progesterone from the normal estrus cycle suppresses growth in response to physiological levels of estrogen (Kirkman H and Robbins M (1959) In: *National Cancer Institute Monograph No. 1*, National Institutes of Health, Bethesda, Md.). Second, these cells only form tumors in response to estrogens. The other major classes of steroid hormones are ineffective in vivo. The relative effectiveness of the three estrogens with H301 cells was investigated (FIG. 12). Their potency was $E_2 > E_1 > E_3$. As with rat tumor cells, $E_3$ was markedly less effective than $E_2$ or $E_1$. $E_2$ and $E_1$ required $1.0 \times 10^{-11}$ M and $1.0 \times 10^{-10}$ M, respectively, to achieve significant ($p<0.05$) growth. The $ED_{50}$ concentration of $E_2$ is about 5 to $9 \times 10^{-11}$ M. As expected from in vivo results (Sirbasku D A and Kirkland W L (1976) *Endocrinology* 98, 1260-1272), this concentration was higher than for the rat pituitary tumor cells (FIG. 11) or rat mammary tumor cells (FIG. 3). In fact, they were as much as 100 to 1000-fold higher than for human breast cancer cells (FIG. 10). In other tests shown in FIG. 12, progesterone, cortisol, T and DHT were all inactive. The higher estrogen concentrations required for significant growth of the H301 cells in culture, coupled with the marked estrogen specificity as is seen in vivo (Sirbasku D A and Kirkland W L (1976) *Endocrinology* 98, 1260-1272), indicate that the medium conditions used in this study yielded physiologically germane results.

Figure 13:
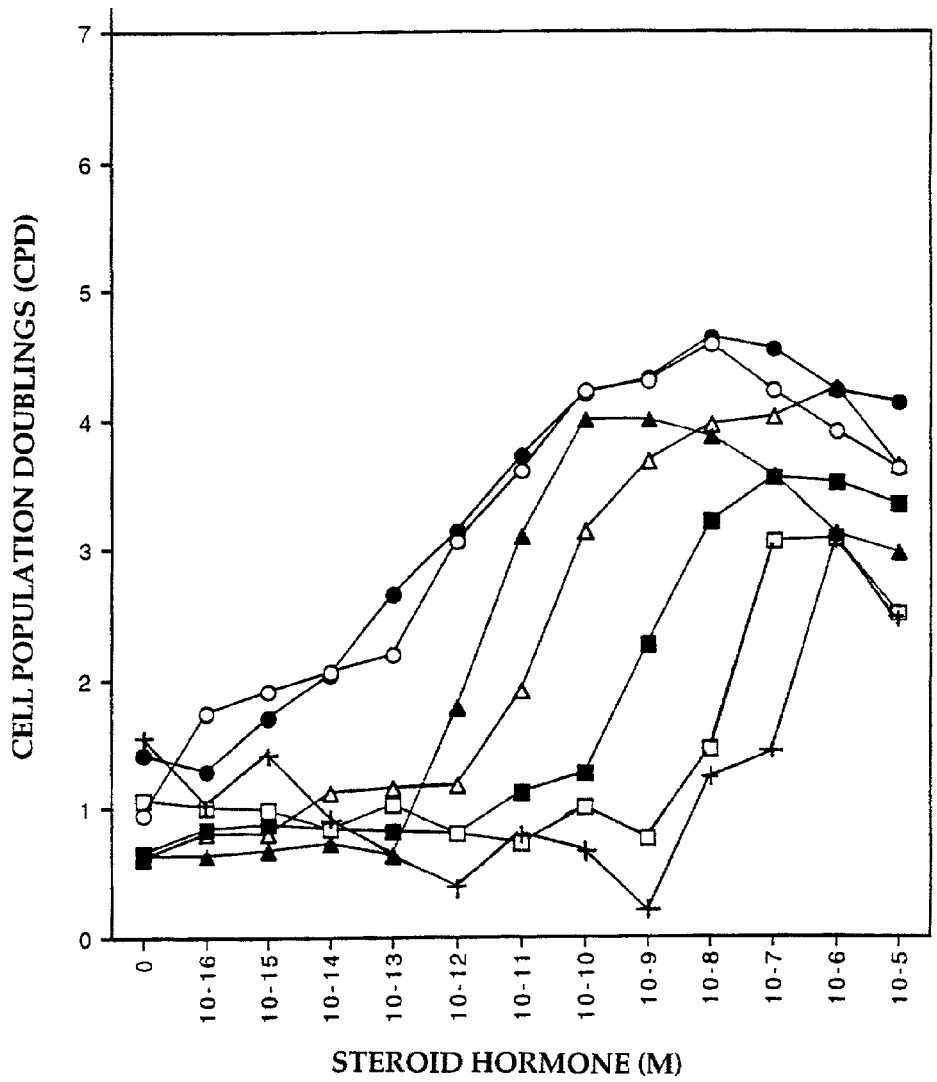
FIG. 13. Dose-Response of Steroid Hormones with LNCaP Cells in 50% CDE-horse Serum.

Dose-response Effects of Steroid Hormones with Human Prostatic Carcinoma Cells in CDE Serum. In the final dose-response study, the potency of several classes of steroid hormones with the LNCaP cells was analyzed. This was done in D-MEM/F-12 containing 50% (v/v) CDE horse serum. Due to a point mutation which permits binding of both androgen and non-androgen hormones to the AR of LNCaP cells (Veldscholte J et al. (1990) *Biochem Biophys Res Commun* 173, 534-540; Veldscholte J et al. (1990) *Biochim Biophys Acta* 1052, 187-194), the Inventor expected several classes of steroids to promote growth, albeit at concentrations compatible with their known affinities for the mutated receptor. This proved to be the case, as shown in FIG. 13. DHT and $E_2$ were the most potent steroids. In fact, they were equipotent. Both caused significant ($p<0.05$) growth at $1.0 \times 10^{-12}$ M. Contrary to other reports (Schuurmans A L et al. (1988) *The Prostate* 12, 55-64; Sonnenschein C et al. (1989) *Cancer Res* 49, 3474-3481; de Launoit Y et al. (1991) *Cancer Res* 51, 5165-5170; Lee C et al. (1995) *Endocrinology* 136, 796-803; Kim I et al. (1996) *Endocrinology* 137, 991-999), the present study did not find that high concentrations of DHT inhibited LNCaP growth. The potency of the steroid hormones tested was $DHT=E_2>T>E_1>$progesterone$>E_3>$cortisol. As potencies declined, saturation densities also decreased. The observed relative steroid potencies agreed with those of others (Belanger C et al. (1990) *Ann NY Acad Sci* 595, 399-402), and correlated with the expected binding of the various classes of steroids to the mutated AR of the LNCaP line. Additionally, the presently disclosed methods offered the advantage of greater growth responses. The results in FIG. 13 not only lend support to the view that cultures containing a high concentration of CDE serum yield physiologically relevant information, but they also demonstrate that the new charcoal extraction method disclosed herein effectively depletes several classes of steroid hormones.

Discussion of Example 4. The methods presented in this Example show that mitogenic effects of estrogens and androgens can now be measured at the picomolar level. These highly sensitive assays can be used advantageously to assess clinical samples for inhibitor concentrations (after steroid depletion) of to establish that sufficient estrogens are present to cause growth possibly in postmenopausal women. The concentrations that are measurable fall well below radioimmunoassay concentrations and will give an accurate measure of the active estrogen (i.e. unbound) versus the total determined by conventional procedures akin to radioimmunoassays. The results provided herein present a new approach to the question of why postmenopausal women have sufficient levels of estrogens to promote breast cancer cell growth. It is well known that $\geq 65\%$ of the breast cancers in postmenopausal women are estrogen receptor positive. The results herein indicate that these cancers are so sensitive to estrogens that even a reduced physiological concentration is sufficient to cause growth. Breast cancer prevention by anti-hormone therapy must be evaluated on this new basis.

The results demonstrate clearly that serum contains at least one estrogen reversible inhibitor and that it/they mediates physiologically relevant sex steroid responses. The fact that CDE-horse serum is effective with several cell lines of rodent and human origins indicates that the inhibitor or inhibitors are not species specific. Moreover, the fact that all of the $ER^+$ cell lines responded similarly in these studies to the different types of serum tested indicates that the inhibitor or inhibitors are ubiquitous in mammals. This suggests an important physiologic fact. Estrogen target tissue growth is coordinate in vivo. Administration of the hormone causes mitogenic effects in all of the major target tissues such as breast, uterus, ovaries, female genital tract, pituitary and specialized other tissues and cells. Therefore, the studies presented imply that the inhibitor or inhibitors should be active with several target tissues.

The results presented in this Example have special significance with regard to support for the conclusion that a new ERγ regulates growth. In these studies, growth is one-half maximally stimulated by 10-1,800 fold lower concentrations of $E_2$ than indicated by the Kd values expected of the classical ERα. According to the accepted theory of hormone binding, the $K_d$ value represents the steroid concentration that one-half saturates the existing receptors. The following Table 4 summarizes the $ED_{50}$ concentrations required for a one-half maximum growth in medium containing 30 to 50% (v/v) CDE-serum versus the estrogen receptor $K_d$ measured for the same or closely related cell lines. The new receptor is discussed further in a later Example.

TABLE 4

Comparisons of $ED_{50}$ and $K_d$ as Evidence Supporting a New ER Designated ERγ

| Cell Line | $ED_{50}$ for $E_2$ Induced Growth | $K_d$ for $E_2$ | Fold-higher $K_d$ Concentration Compared to $ED_{50}$ for Growth |
|---|---|---|---|
| MTW9/PL2 | $1 \times 10^{-12}$ M | $1.8 \times 10^{-9}$ M | $1.8 \times 10^3$ |
| T47D | $1 \times 10^{-12}$ M | $0.11 \times 10^{-9}$ M | $1.1 \times 10^3$ |
| $GH_4C_1$ | $1 \times 10^{-11}$ M | $0.25 \times 10^{-9}$ M | 25 |
| H301 | $9 \times 10^{-11}$ M | $0.87 \times 10^{-9}$ M | 10 |

Example 5

Thyroid Hormone Growth Effects in CDE-Horse Serum Prepared at 34° C.

Figure 14:
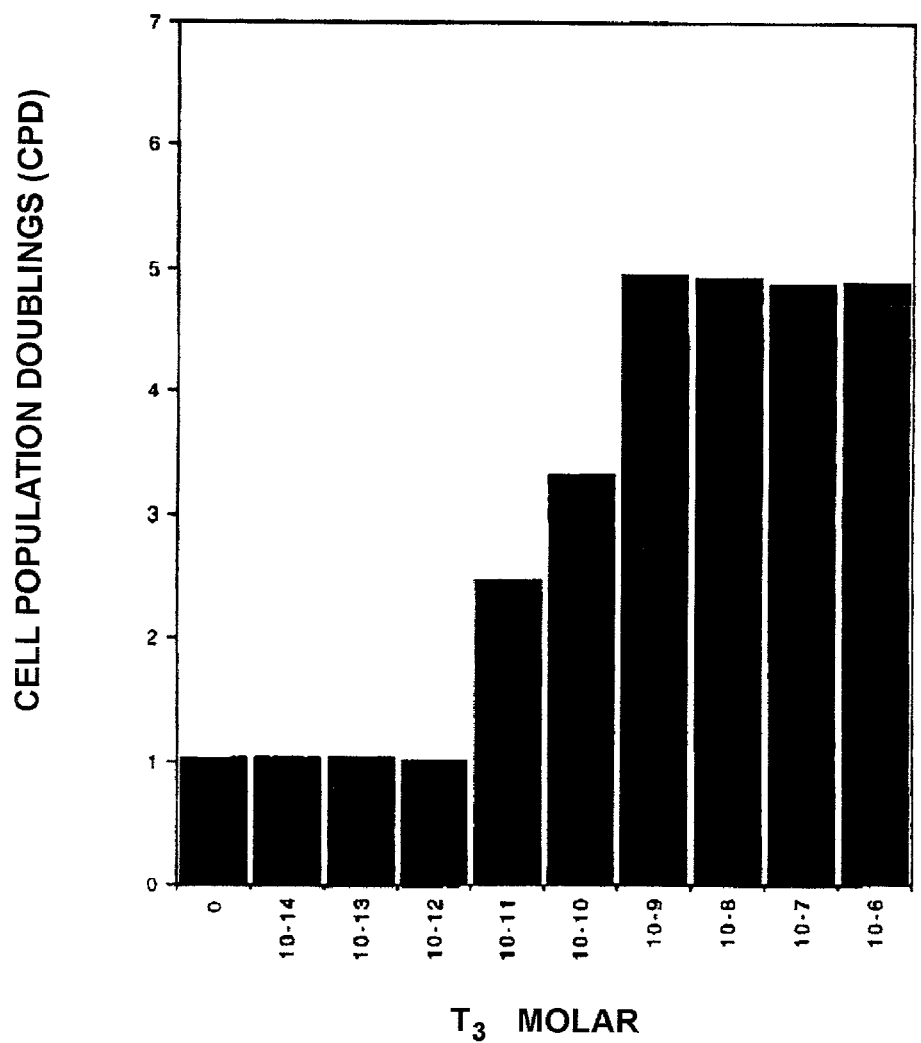
FIG. 14. $T_3$ Growth Effects with $GH_3$ Cells in Serum-free Medium (PCM).
Figure 15:
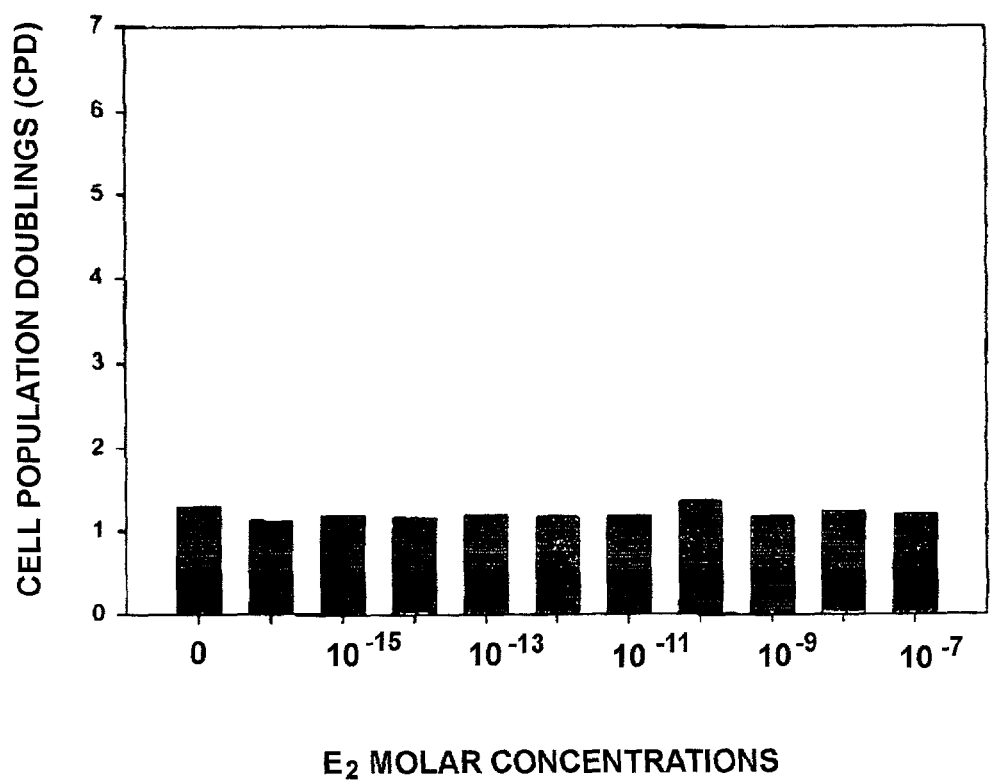
FIG. 15. $E_2$ Growth Effects with $GH_3$ Cells in Serum-free Medium (PCM) Minus $E_2$.
Figure 16:
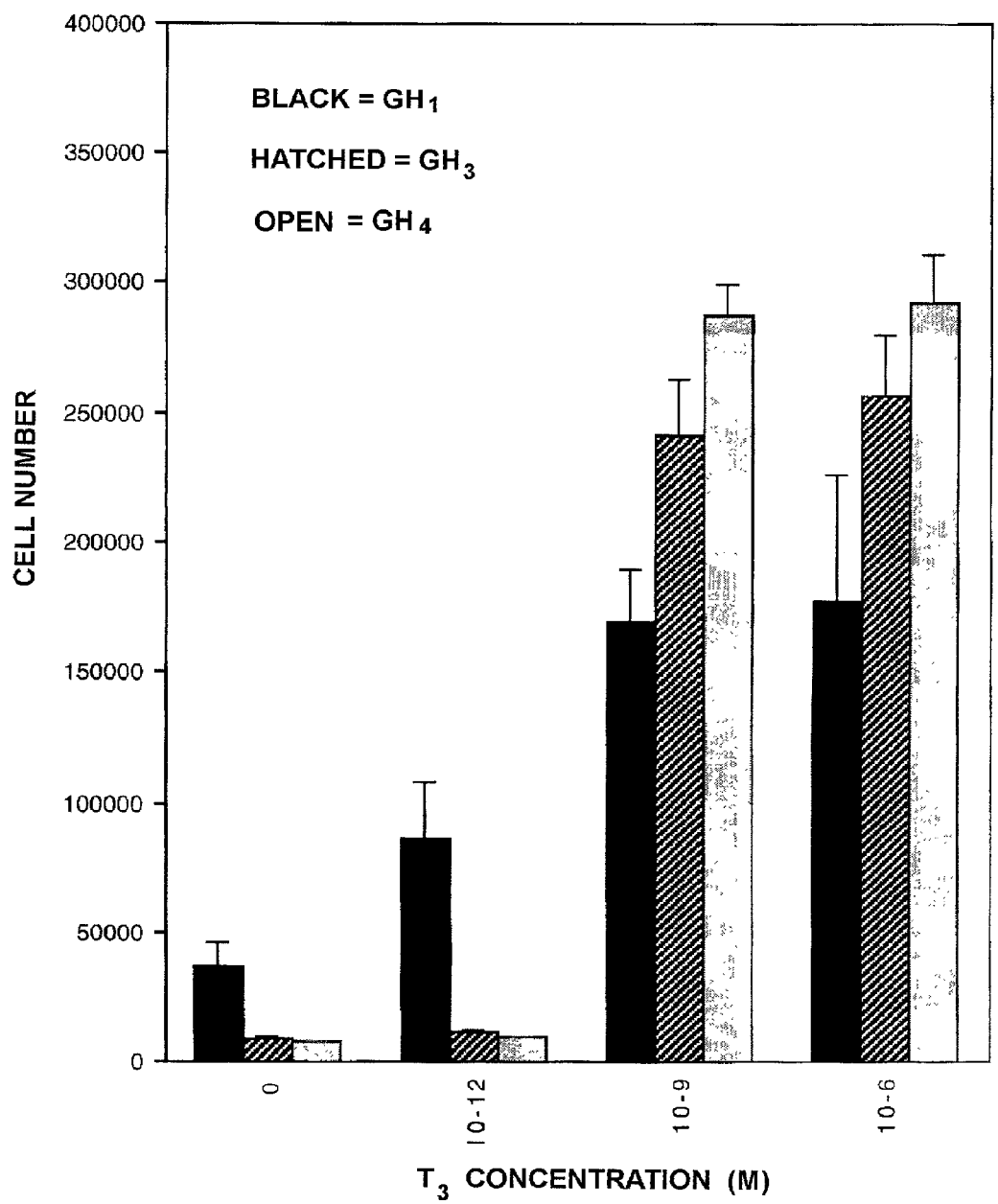
FIG. 16. $T_3$ Growth Effects with Three GH Cell Lines in 2.5% CDE-horse Serum.
Figure 17:
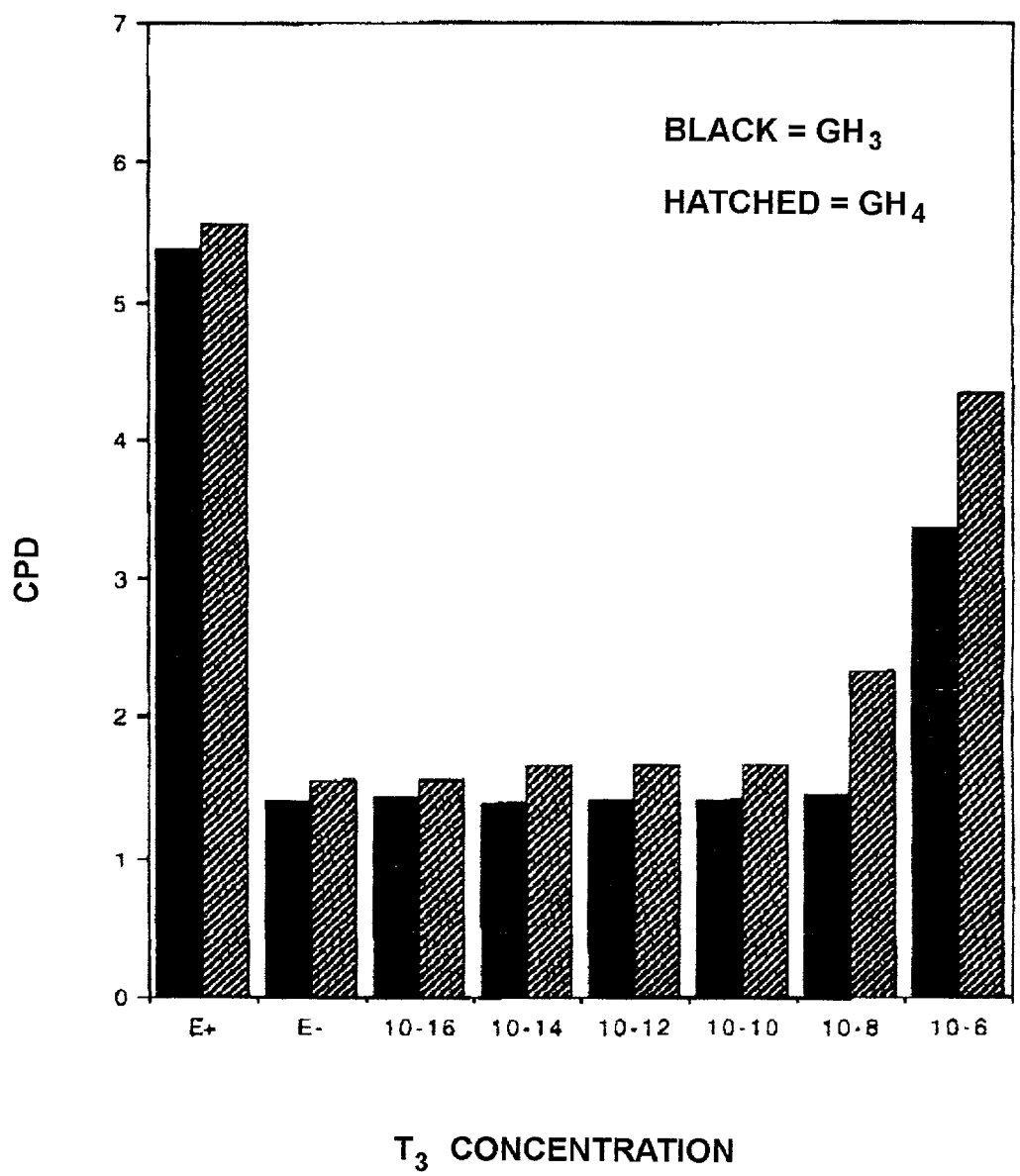
FIG. 17. $T_3$ Growth Effects with Two GH Cell Lines in 50% CDE-horse Serum.

In this Example an assay system is described for testing substances expected to have thyroid hormone like activity. GH rat pituitary tumor cells are highly thyroid hormone responsive in serum-free defined medium (Eby J E et al. (1992) *Anal Biochem* 203, 317-325; Eby J E et al. (1992) *J Cell Physiol* 156, 588-600; Sato H et al. (1991) *In Vitro Cell Dev Biol* 27A, 599-602). An example of this responsiveness with the $GH_3$ line is shown in FIG. 14. However, in serum-free defined medium, these cells are not $E_2$ responsive when $T_3$ is omitted from the medium (FIG. 15). During evaluation of the role the GH cell lines in CDE-serum, it was found that in D-MEM/F-12 with 2.5% (v/v) CDE-horse serum, $T_3$ caused substantial growth of the $GH_4C_1$, $GH_1$ and $GH_3$ rat pituitary tumor cell lines (FIG. 16). However, at 50% (v/v) CDE-horse serum, only supraphysiologic concentrations of thyroid hormone showed growth effects (FIG. 17). Nonetheless, the 34° C. CDE method described in the preceding Examples is clearly functional to demonstrate both steroid hormone and thyroid hormone growth effects in culture. It is known that the thyroid hormone receptor is a member of a superfamily of receptors that also includes the steroid hormone receptors (Evans R M (1988) *Science* (Wash D.C.) 240:889-895). Testing of substances expected to have thyroid hormone like activity can be performed with the GH cell lines in the presence of low concentrations of CDE-serum.

Discussion of Example 5. The removal of thyroid hormones from serum has been described before using the Bio-Rad™ AG-1 X8 ion exchange resin (Samuels H H et al. (1979) *Endocrinology* 105, 80-85). Removal of $T_3/T_4$ by this method relies on their negative carboxylic acid charge at neutral pH. That method also removes most of the other lower molecular weight charged substances from serum. For some applications, this is not beneficial, particularly to the demonstration of steroid hormone responsive cell growth in culture. Also, the ion exchange method does not remove the uncharged/hydrophobic steroid hormones. Therefore, the AG-1 X8 method is more limited than the 34° C. CDE method described herein.

Example 6

Estrogenic Effects in XAD-4™ Resin Treated Horse Serum

Figure 18:
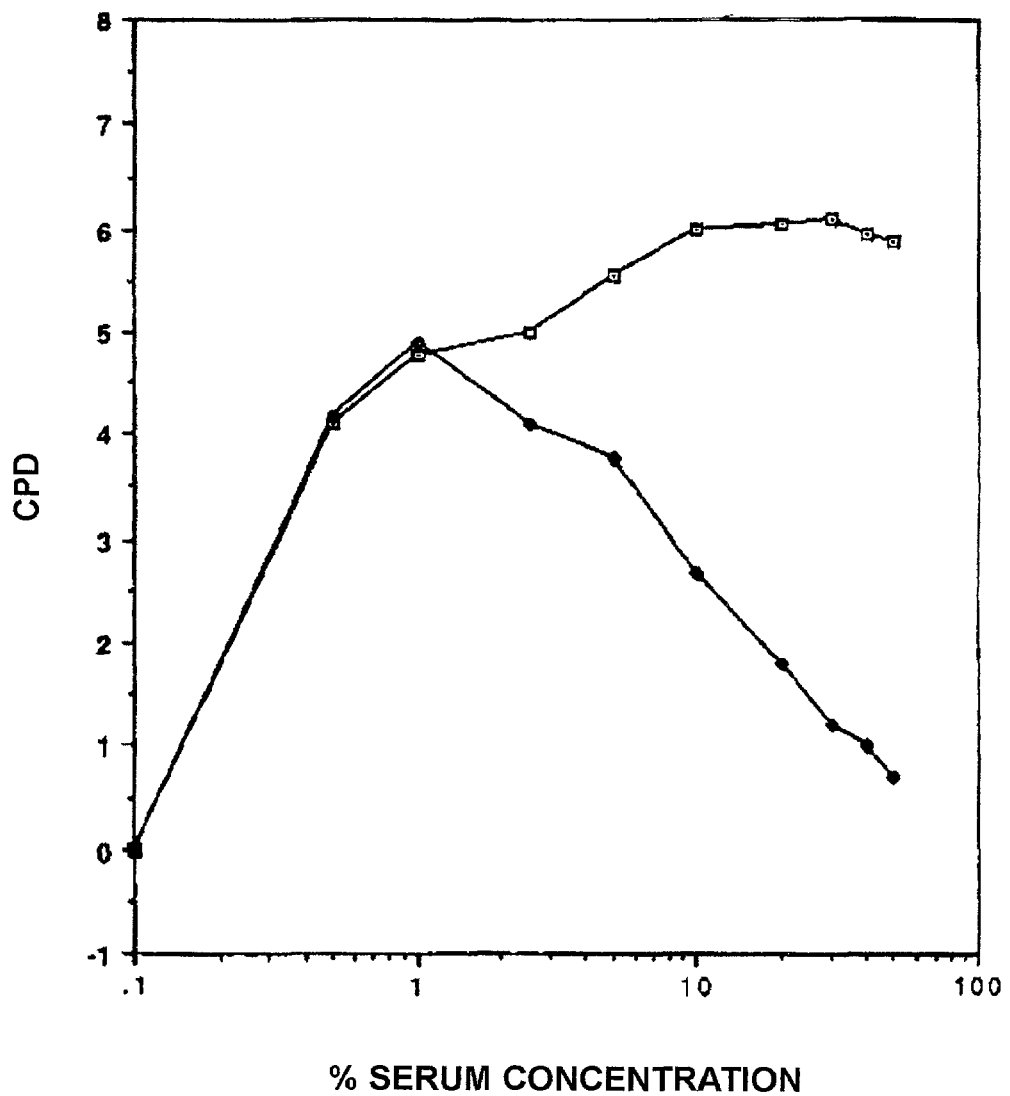
FIG. 18. Effect of XAD-4™ Resin Treated Horse Serum on MTW9/PL2 Cell Growth ±$E_2$.
Figure 19:
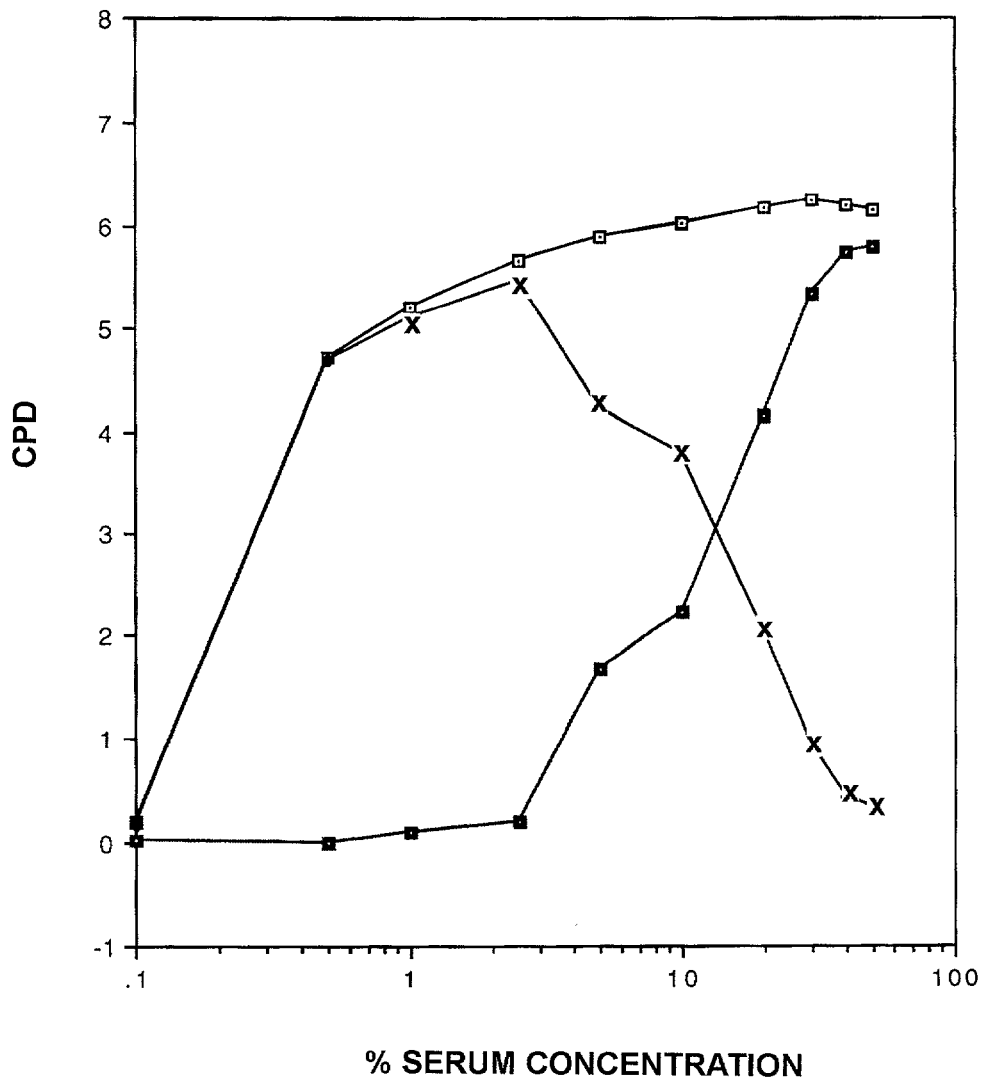
FIG. 19. Effect of XAD-4™ Resin Treated Horse Serum on T47D Cell Growth ±$E_2$.

Horse serum depleted of steroid hormones by XAD-4™, prepared as described in Example 2, was assayed to determine if it demonstrated estrogen reversible inhibition of $ER^+$ cancer cell growth in culture. FIG. 18 shows the effects of XAD-4™ treated horse serum ±10 nM $E_2$ with the MTW9/PL2 cell line. Unmistakably, the pattern of cell response was the same as seen with CDE-horse serum. At 50% XAD-4™ serum (v/v), an estrogenic effect of 5.2 CPD was observed in 7 days. FIG. 19 shows a similar experiment with T47D cells after 14 days. At 50% (v/v) XAD-4™ treated serum, an estrogenic effect with T47D cells of 5.3 CPD was observed. The magnitudes of the estrogenic effects with both cell lines were the same as observed with CDE-horse serum. Because both MTW9/PL2 and T47D cells are sensitive to picomolar concentrations of estrogen, it was evident that the XAD-4™ resin treatment effectively removed the endogenous sex steroids present in serum.

Discussion of Example 6. There is no previous report of the preparation steroid depleted serum by this resin treatment method. As indicated in Example 2, the XAD-4™ treatment method has particular applicability for the industrial preparation of large volumes of steroid hormone depleted serum, and will allow the commercial supply of steroid depleted serum at reasonable cost. A preferred application for this steroid hormone stripped serum is in the biotechnology industry, in which cell culture is used to produce medically and otherwise commercially significant proteins and cellular products. Steroid hormone depleted serum has applicability beyond the $ER^+$ and $AR^+$ cells described in this report. For example, hybridoma cells are the sources of many important monoclonal antibodies. Depletion of steroids from the serum used to grow these cells will increase cell viability (e.g. cortisol is a potent cytotoxic agent for leukocyte cell types), and therefore increase product yield. Moreover, steroid-stripped sera prepared in this way may stabilize hybridoma production of desirable immunoglobulins. The use of XAD™-4 extracted serum is also applicable to development of hybridoma cells of medical significance and therapeutic value. These and other applications of the XAD™-4 treated serum for both commercial and diagnostic testing as well as for industrial production of valuable cellular products are foreseen.

Example 7

Testing of Substances for Estrogenic Activity

The purported estrogenic effects of phenol red were tested and proven to be unfounded. Further, the methods described in this Example exemplify methods that are generally effective for assessing the steroidogenic activity of any substance.

Examination of Phenol Red Indicator as an Estrogenic Substance. The reported estrogenic action of phenol red and/or its lipophilic contaminants has led to the widespread use of indicator free culture medium to conduct endocrine studies in vitro (Berthois Y et al. (1986) *Proc Natl Acad Sci USA* 83, 2496-2500; Bindal R D et al. (1988) *J Steroid Biochem* 31, 287-293; Bindal R D and Katzenellenbogen J A (1988) *J Med Chem* 31, 1978-1983). The generally accepted view is that the 8.1 mg/mL (i.e. about 23 µM) of phenol red present in the D-MEM/F-12 medium (Gibco-BRL) alone was sufficient to cause estrogenic effects. Despite this, the results presented thus far in this disclosure show large magnitude estrogen effects in D-MEM/F-12 tissue culture medium containing the standard concentration of the indicator phenol red. To ensure that this potential problem was avoided in subsequent studies, the phenol red matter was further investigated, as reported (Moreno-Cuevas J E and Sirbasku D A (2000) *In Vitro Cell Dev Biol* 36, 447-464). In so doing, nine estrogen receptor positive ($ER^+$) cell lines representing four target tissues and three species were selected. Phenol red was investigated using five different experimental protocols. First, $E_2$ responsive growth of all nine $ER^+$ cells lines was compared in medium with and without the indicator. Second, using representative lines it was determined whether phenol red was mitogenic in indicator free medium. The dose-response effects of phenol red were compared directly to those of $E_2$. Third, it investigated whether tamoxifen inhibited growth equally in phenol red containing and indicator free medium. This study was based on a report indicating that antiestrogen effects should be seen only in phenol red containing medium. Fourth, it was investigated whether phenol red displaced the binding of $^3H$-$E_2$ using $ER^+$ intact human breast cancer cells. Fifth, it was investigated whether $E_2$ and phenol red both acted as inducers of the progesterone receptor using a human breast cancer cell line well known for this property (Horwitz K B and McGuire W L (1978) *J Biol Chem* 253, 2223-2228). All of the experiments presented in this disclosure support the conclusion that the concentration of phenol red contaminants in a standard culture medium available today is not sufficient to cause estrogenic effects. The studies presented indicate that the real issue of how to demonstrate estrogenic effects in culture resides elsewhere than phenol red (Moreno-Cuevas J E and Sirbasku D A (2000) *In Vitro Cell Dev Biol* 36, 447-464). It was found that demonstration of sex steroid hormone mitogenic effects in culture depends upon conditions that maximize the effects of a serum-borne inhibitor(s). When the effects of the inhibitor are optimized, the presence or absence of phenol red makes no everyday difference to the demonstration of estrogen mitogenic effects with several target cell types from diverse species (Moreno-Cuevas J E and Sirbasku D A (2000) *In Vitro Cell Dev Biol* 36, 447-464).

Phenol Red Testing for Estrogenic Activity with MCF-7A Cells. The original reports of the effect of phenol red or its impurities had used the MCF-7 human breast cancer cells to assess estrogenic activity (Berthois Y et al. (1986) *Proc Natl Acad Sci USA* 83, 2496-2500; Bindal R D et al. (1988) *J Steroid Biochem* 31, 287-293; Bindal R D and Katzenellenbogen J A (1988) *J Med Chem* 31, 1978-1983). The initial study began with the MCF-7A strain of this population. As shown in FIG. 20A, growth was measured in the presence of increasing concentrations of CDE-horse serum with and without phenol red in the medium and $\pm E_2$. Concentrations of $\leq 10\%$ (v/v) CDE-horse serum supported more than 5 CPD. Higher concentrations progressively inhibited in both indicator containing and indicator free medium. In both types of medium, $E_2$ was required to reverse the serum inhibition. To confirm that $E_2$ was equally effective in phenol red free and phenol red containing medium, the estrogenic effects shown in FIG. 20A were compared in both types of medium and at each serum concentration. The results of this analysis are presented in FIG. 20B. The maximum estrogenic effect at 50% (v/v) serum was 2.38 CPD (i.e. 2238 or 5.2-fold) in medium without indicator and 2.56 CPD (i.e. $2^{2.56}$ or 5.9-fold) with phenol red. This difference was not significant. Only at 5% (v/v) serum was there a significantly ($p<0.05$) greater estrogenic effect in phenol red free medium. However, in replicate experiments this $\leq 1.0$ CPD effect was inconsistent. At all other serum concentrations, the growth differences between plus and minus phenol red were not significant.

Test of Phenol Red Effects with MCF-7K Cells. The MCF-7K strain was routinely more estrogen responsive than the MCF-7A line (Sirbasku D A and Moreno-Cuevas J E (2000) *In Vitro Cell Dev Biol* 36, 428-446). The MCF-7K cells also showed a serum concentration dependent growth inhibition (FIG. 20C). The final degree of inhibition at 50% (v/v) serum was independent of phenol red. Only in the presence of 2.5, 5, 10 and 20% (v/v) CDE-horse serum were the estrogenic effects significantly greater in phenol red free (FIG. 20D). It is important to note that while these differences were identified more often with the MCF-7K strain than the MCF-7A line, they were invariably small. Plainly, no serum concentration supported $\geq 1.0$ CPD estrogenic effects in phenol red free medium compared to indicator free medium (FIG. 20D). In fact, deletion of phenol red improved estrogen responsiveness by an average of only 0.6 CPD with the MCF-7K line. When judged by the maximum estrogenic effects achievable with MCF-7K cells in 50% (v/v) CDE-horse serum, plus and minus phenol red gave indistinguishable results of CPD 3.01 (8.0-fold) and CPD 2.99 (7.9-fold), respectively (FIG. 20D).

Phenol Red Testing for Estrogenic Activity with T47D and ZR-75-1 Cells. The same experiments just described above with the MCF-7 cell strains were repeated with T47D and ZR-75-1 cells. These lines were substantially more estrogen stimulated in CDE-serum than MCF-7 cells (Sirbasku D A and Moreno-Cuevas J E (2000) *In Vitro Cell Dev Biol* 36, 428-446) and hence were expected to be more sensitive to phenol red/contaminants.

Phenol Red and T47D Cells. T47D cells were grown in medium with CDE-horse serum both with and without phenol red (FIG. 21A). Low concentrations of serum (i.e. $\leq 2\%$) promoted growth. Higher concentrations progressively inhibited growth irrespective of indicator content. In both media, $E_2$ was required to reverse the inhibition (FIG. 21A). In 50% (v/v) CDE-horse serum, the maximum $E_2$ responses were $2^{5.35}$ (41-fold) and 25.29 (39-fold) in phenol red containing and indicator free medium, respectively (FIG. 21B). Only at low serum concentrations were phenol red effects observed in any experiment. In some replicates, the phenol red effect was opposite to that expected. For example, in the experiment shown in FIG. 21B, 0.5 to 2.5% serum showed significantly ($p<0.05$) greater estrogenic effects in the presence of phenol red. These results graphically illustrate the hazards of interpreting 1.0 CPD responses either in favor of phenol red/contaminants as estrogens or in opposition to this proposal.

Phenol Red and ZR-75-1 Cells. ZR-75-1 cells showed similar results as the T47D line. Serum caused an inhibition of growth that was undoubtedly unrelated to phenol red (FIG. 21C). In both types of medium, and at every serum concentration tested, $E_2$ was required to reverse the inhibition (FIG. 21C). In 50% (v/v) serum, ZR-75-1 cells showed maximum estrogenic effects of $2^{3.39}$ (10.5-fold) and $2^{3.49}$ (11.2-fold) in medium with and without indicator, respectively (FIG. 21D). As seen with T47D cells, the ZR-75-1 line showed greater estrogenic effects in medium with phenol red than in medium without indicator when the serum was 0.5, 5 or 10% (v/v) (FIG. 21D).

Phenol Red Testing for Estrogenic Activity with MTW9/PL2 Cells. The next experiments were done with MTW9/PL2 rat mammary tumor cells (FIG. 22A). They were inhibited by high concentrations of CDE-horse serum with and without indicator. $E_2$ was required to reverse the inhibition in both types of medium (FIG. 22A). The maximum estrogenic effects in 50% serum were 25.82 (56-fold) and $2^{5.69}$ (52-fold) with and without phenol red, respectively (FIG. 22B). In the experiment shown in FIG. 22B, estrogenic effects were unpredictably greater in phenol red free medium than in medium with indicator. This was observed at low serum concentrations (i.e. 0.5 and 1.0%) and again at higher levels (i.e. 20 and 30%). Although suggesting a phenol red effect, these results in fact only serve to emphasize the pitfalls of accepting small changes as meaningful even though they are significant at $p<0.05$. When estrogenic effects were found with MTW9/PL2 cells in phenol red free conditions, they invariably were $\leq 1.0$ CPD. The sum of the studies with MTW9/PL2 cells did not yield a predictable correlation between estrogenic effects in the absence of the indicator and serum concentrations.

Other Cell Lines Tested for Growth $\pm$Phenol Red and $\pm E_2$. The results presented above were replicated with the $GH_1$ and $GH_4C_1$ rat pituitary tumor cell lines as well as with the H301 cells and the LNCaP cell line (Moreno-Cuevas J E and Sirbasku D A (2000) *In Vitro Cell Dev Biol* 36, 447-464). Again, the presence or absence of the indicator in the medium containing CDE-horse serum had no effect whatever on the demonstration of the usual high estrogenic effects with these cells.

Direct Test of Phenol Red Estrogenic Activity. Three cell lines were selected for a direct test of phenol red as a mitogen.

Figure 23:
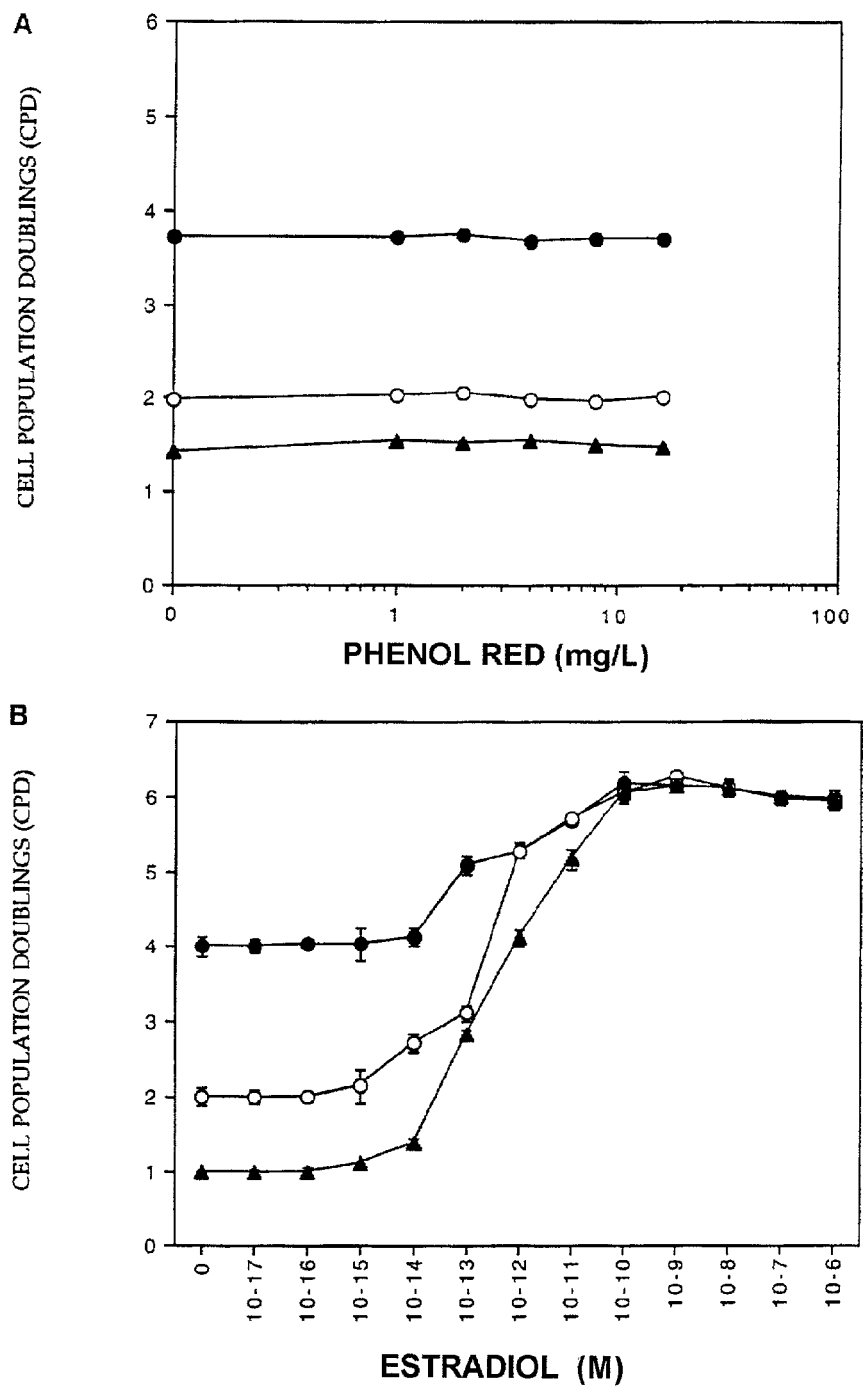
FIG. 23. Dose-Response Effects of Phenol Red versus $E_2$ with Three ER$^+$ Cell Lines. (A) Growth Effects of Phenol Red with MCF-7K, T47D and MTW9/PL2 Cells; (B) Growth Effects of $E_2$ with MCF-7K, T47D and MTW9/PL2 Cells.

The MCF-7A line was used because it most closely approximated the origin and passage age of the cells used to conduct the original study of phenol red as a weak estrogen (Berthois Y et al. (1986) *Proc Natl Acad Sci USA* 83, 2496-2500). The T47D cells were chosen because they are the most estrogen responsive human breast cancer cell line available today (Sirbasku D A and Moreno-Cuevas J E (2000) *In Vitro Cell Dev Biol* 36, 428-446). The MTW9/PL2 cells were chosen as an example of a highly estrogen responsive rodent origin line (Moreno-Cuevas J E and Sirbasku D A (2000) *In Vitro Cell Dev Biol* 36, 410-427; Sirbasku D A and Moreno-Cuevas J E (2000) *In Vitro Cell Dev Biol* 36, 428-446). The assays were done in phenol red free D-MEM/F-12 supplemented with 30% CDE-HS. This concentration was chosen even though it is not as inhibitory as 50% (v/v) serum. This selection was made to reduce possible interactions of the phenol red/contaminant with serum proteins while still retaining a significant inhibitory effect. Phenol red concentrations of up to 16 mg/L were added to this medium. This highest level was twice that in standard commercially formulated Gibco-BRL D-MEM/F-12. Several different manufacturing lots of aqueous phenol red gave equivalent results. The preparations used in this study ranged in age from newly obtained to more than ten year old laboratory stocks. These experiments gave unmistakable results. There was no increase in the growth of any of the cell lines in response to phenol red (FIG. 23A). By comparison, parallel cultures receiving $E_2$ showed sizable 2 to 5 CPD responses to the natural hormone (FIG. 23B). $E_2$ at $1.0 \times 10^{-10}$ M optimized growth of all three cell lines. The $ED_{50}$ concentrations of $E_2$ were $3.0 \times 10^{-12}$ M. Significant (p<0.05) estrogenic effects were observed at $1.0 \times 10^{-12}$ M. The results presented in FIG. 23 indicate that the culture conditions used in this study could reasonably be expected to detect responses due to contaminants present at the concentrations indicated in the original reports (Berthois Y et al. (1986) *Proc Natl Acad Sci USA* 83, 2496-2500; Bindal R D et al. (1988) *J Steroid Biochem* 31, 287-293; Bindal R D and Katzenellenbogen J A (1988) *J Med Chem* 31, 1978-1983).

Comparison of $E_2$ Potency in Medium with and without Phenol Red. As described above in Table 4, the T47D and MTW9/PL2 cells grow significantly in response to $1.0 \times 10^{-12}$ M $E_2$. The D-MEM/F-12 used in those studies also contained about 23 µM phenol red. When the results of those studies were compared with the experiments in FIG. 23B, done in D-MEM/F-12 without indicator, the estrogen dose response curves were very similar. The conclusion is straightforward. $E_2$ dose-responses were not affected by phenol red. If phenol red lipophilic contaminants were present at the concentrations originally suggested (Berthois Y et al. (1986) *Proc Natl Acad Sci USA* 83, 2496-2500; Bindal R D et al. (1988) *J Steroid Biochem* 31, 287-293; Bindal R D and Katzenellenbogen J A (1988) *J Med Chem* 31, 1978-1983) they should have masked the observation of picomolar effects of exogenous estrogens.

Effect of Phenol Red on Binding of $^3H$-$E_2$ to Intact Cells. For the next study, intact T47D cells were used to measure the effects of phenol red on estrogen receptor binding. The cells were incubated with 5 nM $^3H$-$E_2$ and the effects of addition of increasing concentrations of unlabeled $E_2$ assessed (Table 5). A 100-fold excess of unlabeled $E_2$ displaced 75% of the binding of $^3H$-$E_2$. By this criterion, 75% of the binding of $^3H$-$E_2$ was specific to estrogen receptors (Chamness G C and McGuire W L (1975) *Steroids* 26, 538-542). The same analysis was conducted with aqueous preparations of phenol red. Even at 16 mg/L, the indicator did not reduce the binding of $^3H$-$E_2$ (Table 5). This was true no matter which batch of indicator was analyzed (results not shown). The phenol red used for the experiment shown in Table 5 was approximately the same age (purchased in 1986) as the date of the original report (Berthois Y et al. (1986) *Proc Natl Acad Sci USA* 83, 2496-2500). These results raise the question how often preparations of phenol red purchased at that time as an aqueous membrane filtered product contained a sufficient level of contaminants to elicit an estrogenic effect.

TABLE 5

DISPLACEMENT OF $^3H$-$E_2$ BINDING TO INTACT T47D CELLS BY UNLABELED $E_2$ OR UNLABELED PHENOL RED IN INDICATOR FREE AND SERUM-FREE D-MEM/F-12 FOR TWO HOURS AT 37° C.

| | | |
|---|---|---|
| 4 Control-No Additions (5 nM $^3H$—$E_2$ only) | 12,458 ± 1615 | 100% |
| 2.5 nM Unlabeled $E_2$ | 12,177 ± 872 | 98% |
| 5.0 nM Unlabeled $E_2$ | 8,756 ± 588 | 70% |
| 50 nM Unlabeled $E_2$ | 7,898 ± 744 | 63% |
| 250 nM Unlabeled $E_2$ | 4,892 ± 194 | 39% |
| 500 nM Unlabeled $E_2$ | 3,494 ± 127 | 28% |
| 1000 nM Unlabeled $E_2$ | 2,543 ± 304 | 20% |
| 1 mg/L Phenol Red | 12,670 ± 727 | 102% |
| 2 mg/L Phenol Red | 13,874 ± 906 | 111% |
| 4 mg/L Phenol Red | 11,730 ± 566 | 94% |
| 8 mg/L Phenol Red | 12,357 ± 664 | 99% |
| 16 mg/L Phenol Red | 13,748 ± 998 | 110% |

Comparison of the $E_2$ and Phenol Red Induction of Progesterone Receptors. Another putative function of phenol red was to induce progesterone receptors in estrogen sensitive cells. An investigation was made as to whether the indicator induced an increase in the progesterone receptors of T47D cells which contain these sites (Horwitz K B et al. (1978) *Cancer Res* 38, 2434-2437). In a first study, the kinetics of progesterone receptor induction versus estrogen concentration in phenol red free medium were investigated (FIG. 24A). $E_2$ levels as low as $1.0 \times 10^{-12}$ M caused a significant two-fold increase in receptor content in four days. At $1.0 \times 10^{-8}$ M, $E_2$ induced a four-fold increase in progesterone receptors in four days. Clearly, $E_2$ induced a time and concentration dependent increase in the progesterone receptors with T47D cells. Next, this same analysis was done with phenol red over a concentration range of 1 to 16 mg/L (FIG. 24B). Phenol red induced a small increase in progesterone receptors at 8 and 16 mg/L after four days. This induction was about the same as caused by $1.0 \times 10^{-14}$ M $E_2$ (FIG. 24A). These results indicate that if estrogenic contaminants are present in phenol red, they are most likely in the $10^{-14}$ M range even assuming equal receptor binding capacity to $E_2$. This point is important because the active agent is thought to be only a trace impurity in many batches of phenol red (Bindal R D et al. (1988) *J Med Chem* 31, 1978-1983). The impurities bind to the estrogen receptor with only 50% of the affinity of $E_2$. The impurity was expected to be 0.002% of the phenol red concentration. Based on test results that employed many different batches of Gibco-BRL D-MEM/F-12, this concentration of the impurity seems highly unlikely in the medium commercially available today.

Discussion of Example 7. The studies of the effects of phenol red or its lipophilic impurities demonstrate the usefulness of the presently disclosed methods for the assessment of estrogenic and androgenic activity of commercially prepared materials, substances present or extracted from environmental or food sources or other sources that are thought to contain such activities. The testing can be approached by three separate methods, as shown by examples with phenol red. (1) Compounds or other preparations and substances can be tested for growth activity with human or rodent cell lines depending upon the information sought. Potency can be established as UNITS based on $E_2$ or any other estrogen or androgen required. This permits direct expression of the estrogen like activity or androgen like activity per volume or mass of the substance under evaluation. Levels can be measured without regard for expensive development of a radio immunoassay that in the end still does not yield evidence of biological activity as a sex steroid hormone analog (agonist or antagonist). The use of rodent cell lines opens the possibility of direct comparison to in vivo activity if required. The effects of hormone-like substances can be tested with human cell lines in athymic nude mice or SCID mice as required. (2) Another form of analysis is direct measure of potency by $^3H$-$E_2$ or $^3H$-DHT binding displacement analysis from whole cells or extracted estrogen receptors. An example with $^3H$-$E_2$ and whole cells is shown in Table 5. The two different binding assays offer different information. Whole cells have a predominance of hydrophobic sites (i.e. membranes) that absorb lipophilic substances and therefore may attenuate their activity. Use of cell extracted sex steroid hormone receptors permits direct measure of the potential of a substance to act as a hormone independent of its biological effects. (3) Finally, use of the progesterone receptor analysis permits evaluation of substances and preparations by a method entirely independent of growth. This is a gene expression based analysis that permits evaluation that can be used to supplement growth data or be used in place of growth analysis. The MTW9/PL2 cells have been shown above to be suitable for this purpose.

Example 8

Testing of Substances for Inhibitor-Like Activity

In studies described in this Example, TGFα, TGFβ1, EGF, IGF-I, IGF-II and insulin were tested in the cell growth assay described in the preceding Examples, substituting those proteins for the serum-borne inhibitor contained in the preferred CDE serum.

TGFβ1 as a Substitute for the Serum-borne Estrogen Reversible Inhibitor. Normal mouse mammary (Silberstein G B and Daniel C W (1987) *Science* (Wash D.C.) 237, 291-293; Silberstein G B et al. (1992) *Dev Biol* 152, 354-362) and normal human breast epithelial cell growth is inhibited by TGFβ(Bronzert D A et al. (1990) *Mol Endocrinol* 4, 981-989). Additionally, human breast cancer cells are inhibited by TGFβ (Knabbe C et al. (1987) *Cell* 48, 417-428; Arteaga C L et al. (1988) *Cancer Res* 48, 3898-3904; Arteaga C L et al. (1990) *Cell Growth Diff* 1, 367-374). TGFβ also inhibits the $GH_4C_1$ rat pituitary tumor cells (Ramsdell J S (1991) *Endocrinology* 128, 1981-1990) and the LNCaP human prostatic carcinoma cells (Schuurmans A L et al. (1988) *The Prostate* 12, 55-64; Wilding G et al. (1989) *Mol Cell Endocrinol* 62, 79-87; Carruba G et al (1994) *Steroids* 59, 412-420; Castagnetta L A and Carruba G (1995) *Ciba Found Symp* 191, 269-286; Kim I Y et al. (1996) *Endocrinology* 137, 991-999). In studies presented next, replacement of the serum-borne inhibitor with TGFβ was attempted. A number of related forms of this inhibitor are known (Clark D A and Coker R (1998) *Int J Biochem Cell Biol* 30, 293-298; Massagué J (1998) *Annu Rev Biochem* 67, 753-791). TGFβ1 and TGFβ2 are most often studied and commonly have similar potencies. For example, they are equipotent with human breast cancers cells (Zugmaier G et al. (1989) *J Cell Physol* 141, 353-361). TGFβ was chosen for the instant study. Without a doubt, a number of the key cell lines used throughout the Examples were inhibited by TGFβ. It was therefore considered essential to ask if TGFβ was the estrogen reversible inhibitor.

TGFβ1 and MCF-7 Cells. Because MCF-7 cells are probably the most studied human breast cancer line today, this next work began with those cells. TGFβ has been described as a hormone regulated autocrine inhibitor of the $ER^+$ MCF-7 human breast cancer cell growth (Knabbe C et al. (1987) *Cell* 48, 417-428). In the present study, to test if TGFβ substituted for the serum-borne inhibitor with these cells, they were grown in D-MEM/F-12 containing 2.5% (v/v) CDE-horse serum plus increasing concentrations of transforming growth factor and $\pm E_2$. The results in FIG. 25A show that even 50 ng/mL of TGFβ1 caused only a modest inhibition of MCF-7K cell growth. Cell numbers were reduced from 350,000 to 200,000 per dish. This difference was significant (p<0.05). Nevertheless, the estrogen reversal of the inhibition was no larger than the $E_2$ effect observed in D-MEM/F-12 containing 2.5% (v/v) horse serum without TGFβ1 FIG. 25A. Furthermore, when the cell number data were expressed as CPD (insert FIG. 25A), it was definite that TGFβ 1 was at best a very modest inhibitor and that there was no TGFβ1 related estrogenic effect.

TGFβ1 and MTW9/PL2 Cells. The next study was performed because the MTW9/PL2 cells are the only known estrogen growth responsive rat cell line derived from a hormone responsive carcinogen induced tumor. A similar analysis was done with the MTW9/PL2 rat mammary tumor cells (FIG. 25B). TGFβ1 reduced cell numbers from 350,000 to 100,000 per dish. This was significant (p<0.05). However, the presentation of cell number results only tends to exaggerate the effects of TGFβ1. When the results were converted to CPD (insert FIG. 25B), the actual inhibition was 1.5 CPD. This was at most a 25% decrease in growth rate. As shown, there was no estrogen reversal of the TGFβ1 inhibition with MTW9/PL2 cells.

TGFβ1 and other $ER^+$ Cell Lines. The effects of TGFβ1 at 50 ng/mL $\pm E_2$ were also investigated with the other cell lines used in this study. The MCF-7A, T47D and ZR-75-1 human breast cancer cells were inhibited by TGFβ1 (FIG. 26A). From these results, and those in FIG. 25A, it was clear that the MCF-7 cells were the most sensitive of the $ER^+$ human breast cancer lines tested. Irrespective of the line, $E_2$ had no influence on the TGFβ1 mediated inhibitions (FIG. 26A). The same experiments were done with the LNCaP cells and the $GH_4C_1$ pituitary line (FIG. 26A). They were more sensitive to TGFβ1 than breast cancer cells. Nonetheless, the TGFβ1 effects were not reversed by $E_2$. When the cell number decreases presented in FIG. 26A were converted to CPD, it was clear that the TGFβ1 effects were negligible and that $E_2$ was of no significant consequence (FIG. 26B). Thus, TGFβ1 did not substitute for the estrogen reversible inhibitor(s) in CDE serum with any of the sex steroid sensitive $ER^+$ cell lines tested.

TGFα and EGF as Substitutes for the Estrogen Reversible Inhibitor in CDE Serum. The EGF family of mitogens and receptors has been linked to breast cancer proliferation, invasion and progression (Dickson R B and Lippman M E (1987) *Endocr Rev* 8, 29-43; Norman no N et al. (1994) *Breast Cancer Res Treat* 29, 11-27; Ethier S P (1995) *J Natl Cancer Inst* 87, 964-973; de Jung J S et al. (1998) *J Pathol* 184, 44-52 and 53-57). Most prominent among these polypeptide mitogens has been the EGF analogue, TGFα (Dickson R B and Lippman M E (1987) *Endocr Rev* 8, 29-43; de Jung J S et al. (1998) *J Pathol* 184, 44-52 and 53-57). Estrogen induced secretion of TGFα is thought to create an autocrine loop that promotes breast cancer cell growth (Dickson R B et al. (1985) *Endocrinology* 118, 138-142; Dickson R B et al. (1986) *Cancer Res* 46, 1707-1713; Dickson R B et al. (1986) *Science* (Wash D.C.) 232, 1542-1543; Dickson R B and Lippman M E (1987) *Endocr Rev* 8, 29-43; Derrick R (1988) *Cell* 54, 593-595; Arrack B A et al. (1990) *Cancer Res* 50, 299-303; Kenney N J et al. (1993) *J Cell Physiol* 156, 497-514; Normanno N et al. (1994) *Breast Cancer Res Treat* 29, 11-27; Dickson R B et al. (1987) *Proc Natl Acad Sci USA* 84, 837-841; Salomon D S et al. (1984) *Cancer Res* 44, 4069-4077; Liu S C et al. (1987) *Mol Endocrinol* 1, 683-692). TGFα is also thought to potentiate estrogen action in uterus (Nelson K G et al. (1992) *Endocrinology* 131, 1657-1664) as well as to regulate the EGF receptor in this tissue (DiAugustine R P et al. (1988) *Endocrinology* 122, 2355-2363; Huet-Hudson Y M et al. (1990) *Mol Endocrinol* 4, 510-523; Mukku V R and Stancel G M (1985) *J Biol Chem* 260, 9820-9824). The culture conditions described herein offer a new opportunity to test the autocrine growth model under conditions not previously available. Application of the new cell growth assays allowed a direct test to determine if an autocrine/intacrine growth factor loop explains the estrogen reversal of the serum inhibition.

EGF and TGFα as Substitutes for $E_2$. Growth of the MCF-7A, MCF-7K, T47D and ZR-75-1 cells was measured in D-MEM/F-12 containing increasing concentrations of CDE horse serum with and without exogenous EGF or TGFα. The results with the four cell lines are shown in FIGS. 27A, 27B, 27C, and 27D, respectively. As expected, CDE horse serum was progressively inhibitory at concentrations ≧5% (v/v). The addition of growth saturating concentrations (Karey K P and Sirbasku D A (1988) *Cancer Res* 48, 4083-4092) of EGF or TGFα did not reverse the effects of the serum-borne inhibitor. In control cultures without added polypeptide mitogens, $E_2$ completely reversed the serum inhibition. These results again confirm the same conclusion arrived at earlier using an entirely different approach (Karey K P and Sirbasku D A (1988) *Cancer Res* 48, 4083-4092). Direct evidence for obligatory EGF/TGFα autocrine loops in estrogen responsive cell growth simply has not yet been established. In fact, there is solid in vivo evidence that challenges an EGF/TGFα autocrine loop as active in the action of estrogens (Arteaga C L et al. (1988) *Mol Endocrinol* 2, 1064-1069).

IGF-I, IGF-II and Insulin as Substitutes for Estrogen Action. Insulin-like growth factors I and II (IGF-I and IGF-II) promote breast cancer cell growth (Furlanetto R W and DiCarlo J N (1984) *Cancer Res* 44, 2122-2128; Myal Y et al. (1984) *Cancer Res* 44, 5486-5490; Dickson R B and Lippman M E (1987) *Endocr Rev* 8, 2943; Karey K P and Sirbasku D A (1988) *Cancer Res* 48, 4083-4092; Ogasawara M and Sirbasku D A (1988) *In Vitro Cell Dev Biol* 24, 911-920; Stewart A J et al. (1990) *J Biol Chem* 265, 2172-2178). IGF-I related proteins (Huff K K et al. (1986) *Cancer Res* 46, 4613-4619; Huff K K et al. (1988) *Mol Endocrinol* 2, 200-208; Dickson R B and Lippman M E (1987) *Endocr Rev* 8, 2943; Minute F et al. (1987) *Mol Cell Endocrinol* 54, 17-184, as well IGF-II (Yee D et al. (1988) *Cancer Res* 48, 6691-6696; Osborne C K et al. (1989) *Mol Endocrinol* 3, 1701-1709), are thought of as possible autocrine/paracrine mitogens. Their secretion in response to hormones has been proposed (Dickson R B and Lippman M E (1987) *Endocr Rev* 8, 2943; Huff K K et al. (1988) *Mol Endocrinol* 2, 200-208; Osborne C K et al. (1989) *Mol Endocrinol* 3, 1701-1709). Insulin itself is likely an endocrine mediator. In the instant study, it was investigated whether exogenous IGF-I addition to cultures containing CDE-horse serum substituted for the inhibition reversing effects of estrogens with human breast cancer cells. FIG. 28A and FIG. 28B show the results with the MCF-7K and MCF-7A cells, respectively. Clearly, 1.0 µg/mL IGF-I did not reverse the serum inhibition. This was true despite the fact that this concentration of added IGF-I was much more than growth saturating (Karey K P and Sirbasku D A (1988) *Cancer Res* 48, 4083-4092). Duplicate studies with the T47D cells gave the same results (FIG. 28C). It should be noted that IGF-I is active with breast cancer cells even in the presence of serum (Furlanetto R W and DiCarlo J N (1984) *Cancer Res* 44, 2122-2128; Myal Y et al. (1984) *Cancer Res* 44, 5486-5490; Osborne C K et al. (1989) *Mol Endocrinol* 3, 1701-1709; Stewart A J et al. (1990) *J Biol Chem* 265, 2172-2178; Cullen K J et al. (1990) *Cancer Res* 53, 48-53) that contains specific growth factor binding proteins (Rechler M et al. (1980) *Endocrinology* 107, 1451-1459). Human breast cancer cells also secrete binding proteins for the insulin-like growth factors (Yee D et al. (1991) *Breast Cancer Treat Res* 18, 3-10). Binding of the insulin-like factors to carrier proteins may attenuate activity (Zapf J et al. (1978) *J Clin Invest* 63, 1077-1084), have both inhibiting and activating effects (De Mellow J S et al. (1988) *Biochem Biophys Res Commun* 156, 199-204), or enhance biological action (Elgin R et al. (1987) *Proc Natl Acad Sci USA* 84, 3254-3258; Blum W F et al. (1989) *Endocrinology* 125, 766-772). In parallel studies (data not shown), the effects of IGF-II were assayed with the same breast cancer lines under the conditions used with IGF-I. Even at 500 ng/mL, IGF-II did not reverse the inhibitory effects of 10 to 50% (v/v) CDE serum. In another related test, insulin at 10 ng/mL to 10 µg/mL did not reverse the inhibition caused by 50% (v/v) CDE serum. The results with insulin, IGF-I and IGF-II were mutually supportive because these mitogens promote growth via a common receptor (Rechler M et al. (1980) *Endocrinology* 107, 1451-1459; Karey K P and Sirbasku D A (1988) *Cancer Res* 48, 4083-4092; Osborne C K et al. (1989) *Mol Endocrinol* 3, 1701-1709; Stewart A J et al. (1990) *J Biol Chem* 265, 2172-2178). The insulin results were also important in another way. This hormone does not interact with binding proteins and hence their presence in medium will not influence insulin action. These results again confirm the same conclusion arrived at earlier using an entirely different approach (Karey K P and Sirbasku D A (1988) *Cancer Res* 48, 4083-4092). Direct evidence for obligatory IGF-1/IGF-II autocrine loops in estrogen responsive cell growth simply has not been confirmed yet. In fact, there is solid in vivo evidence to the challenge IGF-1/IGF-II autocrine loop participation in the action of estrogens (Arteaga C L et al. (1989) *J Clin Invest* 84, 1418-1423).

Discussion of Example 8. From this series of experiments, it can be readily appreciated that any other natural or synthetic protein or other substance can be similarly tested for cancer cell growth inhibiting activity akin to the serum-derived inhibitor in the CDE horse serum. Also, the same XAD™-4 and CDE extraction protocols may also be applied to body fluids and secretions other than serum, and the extracted fluids may be assayed as described for inhibitor activity. Such fluids or secretions include plasma, urine, seminal fluid, milk, colostrum and mucus. An XAD™-4 column is especially suited for preparing a steroid hormone depleted specimen from a small sample of body fluid.

Conceptual Derivations from this Study. These results also have a direct bearing on a number of hypotheses advanced to explain how estrogens cause target tissue cell growth. The development of the new methods herein provided a unique opportunity to reevaluate the most widely cited proposals under consideration. It was concluded that serum contains an inhibitor that effectively blocks $ER^+$ and $AR^+$ cell growth. Furthermore, physiologic concentrations of sex steroid hormones reverse this inhibition. The results were uniformly the same no matter from which species the cell lines were derived or which species was the source of the serum. In every case, the effects of the various classes of steroid hormones on the different cell lines were consistent with their known tumor forming/growth properties in vivo or published responses in vitro. These results provide new insights into the following proposed mechanisms.

Serum Factor Regulation—Demonstration of Estrogen Responsiveness. The literature describing positive sex steroid hormone growth effects is notably weighted in favor of the use of serum-supplemented cultures. In fact, a review made of the literature (Briand P and Lykkesfeldt A E (1986) *Anticancer Res* 6, 85-90; Wiese T E et al. (1992) *In Vitro Cell Dev Biol* 28A, 595-602) indicates that most past studies have used medium containing ≦20% (v/v) steroid hormone depleted serum. Although other investigators have reported estrogenic effects in "serum-free defined culture", these studies actually used conditions that included a prolonged preincubation in the presence of serum (Allegra J C and Lippman M E (1978) *Cancer Res* 38, 3823-3829; Briand P and Lykkesfeldt A E (1986) *Anticancer Res* 6, 85-90; Darbre P D et al. (1984) *Cancer Res* 44, 2790-2793). The results presented in preceding Examples demonstrate clearly that large magnitude effects are readily demonstrable in medium with CDE-serum and that as the CDE-serum concentrations increase to a maximum useable level of 50%, cell growth is inhibited and estrogens invariably reverse these effects. In light of those results, it was clear that the presence of serum, or a factor(s) contained in serum, made possible the demonstration of sex hormone dependent growth in culture.

The Endocrine Estromedin Hypothesis—Positive Indirect Control. In 1978 it was proposed (Sirbasku D A (1978) *Proc Natl Acad Sci USA* 75, 3786-3790) that growth of estrogen target tissues was not mediated directly by these hormones, but was instead controlled indirectly by steroid inducible circulating growth factors (i.e. endocrine estromedins). Estromedins were proposed to be secreted by target tissues such as uterus, kidney and pituitary, and to act in concert to simultaneously promote the growth of all $ER^+$ target tissues (Sirbasku D A (1978) *Proc Natl Acad Sci USA* 75, 3786-3790; Sirbasku D A (1981) *Banbury Report* 8, 425-443; Ikeda T et al. (1982) *In Vitro* 18, 961-979). The estromedin hypothesis arose from the observation that reproducible in vitro direct estrogen mitogenic effects were not identifiable (Sirbasku D A (1978) *Proc Natl Acad Sci USA* 75, 3786-3790; Sirbasku D A (1981) *Banbury Report* 8, 425-443; Ikeda T et al. (1982) *In Vitro* 18, 961-979). It must be emphasized that the original estromedin hypothesis rested entirely upon the failure to demonstrate large magnitude estrogen mitogenic effects in culture with cell lines confirmed to form steroid hormone responsive tumors in host animals. When estrogen effects were clearly observed with the MTW9/PL2 rat mammary tumor cells in culture, as described herein and reported (Moreno-Cuevas J E and Sirbasku D A (2000) *In Vitro Cell Dev Biol* 36, 410-427; Sirbasku D A and Moreno-Cuevas J E (2000) *In Vitro Cell Dev Biol* 36, 428-446), it was apparent that the endocrine estromedin model required further evaluation. It was reasoned that extension of these results to additional $ER^+$ cell lines, including those from other species and diverse target tissues, would either provide important support for the earlier hypothesis or disprove it. In the work disclosed herein, this reassessment has been accomplished. All of the $ER^+$ cells tested, as well as one androgen sensitive $AR^+$ human cancer line, manifested substantial growth in response to the appropriate steroid hormones in cultures containing inhibiting concentrations of CDE serum. There can be no doubt that steroid hormones act positively to promote target tumor cell growth. The results presented in this report plainly nullify the previous endocrine estromedin model of steroid hormone responsive cell growth. The disapproval of the earlier endocrine estromedin model reopened the question of how estrogens and other factors regulate sex steroid responsive growth.

The Autocrine and Paracrine Models—Positive Indirect Control. In the studies described in this Example, it was investigated whether exogenous growth factors mimic the inhibitor reversing effects of estrogens. The EGF/TGFα and insulin-like families were focused on because of their high biological potencies and physiologic relevance. These growth factors were expected to substitute for steroid hormones based on the autocrine loop mechanisms proposed earlier. Despite this expectation, polypeptide growth factors did not substitute for the estrogens. They were inactive in the presence of the serum-borne inhibitor. In point of fact, deduction indicates that it makes no practical difference whether the growth factors were autocrine or paracrine in origin. The presence of the serum inhibitor in effect blocks all mitogenic action except that exerted by the steroid hormones. This is a preferred feature of the serum-borne inhibitor(s) disclosed herein, and is further described in Examples which follow, when the use of serum-free defined culture is described. These results also indicate that the search for the regulatory mechanism controlling estrogen dependent growth must seek new directions. Since the estrogenic effects seen in CDE-serum are the largest yet recorded, CDE is the preferred source of the regulator in the cell growth assays.

Culture Parallels in vivo Growth Regulation. The results shown in this Example have another important implication. Usually normal in vivo tissues are bathed in growth factor containing fluids. Mitogens within tissues may be of local origin or may be derived from the circulation (Gospodarowitz D and Moran J S (1976) *Annu Rev Biochem* 45, 531-558; Goustin A S et al. (1986) *Cancer Res* 46, 1015-1029). If growth factors have unrestricted freedom to stimulate cell proliferation, normal formation and architecture of the tissues would not develop nor could they be maintained. Manifestly, tissue architecture would be disrupted. In fact, this is one definition of cancer (Sonnenschein C and Soto A M (2000) *Molecular Carcinogenesis* 29, 205-211). The properties of a serum-borne inhibitor that counterbalances unrestricted growth merit serious further consideration with regard to how cancers develop in steroid hormone sensitive tissues. Others researchers have also arrived at this conclusion (Soto A M and Sonnenschein C (1985) *J Steroid Biochem* 23, 87-94).

The Estrocolyone Hypothesis—Negative Indirect Regulation. The estrocolyone model (Soto A M and Sonnenschein C (1987) *Endocr Rev* 8, 44-52) is an indirect negative mechanism based on regulation of sex steroid hormone dependent cells via a serum-borne inhibitor. The inhibitor blocks growth promoted by non-steroidal mitogens such as growth factors and diferric transferrin. Sonnenschein and Soto first proposed that estrocolyone acted at the cell surface via specific receptors. The effects of sex steroid hormones were to bind estrocolyone and prevent it from associating with the cells. Only low physiologic concentrations of sex steroid hormones were needed for this function. The special emphasis of this model was that sex steroid hormones did not act through intracellular located DNA binding receptors (i.e. cytosolic or nuclear sites). These intracellular sites had no growth function. Hence, this was an indirect negative mechanism (Soto A M and Sonnenschein C (1987) *Endocr Rev* 8, 44-52). The results presented in this disclosure are in agreement with the serum-borne mediator aspect of the estrocolyone hypothesis. There is no doubt that serum from several species contains a steroid hormone reversible inhibitor and that its isolation and molecular characterization will be a major advance with both practical and conceptual applications. With regard to the action site of the steroid hormones, these results differ from the estrocolyone hypothesis as described (Soto A M and Sonnenschein C (1987) *Endocr Rev* 8, 44-52). The tentative identification of several estrocolyone candidates have been described, and in U.S. Pat. No. 4,859,585 (Sonnenschein) and U.S. Pat. No. 5,135,849 (Soto), the issue of properties was raised again, but with different conclusions than published earlier.

The Positive Direct Model—Steroid Hormone Receptor Mediation. The one mechanism most widely accepted regarding steroid hormones and growth involves the nuclear located DNA binding ERα receptor (Gorski J and Hansen J C (1987) *Steroids* 49, 461-475). Growth is thought to be mediation by specific cytosolic and/or nuclear located receptors that ultimately alter DNA transcription to regulate gene activity. Results from many laboratories support this mechanism (Jensen E V and Jacobson H I (1962) *Recent Prog Horm Res* 18, 387-414; Gorski J et al. (1968) *Recent Prog Horm Res* 24, 45-80; Jensen E V et al. (1968) *Proc Natl Acad Sci USA* 59, 632-638; Jensen E V and DeSombre E R (1973) *Science* (Wash D.C.) 182, 126-134; Anderson J N et al. (1974) *Endocrinology* 95, 174-178; O'Malley B W and Means A R (1974) *Science* (Wash D.C.) 183, 610-620; Lippman M E (1977) *Cancer Res* 37, 1901-1907; Harris J and Gorski J (1978) *Endocrinology* 103, 240-245; Markaverich B M and Clark J H (1979) *Endocrinology* 105, 1458-1462; Katzenellenbogen B S (1980) *Annu Rev Physiol* 42, 17-35; Katzenellenbogen B S (1984) *J Steroid Biochem* 20, 1033-1037; Clark J H and Markaverich B M (1983) *Pharm Ther* 21, 429-453; Darbre P et al. (1983) *Cancer Res* 43, 349-355; Darbre P D et al. (1984) *Cancer Res* 44, 2790-2793; Huseby R A et al. (1984) *Cancer Res* 44, 2654-2659; Gorski J and Hansen J C (1987) *Steroids* 49, 461-475; Katzenellenbogen B S et al. (1987) *Cancer Res* 47, 4355-4360; O'Malley B W (1990) *Mol Endocrinol* 4, 363-369). As discussed elsewhere herein, the preferred positive action of estrogens is activation of a new ERγ that saturates/activates at lower steroid concentrations than the ERα or the ERβ.

Serum Proteins with Estrocolyone Steroid Binding Characteristics. If the estrocolyone mechanism is in fact correct, one must be able to identify at least one serum protein with very high affinity binding (ie. $K_d$ picomolar) for sex steroids. There is, however, a major unresolved problem with that hypothesis. Other than sex hormone binding globulin (SHBG), additional high affinity estrogen binding in CDE human serum has not been found. SHBG has $K_d$ of $1.7 \times 10^{-9}$ M for $E_2$ at 37° C. (Rosner W and Smith R N (1975) *Biochemistry* 14, 4813-4820). This affinity does not qualify as the high binding expected of estrocolyone. Also, a search for estrocolyone in human serum only resulted in identification of SHBG (Reny J-C and Soto A M (1992) *J Clin Endocrinol Metab* 68, 938-945). No higher affinity binding site/protein was found. The binding of labeled steroid hormones with CDE-horse and CDE-rat serum was studied (results presented in an Example which follows), and $^3H$-$E_2$ specific binding at $K_d$ of 20 to 50 nM was found. This is a significant matter because estrogenic effects are demonstrated in this disclosure at 1 to 10 picomolar. As further support for this point, the estrocolyone authors found estrogenic effects at 10 to 30 picomolar $E_2$ (Soto A M and Sonnenschein C (1985) *J Steroid Biochem* 23, 87-94; Soto A M and Sonnenschein C (1987) *Endocr Rev* 8, 44-52). The lack of correlation between the concentration of steroid that promotes growth and affinity of sex steroids for serum components raises serious questions about this aspect of the estrocolyone hypothesis. These observations also suggest that a very high affinity intracellular ERγ regulates growth.

A New Model of Steroid Hormone Responsive Cell Growth. A new model best fits the available data. It brings together aspects of both the direct positive mechanism and indirect negative control. According to this model, regulation of steroid hormone target tumor cell growth is a balance between positive and negative control signals. This balance dictates either growth (i.e. cell division) or quiescence (i.e. cell metabolism and tissue specific function but without cell division). Direct positive control is mediated by a high sensitivity intracellular sex steroid receptor (yet to be defined) that ultimately activates gene expression whereas negative regulation is exerted by a serum-borne inhibitor that acts at the cell surface. The results disclosed herein support the view that growth is controlled directly by both negative and positive mediators. The results presented further define the molecular properties of the serum-borne inhibitor by eliminating TGFβ1 as a candidate. This is an important issue because of the well-known effects of TGFβ on normal breast epithelial cells (Hosobuchi M and Stampfer M R (1989) *In Vitro Cell Dev Biol* 25, 705-713) and ER⁻ estrogen insensitive breast cancer cells (Arteaga C L et al. (1988) *Cancer Res* 48, 3898-3904). The results herein continue to confirm a previously unrecognized entity that serves as the estrogen reversible inhibitor in serum. Inhibitors that lack estrogen reversibility can be eliminated from consideration.

Example 9

Serum-Free Defined Culture Medium Formulations

In this Example, formulations of various serum-free defined culture media are discussed. Among other features, the preferred embodiments of the present media provide useful tools for detecting estrogenic effects.

Serum-free Defined Mammalian Cell Culture—Development Background. The use of serum-free defined medium to grow diverse cell types in culture gained national and international recognition with the publication by Hayashi and Sato (Hayashi I and Sato G H (1976) *Nature* (Lond) 259, 132-134). They demonstrated a breakthrough. The serum supplement commonly used in cell culture medium could be replaceable entirely by mixtures of nutrients and hormones in serum-free medium. This observation was expanded to include cell types from many mammalian tissues (Barnes D and Sato G (1980) *Anal Biochem* 102, 255-270; Barnes D and Sato G (1980) *Cell* 22, 649-655; Bottenstein J et al. (1979) *Methods Enzymol* 58, 94-109; Rizzino A et al. (1979) *Nutr Rev* 37, 369-378). Further development and application of this technology has been reported (Barnes D W, Sirbasku D A and Sato G H (Volume Editors) (1984) *Cell Culture Methods for Molecular Biology and Cell Biology*, Volume 1: *Methods for Preparation of Media, Supplements, and Substrata for Serum-free Animal Cell Culture*; Volume 2: *Methods for Serum-free Culture of Cells of the Endocrine System*; Volume 3: *Methods for Serum-free Culture of Epithelial and Fibroblastic Cells*; Volume 4: *Methods for Serum-free Culture of Neuronal and Lymphoid Cells*, Allan R. Liss/John Wiley, New York). A national/international symposium organized and directed by Drs. Gordon Sato, Arthur Pardee and David Sirbasku was held at the Cold Spring Harbor Laboratory to address the unfolding technology required for serum-free defined medium growth of cells in culture and to discuss its applications (Sato G H, Pardee A B and Sirbasku D A (1982) Volume Editors, *Cold Spring Harbor Conferences on Cell Proliferation*, Volume 9, Books A and B, *Growth of Cells in Hormonally Defined Media*, Cold Spring Harbor, N.Y.).

Serum-free Defined Culture—Nutrient Additions. A number of nutrient additions to D-MEM/F-12 are needed to grow the cells used in the presently described studies. The formulations of serum-free defined medium employed are specific optimizations, modifications, or necessary changes of earlier media that have been described (Riss T L and Sirbasku D A (1987) *Cancer Res* 47, 3776-3782; Danielpour D et al. (1988) *In Vitro Cell Dev Biol* 24, 42-52; Ogasawara M and Sirbasku D A (1988) *In Vitro Cell Dev Biol* 24, 911-920; Karey K P and Sirbasku D A (1988) *Cancer Res* 48, 4083-4092; Riss T L et al. (1988) *In Vitro Cell Dev Biol* 24, 1099-1106; Riss T L et al. (1988) *In Vitro Cell Dev Biol* 25, 127-135; Riss T L and Sirbasku D A (1989) *In Vitro Cell Dev Biol* 25, 136-142; Riss T L et al. (1986) *J Tissue Culture Methods* 10, 133-150; Sirbasku D A et al. (1991) *Mol Cell Endocrinol* 77, C47-C55; Sirbasku D A et al. (1991) *Biochemistry* 30, 295-304; Sirbasku D A et al. (1991) *Biochemistry* 30, 7466-7477; Sato H et al. (1991) *In Vitro Cell Dev Biol* 27A, 599-602; Sirbasku D A et al. (1992) *In Vitro Cell Dev Biol* 28A, 67-71; Sato H et al. (1992) *Mol Cell Endocrinol* 83, 239-251; Eby J E et al. (1992) *Anal Biochem* 203, 317-325; Eby J E et al. (1993) *J Cell Physiol* 156, 588-600; Sirbasku D A and Moreno-Cuevas J E (2000) *In vitro Cell Dev Biol* 36, 428-446).

Serum-free Defined Medium Nutrient Supplements—Bovine Serum Albumin. Bovine serum albumin (BSA) (Sigma Catalog No. A3912) was made by "initial fractionation by heat shock and Fraction V", minimum purity 98% (electrophoresis), according to the supplier. A 50 mg/mL stock solution of BSA was prepared in normal saline and was sterilized using 0.2 µm pore membrane filters. Aliquots are stored at $-20°$ C. in plastic tubes. As will be discussed below, the "heat shock" step that was used in most albumin preparation methods inactivates the estrogen reversible inhibitor disclosed herein.

Serum-free Defined Medium Nutrient Supplements—Linoleic Acid—Albumin (Lin-Alb). This preparation was purchased from Sigma as Linoleic Acid Albumin Conjugate (Catalog No. L8384). The conjugate is supplied as a powder sterilized by irradiation. The fatty acid content is 1% (w/w) linoleic acid. A stock solution was typically prepared by dissolving the contents of a 500 mg bottle in 10 mL of sterile normal saline to give a final concentration of 50 mg/mL. Aliquots are stored at 4° C. in polystyrene tubes. This solution is never frozen. Mammalian cells cannot produce polyunsaturated fatty acids. They must be supplied in a soluble form. Fatty acids are carried physiologically bound to albumin.

Serum-free Defined Medium Nutrient Supplements—Ethanolamine (ETN). ETN was purchased from Sigma (Catalog No. A5629) (FW 61). This liquid has a density of 1.0117 grams/mL. Using 0.610 mL in 100 mL of water, a 100 mM stock solution was prepared which was sterilized using the 0.2 um pore membrane filters. The ETN was stored at $-20°$ C. in polystyrene tubes. This nutrient is required to sustain phospholipid metabolism required for all membrane biosynthesis.

Serum-free Defined Medium Nutrient Supplements—Phosphoethanolamine (PETN). This solid material was purchased as o-phosphoryl-ethanolamine (FW 141) (Sigma Catalog No. P0503). A 10 mM stock of PETN was prepared by dissolving 141 mg in 100 mL of water and sterilizing with 0.2 µm pore membrane filters. Aliquots were stored at $-20°$ C. in polystyrene tubes. This component is an adjunct to ETN.

Serum-free Defined Medium Nutrient Supplements—Glutamine (GLUT). This essential amino acid was purchased from Sigma (Catalog No. G5763). It is "cell culture tested" according to the manufacturer. Addition of glutamine (FW 146.1) to the culture media is necessary because of its relatively short half-life (i.e. about 80% is lost in 20 days at 35° C.). See the Sigma product information for the decay curves at different temperatures and pH. Purchased D-MEM/F-12 stored in the refrigerator for about three weeks lost most of the original glutamine present. For serum-free applications, additional supplementation is required to sustain growth. For a preparation, 11.7 g was dissolved in 400 mL of water to give 200 mM glutamine. This solution was sterilized using 0.2 µm pore filter membranes. Aliquots are stored at $-20°$ C. polystyrene tubes. The final glutamine concentration added to serum-free defined medium is 2 mM. Glutamine is a major metabolite and energy source for cells growing in culture.

Serum-free Defined Medium Nutrient Supplements—Reduced Glutathione (GSH). Crystalline reduced glutathione (FW 307.3) was purchased from Sigma (Catalog No. G4251). A stock of 40 mg/mL was prepared by dissolving 400 mg in 10 mL of water. This stock was very quickly sterilized with a 0.2 µm pore filter unit. Aliquots were quickly stored at $-20°$ C. in polystyrene tubes. According to Sigma technical service, this sulfhydryl (—SH) compound is unstable in aqueous solutions, including tissue culture medium, and is rapidly converted to the oxidized GS-SG form by exposure to air. Addition every two to four days to the culture medium may be required for reducing agent requiring cells. Another reducing agent that also is effective is mercaptoethanol. It is more stable and often effective at lower concentrations than GSH. Preferably the concentrations are controlled effectively. Reducing agents act as "scavengers" of free radicals generated by the oxygen atmosphere of cell culture.

Serum-free Defined Medium Nutrient Supplements—Selenium (Se). A powder of sodium selenite (100 mg/vial) is obtained from Collaborative Research or Sigma (Catalog No. S5261). It has been sterilized by irradiation. The contents of a single vial are dissolved in 100 mL of sterile water to give final stock of 1.0 mg/mL. This preparation should not be filter sterilized because Se binds to filters. The final volume was diluted to 100 mL with sterile saline. Aliquots are stored at $-20°$ C. in polystyrene tubes. Selenium is an important cofactor for enzyme systems that protect the cells from oxidation effects.

Serum-free Defined Medium Nutrient Supplements—Diferric Transferrin (2FeTf). Iron Fe (III) saturated (98%) human transferrin (diferric transferrin) was purchased from Collaborative Research (Catalog No. 40304) or Sigma (Catalog No. T3309) as bottles containing 1 gram of red colored powder. The contents of one bottle are dissolved in 100 mL of normal saline. This red colored solution is sterilized using 0.2 µM pore membrane filters. This stock is 10 mg/mL. Aliquots are stored at $-20°$ C. in polystyrene tubes. All growing cells require diferric transferrin as a source of iron for a great many metabolic processes, except for a few known cell types in which free Fe (III) or chelated Fe (III) can be substituted for diferric transferrin. The cell lines employed in the present Examples do not include those exceptional cell types, however.

Serum-free Defined Medium Growth Factor Supplements—Epidermal Growth Factor (EGF). EGF prepared from mouse submaxillary gland (tissue culture grade) was purchased from Collaborative Research (Catalog No. 40001) as 100 µg in a sterile vial or from Sigma (Catalog No. E4127). The original vials are stored at 4° C. according to the manufacturer's instructions. To prepare a stock solution, 5.0 mL of sterile saline was added to a vial to yield a 20 µg/mL EGF solution. Aliquots are stored frozen at $-20°$ C. polystyrene tubes. Repeated freeze-thaw must be avoided. This growth factor is useful because of its very broad cell specificity range.

Serum-free Defined Medium Growth Factor Supplements—Acidic Fibroblast Growth Factor (aFGF). Acidic FGF is purchased from Sigma (Catalog No. F5542). It is the human recombinant product from *E. coli*. This product has very specific handling requirements. It is provided sterilized in 25 µg vials lyophilized from PBS containing 1.25 mg of BSA. The contents of each vial are reconstituted in 25 mL of sterile PBS containing 1.0 mg/mL of BSA and 10 µg/mL of heparin. Filtration of this product at this concentration must absolutely be avoided. This solution is stored at −20° C. in polystyrene tubes. The solutions of aFGF definitely cannot be freeze-thawed more than twice. This growth factor is highly labile. Careless handling will result in problems. Keratinocyte growth factor (KGF) can substitute for aFGF. The fibroblast growth factor family is important in growth of urogenital tissues including bladder and prostate (Liu W et al. (2000) *In Vitro Cell Dev Biol* 36, 476-484).

Serum-free Defined Medium Growth Factor Supplements—Heparin. Heparin is used to stabilize FGF in cell culture (Gospodarowitz D and Cheng J (1986) *J Cell Physiol* 128, 475-484). Heparin is obtained from Sigma (Catalog No. H3149) as the sodium salt, Grade 1-A, from porcine intestinal mucosa. A solution of 1.0 mg/mL is made in saline and sterilized with 0.2 µm pore membrane filters. An aliquot of 250 µL is added to the 25 mL of aFGF reconstitution solution used above. Sterile heparin is stored at 4° C.

Serum-free Defined Medium Adhesion Protein Supplement—Fibronectin (Fbn). Human plasma derived fibronectin can be purchased from many commercial sources. Bovine fibronectin is also available and is effective. Fibronectin is prepared from units of fresh human plasma (unfrozen) or fresh bovine (unfrozen) plasma by two methods (Retta S F et al. (1999) *Methods in Molecular Biology* 96, 119-124; Smith R L and Griffin C A (1985) *Thrombosis Res* 37, 91-101). Purity is evaluated by SDS-PAGE with Coomassie Brilliant Blue staining or silver staining (Pierce Chemicals® kits). Adhesion activity is confirmed with cells in serum-free defined medium. Vitronectin can substitute for fibronectin.

Serum-free Defined Medium Iron (Fe (III) Chelator Supplements—Deferoxamine Mesylate (DFX). Deferoxamine (FW 656.8) is purchased from Sigma (Catalog No. D9533). The stock solution is made at 10 mM by adding 131 mg to 20 mL of highly purified water as described above. The solution is sterilized by filtration with 0.2 µM pore membranes. Aliquots are stored at −20° C. in polystyrene tubes.

Serum-free Defined Medium Iron (Fe (III) Chelator Supplements—Apotransferrin (apoTf). Human serum apotransferrin can be purchased from Sigma (Catalog No. T4382). It is minimum 98% iron-free. Alternatively, apotransferrin is prepared as described previously (Sirbasku D A et al. (1991) *Biochemistry* 30, 295-304; Sirbasku D A et al. (1991) *Biochemistry* 30, 7466-7477). Apotransferrin is prepared by dialysis against citrate buffer pH 5.0-5.5 with 1 µg/mL DFX present to chelate ≧98% of the iron. Handling and storage were as described for diferric transferrin but with great care to avoid contact with iron sources.

Serum-free Defined Medium Nutrient Supplements—Bovine Insulin (INS). This hormone was purchased from either of two sources. From Gibco-BRL it is Insulin, Bovine Zinc Crystals for Cell Culture Applications (Catalog No. 18125-039). It was also obtained from Collaborative Research (Catalog No. 40305) and stored at 4° C., according to that manufacturer's recommendation. Gibco-BRL recommends solid insulin storage at −5° C. to 20° C. A stock of 10 mg/mL in 0.01 N HCl was prepared by adding 250 mg of insulin to 25 mL of the acid. The HCl was made by adding 172 µL of concentrated (11.6 N) HCl to 100 mL of water. The final stock solution of 10 mg/mL of insulin is filter sterilized using 0.2 µm pore diameter membranes. Aliquots are stored at 4° C. in polystyrene tubes. Care was taken not to freeze-thaw the aliquots of stock solution. Insulin is a very broad range cell growth-stimulating factor as well as a regulator of specific metabolic processes. At sufficiently high concentrations (i.e., usually >1 µg/mL, insulin causes growth via binding to the IGF-I Type I receptor (Karey K P and Sirbasku D A (1988) *Cancer Res* 48, 4083-4092).

Serum-free Defined Medium Nutrient Supplements—Thyroid Hormones. The preferred thyroid hormone is $T_3$ (3',5-Triiodothyronine (FW 673)), purchased from Sigma as Catalog No. T2752). It is stored desiccated at −20° C. To prepare stocks, 0.5 N NaOH was made by addition of 20 grams of pellets to one liter of water. Then, 67.3 mg of $T_3$ was added. After dissolving the $T_3$ with stirring for a few minutes, 25 mL of this stock was diluted up to 250 mL with water, for a final concentration of 0.05 N NaOH. This dilution was sterilized using the 0.2 µm pore diameter filter. At this point, the final stock for storage was 10 µM $T_3$. Aliquots of this final stock are stored in polystyrene tubes at −20° C. The second thyroid hormone, thyroxin ($T_4$, sodium salt, pentahydrate FW 888.9), is prepared by the same procedure. For this stock solution, 88.9 mg of $T_4$ are used. $T_4$ is purchased from Sigma (Catalog No. T2501). $T_4$ is used at 10 to 20 times higher concentrations than $T_3$. Care is taken not to freeze-thaw these preparations. Thyroid hormones have a very broad range of metabolic and growth effects, and many different types of cells require thyroid hormones for growth in serum free culture.

Compositions of Serum-free Defined Media. TABLE 6 presents the formulations of the preferred serum-free defined media developed for use in detecting high-level steroid hormone reversible inhibition by steroid hormone-depleted ("steroid hormone stripped") serum fractions and by purified inhibitors in serum-free cell growth assays. As indicated in the footnotes to the table, when a particular component is included in one of the formulations, the concentration that provides a suitable cell growth medium can fall within the indicated range.

TABLE 6

Composition of Serum-free Defined Media Based on Standard Gibco-BRL D-MEM/F-12

| CELL TYPE<br>MEDIUM NAME | Human<br>Breast<br>DDM-2MF | Human<br>Prostate<br>CAPM | Rat<br>Mammary<br>DDM-2A | Rat<br>Pituitary<br>PCM-9 | Hamster<br>Kidney<br>CAPM |
|---|---|---|---|---|---|
| COMPONENT FINAL CONCENTRATIONS IN THE DEFINED MEDIA | | | | | |
| Insulin[1] | 500 ng/mL | 10 µg/mL | 10 µg/mL | 10 µg/mL | 10 µg/mL |
| EGF[2] | 20 ng/mL | 20 ng/mL | 20 ng/mL | None | 20 ng/mL |
| AFGF[3] | None | 10 ng/mL | None | None | 10 ng/mL |
| Triiodothyronine[4] | 0.3 nM | 1.0 nM | 0.3 nM | 1.0 nM | 1.0 nM |
| Diferric transferrin[5] | 10 µg/mL | 10 µg/mL | 10 µg/mL | 10 µg/mL | 10 µg/mL |

TABLE 6-continued

Composition of Serum-free Defined Media Based on Standard Gibco-BRL D-MEM/F-12

| CELL TYPE<br>MEDIUM NAME | Human<br>Breast<br>DDM-2MF | Human<br>Prostate<br>CAPM | Rat<br>Mammary<br>DDM-2A | Rat<br>Pituitary<br>PCM-9 | Hamster<br>Kidney<br>CAPM |
|---|---|---|---|---|---|
| Ethanolamine[6] | 50 μM | 50 μM | 50 μM | 10 μM | 50 μM |
| Phosphoethanolamine[7] | 5 μM | None | 5 μM | None | None |
| Bovine Serum Albumin[8] | 500 μg/mL | 1.0 mg/mL | 500 μg/mL | 500 μg/mL | 1.0 mg/mL |
| Linoleic acid-BSA[9] | 150 μg/mL | None | 150 μg/mL | None | None |
| Selenium[10] | 20 ng/mL | 10 ng/mL | 20 ng/mL | 10 ng/mL | 10 ng/mL |
| Reduced glutathione[11] | 20 μg/mL | None | 20 μg/mL | None | None |
| Glutamine[12] | 2.0 mM | None | 2.0 mM | None | None |
| Heparin[13] | None | 7.5 μg/mL | None | None | 7.5 μg/mL |
| Deferoxamine[14] | 5 μM | 10 μM | 5 μM | 10 μM | 10 μM |
| Human Fibronectin[15] | 25 μg | 20 μg | None | None | 20 μg |

When a component is added, the following are the effective concentration ranges used:
[1]INS range 100 ng/mL to 10 μg/mL
[2]EGF range 1 ng/mL to 50 ng/mL
[3]aFGF range 0.2 ng/mL to 20 ng/mL
[4]$T_3$ range 0.3 nM to 10 nM
[5]2FeTf range 2 μg/mL to 50 μg/mL
[6]ETN range 5 μM to 100 μM
[7]PETN range 5 μM to 50 μM
[8]BSA range 0.2 mg/mL to 5.0 mg/mL
[9]Lin-Alb range 50 μg/mL to 500 μg/mL
[10]Se range 5 ng/mL to 20 ng/mL
[11]GSH range 1 μg/mL to 50 μg/mL
[12]Glut range 0.5 mM to 2.0 mM
[13]Heparin range 1 μg/mL to 10 μg/mL
[14]DFX range 2 μM to 20 μM
[15]Fbn range 15 μg to 50 μg per 35-mm diameter dish Serum-free Media Variations. The variations described next are applicable to the defined media in TABLE 6. Standard phenol red-containing Gibco-BRL D-MEM/F-12 is a preferred basal medium to which the defined media components are added. It contains 0.6 mM to 1.0 M $CaCl_2$. D-MEM/F-12 can be purchased from Gibco-BRL in the liquid form or can be prepared from the powder formulation using only highly purified water. Alternatively, another suitable basal medium could be used as long as it provides at least the required minimum amounts of necessary nutrients, vitamins and minerals to maintain cell viability of the desired cell line. The calcium concentration range preferred is 0.6 to 10 mM. Calcium stabilizes the inhibitor in cell culture without impairing cell growth. The human breast cancer cell medium, DDM-2MF, was a modification of the original DDM-2 medium (Danielpour D et al. (1988) *In Vitro Cell Dev Biol* 24, 42-52) and MOM-1 (Ogasawara M and Sirbasku D A (1988) *In Vitro Cell Dev Biol* 24, 911-920) and contained modified hormone concentrations, deferoxamine (DFX) and fibronectin. Aqueous salt solutions such as tissue culture medium contain hydrolytic polymeric forms of Fe (III) (Spiro T G et al. (1966) *J Am Chem Soc* 88, 2721-2726). DFX binds this form of Fe (III) with very high affinity (Schubert J (1964) In; *Iron Metabolism: The Chemical Basis of Chelation*, Springer, Berlin, pp 466-498). If not removed, Fe (III) inhibits hormone-responsive growth in serum-free defined medium (Sirbasku D A et al. (1991) *Mol Cell Endocrinol* 77, C47-C55; Sato H et al. (1992) *Mol Cell Endocrinol* 83, 239-251; Eby J E et al. (1993) *J Cell Physiol* 156, 588-600; Eby J E et al. (1992) *Anal Biochem* 203, 317-325). The preferred cell growth media for conducting cell growth assays are substantially devoid of unbound Fe (III), i.e., preferably containing less than 1 μM Fe (III), and more preferably containing no more than about 0.15 μM. In preferred growth assay systems described herein, which are substantially devoid of unbound Fe (III), the concentration of free, or active Fe (III) in the medium is less than a cell growth inhibiting amount.

Fibronectin was used with DDM-2MF to promote cell attachment. The 35-mm diameter assay dishes were pre-coated by incubation with the designated amount of fibronectin (TABLE 6) for 16 to 48 hours at 37° C. in 2.0 mL of D-MEM/F-12. CAPM human prostatic cancer cell medium was developed to support the growth of tumor cells from this tissue. The composition of CAPM is described in TABLE 6. CAPM also supports the growth of the H301 Syrian hamster kidney tumor cells. DDM-2A, which is a modified form of DDM-2 (Danielpour D et al. (1988) *In Vitro Cell Dev Biol* 24, 42-52), was preferred for growing MTW9/PL2 cells. PCM-9 defined medium was developed for growing the rat pituitary cell lines. This medium differs from previous PCM formulations (Sirbasku D A et al. (1991) *Mol Cell Endocrinol* 77, C47-C55; Sato H et al. (1992) *Mol Cell Endocrinol* 83, 239-251; Eby J E et al. (1993) *J Cell Physiol* 156, 588-600; Eby J E et al. (1992) *Anal Biochem* 203, 317-325) in that DFX was substituted for apotransferrin and the triiodothyronine concentration was increased to 1.0 nM. Although DFX and apotransferrin (2 to 50 μg/mL) are the preferred chelators based on their very high specificity and affinities for Fe (III), EDTA at 1 to 10 μM or sodium citrate at 10 to 1000 μM also effectively neutralize the cytotoxic effects of Fe (III) (Eby J E et al. (1993) *J Cell Physiol* 156, 588-600). Ascorbic acid (vitamin C) also chelates Fe (III), but is used less often because it is unstable in cell culture medium at 37° C. in an oxygen environment in the presence of salts and metals in the medium. Also, at concentrations of 50 to 100 μg/mL, apo-ovotransferrin and apo-lactoferrin also were effective Fe (III) chelators in serum-free defined medium (Eby J E et al. (1993) *J Cell Physiol* 156, 588-600). Although EGF, aFGF and insulin are the preferred growth factors, several other human recombinant proteins are effective. They have either been purchased or obtained as gifts from Gibco-BRL, Sigma or IMCERA Bioproducts. Insulin-like growth factors I and II (IGF-I and IGF-II) can be used to replace insulin, transforming growth factor α (TGFα) replaces EGF, TGFβ as an inhibitory supplement, and basic fibroblast growth factor (bFGF) partially replaces aFGF. Insulin can be used to replaced IGF-I and IGF-II. All of these protein growth factors are dissolved under sterile conditions according to manufacturers' instructions and stored as indicated.

Discussion of Example 9. The preferred serum-free media described above provide an ideal scenario for the study of growth responses of hormone responsive cancers without the myriad of potential interactions accompanying the presence of serum with its 5000+ proteins and other compounds. The formulations presented permit dissection of growth into its individual parts caused by different stimulators. When of interest, a combination of a few factors can be investigated to achieve an understanding of growth promoter/inhibitor interactions (i.e. cross-talk). This is exceptionally difficult to achieve in the presence of full serum. The serum-free medium described herein provided a tool for the assessment of growth inhibitor(s) isolated from CDE-horse serum, whose actions are reversed by sex-steroid hormones, as mentioned at the beginning of this Example and also discussed elsewhere herein. These serum-free defined media will allow direct analysis of the final purified serum-borne inhibitors under the most defined conditions available for cell culture. This feature brings the regulation of steroid hormone dependence up to the conditions that have been the most sought after over the past fifteen years. The preferred serum-free media of the present invention raise hope for the provision of new insight that could help to clarify the mechanisms involved in the control of breast, prostatic and other mucosal cancers under conditions not previously available.

Moreover, because of widespread concern today about possible contamination of commercial animal sera by disease causing agents such as bovine spongiform encephalopathy ("mad cow disease"), there is a great need for serum-free cell culture media that can support a variety of cell types. The new media compositions fill that need. The new serum-free media can be used not only for assays but also for large scale testing purposes and industrial uses such as cell culture production of a desirable protein. For example, an antigen for vaccine production, or a monoclonal antibody can be prepared without fear of contamination by a serum-derived agent. The serum-free media are also useful for producing quantities of virus for vaccine manufacture or for producing recombinant viruses for gene therapy, and can be substituted for a conventional serum-based medium in a basic cell culture method for producing quantities of proteins or viruses. Such basic cell culture methods are well known in the art and have been described in the literature.

Example 10

Serum-Free Defined Medium Supports Both Hormone Sensitive and Autonomous Cancer Cell Growth In this Example, it is shown that media derived according to the present methods are effective for supporting hormone sensitive and autonomous cancer cell growth.

Figure 29:
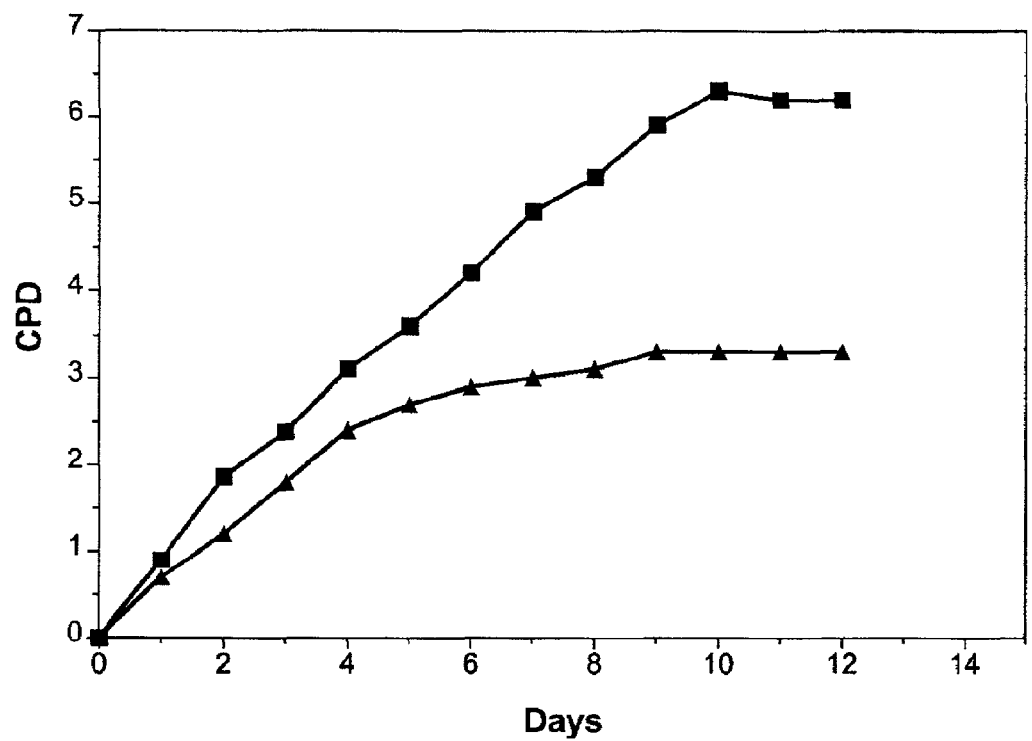
FIG. 29. Growth of T47D Human Breast Cancer Cells in Standard and "low-Fe" D-MEM/F-12.
Figure 30:
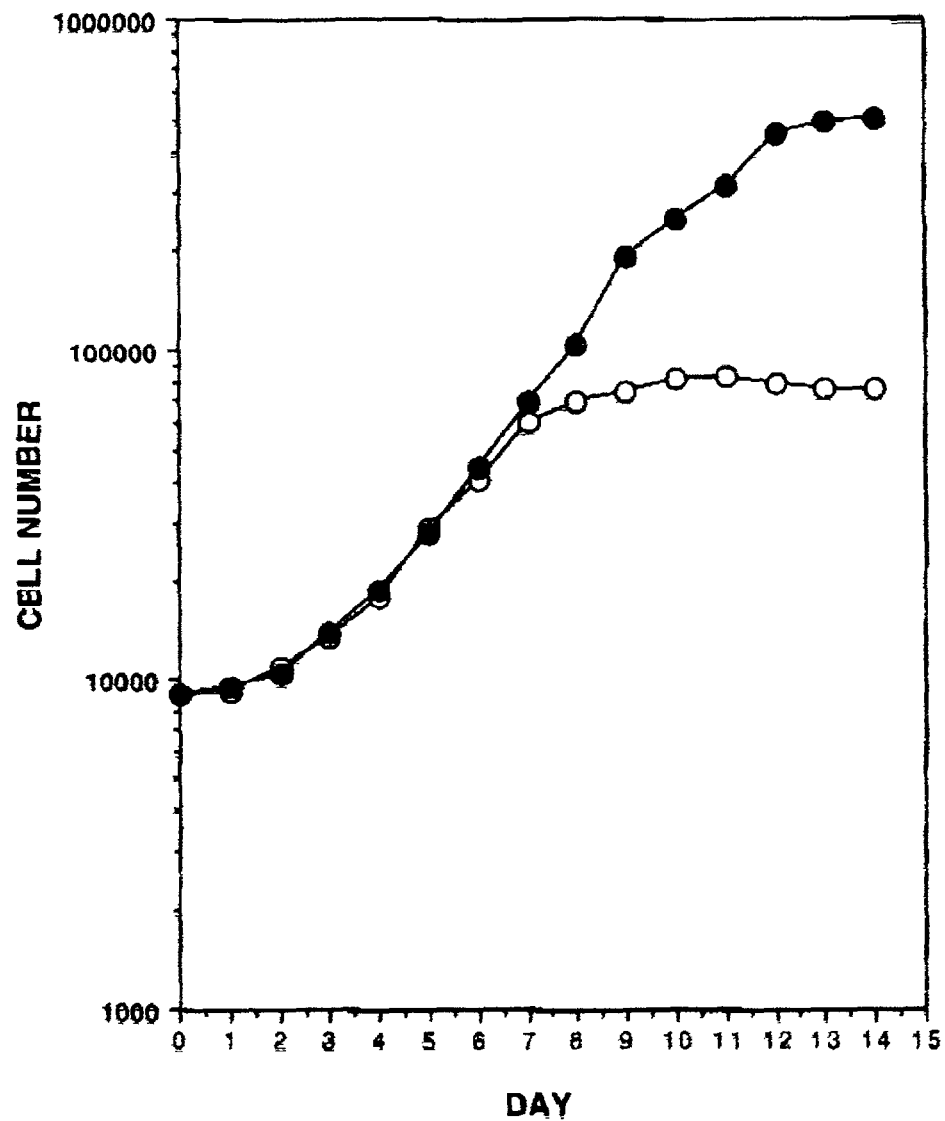
FIG. 30. Growth of LNCaP Human Prostate Cancer Cells in Standard and "low-Fe" D-MEM/F-12.
Figure 31:
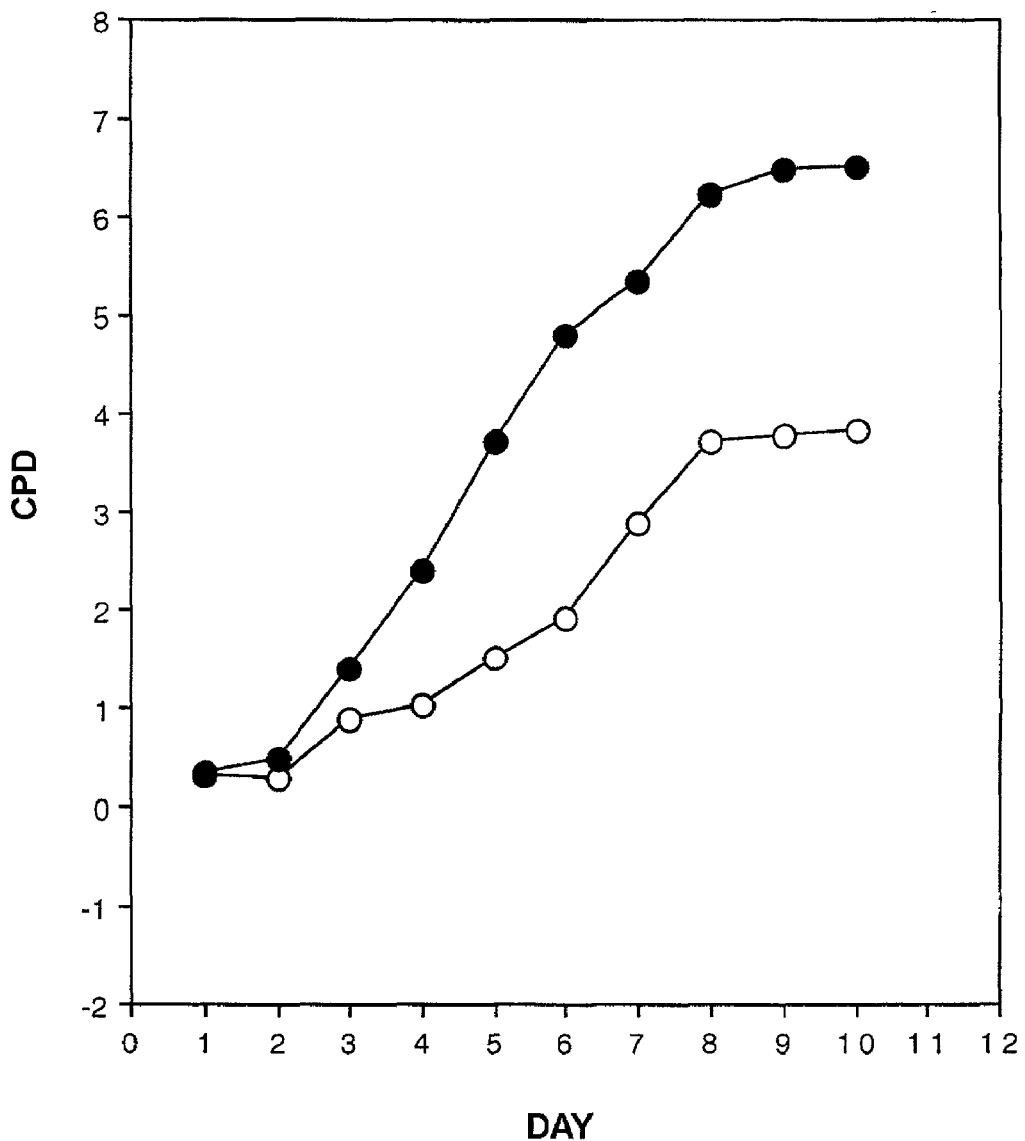
FIG. 31. Growth of MDCK Dog Kidney Tubule Cells in Standard and "low-Fe" D-MEM/F-12.

Selection of Models to Study Hormone Dependence and Autonomy in Serum-free Defined Culture Media. One goal was to develop serum-free defined media that can be used to directly compare negative serum factor regulation with steroid hormone responsive and steroid hormone autonomous cancers of the same tissue. That meant establishing a medium that supported the growth of both cell types. As models, human prostatic carcinoma and human breast carcinoma cells were chosen because responsive and autonomous (unresponsive) cell lines are currently available for both types of cancers. Furthermore, as discussed above, these cancers have many common characteristics including their tendency to pass from steroid hormone receptor positive to steroid hormone receptor negative in a process called tumor progression. During the course of development of such defined media, one observation was made consistently: breast cancer cells that were $ER^+$ (i.e. estrogen sensitive) and prostate cancer cells that were $AR^+$ (i.e. androgen sensitive) grew less well in defined medium based on standard D-MEM/F12 than in defined medium based on "low-Fe" D-MEM/F12. The results of an example with T47D cells in DDM-2MF are shown in FIG. 29. The example with LNCaP cells in CAPM is shown in FIG. 30. Another example is the thyroid hormone responsive MDCK kidney tubule epithelial cells in CAPM as shown in FIG. 31. Standard D-MEM/F-12 contains both ferric nitrate and ferrous sulfate as nutrient additions. When purchased without these salts, the medium was designated "low-Fe" D-MEM/F-12. The iron concentrations in standard and "low-Fe" D-MEM/F-12 were 1.0 µM and 0.15 µM, respectively (Eby J E et al (1992) *Anal Biochem* 203, 317-325). Even in "low-Fe" medium, iron is present as a contaminant in the chemicals used to make the formulation, the 2.2 g/L $NaHCO_3$ added as a metabolic requirement and buffer, and the 15 mM HEPES buffer necessary for stabilizing the pH under serum-free conditions (Eby J E et al (1992) *Anal Biochem* 203, 317-325). It is noteworthy that as low as 1.0 µM Fe (III) inhibits epithelial cell growth completely within five to seven days. In another test the thyroid hormone responsive human HT-29 colonic carcinoma cells in CAPM also grew better in "low-Fe" than standard D-MEM/F-12 (data not shown). This indicates that restriction of Fe (III) in culture medium will have implications even beyond sex steroid hormone dependent cells.

Modifications of the Usual Growth Assays for Experiments in "low-Fe" Medium Versus "Standard" Medium. Specific modifications of the customary cell growth assays were required for assays done under iron-restricted conditions. For example, the 35-mm assay dishes were incubated for 16 to 24 hours prior with 20 to 25 µg of fibronectin in 2 mL of "low-Fe" D-MEM-F12 medium. Serum-free components were added to "low-Fe" D-MEM/F-12 at double the concentrations needed (2×) or to "standard" D-MEM/F-12 at (2×) as the experiments dictated. Each assay dish received 1.0 mL of this solution. Next, the cells to be used in the assays were washed three times in either "low-Fe" medium or "standard" medium depending upon the experimental protocol. These washes were done with the same care as discussed above in the general materials and methods described in Example 1. Each dish received 1.0 mL of cells in the appropriate medium. At this point, the components final concentrations were (1×) as summarized in TABLE 6. Also, TABLE 6 describes medium containing deferoxamine as the Fe (III) chelator. Although less preferred, due in part to cost considerations, specificity, and affinity for Fe (III), as noted above, apotransferrin is also effective, especially at the preferred apotransferrin concentration of 50 µg/mL. When apotransferrin binds Fe (III), it is converted to one of three forms of ferric transferrin (Eby J E et al (1992) *Anal Biochem* 203, 317-325). These three forms become additional support for cell growth in defined medium, thereby converting a toxic substance to a useable natural nutrient.

Figure 32:
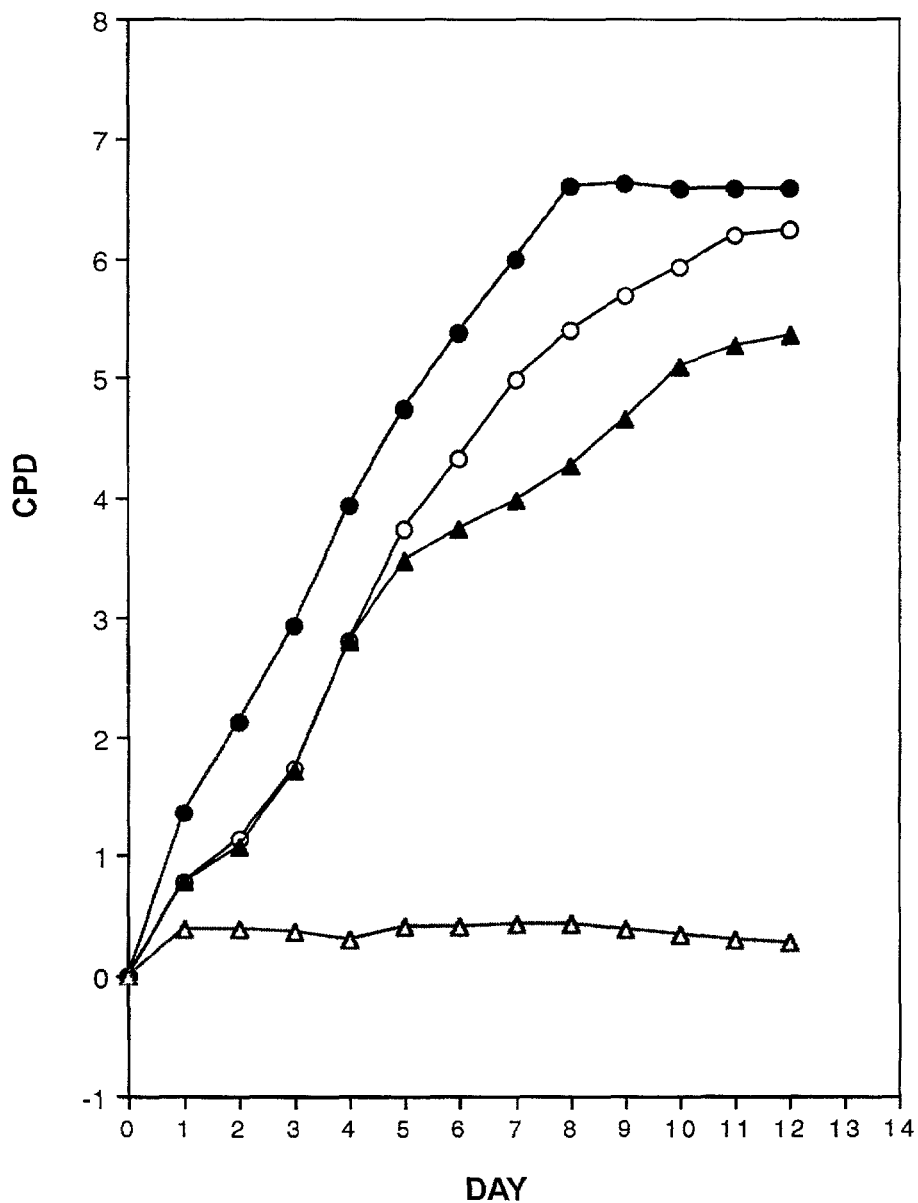
FIG. 32. Growth of AR$^+$ LNCaP Cells in CAPM ±DHT versus Growth in D-MEM/F-12 Containing 10% Fetal Bovine Serum.
Figure 33:
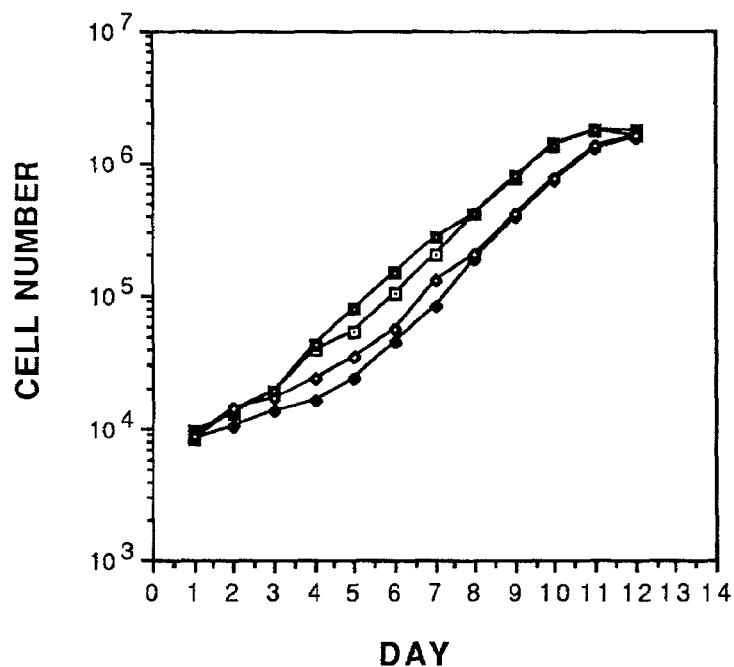
FIG. 33 Growth of the AR$^-$ DU145 and AR$^-$ PC3 Cells in CAPM versus Growth in D-MEM/F-12 Containing 10% Fetal Bovine Serum.

Growth in Serum-free Defined Medium Versus D-MEM/F-12 with 10% (v/v) Fetal Bovine Serum. To demonstrate the utility of the formulations in TABLE 6, cell growth was compared in serum-free defined medium ±steroid hormone versus growth supported by fetal bovine serum. It is generally accepted that fetal bovine serum represents one of the most effective sera for tissue culture. As an example, growth of the LNCaP cells was compared in CAPM ±DHT versus growth in 10% (v/v) fetal bovine serum (FIG. 32). CAPM plus 10 nM DHT supported growth at about 80 to 90% of the rate of fetal bovine serum. Growth promoted by 10% fetal bovine serum, typically obtained from conventional commercial sources, reached 6.57 (±0.48) CPD or, a 96-fold increase on cell number in 12 days. By day 12, cell densities in CAPM nearly equaled those in serum. Growth promoted by the serum-free medium reached 6.22 (±0.35) CPD or 84-fold increase. CAPM was able to support LNCaP growth even in the absence of sex-steroid hormones. Maximum growth obtained without sex-steroid hormones was of 5.35 (±0.12) CPD or a 49-fold increase. The androgenic effect is therefore marginal, with differences of less than one CPD between the presence and absence of DHT. Also shown, the cells did not grow in D-MEM/F-12 without any additions (FIG. 32). Similar studies were done with other cell lines to determine growth rates versus serum and to establish the periods for single time assays (e.g. 7, 10, 12 or 14 days). FIG. 33 shows the same analysis with DU145 and PC3 cells in CAPM and in D-MEM/F-12 with 10% fetal bovine serum. As the cell number data show, growth was logarithmic. After 12 days, growth in the serum-free medium was identical to that in 10% fetal bovine serum for both cell lines. Growth of PC3 in 10% serum reached 6.98 (±0.71) CPD or a 112-fold increase in cell number versus 6.97 (±0.44) CPD or the same fold increase for cell numbers in serum-free medium. Growth of DU145 in 10% fetal bovine serum was 6.71 (±0.58) CPD versus 6.73 (±0.18) CPD in serum-free conditions. The results in FIGS. 32 and 33 demonstrate by example that the serum-free defined media in TABLE 6 are effective with both hormone sensitive and hormone autonomous cells.

Figure 35:
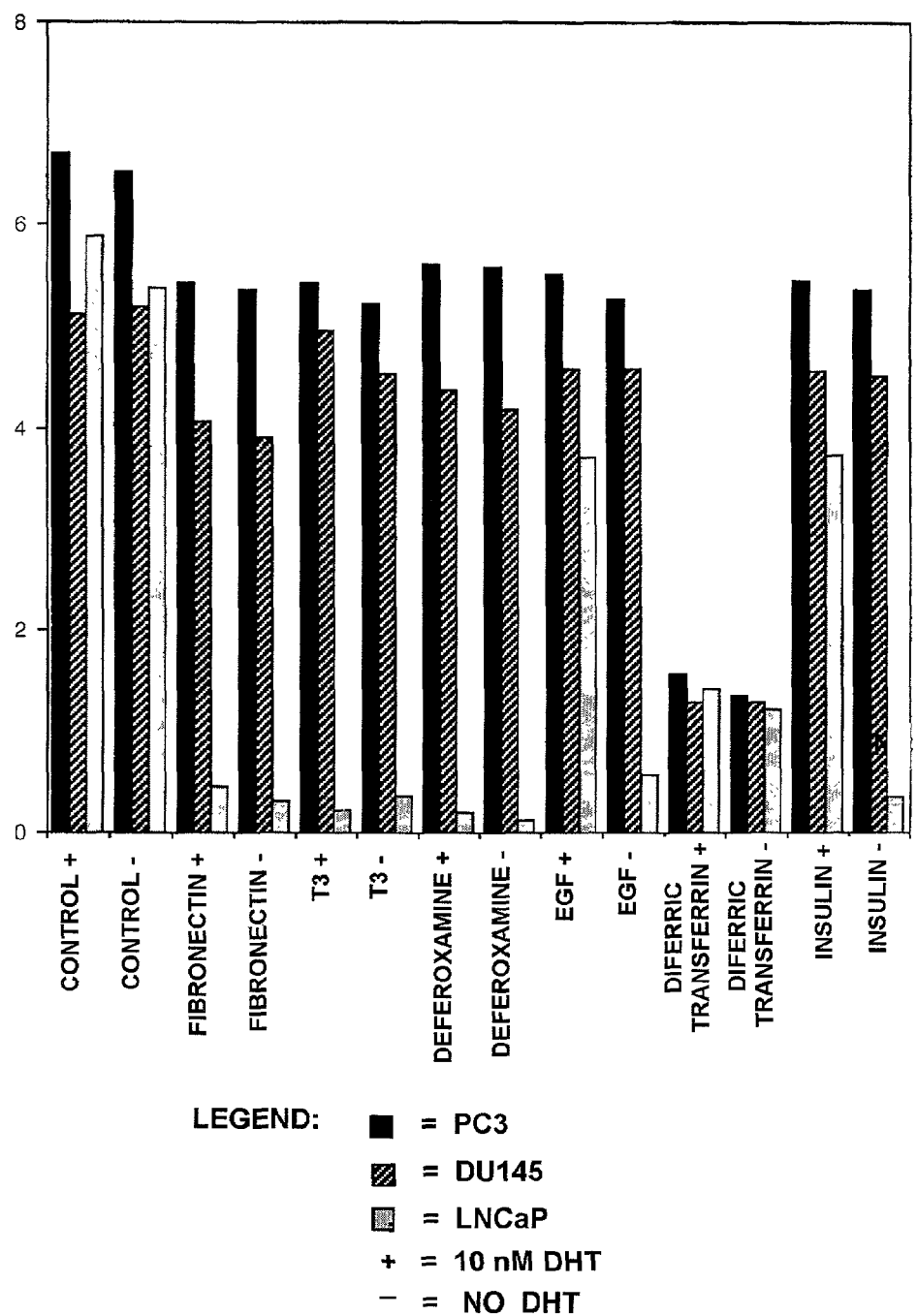
FIG. 35. Effects of Deletion of Individual Components from CAPM Serum-free Medium on LNCaP, DU145 and PC3 Cell Growth ±DHT.

Determination of Component Concentrations and the Requirement for a Fe (III) Chelator. The optimum concentration of each single component was determined by dose-response analysis in the presence of other components. The technology used to establish early forms of serum-free defined media has been described (Danielpour D et al. (1988) *In Vitro Cell Dev Biol* 24, 42-52; Ogasawara M and Sirbasku D A (1988) *In Vitro Cell Dev Biol* 24, 911-920). An example of this process is shown in FIG. 34 with LNCaP cells. Dose-response effects of bovine serum albumin, apotransferrin, $T_3$, ethanolamine, selenium, and EGF are shown. The results show clearly that the addition of the iron chelator apotransferrin was required for cell growth. After determining optimum concentrations for each component, the contribution of each to the total was assessed by another assay. Individual components were deleted one at a time. As an example, the three most widely used prostatic carcinoma cell lines were compared (i.e. LNCaP, PC3 and DU145) in CAPM that contained deferoxamine in place of apotransferrin (FIG. 35). The deletions were done ±DHT. The first and most striking result was the major differences between the growth requirements of the DHT sensitive LNCaP cells and those of the autonomous DU145 and PC3. Only the deletion of diferric transferrin substantially prevented the growth of autonomous cells. Also, it was clear that deletion of deferoxamine had only a small (i.e. <20%) effect on growth of the DU145 and PC3 cells. The DU145 and PC3 cell lines also were $T_3$, insulin, EGF, fibronectin and deferoxamine independent. As expected ±DHT had no significant effect on DU145 or PC3. By contrast, LNCaP growth was significantly (p<0.01) reduced or arrested completely by deletion of fibronectin, T3, diferric transferrin or deferoxamine. LNCaP growth also was inhibited by deletion of EGF or insulin, but these effects were pronounced only in the absence of DHT.

Discussion of Example 10. The media described in TABLE 6 were optimized for the specific cell types designated. Additionally, they were optimized to permit direct comparison of the growth properties of $ER^+$ and $AR^+$ steroid hormone sensitive tumor cell lines to their $ER^-$ and $AR^-$ steroid hormone insensitive (also called autonomous) counterparts. This careful optimization was done originally to study rat mammary tumor cells of both types in DDM-2A defined media. The appropriate cell lines for this approach have been developed from the MTW9/PL2 population and described (Danielpour D and Sirbasku D A (1984) *In Vitro* 20, 975-980). The medium DDM-2MF has been developed for the same purpose only for comparisons of $ER^+$ and $ER^-$ forms of these cancers. TABLE 1 lists the most important $ER^+$ human breast cancer cell lines in use today. In addition a number of other $ER^-$ human breast cancer cells lines have been evaluated. They are the MDA-MB-231 (Cailleau R et al. (1974) *J Natl Cancer Inst* 53, 661-674), BT-20 (Lasfargues E Y and Ozzello L (1958) *J Natl Cancer Inst* 21, 1131-1147), Hs0578T (Hackett A J et al. (1977) *J Natl Cancer Inst* 58, 1795-1806), MDA-MD-330 (Cailleau R et al. (1978) *In Vitro* 14, 911-915), and the myoepithelial HBL-100 (Gaffney E V (1982) *Cell Tissue Res* 227, 563-568). The demonstration of $ER^-$ status of these lines has been described (Reddel R R et al. (1985) *Cancer Res* 45, 1525-1531). With regard to human prostatic cancer, the only reliable androgen responsive cell line available today is the LNCaP (TABLE 1). Another, the ALVA-41, has been described as androgen growth responsive (Nakhla A M and Rosner W (1994) *Steroids* 59, 586-589). However, as shown in subsequent Examples, this line is autonomous by the criterion of a lack of DHT effects in CDE-horse serum. Two other human prostate cancer cell lines are commonly used as autonomous examples. These lines are the DU145 (Stone K R et al. (1978) *Int J Cancer* 21, 274-281) and the PC3 (Kaighn M E et al. (1979) *Invest Urol* 17, 16-23). Previously, there was a defined medium established for PC3 cells (Kaighn M E et al. (1981) *Proc Natl Acad Sci USA* 78, 5673-5676). This medium was evaluated and did not support LNCaP cell growth. However, others have reported "serum-free" media that was stated to be effective with LNCaP, DU145, PC3 and ALVA-31 cells (Hedlund T E and Miller G J (1994) *The Prostate* 24, 221-228). The problem was this medium was not serum-free nor was it defined. The experiments began with cells plated into 5% serum and then preceded to use a serum fraction called fetuin to support growth. Fetuin is a complex undefined mixture of ≧4% of the proteins in serum. Under those conditions, an accurate analysis of hormonal and growth factor effects (Ogasawara M and Sirbasku D A (1988) *In Vitro Cell Dev Biol* 24, 911-920) cannot be done satisfactorily. The completely serum-free CAPM in TABLE 6 supports the growth of all of these prostate cell lines. In addition, CAPM has been applied to the $ER^+$ estrogen growth stimulated H301 Syrian hamster kidney cells (Sirbasku D A and Moreno J E (2000) *In Vitro Cell Dev Biol* 36, 428-446) and its autonomous derivative cell line A195. As has been reviewed (Evans R M (1988) *Science* (Wash D.C.) 240, 889-895), steroid hormones and thyroid hormones belong to the same superfamily of receptors. Both are important in growth. Therefore, it was expected that some tissues might be thyroid hormone positive regulated, while others might be positive regulated by steroid hormones. CAPM has also been applied to the study of thyroid hormone reversal of purified inhibitors with the human colon carcinoma cell line HT-29. Similar use has been made of CAPM with the MDCK dog kidney tubule cell line (Leighton J et al. *Science* (Wash D.C.) 158, 472-473). CAPM replaces a different defined medium prepared for MDCK cells (Taub M et al. (1979) *Proc Natl Acad Sci USA* 76, 3338-3342). It is likely that the prostaglandin in that earlier medium interfered with the action of the thyroid hormones. In any case, that medium was not useful for demonstration of thyroid hormone reversal of purified MDCK cell growth inhibitors. All of these observations support the view that a series of uniquely optimized media have been formulated to define the growth requirements of epithelial cells from several of the very prominent cancers of humans. Furthermore, the technology developed promises application to the optimization of growth of other types cells from a variety of epithelial/mucosal tissues. Epithelial/mucosal cancers comprise 80% of those in humans.

Example 11

Differential Effects of Fe (III) on the Growth of Hormone Responsive and Autonomous Human Breast and Human Prostate Cancer Cells This Example demonstrates that iron has an inhibiting effect on steroid responsive cell growth, independent of the above-described immunoglobulin effects, and which is distinguishable from its effect on autonomous cells.

Approaches to Demonstration of Iron Toxicity. Standard D-MEM/F-12 appeared to contain sufficient Fe (III) to inhibit hormone responsive cell growth (FIGS. 29 and 30). Accordingly, other approaches were used to further demonstrate the deleterious effects of Fe (III) on hormone responsive tumor cell growth. To add Fe (III) to culture medium, it must be in a soluble form. Ferric ammonium citrate was selected for use. However, ferric ammonium sulfate is also effective. Other salts such as ferric chloride or ferric nitrate or ferrous sulfate can be used. Ferric ammonium citrate is a mixture that contains 16.6% of ferric iron by weight. The amount of mixture added to each dish was adjusted to achieve the desired Fe (III) concentrations. Due to the light sensitivity of the mixture, the solutions were prepared fresh daily and the experiments carried out under restricted light conditions. Also, the mixture was prepared in water. Buffers without phosphate may be used, but they are generally less effective due to formation of insoluble materials. The ferric mixtures and the iron chelators EDTA, deferoxamine mesylate and sodium citrate were purchased from Sigma.

Figure 36:
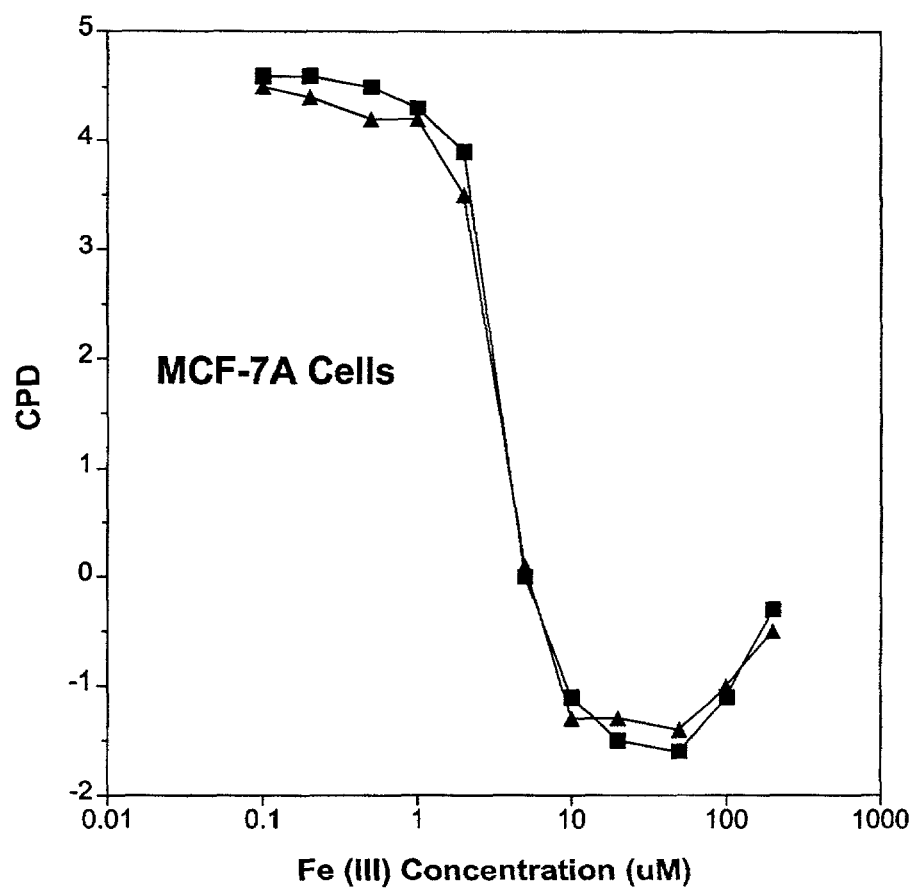
FIG. 36. Effect of Fe (III) on MCF-7A Cell Growth in DDM-2MF Serum-free Defined Medium.
Figure 37:
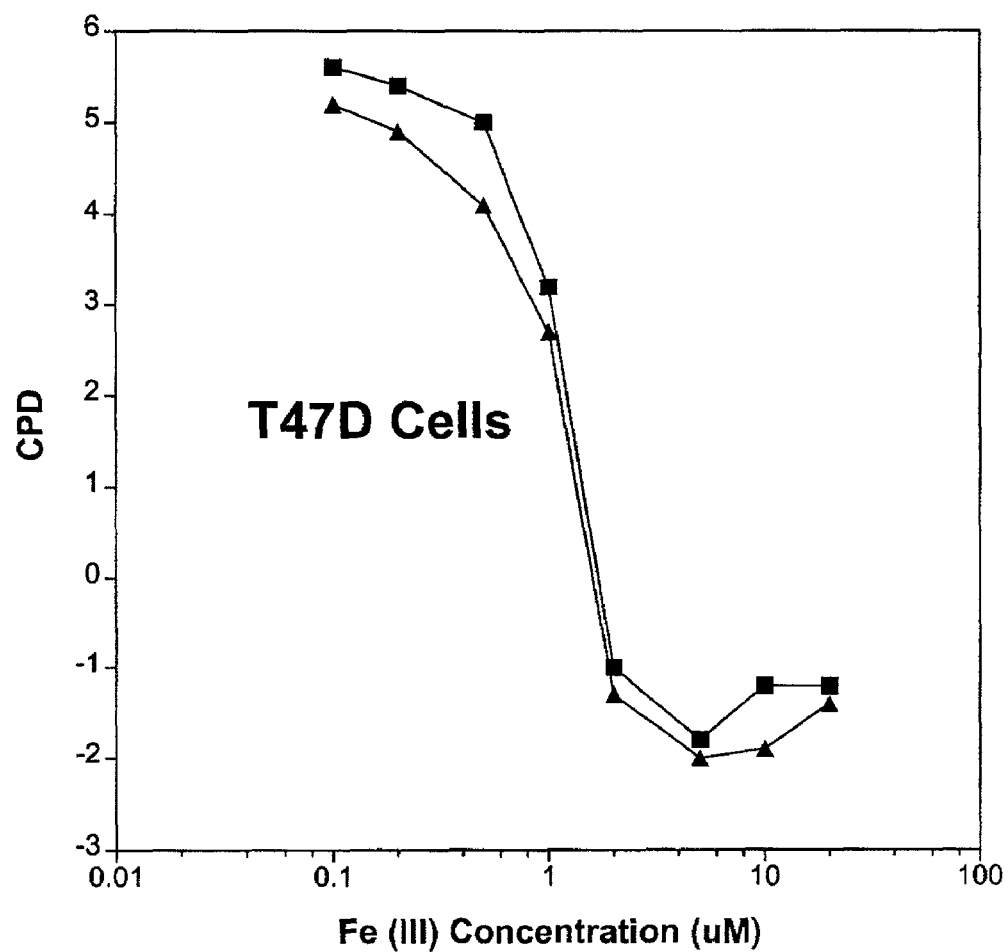
FIG. 37. Effect of Fe (III) on T47D Cell Growth in DDM-2MF Serum-free Defined Medium.

Iron Toxicity with Human $ER^+$ Breast Cancer Cells. In the first experiments, two $ER^+$ cell lines were evaluated for Fe (III) sensitivity in DDM-2MF defined medium prepared with 10 µg/mL apotransferrin in place of the deferoxamine shown in TABLE 6. The effect of addition of ferric ammonium citrate on MCF-7A growth $\pm E_2$ at 10 days is shown in FIG. 36. Either with or without steroid hormone, Fe (III) was completely inhibitory at 10 µM. There were no viable cells in the dishes at $\geq$10 µM. The $EI_{50}$ of Fe (III) with MCF-7A cells was 5 to 7 µM. A similar analysis with T47D cells in DDM-2MF with 10 µg/mL apotransferrin instead of deferoxamine showed complete inhibition at 10 days with 2 µM Fe (III) (FIG. 37). At $\geq$2 µM there were no viable cells in the dishes either with or without ($\pm$) $E_2$. The $EI_{50}$ of Fe (III) with T47D cells was 1 µM.

Figure 38:
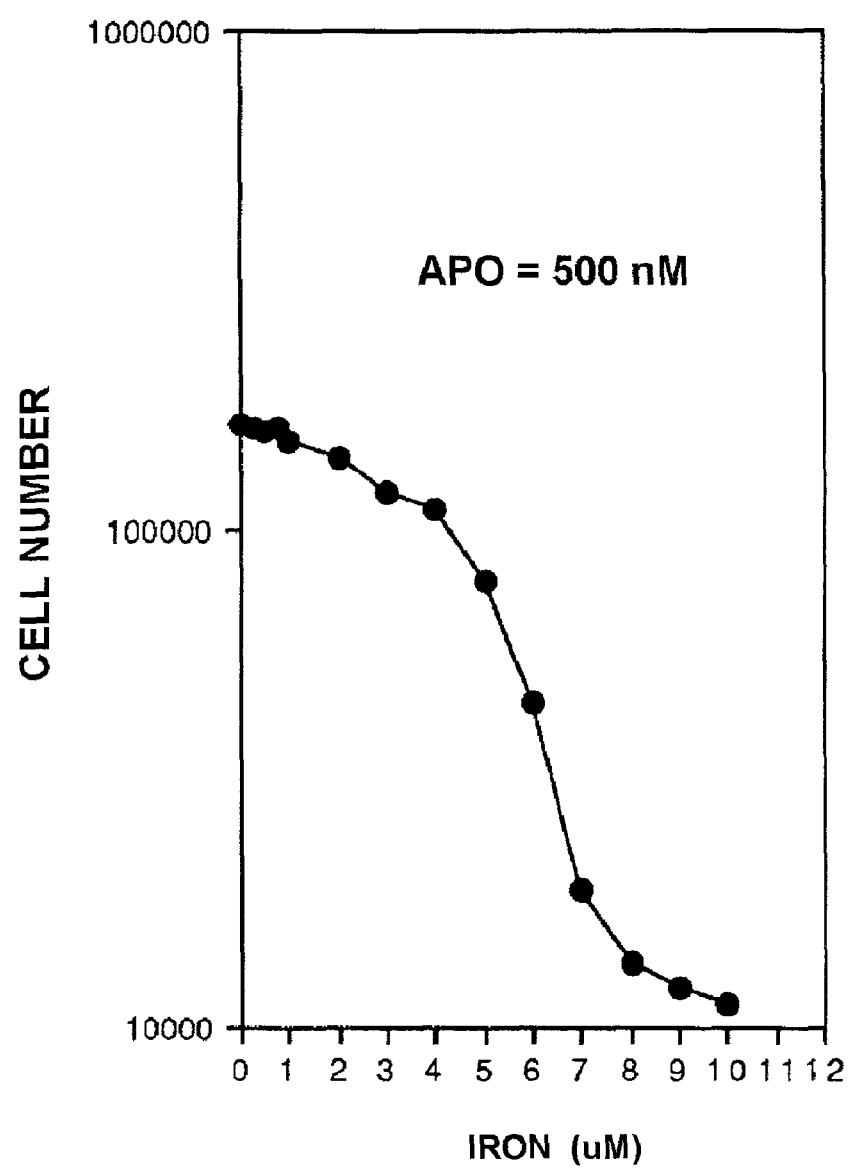
FIG. 38. Effect of Fe (III) on LNCaP Cell Growth in CAPM Plus Apotransferrin.
Figure 39:
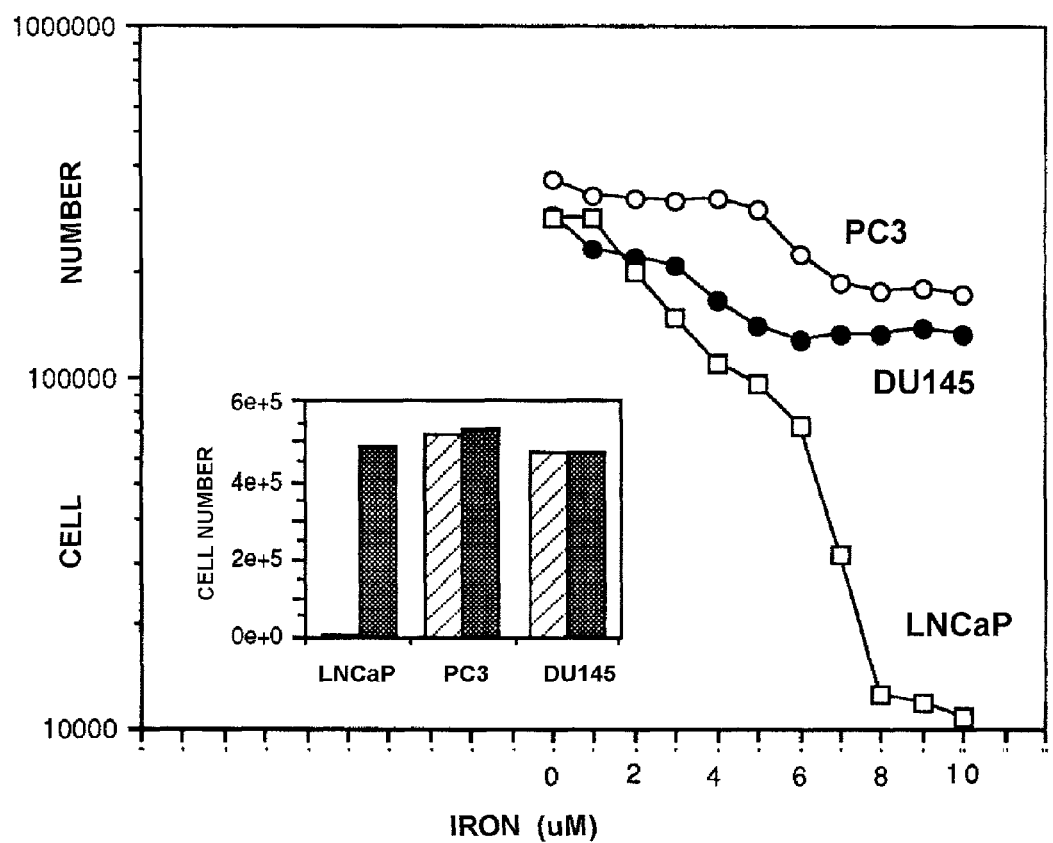
FIG. 39. Comparative Effect of Fe (III) on LNCaP, DU145 and PC3 Cell Growth in CAPM.

Iron Toxicity with $AR^+$ and $AR^-$ Human Prostate Cancer Cell Lines. The effect of Fe (III) on $AR^+$ LNCaP cell growth was assessed in CAPM defined medium in which apotransferrin (500 nM) was substituted for deferoxamine, and the results are shown in FIG. 38. Clearly, 10 µM Fe (III) arrested growth to seed density levels (i.e. 12,000 cells per dish) in a 12-day assay. The $EI_{50}$ for LNCaP cells was 5 µM. In another experiment in CAPM, the effects of ferric ammonium citrate were evaluated with $AR^+$ LNCaP cells and $AR^-$ PC3 and DU145 cells (FIG. 39). Again, Fe (III) inhibited LNCaP cells to seed densities levels by 8 to 10 µM. However, effects on the androgen autonomous PC3 and DU145 cells were markedly less (FIG. 39). Reductions of 10 to 30% in cell number for PC3 and DU145, respectively, were observed in 10 µM Fe (III). The inhibitory effects of Fe (III) on the androgen independent PC3, DU145 and ALVA-41 cells were variable, and never as marked as with the steroid hormone responsive LNCaP cells. The insert in FIG. 39 shows a correlation between hormone responsiveness and Fe (III) effects. The results show a correlation between iron effects and thyroid hormone responsiveness. LNCaP cells are $T_3$ responsive whereas PC3 and DU145 are not.

Figure 40:
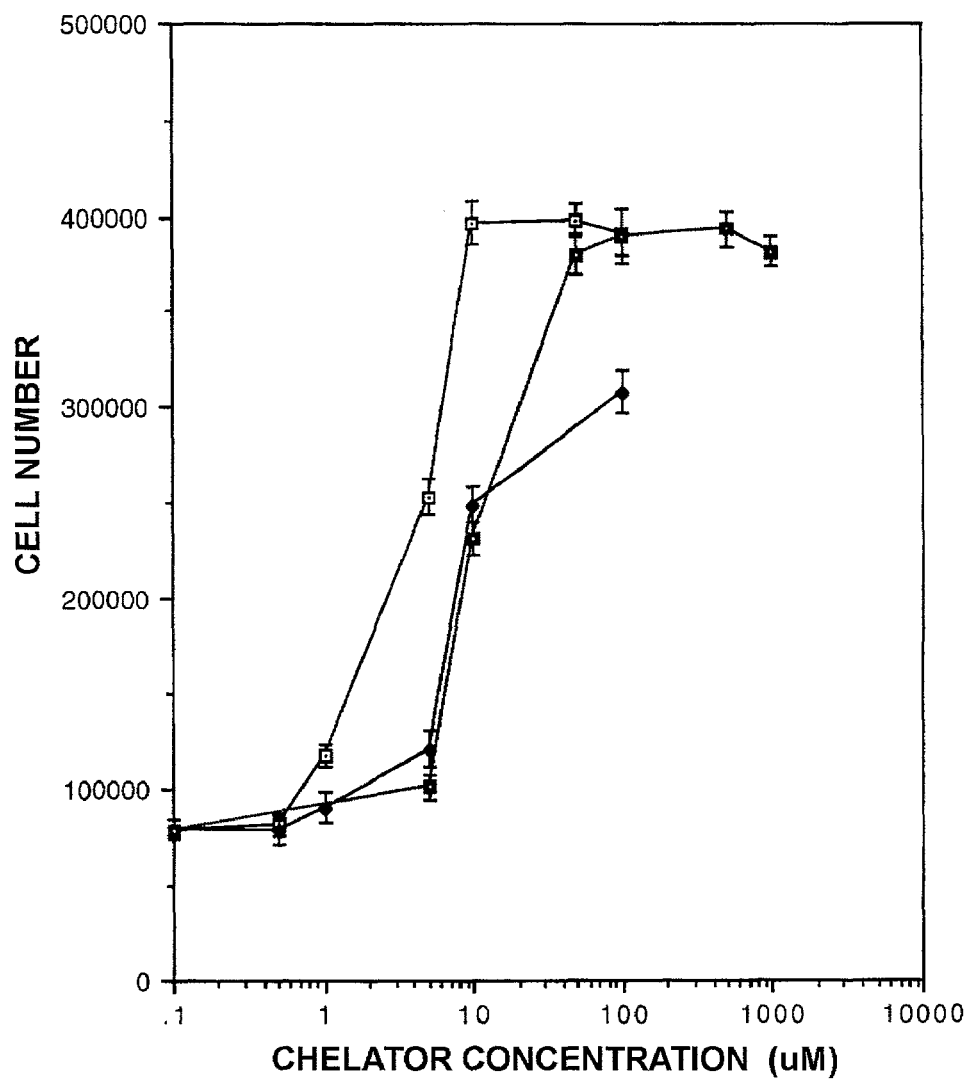
FIG. 40. Growth Restoring Effect of Fe (III) Chelators in serum-free medium with T47D Cells.
Figure 41:
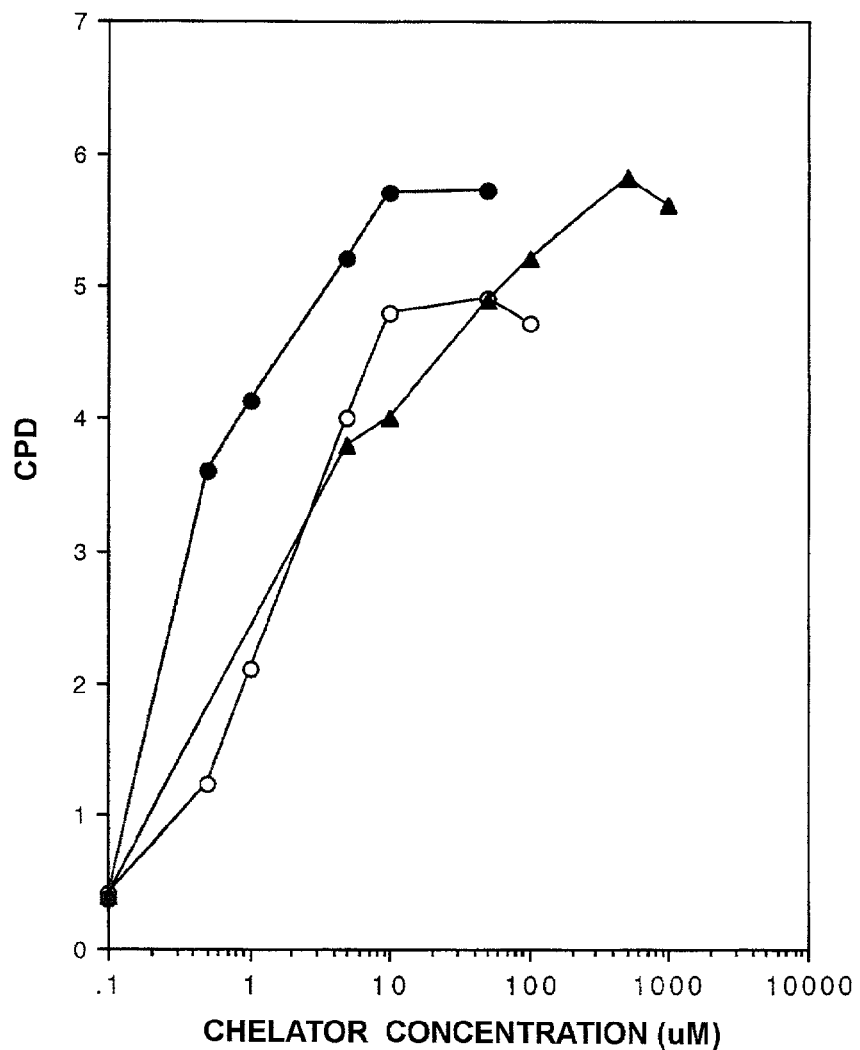
FIG. 41. Growth Restoring Effect of Fe (III) Chelators in serum-free medium with LNCaP Cells.

Reversal of Fe (III) Inhibition by Iron Chelators. The inhibitory/cytotoxic effects of Fe (III) were reversible by the addition of iron chelators. Those studied were selected based on data showing their relative affinities and specificities for Fe (III) (Schubert J (1963) In: *Iron Metabolism*, Gross F, ed, Springer-Verlag, Berlin, pp 466-496). Deferoxamine is most specific and has the highest affinity for Fe (III). Citrate is next most effective. EDTA is not as effective nor is it as specific as the first two chelators. In experiments with T47D cells, the deferoxamine usually present in the DDM-2MF medium was removed and an additional 1.5 µM Fe (III) added to ensure complete inhibition of the cells. FIG. 40 shows the relative effects of addition of these three chelators to T47D serum-free defined medium cultures. The order of effectiveness was as expected from the affinities and specificities of these chelators. Clearly, addition of Fe (III) chelators restored growth. FIG. 41 shows a similar study with LNCaP cells in CAPM defined medium from which the deferoxamine also was removed and 1.5 µM Fe (III) added. It was clear that chelation of the Fe (III) restored growth. It should be noted that this conclusion is reasonable based on the fact that deferoxamine has near absolute specificity for Fe (III). Concentrations as low as 0.5 µM of deferoxamine were sufficient to induce 3.5 CPD with LNCaP cells. Maximum growth with this chelator (5.81 CPD) was obtained at 10 µM. Citrate and EDTA were also effective growth stimulators of LNCaP cells incubated at high iron concentrations. Their maximum effects were with the addition of 500 µM and 10 µM respectively. The growth induction achieved with EDTA is lower than with citrate or deferoxamine. This probably could be explained by the fact that EDTA is a less discriminatory chelator, and essential metals other than iron were affected. Concentrations of the chelators higher than those shown in FIGS. 40 and 41 were associated with cell damage and death. In particular, chelation of calcium by citrate and EDTA will cause cell death in culture. The effect of the chelators was prevented by addition of more Fe (III) (data not shown).

Figure 42:
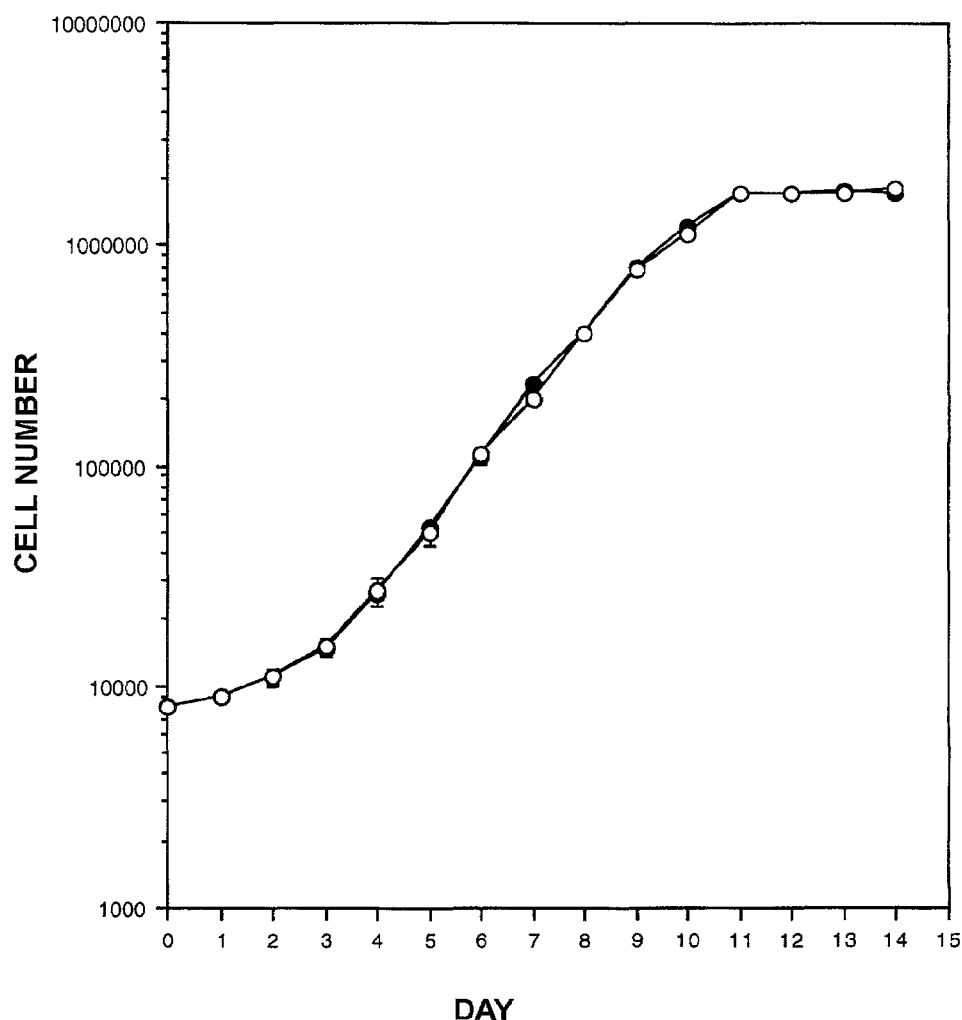
FIG. 42. Comparison of DU145 Cell Growth in "low-Fe" and "standard" D-MEM/F-12 Based Serum-free Defined Medium CAPM.
Figure 43:
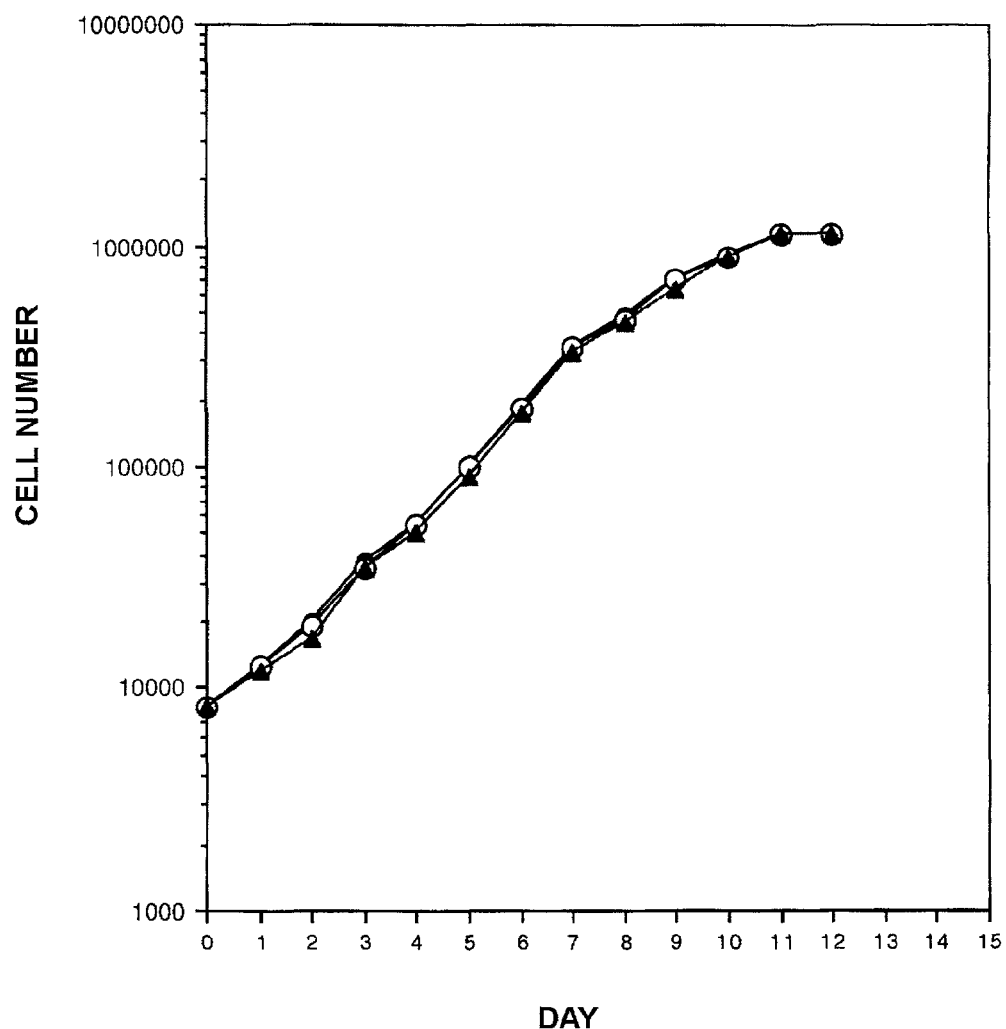
FIG. 43. Comparison of PC3 Cell Growth in "low-Fe" and "standard" D-MEM/F-12 Based Serum-free Defined Medium CAPM.
Figure 44:
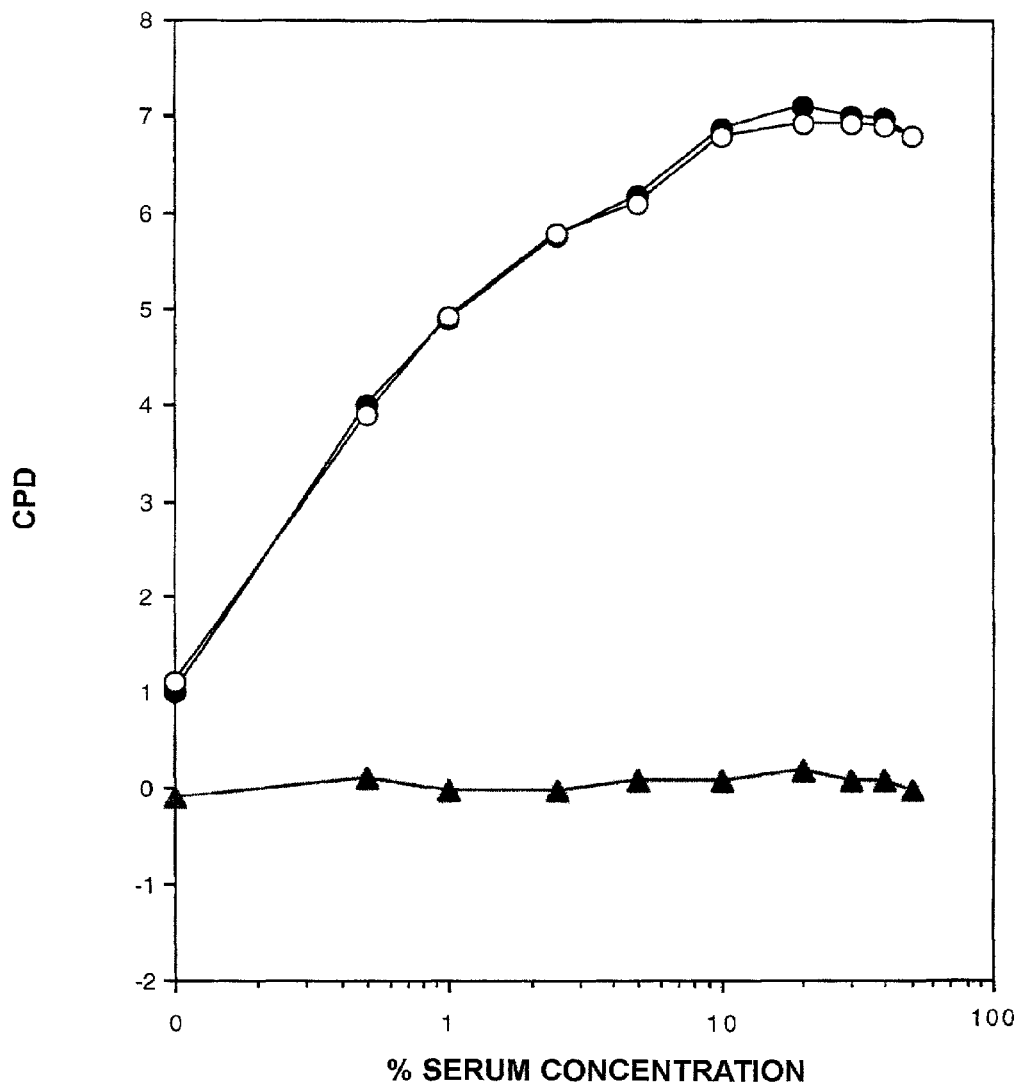
FIG. 44. Growth of the DU145 Cells in CDE-horse Serum ±DHT.
Figure 45:
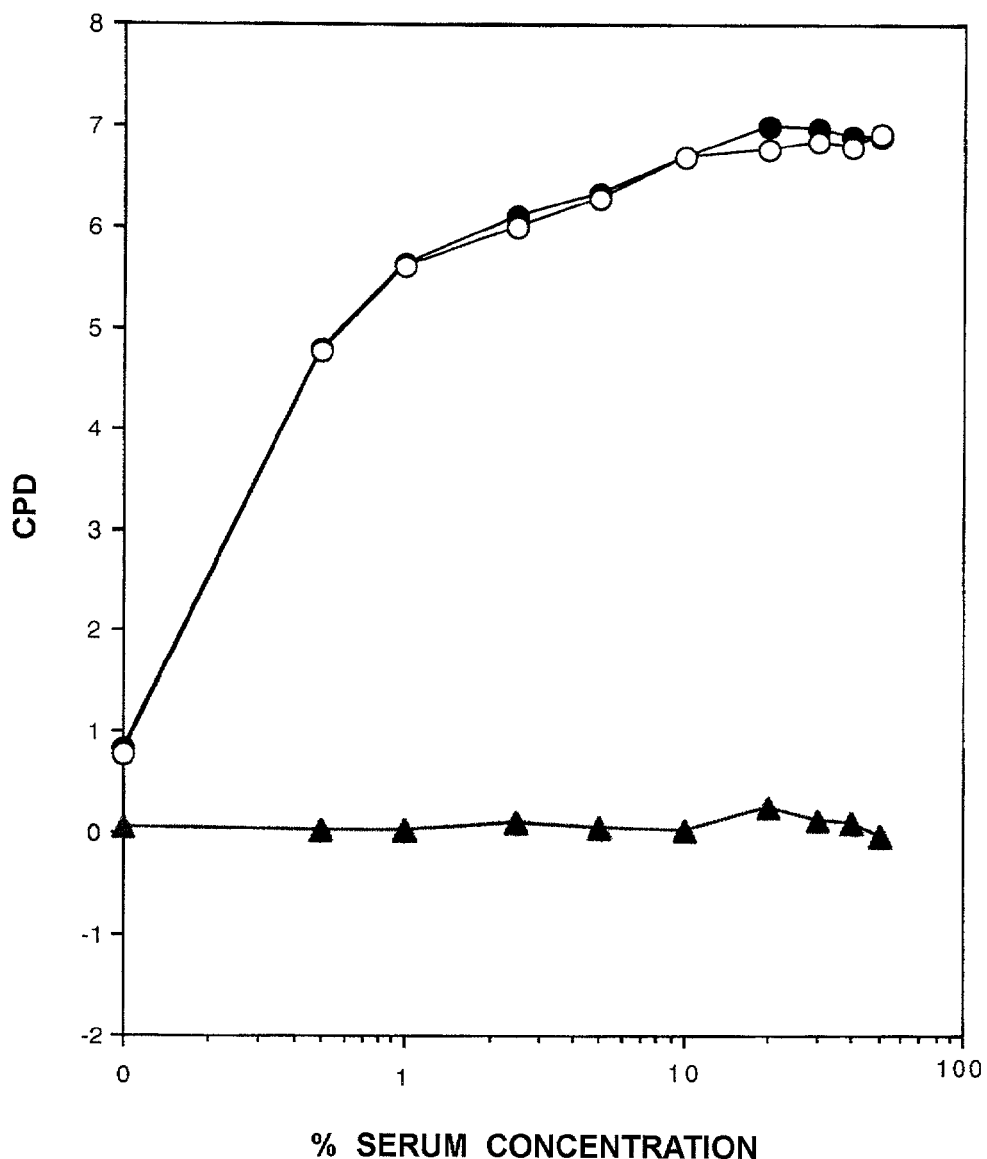
FIG. 45. Growth of the PC3 Cells in CDE-horse Serum ±DHT.
Figure 46:
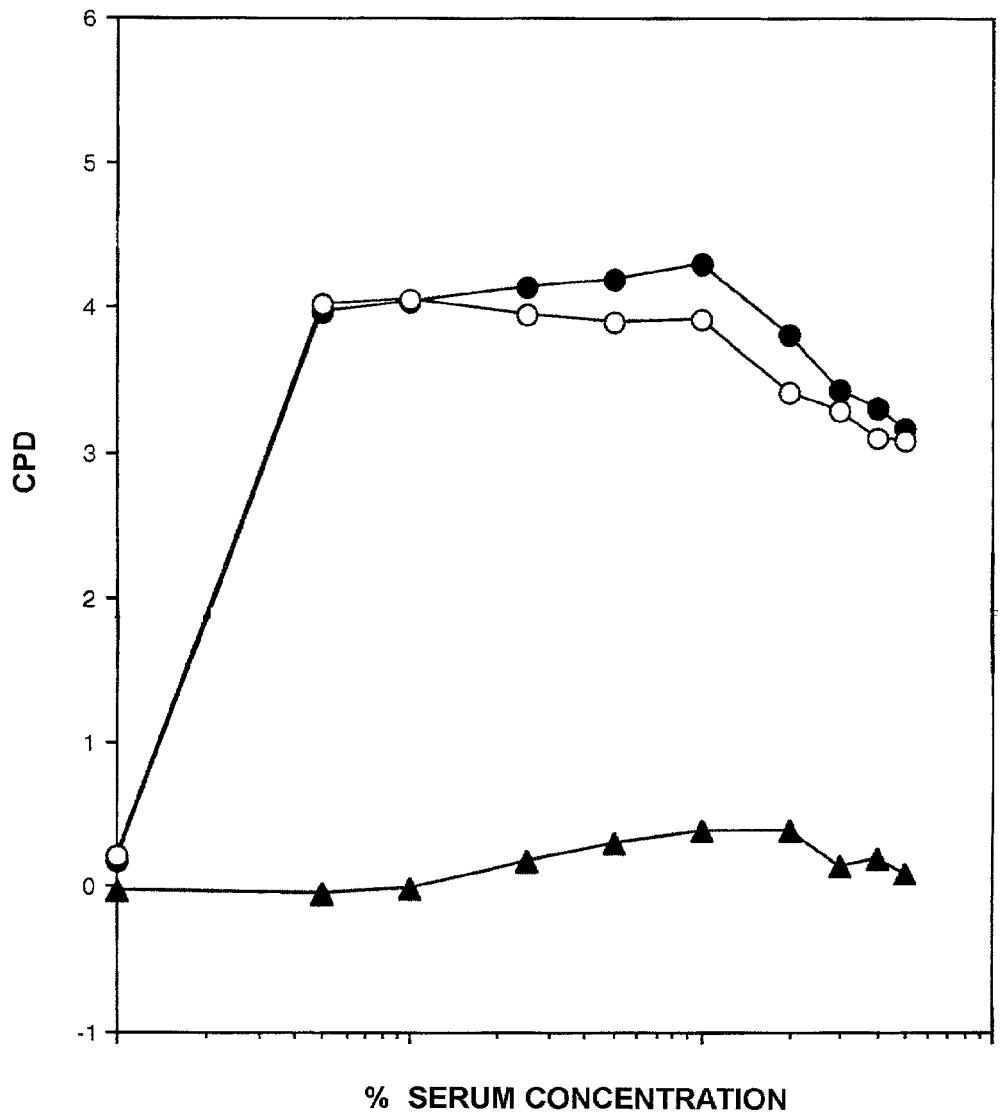
FIG. 46. Growth of the ALVA-41 Cells in CDE-horse Serum ±DHT.

Correlation Between Hormone Autonomy and Lack of Iron Effects. In the next series of studies, data was sought supporting the concept that loss of steroid hormone dependence correlates positively with loss of Fe (III) effects. As shown in FIG. 30, LNCaP cells grew better in "low-Fe" serum-free defined medium than in defined medium based on "standard" D-MEM/F-12. This difference was also evaluated with the androgen insensitive DU145 (FIG. 42) and PC3 (FIG. 43) cells. The results were clear. The autonomous lines grew equally well in CAPM based on both types of D-MEM/F-12. The presence of the higher Fe (III) level in CAPM based on standard D-MEM/F-12 had no effect. To confirm that these cell lines were androgen autonomous as defined by the loss of steroid and inhibitor growth regulation in CDE-serum, the next studies were done. DU145 cells showed no inhibition of growth in 50% CDE-serum (FIG. 44). There was no androgenic effect whatsoever. A similar assay with PC3 cells showed essentially the same results (FIG. 45). There was no inhibition even in 50% CDE-horse serum, and no androgenic effect. Additionally, ALVA-41 cells are not iron sensitive (results not shown), and also are not sensitive to the serum-borne inhibitor (FIG. 46).

Discussion of Example 11. Together with the studies presented above, it appears that $AR^+$ cells are sensitive to the serum-borne inhibitor, sensitive to the positive effects of steroid hormone and sensitive to Fe (III) inhibition. In contrast, the DU145 and PC3 cells are insensitive to the serum-borne inhibitor, insensitive to the positive effects of androgen, and insensitive to Fe (III). The results presented in this example continue to demonstrate the requirement for the action of a serum-borne mediator to demonstrate steroid hormone responsive cell growth in culture. In addition, autonomy may be the loss of the receptor for the serum factor and/or the loss of the intracellular steroid hormone receptor. If this hypothesis is correct it should be possible to identify cells that possess steroid receptors but still have lost "sensitivity" to the hormone by virtue of the lack of the effect of the inhibitor. Most notably, this is the case with DU145 and ALVA-41 cells. As defined by immunohistochemistry, the DU145 cells are definitely $AR^+$ (Brolin J et al. (1992) *The Prostate* 20, 281-295). As defined by a number of criteria, the ALVA-41cells are $AR^+$ (Nakhla A M and Rosner W (1994) *Steroids* 59, 586-589). A new concept explaining the progression of normal tissue cells to hormone autonomous cancers is provided herein and discussed in more detail in an Example below.

The use of CDE-serum is essential for the demonstration of androgen and other steroid hormone responsiveness in culture, but also limits the understanding of stimulatory or inhibitory roles of hormones or factors on prostate and other cancer cells because of the inclusion of an undetermined amount of undefined components. Serum-free medium will circumvent this problem.

In these studies, it is clear that exposure of androgen responsive prostate cancer cells to Fe (III) results in cell death. Compounds containing available Fe (III) offer the possibility of new therapies for prostate cancer localized to the tissue. It is proposed that deprivation of iron will be a highly effective means of eliminating the most dangerous hormone autonomous forms of prostate cancer. The most impressive growth requirement of hormone autonomous prostate and breast cancer cells is for diferric transferrin as a source of essential iron for growth. Without this iron source, none of the epithelial cancer cell examined could proliferate. In fact, within a two to three week period all cells in the cultures were dead.

The measurement of thyroid hormone receptors in prostate cancer should be initiated as a diagnostic tool to determine iron sensitivity. Moreover, a new therapy mode for tumors containing mixtures of both hormone responsive and autonomous cells is suggested, based on the observation that deprivation of iron can equally kill both types of cancer. This suggests that systemic Fe (III) therapy for disseminated prostate cancer may be efficacious. It is definitely possible that iron in the Fe (III) form and compounds containing it will be effective anti-prostate cancer treatments, and that direct injection (or painting) of localized prostate tumors or metastasis at other sites (e.g. bone) might effectively kill these cancers without concomitant systemic effects. This therapy potentially could replace such protocols as systemic chemotherapy (physically damaging), radiotherapy (damage to collateral tissues) or the use of locally acting radioactive gold chips that are complex to handle in the surgical environment and must be implanted and removed surgically. Furthermore, iron therapies can be repeated frequently by application via transrectal or transurethral access, using conventional techniques. This approach is unique and has not been discussed or suggested anywhere else in the literature. Such iron treatments may be a useful therapy for benign prostatic hypertrophy (BPH). As discussed above, this condition is very common in older men and is treated usually by surgery. Application of iron compounds is a new approach to treatment of BPH. Iron treatment also offers a unique approach to the problem of residual breast cancer cells in mastectomy sites or after lumpectomy. The present studies suggest that these sites be "painted", injected or otherwise treated locally with a Fe (III)-containing solution to destroy residual early ($ER^+$) breast cancer cells not detected at surgery. Subsequent treatments of these sites by injection can be used as follow-up therapy alone or with the current adjuvant chemotherapy or radiation therapy common in lumpectomy treated patients.

Example 12

Growth in Serum-Free Defined Medium Versus Growth in CDE-Serum $\pm E_2$

Figure 48:
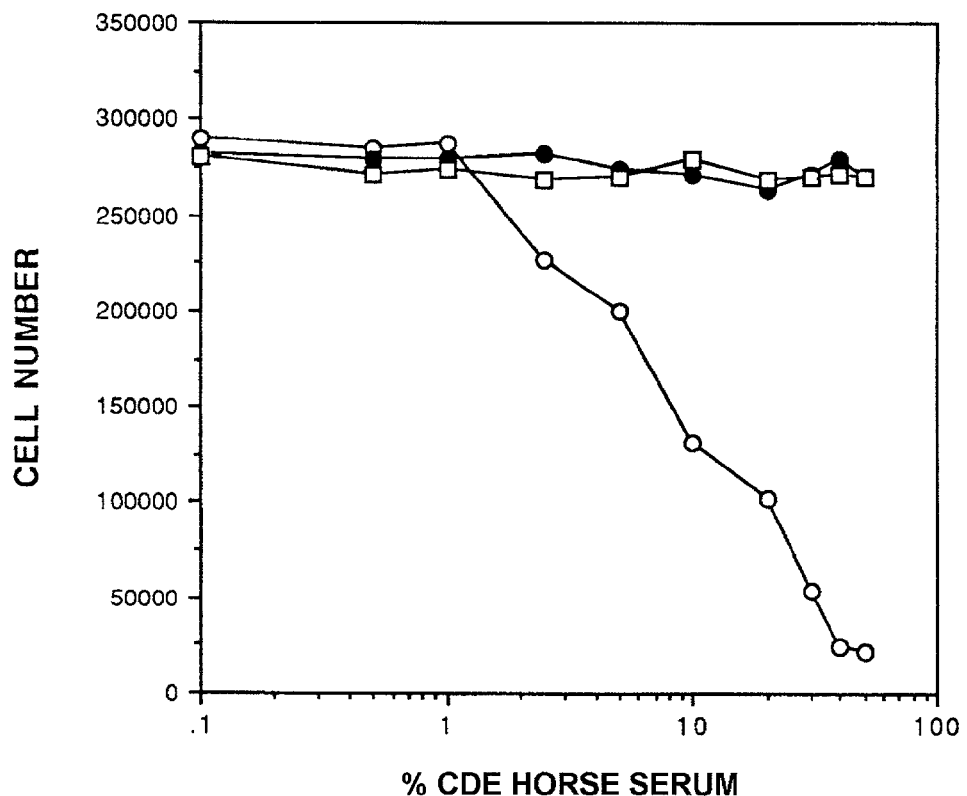
FIG. 48. Effect of CDE-horse Serum on LNCaP Cell Growth in Serum-free CAPM ±$E_2$ and ±DHT.

Use of Defined Media to Verify the Presence of a Serum-borne Inhibitor. The defined media described in Example 9 were used to verify the presence of a serum-borne inhibitor. The growth of six different $ER^+$ cell lines was compared in serum-free defined media (TABLE 6) to the effects seen in cultures supplemented with CDE-horse serum. These studies are shown in FIGS. 47 and 48. Estrogenic effects are recorded for each set of conditions with each cell line.

MCF-7K Cells in Serum-free and Serum Containing Medium $\pm E_2$. The first studies were done with steroid hormone responsive human cancer cell lines. FIG. 47A shows MCF-7K cell growth in serum-free DDM-2MF ±10 nM $E_2$. The population replicated logarithmically for 12 days. $E_2$ had no effect on growth rate or saturation density. These results were in contrast to assays done in D-MEM/F-12 supplemented with CDE horse serum (FIG. 56B). Above 10% (v/v) serum, growth was progressively inhibited. The inhibition caused by any serum concentration was reversed by $E_2$. Measured on assay day 10, a 3 CPD estrogenic effect was observed which was a $2^3$ or 8-fold cell number increase. The experiments were also done with MCF-7A cells with similar results (data not shown). This effect in CDE-serum was as great as that reported for a special response clone of the MCF-7 cell line (Wiese T E et al. (1992) *In Vitro Cell Dev Biol* 28A, 595-602).

T47D Cells in Serum-free and Serum Containing Medium $\pm E_2$. FIG. 47C shows the growth of T47D cells in serum-free defined DDM-2MF ±10 nM $E_2$. Although a small effect of estrogen was observed on growth rate, the most significant effect was an increase in stationary densities by 0.5 to 1.0 CPD. In contrast, the effect of $E_2$ was much greater in medium containing CDE horse serum (FIG. 47D). At 50% (v/v) CDE-serum, growth was completely inhibited. The estrogenic effect under these conditions was >5 CPD. This was more than a $2^5$ or 32-fold hormone effect on cell number. Comparison of these results with those of others (Chalbos D et al (1982) *J Clin Endocrinol Metab* 55, 276-283; Schatz R W et al. (1985) *J Cell Physiol* 124, 386-390); Soto A M et al. (1986) *Cancer Res* 46, 2271-2275; Soto A M and Sonnenschein C (1987) *Endocr Rev* 8, 44-52; Reese C C et al. (1988) *Ann NY Acad Sci* 538, 112-121) confirmed that the conditions in FIG. 47D were substantially more effective. Comparable experiments with the ZR-75-1 line gave results intermediate between MCF-7 and T47D cells (data not shown). ZR-75-1 cells showed no effect of $E_2$ in serum-free defined DDM-2MF. This line grows more slowly than MCF-7 or T47D cells in defined medium and in serum-supplemented cultures (Ogasawara M and Sirbasku D A (1988) *In Vitro Cell Dev Biol* 24, 911-920). The maximum estrogenic effects of the preferred embodiment recorded with ZR-75-1 cells in D-MEM/F-12 with 50% (v/v) CDE-horse serum ranged between 3 and 4 CPD after 14 days. This was greater than reported by others in serum containing (Darbre P et al. (1983) *Cancer Res* 43, 349-355; Kenney N J et al. (1993) *J Cell Physiol* 156, 497-514) or "serum-free" medium (Allegra J C and Lippman M E (1978) *Cancer Res* 38, 3823-3829; Darbre P D et al. (1984) *Cancer Res* 44, 2790-2793).

LNCaP Cells in Serum-free and Serum Containing Medium $\pm E_2$. In another study, the effects of $E_2$ on the growth of the LNCaP human prostatic carcinoma cell lines in defined medium and in serum-supplemented culture were compared. This cell line bears a point mutation in the AR that permits high affinity binding of estrogens to the altered receptor (Veldscholte J et al. (1990) *Biochem Biophys Res Commun* 173, 534-540; Veldscholte J et al. (1990) *Biochim Biophys Acta* 1052, 187-194). In addition, it is possible that estrogens cause LNCaP growth via a separate functional ER (Castagnetta L A and Carruba G (1995) *Ciba Found Symp* 191, 269-286). Irrespective of mechanism, estrogens are known to promote LNCaP growth (Belanger C et al. (1990) *Ann NY Acad Sci* 595, 399-402; Veldscholte J et al. (1990) *Biochem Biophys Res Commun* 173, 534-540; Veldscholte J et al. (1990) *Biochim Biophys Acta* 1052, 187-194; Castagnetta L A and Carruba G (1995) *Ciba Found Symp* 191, 269-286). As presented herein (FIG. 47E), this cell line in serum-free defined CAPM showed essentially no $E_2$ effect on growth rate and $\leq 1.0$ CPD on saturation density. When LNCaP growth assays were done in medium with CDE-horse serum, the mitogenic effect of $E_2$ was >5 CPD (FIG. 47F). Estrogenic effects herein were larger than reported by others with LNCaP cells in serum containing culture (Bélanger C et al. (1990) *Ann NY Acad Sci* 595, 399-402; Castagnetta L A and Carruba G (1995) *Ciba Found Symp* 191, 269-286).

LNCaP Cell Growth in CAPM Defined Medium with CDE-Horse Serum and ±DHT or $E_2$. To confirm that the serum-borne inhibitor can be assessed even in the presence of all of the components of serum-free defined medium, an example experiment is shown in FIG. 48. The LNCaP cells were grown in serum-free CAPM supplemented with increasing concentrations of CDE-horse serum without steroids and in assay dishes with the CDE-serum plus 10 nM $E_2$ or 10 nM DHT. Without steroid, the CDE-horse serum showed the expected progressive inhibition. Both the estrogen and androgen reversed this inhibition completely at every serum concentration. Clearly, the inhibitor in serum possesses a very special quality that blocks the action of the many mitogenic agents present in defined media.

$GH_4C_1$ Cells in Serum-free and Serum Containing Medium $\pm E_2$. In the next studies, shown in FIG. 49, growth of rodent ER$^+$ cell lines in defined medium and CDE serum-containing medium with and without $E_2$ were compared. The study was with the $GH_4C_1$ rat pituitary tumor cell line. In serum-free PCM-9, $E_2$ had no effect on growth rate or saturation density (FIG. 49A). In contrast, the cells were highly estrogen responsive in CDE-horse serum (FIG. 49B). In $\geq 30\%$ (v/v) CDE-serum, the estrogenic effect was >4.5 CPD (i.e. >22-fold cell number increase). The $GH_4C_1$ response obtained was substantially greater than that previously reported in cultures containing serum from a gelded horse (Amara J F and Dannies P S (1983) *Endocrinology* 112, 1141-1143). Replicate studies with the GH1 and GH3 rat pituitary tumor cells gave results equivalent to those shown in FIGS. 49A and 49B (results not shown).

MTW9/PL2 Cells in Serum-free and Serum Containing Medium $\pm E_2$. FIG. 49C shows the effect of $E_2$ on growth of the MTW9/PL2 rat mammary tumor cells in serum-free DDM-2A. There was a small effect on growth rate and a $\leq 1.0$ CPD effect on saturation density. When the same cells were assayed in D-MEM/F-12 containing CDE horse serum, the effect of $E_2$ was remarkable (FIG. 49D). Cell number differences of 26 (i.e. 64-fold) were recorded in 50% (v/v) serum in a seven-day assay. This result agrees with those presented above in this disclosure. Furthermore, comparison of MTW9/PL2 responses (FIG. 49D) to those of the human breast cancer cell responses (FIGS. 47B and 47D) confirms that the ER$^+$ rat cells are the most estrogen responsive mammary origin line yet developed.

H301 Cells in Serum-free and Serum Containing Medium $\pm E_2$. In the final studies, the effect of $E_2$ on the growth of the H301 hamster kidney tumor cells in serum-free medium was compared to that in CDE horse serum containing medium. Estrogen had no effect on H301 cell growth in serum-free defined CAPM (FIG. 49E). In contrast, $E_2$ induced H301 cell number increases of >$2^4$ (i.e. >16-fold) were recorded in D-MEM/F-12 containing $\geq 30\%$ (v/v) CDE serum (FIG. 49F). The H301 response was similar to the MCF-7 cells in that 50% (v/v) CDE-serum did not fully inhibit. The magnitude of the estrogenic effect with H301 cells was equal to that reported by others studying this line in cultures supplemented with CDE serum prepared by different methods (Soto A M et al. (1988) *Cancer Res* 48, 3676-3680).

Discussion of Example 12. The serum-free defined medium provide a model system for identifying physiologically relevant new molecules. When completely serum-free defined conditions were employed in the past, the effects of estrogens were either marginal or insignificant as has been discussed above. The earlier observations in completely serum-free defined culture medium have been extended in the present investigation. Direct comparisons were made between estrogenic effects in serum-free defined culture and estrogenic effects in medium containing CDE serum. The results were unequivocal. With every cell line tested, CDE serum was required to demonstrate significant estrogenic effects on logarithmic cell growth rates. A major advance provided was the clear demonstration that high concentrations of serum are required to observe large magnitude estrogenic effects. Furthermore, the inhibitory effects of serum are dose dependent even in the presence of the components used to formulate serum-free medium. This indicates that growth is progressively negatively regulated. This observation has physiological implications. Changes in the serum concentration of the inhibitor, or changes in availability to target tissues, will have direct effects on the rate of cell replication. The results in FIGS. 47 to 49 point to serum as the best source yet identified to obtain the component that regulates sex steroid responsive growth. The tissue origin of the serum regulator remains to be investigated.

Example 13

Action of DES on Human AR$^+$ LNCaP Prostate Cancer Cells

LNCaP Cells and DES Action. Diethylstilbestrol (DES) is now used as one of the primary treatments for prostatic cancer (Seidenfeld J et al. (2000) *Ann Intern Med* 132, 566-577). Its action is likely mediated through the hypothalamus-pituitary axis (Seidenfeld J et al. (2000) *Ann Intern Med* 132, 566-577).

DES causes suppression of anterior pituitary hormones (e.g. LH and FSH) and therefore suppresses testicular output of androgens. Although it is thought that DES has no direct effects on prostate cancer cells, the development of the assay methodology set out herein permitted a direct assessment of this issue. The AR$^+$ LNCaP cells were used as a model for these tests (FIG. 50). As shown in FIG. 50A, 10 μM DHT effectively reversed the inhibition caused by higher concentrations of CDE-horse serum in D-MEM/F-12. Likewise, 10 nM $E_2$ also reversed the CDE-serum caused inhibition completely (FIG. 50B). However, the same concentration of DES was entirely ineffective (FIG. 50C). DES did not reverse the serum caused inhibition. The synthetic estrogen had no direct positive effect on LNCaP cell growth. In the final study of this series, DES addition to medium containing DHT or $E_2$ did not affect the reversal caused by these two natural steroids (FIG. 50D). Therefore, DES is not a direct inhibitor of androgen or estrogen promoted LNCaP cell growth. The view that DES acts indirectly to cause chemical castration is consistent with the present results. These results are supported by other studies indicating that DES does not bind to the AR of LNCaP cells (Montgomery B T et al. (1992) *The Prostate* 21, 63-73).

Discussion of Example 13. The fact that DES is a major treatment for prostate cancer but does not act directly on the tissue has therapeutic implications. For prostate cancer localized to the organ, or specific metastases in other locations (e.g. bone, liver or lung), direct application of Fe (III) offers a therapy with a different mode of action. It is also possible that local Fe (III) therapy (as described in Example 12) can be used in conjunction with conventional systemic DES treatment to increase effectiveness above that with either treatment alone. There is another potential advantage of local Fe (III) treatment over systemic DES treatment. DES has many side-effects in males. Some present considerable discomfort or medical problems. Locally applied Fe (III) is absorbed by the body to form non-toxic mono ferric and diferric transferrin by chelation with the large pool of available apotransferrin. The iron containing proteins formed are no problem for the body because they are the natural physiological forms of iron delivered to all tissues.

Example 14

Properties and Rationale for Serum Purification Source

Properties of the Serum-borne Inhibitor(s). It is clear from the results presented herein, and described in co-owned, concurrently filed U.S. patent application Ser. No. 09/852,958/ PCT/US2001/15183 entitled "Compositions and Methods for Demonstrating Secretory Immune System Regulation of Steroid Hormone Responsive Cancer Cell Growth," which is hereby incorporated herein by reference, that charcoal-dextran treated serum contains a sex steroid hormone reversible inhibitor(s) of target tumor cell growth in culture. This activity was identified as a progressive cell growth inhibition in culture medium containing 10% to 50% (v/v) hormone depleted serum. Despite its first proposal more than fifteen years ago, until the present invention, the inhibitor had yet to be purified, partially because of its instability. In an initial phase of investigations, a highly enriched fraction of serum protein was produced whose estrogen reversible inhibitory activity was stable and whose cell growth inhibitory effects replicate those seen with full serum with a variety of sex steroid hormone target tumor cell types in culture. Isolation was first attempted using an array of standard protein purification methods. Although they were expected to enhance stability, inhibitor activity was either not recovered after one only step or it was lost within two fractionation steps. In earlier work (Sirbasku D A et al. "Serum factor regulation of estrogen responsive mammary tumor cell growth." Proceedings of the 1997 Meeting of the "Department of Defense Breast Cancer Research Program: An Era of Hope", (Abstract) pp. 739-740, Washington, D.C., Oct. 31-Nov. 4, 1997) indicated that the inhibitor shared some properties with sex hormone binding globulin (SHBG). These results were obtained with a purification protocol known to simultaneously yield purified corticosteroid binding globulin (CBG) and SHBG from human cord serum (Fernlund P and Laurell C-B (1981) *J Steroid Biochem* 14, 545-552). Additionally, it had been observed that the effect of calcium on both the estrogenic activity and the binding of $^3$H-DHT to CDE-serum was remarkably similar to data presented by others concerning the stability of human SHBG (Rosner W et al. (1974) *Biochim Biophys Acta* 351, 92-98). Different laboratories have raised the issue of classical SHBG as the sex hormone reversible inhibitor of target cell growth. That protein binds both androgens and estrogens in plasma and acts as a carrier system with cell signaling characteristics (Rosner W (1990) *Endocr Rev* 11, 80-91). However, in view of the results presented herein and in U.S. patent application Ser. No. 09/852, 958/PCT/US2001/15183, SHBG was considered an unlikely candidate for the inhibitor. Both CDE-horse serum and CDE-rat serum contain concentrations of inhibitor about equal to any of the other serum types investigated but they do not contain SWIG (Corvol P and Bardin C W (1973) *Biol Reprod* 8, 277-282; Renior J-M et al. (1980) *Proc Natl Acad Sci USA* 77, 4578-4582; Wenn R V et al. (1977) *Endokrinologie* 69, 151-156). Nevertheless, rabbit anti-human SHBG purchased from Accurate Chemicals not only immunoprecipitated the estrogenic activity in CDE-horse and rat serum, but also precipitated the $^3$H-DHT (i.e. SHBG-like) binding activity in these sera. This coincidence initially led to the mistaken conclusion that the inhibitor was SHBG-like (Sirbasku D A et al. "Serum factor regulation of estrogen responsive mammary tumor cell growth." Proceedings of the 1997 Meeting of the "Department of Defense Breast Cancer Research Program: An Era of Hope", (Abstract) pp. 739-740, Washington, D.C., Oct. 31-Nov. 4, 1997). This misconception turned out to be fortuitous, however, as it led to a further exploration of the products obtained by the two-step cortisol agarose affinity and phenyl-Sepharose chromatography protocol. This protocol, when used with horse and rat serum, provided material that at concentrations of 10 to 15 μg/mL replicated the $E_2$ reversible inhibition caused by 30 to 50% (v/v) serum with steroid responsive human breast cancer cells, and responsive rat mammary, rat pituitary and Syrian hamster kidney tumor cells in culture. The inhibitor retained full activity for three years when stored unfrozen at −20° C. in the presence of calcium, DHT and glycerol. As demonstrated herein, the long-standing problem of inhibitor instability has been overcome, and a highly active preparation became available to further probe molecular identity and mechanism(s) of action.

Mechanisms and Inhibitor Candidates. The regulation estrogen target tissue cell growth has been a topic of dynamic experimental interest beginning several years ago (Jensen E V and DeSombre E R (1973) *Science* (Wash D.C.) 182, 126-134; O'Malley B W and Means A R (1974) *Science* (Wash D.C.) 183, 610-620). Today, it is generally accepted that estrogen interaction with specific nuclear located DNA binding receptors is necessary to initiate critical cell cycle events (Dickson R B and Stancel G M (1999) *J Natl Cancer Inst Monograph No.* 27, 135-145). It is also highly likely that other non-steroid factors are essential participants in this process (Sirbasku D A (1978) *Proc Natl Acad Sci USA* 75, 3786-3790; Sirbasku D A (1981) *Banbury Report* 8, 425-443; Dickson R B and Lippman (1987) *Endocr Rev* 8, 29-43; Soto A M and Sonnenschein C (1987) *Endocr Rev* 8, 44-52). A number of years ago, studies were reported that indicated that serum-borne inhibitors, later named "estrocolyones", had an important if not essential role (Soto A M and Sonnenschein C (1985) *J Steroid Biochem* 23, 87-94; Soto A M and Sonnenschein C (1987) *Endocr Rev* 8, 44-52). Estrocolyones were proposed to act as estrogen reversible inhibitors of steroid hormone target tissue cell growth. The results herein support this concept. Over the course of several years, the inhibitor has been variously identified as an unstable $M_r$ 70,000 to 80,000 protein (Soto A M et al. (1992) *J Steroid Biochem Mol Biol* 43, 703-712), the intact serum albumin molecule (Laursen I et al. (1990) *Anticancer Res* 10, 343-352; Sonnenschein C et al. (1996) *J Steroid Biochem Mol Biol* 59, 147-154), two domains of serum albumin (Sonnenschein C et al. (1996) *J Steroid Biochem Mol Biol* 59, 147-154) and SHBG (Reese C C et al. (1988) *Ann NY Acad Sci* 538, 112-121). However, the roles of albumin and SHBG as estrogen related serum-borne growth regulators have been challenged (Sirbasku D A and Moreno-Cuevas J E (2000) *In Vitro Cell Dev Biol* 36, 447-464; Moreno-Cuevas J E and Sirbasku D A (2000) *In Vitro Cell Dev Biol* 36, 447-464; Soto A M et al. (1992) *J Steroid Biochem Mol Biol* 43, 703-712; Damassa D A et al. (1991) *Endocrinology* 129, 75-84). Prior to the present invention, no serum-derived inhibitor has been isolated, or otherwise identified at the molecular level, that replicates the large magnitude estrogen reversible inhibitory effects of the presently disclosed inhibitors.

Discussion of Example 14. Purification of Source Serum. A goal of these studies was to obtain a high specific activity preparation of the serum inhibitor and to define isolation and storage conditions that will permit its study over long experimental durations. Horse serum was selected for the initial studies because it had several adventitious properties. First, it is a high content source of the estrogen reversible inhibitor that has biological activity with a broad range of human and rodent sex steroid hormone target cells in culture. Second, when horse serum was steroid hormone depleted by charcoal extraction, the activity remained relatively stable at room temperature for a few weeks. Third, horse serum did not contain SHBG. This bypassed the issue of classical $M_r$ 94,000 dimeric SHBG as inhibitor. Additionally, horse serum is inexpensive, readily available, and presented minimum biohazard during the application of the purification protocol.

Discovery Based on Serum Inhibitor Isolation. The fact that the estrogen reversible inhibitory activity was ubiquitous in mammalian serum suggested that isolation from any one active species would lead to identification in the others, possibly without purification. This is exactly what happened. The final estrogen-reversible inhibitors isolated led to a major discovery of physiologic importance and revealed the first known link between the secretory immune system and mucosal cancer development and growth.

Example 15

Cortisol Affinity and Phenyl Sepharose Isolation of the "SHBG-Like" Estrogen Reversible Inhibitor from CDE-Horse Serum Outcome of the Search for the Estrogen Reversible Inhibitors. As cited above, neither horse or rat serum contains SHBG. Therefore, these were the preferred sera to begin isolation. Partial purification of the inhibitor from serum has been achieved initially by a two-step procedure. The partially purified inhibitor fractions are different than the serum derived inhibitor described in U.S. Pat. No. 4,859,585 (issued to Sonnenschein and Soto), which has been more recently identified as a subtype domain of albumin. By contrast, IgA and IgM, preferably in dimeric/polymeric form, are steroid hormone reversible inhibitors of cell growth. The discovery of immune regulation of sex hormone dependent growth is unique.

Two-step Cortisol-agarose and Phenyl Sepharose Isolation Method. Based on the perceived SHBG-like properties described above, a new approach to the purification was taken. This method used a two-step cortisol-agarose affinity and phenyl-Sepharose chromatography protocol. It had been employed by others to simultaneously yield purified human cord serum CBG and SHBG (Fernlund P and Laurell C-B (1981) *J Steroid Biochem* 14, 545-552). The method first required the synthesis of the cortisol affinity matrix. The cortisol-agarose affinity matrix was synthesized and the initial purifications done as described (Fernlund P and Larell C-B (1981) *J Steroid Biochem* 14, 545-552). An 80 mL bed volume cortisol-agarose column (2.5 cm×17.8 cm) was equilibrated with a buffer containing 0.05 M piperazine, pH 5.5, with 0.2 M NaCl. Two liters of horse serum were charcoal-dextran extracted at 34° C. as described above. For two of the six preparations used in these studies, the serum was depleted of steroid hormones by the Amberlite™ XAD-4™ resin method. There was no resulting difference in the purifications. After removing a 30 mL sample for pre-column activity assay, the remaining volume was adjusted to pH 5.5 with 1.0 N HCl. This was applied to the column at a flow rate of 30 to 40 mL per hour. Throughout the purification, the flow rates were maintained with a peristaltic pump. The effluent was collected and a sample and adjusted to pH 7.2 for post-column assessment of estrogen reversible inhibitory activity. After all of the serum had been applied, the column was washed for 7 days at the same flow rate with the equilibration buffer until the $A_{280nm}$ of the effluent was <0.06 versus water.

To recover the activity, the cortisol-agarose column was eluted with a 500 mL linear gradient formed with 250 mL of the piperazine/NaCl buffer and 250 mL of the buffer with 1.0 mg/mL cortisol and 10% (v/v) methanol. After completion of the gradient, the column was washed with one volume of the cortisol/methanol buffer. A total volume of 600 mL was collected as 10 mL fractions. As reported by Fernlund & Laurell (Fernlund P and Laurell C-B (1981) *J Steroid Biochem* 14, 545-552), two separate $A_{280nm}$ or protein concentration ranges could be recognized, but their separation and individual chromatography on phenyl-Sepharose was no more effective than pooling the entire 600 mL gradient elution and using it for the next step. The total volume from the cortisol gradient was reduced 5 to 8-fold by nitrogen gas pressure Amicon ultrafiltration (YM-10 membrane) and applied directly to the next column without dialysis or pH adjustment.

A 28 mL bed volume phenyl-Sepharose (1.5 cm×16 cm) was equilibrated with 0.05 M Tris-HCl, pH 7.5, containing 0.5 M NaCl. The concentrated cortisol gradient volume was applied at a flow rate of 60 mL/hour (10 mL fractions). The first $A_{280nm}$ peak observed was a mixture of cortisol and CBG (Fernlund P and Laurell C-B (1981) *J Steroid Biochem* 14, 545-552). These fractions were combined as cortisol affinity-phenyl Sepharose pool I (CA-PS-pool I). The column was then washed with equilibration buffer until the $A_{280min}$ was reduced to 0.002 versus water. The next buffer applied was 0.05 M Tris-HCl, pH 7.5 (60%, v/v) containing 40% (v/v) ethylene glycol. The $A_{280nm}$ peak observed with this wash was combined to form CA-PS-pool II that corresponded to SHBG from human serum (Fernlund P and Laurell C-B (1981) *J Steroid Biochem* 14, 545-552). The two pools were separately concentrated to approximately 40 mL each and dialyzed separately against storage buffer which was 0.05 M Tris-HCl, pH 7.5, containing 0.15 NaCl, 0.05 M $CaCl_2$ and 60% (v/v) glycerol. The dialysis further concentrated each sample. As last additions, 0.1 mM cortisol was added to CA-PS-pool I and 0.1 mM DHT was added to CS-PS-pool II. The pools were stored unfrozen at −20 C. Six replicate isolations were done. The protein yields ranged from 22.8 to 37.7 for CA-PS-pool I and 5.82 to 12.2 mg for CA-PS-pool II. Based on an average of 60 grams of protein per two liters of CDE-horse serum (i.e. 30 mg/mL), CA-PS-pool II represented about 0.013% of the total protein in serum.

Cortisol Affinity and Phenyl Sepharose Isolation Results and SDS-PAGE Molecular Weight Estimation. The chromatography profiles from the two-step cortisol affinity and phenyl Sepharose isolation of the inhibitor(s) activity from CDE-horse serum are shown in FIG. 51. The elution from phenyl Sepharose gave the CA-PS-pools I and II. CA-PS-pool I contained predominantly 58 kDa CBG (Rosner W and Bradlow H L (1971) *J Clin Endocrinol Metab* 33, 193-198) as confirmed by SDS-PAGE and Western immunoblotting with rabbit anti-horse CBG as well as by partial $N^\alpha$ amino acid sequencing of the first 10 to 20 residues (results not presented). SDS-PAGE analyses of three example preparations of CA-PS-pool II are shown in FIG. 52A. Components of 67, 58, 54, and 29 kDa were identified. These were compared to the 48 and 46 kDa units identified for purified human SHBG (Khan M S et al. (1985) Steroids 45, 463-472) (FIG. 52A).

Native Molecular Weight Estimation. Analyzes done under non-reducing and non-denaturing conditions using Superdex molecular sieve FPLC at neutral pH in buffers identified components CA-PS-pool I in the exclusion volume at $\geq 900$ kDa, and components approximately 350 and 168 kDa (Sirbasku D A et al. "Serum factor regulation of estrogen responsive mammary tumor cell growth." Proceedings of the 1997 Meeting of the "Department of Defense Breast Cancer Research Program: An Era of Hope", (Abstract) pp. 739-740, Washington, D.C., Oct. 31-Nov. 4, 1997). Comparison of the results from denaturing and non-denaturing conditions confirmed that the CA-PS-pool II was still heterogeneous and that the activity was most likely a subunit containing high molecular weight protein(s).

Removal of Storage Solution Components before Bioassay. Before conducting bioassays of the inhibitory activity in the phenyl-Sepharose pools, the glycerol and steroid hormones in the storage buffers were removed. If DHT is not removed completely from CA-PS-pool II, the inhibitory activity was substantially diminished or eliminated entirely. Samples (0.5 to 15 mL) were introduced into Slide-A-Lyzer® (Pierce) cassettes of molecular weight cutoff 10,000. The cassettes were incubate twice with stirring in two liters of Tris-HCl, pH 7.4, containing 10 mM $CaCl_2$ for four hours at 34° C. to remove excess free steroids and glycerol. Next, the cassettes were transferred to the same buffer containing 20% (v/v) of a charcoal-dextran mixture prepared as described above. After 18 hours at 37° C., the cassettes were transferred to another two-liter volume of the same buffer containing 10% (v/v) of the charcoal-dextran mixture and dialysis continued with stirring for another 6 to 8 hours. Finally, the cassettes were rinsed lightly with water and the dialyzed material recovered according to manufacturers instructions. The contents were sterilized by 0.2-µm-pore membrane filtration and stored at 4° C. These preparations were usually used within a few weeks.

Assay of CA-PS-pool I Estrogen Reversible Inhibitory Activity with MTW9/PL2 Cells. When assayed with MTW9/PL2 cells, CA-PS-pool I contained 20 to 25% of the units of estrogen reversible inhibitory activity recovered from the phenyl Sepharose column (data not shown). With two preparations not presented, the cortisol gradient pool shown in FIG. 51 was made 1.5 M NaCl before application to the phenyl Sepharose column equilibrated at the same higher salt concentration. Under these conditions, the CA-PS-pool I contained >90% CBG, as estimated by SDS-PAGE, but showed either no estrogen reversible activity or only traces (results not presented). Irrespective of the ionic strength or pH of the cortisol affinity pool applied to phenyl Sepharose, ethylene glycol was required to elute the majority of the activity.

Assay of CA-PS-pool II Estrogen Reversible Inhibitory Activity with Several $ER^+$ Cell Lines. Despite method variations with phenyl Sepharose, CA-PS-pool II always contained $\geq 75\%$ of the activity recovered. In a crucial test of significance, CA-PS-pool II was assayed to determine if it replaced the effects of CDE-serum with eight different $ER^+$ cell lines. The results are shown in FIG. 53. The estrogen reversible inhibitory effects of CA-PS-pool II were investigated with five rodent tumor cell lines derived from three different estrogen target tissue tumors, and three separate estrogen sensitive human breast cancer cell lines. The cells were added to medium with 2.5% (v/v) CDE-horse serum plus increasing concentrations of CA-PS-pool II ±10 nM $E_2$. The first lines evaluated were the $GH_1$, $GH_3$, and $GH_4C_1$ rat pituitary tumor cells (FIGS. 53A, 53B and 53C, respectively). They were chosen first because these lines are well known for hormone regulation of differentiated tissue specific functions in culture and exceptional sensitivity to a variety of hormones including estrogens (Tashjian A H Jr (1979) *Methods Enzymol* 58, 527-535; Haug E and Gautvik K M (1976) *Endocrinology* 99, 1482-1489; Haug E (1979) *Endocrinology* 104, 429-437; Amara J F and Dannies P S (1983) *Endocrinology* 112, 1141-1143). At 10 µg/mL, CA-PS-pool II was fully inhibitory with all three GH lines. Growth was reduced to near seed density levels (i.e. <0.5 CPD). By this measure, >1,700-fold increase in potency had been achieved versus full CDE-serum. The $ED_{50}$ with the GH cells was 6 to 8 µg/mL which was a 300 to 800-fold specific activity increase compared to full serum. $E_2$ reversed the effects of the CA-PS-pool II at every inhibitory concentration. CA-PS-pool II replaced the effects of full CDE-serum with these cells. FIGS. 53D and 53E show similar experiments with the estrogen sensitive H301 hamster kidney tumor cells and the MTW9/PL2 rat mammary cells, respectively. CA-PS-pool II was most inhibitory at 15 µg/mL with both lines. The $ED_{50}$ were in the range of 5 to 10 µg/mL. As with the GH lines, $E_2$ completely reversed the effects of the inhibitor. Again, CA-PS-pool II replaced the effects of full CDE-serum with these cells. With human breast cancer cell lines MCF-7K, ZR-75-1 and T47D, the results were similar (FIGS. 53F, 53G, and 53H, respectively). Addition of 10 to 15 µg/mL of CA-PS-pool II caused maximum inhibition. The $ED_{50}$ concentrations were 6 to 9 µg/mL. As with $ER^+$ rodent cell lines, $E_2$ completely reversed the inhibition caused by CA-PS-pool II. Again, CA-PS-pool II replaced the effects of full CDE-serum with these cells.

Cortisol-agarose Affinity Removal of the Inhibitor from CDE-serum. Next it was determined if the cortisol affinity chromatography had not removed the majority of the activity from serum. To test this, three cell lines were analyzed with pre- and post cortisol column samples. FIGS. 54A and 54B show the effect of a single column passage on the inhibitory activity for T47D human breast cells. The $ED_{50}$ of the pre-column CDE-serum was 7% (v/v) (FIG. 54A). Post-column, even 50% (v/v) serum did not achieve $ED_{50}$ (FIG. 54B). FIGS. 54C and 54D show the same studies with the $GH_3$ rat pituitary cells. In this case, a single column passage completely depleted the activity. Complete depletion was also observed with the H301 hamster kidney cell line (FIGS. 54E and 54F).

Storage Conditions and SHBG Related Properties. At completion of the two-step isolation, the pools were stored in the presence of sufficient glycerol to prevent freezing at $-20°$ C. In experiments not shown, the estrogen reversible inhibitor was progressively less stable without addition of glycerol, calcium and/or steroid hormone. Dialysis against buffers without calcium is most definitely to be avoided. Freeze/thaw is very harmful, even with calcium and DHT present. Assays of $-20°$ C. glycerol stored CA-PS-pool II over a two year period indicated no decay in activity. Clearly, the storage conditions known to stabilize functional SHBG (Fernlund P and Laurell C-B (1981) *J Steroid Biochem* 14, 545-552; Rosner W et al. (1974) *Biochim Biophys Acta* 351, 92-98) also favored retention of estrogen reversible inhibitor activity in CA-PS-pool II.

Labeled Steroid Hormone Binding to CA-PS-pool I. CA-PS-pool I was determined to contain CBG by criteria cited above. Additionally, this pool was examined by Scatchard analysis for binding of tritium labeled steroid hormones. The results are summarized in TABLE 9. The association constants ($K_a$) of the labeled hormones showed the order cortisol>progesterone>>>sex steroid hormones. The $K_a$ of cortisol binding at 34° C. was $1.41 \times 10^{-9}$ M$^{-1}$ that was equal to that of native rat CBG when analyzed at 4° C. (Rosner W (1990) *Endocr Rev* 11, 80-91). However, it was higher than the $K_a$ of $5.2 \times 10^7$ M$^{-1}$ for human CBG measured at 23° C. (Rosner W and Bradlow H L (1971) *J Clin Endocrinol Metab* 33, 193-198). The binding characteristics of steroids to CBG from several species have been studied (Rosner W (1972) *J Steroid Biochem* 3, 531-542). The similarity of the results herein further supports the conclusion that CA-PS-pool I contains predominantly CBG.

Labeled Steroid Hormone Binding to CA-PS-pool II. The estrogen reversible inhibitor activity in CDE-serum correlated with the binding of tritium labeled sex steroid hormones. This suggested a relationship between the estrogen reversible inhibitor and SHBG. However, the $K_a$ for $^3$H-DHT binding to CDE-serum at 34° C. was $3.90 \times 10^{-7}$ M$^{-1}$. However, it is important to note that this was at least 20 times lower than that of purified human SHBG at $0.99 \times 10^9$ M$^{-1}$ for DHT or $2.2 \times 10^8$ M$^{-1}$ for $E_2$ at 37° C. (Rosner W and Smith R N (1975) *Biochemistry* 14, 4813-4820). To determine if CA-PS-pool II possessed the same sex hormone binding properties as whole CDE-serum, and/or human SHBG, the next study was conducted. Scatchard analysis of $^3$H-DHT binding to CA-PS-pool II was done at 34° C. The estimated $K_a$ was $5.88 \times 10^7$ M$^{-1}$. Replicates (N=3) gave a $K_a$ range $4.5-10 \times 10^7$ M$^{-1}$. Computer analysis indicated a single class of binding sites although correlation coefficients were approximately 0.7. Similar analyses were done with $^3$H-$E_2$, $^3$H-progesterone and $^3$H-cortisol. The results with all four labeled steroids are summarized in TABLE 7. The $K_a$ order was DHT>$E_2$>>>cortisol>progesterone. The $K_a$ for sex steroid hormone binding to the CA-PS-pool II was similar to whole CDE-serum but 20 to 50-fold lower than human SHBG.

TABLE 7

Summary of the Scatchard Analysis of phenyl-Sepharose pools I and II with four labeled steroid hormones

| Steroid Hormone ($^3$H-labeled) | CA-PS-Pool I | | CA-PS-Pool II | |
|---|---|---|---|---|
| | $K_d$ (M) | $K_a$ (M$^{-1}$) | $K_d$ (M) | $K_a$ (M$^{-1}$) |
| Cortisol | $7.10 \times 10^{-10}$ | $1.41 \times 10^9$ | $1.89 \times 10^{-6}$ | $5.30 \times 10^5$ |
| Progesterone | $1.70 \times 10^{-9}$ | $5.90 \times 10^8$ | $7.89 \times 10^{-6}$ | $1.17 \times 10^5$ |
| 17β-estradiol | $1.05 \times 10^{-5}$ | $9.51 \times 10^4$ | $2.83 \times 10^{-8}$ | $3.55 \times 10^7$ |
| Dihydro-testosterone | $6.05 \times 10^{-6}$ | $1.64 \times 10^5$ | $1.43 \times 10^{-8}$ | $6.99 \times 10^7$ |

Western Immunoblotting with Anti-human SHBG. The above shows that the estrogen reversible inhibitor shared immunological properties with human SHBG. To investigate further, Western immunoblotting of CA-PS-pool II was done with anti-human SHBG. The results are presented in FIG. 52B. Western analysis with the anti-SHBG recognized the same four components seen with Coomassie Blue staining in FIG. 52A. These same four components have also been identified with whole CDE-serum using Western analysis with anti-human SHBG (data not shown). In Western immunoblotting studies not presented, anti-human SHBG did not identify horse serum albumin. This confirmed that the 67 kDa Coomassie Blue stained component present in the CA-PS-pool II was not 68 kDa horse serum albumin. These results provided additional support for the conclusion that albumin is not the estrogen reversible inhibitor activity of serum. These results also very clearly demonstrated that the SHBG used to raise antibodies in rabbit had not been purified to homogeneity, but rather had been used at a more "crude" state. (In a personal communication, it was also confirmed by the manufacturer of the anti-SHBG antibody that the SHBG fraction used for antibody production was not highly purified and had not been size fractionated.)

Discussion of Example 15. There has been one very critical problem with the estrocolyone hypothesis. Estrocolyone has never been purified and shown to act as described (Soto A M and Sonnenschein C (1987) *Endocr Rev* 8, 44-52). The active pool isolated from the two-step procedure (i.e. CA-PS-pool II) certainly does not bind steroid hormones with sufficient affinity to act as estrocolyones (TABLE 7). Growth is activated at picomolar concentrations while the affinity (Kd) of $E_2$ with CA-Pool II is about $10^{-8}$ M. This discrepancy is simply far too large to accept the role of estrogens in growth as binding the inhibitor and thereby preventing its action on target cells (Soto A M and Sonnenschein C (1987) *Endocr Rev* 8, 44-52). The fact that proteins in CA-PS-pool II bind steroids is not germane to the mechanism of action of these hormones in growth regulation under physiological conditions.

The results of steroid hormone binding may however be germane to the use of high dose treatments of breast cancer. Care must be taken when considering that high doses of estrogen, androgen, progesterone and cortisol all have the potential for binding the active agent in CA-PS-pool II and therefore may reduce the effective concentration of inhibitor. The assays described in this Example can be applied to biological fluids and plasma to determine if steroid concentrations are excessive and to evaluate proper levels with changes in treatment regimes.

The results presented herein indicate that the proposed new model of cell growth is a favored mechanism. Steroid hormones appear to act as positive agents via internal high affinity receptors (e.g. ERγ) whereas serum-borne inhibitors act at the surface to block growth. The combination of the two signals dictates cell proliferation rates. This data further supports the assertion that the ERγ can be used for diagnostic purposes in ER$^+$ cancers, preferably in the same way that conventional ER receptor screening is now performed.

A highly enriched fraction of serum protein was prepared whose estrogen reversible inhibitory activity is stable and whose effects replicate those seen with full serum with a variety of sex steroid hormone target tumor cell types in culture. Because early studies mistakenly indicated that the inhibitor shared various properties with SHBG, a two-step cortisol-agarose affinity and phenyl-Sepharose chromatography protocol was applied. A highly enriched "SHBG-like" preparation was obtained. At 10 to 15 μg/mL, it replicated the $E_2$ reversible inhibition caused by 30 to 50% (v/v) serum with steroid responsive human breast cancer cells, and responsive rat mammary, rat pituitary and Syrian hamster kidney tumor cells in culture. The inhibitor retained full activity for more than one year when stored unfrozen at −20° C. in the presence of calcium, dihydrotestosterone and glycerol. This study demonstrated that the longstanding problem of inhibitor stability has been overcome and that a high specific activity preparation was now available to further probe molecular identity. These results clearly differentiate this inhibitor preparation from any previously described type of estrogen reversible inhibitor (i.e. estrocolyone). Moreover, no previous inhibitor composition, at a concentration $\leq 15$ μg/mL, can supplant the effects of full serum to give estrogenic effects $\geq 3$ CPD with several ER$^+$ cell lines from different tissues and different species.

The most active inhibitor preparation obtained in this study appeared to have multiple components present. The separation and identification of these components would yield additional assays and preferred reagents and methodologies for testing new hormone-like and anti-hormone like substances. The results in FIG. 52 suggest that there may be more than one inhibitor. The active serum-derived inhibitor fraction can be used directly in tests of new compounds, substances, mixtures and preparations from natural and synthetic sources to estimate both estrogenic and androgenic activity in culture. Large-scale preparation of this purified serum fraction is possible by using larger affinity columns and proportionately increased serum volumes, similar to existing technology employed for purifying other biological products. It is advantageous that only small quantities of the purified serum fraction are needed for cell growth Example 16

Serum-free Assay Systems for Measuring Large Magnitude Steroid Hormone Mitogenic Responses with the Two-Step Purified Inhibitor The above-described studies with several different sex steroid sensitive cell lines demonstrated that the effects of a partially purified estrogen reversible inhibitor could readily be assayed in the presence of a low concentration (i.e. 2.5%) of CDE-serum. The next step was to eliminate the serum completely and to show estrogen responsiveness under far more defined conditions.

Second Analysis of Serum-free Growth ±$E_2$. Experiments were conducted using completely serum-free medium, and the magnitude of the estrogenic effects observed in defined medium was again compared to those seen in medium containing CDE-serum. ER$^+$ tumor cell growth was measured first in serum-free defined culture ±10 nM $E_2$. Similar experiments have been reported in FIGS. 47 and 48. The new assays were included here because the first experiments were done two years earlier. The results show the stability of the cell lines used and the fact that serum-free defined medium is highly reproducible. More recent results are shown with the MCF-7K human breast cancer cells (FIG. 55A), the T47D human breast cancer cells (FIG. 55B), the $GH_4C_1$ rat pituitary tumor cells (FIG. 55C), and the H301 Syrian hamster kidney tumor cells (FIG. 55D). All four-cell lines grew logarithmically for several days in defined and reached densities of 0.5 to $1.0 \times 10^6$ cells per 35-mm dish. The media formulations were based on standard D-MEM/F-12 as described in TABLE 6. Growth rates were optimized to 70% or more of D-MEM/F-12 containing 10% (v/v) fetal bovine serum. The results presented in FIG. 55 show little or no $E_2$ effect on growth in defined medium. Barnes and Sato (Barnes D and Sato G (1980) *Nature* (Lond) 281, 388-389) have reported similar negative results with another strain of MCF-7 cells in a different formulation of defined medium. Considering the variety of cell types assayed herein, the present results and the results of others, the lack of estrogenic effects in serum-free defined medium was not related to chemical composition of any one medium nor was there a major problem with time dependent variation of cell line properties.

Effects of CDE-Serum on ER$^+$ Cells in Different Formulations of Serum-free Defined Medium. The experiments in FIG. 56 were done to show that serum could be added different formulations of defined medium and still cause estrogen reversible inhibition. Effects are shown with CDE-horse serum ±10 nM $E_2$ and T47D cells DDM-2MF (FIG. 56A), MTW9/PL2 cells in DDM-2A (FIG. 56B) and $GH_4C_1$ cells in PCM-9 (FIG. 56C). Definitely, the serum-borne inhibitor(s) was fully effective in three different formulations of defined medium and with three different estrogen target tissue cell types.

Effects of CA-PS-pool II on ER$^+$ Cell Growth in Serum-free Defined Medium. The estrogen reversible inhibitory effects of CA-PS-pool II were examined with eight ER$^+$ cell lines growing in different serum-free defined media (FIG. 57). The cell lines were the MCF-7K cells (FIG. 57A), the T47D cells (FIG. 57B), the ZR-75-1 human breast cancer cells (ATCC) (FIG. 57C), the $GH_1$ (ATCC) (FIG. 57D), $GH_3$ (ATCC) (FIG. 57E), and $GH_4C_1$ (FIG. 57F) rat pituitary tumor cells, the MTW9/PL2 rat mammary tumor cells (FIG. 57G), and the H301 Syrian hamster kidney tumor cells (FIG. 57H). At 20 to 30 μg/mL, this fraction completely inhibited growth. The inhibition was totally reversed by 10 nM $E_2$. The $E_2$ effects on cell number were in the range from 33 to 72-fold (i.e. CPD=$2^{5.04}$ to $2^{6.18}$). The activity was not replaced by serum albumin at 5 mg/mL (data not shown). The estrogen mitogenic effects seen in defined medium containing only a few μg/mL of protein were equal to or greater than those seen in medium containing 30 to 50% (v/v) CDE-horse serum with every ER$^+$ cell line tested (TABLE 8). Plainly, the serum-free conditions established herein are the most defined model assay systems yet established to demonstrate estrogen responsiveness in vitro.

TABLE 8

Summary of the Maximum Estrogenic Effects in D-MEM/F-12 plus CDE-horse Serum 10 nM $E_2$ versus those in Serum-free Defined Medium Supplemented with CA-PS-pool II

| CELL LINES | MAXIMUM ESTROGENIC EFFECTS IN CDE-SERUM | MAXIMUM ESTROGENIC EFFECTS IN SERUM-FREE MEDIUM PLUS CA-PS-POOL II |
|---|---|---|
| MCF-7K | 3.40 CPD ($2^{3.40}$ = 10.5-fold) | 5.84 CPD ($2^{5.84}$ = 57.3-fold) |
| T47D | 5.38 CPD ($2^{5.38}$ = 41.6-fold) | 5.88 CPD ($2^{5.88}$ = 58.9-fold) |
| ZR-75-1 | 3.84 CPD ($2^{3.84}$ = 14.3-fold) | 5.21 CPD ($2^{5.21}$ = 37.0-fold) |
| $GH_1$ | 4.71 CPD ($2^{4.71}$ = 26.2-fold) | 5.04 CPD ($2^{5.04}$ = 32.9-fold) |
| $GH_3$ | 4.78 CPD ($2^{4.78}$ = 27.4-fold) | 5.04 CPD ($2^{5.04}$ = 32.9-fold) |
| $GH_4C_1$ | 4.82 CPD ($2^{4.82}$ = 28.2-fold) | 5.11 CPD ($2^{5.11}$ = 34.5-fold) |
| MTW9/PL2 | 6.22 CPD ($2^{6.22}$ = 74.5-fold) | 6.18 CPD ($2^{6.18}$ = 72.5-fold) |
| H301 | 4.33 CPD ($2^{4.33}$ = 20.1-fold) | 6.01 CPD ($2^{6.01}$ = 64.4-fold) |

CPD ($2^{CPD}$=Fold Cell Number Increases Above Controls Without Estrogen)

Discussion of Example 16. The studies presented in FIG. 57 and TABLE 8 summarized unequivocally, and for the very first time, demonstrate that large magnitude estrogen mitogenic responses can be observed in completely serum-free defined media containing 2 mg/mL total protein. Furthermore, the responses shown in FIG. 57 either equal or exceed others previously observed in partially serum-free media with ZR-75-1 human breast cancer cells (Allegra J C and Lippman M E (1978) *Cancer Res* 38, 3823-3829; Darbre P D et al. (1984) *Cancer Res* 44, 2790-2793) or with a variety of other estrogen sensitive ($ER^+$) human and rodent cell lines in medium with hormone depleted or deficient serum (Amara J F and Dannies P S (1983) *Endocrinology* 112, 1141-1143; Natoli C et al. (1983) *Breast Cancer Res Treat* 3, 23-32; Soto A M et al. (1986) *Cancer Res* 46, 2271-2275; Wiese T E et al. (1992) *In Vitro Cell Dev Biol* 28A, 595-602).

These results have a number of important implications, one of which is that they support the aspect of the estrocolyone hypothesis (Soto A M and Sonnenschein C (1987) *Endocr Rev* 8, 44-52) that relates to the presence in serum of a meaningful inhibitor(s). Also, in view of the present results, there is no doubt that the inhibitor(s) is/are completely estrogen reversible. However, the present experimental results do not confirm that the steroid hormones interact with the inhibitor with sufficient affinity to support that aspect of the estrocolyone hypothesis. The results in TABLE 7 indicate that this steroid hormone binding aspect of the estrocolyone hypothesis is highly unlikely.

The estrogen reversibility of the inhibitor with every target cell type studied under the rigorous conditions of serum-free defined culture suggests physiologic relevance. The large magnitude of the effects is a strong statement in favor of significance. This is especially clear when considering the fact that the first experiments with 30 to 50% (v/v) serum contained 15 to 25 mg/mL of protein, whereas the later tests using serum-free medium required only 20 µg/mL of isolated protein.

The active fraction isolated from horse serum represented only 0.01 to 0.04% (w/w) of the total protein. Nonetheless, it effectively regulated eight $ER^+$ cell lines derived from three species and three different target tissues. These observations are evidence that a broadly applicable serum fraction has been identified. Furthermore, the serum-free medium results suggest that a common agent(s) may coordinately regulate estrogen responsive tissue growth in vivo and that the concept of estrogen reversible negative control may be far-reaching. The results support the conclusion that in vitro studies can be used to identify important new aspects of in vivo endocrine physiology. The results of the cell growth experiments in defined medium have many practical applications. It has been demonstrated herein that a model cell growth assay system now exists that is valuable for assessing a wide variety of cell growth effects.

Cells in serum-free medium grow in response to nutrients, growth factors, metal delivery proteins, adhesion proteins, and various classes of hormones. All of these components are mitogenic in the sense that they contribute to cell replication. Nonetheless, the addition of only 20 µg/mL of inhibitor to block growth completely bears directly on the question of the progression of normal steroid target cells to fully hormone autonomous cancers. The inhibitor preparation used herein has the properties of a family of tissue regulators first named "chalones". These proposed cell regulators are water-soluble and tissue specific (but not species specific) proliferation inhibitors that are reversible by physiologic stimuli including hormones (Bullough W S (1975) *Life Sci* 16, 323-330; Finkler N and Acker P (1978) *Mt Sinai J Med* 45, 258-264). The studies presented herein support this classic concept as it applies to sex steroid hormone target tissues. The molecular identification of the serum inhibitor(s) promises not only to further support the role of estrogens as "necessary", but also to establish that "chalone-like" entities likely are the missing "sufficient" components that account for estrogen regulation of tissue growth. The application of serum-free defined medium conditions along with the use of a high specific activity fraction to demonstrate estrogen responsiveness in culture is unique. It should be noted that "chalones" have never before been identified. The results presented herein indicate, and in U.S. patent application Ser. No. 09/852,958/PCT/US2001/15183 entitled "Compositions and Methods for Demonstrating Secretory Immune System Regulation of Steroid Hormone Responsive Cancer Cell Growth," hereby incorporated herein by reference, that the immune system is the long sought after source of these tissue specific inhibitors. In the series of studies described herein, the tissues are the mucosal tissues.

Example 17

Chemical and Immunological Properties of the Partially Purified CA-PS-Pool II Inhibitors and Identification as IgA and IgM This Example describes chemical and physical confirmation that the sought-after serum-borne cancer cell growth inhibitor(s) include at least IgA and IgM.

Antibodies Against the CA-PS-Pool II Components. Preparative SDS-PAGE was done on the CA-PS-pool II fraction, and after localization of the 54 kDa band, the 54 kDa band was eluted and prepared for rabbit antibody production by HTI (Ramona, Calif.). The antibodies raised were very potent and reacted with CA-PS-pool II (FIG. 58). They did not cross react with CBG (CA-PS-pool I). However, despite great care, it was evident that the anti-54 kDa was raised against a mixture of 67, 58 and 54 kDa subunits (FIG. 58). The reaction was definitely strongest with the 54 kDa component, but clearly identifiable with the 67 kDa and 58 kDa bands as well. This apparent problem turned out to be an advantage, and allowed positive identification of the active agents in CA-PS-pool II. It was investigated whether the activity in CA-PS-pool II might have been isolated because of affinity for the agarose matrix rather than as a consequence of the steroid hormone ligand attached to agarose, noting from interpretation of unrelated studies, that agarose alone can bind immunoglobulins and give SDS-PAGE bands at 67, 58 and 54 kDa. Therefore, it was thought possible that IgG was the estrogen reversible inhibitor.

Antibodies Against the 54 kDa Component of CA-PS-Pool II and Blocking of the Estrogen Reversible Inhibitor Activity. Based on the results in FIG. 58, it was apparent that the 54 kDa antiserum might be used to determine if the biological activity resided in any of the 67, 58 or 54 kDa bands. The next study was done to resolve this important issue. The results were pivotal. FIG. 59 shows that the purified material in CA-PS-pool II was completely inhibitory at 20 to 40 µg/mL. Addition of even a 1:5000 dilution of anti-54 kDa blocked the effect of the inhibitor. In control studies, rabbit pre-immune serum had no effect even at 1:100 a dilution (data not shown). It was evident that anti-54 kDa serum contained the antibody to the activity.

Anti-54 kDa Serum Recognizes Authentic Horse IgA, IgM and IgG. Next, authentic horse IgA was obtained from Accurate Chemicals, and horse IgM was obtained from Accurate Chemicals and Custom Monoclonal International. The material from Custom Monoclonals was custom purified by an affinity method with a monoclonal antibody against horse IgM Fc and further purified by molecular sieve chromatography to be sure of elimination of other immunoglobulins (a common problem). IgGs were obtained from Zymed (San Francisco, Calif.), Sigma (St. Louis, Mo.) or The Binding Site (San Diego, Calif.). The Western analysis shown in FIG. 60 demonstrates these results. The results show clear cross-reaction with 67 kDa IgM heavy chain, 58 kDa IgA heavy chain and 54 kDa IgG heavy chain but no reaction with horse albumin.

Assay of Estrogenic Effects Controlled by Commercially Purchased Horse IgG, IgA and IgM in 2.5% CDE-horse Serum with MTW9/PL2 Cells. FIG. 61 demonstrates that at concentrations up to 59 µg/mL, horse IgG did not cause inhibition of MTW9/PL2 cell growth in 2.5% CDE-horse serum. There was no significant estrogenic effect caused by IgG. FIG. 62 shows very clearly that commercially prepared horse serum derived IgM (Custom Monoclonals), was very active. At concentrations of 20 to 50 µg/mL, IgM completely inhibited the growth of the MTW9/PL2 cells (i.e. <1.0 CPD). Addition of 10 nM $E_2$ reversed the inhibition nearly completely. Estrogenic effects of 4 to 5 CPD were seen (FIG. 62). FIG. 63 shows the same general results with commercially prepared horse serum derived IgA (Accurate). The only apparent difference was that IgA was slightly more effective than IgM. These results clearly proved that the active components in CA-PS-pool II were IgA and IgM. This was a clear sequence of studies culminating in evidence supporting IgA and IgM. That these immunoglobulins would prove to be the inhibitor was completely unexpected. Although these two active classes of immunoglobulins (IgA and IgM) are well-established secretory products of normal breast cells, there was no previous suggestion in the prior art that they play a role in the negative regulation of estrogen-dependent cell growth. These immunoglobulins are major proteins in milk whose hormone-related local production in breast tissue is well documented, and their function in the body's secretory immune system is well known.

Alternate Methods of Obtaining Horse Serum IgG, IgM and IgA. IgG can be purified using a Hytrap matrix, which is a mixture of immobilized Protein A and Protein G, employing a technique described by others (Lindmark R et al. (1983) *J Immunol Meth* 62, 1-13; Kronvall G et al. (1969) *J Immunol* 103, 828-833; Akerstrom B et al. (1986) *J Biol Chem* 261, 10240-10247). IgM can be obtained using a mannan binding protein isolation method normally applied with human serum (Nevens J R et al. (1992) *J Chrom* 597, 247-256). However, yields are low. Another method based on anti-IgM immunoglobulins linked covalently to Sepharose is far more effective. This same procedure with immobilized anti-IgA immunoglobulins can be used to isolate IgA (Tharakan J In: Antibody Techniques, Malik V S & Lillehoj E P, Eds, 1994, Academic Press, San Diego, Calif., Chapter 15). Horse IgA can also be purified using an immobilized Jacalin lectin method usually reserved for human samples (Roque-Barreira M C et al. (1986) *Braz J Med Biol Res* 19, 149-157). However, it can be modified for non-human species. The buffers are modified to contain 10 to 50 mM $CaCl_2$ to bind IgA from other species. Even then, yields are not high. The preferred methods for horse IgA and IgM use immobilized antibodies.

Purification of Rat Serum Immunoglobulins. Three isolations of the estrogen reversible inhibitor from separate one-liter batches of adult rat serum were conducted. This was done for two important reasons. First, the estrogen reversible activity in all types of adult serum, including rat, were assayed with a highly estrogen sensitive MTW9/PL2 rat mammary tumor cell line. It was useful to confirm the horse serum purification results with a homologous experimental system. Second, the confirmation that rat IgA and IgM regulated rat mammary tumor cell growth would open the possibility of combined testing of new therapeutic substances both in vitro and in vivo. To summarize, the same "CBG" and "SHBG" fractions were obtained from rat serum by the methods of Fernlund & Laurell as had been obtained from horse serum. The chromatography profiles of the rat separations (not presented) were very similar to those presented in FIG. 51. The only major difference was that with rat serum, the first peak (i.e. CA-PS-pool I) contained no CBG. At pH 5.5, rat CBG did not significantly bind to the affinity matrix. Rat serum CA-PS-pool I and CA-PS-pool II both contained only two Coomassie Blue stained bands when analyzed by SDS-PAGE (FIG. 64A). These were approximately 55 kDa and 54 kDa. They were somewhat lower molecular weights than found with horse, and there were fewer bands. To test if either rat band was IgG, a Western analysis was performed with rabbit anti-rat IgG (FIG. 64B). The antibody did not recognize the Coomassie stained bands but did react with control IgG. However, when examined with very specific heavy chain monoclonal antibodies raised to rat IgG1, IgA, and IgM (purchased from Zymed), the Western analysis was clear (FIG. 65). Both the commercially purified rat immunoglobulins (purchased from Zymed) and the two-step purified pools showed cross-reaction with anti-IgA (weakly), anti-IgG1 subtype (strong reaction) and anti-IgM (moderate reaction) (FIGS. 65A, 65B, 65C, respectively).

Rat and Horse Serum Active Pools Isolated by the Two-Step Procedure of Fernlund and Laurell have the same Classes of Immunoglobulins. The same classes of immunoglobulins obtained by the two-step procedure of Fernlund and Laurell (Fernlund P and Laurell C-B (1981) *J Steroid Biochem* 14, 545-552) with horse serum were found when rat serum was the starting material. This was considered to be further confirmation that binding to the agarose matrix was more important than to the immobilized cortisol. It should be noted that in the original Fernlund and Laurell report using human cord serum does not address possible immunoglobulin contamination, however (Fernlund P and Laurell C-B (1981) *J Steroid Biochem* 14, 545-552). This is particularly curious because human immunoglobulins bind to agarose (Smith R L and Griffin C A (1985) *Thombosis Res* 37, 91-101).

Labeled Steroid Hormone Binding to The "SHBG-like" Pools from Rat Serum. As described in TABLE 6, CA-PSpool II from horse serum binds sex steroids with an affinity of about $10^{-8}$ M. This same Scatchard analysis was done with an active fraction from rat serum. TABLE 9 shows the results of these studies with four labeled steroid hormones. It is clear that sex steroid hormones bind with a higher affinity than progesterone or cortisol. The binding affinities of rat and horse preparations were very similar. In both cases, the affinities tend to rule out the estrocolyone hypothesis because it requires $E_2$ binding in the picomolar range.

TABLE 9

Summary of the Scatchard Analysis of the "SHBG-like" Pools from Rat Serum with Labeled Steroid Hormones

| Steroid Hormone | CA-PS-Pool II | |
| --- | --- | --- |
| (3H-labeled) | $K_d$ (M) | $K_a$ (M$^{-1}$) |
| Cortisol | $5.7 \times 10^{-6}$ | $1.8 \times 10^5$ |
| Progesterone | $6.9 \times 10^{-6}$ | $1.4 \times 10^5$ |
| 17β-estradiol | $4.1 \times 10^{-8}$ | $2.4 \times 10^7$ |
| Dihydrotestosterone | $2.4 \times 10^{-8}$ | $4.1 \times 10^7$ |

Evaluation of the Rabbit Anti-SHBG Cross-Reaction with the Active Pools from the Two-Step Isolation of Fernlund and Laurell. As shown above in FIG. 52B, Western analysis with the anti-SHBG detected horse IgA, IgM and IgG. Additionally, anti-SHBG immunoprecipitated the estrogenic activity of horse serum (results not presented). To extend these results, it was established that rabbit anti-human SHBG recognized a number of the major classes and subclasses of rat immunoglobulins. SDS-PAGE with Coomassie blue staining (FIG. 66A) was compared to identification of the same proteins by Western analysis with anti-SHBG (FIG. 66B). These results leave very little doubt that the human plasma derived SHBG used to raise antibodies in rabbits was not homogeneous but in fact was a "crude" preparation contaminated with several immunoglobulins.

Test of Rat IgG, IgA and IgM for Estrogen Reversible Inhibitory Activity with MTW9/PL2 Rat Mammary Tumor Cells. All of the rat immunoglobulins described in this section were purchased from Zymed as the highest quality available. Their activity was assessed with MTW9/PL2 cells in 2.5% (v/v) CDE-rat serum, as described above. The activity of rat IgG (all subclasses combined) was assessed (FIG. 67). There was no inhibitory effect at up to 50 μg/mL. Rat IgA was a potent estrogen reversible inhibitor (FIG. 68). At 20 to 50 μg/mL, it completely inhibited growth. Addition of 10 nM $E_2$ completely reversed the inhibition. The estrogenic effects recorded were >5 CPD. The results with rat IgM were very similar (FIG. 69). At 20 to 50 μg/mL, it completely inhibited growth. Addition of 10 nM $E_2$ reversed the inhibition. The estrogenic effects recorded were >5 CPD. It is essential to note that IgA or IgM replaced the effect of full CDE-rat serum with MTW9/PL2 cells. With a completely homologous system (i.e. cell line, basal 2.5% CDE-serum, and immunoglobulins), the results were clear. IgA and IgM were the sought after serum-borne inhibitors from rat.

Discussion of Example 17. The identification of IgA and IgM as serum-borne inhibitors fully separates these inhibitors from the teachings of U.S. Pat. No. 4,859,585 (Sonnenschein) and U.S. Pat. No. 5,135,849 (Soto), which arrived at no molecular identification of the inhibitor. The series of investigations described above demonstrate that a very longstanding problem has been solved. While the solution is significant, an even more an important consequence of this knowledge is the fact that for the very first time, mucosal cell hormone dependent growth has been linked to a natural immune regulation. Moreover, this information has direct application to the diagnosis, genetic screening, prevention and therapy of breast and prostate cancer and a high likelihood of applications to other mucosal cancers, as also described elsewhere herein.

During the purification of both the horse serum and the rat serum estrogen reversible activity, SUPERDEX™ (Pharmacia) molecular sieve chromatography of the final mixtures indicated the presence of <20% 160 kDa monomeric immunoglobulins. The majority of the material was of much larger mass. Because IgA exists naturally as monomer, dimer and polymers, there was a question concerning which of these is/are inhibitory form(s). The SUPERDEX™ results strongly favor the dimer/polymer form. This was confirmed also with commercially prepared IgA that was obtained from hybridoma and myeloma cell lines. The IgA from these was >80% dimer/polymer. It was very active as an inhibitor. In light of these results, it is suggested that these forms are the "good" type of IgA in the body, and that direct measurement of their concentration in plasma and body fluids has diagnostic and prognostic applications.

Test methods similar to those described above, but performed with a defined, preferably minimum serum, plus purified immunoglobulin inhibitor ("inhibitor spiked serum") provide a new approach to evaluating potentially cell growth affecting substances, mixtures and compounds that might be influenced by serum components. For example, a serum composition might contain steroid hormone free serum, such as a standard, commercially available fetal bovine serum preparation, and a predetermined amount of an immunoglobulin inhibitor, i.e., one or more of IgA, IgM or IgG. Testing under these conditions, with a known amount of inhibitor in the serum, may be desirable or required when the substance has potential for inactivation/activation by a serum component or when it has lipophilic properties that require a minimum protein concentration in the medium to prevent loss.

Another valuable application of the immunoglobulin inhibitors will be in identifying substances that may have direct effects on the action of the immunoglobulins to cause inactivation. An assay of this nature is unique in the sense that incubation of substances with the immunoglobulin can be done before the assay to determine effects on natural immune responses. Changes in environmental/chemical factors that affect the body's immune system are of major medical concern. They also are of great concern to veterinary medicine. Chemicals/nutritional supplements may affect immune function of domestic animals and thereby affect human food supplies.

This series of investigations demonstrate at least two immunoglobulin inhibitors in serum. More than one inhibitor was suggested by the conventional purification data in a preceding Example, and was proved true in succeeding examples. There may still be other useful estrogen reversible immunoglobulin inhibitors in serum that are yet to be identified from serum or tissue sources. The methods described in this Example have direct application to the search for new compounds that mimic the effect of the immunoglobulins as estrogen reversible inhibitors. Such application opens a new avenue of search for anticancer drugs.

Example 18

Regulation of Steroid Hormone-Responsive and Thyroid Hormone-Responsive Cancer Cell Growth in Serum-Free Defined Medium by Secretory and Plasma Forms of IgA and Plasma and Cell Culture Derived IgM The determination of whether purified IgA and IgM from several species mimicked the sex steroid hormone reversible inhibitors isolated from horse in serum was sought. These studies included ER+ tumor cells derived from rodents as well ER+ and AR+ cells from human cancers. Completely serum-free defined culture conditions were used to perform cell growth assays using the purified inhibitors. The total protein concentration in the media was <2 mg/mL. The estrogenic and androgenic effects observed in these assays are unique, as like effects have not been achieved previously in completely serum-free defined medium.

Sources of Purified IgA and IgM. Human IgM was purified from human plasma as described using immobilized mannan-binding protein (Nevens J R et al. (1992) *J Chromatography* 597, 247-256). As an example of the effectiveness of this isolation, FIG. 70 shows SDS-PAGE and Coomassie Blue Staining with two preparations of human plasma IgM prepared. Human IgA1 and IgA2 were purified using immobilized Jacalin (Roque-Barreira M C and Campos-Neto A (1985) *J Immunol* 134, 1740-1743; Kondoh H et al. (1986) *J Immunol Methods* 88, 171-173; Pack T D (1999) *American Biotechnology Laboratory* 17, 16-19; Loomes L M et al. (1991) *J Immunol Methods* 141, 209-218). Rat IgA and IgM were purchased from Zymed. The effectiveness of the Jacalin method with human plasma is shown in FIG. 71. Horse IgA and IgM were purchased from Accurate, Sigma and Custom Monoclonals. IgA and IgM from other species or as products from cell culture are purchased from Sigma or Accurate. Human IgA and IgM were bought also from Sigma and Accurate. Human secretory (milk) IgA (sIgA) was purchased from Sigma or Accurate.

MTW9/PL2 rat mammary tumor cells. For this series of experiments the serum-free defined medium was the preferred formulation of DDM-2A described in TABLE 6. The cell growth assays with this cell line in DDM-2A testing increasing concentrations of human plasma IgM is shown in FIG. 72. Human plasma IgM completely inhibited growth by 20 to 60 µg/mL. The $ED_{50}$ was about 12 µg/mL. Based on an IgM $M_r$ of 950,000, the $ED_{50}$ concentration was $1.3 \times 10^{-8}$ M. Complete inhibition was at $2.2 \times 10^{-8}$ M. These concentrations are certainly within the physiological range of IgM in the plasma and body fluids such as breast milk. Based on these studies, a comparison was done in completely serum-free defined DDM-2A medium of the effects of 40 µg/mL of rat plasma IgA $\pm E_2$, rat plasma IgM $\pm E_2$, and horse plasma IgM $\pm E_2$ (FIG. 73, expressed as (A) cell numbers and (B) CPD). From the CPD calculations it was clear that no matter the species source, IgA and IgM were very potent estrogen reversible inhibitors of MTW9/PL2 cell growth.

One problem occurred with the MTW9/PL2 cell assays that initially caused concern. Human IgA was purchased from Sigma as the milk derived immunoglobulin. It was far less expensive than plasma IgA. For reasons that at first were not clear, this material was at best only partially inhibitory and often not inhibitory. As will be discussed below with $GH_1$ cells, this turned out to be a significant clue to the mechanism of action of the immunoglobulins. Nonetheless, it is known that the heavy chains of IgM and IgA from different species share primary structure homology. This is not true of the variable regions of the light chains. The results presented support the possibility of Fc-like receptor mediation of the IgA and IgM effects on MTW9/PL2 cells.

$GH_1$, $GH_3$ and $GH_4C_1$ rat pituitary tumor cells. For this series of experiments the serum-free defined medium was the preferred formulation of PCM-9 described in TABLE 6. The next serum-free defined medium studies were done with $GH_1$ cells. Example assays are shown. This cell line was highly estrogen responsive in the presence of homologous rat myeloma derived IgA (FIG. 74). Maximum estrogenic effect was >5 CPD or more than a 32-fold estrogen-induced increase in cell number in 10 days. A similar assay with human plasma derived IgA showed nearly the same results (FIG. 75). Indeed, human IgA showed greater inhibition at 10 µg/mL. Another study with human IgM demonstrated that it was also an estrogen reversible inhibitor of $GH_1$ cell growth (FIG. 76). It was not as inhibitory as IgA with this cell line, but certainly still effective. As discussed above, in the Background of the Invention, during the secretion process a fragment of about 80% of the poly-Ig receptor (including the five extracellular domains) becomes attached to the dimeric/polymeric form of IgA to form secretory IgA or sIgA. The receptor fragment is called the "secretory component". After secretion, sIgA can be readily isolated from human milk. The effect of milk derived secretory IgA (sIgA) was evaluated with the $GH_1$ cells in PCM-9, and the results of a representative study are shown in FIG. 77. These results were strikingly different than those obtained with plasma derived IgA (pIgA). SIgA was not inhibitory even at 20 µg/mL. Considering why the two different forms of IgA behaved so differently in the $GH_1$ cells, the poly-Ig receptor was recognized as a potential candidate for the mediator of the action of IgA/IgM. The poly-Ig receptor has not been previously associated with any growth related function. The poly-Ig receptor is concerned with process of transcytosis of IgA/IgM, as conceptually illustrated in (FIG. 78). SIgA already has the receptor bound in the sense of the secretory piece in association with the Fc domains of the dimer. FIG. 79 illustrates schematically the structures of inactive monomeric IgA, the connecting or joining "J" chain, the structure of the active dimer with "J" chain, the secretory piece or secretory component, and the dimeric IgA structure plus secretory component attached, as generally understood. The illustration shows that the Fc domains of dimeric IgA are blocked by the secretory piece/component. Access to the Fc domains is required for binding to the poly-Ig receptor.

The present series of cell growth assays above were continued with the related $GH_3$ cells, again in serum-free defined the preferred formulation of PCM-9 medium. Rat myeloma derived IgA was an effective estrogen reversible inhibitor of these cells in a 9 day growth assay (FIG. 80). The maximum estrogenic effect exceeded 5 CPD. A similar assay with rat IgM was conducted (FIG. 81). It showed even greater inhibition at 10 µg/mL than with IgA. The estrogenic effect recorded in 10 days was nearly 6 CPD. These same assays were next repeated with the human immunoglobulins. Human pIgA was an estrogen reversible inhibitor of $GH_3$ cell growth (FIG. 82). It was not as effective as its rat counterpart, but the estrogenic effect with the human immunoglobulin was still 4 CPD. Also, human IgM was effective with $GH_3$ cells (FIG. 83). Again the estrogenic effect was about 4 CPD. In the final study with $GH_3$ cells, it was again apparent that human milk derived sIgA was not inhibitory (FIG. 84).

The studies above with $GH_1$ and $GH_3$ cells were continued with the related $GH_4C_1$ line, again in serum-free defined PCM-9 medium. Rat myeloma derived IgA was an effective estrogen reversible inhibitor of these cells in a 9 day growth assay (FIG. 85). The maximum estrogenic effect approached 5 CPD. A similar assay with rat plasma IgM was conducted (FIG. 86). It showed slightly less inhibition than IgA. The estrogenic effect recorded in 10 days was nearly 4 CPD. These same assays were next repeated with the human immunoglobulins. Human pIgA was an estrogen reversible inhibitor of $GH_4C_1$ cell growth (FIG. 87). It was not as effective as its rat counterpart, but the estrogenic effect with the human immunoglobulin was still almost 4 CPD. Also, human pIgM was effective with $GH_4C_1$ cells (FIG. 88). The estrogenic effect was about 5 CPD. In the final study with $GH_4C_1$ cells it was again apparent that human milk derived sIgA was not inhibitory (FIG. 89).

H301 Syrian hamster kidney tumor cells. The studies with this cell line were done in the preferred formulation of CAPM defined medium described in TABLE 6. Because hamster IgA and IgM were not available, these experiments began with plasma IgA from mouse (FIG. 90). Mouse IgA was very effective with hamster H301 cells. The estrogenic effect was >5 CPD. Human plasma IgA was also effective (FIG. 91A). The maximum estrogenic effect reached 4 CPD. Secretory IgA was inactive (FIG. 91B). With this cell line, human IgM also was an estrogen reversible inhibitor. As shown in FIG. 92, a dose-response study demonstrated that in serum-free defined medium with 40 µg/mL of human plasma IgM, concentrations of 0.1 to 1.0 picomolar $E_2$ caused significant growth (p<0.01). This data demonstrate the extraordinary sensitivity of the serum-free defined cell growth assays in the presence of immunoglobulin. The data in FIG. 92 provide strong support for the view that the H301 cells can be used to characterize the new ERγ proposed in this disclosure. Further description of the rationale and evidence for a new growth regulation very high affinity estrogen receptor, ERγ, is found in a following Example.

MCF-7A and MCF-7K human breast cancer cells. For this series of experiments the serum-free defined medium was the preferred formulation of DDM-2MF described in TABLE 6. Two highly applied MCF-7 human breast cancer cell strains were applicable to this series of investigations. As shown with MCF-7A cells in DDM-2MF serum-free defined medium, plasma IgA was highly effective as an estrogen reversible inhibitor. The estrogenic effect exceeded 4 CPD in 10 days (FIG. 93A). In contrast, sIgA was inactive (FIG. 93B). With the MCF-7K strain, the results were nearly identical. Plasma IgA was effective (FIG. 94A) and sIgA was inactive (FIG. 94B). The estrogenic effects caused by pIgA were replicated by substitution of plasma IgM. With MCF-7A and MCF-7K, pIgM was an effective estrogen reversible sustaining estrogenic effects of >4 CPD (FIGS. 95 and 96, respectively). In a final study of this series, an $E_2$ dose-response experiment was conducted with MCF-7K cells in DDM-2MF plus 40 µg/mL of plasma IgM. The results were remarkable. Estrogen at as low as 0.1 picomolar caused more than one-half maximum growth response (FIG. 97). The extraordinary sensitivity of this assay methodology is clearly established. These results add more evidence that a very high affinity estrogen receptor (i.e. ERγ) regulates growth and is yet to be defined in human breast cancer cells.

T47D human breast cancer cells. The T47D cell line was assayed for immunoglobulin effects in the preferred formulation of serum-free defined medium DDM-2MF described in TABLE 6. As shown in FIG. 98A, human plasma IgA was a very effective estrogen reversible inhibitor with T47D cells. The maximum estrogenic effect was 6 CPD or a 72-fold cell number increase in 12 days. In contrast, sIgA was inactive at up to 20 µg/mL (FIG. 98B). Likewise, human plasma IgM is effective (FIG. 99), demonstrating complete inhibition of cell growth by 20 µg/mL IgM. The estrogenic effect was 5 CPD in 12 days. In experiments not shown, the effects of plasma derived IgM were compared to myeloma derived IgM. This study yielded the same estrogenic effects with both sources of IgM. Again, the antigenic determinant appears to be unimportant. The results support the view that the heavy chains dictate the activity. In other studies with T47D cells in defined medium containing 40 µg/mL, the dose-response effects with $E_2$ showed more than one-half maximum growth at 0.1 picomolar (FIG. 100). These results continue to fortify the theme that the methods described in this Example allow investigation of potential estrogenic compounds and substances that might be present in samples of industrial or biological materials at very low concentrations. It is also apparent that the data supports the view that a high affinity ERγ regulates growth.

ZR-75-1 human breast cancer cells. For these experiments the serum-free medium was the preferred formulation of DDM-2MF described in TABLE 6. Plasma IgA was an estrogen reversible inhibitor with ZR-75-1 cells (FIG. 101A). The estrogenic effect was recorded at 5 CPD in 14 days. As seen before with the other ER⁺ cell lines above, sIgA was not an inhibitor with ZR-75-1 cells (FIG. 101B). Plasma IgM was also assayed with the ZR-75-1 cells (FIG. 102). It was a potent estrogen reversible inhibitor under these completely serum-free defined conditions. As discussed above, this line had been thought to be estrogen responsive in serum-free culture. However, the former methods were not serum-free. As disclosed herein, it has now been established in entirely different culture conditions and shown that this line is truly estrogen growth responsive in culture.

HT-29 human colon cancer cells. For this series of experiments the serum-free defined medium was the preferred formulation of CAPM described in TABLE 6. As expected from endocrine physiology, colon is not a sex steroid hormone growth regulated tissue as are others such as breast, uterus, ovary and pituitary. However, it was discovered that this tissue is thyroid hormone growth responsive. As shown in FIG. 103, HT-29 human colonic carcinoma cells grow in CAPM independently of the presence of thyroid hormone. This growth is promoted by the other factors present in CAPM minus $T_3$. However addition of plasma IgM at 40 µg/mL had a dramatic effect. In the absence of $T_3$ HT-29 cell growth was inhibited to ≦1.0 CPD in 10 days. Addition of increasing concentrations of $T_3$ restored growth (FIG. 103). This demonstrates that colonic cancer cells respond to thyroid hormones in the same manner that ER⁺ cells respond to $E_2$. Estrogens and thyroid hormones belong to the same superfamily of receptors and both are required for normal physiologic growth and development (Williams G R and Franklyn J A (1994) *Baillieres Clin Endocinol Metab* 8, 241-266; Tsai M J and O'Malley B W (1994) *Annu Rev Biochem* 63, 451-486). This is the first demonstration of a secretory immunoglobulin acting directly as a thyroid hormone reversible growth inhibitor of a human origin colon cancer cell line.

LNCaP human prostatic carcinoma cells. For this series of experiments the serum-free defined medium was the preferred formulation of CAPM described in TABLE 6. LNCaP cells were negatively regulated by plasma IgA (FIG. 104A). The immunoglobulin was a DHT reversible inhibitor that was completely effective at 10 µg/mL. The androgenic effect was >5 CPD in 12 days. As seen with the ER⁺ cell lines above, sIgA was not inhibitory with LNCaP cells (FIG. 104B). Two different types of human IgM were also compared with LNCaP cells (FIG. 105). They were plasma derived and myeloma derived IgM. Despite the differences in antigen binding domains, both forms were equally inhibitory and both forms were reversed by 10 nM DHT. These results indicate that the Fc/heavy chain of IgM is the functional activator of the inhibition.

Summary of the estrogenic effects of IgM on ER⁺ cell growth. FIG. 137 presents a summary of the effects of IgM derived from different species with a variety of ER⁺ cell lines. This summary presents the maximum estrogenic effects recorded under conditions described above in serum-free defined medium with each cell line ±10 nM $E_2$. Estrogenic effects ranged from 4 to >7 CPD. Comparison of the results in FIG. 106 with those in TABLE 8 show in general that the results achieved in completely defined medium are equal to or greater than those seen in CDE-serum cultures.

Discussion of Example 18. These methods will permit evaluation of industrial, environmental, biological, medical, veterinary medicine and other potential sources of estrogenic or androgenic activity under the most sensitive conditions yet developed. Estrogenic activity is measurable at ≦1.0 picomolar concentrations. Two cell lines, MTW9/PL2 and H301, are preferred potential sources of identification of the new growth regulatory ERγ. The evidence presented with MCF-7 and T47D human breast cancer cells support the presence of a new growth regulatory ERγ. The serum-free methods described herein provide unique tools to search for ERγ. Assays conducted under these conditions permit estimation of estrogen sensitivities in ranges not approachable by other technology. These methods can also be adapted to measurement of the inhibitor in biological fluids available in only small supply. For example, coupled with use of XAD-4™ resin extraction to remove steroids, bodily fluids and other source materials can be assayed on small scale to determine the concentration of effective inhibitor. This is of particular interest because IgA in plasma is >90% inactive monomer and <10% active dimer/polymer. Measurement of IgA by conventional methods gives total concentrations, and does not determine the concentration/presence of active inhibitor. The present biological activity method has distinct features and advantages, and can serve as an adjunct measurement.

The serum-free defined medium assays described herein can be used to search for new compounds that mimic the action of immunoglobulins to block cancer cell growth in its early stages. This screening can be done under conditions in which serum proteins might interfere. Compounds so-identified can next be evaluated by addition of CDE-serum or XAD-4™ treated serum to determine if serum proteins interfere and to determine drug efficacy in vitro under both serum-free defined medium conditions and serum supplemented conditions. Serum-free defined medium methods can be used for screening of compounds that may either enhance or inhibit immune function at the epithelial cell level. Compounds with these activities may have utility as immune enhancers to help reduce the risk of cancer development. These assay methods offer a screening tool for such compounds that has not been available before. Larger magnitude effects permit greater accuracy with the new assay methods when estimating effects of substances that are less potent than natural estrogens.

Example 19

A New High Estrogen Affinity Growth Regulating Estrogen Receptor (ERγ)

This Example provides evidence of a never before recognized receptor that mediates estrogen responsive cell growth, and discusses potential applications for the receptor as a diagnostic and prognostic tool.

Steroid Hormone Superfamily of Receptors. Estrogens, androgens, progestins, corticosteroids, mineral steroids, vitamin D, retinoic acid and thyroid hormone receptors all belong to a family of DNA binding intracellular receptors that are activated by binding of the appropriate hormone/ligand (Evans R M (1988) *Science* (Wash D.C.) 240, 889-895; Giguere V (1990) *Genetic Eng* (NY) 12, 183-200; Williams G R and Franklyn J A (1994) *Baillieres Clin Endocrinol Metab* 8, 241-266; Kumar R and Thompson E B (1999) *Steroids* 64, 310-319; Pemrick S M et al. (1994) *Leukemia* 8, 1797-806; Carson-Jurica M A et al. (1990), *Endocr Rev* 11, 201-220; Tsai M J and O'Malley B W (1994) *Annu Rev Biochem* 63, 451-486; Alberts B et al. (1994) *Molecular Biology of The Cell,* 3rd edition, Garland Publishing, New York, pp 729-731). The estrogen receptor described in the citations above is now designated the classical estrogen receptor alpha (ERα). Its role in steroid regulated gene expression has been studied extensively and often reviewed (Yamamoto K R (1985) *Annu Rev Genet* 19, 209-252; Green S and Chambon P (1991) In: *Nuclear Hormone Receptors*, Academic Press, New York, pp 15-38; Tsai M-J and O'Malley B W (1994) *Annu Rev Biochem* 63, 451-486; McDonnell D P et al. (1992) *Proc Natl Acad Sci USA* 89, 10563-10567; Landel C C et al. (1994) *Mol Endocrinol* 8, 1407-1419; Landers J P and Spelsberg T C (1992) *Crit Rev Eukary Gene Exp* 2, 19-63; Cavailles V et al. (1994) *Proc Natl Acad (Sci USA* 91, 10009-10013; Halachmi S et al. (1994) *Science* (Wash D.C.) 264, 1455-1458; Brasch K and Ochs R L (1995) *Int rev Cyto* 159, 161-194; Hard T and Gustafsson J-Å (1993) *Acc Chem Res* 26, 644-650).

Human Mutation and Mouse Knock-out Studies of ERα and ERβ. It is noteworthy that estrogen resistance in man is caused by a mutation in the ERα (Smith E P et al. *N Eng J Med* 331, 1056-1061). The most startling fact is that this point mutation (i.e. cytosine→thymidine) generated a premature stop codon, but was not lethal. Although many metabolic abnormalities were noted, development into adulthood was observed without expression of a functional ERα. This fact is further strengthened by the experiments with ERα gene knockout mice (Couse J F and Korach K S (1999) *Endocr Rev* 20, 358-417). Those authors state "the list of unpredictable phenotypes in the α ERKO (estrogen receptor knockout) must begin with the observation that generation of an animal lacking a functional ER α gene was successful and produced animals of both sexes that exhibit a life span comparable to wild-type". Furthermore, in the review of the ERKα results it was not possible to conclude that the ERα regulated estrogen responsive cell growth. Indeed, functions normally ascribed to the ERα seemed unaffected. In fact, only development in tissues such as breast seemed best correlated (Boccchinfuso W P and Korach K S (1997) *J Mammary Gland Biol Neoplasia* 2, 323-334). The situation with ERKO mice and ERβ is similar (Couse J F and Korach K S (1999) *Endocr Rev* 20, 358-417). The results from ERβ knockout suggest an indirect role of this receptor via stromal tissue (Gustafsson J-Å and Warner M (2000) *J Steroid Biochem Mol Biol* 74, 254-248). Certainly a direct growth role for ERβ in breast epithelial cells was not established. The results available from ERKO do not yet provide confidence that either the ERα or the ERβ mediate estrogen responsive cell growth.

ERα and Growth Regulation. There are other pertinent lines of evidence that relate to the role of the ERα and growth. The first is from a study of transfection of estrogen receptor negative cells with the full length functional ERα (Zajchowski D A et al. (1993) *Cancer Res* 53, 5004-5011). The investigators arrived at a remarkable result. They had expected to regain estrogen responsive growth in the transfected hormone independent cells. This was definitely not the case. Instead, addition of $E_2$ caused cell growth inhibition. The results indicated that ERα was not a positive mediator, but instead a negative regulator. However, similarly transfected estrogen responsive cell lines such as MCF-7 and T47D were not $E_2$ inhibited.

As previously mentioned herein, considering the results of the present investigations, it is concluded that another positive acting ER exists in the MCF-7 and T47D cells and that its function is dominant and sustains growth related gene expression even with the inhibitory ERα present. The existence of two ER receptors is also indicated in an older study of the growth of the $GH_4C_1$ rat pituitary tumor cells in culture (Amara J F and Dannies P S (1983) *Endocrinology* 112, 1141-1143). Those investigators demonstrated a biphasic effect of $E_2$ on these cells. At picomolar concentrations, $E_2$ caused growth. At higher concentrations, $E_2$ induced prolactin production secretion and inhibited growth. If two receptors are operating, the growth receptor is more sensitive to $E_2$ whereas the ER regulating gene expression (e.g. prolactin mRNA production) is activated by higher concentrations of estrogen. This same biphasic action of estrogen on the growth of T47D human breast cancers cells has also been noted (Chalbos D et al. (1982) *J Clin Endocrinol Metab* 55, 276-283). Low concentrations promoted growth, whereas higher levels were inhibitory. Indeed, a biphasic effect also was noted with the MCF-7 cell line (Soto A M and Sonnenschein C (1985) *J Steroid Biochem* 23, 87-94). When this observation is coupled with the clear statements of Soto et al (Soto A M et al. (1986) *Cancer Res* 46, 2271-2275) that "the free estradiol levels needed for maximum response are significantly lower than estrophilin (i.e. ERα) $K_d$s", there is further support for the view that an ER exists that regulates growth and is more estrogen sensitive (i.e. lower $K_d$) than the classical ERα. While those investigators conclude that the results exclusively supported their estrocolyone hypothesis, and excluded ERα as the positive growth regulator, there was no recognition of the possibility of a much higher affinity receptor different than ERα. Finally, there is one other issue that has perplexed endocrinologists and cancer biologists for several years. Breast cancer is sometimes treatable with high doses of estrogen (Segaloff A (1981) *Banbury Report* 8, 229-239). If the ERα is the only growth mediator, one is forced into many other postulates to explain this observation (Reese C C et al. (1988) *Ann NY Acad Sci* 538, 112-121). Indeed, it may be that full occupation of ERα is inhibitory and that another receptor is the positive signal. One other issue that is of special interest with regard to the ERα is the fact that many tissues are known to express ERα but are not growth responsive to estrogen. Instead, estrogens cause tissue specific gene expression. Considering the results of the present investigations, it is proposed that those tissues lack ERγ, and are therefore not growth responsive.

Variant Estrogen Receptors. Certain variant estrogen receptors have been identified recently by others. For example, from the estrogen growth responsive T47D human breast cancer cell line, there have been three isoforms of the ERα identified in one study (Wang Y and Miksicek R J (1991) *Mol Endocrinol* 5, 1707-1715) and another three in a different study (Graham M L et al (1990) *Cancer Res* 50, 6208-6217). With another two estrogen growth responsive human breast cancer cells lines, the MCF-7 and ZR-75-1, another ERα variant was identified that lacked the entire exon 4 of the receptor (Pfeffer U et al. (1993) *Cancer Res* 53, 741-743). Variant receptors have also been identified from human breast cancer biopsy specimens (Murphy L C and Dotzlaw H (1989) *Mol Endocrinol* 3, 687-693). Another truncated variant of ERα acts as a natural inhibitor of the action of the wild-type ERα (i.e. unchanged receptor) (Fuqua S A et al. (1992) *Cancer Res* 52, 483-486). Another type of variant has received wide attention because it has constitutive transcriptional activity without the steroid hormone ligand bound (Fuqua S A et al. (1991) *Cancer Res* 51, 105-109). Even normal human breast epithelial cells show several natural variants of ERα (Yang J et al. (2000) *Endocrine* 12, 243-247). When all of these results are considered as a group, it is clear that different forms of the ERα are possible in cells, and it is reasonable to conclude that an alternate form of ERα, possibly formed by alternate splicing, or possibly arising from an as yet unrecognized gene, may regulate estrogen dependent/responsive tumor cell growth.

Characterization of ERβ. More recently, another estrogen receptor has been cloned and cDNA sequenced from rat prostate and ovary (Kuiper G G et al. (1996) *Proc Natl Acad Sci USA* 93, 5925-5930). It has now also been cloned from mouse (Tremblay G B et al. (1997) *Mol Endocinol* 11, 353-365) and human (Mosselman S et al. (1996) *FEBS Lett* 392, 49-53). This new receptor has been named estrogen receptor beta (ERβ). Evidence that ERβ is separate from ERα comes from the fact that the genes are located on different chromosomes (Enmark E et al. (1997) 82, 4258-4265). Therefore, ERβ is not simply an alternate splicing product of the ERα gene. Furthermore, ERβ is distinguishable from ERα based on critical differences in the amino acid sequences of functional domains (Kuiper G G et al. (1996) *Proc Natl Acad Sci USA* 93, 5925-5930; Enmark E et al. (1997) 82, 4258-4265; Dickson R B and Stancel G M (2000) *J Natl Cancer Inst Monogr No.* 27, 135-145). For example, the sequence homology between the two receptors is 97% in the DNA binding domain, but 59% in the C-terminal ligand-binding (i.e. steroid hormone-binding) domain, and only 17% in the N-terminal domain. The ERβ N-terminal domain is much abbreviated compared to the ERα (Enmark E et al. (1997) 82, 4258-4265). Rat ERβ contains an 18 amino acid insert in the domain binding the ligand. Despite the significant differences in structure, ERα and ERβ bind $E_2$ with the same affinity (Kuiper G G et al. (1996) *Proc Natl Acad Sci USA* 93, 5925-5930; Dickson R B and Stancel G M (2000) *J Natl Cancer Inst Monogr No.* 27, 135-145). In fact, others (Tremblay G B et al. (1997) *Mol Endocrinol* 11, 353-365) have stated that ERβ has a slightly lower affinity for $E_2$ than ERα (Tremblay G B et al. (1997) *Mol Endocrinol* 11, 353-365). Therefore, it is important to note that if either of these receptors mediates estrogen-induced growth, the steroid hormone concentrations required for one-half maximum growth (i.e. $ED_{50}$), or for optimum growth (i.e. $ED_{50}$), are expected to be about the same. The issue of estrogen concentrations for growth required for $ED_{50}$ versus those required for one-half maximum saturation of the receptors (i.e. the dissociation constant $K_d$) will be further discussed in Examples that follow.

ERα and ERβ Interrelationships. Some investigators have suggested that ERα and ERβ are functionally interrelated (Kuiper G G et al. (1998) *Endocrinology* 139, 4252-4263) and that one role of ERβ is to modulate the transcriptional activity of ERα (Hall J M and McDonnell D P (1999) *Endocrinology* 140, 5566-5578). Clearly however, there are significant functional differences between ERα and ERβ. These have discussed (Gustafsson J-Å (1999) *J Endocrinol* 163, 379-383). Also, there are functional differences expected because of the different pattern of steroid hormone binding shown by ERβ (Kuiper G G et al. (1996) *Proc Natl Acad Sci USA* 93, 5925-5930). For example, ERβ binds androgens whereas ERα does not. This fact, plus the location of ERβ in prostate indicates a new function that may be androgen related.

Estrogen Related Orphan Receptors. There is also another dimension of the estrogen receptor literature that deserves special comment. There have been "estrogen related receptors" (ERR 1 and 2) or "orphan" receptors identified that share properties with ERα but do not have a known function and do not have a known ligand (Giguere V et al. (1988) *Nature* (Lond) 331, 91-94; Gustafsson J-Å (1999) *J Endocrinol* 163, 379-383). Whatever mechanism is proposed for the action of the steroid hormone (i.e. on growth), it can be seen from the data presented herein, and subsequently reported elsewhere (Sirbasku D A and Moreno-Cuevas J E (2000) *In Vitro Cell Dev Biol* 36, 428-446), it takes a significant period to reverse the effects of the inhibitor. This process cannot be simply due to a rapid effect on transcription caused by steroid hormones (e.g. via a known estrogen receptor). Cellular metabolic events, including the transformation of $E_2$ to an active steroid metabolite, may provide the growth regulating ligand for one of the "orphan" estrogen receptors. An alternative possibility is that the receptor may be activated by metabolites formed from cholesterol metabolism (Gustafsson J-Å (1999) *Science* (Wash D.C.) 284, 1285-1286). In fact, today, there are more than 70 "orphan" receptors seeking ligands and functions (Gustafsson J-Å (1999) *Science* (Wash D.C.) 284, 1285-1286).

Comparison of the Labeled $E_2$ Binding Dissociation Constants ($K_d$) of Several Estrogen Sensitive Cell Types. Clearly, the assays with extracts measured the same affinity binding sites as analyses with whole cells. This offers reasonable evidence that the standard binding technology employed in these studies is measuring the most common form of receptor present in cells, no matter whether whole cells are assayed or cell extracts. The affinity of the MTW9/PL2 estrogen receptor is that which is characteristic of the ERα. The $K_d$ of the receptor measures the concentration of ligand that one-half saturates the sites. In TABLE 10, the $K_d$ values for labeled $E_2$ are presented as reported and presumably represent the ERα. Only when the measurements are specific for the β form is the designation (ERβ) included.

TABLE 10

Comparison of $E_2$ Binding Affinities Expressed as Dissociation Constants ($K_d$)

| CELL LINES | WHOLE CELLS $K_d$ for $E_2$ | CELL EXTRACTS $K_d$ for $E_2$ | REFERENCES |
|---|---|---|---|
| MTW9/ PL2 | $2.78 \times 10^{-9}$ M | $1.89 \times 10^{-9}$ M | Moreno-Cuevas JE and Sirbasku DA (2000) In Vitro Cell Dev Biol 36, 410–427 |
| MCF-7 | $0.58 \times 10^{-9}$ M | $1.77 \times 10^{-9}$ M | MacIndoe JH et al. (1982) Steroids 39, 247–258 |
| MCF-7-Mason | | $4.0 \times 10^{-9}$ M Unfilled nuclear | Horwitz KB et al. (1978) Cancer Res 38, 2434–2437 |
| MCF-7-Mason | | $\times 10^{-9}$ M Filled nuclear | Horwitz KB et al. (1978) Cancer Res 38, 2434–2437 |
| MCF-7 | | $\times 10^{-9}$ M | Reddel RR et al. (1985) |
| MCF-7-L | | $0.08 \times 10^{-9}$ M | Cancer Res 45, 1525–1531 |
| MCF-7-M | | $0.07 \times 10^{-9}$ M | |
| T47D | | $\times 10^{-9}$ M Unfilled nuclear | Horwitz KB et al. (1978) Cancer Res 38, 2434–2437 |
| T47D | | $4.0 \times 10^{-9}$ M Filled nuclear | Horwitz KB et al. (1978) Cancer Res 38, 2434–2437 |
| T47D | | $0.11 \times 10^{-9}$ M | Reddel RR et al. (1985) Cancer Res 45, 1525–1531 |
| ZR-75-1 | | $0.09 \times 10^{-9}$ M | Reddel RR et al. (1985) Cancer Res 45, 1525–1531 |
| ZR-75-1 | | $1.3 \times 10^{-9}$ M | Engel LW et al. (1978) Cancer Res 38, 3352–3364 |
| H301 | $1.0 \times 10^{-9}$ M | | Liehr JG and Sirbasku DA (1985) In: Tissue Culture of Epithelial Cells, Taub M, ed, Plenum, New York, pp 205–234 |
| H301 | | $0.87 \times 10^{-9}$ M | Soto AM et al. (1988) Cancer Res 48, 3676–3680 |
| $GH_3$ | | $0.25 \times 10^{-9}$ M | Moo JB et al (1982) In: Growth of Cells in Hormonally Defined Media, Vol. 9, Cold Spring Harbor, New York, pp 429–444 |
| $GH_3$ | $0.31 \times 10^{-9}$ M | | Haug E et al. (1978) Mol Cell Endocrinol 12, 81–95 |
| Prostate and Ovary | | $\times 10^{-9}$ M (ERα) $0.5 \times 10^{-9}$ M (ERβ) | Tremblay GB et al. (1997) Mol Endocrinol 11, 353–365 |
| Transfection Studies | | 0.05 to $0.1 \times 10^{-9}$ M (ERβ only) | Kuiper GC et al. (1998) Endocrinology 139, 4252-42-63 |

TABLE 10 presents only a fraction of the estrogen binding data available in the literature. However, the $K_d$ values presented are representative and do show a discernable pattern. The lowest $K_d$ identified in a literature search was in the range $5 \times 10^{-11}$ M to $1.0 \times 10^{-10}$ M for the ERβ and $7 \times 10^{-11}$ M to $1.1 \times 10^{-10}$ M for the ERα. In general, the binding affinities as estimated by $K_d$ are lower for receptors from human cells than those from rodent lines. It is important to note that the results presented in TABLE 10 indicate that the lower limit of measuring estrogen receptor affinities most likely has been reached. The use of the highest specific activity tritium labeled steroids has been optimized and simply cannot be used to measure 10 to 100-fold lower $K_d$ concentrations. This opens the possibility of an as yet unrecognized ER that mediates growth effects at lower concentrations of estrogen than either the ERα or the ERβ.

Discussion of Example 19. Evidence is provided herein that all of the ER+ cell lines analyzed in this presentation show estrogenic effects (i.e. positive growth responses significant to p<0.05 or P<0.01) obtained at 10 to more than 1000-fold lower $E_2$ concentrations than expected from the measurement of $K_d$, with these and related cell lines. It is proposed herein that estrogen promoted growth is mediated by an as yet to be characterized estrogen receptor designated ERγ. In accordance with this proposal, the ligand that activates ERγ may be $E_2$ or another cellular component induced, changed or modified by the action of estrogen. For example, the ligand may be a lipophilic compound such as one of the intermediates of the cholesterol biosynthetic pathway or the phospholipid biosynthetic pathways. There is a relationship between the ERα and the ERγ, as cells that are growth responsive to estrogens express the ERα. This suggests that ERα has a functional, regulatory, gene, expression, or other types of control relationship to ERγ in growth activated target tissues. Accordingly, ERγ may be the most accurate estimation of breast and other cancer cell growth sensitivity to estrogens, and its measurement could serve as a valuable adjunct or replacement for the current protocols relying on the measurement of ERα in breast cancer.

The ERγ is also suitable for application as a diagnostic and prognostic tool for other cancers such as those of the female urogenital tract including ovary, uterus cervix and vagina, as well as bladder, kidney, liver, melanoma, Hodgkin's disease, pituitary adenomas and other target tissues.

Example 20

Effect of Tamoxifen Antiestrogen in Serum-free Defined Medium

In this Example the use of one of the present cell growth assays was used to evaluate the effects of this classical antiestrogen with "mixed" functions. A new type of growth inhibiting function for tamoxifen is identified.

Background of Tamoxifen Effects and Clinical Applications. The antiestrogenic effects of tamoxifen are well documented. Most evidence suggests this compound and its active metabolite 4-hydroxyl-tamoxifen prevent growth of ERα positive cells via interaction with the receptor (Coezy E et al. (1982) *Cancer Res* 42, 317-323; Bardon S et al. (1984) *Mol Cell Endocrinol* 35, 89-96; Reddel R R et al. (1985) *Cancer Res* 45, 1525-1531). However, it has also been suggested that tamoxifen blocks growth factor promoted MCF-7 breast cancer cell growth (Vignon F et al. (1987) *Biochem Biophys Res Commun* 146, 1502-1508). Also, tamoxifen has high affinity binding sites and actions distinct from the estrogen receptor (Sutherland R L et al. (1980) *Nature* (Lond) 288, 273-275; Phaneuf S et al. (1995) *J Reprod Fertil* 103, 121-126). Despite its complex actions, tamoxifen has widespread use as a treatment for breast cancer (Fisher B et al. (1998) *J Natl Cancer Inst* 90, 1371-1388; Jaiyesimi I A et al (1995) *J Clin Oncol* 13, 513-529; Clinical Trial Report (1997) *J Clin Oncol* 15, 1385-1394; Clinical Trial Report (1987) *Lancet* 2(8552), 171-175; Forrest A P et al. (1996) *Lancet* 348(9029), 708-713; Tormey D C et al. (1996) *J Natl Cancer Inst* 88, 1828-1833; Gundersen S et al (1995) *Breast Cancer Res Treat* 36, 49-53; Gelber R D et al. (1996) *Lancet* 347(9008), 1066-1071; Raabe N K et al. (1997) *Acta Oncol* 36, 2550-260).

Serum-free Medium Effects of Tamoxifen. In the present series of tests, the effects of tamoxifen (TAM) were reexamined under completely serum-free defined conditions. It is important to note that throughout the Examples herein, data is presented showing that estrogens alone have either had no effect on growth in defined medium or at most a 1.0 CPD effect that was related to saturation density. This was true no matter if phenol red was present or absent from the medium, as shown herein and also reported (Moreno-Cuevas J E and Sirbasku D A (2000) *In Vitro Cell Dev Biol* 36, 447-464). In similar assays, $1.0 \times 10^{-7}$ M tamoxifen was completely inhibitory with T47D cells in culture, as shown in FIG. 107. The study shown in FIG. 107 examined the concentrations of tamoxifen needed to fully inhibit T47D cell growth in the preferred formulation of DDM-2MF serum-free defined medium without any source of estrogens. Even phenol red was eliminated. The expected outcome was no tamoxifen inhibition. As shown, estrogen alone had only a 1.0 CPD effect in serum-free defined medium. However, tamoxifen had unexpected effects revealed by the use of serum-free defined medium. Tamoxifen effectively arrested growth at $1.0 \times 10^{-7}$ M. Higher concentrations were cytotoxic. It was observed in these assays that tamoxifen had the same effect as immunoglobulins IgA and IgM. To demonstrate this fact another way, the experimental results presented in FIG. 108 show that estrogens completely reversed the effect of $1.0 \times 10^{-7}$ M tamoxifen. This sequence of experiments showed the same results as those shown above with plasma IgA and IgM and ER$^+$ cell lines.

Discussion of Example 20. The observation of inhibition of cell growth by a classical antiestrogen demonstrates the utility of this technology to search for other antiestrogenic compounds. Furthermore, because of the current intense focus on the search for SERMs (i.e. Selective Estrogen Receptor Modulators) the serum-free technology disclosed herein has particularly useful applications. Specific types of SERMS can be sought for different cell types. Those SERMs that do not cause breast cancer cell growth can be readily identified by this technology. Those SERMs with multiple activities can be identified before conducting expensive animal testing.

The technology presented permits a clear definition of antiestrogens with "mixed" functions (e.g. tamoxifen-like, that act at several sites) versus those with a "pure" function mediated only by the estrogen receptor. To date, no similar easily applied in vitro method based on serum-free defined medium and secretory immunoglobulins is available that produces growth as an endpoint of the assay.

An entirely new function is proposed for the well-known drug tamoxifen, in which tamoxifen mimics the immune system effects on ER$^+$ cancers, thereby inhibiting growth. It is believed that estrogen reverses these effects, not as a consequence of interaction with the classical ERα, but as a consequence of the ERγ. This mechanism is closely parallel to that observed with IgA/IgM and E$_2$, disclosed herein. Prior to the present invention, tamoxifen has never been linked to growth regulatory changes in the secretory immune system, nor has there been any suggestion that tamoxifen in any way mimics the inhibitory action of IgA/IgM on mucosal cells. Accordingly, certain embodiments of the present invention offer new uses for tamoxifen based on diagnostic testing to identify human breast, prostate, colon and other mucosal cancers that are poly-Ig receptor/secretory component positive. For example, such identification could be determined by immunohistochemistry or radioimmunoassay or other suitable tests that have clinical applicability. Those tissues determined to be poly-Ig receptor/secretory component positive are then candidates for tamoxifen treatment either alone or in conjunction with other treatment modalities. The new, preferred applications of tamoxifen described herein is not based on the classical ERα, which has different criteria for its use and different tissues as potential targets.

The serum-free assay methodology described herein will be directly applicable to a search for tamoxifen derivative compounds showing more "immune-like" activity or other compounds with a similar activity. The assay method is unique because of the discovery of the estrogen reversible effects of IgA and IgM and because of the results showing that tamoxifen inhibits in the complete absence of estrogens and is reversed by natural estrogen just as happens with IgA/IgM.

The results presented show that tamoxifen inhibits the mitogenic action of a variety of growth factors and nutrients in completely serum-free defined culture. This effect shows the same type of "master switch" action as demonstrated by immunoglobulins, and has mechanistic implications. The immunoglobulins shut off all growth, as did tamoxifen in these studies. As is discussed further hereinbelow, the receptor mediating the effects of the immunoglobulins must possess the property of a "master switch" to shut down all but steroid hormone responsive growth. Notably, both the immunoglobulins and tamoxifen have this effect even when a large number of "mitogens" are present. Others have reported that tamoxifen inhibits growth factor dependent growth (Vignon F (1987) *Biochem Biophys Res Commun* 146, 1502-1508), but only concluded that tamoxifen was not a "pure" estrogen. An entirely new site of action for tamoxifen is arrived at in the present disclosure.

Tamoxifen may also be an antagonist of ERγ, and may be useful in that capacity. The assay methods presented herein can be used to distinguish those antiestrogens that act only on the growth estrogen receptor from those acting elsewhere as well. The serum-free defined medium technology presented herein has direct application to the assay of a great variety of drugs now in use by women either before the onset of breast cancer or after the onset. Drugs or preparations such as antidepressants, herbal extracts, soy products, other food, plant or microorganism extracts, estrogenic creams and cosmetic preparations can be assessed for antiestrogenic or estrogenic activity. These methodologies are also applicable to exploration of additional anti-androgenic compounds. Furthermore, in view of the possible role of estrogens as well as androgens in prostate growth, this technology can be used to search for compounds with both activities.

Example 21

Effect of Long-Term Exposure of Breast Cancer Cells to IgM Under Serum-Free Defined Conditions IgM Cytotoxicity after Long-Term Exposure—MTW9/PL2 Cells. In the above examples, IgM has been demonstrated to be an estrogen reversible inhibitor of ER+ rodent tumor and human cancer cell growth. During these studies, visual inspection of the cultures indicated that experiments carried beyond 7 days with the MTW9/PL2 cells showed a marked deterioration of morphology. This suggested that exposure of the MTW9/PL2 cells to IgM might in fact be causing cell death. Such observations wee immediately recognized as having potential therapeutic applications. To examine this further, MTW9/PL2 cells were incubated in serum-free defined medium DDM-2A for up to 10 days in the presence of 40 µg/mL horse IgM (prepared by Custom Monoclonals International). On days 0, 2, 4, 6, 8, and 10 after seeding, 10 nM $E_2$ was added to cultures and growth effects measured as cell number increases (FIG. 109). These results, presented as cell numbers versus days, show that addition of $E_2$ on or after day 8 no longer had an estrogenic effect. Conversion of the data in FIG. 109 to CPD estrogenic effects showed very clearly that $E_2$ addition after eight days no longer caused reversal of the IgM (FIG. 110). The CPD after eight days with IgM were no different than the controls held in the absence of $E_2$ throughout the study. Clearly, IgM was cytotoxic in eight days with MTW9/PL2 rat mammary tumor cells.

IgM Cytotoxicity after Long-Term Exposure—Human Cancer Cells. Similar studies were done with the T47D and MCF-7A human breast cancer cells in serum-free defined medium DDM-2MF. Two examples are presented in FIG. 111 and FIG. 112, respectively. In the presence of 40 µg/mL human pIgM, the T47D cells and the MCF-7A cells no longer responded to 10 nm $E_2$ by day 13. Control studies indicated the killing was IgM mediated. The conclusion was clear. IgM was cytotoxic to human breast cancer cells within two weeks. In a partial replica study with LNCaP cells (results not shown), human pIgA exposure for 14 days caused cell death as IgM had done with T47D cells. These results have important therapeutic implications.

Discussion of Example 21. The results presented are the first evidence that exposure of breast and prostate cancer cells to IgA and IgM for periods of two weeks or longer can cause growth inhibition leading to cell death. At present, it is not known if this represents some form of cytotoxicity or is due to a natural process such as apoptosis. Certainly apoptosis and cancer therapy is a dynamic current research theme, however there are no apparent previous reports in the literature related to IgA and IgM action on mucosal cell growth and apoptosis.

A dilemma has existed for many years regarding the frequency of metastasis in breast, prostate and other epithelial cancers. It would seem that the malignant cells should populate many more new sites much more rapidly than actually happens in patients. To be sure, metastases occur at many sites, and do occur simultaneously or nearly so. However, IgA and IgM in the plasma may act to suppress the number of disseminated cancer cells. An implication of the results of the present investigations is that cancer cells in the general circulation are exposed to the effects of IgA and IgM and therefore remain inhibited or are in fact killed. Only after they are located in relatively inaccessible sites do they not feel the full effects of IgA and IgM, and therefore proliferate more rapidly. One example of this is the very well known propensity of prostate cancers to locate in bone. This is also true of breast, to a significant extent. Metastatic breast and prostate cancers are very often autonomous, consistent with the present experimental results. Autonomous cancer cells are not inhibited by IgA and IgM, and are, therefore, free to move in plasma and proliferate at new sites without negative immune surveillance.

Notably, the most well known human breast cancer cell line, MCF-7, was obtained from a pleural effusion of a patient with an estrogen responsive cancer (Soule H D et al (1973) *J Natl Cancer Inst* 51, 1409-1416). Indeed, many researchers have sought breast cancer cell lines from this fluid. The question of why this estrogen responsive and highly immunoglobulin sensitive line survived at this new site becomes clearer, in light of the present disclosure, when it is recognized that plural fluid is not rich in plasma immunoglobulins. Pleural fluid is a filtrate of plasma. Elevation of plasma IgA and IgM levels may have preventative value with regard to metastasis, and therapeutic value with respect to those tumors that are accessible to the plasma immunoglobulins.

Example 22

The Role of the Poly-Ig Receptor in Hormone Responsive and Autonomous Breast and Prostate Cell Growth Regulation In this Example it was shown that the poly-Ig receptor or a poly-Ig like receptor mediates the inhibition of cell growth by IgA/IgM. Methods of identifying genetic or expression defects in that receptor, and screening methods for assessing susceptibility, and for establishing a diagnosis or prognosis in mucosal cancers are described.

Structural Properties of the Poly-Ig Receptor. The negative response to IgA and IgM is mediated by the mucosal poly-Ig receptor or a very similar structure with the same immunoglobulins specificity as well as the same immunological and $M_r$ properties. The poly-Ig receptor is a $M_r$ 100,000 transmembrane protein with several properties that place it in the Ig superfamily of receptors (Krajči P et al. (1992) *Eur J Immunol* 22, 2309-2315; Williams A F and Barclay A N (1988) *Annu Rev Immunol* 6, 381-405). The poly-Ig receptor and the secretory component from human has been cDNA cloned and DNA sequenced (Krajči P et al. (1992) *Eur J Immunol* 22, 2309-2315; Krajči P et al. (1995) *Adv Exp Med Biol* 371A, 617-623; Krajči P et al. (1991) *Hum Genet* 87, 642-648; Krajči P et al. (1989) *Biochem Biophys Res Commun* 237, 9-20) as has the poly-Ig receptor from mouse (Kushiro A and Sato T (1997) *Gene* 204, 277-282; Piskurich J F et al (1995) and bovine tissue (Verbeet M P et al. (1995) *Gene* 164, 329-333). Altogether, the human poly-Ig receptor coding sequence encompassed 11 exons. The extracellular five domains originate from exons 3 (D1), exon 4 (D2) exon 5 (D3 and D4), exon 6 (D5), exon 7 (the conserved cleavage site to form the secretory component), exon 8 (the membrane spanning domain), exon 9 (a serine residue required for transcytosis), exon 9 (sequence to avoid degradation), exon 10, no known function) and exon 11 (sequence contains a threonine residue and the COOH terminus) (Krajči P et al (1992) *Eur J Immunol* 22, 2309-2315).

With the exception of domains 3 and 4 (both from one exon), the receptor structure follows the rule of one domain/one exon. The poly-Ig receptor binds IgA and IgM via their Fc domains, and more particularly, via a specific amino acid sequence (15→37) of domain 1 (Bakos M-A et al. (1991) *J Immunol* 147, 3419-3426). Of the other extracellular domains, only D5 is known for a specific function. It contains the disulfide bonds that covalently exchange with dimeric/polymeric IgA to form sIgA during transcytosis. The role of this receptor in transcytosis of IgA/IgM has been well studied with mucosal tissues and epithelial cells in culture (Vaerman J P et al (1998) *Eur J Immunol* 28, 171-182; Fahey J V et al (1998) *Immunol Invest* 27, 167-180; Brandtzaeg P (1997) *J Reprod Immunol* 36, 23-50; Loman S et al (1997) *Am J Physiol* 272, L951-L958; Mostov K E et al. (1995) *Cold Spring Harbor Symp Quant Biol* 60, 775-781; Schaerer E et al (1990) *J Cell Biol* 110, 987-998). One serine residue is particularly important for transcytosis (Hirt R P et al (1993) *Cell* 74, 245-255).

Lines of Evidence Supporting Poly-Ig Receptor or a Poly-Ig Like Receptor in Negative Growth Regulation. A series of studies and observations disclosed herein indicate that the IgA/IgM inhibition mediating receptor has the properties of the poly-Ig receptor or another receptor ("poly-Ig like receptor") with properties very similar to those of the poly-Ig receptor. From those studies, the following supporting facts were gained: (1) The source of the active IgA is not the deciding factor. Plasma or myeloma derived IgA are equally effective. Also, species makes little or no apparent difference in activity. IgA isolated from various species has major sequence homology in the α heavy chains but differences in the variable chains. This is consistent with mediation by an Fc superfamily receptor. The poly-Ig receptor is a member of this Fc binding family. (2) IgA obtained from commercial myeloma cell sources (especially from Zymed) contains predominantly dimeric and polymeric immunoglobulin. It is highly active. This is consistent with mediation by the poly-Ig receptor because it binds only dimeric/polymeric IgA. (3) Cultures containing the active CA-PS-pool II material are ≧90% dimeric/polymeric forms of immunoglobulins. Experiments described herein demonstrated clearly that this material is as active as any commercially prepared IgA in both serum-supplemented and serum-free defined medium. This is consistent with the expected binding of IgA to the poly-Ig receptor. (4) IgM is at least as active, or two to three times as active as dimeric IgA, on a molar basis. Dimeric IgA is a 350 kDa complex. IgM is a 950 kDa pentamer. These masses favor IgM by two to three-fold on a molar basis. Also, IgM has five Fc domains for binding, and dimeric IgA two Fc domains. The source of the IgM can be from plasma or myeloma cells. They are equally effective. This is expected of the poly-Ig receptor. (5) Secretory IgA is invariable inactive as an inhibitor. It has the five extracellular domains of poly-Ig receptor attached. Plasma derived IgA is in contrast fully active (see FIG. 79 for IgA structures). To prove that pIgA does not have the secretory component whereas sIgA contains the 80 kDa receptor fragment, the Western analysis in FIG. 113 was performed. Secretory IgA shows an 80 kDa cross-reaction band with anti-secretory component whereas pIgA shows no reaction. This was the expected result and provides solid support for the view that the poly-Ig receptor is the mediator. Because secretory component is isolated from milk sIgA, these results show that the secretory component used for immunization of the rabbits was free of the other subunits in IgA. This was a meaningful control for the next experiments.

In the next experiments, anti-human secretory component antiserum was used to block the inhibiting effects of IgA and IgM. FIG. 114 shows the results with the T47D cells in serum-free defined medium DDM-2MF with human plasma IgM alone and with a series of dilutions of the antiserum. As shown, 10 nM $E_2$ completely reversed the IgM inhibition. Dilutions of 1:500 to 1:5000 also blocked the inhibition. In the insert in FIG. 114, it is shown that a control study with pre-immune rabbit serum demonstrated that it had no inhibitor blocking activity. A similar study was done with LNCaP cells in serum-free defined CAPM with human pIgA (FIG. 115). As shown, 10 nM $E_2$ completely reversed the pIgA inhibition. Anti-serum dilutions of 1:00 and 1:1000 also reversed the inhibition. Differences between the effective dilutions with T47D and LNCaP cells was due to changes in lots of commercially prepared antiserum. Anti-secretory component antibodies completely blocked the inhibitory effects of IgA and IgM. These studies not only indicate poly-Ig receptor mediation, but they support the view that IgA and IgM act via the same receptor. The poly-Ig receptor is known to conduct transcytosis of both of these immunoglobulins with very high efficiency.

To determine if IgA/IgM responsive cells expressed 1000 kDa poly-Ig receptor, the Western analysis shown in FIG. 116 was done. Amounts of extracts of the designated cell types were analyzed with a 1:1000 dilution of rabbit anti-human secretory component. As expected MDCK cells were positive. This cell line has been studied for several years as a model of poly-Ig receptor sorting and function. LNCaP cells showed the same receptor (FIG. 116). Cell lines that were negative were ALVA-41, DU145, human fibroblasts, and PC3 cells (FIG. 116). As shown in multiple experiments described herein, LNCaP cells are IgA/IgM inhibited. The results of the Western analyses show that they express the poly-Ig receptor.

In the final experiments of this series, pIgA was tested with two of the cell lines that were poly-Ig receptor negative by the Western analysis shown in FIG. 116. The results with DU145 cells are shown in FIG. 117. Plasma IgA was not an inhibitor. A similar study with PC3 cells is shown in FIG. 118. Again, pIgA was not an inhibitor even at 50 g/mL. These results demonstrate cells that lack the poly-Ig receptor are also insensitive to pIgA.

The HT-29 colon cancer cells are known to express only the authentic form of the poly-Ig receptor. They are also negatively growth regulated by IgM (FIG. 103). This implies that the poly-Ig receptor has more function than transcytosis only. This is very strong evidence in favor of the authentic poly-Ig receptor having a heretofore unrecognized growth regulating function in early stage cancers of colon. The HT-29 colon cancer cells are the source of a cDNA sequence for the poly-Ig receptor deposited in GENBANK. This sequence, hereby incorporated herein by reference, is very often referred to in published reports and shown to be equal to the exons identified from normal human leukocytes that were the source of the genomic sequence of the poly-Ig receptor. Taken together, all of the available data indicate that the authentic poly-Ig receptor has a new function, as identified and described herein.

Discussion of Example 22. For the first time, a relationship between immunoglobulin growth regulation and the poly-Ig receptor is demonstrated. This receptor has in the past been studied from the perspective of a transcytosis receptor; however, a new function for this receptor is now described. Gene changes in the authentic poly-Ig receptor gene may include point mutations, deletions, insertions, and premature termination. The receptor mediating the effects of IgA/IgM may be a form arising from alternate splicing of the original transcytosis receptor. Changes in the regulation of expression may influence the presence or absence of this receptor. Changes in allelic balance may affect the expression of this receptor and hence its function in normal, early stage cancers and in autonomous cancers. The positive correlation between the presence of ER and AR and expression of the poly-Ig receptor indicates regulation or positive influence by steroid hormones. Without wishing to be bound by a particular theory, it is suggested that this regulation may be at the gene expression level or at another down-stream processing point. The actual mechanism has not yet been identified.

One of the primary themes of cancer research has been that loss of "tumor suppressor genes" causes the release of cells from negative regulation and thereby contributes to the progression to cancer. The evidence disclosed herein indicates that the poly-Ig receptor has a "tumor suppressor" function. It is present in cells that are regulated by IgA/IgM and absent in cells that are insensitive to immune inhibitors. This is a new aspect of cancer immunology that had not been recognized before the present invention.

For the first time, the poly-Ig receptor is connected to the D1S58 linked locus that is a "hot spot" for genetic changes in breast cancer. This disclosure proposes that this locus or near neighbors contain the growth regulating form of authentic transcytosis poly-Ig receptor or a very similar immunoglobulin superfamily receptor. Alternately, the 1q31-q41 region of chromosome 1 contains several other genes of immunological interest that might include the poly-Ig receptor or another related receptor mediating the effects of IgA/IgM.

These genes are applicable for use as screens for breast and other mucosal cell cancers. They are expected to indicate susceptibility and to be used in prognosis and other diagnostic applications with human tissue and cancer samples. Analyses of allelic imbalances in the receptor gene are also foreseen as a new tool to determine susceptibility and prognosis for development of breast and other mucosal cancers, as will be the detection of mutations in the growth regulating intracellular domains of the receptor. The known amino acid sequence of the poly-Ig receptor does not contain the immunoreceptor tyrosine-based inhibitory motif (ITIM) common to a new family of inhibitory motif receptors (Cambier J C (1997) *Proc Natl Acad Sci USA* 94, 5993-5995). Other amino acid sequences may serve this same function.

Example 23

IgG1 and IgG2 as Immunoglobulin Regulators of Estrogen and Androgen Responsive Cancer Cell Growth A role for IgG1 and IgG2 as immunoglobulin regulators of estrogen and androgen responsive cancer cell growth is described in this Example, together with methods describing how to use those IgG subclasses to identify the Fcγ receptor that mediates their inhibitory effect. Use of the receptor, and its gene for assessing susceptibility to cancer, and in diagnostic, gene screening and other applications is also addressed.

Background Regarding IgG Subclasses. The major immunoglobulins secreted as mucosal immune protectors include IgA, IgM and IgG. In human serum, the percent content of IgG, IgA and IgM are 80, 6 and 13%, respectively. In humans, the major subclasses of IgG are IgG1, IgG2, IgG3 and IgG4. These are 66, 23, 7 and 4% of the total IgG, respectively. The relative content of human immunoglobulin classes/subclasses in adult serum follow the order IgG1>IgG2>IgA1>IgM>IgG3>IgA2>IgD>IgE (Spiegelberg H L (1974) *Adv Immunol* 19, 259-294). When the serum concentrations of immunoglobulins are compared to those in exocrine secretion fluids, the relative contents change dramatically (Brandtzaeg P (1983) *Ann NY Acad Sci* 409, 353-382; Brandtzaeg P (1985) *Scand J Immunol* 22, 111-146). For example in colostrum (a breast fluid secretion), secretory IgA is ≧80% of the total immunoglobulins. IgM is ≦10% of the total. IgG represents a few percent. In human colostrum and milk, IgG1 and IgG2 are the major subclasses of IgG (Kim K et al. (1992) *Acta Paediatr* 81, 113-118). Clearly, comparison of serum and mucosal fluid concentrations indicate selective immunoglobulin secretion. The secretion mechanism for IgA and IgM are well described. Conversely, there is a fundamental question surrounding IgG secretion. There is no "J" chain present in IgG1 and IgG2. From the known facts of transcytosis/secretion of immunoglobulins (Johansen F E et al. (2000) *Scand J Immunol* 52, 240-248), it is unlikely that IgG secretion is mediated by the poly-Ig receptor. An epithelial receptor specific for IgG1 has been reported in bovine mammary gland (Kemler R et al. (1975) *Eur J Immunol* 5, 603-608). Apparently, it preferentially transports this class of immunoglobulins from serum into colostrum. Despite this 1975 report however, the receptor has not been chemically or structurally identified nor has the mechanism of transport of IgG monomers been satisfactorily defined. Certainly no growth function was ascribed to this "IgG1 receptor" in the 1975 Kemler et al. report. It is possible that this receptor is a member of a large group now designated as Fc receptors (Fridman W H (1991) *FASEB J* 5, 2684-2690), but there is one study with IgG showing that, of 31 different long-term human carcinoma cell lines, including breast, "all lines were found to be consistently Fc receptor negative" (Kerbel R S et al. (1997) *Int J Cancer* 20, 673-679). One possible candidate for the epithelial transport of IgG1 is the neonatal Fc receptor (Raghavan M and Bjorkman P J (1996) *Annu Rev Cell Dev Biol* 12, 181-220). However, there is no indication yet of the presence of this receptor in adult mucosal tissues.

Value of Assessing IgG Subclasses for Activity. Although the IgG class is lowest in concentration in secretory fluids, it is still physiologically important because of its capacity to neutralize pathogens by various mechanisms. The human clinical importance of understanding and measuring IgG subclasses has been growing steadily. From a few clinical reports per year in 1970, the literature now exceeds four hundred reports a year. These assays are valuable for several reasons, including the following: (1) they provide a clearer picture of an individual's susceptibility to disease; (2) an awareness that treatment for subclass deficiencies is important; (3) the subclasses can be used to assess the state of a number of diseases; and (4) the IgG subclass difference between ethnic groups and different races is a potential area for expanded control of disease. The present investigations showed that bulk purified mixtures of all subclasses of horse and rat IgG were not estrogen reversible inhibitors for MTW9/PL2 rat mammary tumor cells. These results were further examined, as described below.

Test of Rat IgG Subclasses as Estrogen Reversible Inhibitors of MTW9/PL2 Rat Mammary Tumor Cell Growth. The IgG subclasses of rat are IgG1, IgG2A, IgG2B and IgG2C. These IgGs, obtained from commercial sources previously identified herein, were tested at 15 µg/mL with MTW9/PL2 cells in DDM-2A serum-free defined medium (FIG. 119). All four IgG subclasses were compared to rat pIgA and rat pIgM. The latter two were estrogen reversible inhibitors, as expected (FIG. 119). However, the four IgG subclasses were not inhibitors at a concentration that was effective with IgA or IgM. The estrogenic effects recorded in cultures with them were no larger than seen in serum-free defined medium alone (FIG. 119). Clearly, IgG are not effective steroid hormone modulators in rat.

Test of Human IgG Subclasses as Estrogen Reversible Inhibitors of Breast and Prostate Cancer Cell Growth. The subclasses of human IgG are IgG1, IgG2, IgG 3 and IgG4. They are formed with both λ and κ light chains. A series of studies was performed, and it was found that with human breast cancer cells, only IgG1κ was a significant estrogen reversible inhibitor. FIG. 120 shows a comparison of its activity to human pIgA and pIgM. At 40 µg/mL, it was 37% as effective as pIgM. A similar study with LNCaP cells showed that only IgG1κ had activity greater than the estrogenic effect seen in CAPM serum-free defined medium only (FIG. 121). However, in some experiments with prostate cells, IgG2K also showed androgen reversible inhibitory activity (FIG. 122). Based on these studies, it is concluded that IgG1 and IgG2 have small but measurable androgen reversible activity with AR+ human prostate cancer cells.

Discussion of Example 23. The effect of IgG1κ raises an issue not encountered with IgA or IgM. The preference for the K light chain implies that a different receptor mediates the effects of this immunoglobulin. This immunoglobulin may have greater inhibitory effects on normal breast or prostate cells that it has on ER+ and AR+ cancer cells. Part of the transformation/progression process leading to hormone responsive cancers may be an attenuation of the effectiveness of IgG1κ as an inhibitor. The present IgG1 observations have other applications, as well, including the measurement of the IgG1κ subclass in different populations such as black American, Asian, white, Native American and Hispanic with contrasting susceptibilities to breast and prostate cancer, or individuals within any one ethnic group, may provide additional information and confirmation of the usefulness of such measurements. These measurements can be made in bodily fluids or plasma. Measurement in milk and breast fluid may provide an indication of susceptibility to the development of breast cancer.

Irrespective of the receptor that mediates the growth response of IgG1κ or IgG2, this receptor will be a candidate for the missing transcytosis receptor for IgG. Its molecular identification has utility in diagnostic specimens of breast, prostate and other cancers and can be used to determine new uses of the immune system for therapeutic applications. Once it is completely identified, the receptor that mediates the IgG1/IgG2 growth inhibition effects will provide another target for development of compounds that mimic the immune system inhibition of cancer cell growth. As described above with respect to the gene for the poly-Ig receptor, the gene encoding this IgG receptor will also be useful as a locus for analysis of genetic susceptibility to breast and prostate cancers, as well as other types of mucosal and epithelial cancers of humans.

Example 24

Mediation of IgG1κ Effects by a Fc-Like Receptor

In this example the probable mediating receptor for IgG1κ cancer cell growth inhibiting effects is further described and applications for using the gene encoding this receptor as a genetic screening tool to aid in assessing genetic susceptibility are discussed.

It is Highly Unlikely that IgG1 Acts via the Poly-Ig Receptor. The poly-Ig receptor has a requirement for "J" chain for binding (hence its specificity for dimeric/polymeric IgA or pentameric IgM each of which has one J chain). Also, as shown in TABLE 11, Fcγ receptors are localized in leukocyte series or bone marrow origin cells. There is no convincing evidence in the literature of their presence in epithelial cells or in secretory cells of the mucosa. The IgG1 inhibition-mediating receptor sought in the present study is one analogous to the Fcγ in two significant properties. First, it binds monomeric IgG1 via the Fc domain of the immunoglobulin with some participation of the K light chain. Second, the receptor has inhibitory activity akin to a new family of Fc receptors. The amino acid sequence of the new IgG1κ receptor is expected to have an immunoreceptor tyrosine-based inhibitory motif (ITIM) (VxYxxL) common to a new family of inhibitory motif receptors (Cambier J C (1997) $Proc\ Natl\ Acad\ Sci\ USA$ 94, 5993-5995). Alternatively, other amino acid sequences may serve this same function. The Fcγ family of receptors contains members that possess a very special property. They are expected to mediate growth inhibition. The methods of identification are outlined below.

TABLE 11

Properties of the Fc γ Family of Receptors

| | Fc γ RI (CD64) | Fc γ RII (CD32) | Fc γ III (CD16) |
|---|---|---|---|
| IgG1 Binding | $K_a \sim 10^8\ M^{-1}$ | $K_a = 2 \times 10^6\ M^{-1}$ | $K_a = 5 \times 10^5\ M^{-1}$ |
| Binding Order | IgG1> | IgG1> | IgG1= |
| | IgG3= | IgG3= | IgG3 |
| | IgG4> | IgG4> | |
| | IgG2 | IgG2 | |
| Found in these Cell Types | Macrophages Neutrophils Eosinophils | Macrophages Neutrophils Eosinophils Platelets B Cells | Natural Killer Cells Macrophages Neutrophils Eosinophils |

It should be noted that none of these receptors has previously been identified in mucosal cells. Identification of one of these, or a highly related growth inhibitory Fc receptor, in mucosal cells will be a significant advance with many practical and clinical applications.

Discussion of Example 24. The amino acid sequence of a new Fc family receptor may include immunoreceptor tyrosine-based inhibitory motif (ITIM) common to a new family of inhibitory motif receptors (Cambier J C (1997) $Proc\ Natl\ Acad\ Sci\ USA$ 94, 5993-5995). Fc receptors of mucosal cells that may include one of the known members of the family of ITIMs, or may contain another amino acid sequence or sequences that serve this same function, are the subject of ongoing investigation. Once the sequence is identified, the genetic mapping to a specific chromosome number and locus is expected. The genomic DNA sequence of the new receptor (or existing receptor, if already known), including introns and exons, is also expected. Once identified, this receptor will find use as a genetic screening tool for genetic susceptibility to breast and prostate and other mucosal cancers, in addition to, or analogous to, conventional breast and prostate screening technologies. Additionally, the IgG1 mediating receptor will be employed for diagnostic and clinical applications, as further discussed hereinbelow. Detection of mutations and changes associated with progression from normal cells to autonomous cancer cells are using this receptor gene is foreseen. Methods of detecting changes in regulation or expression of the receptor due to allelic imbalances in the receptor gene are also foreseen as a new tool to determine susceptibility and prognosis for development of breast and other mucosal cancers. Detection of other regulatory and developmental changes are also made possible by this receptor and its gene.

Example 25

Immunoglobulin Inhibitors as Tools for Identifying the Receptors that Mediate the IgA/IgM/IgG Cell Growth Regulating Effects This Example describes how IgA, IgM and IgG1 can serve as biological reagents or tools in establishing the identity of the inhibition mediating receptors.

The Mediating Receptors—Inhibitory Function. It has been made clear by the results presented herein, and in co-owned concurrently-filed U.S. patent application Ser. No. 09/852,958/PCT/US2001/15183 entitled "Compositions and Methods for Demonstrating Secretory Immune System Regulation of Steroid Hormone Responsive Cancer Cell Growth," hereby incorporated herein by reference, that the mediating receptor for the serum-borne agent has special properties. As discussed above, serum contains a great variety of mitogenic agents. On this point, the present results in 50% (v/v) serum were especially relevant. This concentration of serum is a rich source of mitogens including insulin and the insulin-like growth factors. Nutrients and other serum components also have growth-promoting effects. Examples include diferric transferrin, unsaturated fatty acids bound to albumin, complex lipids and ethanolamine. The broad range of different "mitogens" present in defined medium are described elsewhere (Riss T L and Sirbasku D A (1987) *Cancer Res* 47, 3776-3782; Danielpour D et al. (1988) *In Vitro Cell Dev Riot* 24, 42-52; Ogasawara M and Sirbasku D A (1988) *In Vitro Cell Dev Biol* 24, 911-920; Karey K P and Sirbasku D A (1988) *Cancer Res* 48, 4083-4092; Riss T L et al. (1988) *In Vitro Cell Dev Biol* 24, 1099-1106; Riss T L et al. (1988) *In Vitro Cell Dev Biol* 25, 127-135; Riss T L and Sirbasku D A (1989) *In Vitro Cell Dev Biol* 25, 136-142; Riss T L et al. (1986) *J Tissue Culture Methods* 10, 133-150; Sirbasku D A et al. (1991) *Mol Cell Endocrinol* 77, C47-C55; Sirbasku D A et al. (1991) *Biochemistry* 30, 295-304; Sirbasku D A et al. (1991) *Biochemistry* 30, 7466-7477; Sato H et al. (1991) *In Vitro Cell Dev Biol* 27A, 599-602; Sirbasku D A et al. (1992) *In Vitro Cell Dev Biol* 28A, 67-71; Sato H et al. (1992) *Mol Cell Endocrinol* 83, 239-251; Eby J E a al. (1992) *Anal Biochem* 203, 317-325; Eby J E et al. (1993) *J Cell Physiol* 156, 588-600; Sirbasku D A and Moreno-Cuevas J E (2000) *In vitro Cell Dev Biol* 36, 428-446). From the present results, clearly, the immunoglobulin inhibitor(s) also block the growth effects of all those mitogens, and steroid hormones are selectively capable of reversing the effects of the inhibitor(s). Plainly, as predicted by the estrocolyone hypothesis, serum contains an inhibitor that has a dominant role in the regulation of proliferation of steroid hormone target cells. These inhibitors will have biological implications extending well beyond estrogen and androgen target tissues. Because of its "master switch" character, the newly identified immunoglobulin inhibitors have many practical industrial testing and manufacturing uses as well as many beneficial clinical applications.

The Receptor Mediating IgA/IgM/IgG Inhibitory Effects. The results shown herein strongly indicate that the Ig/IgM growth inhibition is mediated either by the poly-Ig receptor or a very closely related receptor. Establishing a growth regulating function for this "transcytosis" receptor will open new directions in medical diagnosis, treatment and prevention of cancers of mucosal epithelial tissues. It will be determined whether the poly-Ig receptor, or a poly-Ig like receptor, mediates the growth regulating effects of IgA on human breast and prostate cancer cells in culture. For this study, the poly-Ig receptor in these cancer cells will be identified using well-known PCR cloning technology, $^{125}$I-labeled IgA chemical cross-linking and Western and immunohistochemistry methods that have been described in the literature.

Next, blocking polyclonal antibodies or blocking monoclonal antibodies will be employed to show that the poly-Ig receptor mediates the growth response. The antibodies will be raised against the poly-Ig receptor using known techniques. Reversal of the inhibitory effect of IgA and IgM by blocking the poly-Ig receptor will suggest that the poly-Ig receptor is not just a simple transport receptor, but that it has a central role in breast and prostate cancer cell growth regulation. There is no existing paradigm for breast or prostate cell growth regulation that involves the poly-Ig receptor or for that matter any receptor specific for the IgA class of immunoglobulins including Fcε receptors (Fridman W H (1991) *FASEB J* 5, 2684-2690).

The different forms and domains of IgG, IgA and IgM that act as inhibitors of normal prostate and breast and other mucosal epithelial cell growth and the hormone responsive and hormone autonomous forms of these cancers in serum-free defined culture medium will be determined and used as tools to evidence or confirm the identity of the receptor(s) responsible for mediating the growth regulatory effect. The properties of the ligand that elicits a response will be evidence supporting the identity of the receptor. Poly-Ig receptor is activated by Fc-domains as are Fcγ receptors. Normal cells are likely to be most inhibited by IgG, IgA and IgM, whereas the ER$^+$ and AR$^+$ cells will likely be inhibited primarily by IgA/IgM, and ER$^-$ and AR$^-$ cells will likely not be inhibited by any of the three classes of immunoglobulins, as predicted by the conceptual model described below. The methods employed will include direct tests of the activity of IgG, IgA and IgM on cell growth as well as assessment of the activity of specific size forms and Fc versus Fab fragments. Antibodies such as anti-J chain and anti-Fc will be used to extend these studies to demonstrate that the Fc is the active domain and that Fc binding receptors are involved.

More specifically, AR$^+$ LNCaP cells, the AR PC3 and DU145 cells, and the AR$^+$ ALVA-41 cells will be studied. Normal human prostate and breast epithelial cells will be obtained from Clonetics. Growth assays will be done in completely serum-free CAPM (prostate) and DDM-2MF (breast), as described above. IgA1 and IgA2 will be purified from human serum and colostrum, using techniques that are well known and have been described in the literature. Initial small samples will be obtained from a commercial supplier such as The Binding Site (San Diego, Calif.). The monomeric, dimeric and polymeric forms of IgA will be separated using techniques that are well known and have been described in the literature. If only IgA2 has activity, it will be further separated into the A2(m)1 and A2(m)2 allotypes, using well-known techniques that have been described in the literature. Because the initial IgA/IgM inhibitor preparations evaluated in the present studies were mostly dimeric and monomeric, those forms are expected to be the most active in the future series of tests. Confirmation that the most active forms are dimeric/polymeric IgA/IgM will be strong evidence for poly-Ig receptor mediation. Should the monomers be revealed as the only active inhibitor forms, however, it would favor Fc or Fc super-family receptors, in which case the Fcα will be investigated as a possible mediator.

IgA will be fragmented with a specific protease to yield Fc and Fab fragments from IgA, using techniques that are well known and have been described in the literature. The Fab and Fc fragments of IgM will be obtained using a Pierce Chemicals kit based on immobilized trypsin. Fab and Fc fragments of IgG1 will be obtained using another Pierce kit. If only Fc fragments of IgA and IgM are active, mediation by the poly-Ig receptor is likely. If the Fc of IgG1 is active, it will indicate an Fc receptor as the mediator.

The immunoglobulin inhibitors will also be used as tools or biological reagents to confirm whether IgG acts via a receptor different than IgA/IgM. Based on the results reported above, identification of Fcγ like receptors and the poly-Ig receptor (or related receptor) with normal cells, $ER^+$ cells and $AR^+$ cells is expected, and no functional receptors are expected in $ER^-$ cells or $AR^-$ cells. $^{125}$I-labeled IgG1, IgA and IgM will be prepared using chloramine T or Iodogen® beads or coated tube (Pierce Chemicals kits). Binding parameters, binding constants, analyses of the effects of reciprocal additions of labeled and unlabeled immunoglobulins to identify separate or similar binding sites, and determination of the effects of addition of purified secretory component on IgA and IgM binding will be performed as previously described or using well known published techniques. Specific binding will be as total binding minus binding in a 100-fold excess of unlabeled protein. For each form with activity, time, concentration and temperature dependence of binding will be assessed. Scatchard analysis will be used to estimate the number of sites per cell and the association constants ($K_a$). Reciprocal competitions with unlabeled and labeled immunoglobulins will be used to define interaction with the same or different receptors. This latter point is important because binding of both IgA and IgM to the same site strongly favors the poly-Ig receptor and plainly contra-indicates Fcα (IgA) or Fcμ (IgM) receptors, which are members of a superfamily in which each member is specific for a (monomer) class of immunoglobulins. In addition, the effects of blocking antibodies such as anti-secretory component, anti J chain and anti Fc will be assessed with all three cell types. Where indicated, chemical cross-linking with $^{125}$I-labeled Ig will be performed to define the mass of the receptors. Optionally, metabolic labeling and/or immunoprecipitation techniques will be used instead, employing well-known techniques that have been described in the literature.

Western immunoblotting with normal, steroid hormone receptor positive and steroid hormone receptor negative cell types will be performed to identify the receptors present. Immunohistochemistry will be applied to identify the poly-Ig receptor and Fcγ receptors on all three types of cells using the blocking antibodies. Using a full-length human poly-Ig receptor cDNA clone, S1 nuclease protection assays will be conducted with RNA from normal prostate and breast cells, $ER^+$ and $ER^-$ breast cancer cells, and $AR^+$ and $AR^-$ prostate cancer cells to identify mRNA. In the cases of $ER^+$ and $AR^+$ or $ER^-$ or $AR^-$ cells, this method will help to identify truncated or otherwise altered receptors or non-functional receptors. As described in certain of the preceding examples, Western blots have already been conducted, as well as cell growth assays with receptor blocking antibodies. The remaining analyses will be done with normal cells as well as all other $ER^-$ or $AR^-$ lines. All blocking antibodies are dialyzed against buffer containing charcoal to remove interfering steroid hormones. Rabbit polyclonal anti secretory component will be raised (e.g., by HTI BioProducts, Ramona, Calif.) and rabbit polyclonal anti-human J chain and specific antibodies against the Fc receptors for IgG and IgA are commercially available (Accurate). The specificity of all antiserum will be checked by Western analysis.

To identify the receptors mediating the androgen reversible inhibition of normal and/or $AR^+$ cells, PCR cloning methods will additionally be used to determine the cDNA sequences of the poly-Ig receptor and Fcγ receptors from normal, $AR^+$ and, if indicated, from $AR^-$ cells. This method will provide clear answers to the question of the relationship of the human poly-Ig receptor and Fcγ receptors to immune system negative regulation. It is expected that the receptors will be found to be either identical to known sequences or altered in sequence to convert them to "inhibitory motif" receptors. Based on the known cDNA sequence of the poly-Ig receptor from HT-29 cells, PCR cloning technology will be applied to obtain a full-length clone from the LNCaP and T47D cells. Ongoing investigations are directed to comparing receptor sequences from normal prostate and breast cells to identify any changes. Based on the known sequence of the FcγRIIB1 receptor, these same studies will be repeated. The receptors identified by cloning will be examined for the immunoreceptor tyrosine-based inhibitory motif (ITIM) amino acid sequence I/VxYxxL or related sequences. Concomitantly, the cells will be examined by Western analysis for SHP-1 and SHP-2 phosphatase mediators of the inhibition of growth factor activity. These markers are not only associated with the inhibitory motif but also other inhibitory receptors. More specifically, an LNCaP and T47D full-length poly-Ig receptor clone will be prepared and compared to the reported sequence of the poly-Ig receptor. The same technology will be applied to the poly-Ig receptor from normal prostate cells, and, if indicated, from the $AR^+$ lines. Because these cell lines are expected to express the known poly-Ig receptor, or a related form, the PCR approach is applicable. The same approach will be used with the Fcγ like receptor. However, in this case, because these receptors are predominantly lymphoid origin, the form in epithelial cells may be substantially different. Standard cloning methods will be employed to obtain the complete cDNA sequence of the Fcγ like receptor from normal and LNCaP cells. Total RNA will be extracted and mRNA purified by oligo dT cellulose chromatography (also for Northern analysis). cDNA synthesis will be done with oligo dT primers and AMV reverse transcriptase followed by Rnase H to remove RNA. Second strand synthesis will be done with hexameric random primers and DNA pol. I. Treatment with T4 DNA pol, Rnase H and Rnase A creates blunt ends. EcoR1 methylation is followed by EcoR1 linkers and ligation into a cloning vector. (Stragene) vectors based on λgt10 (hybridization screening) and λgt11 (secretory component antibody screening). Both vectors will accept inserts larger than the receptor. The cDNA sequence of human poly-Ig receptor known is the genomic sequence. These will be used to prepare sequence specific primers for PCR. The primers will encompass the 5' and 3' non-coding sequences to ensure a complete cDNA. The PCR products will be subcloned using the TA kit from Invitrogen. The sequencing of PCR clones will be done by the dideoxy chain termination method (Lone Star Labs, Houston, Tex.). From these, determination of whether there have been significant alterations in the receptor during the transition from normal to $ER^-$ and $AR^-$ cancer cells is expected. From sequence data, the ITIM amino acid sequences indicating an inhibitory motif receptor will be sought. It is important to note, however, that the absence of these sequences does not necessarily rule out an inhibitory function. The Western analyses for SHP-1 and SHP-2 will be valuable as an indication of an inhibitory function even in the absence of ITIM or when the ITIM is in a modified form.

Discussion of Example 25. Without wishing to be bound by a particular theory, it is proposed that the inhibitory effect of IgG1 is more marked with normal cells than with ER+ or AR+ cancer cell lines and an early step in the pathway to malignancy involves loss by the cell of IgG1 regulation. From preliminary investigations, it appears likely that the IgA and IgM receptors are a common poly-Ig receptor (or a poly-Ig like receptor), which in normal cells is expected to be the same as in steroid hormone receptor positive cell lines. In contrast, the IgG1 receptor, likely an Fc gamma type receptor, is expected to either be either genetically altered, or its expression altered by changes in other controls, to reduce the receptors in ER+ and AR+ cell lines. The demonstration that IgG1 has a major growth inhibiting effect on normal cells may lead to immunization against breast cancer by administering or enhancing IgG1 in at-risk tissues. Characterization of an inhibitory role for IgG1 via an Fcγ-like receptor is expected to lead to important innovations in medical diagnosis, treatment and prevention of cancers of mucus epithelial tissues.

Example 26

Conceptual Model for Cascading Loss of Immunoglobulin Control in Progression from Normal Cells to Steroid Hormone Responsive and Autonomous Cancers Concept. The isolated inhibitors, now identified as IgA, IgM and IgG1, controlled breast and prostate cell growth by acting as a steroid hormone reversible inhibitor even when tested under the very rigorous conditions of serum-free defined culture. These active natural inhibitors are present in blood, bodily secretions and mucosal epithelial tissues. The isolated inhibitors readily prevented the growth of these types of cancer cells when they were still in the early (i.e., hormone responsive) stage, but not in the late, non-hormone responsive stage. These results have many implications with regard to the diagnosis, genetic screening, treatment and prevention of breast, prostate, colon and other mucosal cancers. Without wishing to be bound by a particular theory, considering the present discoveries and experimental results and, a new conceptual model for understanding how estrogens cause ER+ breast cancer cell growth and for understanding how the natural progression of breast cancers occurs to give rise to highly malignant (and dangerous) hormone autonomous forms is proposed. This same model is applicable to other mucosal tissues that respond to the steroid hormone family of hormones, including androgens and thyroid hormones.

Progression Concept Based on the Breast Cancer Model—Generally Applicable to Mucosal Tissue Cancers. It is well established that breast cancers pass through a characteristic natural history that involves a gradual evolution from near normal growth patterns into cancers that are completely steroid hormone autonomous (i.e. they are no longer stimulated by steroid hormones). These are usually designated estrogen receptor negative (ER−). As disclosed herein, it has been found that autonomous (ER−) breast cancer is accompanied by a loss in sensitivity to IgA or IgM. Fully autonomous breast cancers are not inhibited by these secretory immunoglobulins. In light of the results described herein, it appears that autonomous breast cancers lack the poly-Ig receptor that mediates the growth inhibiting effects of IgA and IgM. These results are of special significance because for the first time they pinpoint a specific genetic change (i.e. in the poly-Ig receptor) that might account for the majority (i.e. approximately 75%) of breast cancers termed "sporadic" and for which there is as yet no clear genetic change identified. Indeed, these results also provide an excellent opportunity to implement gene therapy based on reintroduction of the poly-Ig or poly-Ig like receptor into completely autonomous cancers to regain immunological regulation.

It is well established in the literature that IgG1 is present in serum during childhood, when breast tissue growth is precisely regulated to body size (isometric growth). The other inhibitors, IgA and IgM, are very low at this time, but increase in serum at puberty. Because adult women have increased positive stimuli for breast cell proliferation due to estrogen production, the presence of IgA and IgM may provide additional protection. It is now proposed that alterations in immune regulation lead to the progression of breast and prostate cells from normal control to ER+ and AR+ cancer cells and that additional alternations in immune control contribute to the development of fully autonomous cancers, according to the following model presented in TABLE 12:

TABLE 12

Model for Progression of Steroid Hormone Dependent Cancers from Normal Growth Regulation by the Immune System to Steroid Responsive Cancers and on to Fully Hormone Autonomous Cancers

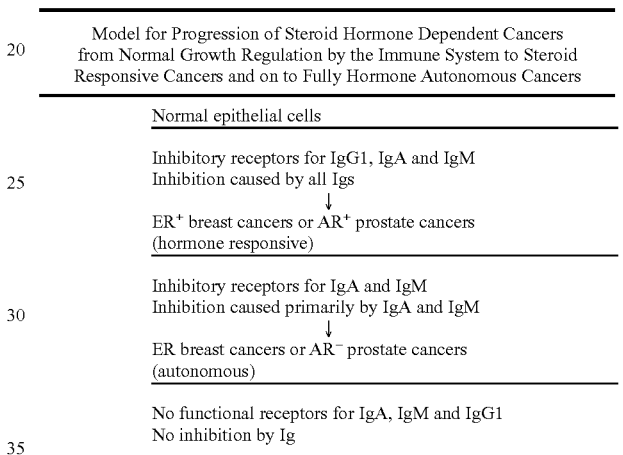

Inhibitory Motif Receptors. The receptors mediating the immune response regulation must be at or very near the beginning of the onset of breast cancer. Using the tools developed in the present series of investigations, it is expected that inhibitory motif receptors for these immunoglobulins will be identified. It is now proposed that the mediating receptors are members of the Ig superfamily, which includes Fc receptors and a new class of Ig inhibitory motif receptors. This new class of receptors has emerging importance because of the increasing recognition of the role of negative regulation of cell growth. These receptors have both common and unique properties. They bind immunoglobulins via the Fc domains and hence can be classified as Fc receptors. One of these is, in fact, FcγRIIB that binds IgG1 (TABLE 12) and causes inhibition of antigen activation of B cells. There are many other examples (Cambier J C (1997) Proc Natl Acad Sci USA 94, 5993-5995). Among these are more than 15 receptors now designated Signal-Regulatory Proteins (SIRPs). These all express a special inhibitor motif of six amino acids (I/Vx-YxxL) that is now referred to as the "immunoreceptor tyrosine-based inhibitory motif" or ITIM. One of the most marked characteristics of the ITIM containing SIRPs is that this motif recruits two phosphatases (SHP-1 and SHP-2) to result in the inhibition of all growth factor dependent proliferation. This is similar to what was observed with IgG1, IgA and IgM and ER+ breast cancer cells and AR+ prostate cancer cells serum-free defined medium. This work is expected to aid in the identification of the missing genes for sporadic breast cancers and a more complete understanding of the cascade of gene changes that lead to complete loss of immune control of breast cell growth.

Similarly, it is suggested that alterations in immune regulation also lead to the progression of prostate cells from normal control to AR+ cancer cells and that additional alterations in immune control contribute to the development of AR fully autonomous cancers. Further studies are directed at identifying a cascade of gene changes leading to complete loss of immune control of cell proliferation.

Similarly, it is also proposed that alterations in immune regulation also lead to the progression of colon cancer cells from thyroid hormone receptor (THR) normal control to THR+ cancer cells and that additional alterations in immune control contribute to the development of THR− fully autonomous cancers. Further studies are directed at identifying a cascade of gene changes leading to complete loss of immune control of cell proliferation Tests to determine whether steroid hormone independent breast and prostate cancer cell growth results from either the loss of the poly-Ig receptor or an inactivation of its function are a focus of continuing investigations. A series of steroid hormone dependent and steroid hormone independent breast and prostate cancer cell lines will be compared for their inhibitory growth responses to IgA, the presence of poly-Ig receptor m-RNA, the expression of the receptor by $^{125}$I-IgA binding analysis and immunohistochemistry localization of receptor. Detection of an absence of the receptor or an inability to bind IgA will suggest that cancer cell autonomy arises due to a loss of secretory immune system regulation. Such a result would be entirely new in the field of hormone dependent cancers and would provide a new immune mechanism responsible for conversion from hormone dependence to autonomy. New immunotherapies can be developed based on activating the receptor in hormone responsive cancers and new gene therapies based on reestablishing the function of this receptor in autonomous breast cancers.

Ongoing investigation is directed at resolving whether hormone autonomous breast cancer cell lines have functional poly-Ig receptors. The ER− cell lines to be studied are the MDA-MB-231, BT-20, MDA-MB-330 the non-tumorus HBL-100, and the Hs578t and Hs578Bst. Each will be evaluated for growth in serum-free medium ±IgA and ±$E_2$. This study will determine if autonomous cells have lost immune system negative regulation. To determine if the receptor is lost, the S1 nuclease protection assays will be used to seek its mRNA. A kit from AMBION will be used. In addition, $^{125}$I-I labeled IgA will be used to determine specific binding characteristics as described above. Immunohistochemistry will be used to confirm and/or extend the binding data. If the receptor mRNA and protein are absent, these methods should confirm that fact. Alternatively, if they are present but nonfunctional, these methods should also confirm that fact.

Discussion of Example 26. The proposed model of progression of mucosal cancers from normal cells to fully autonomous cancers is based on the experimental results presented, and has not been suggested prior to the present invention. As previously stated, there has also been no previous recognition of the roles of IgA, IgM and IgG1 in breast, prostate, or other mucosal cancers. The cancer progression model has diagnostic implications. For example, breast, prostate and other cancers can be examined for content of the IgA, IgM and IgG1 receptors, as an indicator or aid to determining the stage of the cancer. This information can be compared to the determination of estrogen receptor and progesterone receptor status to aid in decisions regarding immunotherapy with immune modulators or the immunoglobulins or the use of combined anti-hormone and immune therapy modalities. Tumors that are negative for all of the immunoglobulin receptors are prime candidates for gene therapy to replace the receptors and thereby reestablish immune surveillance, as further described in a subsequent example.

Example 27

Role of TGFβ in Breast Cancer Predicts the Cellular Progression in Early Onset Breast Cancer This Example describes a new model for TGFβ and secretory immune system roles in cancer progression in early onset breast cancer. A "linear" progression model (e.g., normal breast cell→ER+ cancer cell→ER− cancer cell) has been generally accepted for many years (Furth J (1959) *Cancer Res* 3, 241-265; Heppner G H (1984) *Cancer Res* 44, 2259-2265). In conformity with the linear progression concept, a modified model of human mucosal cell progression is presented (shown in TABLE 12) that outlines sequential passage of normal cells to steroid hormone stimulated cancers that in turn give rise to steroid hormone autonomous cancers, and includes the proposed roles played by the immunoglobulin inhibitors.

There exist, however, pronounced factual issues that are not adequately addressed by the linear progression model. For example, it is known that early onset (i.e. pre-menopausal) breast cancers are 60 to 70% ER− or steroid autonomous. This fact is difficult to explain under a strictly linear progression model because during this time (i.e., the pre-menopausal stage) female levels of estrogen are high, and therefore should favor outgrowth of estrogen responsive tumors. Considering all of the foregoing and a number of seemingly unrelated observations, in light of the TGFβ experimental results obtained herein, an alternative new concept, or model, of "progression" in early onset breast cancer has been reached. This proposed model is illustrated as a schematic flow diagram in FIG. 123. This model suggests an alternative or additional sequence for cancer progression that does not in all cases require the transition to ER+ or AR+. As shown previously herein, TGFβ has little if any inhibitory effect on ER+ breast cancer cells (FIGS. 25 and 26). However, it is also well established that TGFβ is a very potent inhibitor of normal breast epithelial cell growth (Hosobuchi M and Stampfer M R (1989) *In Vitro Cell Dev Biol* 25, 705-713; Daniel C W et al. (1996) *J Mammary Gland Biol Neoplasia* 1, 331-341). Furthermore, it is equally well established that TGFβ remains an inhibitor for ER− autonomous cells (Arteaga C L et al. (1988) *Cancer Res* 48, 3898-3904; Osborne C K et al (1988) *Breast Cancer Res Treat* 11, 211-219). Drawing from the fact that ER+ breast cancer cells lack TGFβ receptors (Arteaga C L et al. (1988) *Cancer Res* 48, 3898-3904; Brattain M G et al (1996) *J Mammary Gland Biol Neoplasia* 1, 365-372), early onset autonomous breast cancer very likely does not arise from responsive cancer cells, but instead arises directly from normal cells as outlined in FIG. 123 by the loss of immune surveillance. The term "immune surveillance" means that cell growth inhibitory immunoglobulins in the general circulation, and/or secreted by or bathing the mucosal/epithelial tissues, are present and are in sufficient amounts to deter or prevent cancer cell proliferation. This model has many clinical implications and applications for diagnosis and genetic screening to identify young women at greatest risk of developing breast cancer. Early onset markers will be loss of immune surveillance without obligatory loss of TGFβ effects. The fact that ER+ breast cancer cells lack TGFβ receptors while ER− breast cancer cells do have the TGFβ receptor mitigates in favor of the new bifurcated progression model, in which both ER+ and ER− cancers arise directly out of normal breast cells. Because it is statistically very unlikely that an ER⁺ cancer cell, after having lost the TGFβ receptor, would somehow regain that receptor before passing continuing onward to become an ER⁻ cancer cell, this non-linear alternative model is reasonable.

Discussion of Example 27. The therapeutic implications of the TGFβ system have been reviewed (Arrick B A (1996) *J Mammary Gland Biol Neoplasia* 1, 391-397; Reiss M and Barcellos-Hoff M H (1997) *Breast Cancer Res Treat* 45, 81-95). However, the model presented in the present Example integrates the investigator's discovery of the involvement of the secretory immune system with the well known but complex (Koli K M and Arteaga C L (1996) *J Mammary Gland Biol Neoplasia* 1, 373-380) effects of TGFβ on breast cancer cells. It is expected that a lesion in the genetics or expression of TGFβ and/or its isoform system of three receptors (Chakravarthy D et al. (1999) *Int. J Cancer* 15, 187-194) will have importance in modulating the estrogen reversible effects of the secretory immunoglobulins.

Conversion of normal cells to ER⁺ responsive breast cancers involves the loss of expression of the TGFβ receptor system including one or more of the three different forms of the receptor. Changes in these receptors, either individually or in unison are indicated in development of steroid hormone dependent cancers. It is possible that TGFβ receptor II is of greatest importance of the three forms (Gobbi H et al. (1999) *J Natl Cancer Inst* 91, 2096-2101). Nonetheless, other studies suggest receptor forms I, II and II as important. As yet, those results have not been applied to genetic screening related to ER⁺ breast cancers. According to the presently proposed model, lesions in the TGFβ system precede lesions or other types of losses of the receptors for secretory immunoglobulins. The loss of TGFβ inhibitory responses may represent the earliest receptor change identifiable in estrogen responsive breast cancer. The view that early onset breast cancer is a failure in immune surveillance and not necessarily related to TGFβ provides a new focus for genetic screening and other diagnostic tools.

Prior to the present invention, there has been no report linking the inhibitory effects of TGFβ with the inhibitory effects of the secretory immunoglobulins. It has been reported that TGFβ is an immune modulator (Palladino M A et al. (1990) *Ann NY Acad Sci* 593, 181-187; Letterio J J and Roberts A B (1998) *Annu Rev Immunol* 16, 137-161). It is a member of the cytokine family, and as such has effects on cells of the immune system. It is known that TGFβ has bifunctional effects on mucosal IgA responses (Chen S-S and Li Q (1990) *Cell Immunol* 128, 353-361) and inhibits IgG, IgM and IgA production by human lymphocytes (van den Wall Bake A W et al. (1992) *Cell Immunol* 144, 417-428). The discovery of the growth-regulating role of the immunoglobulins places the complex effects of TGFβ in a new perspective. Increased TGFβ production can lead to suppression of the immunoglobulins and therefore positive growth effects on breast cancer cell growth. In the past other investigators have noted a positive effect of TGFβ on breast cancer cell growth under some circumstances, but had no explanation for this observation (Arteaga C L et al. (1996) *Breast Cancer Res Treat* 38, 49-56). The results herein now suggest a mechanism for TGFβ positive effects on breast cancer cell growth. Overproduction of TGFβ is a potential issue that is pertinent to the growth of estrogen responsive breast cancers.

Example 28

Windows of Breast Susceptibility to Carcinogenesis and Mutation and the Levels of Immunoglobulin Inhibitors In this Example, age-related changes (i.e. a reduction) in immunoglobulin concentrations in the plasma of rats are correlated with carcinogenesis of the mammary gland.

"Windows" and Breast Cancer. Mutations leading to breast cancer may occur early in life, during puberty and young adulthood, and control of DNA synthesis by IgA/IgM during this critical period may attenuate the action of carcinogens and reduce the risk of breast cancer later in life (Marshall E (1993) *Science* (Wash D.C.) 259, 618-621). Human female breast cancer incidence rates increase dramatically after age 50 and now approach one in ten by age 75. The existing data suggest that the causal mutations most likely occur at earlier ages. In view of the fact that milk/breast secretions decrease dramatically after menopause, it remains to be determined whether mutations can arise later in life due to the natural age-related reduction in the growth inhibitory function of the secretory immune system IgA and IgM. An entirely new approach to the prevention of breast cancer is proposed, which includes administering IgA and IgM to young female rats, initially, to diminish the effects of carcinogens by IgA/IgM control of DNA synthesis. These treatments are then followed by oral "immunizations" to increase the natural levels of immunoglobulin secreting B-cells within the mammary tissue. This new oral immunization plan is the first attempt to prevent breast cancer by this strategy by enhancing immune surveillance in the individual.

Entry into Phase II—in vivo Studies with Rats. The studies described hereinabove were performed in cell culture, and constitute the Phase I studies. That work employed well-established in vitro cell culture models recognized generally to yield physiologically relevant information. Following the in vitro studies, is Phase II, using animal models to further define the role of the secretory immune system in breast cancer etiology and growth in vivo.

Mammary Carcinogenesis Literature Background. Mammary carcinogenesis in female rodents is most effective during the developmental period that spans early puberty through early young adulthood (Welsch C W (1985) *Cancer Res* 45, 3415-3443; Huggins C et al. (1961) *Nature* (Lond) 189, 204-207; Janns D H and Hadaway E I (1977) *Proc Am Assoc Cancer Res* 18, 208; Moon R C (1969) *Int J Cancer* 4, 312-317; Russo J and Russo I H (1978) *J Natl Cancer Inst* 61, 1451-1459; Dao T L (1969) *Science* (Wash D.C.) 165, 810-811; Meranze D R et al. (1969) *Int J Cancer* 4, 480-486; Haslam S Z (1979) *Int J Cancer* 23, 374-379; Russo J et al. (1979) *Am J Pathol* 96, 721-736; Gullino P M et al. (1975) *J Natl Cancer Inst* 54, 401-414; Grubbs C J et al. (1983) *J Natl Cancer Inst* 70, 209-212). Single challenges with mammary specific carcinogens during this time cause tumors in the majority of animals within one year. Similar challenges later during adulthood are far less effective. The results of a typical carcinogen experiment with female rats are shown in FIG. 124. Those results show the effects of 3-methylcholanthrene (3MCA) and dimethylbenz[a]anthracene (DMBA). Both carcinogens are commonly used to induce hormone responsive rat mammary tumors. Carcinogenesis is most effective between the ages of 30 days and 100 days, and far less effective in rats beyond 150 days. These data support the conclusion that a "window" exists during which mutations can be induced that lead to breast cancer later in life. There is a strong correlation of this "window" to the timing of "terminal end bud" development in the breast tissue of female rats (Russo I H and Russo J (1978) *J Natl Cancer Inst* 61, 1439-1449). The age relatedness of carcinogenesis in rat mammary gland is paralleled in rat ovary and rat prostate.

There is an expanding body of evidence that indicates that there is a "window" in human females in which the breast is more susceptible to cancer causing changes than at other times in life (Bhatia S et al. (1996) *New Eng J Med* 334, 745-793; Boice J D and Monson R R (77) *New Eng J Med* 59, 823-832; McGregor D H et al. (1977) *J Natl Cancer Inst* 59, 799-811; Kaste S C et al. (1998) *Cancer* 82, 784-792; Boice J D (1996) *Med Pediatr Oncol* (Supplement 1), 29-34; Cook K L et al. (1990) *AJR Am J Roentgenol* 155, 39-42; Beaty O III et al. (1995) *J Clin Oncol* 13, 603-609; Shapiro C L and Mauch P M (1992) [Editorial] *J Clin Oncol* 10, 1662-1665). Exposure of 10 to 19 year old human females to ionizing radiation or chemical mutagens (e.g. atomic bomb survivors and patients treated by chemotherapy and radiation for Hodgkin's disease and other cancers) leads to higher than expected breast cancer rates later in life. Similar exposures of adult human females were far less deleterious. The explanation for these observations is the fact that mammary gland DNA synthesis increases during puberty and young adulthood is due to the onset of the differentiation program (Russo J et al. (1982) *Breast Cancer Res Treat* 2, 5-73) and sex hormone secretion. As gland terminal end buds develop, they are the sites for mutagenesis (Russo J et al. (1982) *Breast Cancer Res Treat* 2, 5-73). Clearly, DNA synthesis is required for carcinogenesis of mammary gland (Welsch C W (1985) *Cancer Res* 45, 3415-3443; Gullino P M et al. (1975) *J Natl Cancer Inst* 54, 401-414; Grubbs C J et al. (1983) *J Natl Cancer Inst* 70, 209-212; Dao T L (1962) *Cancer Res* 22, 973-981; Dao T L and Sunderland J (1959) *J Natl Cancer Inst* 23, 567-581; Dao T L (1981) *Banbury Report* 8, 281-298; Huggins C et al. (1959) *J Exptl Med* 109, 2542; Nagasawa H and Yanai R (1974) *J Natl Cancer Inst* 52, 609-610; Sinha D K and Dao T L (1980) *J Natl Cancer Inst* 64, 519-521; Sinha D K and Pazik J E (1981) *Int J Cancer* 27, 807-810). It is now proposed that this carcinogenesis timing may be due to changes in the secretory immune system negative regulation during this critical "window" period.

Correlation of Immunoglobulin Concentrations and Carcinogenesis in Rat Mammary Gland. Studies were conducted to demonstrate for the first time that the period of maximum sensitivity of the mammary gland to carcinogenesis correlates with times of lowest IgG, IgA and IgM concentrations in the plasma of female Sprague-Dawley (S-D)-rats. Because all three immunoglobulin classes are believed to inhibit normal mammary cell replication (TABLE 12), an antibody was selected that would identify all three classes of immunoglobulins. This choice was rabbit anti-human SHBG, which recognizes the three classes of rat Ig that are of interest (FIG. 66). Before initiating these studies, two control studies were done to ensure that the anti-SHBG obtained from a commercial source (Accurate) effectively recognized all of the growth inhibiting activity in serum.

Immunoprecipitation of the Estrogenic Activity in CDE-horse Serum and CDE-rat Serum. The addition of various dilutions of anti-human SHBG to horse serum effectively reduced the estrogenic activity of this serum (FIG. 125). The experiments were performed by incubation of the serum with the designated dilution of antiserum followed by addition of immobilized protein A/G to absorb the rabbit antibody complexes. Each assay started with 40% CDE-horse serum. Addition of antibody progressively reduced the estrogenic effect. The results in FIG. 125 show that this was due to a removal of the inhibitor. A similar analysis was repeated with CDE-rat serum from adult animals >270 days of age. The results are shown in FIG. 126. Anti-SHBG effectively neutralized the estrogen reversible inhibitor in serum. Additionally, the studies herein have demonstrated that the active fraction containing the growth regulating activity binds sex steroid hormones. To further verify that anti-SHBG was an appropriate antibody, the experiments shown on FIG. 127 were performed. The specific binding of $^3$H-DHT to the serum was measured as described (Mickelson K E and Petra P H (1974) *FEBS Lett* 44, 34-38), followed by addition of anti-human SHBG and immunoabsorption with protein A/G. The anti-serum neutralized the labeled steroid hormone binding in both rat and horse serum.

Immunoglobulins in the Serum of Female Rats from Various Age Groups. FIG. 128 shows that the serum content of the immunoglobulins varied versus age, as determined by Western analysis. FIG. 128 also shows the densitometry of the Western results with each age group. Initially at 20 to 21 days of age (i.e. weaning), the Ig concentrations were at adult levels. IgG is high immediately after weaning because of gut absorption and placental transfer from mother's milk. Between days 34 and 60, the concentrations of total immunoglobulins (i.e. IgG, IgA and IgM) fell by 80%. Estrus begins gradually, but is active by day 41 and reaches full adult expression by 120 days (Döhler K D and Wuttke W (1975) *Endocrinology* 97, 898-907; Ojeda S R et al. (1976) *Endocrinology* 98, 630-638; Döhler K D and Wuttke W (1974) *Endocrinology* 94, 1003-1008). At 120 days, the immunoglobulin content of the serum was again substantially increased. The content was even higher in multiparous retired breeders of >250 days age. Comparison of the results in FIG. 128 with those in FIG. 124 indicates that immunoglobulin levels are lowest in rats when carcinogens are most effective. Notably, IgA levels in human females are low during childhood and early adolescence, and reach adult concentrations only after 16+ years (Leffell M S et al. (1997) *Handbook of human Immunology*, CRC Press, Boca Raton, pp 86-90). These observations suggest that rat and human females have the same "window" with regard to Ig including IgG, IgA and IgM. This set of facts are also addressed in examples that follow.

Discussion of Example 28. This is the first study to correlate changes (i.e. a reduction) in immunoglobulin concentrations in plasma with carcinogenesis of the mammary gland. Continuing Phase II studies will include an animal testing program to define the specific inhibitory roles of IgG, IgA and IgM in mammary gland growth in vivo.

This study has additional implications. It is well known that mammary gland of multiparous females is resistant to carcinogenesis. In fact, longer-term nursing significantly reduces the risk of breast cancer. It is also well known that the hormonal environment that accompanies nursing establishes the secretory immune system in breast. The studies herein lead to the concept that female hormones or other developmental changes increase the content of the secretory system including B cells in breast tissue. This implies that hormone therapies must be examined for effects on the secretory system content of breast. This in turn can be used to develop new agents and drugs that increase content, and hence reduce the susceptibility of breast to carcinogens or any of many other potential mutation causing agents or effects. Further studies are directed at addressing this issue using carcinogen sensitive adolescent female rats, as well as sexually mature females and multiparous females, both of which are more carcinogen resistant than the younger females (Moon R C (1969) *Int J Cancer* 4, 312-317; Russo J and Russo I H (1978) *J Natl Cancer Inst* 61, 1451-1459; Dao T L et al. (1960) *J Natl Cancer Inst* 25, 991-1003). The rat mammary tumor model was chosen because of the large carcinogenesis data base available (Welsch C W (1985) *Cancer Res* 45, 3415-3443; Huggins C et al. (1961) *Nature* (Lond) 189, 204-207; Janns D H and Hadaway E I (1977) *Proc Am Assoc Cancer Res* 18, 208; Moon R C (1969) *Int J Cancer* 4, 312-317; Russo J and Russo III (1978) *J Natl Cancer Inst* 61, 1451-1459; Dao T L (1969) *Science* (Wash D.C.) 165, 810-811; Meranze D R et al. (1969) *Int J Cancer* 448-486; Haslam S Z (1979) *Int J Cancer*

23, 374-379; Russo J et al. (1979) *Am J Pathol* 96, 721-736; Gullino P M et al. (1975) *J Natl Cancer Inst* 544-1414; Grubbs C J et al. (1983) *J Natl Cancer Inst* 70, 209-212), and the abundance of applicable methodologies. Also, there is convincing evidence that carcinogen induced rat mammary cancers are histologically similar to those of human breast (Russo J and Russo I H (1978) *J Natl Cancer Inst* 61, 1451-1459; Russo J et al. (1982) *Breast Cancer Res Treat* 2, 5-73; Dao T L (1964) *Prog Exp Tumor Res* 5, 157-216; Russo J et al. (1977) *J Natl Cancer Inst* 59, 435-445; Murad T and vov Haam E (1972) *Cancer Res* 32, 1404-1415). Additionally, environmentally relevant carcinogens (El-Bayoumy K (1992) *Chemical Research Toxicology* 5, 585-590; Wakabayashi K et al (1992) *Cancer Res Supplement* 52, 20922-2098s; El-Bayoumy K et al. (1995) *Carcinogenesis* 16, 431-434) were selected for testing the inhibitory roles of IgG, IgA and IgM in attenuating carcinogenic effects. It is noteworthy that lipophilic polycyclic hydrocarbons such as DMBA and 3MCA and the soluble alkylating agent NMU effectively transform mammary tissue with single doses (Welsch C W (1985) *Cancer Res* 45, 3415-3443; Huggins C et al. (1961) *Nature* (Lond) 189, 204-207; Janns D H and Hadaway E I (1977) *Proc Am Assoc Cancer Res* 18, 208; Moon R C (1969) *Int J Cancer* 4, 312-317; Russo J and Russo I H (1978) *J Natl Cancer Inst* 61, 1451-1459; Dao T L (1969) *Science* (Wash D.C.) 165, 810-811; Meranze D R et al. (1969) *Int J Cancer* 4, 480-486; Haslam S Z (1979) *Int J Cancer* 23, 374-379; Russo J et al. (1979) *Am J Pathol* 96, 721-736; Gullino P M et al. (1975) *J Natl Cancer Inst* 54, 401-414; Grubbs C J et al. (1983) *J Natl Cancer Inst* 70, 209-212) but are not found in our environment (El-Bayoumy K (1992) *Chemical Research Toxicology* 5, 585-590; Wakabayashi K et al (1992) *Cancer Res Supplement* 52, 20922-2098s; El-Bayoumy K et al. (1995) *Carcinogenesis* 16, 431-434). NMU has been excluded from these studies because it causes specific changes in the ras proto-oncogene (Sukumar S et al. (1983) *Nature* (Lond) 305, 658-661; Zarbl H et al. (1985) *Nature* (Lond) 315, 382-385) which are not common in human breast cancers. It has been previously suggested that as many as 80 or 90% of human breast cancers are caused by environmental carcinogens (Higginson J (1972) In: *Environment and Cancer: 24th Symposium on Fundamental Cancer Research*, Williams and Wilkins, Baltimore, pp 69-92; Haenszel W and Kurihara M (1968) *J Natl Cancer Inst* 40, 43-68). To date, however, this remains to be established.

In this series of studies, DNA synthesis will be monitored in the age groups spanning 20 days to 270 days. When the period of maximum DNA synthesis is identified, IgA and IgM compositions will be administered, as injections, to suppress DNA synthesis during this time. After an effective immunoglobulin dose is found, the appropriate age group will be treated with IgA/IgM and the effects on carcinogenesis assessed versus control animals. The expected result is that carcinogens will be less effective in those rats receiving DNA synthesis inhibiting doses of IgA/IgM. In another series of studies, conditions for increasing B-cell populations in breast tissue will be determined. To begin, B cell content of mammary tissue will be monitored as a function of age. This control study will then be correlated with the time period of maximum DNA synthesis. It is expected that the content of B cells will be low in those age groups showing a maximum DNA synthesis rate. Next, using oral challenges, it will be determined what is the most effective "immunogen" to induce an increase in B cells in mammary tissue. The end point of these studies will be to induce sufficient numbers of B cells to prevent the "window" increase in DNA synthesis. When conditions have been established to prevent this rise, the animal will be treated with carcinogens and monitored for tumor development and survival. This study is expected to provide Phase II evidence supporting an oral "immunization" to reduce the effectiveness of carcinogens.

Other ongoing studies will include disruption of the function of the secretory immune system in adult and multiparous female rats to determine if they become more sensitive to carcinogens. Virgin females of 114 days or older will be studied as will breeders of more than 250 days age. These animals will be treated with antibody against the poly-Ig receptor. The doses of antiserum to disrupt the secretory immune system will be established by monitoring IgA/IgM secretion into bile, uterine fluids and breast milk. Also, mammary DNA synthesis will be monitored. When secretion has been blocked effectively, susceptibility to carcinogens will be explored. It is expected that the disruption of the interaction of IgA/IgM with the poly-Ig receptor will increase DNA synthesis in the mammary gland and therefore increase susceptibility to carcinogens. Other ongoing work will determine if mutations leading to breast cancer occur early in life during puberty and young adulthood and whether control of DNA synthesis by IgA/IgM during this critical period will attenuate the action of carcinogens and reduce the risk of breast cancer later in life.

Example 29

Risk Factors: IgA/IgM Based Test to Detect Lowered Levels of Steroid Hormone Reversible Cell Growth Inhibitors in Plasma or Body Secretions IgA/IgM and Cancer Susceptibility. Toward identifying individuals with high susceptibility to breast cancer or prostate cancer, the level of the inhibitory form of IgA (i.e., IgA dimer) will be measured in an individual's plasma, or the secretory IgA and polymeric IgM will be measured in a bodily secretion. Decreases in plasma levels of IgA or decreased secretory capacity into milk or structural alterations in IgA may confer greater susceptibility to breast cancer. Levels are expected to be low in susceptible individuals and to fall with increasing age in normal individuals, substantially mirroring the age distribution pattern associated with breast and prostate cancer incidence. One way to assay for the dimeric/polymeric form of IgA is via a conventional antibody binding test using antibody raised against the D5 domain disulfide regions with IgA attached. In secretory fluids, direct measure of sIgA can be done along with a measure of secretory component by radioimmunoassay or other methods using enzyme linked immunosorbent assay (ELISA) or biotin-avidin technology, each of which are well known in the art and have been described in the literature. The levels of IgM can be measured directly although their levels are more subject to wide variations. Also, "J" chain can be measured, but only in samples treated to remove the free (unbound) form known to be in plasma.

Secretory Immune System Status Test. Another informative test process will be to use rectal or nasal passage antigen challenge and then measure the appearance of the specific antibody against the antigen in plasma and secretory fluids, using standard high capacity clinical test methods. This will directly measure the immune status of the individual. Those with optimum capacity can be separated from individuals with impaired secretory immune system function. Impaired function of the secretory immune system may indicate susceptibility to cancer.

Cell Growth Testing for Inhibitors. In those cases where direct assessment of inhibitor in fluids is required, these can also be measured by cell growth assays on reduced microwell scale using automated colorimetric assays. The testing is carried out by first treating a plasma specimen to deplete or substantially remove the steroid hormone content without inactivating or removing the endogenous poly IgA dimer and poly IgM molecules. The hormone depleted specimen is then tested for cell growth inhibitory activity in the presence of added steroid hormone in an in vitro assay employing cultured tumor cells incubated in a defined serum-free medium. Procedures for preparing the steroid hormone depleted plasma or serum and for conducting the assay are described in preceding examples and in U.S. patent application Ser. No. 09/854,958/PCT/US2001/15183 entitled "Compositions and Methods for Demonstrating Secretory Immune System Regulation of Steroid Hormone Responsive Cancer Cell Growth," hereby incorporated herein by reference. Application of the XAD-4™ resin treatment is preferred for small samples. These extraction methods are capable of yielding steroid hormone depleted serum that allows identification of 30 to 100-fold estrogen and androgen growth effects (cell number measurement) in culture in 7 to 14 days with human breast and human prostate cancer cells, as well at rat mammary, rat pituitary and Syrian hamster kidney tumor cells.

Comparison of in vitro and in vivo. The results are compared to similar tests using positive and negative control plasmas or serums, which have defined levels of IgA dimer and poly IgM. In this way the tumor cell growth inhibitory activity of the individual's plasma is measured. Because the in vitro assay system employs a cell line that forms breast or prostate tumors when implanted in vivo, the in vitro assay results are believed to be suggestive of the in vivo condition of the individual.

Discussion of Example 29. Rats and humans process plasma and locally produced IgA very differently. This topic is covered in detail (Conley M E and Delacroix D L (1987) *Ann Internal Medicine* 106, 892-899). In rat, pIgA equilibrates with locally produced IgA and is therefore a major source of the immunoglobulin found in secretions. This means the IgA from plasma readily leaves this compartment to arrive at mucosal surfaces and be transported by the poly-Ig receptor into the lumen of mucosal tissues or into secretions such as bile. This physiology makes the rat a very useful experimental tool to determine some of the cancer related effects of IgA and IgM. However, caution is necessary when extrapolating rat results to humans (Conley M E and Delacroix D L (1987) *Ann Internal Medicine* 106, 892-899). Human plasma IgA (pIgA) does not appear to be as available to local tissues for secretion. Indeed, only a small fraction of the secreted IgA in humans comes from plasma IgA. The vast majority arises locally in mucosal tissues from B cells located there and functioning on site. In light of this difference between rat and human IgA processing, measurement of IgA in the plasma is best approached from the IgA deficiency perspective described below. Measurement of the capacity of the secretory immune system in all subjects by direct measurement in fluids (e.g. breast fluid, saliva, tears, seminal fluid, bile or vaginal washes) is preferred.

One of the best approaches to measurement of secretory immunoglobulins in small volumes of body fluids is to challenge with an antigen to which different low molecular weight haptens are conjugated by standard chemistry now well known and very widely applied. Haptens are conjugated to common non-antigenic proteins and identified by measuring the appearance of anti-hapten immunoglobulins in the secretory fluids. By changing haptens, this test can be administered many times over a period of years.

Example 30

Risk Factors: IgA Deficiencies and Malignancies

In this Example, measurement of plasma IgA levels are correlated to increased incidence of mucosal cancers. IgA deficiency is the most common primary immunodeficiency encountered in man (Schaffer F M et al. (1991) 3, 15-44). It is very heterogeneous and is associated with infections, allergies, autoimmune disorders, gastrointestinal disease and genetic disorders. An overview of immunodeficiency-associated cancer has been presented (Beral V and Newton R (1998) *J Natl Cancer Inst Monograph* 23, 1-6). Breast cancer risk or incidence was not considered specifically. Other reports have related this deficiency to abdominal T-cell non-Hodgkin's lymphoma (Ott M M et al. (1998) *Am J Surg Pathol* 22, 500-506; Zenone T et al. (1996) *J Intern Med* 240, 99-102; Filipovich A H et al. (1994) *Immunodeficiency* 5, 91-112) and other malignancies (Pongracz K et al. (1994) *Orv Hetil* 135, 2863-2866). One of the most significant aspects of these reports is the correlation to gastric lymphoma that is currently thought to originate from a bacterial cause. Again, breast cancer and several other mucosal cancers were either not considered or were discussed not considered specifically (Butler J E and Oskvig R (1974) *Nature* (Lond) 249, 830-833). Other than the well-known relationship between ataxia telangiectasia with its characteristic IgA deficiency, and breast cancer, there are no other studies of this issue known to the inventor. This fact also extends to prostate cancers and IgA deficiencies. Measurement of plasma IgA as a measure of propensity to develop breast, prostate and other mucosal cancers is believed to be applicable for conducting widespread screening programs.

IgM Compensation for IgA Deficiency. It is of interest to note that IgA deficiency is accompanied by a compensatory increase in IgM (Brandtzaeg P et al. (1968) *Science* (Wash D.C.) 160, 789-791). Analysis of milk from IgA deficient women indicates substantial increases in IgG subclasses and IgM (Hahn-Zoric M et al. (1997) *Pediatr Allergy Immunol* 8, 127-133; Thom H et al. (1994) *Acata Paediatr* 83, 687-691). In combined deficiency patients, IgM levels rise sufficiently to cause IgM nephropathy (Oymak O (1997) *Clin Nephrol* 47, 202-203). Measurement of plasma IgA, as a tool to determine predisposition to breast cancer, can be accomplished by standard clinical assays with high specificity antibodies to human IgA, prepared according to methods known to those skilled in the art. IgM levels can be measured similarly.

Example 31

Risk Factors: Autoimmunity Test for Anti-IgA and IgM in Plasma

Methods and immunoglobulin inhibitors described in preceding examples are useful for conducting studies to identify factors that are capable of neutralizing the IgA/IgM inhibitory effects on cancer cell growth.

General Applicability. IgA and IgM are estrogen reversible inhibitors of $ER^+$ breast cancer cell growth in the classical sense of the long sought after chalones. They arrest cell growth and are readily reversed within one week in culture and appear to be mucous epithelial cell specific in function. These results may have implications for epithelial cancers beyond those of breast.

Auto-Antibody Properties and Source. Anti-IgA antibodies purified from normal female plasma will be tested to determine if they neutralize IgA as a negative growth regulator for breast cancer cells in serum-free defined culture, employing the cell growth assay procedures described hereinabove. These immunoglobulins will be isolated by standard methods in the literature and their class and subclass determined. They will be fragmented to determine if activity resides in the Fab component, as expected in view of the results described in preceding Examples. Specific blocking monoclonal antibodies will be raised against the active component to permit measurement in the serum of females. The purpose of this test is to determine if an autoimmune mechanism can abrogate the negative IgA growth regulation exerted on estrogen responsive breast cancer cells. Such studies will assist in identifying new factors involved in breast cancer etiology. To date, autoimmunity has not been given significant attention with this disease. This study is expected to reopen consideration of autoimmunity and breast cancer, and a similar approach is applicable to prostate, colon and other mucosal cancers.

Autoimmunity and Cancer. The concept that autoimmune mechanisms are involved in cancer development is not new. However, the present findings showing a direct cell growth modulating role for the secretory immune system is totally new. It has been reported that serum from 26 (all) normal volunteers had anti-IgA antibodies of the IgG and IgM classes (Jackson S et al. (1987) *J Immunol* 138, 2244-2248). They were purified and were directed against both polymeric and monomeric IgA1 and IgA 2 containing the light chains (Fab fragments). Plasma samples will be used to purify similar antibodies, as described above, except in this case, with the goal of isolation of Fc directed antibodies. The purified antibodies will be identified by class and fragmented into Fe and Fab portions. The anti-IgA antibodies will be assessed for their ability to block the action of IgA as an ER$^+$ breast cancer cell growth mediator as described (Sato J D et al. (1987) *Methods Enzymol* 146, 63-82; Arteaga C L et al. (1988) *Mol Endocrinol* 2, 1064-1069; Sato J D et al. (1983) *Mol Biol Med* 1:511-529; Gill G et al. (1984) *J Biol Chem* 259, 7755-7760). Those that prove effective will be used to raise specific monoclonal antibodies as described (Barret C H (1994) Hybridomas and monoclonal antibodies, In: *Antibody Techniques*, Malik V S & Lillehoj E P, Eds, Acadmemic Press, San Diego, pp 71-102). After confirming by double diffusion tests and other analyses that the monoclonal antibody recognizes only the appropriate anti-IgA in serum, a RIA will be developed for quantification of serum samples (Lauritzen E et al. (1994) In: *Antibody Techniques*, Malik V S & Lillehoj E P, Eds, Academic Press, San Diego, pp 227-258). To establish a control baseline, groups of 100 female serum samples will be obtained and assays done to establish a basal "normal" range for the blocking anti-IgA antibody. The age and hormonal status of the women donors will be determined. This will identify a pattern of age differences should they occur. The effects of estrogen containing contraceptives and estrogen replacement therapy will be evaluated. This is especially valuable information because breast cancer occurrence is highly age dependent. Although a naturally occurring antibody has not yet been identified that can directly block the growth regulating effect of IgA, its identification will provide a new tool to measure breast cancer risk and risk for other mucosal cancers. This study makes use of several of the methods and compositions described hereinabove, including immunoglobulin inhibitors compositions, assay methods, defined media and model cell lines.

Autoimmune Antibodies. Alternatively, or additionally, plasma and bodily fluids may be monitored for autoimmune antibodies that block the inhibitory action of IgA and IgM. An expected increase in autoimmune antibodies with increasing age is expected to coincide with increased cancer incidence, or the incidence of cancer may be high in individuals with early onset disease.

Example 32

Diagnostic and Prognostic Tools: Estrogen Receptor γ (ERγ)

In this Example, a new estrogen receptor is identified and its role in estrogen responsive cell growth is described. Use of the new ERγ as an additional or replacement for ERα in gene screening procedures is also discussed.

ERα as the Basis for Most ER Analyses of Breast Cancer Specimens. In preceding Examples, a new estrogen receptor has been proposed that regulates estrogen responsive target tumor cell growth. The measurement of this new receptor as a diagnostic and prognostic tool has great clinical consequences. Currently, throughout the world, the measurement of the known estrogen receptor a (ERα) is accepted as the standard for determining whether a breast cancer is estrogen sensitive or estrogen insensitive (Henderson I C and Patek A J (1998) *Breast Cancer Res Treat* 52, 261-288; Osborne C K (1998) *Breast Cancer Res Treat* 51, 227-238; Kaufmann M (1996) *Recent Results Cancer Res* 140, 77-87; Allred D C et al. (1998) *Mod Pathol* 11, 155-168).

Candidates for the ERγ. It has been reported that a point mutation in ERα causes it to become hypersensitive to estrogens (Lemieux P and Fuqua S (1996) *J Steroid Biochem Mol Biol* 56, 87-91). The point mutation is located in the hormone-binding domain. Growth of the human MCF-7 breast cancer cells transfected with this point mutation ERα variant is stimulated by $10^{-12}$ to $10^{-11}$ M E$_2$ (Fuqua S A et al. (2000) *Cancer Res* 59, 5425-5428). Those investigators proposed that this variant is a point mutation in the ERα that occurs in premalignant breast tissue lesions. They did not suggest that it is the growth regulating form of the ER that occurs naturally in all target cells. It should be noted that in the preceding examples, dose-response data have been presented with many cell lines of both rodent and human origins. In every case, the concentration that caused growth was well below the affinity constant of the standard ERα. This plainly raises a question about the point mutation variant. It must be common to every cell type in this disclosure as evidenced by the information placed in TABLE 1, TABLE 4 and TABLE 10 and the estrogen dose-response data shown in FIG. 3 (MTW9/PL2 cells), FIG. 10 (T47D cells), FIG. 11 (GH$_4$C$_1$ cells), FIG. 12 (H301 cells), FIG. 23B (MCF-7K, T47D and MTW9/PL2 cells), FIG. 92 (MCF-7K cells) and FIG. 100 (T47D cells). To emphasize again, for this point mutation variant to explain all of the data herein, it must be present in every cell line used in this disclosure. Furthermore, the investigators identifying the point mutation variant made the statement that MCF-7 cells had to be transfected with this variant to become sensitive to one to ten picomolar concentrations of E$_2$. The results of the studies herein show, however, that this is simply not the case with MCF-7 cells (FIG. 97) or any of the other cell lines studied. The cells are already sensitive to one picomolar estrogen without any such transfection.

Search for Point Mutation Variant in the Cell Lines Used in This Disclosure. PCR will be used to search for the point mutation variant in the cell lines listed in TABLE 1. This will provide a definite answer to the question of physiological significance. Two outcomes appear most probable. First, the point mutation receptor is found in all of the cell lines. If so, it will be cloned and transfected into ER⁻ cells to determine if this reestablishes high sensitivity estrogen responsiveness, as measured in the cell growth assays described in preceding Examples. Second, if the point mutation is not found in all of the lines, it will indicate that the original authors were correct in their interpretation that this variant of the ERα receptor is characteristic of some premalignant breast cancer lesions and not of more general significance. In this case, the above-described differential display methods will be continued to identify the ERγ. The general domains and functions for each domain of ERα are shown in FIG. 129. ERγ is expected to be homologous to ERα but to have changes in the hormone-binding domain and possibly in the transacting function and DNA binding domains because of activation of growth related genes instead of the genes activated by ERα.

Applications of ERγ. The newly identified ERγ will be used in conjunction with or as a replacement for the current ERα as described above in the various clinical applications in use today for the diagnosis and prognostic evaluation of breast and other mucosal cancers.

Antagonists of the ERγ. The action of tamoxifen as an antagonist of the ERγ will find use in the evaluation and treatment of estrogen responsive cancers. Better treatment regimes employing tamoxifen can be devised because the clinician can now be better informed about the possible effects of the drug. Development of more effective or specific antagonists will be sought using the recombinant form of the ERγ expressed in estrogen insensitive cells and in extracts of cells expression the transfected receptor.

Example 33

Diagnostic, Prognostic and Treatment Decision Tools: Poly-Ig Receptor (or the Poly-Ig like Receptor)

Definition of the Poly-Ig Receptor. In this Example, the poly-Ig receptor designation is intended to include the authentic poly Ig receptor as defined (Krajči P et al. (1992) *Eur J Immunol* 22, 2309-2315) or a receptor with very similar properties as described in this disclosure. The receptor that mediates the IgA/IgM cell growth inhibitory effect is likely located on chromosome 1, as described below, although it is to some extent possible that it is located on another chromosome but still is a poly-Ig like receptor with the characteristics outlined in this disclosure.

Diagnostic, Prognostic and Treatment Mode Uses of the Poly-Ig-receptor. Breast cancer and other mucosal cancer specimens, including those from prostate, colon, ovary, uterus, cervix, vagina, kidney and bladder, will be assessed for the presence of ERα and/or ERγ and for the poly-Ig receptor. The cell surface receptor is preferably located and quantified by fluorescence immunohistochemistry after an appropriate fixation (Brandtzaeg P and Rognum T O (1984) *Path Res Pract* 179, 250-266) or by radioimmunoassay as described for other surface receptors (Tonik S E and Sussman H-H (1987) *Methods Enzymol* 147, 253-265). Monoclonal antibodies against the whole poly-Ig receptor, the secretory component or specific domains can also be used to quantify the receptor (Trowbridge I S et al. (1987) *Methods Enzymol* 147, 265-279). A variety of new enzyme-linked immunosorbant assays (ELISA) are also available and can be applied at very high sensitivity based on biotin-avidin or chemiluminescence technology. The particular method to be applied will be dictated by the types of specimens supplied.

Applications of Poly-Ig Receptor Positive Results. Cancer specimens expressing high levels of poly-Ig receptor and the ER are likely highly differentiated tumors for which there are treatment options. The prognosis for these tumors is thought to be very good provided the cancer has not moved to new locations. However, metastases are a definite negative prognostic indicator. These tumor foci can be treated with a combination of tamoxifen and immunotherapy either as delivered intravenous immunoglobulins or by a natural boosting mechanism via "oral immunization" to be discussed below. Long-term exposure to both tamoxifen and IgA/IgM is a new non-toxic approach to treating disseminated cancer. Currently, disseminated breast (and other) cancers are treated by chemotherapy or possibly with radiation.

Applications of Poly-Ig Receptor Negative Results. Cancers not expressing the poly-Ig receptor must still be assessed for ER and the progesterone receptor. If ER positive, an appropriate treatment option is tamoxifen or adjuvant chemotherapy. Even though tamoxifen has activity mimicking the immune system inhibitors, it also has activity against the ER (which accounts for its classification as a "mixed" antiestrogen). Immunotherapy will not be effective with these tumors. Cancers that are both poly-Ig receptor negative and ER negative are expected to have poor prognosis. The best treatment options currently are limited to chemotherapy or in some cases therapy with monoclonal anti-HER/NEU. This latter treatment has proven to be of limited application.

Clinical Studies of Secretory Component (Poly-Ig Receptor) Expression in Colon and Breast Cancer. Others have conducted a study of the protein and mRNA expression of the poly-Ig receptor has been done with a sample of human colon cancers (Krajči P et al. (1996) *Br J Cancer* 73, 1503-1510). In that study, expression of secretory component was found in 33 colorectal adenomas (31 patients) and in 19 colorectal carcinomas from 19 patients. Although the study provides evidence that colon adenomas (i.e. a predisposition to colon cancer) and confirmed cancers express poly-Ig receptor, the investigators did not attempt to translate the observations further to than to propose a role in "cellular dysplasia".

Likewise, the levels of secretory component were measured in breast tumors from 95 patients with primary or metastatic disease (Stem J E et al. (1985) *Cancer Immunol Immunother* 19, 226-230). The authors of that study proposed that low levels of secretory component were found in metastatic lesions and that this "could indicate a potential for secretory component/poly-Ig receptor involvement in immune regulation of tumor growth". However, neither the identification of growth effects related to the immunoglobulins IgA/IgM nor the identification of a role of the poly-Ig receptor directly was investigated. That study was also incomplete in that there was no attempt made to determine the estrogen receptor status of the primary or metastatic disease. Therefore, there was no correlation to growth state based on the most accepted criterion of steroid hormone receptor status. This line of study appears to have stopped with 1985 observation. The present series of studies has directly addressed the problem, however, by demonstrating growth regulation by the secretory immune system using several different ER⁺ cancers. These results change the context of the diagnostic analysis of secretory component or poly-Ig receptor.

Example 34

Diagnostic Tools: Monoclonal Antibodies to the Poly-Ig Receptor and Breast Cancer Imaging A two-fold approach to breast cancer imaging has been devised that includes immunoglobulin directed and poly-Ig receptor directed methods.

Current Imaging Methods. Today, X-ray mammography remains the most important method for breast cancer screening (Sabel M and Aichinger H (1966) *Physics in Medicine and Biology* 41, 315-368). Since the 1980s, ultrasound scanning has evolved as an indispensable adjunct to X-ray mammography. Other procedures such as Doppler sonography, diaphanography, contrast enhanced MRI, CT and DSA essentially depend upon the enhanced vascularity of the tumor compared to the surrounding normal tissue. In addition to those methods, computer assistance is used for signal processing which aids diagnosis by texture analysis and pattern recognition. Along with those methods, scintigraphy based on receptors located in the breast tumors has become a new non-invasive modality (Valkema R et al. (1996) *J Cancer Res Clin Oncol* 122, 513-532). The presently disclosed method depends upon expression of a specific receptor, the poly-Ig receptor, in the breast tumor. Monoclonal antibodies to the poly-Ig receptor and/or IgA or IgM (whole molecule or fragments) will be used to image breast tumors at an early stage of development.

Poly-Ig Receptor Directed Methods. Breast and prostate cancer cells bind polymeric IgA and IgM, but in contrast to normal cells, the cancer cells no longer transport the immunoglobulins because of disruption of tissue architecture and loss of baso-lateral orientation required for secretion of the immunoglobulins. As a consequence, the immunoglobulins accumulate in the cells and are partially degraded with time. When the immunoglobulins are radio labeled or contrast labeled, the markers accumulate in the cancer cells compared to the amounts in the surrounding normal cells. The cancer cells are expected to image at very early stages due to the accumulation of the tracer or contrast agent. Most breast and prostate cancers begin at the 1 to 2 mm tumor size, so imaging with the IgA/IgM/poly-Ig receptor should be very sensitive. Consequently, these methods constitute a significant improvement over existing imaging systems. Many of the limitations inherent in each imaging method outlined above will be present even with the use of IgA, IgM or poly-Ig receptor technology. Nonetheless, the knowledge base available for imaging supports the use of labeled IgA/IgM/poly-Ig receptor as an improvement because the target will be very early stage tumors readily recognized by this technology. Monoclonal antibodies will be prepared, and radio labeled or contrast labeled IgA/IgM and receptor will be prepared, using suitable conventional methods and techniques that are well known to those of skill in the art.

Example 35

Diagnostic, Prognostic and Treatment Decision Tools: Fc-Like Receptor for IgG1/IgG2

In this Example, the term "Fc-like receptor" is intended to mean a member of the Fc-superfamily of immunoglobulin-like receptors, possibly with an inhibitor ITIM motif, as described above.

Diagnostic, Prognostic and Treatment Mode Uses of the Fc-like Receptor. Of the mucosal cancers examined, evidence is presented herein for inhibitory effects of IgG on only breast and prostate cells. It is likely that IgG1 and IgG2 will have effects on other early mucosal cancers. Breast cancer and prostate cancer specimens will be assessed for the presence of ERα and/or ERγ and for the Fc-like receptor. The cell surface receptor is preferably located and quantified by fluorescence immunohistochemistry after an appropriate fixation (Brandtzaeg P and Rognum T O (1984) *Path Res Pract* 179, 250-266) or by radioimmunoassay as described for other surface receptors (Tonik S E and Sussman H H (1987) *Methods Enymol* 147, 253-265). Monoclonal antibodies against the whole receptor or specific domains can also be used to quantify the receptor (Trowbridge I S et al. (1987) *Methods Enymol* 147, 265-279). A variety of new enzyme-linked immunosorbant assays (ELISA) are also available and can be applied at very high sensitivity based on biotin-avidin or chemiluminescence technology. The method to be applied will be dictated by the types of specimens supplied.

Applications of Fc-like Receptor Positive Results. Cancer specimens expressing high levels of Fc-like receptor and the ER are likely differentiated tumors. The prognosis for these tumors is expected to be very good. These tumors can be treated with a tamoxifen and immunotherapy delivered as either intravenous immunoglobulins or by a natural boosting mechanism via "oral immunization," which is discussed in an Example that follows. Long-term exposure to both tamoxifen and IgG1κ is a new non-toxic approached to treating these cancers, as indicated by results of studies described in Examples 20 and 24, employing an in vitro model assay system that is useful as an aid for predicting in vivo effects of a given stimulus, such as a chemical of interest.

Applications of Fc-like Receptor Negative Results. Cancers not expressing the Fc-like receptor will also be assessed for ER and the progesterone receptor. If ER positive, the preferred treatment options are, for example, tamoxifen or adjuvant chemotherapy. Even though tamoxifen has activity mimicking the immune system inhibitors, it still has activity against the ER (which accounts for its classification as a "mixed" antiestrogen). Immunotherapy is not expected to be effective with these tumors. Cancers that are both Fc-like receptor negative and ER negative are expected to have poor prognosis. This diagnostic test should indicate selection of a very aggressive chemotherapy or other program.

Example 36

Diagnostic, Prognostic and Treatment Decision Tools: TGFβ Receptors

In this Example, use of TGFβ in detecting early onset breast cancer and for assessing the status of a tumor is described.

TGFβ Receptors. The TGFβ receptors to be monitored will be isoforms Type I, Type II and Type III also designated RI, RII, and RIII as described (Gobbi H et al. (1999) *J Natl Cancer Inst* 91, 2096-2101; Chakravarthy D et al. (1999) *Int J Cancer* 15, 187-194). Although breast cancers express all three forms of TGFβ receptors, only one of these (i.e. TGFβ RIII) has been localized to a "hot spot" for breast cancer on the short arm of chromosome 1 (i.e. 1p33-p32). Prior art studies of TGFβ expression in breast cancer specimens have problems based on the fact that it is not clear which cell types in the tissue in fact have the receptors. Because clinical specimens are mixtures of cells, methods should be considered that establish that the target epithelial cells are either receptor positive or negative. Immunohistochemistry of fixed tissue is the preferred method to examine this issue. Appropriate methods have been described (Gobbi H et al. (1999) *J Natl Cancer Inst* 91, 2096-2101). Based on that study (Gobbi H et al. (1999) *J Natl Cancer Inst* 91, 2096-2101), the Type II receptor is most associated with breast epithelial hyperplastic lesions that increase the risk of later development of invasive breast carcinoma. In tumor systems, Type II receptor is positively associated with TGFβ responsiveness (i.e. growth inhibition). As the matter stands however, the 3p22 loci for Type II TGFβ receptor (Mathew S et al. (1994) *Genomics* 20, 114-115) has not yet been mapped as a "hot spot" for breast cancer.

Diagnosis of Early Onset ER⁻ Breast Cancer. Early onset breast cancers can be classified by measurement of their ER content, the content of TGFβ receptors (particularly Types II and III) and the poly-Ig receptor/Fc-like receptor. Together, these assessments are expected to act as aids to define the cancer type for therapy decisions. While these cancers are expected to be TGFβ receptor positive, therapy with this 25 kDa inhibitor alone has not been effective in the past. These tumors may require aggressive treatment with available tools such as standard chemotherapy or high-dose chemotherapy coupled with bone marrow transplant.

Diagnosis of Early Onset ER⁺ Breast Cancer. However, the methods outlined above can also be used to aid in the classification of the approximately 30% of the early onset tumors that are ER⁺. These tumors are expected to be TGFβ receptor negative. Screening for poly-Ig receptors/Fc-like receptors plus the ERα or ERγ will indicate the use of the combined tamoxifen (and/or newer SERMs) and immune therapy described above. Advantages of this modality are the lack of severe side effects, as well as preservation of fertility, which is often a major consideration.

TGFβ Receptors and ER⁺ Cancers. Although this discussion has been focused on breast cancer, the same screening methods are expected to be applicable to a number of other ER⁺ types of cancers. As shown in FIG. 26, all of the ER⁺ cell lines tested appeared to be unaffected by TGFβ although data presented throughout this disclosure shows these same lines are IgA/IgM inhibited. As can best be appreciated by referring to the cancer progression model of FIG. 123, the combination of positive results with the ER (ERα or ERγ) and poly-Ig receptor (or Fc-like receptor), along with negative results for TGFβ receptor(s) is a defining pattern for the early breast cancers that will be immune system treatable.

Example 37

Ataxia Telangiectasia as an Example of a Human Genetic Disorder with High Rates of Breast Cancer Coupled with an IgA Deficiency In this Example, analogies are drawn between the characteristic IgA deficiency in the genetic disorder ataxia telangiectasia (A-T) and the role of IgA in inhibiting steroid hormone responsive cancer growth in mucosal tissues. Homozygotes have high rates of breast cancer (Olsen J H et al. (2001) *J Natl Cancer Inst* 93, 121-127; Swift M (2001) *J Natl Cancer Inst* 93, 84-85), even in males. Even heterozygotes have high breast cancer rates (Janin N et al. (1999) *Br J Cancer* 80, 1042-1045; Inskip H M et al. (1999) *Br J Cancer* 79, 1304-1307; Lavin M (1998) *Br Med J* 317, 486-487; Athrna P et al. (1996) *Cancer Genet Cytogenet* 92, 130-134; Chen J et al. (1998) *Cancer Res* 58, 1376-1379). The mutated gene is thought to code a product similar to the PI-3 kinase (Savitsky K et al. (1995) *Science* (Wash D.C.) 268, 1749-1753). However, 75% of A-T individuals have IgA absent or deficient. Studies have shown that the A-T lesion is not found in breast cancers (FitzGerald M J et al. (1997) *Nature Genet* 15, 307-310; Bebb D G et al. (1999) *Br J Cancer* 80, 1979-1981; Vorechovsky I et al. (1996) *Cancer Res* 56, 2726-2732). This has perplexed researchers and suggests that the high risk of breast cancer in A-T individuals may be due to factors other than the reported genetic lesion. Secretion of immunoglobulins by mucosal cells is certainly impaired (Bordigoni P et al. (1982) *Lancet* 2(8293), 293-297; Boder E (1975) *Birth Defects Orig Artic Ser* 11, 255-270). Very early on, clinicians noted frequent mucosal infections in A-T individuals.

Based on the results of the studies herein, which establish the role of IgA in mucosal/breast cell growth, it seems reasonable to suggest that the IgA deficiency in A-T has a direct effect on malignancy development in mucosal tissues, particularly breast. It is noteworthy that A-T has been discussed often among breast cancer researchers as a model for the etiology of this disease, and was addressed in an editorial (Swift M (2001) *J Natl Cancer Inst* 93, 84-85). Tests assessing the level and activity of IgA in an individual, according to an above-described cell growth assay method, can be useful for correlating to the presence or development of malignancy.

Example 38

Diagnostic and Predictive: Poly-Ig Receptor, the Fc-Like Receptor and TGFβ Receptors Based Genetic Screening for Breast, Prostate and other Mucosal Cancer Susceptibility The mediating receptors for IgA/IgM and IgG1 inhibition, identified as described in foregoing Examples, and the TGFβ receptor, will be useful for screening individuals for susceptibility to cancer, and for gene therapy applications to restore immune regulation in autonomous tumors.

Background Genetic Properties of the Poly-Ig Receptor. The complete genomic and cDNA sequences of the poly-Ig receptor have been determined (Krajči P et al. (1991) *Hum Genet* 87, 642-648; Krajči P et al. (1992) *Eur J Immunol* 22, 2309-2315). Poly-Ig receptor gene has been localized to chromosome 1 at 1q31-q42 locus Krajči P et al. (1991) *Hum Genet* 87, 642-648; Krajči P et al. (1992) *Eur J Immunol* 22, 2309-2315; Krajči P et al. (1995) *Adv Exp Med Biol* 371A, 617-623). The long arm of chromosome 1 had initially been described as the location of the most frequent cytogenetic abnormalities found in human breast carcinoma (Bieche I et al. (1995), *Clin Cancer Res* 1, 123-127). More recently this conclusion was modified state that distal alterations of the short arm of chromosome 1 are the most frequent cytogenetic abnormalities in human breast carcinoma (Bieche I et al. (1999) *Genes Chromosomes Cancer* 24, 255-263). The gene encoding the poly-Ig receptor is linked to D1S58 on the long arm of chromosome 1 (Krajči P et al. (1992) *Hum Genet* 90, 215-219). This locus (i.e. D1S58) is a known site for "allelic imbalances" in a remarkable 75% of all breast cancers (Loupart M-L et al. (1995) *Genes Chromosomes Cancer* 12, 16-23). Allelic imbalances include "Allelic Loss, Allelic Gain, and Imbalances". Loss of herterozygosity (LOH) is consistently high along the length of the long arm of chromosome 1 at D1S58 (i.e. 46%) in breast cancers (Loupart M-L et al. (1995) *Genes, Chromosomes & Cancer* 12, 16-23). LOH is strongly associated with development of cancer. The observations in this disclosure now bring meaning to this published observation. The report describing changes in D1S58 did not specific what gene or type of gene or function might be impaired by damage to this locus (Loupart M-L et al. (1995) *Genes, Chromosomes & Cancer* 12, 16-23). The Inventor's results indicate this "hot spot" is either the authentic poly-Ig receptor acting in its new capacity as a growth regulator, or a very closely related receptor with similar molecular weight, ligand binding and immunological properties. However, it must be recognized that the functional form of the growth regulatory receptor may arise from alternate splicing of the poly-Ig receptor gene. Alternate splicing of the poly-Ig receptor gene is known in rabbit (Deitcher D L and Mostov K E (1986) *Mol Cell Biol* 6, 2712-2715; Frutiger S (1987) *J Biol*

*Chem* 262, 1712-1715) and bovine tissue (Kulseth M A et al. (1995) *DNA Cell Biol* 14, 251-256). It has yet to be proven (or disproved) in humans. Certainly this possibility is still open with hormone responsive cancer cells. Alternately the 1q31-q41 region of chromosome 1 contains several other genes of immunological interest (Krajči P et al. (1991) *Hum Genet* 87, 642-648; Krajči P et al. (1992) *Eur J Immunol* 22, 2309-2315; Bruns G A P and Sherman S L (1989) *Cytogenet Cell Genet* 51, 67-77). As shown in FIG. 130, the locus of the poly-Ig receptor (PIGR) is distant from the major other loci for breast cancer located on chromosome 1. The Entre Genome NCBI Search listed 31 "hot spots" for mutations occurring in breast cancer specimens. None of these genes were related to the poly-Ig receptor. An expanded diagram of chromosome 1 is shown in FIG. 131. It further emphasizes the fact that the locus of the poly-Ig receptor will represent a new discovery as a breast cancer gene. There can be little doubt that the discovery herein of immune negative regulation of growth mediated by the poly-Ig receptor, or one very related, is an advance. It was arrived at not by the genetic approach described above which screens genes without regard for function, but instead by a functional approach based on the biochemical, endocrine and cell biology studies described above.

Identification of the Poly-Ig Receptor by cDNA Sequencing. Molecular cloning and cDNA sequencing of the IgA/IgM inhibition mediating receptor has been generally described in a preceding Example. Preferred ways of carrying out those procedures for identifying the poly-Ig receptor are provided next. The complete cDNA sequence of the poly-Ig receptor will be established by PCR cloning or cDNA cloning with antibody screening as described in TABLE 13. This will be done with ER$^+$ T47D human breast cancer cell lines and the LNCaP prostate cancer cell line. These lines were chosen because they express either the authentic poly-Ig receptor or one very similar as determined by antibody blocking activity (FIGS. 114 and 115). Also, by Western analysis the LNCaP cells express an anti-secretory cross-reacting band of the same molecular weight as authentic poly-Ig receptor from HT-29 cells (FIG. 116). This same technology will be used to obtain the Fc-like receptor from the same two human cancer cell lines because they were shown to be responsive to IgG1/IgG2 (FIGS. 120, 121, and 122). Two strategies appear useful for this procedure and summarized in (TABLE 13). The selection of the appropriate strategy depends upon the results of the studies outlined above. For example, if a poly-Ig like or an Fc-like receptor is sought, there is sufficient sequence data available to apply PCR cloning. If an entirely new receptor is expected from the receptor biochemistry studies, cDNA cloning will be required with antibody screening. PCR cloning will be done according to published detailed procedures (Current Protocols in Molecular Biology, Volume 3, (2000) Sections 15.6 & 15.7, cDNA Amplification Using One Sided (Anchored) PCR and Molecular Cloning of PCR Products). The cDNA cloning will be done with the Lambda TriplEx® Phagemid which gives a three fold greater chance of finding positive plaques with antibody. The complete manual for cloning and use of this vector has been obtained by Internet from ClonTech, January 1996 CLONTECHNIQUES.

TABLE 13

Molecular Cloning Strategies for the Poly-Ig Receptor and the Fc-like Receptor

| STRATEGY 1: PCR CLONING | STRATEGY 2: cDNA CLONING/ANTIBODY SCREENING |
|---|---|
| 1. Prepare poly (A)$^+$ RNA | 1. Identify inhibitory receptor blocking antibody |
| 2. Use oligo (dT) primer and RT to make cDNA | 2. Prepare poly (A)$^+$ RNA |
| 3. Use cDNA with specific primer plus oligo (dT) primer to amplify with Taq DNA Polymerase | 3. Use oligo (dT) primer and RT to make cDNA |
| 4. Amplify again with cDNA and internal primers plus oligo (dT) with Taq DNA Polymerase | 4. Methylate, make double stranded DNA |
| 5. Check size by agarose gels (single band) | 5. Select Vector (TriplEx in a kit) |
| 6. Clone into AT vector for DNA sequencing | 6. Ligate DNA into vector |
| 7. Primers selected with on-line computer assistance | 7. Introduce vector into *E. coli* |
|  | 8. Screen with blocking antibody |
|  | 9. Amplify clones for DNA sequencing |
|  | 10. Because the 5'-end may be missing, use Rapid Amplification of cDNA ends (5'-RACE) kit (Ambion) to get a full length clone. |

Receptor Identification and Chromosome Localization. The molecular cloning of both receptors will provide structural identification and determine if the poly-Ig receptor is the authentic form previously associated with only transcytosis, or whether it is an altered form. The sequencing results are expected to resolve the alternate splicing issue discussed above. If the sequence results indicate a new receptor, chromosomal localization will be done to determine if it is within the D1S58 linked locus on chromosome 1 or possibly on another chromosome. If it is located on another chromosome, this will be solid evidence of a new Ig superfamily receptor gene that negatively regulates growth. The same discussion applies to the Fc-like receptor. It is expected that the Fc-like receptor will be a new gene because of the data showing localization of the other known forms to leukocyte series cells (TABLE 11). Additionally, the amino acid sequences deduced will be used to match to known ITIMs to determine whether the inhibition regulating receptors are members of this new class of inhibitory receptors, as discussed above.

Transfection Studies to Regain Immune Regulation and Steroid Hormone Responsiveness. One ER$^-$ cell line will be selected for transfection based on Western analysis demonstrating a lack of receptor expression. Also, the DU145 cells and ALVA-41 human prostatic carcinoma cells will be used. These cell lines are AR$^+$ but are not inhibited by immunoglobulins (FIG. 117). Transfection of these cells is expected to restore IgA/IgM inhibition and possibly permit demonstration of androgen reversibility. If this is identified, it is very strong evidence for the positive/negative model proposed herein as the control mechanism for steroid hormone sensitive cells. For the transfection studies, receptor cDNA will be subcloned into a mammalian cell expression vector. A vector with a CMV promoter will be used because of its wide range of tissue expression and high levels of product. This will include a six amino acid sequence of c-myc oncogene to detect transformants. This tag will allow the laboratory to distinguish between low levels of endogenous expression and expression due to transformation. The transfections will be done with cationic detergents. This protocol will use the Green Flourescent Protein (GFP) reporter (CMV promoter) which can be visualized directly without fixation or staining. Transient expression of the receptor will be monitored for 80 hours by c-myc immunodetection. To measure the growth inhibitory effects of the IgA or IgM during this time, tritium labeled thymidine incorporation into DNA will be measured. For longer-term studies, stability-transformed cells will be selected using the antibiotic neomycin and G418. Stable transfectants will be monitored for receptor expression as described above. If stable transfectants regain immune control, this will be reasonable support for the conclusion that an effective receptor has been identified. This is an important precursor study for the use of the receptors in gene therapy of breast and prostate cancers a well as other mucosal cancers.

Site Directed Mutagenesis to Identify Critical Domains. Transfection with the tissue culture models above will be used to identify and/or confirm domains in which mutations cause loss of the receptor function. This is an important control because all genes have variations that may or may not be critical. This has certainly been true of BRCA1 (Iau P T et al. (2001) *Eur J Cancer* 37, 300-321). Standard site directed mutagenesis methods are planned to alter specific amino acids or parts or all of selected domains. These cell culture studies will be matched to the sequences being derived from non-disease females to define natural variations that have no effect versus changes that are significant. In the case of BRCA1, the presence of a specific mutation in families with breast/ovarian cancer was used as an important indication of changes that were significant (Iau P T et al. (2001) *Eur J Cancer* 37, 300-321).

Predictive Genetic Analysis: Germ Line Mutations. Women with family histories of breast cancer especially in first-degree relatives are candidates for genetic analysis of the poly-Ig receptor and/or the Fc-like receptor. These analyses will rely on the knowledge of the important domain or other mutations that have been defined by monitoring women with breast cancer versus those without disease as well as information gained above by site directed mutagenesis. The availability of a direct biological assay of receptor function versus mutation position and/or type is a distinct advantage over the situation with BRCA1 and BRCA2 (Iau P T et al. (2001) *Eur J Cancer* 37, 300-321). The methodology is well described (Malkin D et al. (1990) *Science* (Wash D.C.) 250, 1233-1238). Skin biopsy fibroblasts or blood leukocytes are extracted to obtain DNA. Using PCR, selected exons will be amplified and DNA sequenced. Multiple primers can be used to cover the whole receptor, especially if it is similar to the eleven-exon structure of the poly-Ig receptor. Generally, Fc-like receptors are >70 kDa, indicating even fewer exons. Both DNA strands will be amplified. As technology develops, the traditional slab-gel electrophoresis analysis will preferably be replaced with high throughput mutation screening using automated capillary electrophoresis (Larsen L A et al (2000) *Comb Chem High Throughput Screen.* 3, 393-409). This will facilitate commercial screening of large numbers of DNA samples. A significant mutation in one allele is a potential predisposing factor based on the need for only one additional "hit" to have a loss of a critical receptor. These same changes may be applicable to prostate, colon and other mucosal cancers.

Predictive Genetic Analysis: Other Allelic Imbalances. There are a variety of other potential genetic changes that may predispose women to breast cancer. Changes that are especially relevant to this disclosure include loss of heterozygosity (LOH), concomitant gain and loss of alleles (GAL) and simple gain of alleles (GCN) (Loupart M-L et al. (1995) *Genes Chromosomes Cancer* 12, 16-23). The effect of each of these is to increase genetic instability and contribute to changes that affect the expression of the gene product. These will be further addressed below in Examples related to tumor diagnostics. These same changes may be applicable to prostate, colon and other mucosal cancers.

Predictive Genetic Analysis: Expression Genetics in Cancer. One of the most interesting facts of cancer is that relatively few have been directly related to mutated genes in humans (Sager R (1997) *Proc Natl Acad Sci USA* 94, 952-955). What is far more common is that expression of genes is changed. The definitions of the different types of changes are "Class I genes" that are mutated or deleted at the DNA level, and "Class II genes" that are not altered at the DNA level but are changed in expression level. In this disclosure, both types of changes are included for the poly-Ig receptor (or poly-Ig-like receptor) and the Fc-like receptor. The information gained from characterizing these changes will be used to improve the diagnosis, prognosis, treatment or prevention of mucosal cancers.

TGFβ Receptors and Genetic Analysis. The protocols just described above for application to the poly-Ig receptor and the Fc-like receptor are also applicable to, and are hereby extended to include, the TGFβ Type I, Type II and Type II receptors with breast and prostate cancer, preferably. It can readily appreciated that similar analyses can be applied to other mucosal cancers as they are proven to be regulated by IgA/IgM. The genetic analysis of Class I and Class II changes in TGFβ receptors will preferably be done in combination with evaluations of the status of ERα and/or ERγ and the immunoglobulin receptors, as an aid in selection of the most appropriate therapy for a particular patient.

Primary Tumor Analysis. Primary tumors will be screened for allelic imbalances as described (Loupart M-L et al. (1995) *Genes Chromosomes Cancear* 12, 16-23). Based on the known allelic imbalances associated with breast cancer and locus D1S58, these will be preferred analyses. Other analyses such as chromosomal loss and chromosomal rearrangements are recognized as important aspects of cancer development and progression (Lengauer C et al. (1997) *Nature* (Lond) 386, 623-627) and will be included as receptor identification loci are defined.

Molecular Assessment of Cancer. There are several major advances in cancer genetics arising from the present invention that promise a new clinical future for cancer diagnosis, genetic screening, prevention and therapy. These include: (1) A detailed definition of the genetic (DNA) changes and altered gene expression will become available for mucosal cancers and will include the new receptors disclosed herein. (2) Obtaining the genetic profile of a single patient's primary tumor will become a routine matter and permit far better design of treatment for mucosal cancers. (3) Large scale population based screening will become a reality with samples obtained by non-invasive procedures or from easily assessable body fluids such as saliva, sputum, urine and mucosal washings. Representative applications of these concepts and approaches are described herein. (4) A molecular analysis of surgical margins and lymph nodes and metastases will become routine, particularly for mucosal cancers, as evidenced herein. (5) The information provided in the present disclosure, and the tools and methods developed and described herein will be of especial value when applied to the preinvasive and preneoplastic states of mucosal cancers before they become symptomatic.

Example 39

Breast Cancer Prevention with Applications to Prostate Cancer and Other Mucosal Cancers Oral immunization strategies have been devised to reduce the risk of and/or prevent breast cancer and cancers of other mucosal tissues.

World-Wide Breast Cancer Death Rate by Country. When expressed by death rate per 100,000 population, it is clear that the ranking (1 highest and 44 lowest) is highest in industrial/developed countries of North America and Northern Europe (TABLE 14). Large Asian populations are at the bottom of the ranking. The conventional wisdom is that the populations of high-ranking areas are exposed to more environmental carcinogens and mutagens, and also have the highest dietary caloric and fat intake. This has led to the general acceptance of the idea that diet and environment cause breast cancer.

TABLE 14

World-Wide Death Rates for Breast Cancer
Deaths per 100,000

COUNTRY/RANK

Denmark/1
Ireland/2
Netherlands/3
Israel/4
United Kingdom/5
Hungary/6
New Zealand/7
Germany/8
Trinidad & Tobago/9
Canada/10
Solvenia/11
Czech Republic/12
Austria/13
United States/14
Australia/15
France/16
Norway/17
Lithuania/18
Estronia/19
Croatia/20
Republic of Moldova/21
Portugal/22
Spain/23
Latvia/24
Finland/25
Sweden/26
Greece/27
Russian Federation/28
Poland/29
Macedonia/30
Bulgaria/31
Romania/32
Cuba/33
Kazakhstan/34
Chile/35
Venezuela/36
Kyrgyzstan/37
Turkmenistan/38
Mexico/39
Columbia/40
Mauritius/41
Azerbaijan/42
Japan/43
China/44
Slovakia - no data Comparisons of the World-wide Death Rates for Colon/Rectal, Breast and Prostate Cancer. Of the major mucosal cancers, colon/rectal, breast and prostate are the most common and have high mortality in many countries. FIG. 132 shows a listing from the World Health Organization (1999) of the deaths per 100,000 in 45 countries. Although the correlations are not ideal, the general conclusion is that several of the high ranked countries have above average rates of all three types of cancer. These countries again tend to be the industrialize/developed with the dietary and environmental problems associated with higher standards of living. These statistics show that mucosal cancer is a common problem in more affluent countries and that prevention is a major problem that has significance in broad areas of the world.

Plasma Immunoglobulins and Age in Humans. It is well recognized that during the first few months of life, the immune system of the infant has not yet developed. The immunoglobulins in the child's blood are from the mother and are predominantly IgG subclasses IgG1 and IgG2 (FIG. 133). As shown in FIG. 133, IgM is the next Ig to increase as early as in the first year. This rise is required for the development of the full immune response. Notably, IgA is much slower to reach adult levels and only achieves this after age 10+. The late appearance of plasma IgA is paralleled in some of the mucosal tissues. Reproductive system mucosal immunity of males and females is hormone dependent and does not develop until the onset of puberty, and then only reaches adult levels well after this time. This indicates that during the period of development of the breast adolescent females, the secretory immune system is just developing. This is the "window" of opportunity for mutation described above. If this window were reduced, or its open period decreased, a significant reduction in breast cancer risk could be expected.

Prevention of Breast and Prostate and other Mucosal Cancers by "Oral Immunization". Development of a broadly applicable immunization approach to prevent mucosal cancers is urgent. Today, there is no such immunization method. In the present Example, the observations and data presented above establishing the inhibitory effects of the secretory immune system are extended to the development of an oral immunization method based on induction of increased immunoglobulins in mucosal tissues. This increase is expected to slow DNA synthesis and thereby reduce the effect of mutagens during the adolescent female "window". Furthermore, there is another "window" caused by menopause. At this time, the secretory immune system of breast decreases. This reduces available inhibitors. Existing preneoplastic cells are no longer under sufficient negative control. It is proposed that this natural process is a major contributor to the sharp rise in breast cancer incidence after menopause.

Stimulation of the Body's Natural Immune System to Close "Windows" Periods of Mutagen Susceptibility—Dual Benefits. Breast cancer will be used as a model of mucosal tissues, employing a new approach to preventing or reducing the risk of breast/prostate/mucosal cancer by stimulating the body's natural mucosal immune defense system, preferably via oral immunogens, to prevent early mutations that ultimately lead to cancer later in life. Evidence presented herein shows that longer-term exposure of $ER^+$ breast cancer cells to IgA or IgM will result in cell death within a few weeks in culture. Even given that this process will take longer in vivo, use of oral immunization throughout adult life promises benefits. By approaching oral immunization from this perspective, it becomes both prevention and therapy.

Gastrointestinal Immune System. It is now proposed that "oral immunization" can be administered to men and women of all ages to stimulate the natural secretory immune system to produce increased local tissue antibacterial immunoglobulins IgA and IgM (Del Giudice G et al (1999) *Immunol Methods* 19, 148-155). Because of their well establish natural antimicrobial properties (Heremans J F (1970) In: *Immunoglobulins, Biological Aspects and Clinical Uses*, Merler E ed. National Academy of Sciences, Washington, D.C.), secretory immunoglobulins can be expected to prevent or substantially reduce the risk of breast and prostate cancer. The presently disclosed methods and compositions, directed toward prevention, promise to be applicable to reducing the risk of breast cancer in women without regard to age, race, existing risk factors, ethnic background or socio-economic status. This is true also of the risk of prostate cancer in men.

B Cells and Peyer's Patches. B cells of the lamina propria secrete IgA and IgM in breast and prostate tissue. These cells originate from the Peyer's patches of the small intestine (Owen R L (1999) *Seminars Immunol* 11, 157-163) and migrate to breast and prostate after a maturation process in the circulation. B cells from the gut enter the general circulation after stimulation by oral agents (Boyaka P N et al. (1999) *Am J Trop Med Hyg* 60 (4 suppl), 3545). This includes bacterial and viral challenge. The IgA and IgM produced in breast tissue is secreted into milk (Nathavitharana K A et al. (1995) *Arch Dis Chil Fetal Neonatal Ed* 72, F102-F106). The IgA and IgM produced in prostate tissue is secreted into seminal fluid (Stem J E et al. (1992) *J Reprod Immunol* 22, 73-85). The immunoglobulins are transported across mucosal epithelium by poly-Ig receptor mediated transcytosis (Mostov K E (1994) *Annu Rev Immunol* 12, 63-84). In all secretions of mucosal tissues, IgA and IgM are primary antimicrobial agents. This process has been described in detail (Mestecky J and McGhee J R (1987) *Adv Immunol* 40, 153-245). After identifying the types and strains of bacteria most likely to cause breast and prostate cancer, the researcher proposes to use inactivated forms or attenuated forms as oral challenges to develop mucosal immunity (Viret J F et al. (1999) *Infect Immunol* 67, 3680-3685). As evidence of the feasibility of this concept, this same approach was used by Sabin to develop mucosal immunity against the poliovirus (Valtanen S et al. (2000) *J Infect Dis* 182, 1-5; Fiore L et al. (1997) *J Virol* 71, 6905-6912).

Oral Immunization. Oral immunization can be effective for induction of specific sIgA responses if the antigens are presented to the T and B lymphocytes and accessory cells contained within the Peyer's patches where preferential IgA B-cell development is initiated. The Peyer's patches contain helper T cells (TH) that mediate B-cell isotype switching directly from IgM cells to IgA B cells then migrate to the mesenteric lymph nodes and undergo differentiation, enter the thoracic duct, then the general circulation, and subsequently seed all of the secretory tissues of the body, including the lamina propria of the gut and respiratory tract. IgA is then produced by the mature plasma cells, complexed with membrane-bound secretory component, and transported onto the mucosal surface where it is available to interact with invading pathogens. The existence of this common mucosal immune system explains in part the potential of live oral vaccines and oral immunization for protection against pathogenic organisms that initiate infection by first interacting with mucosal surfaces.

Oral Immunization is not Conventional Tumor Immunization. In view of the foregoing examples, it can be readily appreciated that a primary goal in the present case is not to raise conventional anti-tumor antibodies against the tumor, in contrast to existing approaches commonly used today for cancer immunotherapy. Available mucosal routes for obtaining the desired immune response (i.e., production of IgA/IgM/IgG1) include oral, intragastric, nasal, urogenital and rectal. Oral administration is preferred, however, because of its ease of use, whether for inducing mucosal secretion of cancer-arresting amounts of IgA/IgM/IgG in contact with the gastrointestinal mucosa or at another mucosal site. Nasal administration can be effective and convenient.

Strategies for Immunization. A number of suitable strategies have been developed for oral immunization, including the use of attenuated mutants of bacteria (e.g. Salmonella) as carriers of heterologous antigens, encapsulation of antigens into microspheres composed of poly-DL-lactide-glycolide (PGL), protein-like polymers-proteinoids, gelatin capsules, different formulations of liposomes, adsorption onto nanoparticles, use of lipophilic immune stimulating complexes, and addition of bacterial products with known adjuvant properties, all of which are well known to those of skill in the art and have been described in the literature.

Age to Begin Oral Immunization. Prevention is one of the most important issues in cancer. It is well known that there is a time period, or window, during which young females are most susceptible to mutagenic events (e.g., ionizing radiation and/or exposure to chemical mutagens) that later predispose them to higher than average rates of breast cancer. This window is during puberty (i.e. about 9 to 16 years). An oral "vaccine" will be given to very young females (i.e. starting as early as seven years of age, or less) to induce high levels of tissue B cells that secrete protective dimeric IgA and pentameric IgM. This same protective treatment or preventative may also be administered to women of all ages, with the goal is to "immunize" women against breast cancer by increasing the tissue concentrations and secretion of polymeric IgA and IgM. This very same process can be applied to prostate and many other types of epithelial tissues and cancers.

Rising Risk of Breast Cancer. The risk of developing breast cancer for women in the United States has been rising steadily for the past several decades. It will soon approach one in eight. We are fortunate that new treatments and more effective screening tests have kept mortality rates from also rising as dramatically. Nonetheless, we are still losing more than one hundred women per day to breast cancer in the United States alone. It is generally recognized by breast cancer researchers that the first line of defense against this disease is prevention. In the near future, the present know-how will continue to be used to treat these cancers as they occur. However, in order to improve the long-term outlook for all women, and especially if we wish our daughters to live free of this disease, major efforts must also be focused on prevention.

The Secretory Immune System and Growth Regulation as the Discovery Opening this New Area of Prevention. As detailed in the preceding examples, a major breakthrough has been made in understanding how breast cancers grow. It was found that in its initial stages, breast cancer is inhibited by the secretory immune system. That means this part of our immune system can stop early cancer cells from growing. The well known operation of the secretory immune system includes, during adult life, the production by women's breasts of milk or milk-like fluids. Milk contains high levels of two immunoglobulins IgA and IgM. These are passed from mother to child during breastfeeding. Both IgA and IgM protect the child's digestive system from bacterial infections. Along with protecting the child, we have known for many years that breastfeeding lowers the risk of breast cancer. As a result of this discovery, it is now recognized that the same immunoglobulins that protect a child from bacteria can also be manipulated to protect the mother against breast cancer. This realization also provides new insight with respect to the problem of prevention.

Oral Immunization—Mass Applicability. If the secretory immune system can be stimulated at times when women are known to be most susceptible to environmental and other agents that cause breast cancer, the occurrence of breast cancer might be prevented or at least the risk of developing this disease might be considerably reduced. Although there have been previous studies in the literature relating to cancer prevention, none of the studies contemplating the use of oral immunization to treat cancer or a wide variety of infectious diseases, had pursued that objective beyond initial thoughts. Moreover, the application of oral immunization specifically to breast cancer had not received any attention. One benefit of the new oral immunization strategy for reducing the risk of and/or preventing breast cancer is that oral immunization is readily adaptable to mass populations of women of all ages and all circumstances throughout the world.

Example 40

Rat Model for Testing Oral Immunization Effects on Mammary Gland Carcinogenesis

Rat Mammary Tumor Model For "Windows." In this Example, use of an animal model to test the effectiveness of oral immunization during specific windows of susceptibility to carcinogens is described. This study is intended to be conducted before advancing to any type of human testing. Mammary carcinogenesis in female rodents is most effective during the developmental period that spans early puberty through early young adulthood (FIG. 123). Single challenges with mammary specific carcinogens during this "window" period cause tumors in the majority of animals within one year. Similar challenges later during adulthood are far less effective. The results of two typical carcinogen experiments are shown in FIG. 123. These data support the conclusion that a "window" of increased susceptibility exists during which mutations can be induced that lead to breast cancer later in life. There is a body of evidence that indicates that this is also true of human females. Exposure of 10 to 19 year old females to ionizing radiation or chemical mutagens leads to higher than expected breast cancer rates later in life. Similar exposures of adult human females were far less deleterious. The explanation for these observations is the fact that mammary gland DNA synthesis increases during puberty and young adulthood due to the onset of the differentiation program and sex hormone secretion. This program initiates the full development of the gland. As gland terminal end buds (TEB) develop, they are the sites for mutagenesis. Clearly, DNA synthesis is required for carcinogenesis of mammary gland. Taking advantage of these facts, it is proposed that the secretory immune system can be stimulated to reduce DNA synthesis during this critical "window" and thereby diminish the risk of carcinogen induced breast cancers. In FIG. 128, it was demonstrated that IgA in the plasma of female S-D-rats is significantly reduced at the time when carcinogenesis is most effective.

Carcinogen sensitive adolescent female rats as well as sexually mature females and multiparous females, both of which are more carcinogen resistant than the younger females will be studied. The rat mammary tumor is a suitable model because of the large carcinogenesis database available and the abundance of other applicable methodologies. Also, there is convincing evidence that carcinogen induced rat mammary cancers are histologically similar to those of human breast. Preferably, environmentally relevant carcinogens will be employed in the studies. While lipophilic polycyclic hydrocarbons such as 7,12-dimethylbenz(a)anthracene (DMBA) and 3-methylcholanthrene (3MCA) and the soluble alkylating agent nitrosomethylurea (NMU) effectively transform mammary tissue with single doses, they are not found in our environment. NMU is also excluded from these studies because it causes specific changes in the ras protooncogene that are not common in human breast cancers. Investigators have suggested that 80 to 90% of human breast cancers are likely induced by environmental carcinogens.

Inhibitory compositions containing IgA, IgM and/or IgG1 will be employed to determine whether mutations leading to breast cancer occur early in life during puberty and young adulthood, and if the control of DNA synthesis by IgA/IgM during this critical period will attenuate the action of carcinogens and thereby reduce the risk of breast cancer later in life. IgA and IgM will be administered to young female animals initially to diminish the effects of carcinogens. These studies will then be followed by oral "immunizations" to increase the natural levels of immunoglobulin secreting B-cells within the mammary tissue. The studies will include adolescent females as well as those in mid-life. In treated individuals, there may be some consequential delay of entry into puberty and/or some reduction in breast development, compared to untreated individuals. This oral immunization approach is the first attempt to deter or prevent breast cancer using the new strategy, and is further unprecedented by applying it early in life.

General Materials and Methods. S-D female rats will be purchased from Harlan-Sprague-Dawley. Animal holding rooms are maintained at 23±2° C. at constant humidity on 12 hour light/12 hour dark cycles. After anesthesia, blood will be drawn by cardiac puncture until exsanguination. The blood will be clotted overnight at 4° C. before collection of serum. The serum from individual animals will be stored separately at −20° C. The rats will be fed an AIN-76A high fat diet which was effective in another study of mammary carcinogenesis with S-D rats treated by gavage with the environmentally ubiquitous agents benzo[a]pyrene (B[a]P), 1-nitropyrene (1-NP) and 2-amino-1-methyl-6-phenylimidazol[4,5-b]pyridine (PhiP). This diet supports body weight gain at control levels even after eight weekly carcinogen treatments. Survival rates for 41 weeks after carcinogen treatment did not differ from controls.

Rabbit polyclonal antibodies will be raised against human secretory component, which will be obtained from customary commercial sources. The antibodies will be raised and tested by Western immunoblotting with chemiluminescence detection to confirm specificity and species cross reactivity. The antibodies will be immunoaffinity purified. To measure rat IgA and IgM in serum, tissue extracts or secretion samples, radioimmunoassay (RIA) will be used with antibodies purchased from Zymed. Iodine labeling of IgA, IgM and secretory component will be done by standard methods. A nonradioactive ELISA will also be evaluated to measure IgA, IgM and secretory component. The concentrations of IgA and IgM in secretions can also be estimated by Western analysis with densitometry, according to well known procedures. Secretory component will be measured by RIA. RIA/ELISA data will be analyzed by computer using logit transformations and regression analysis, as in known by those skilled in the art.

Purified rat plasma IgA, IgM and bulk IgG will be purchased initially from Zymed. Human sIgA and human plasma dimeric/polymeric IgA will be purchased from Accurate Chemicals. As larger supplies become necessary for animal tests, plasma IgA and IgM can be purified by the preferred methods described herein, and sIgA from colostrum. Alternatively, another purification method could be substituted, provided that it yields IgA and IgM preparations with cell growth inhibitory activity characteristics and purity at least equal to those described in the present cell growth assays.

The environmental carcinogens to be tested will be B[a]P, 1-NP and PhIP. They will be compared to a trioctanoin vehicle control. Tumors appear in response to B[a]P, PhIP and 1-NP at 5, 9 and 17 weeks, respectively. The carcinogens will be administered for eight weeks at a dose of 50 pmol/rat/week. Body weight versus time will be measured. A repeated measures analysis of variance (ANOVA) will be employed to determine overall group differences in weight. Pair-wise, repeated-measures analysis will be employed to determine where differences occur. Cumulative mortality will be measured. The probability of survival will be evaluated by life-table analysis with death as the end point. The statistical difference between pairs of groups will be evaluated by the log-rank test. Tumor incidence will be evaluated by life-table analysis with time of first appearance of tumor as the end point. Over the planned duration of these experiments, the rate of spontaneous mammary tumors is not significant.

For the quantification of mammary gland development, radioisotope labeling of DNA and estimation of numbers of tumors, applying well described methods. Both right and left cervical, thoracic, abdominal and inguinal glands will be analyzed. Left glands will be fixed for whole mount estimates of the numbers of terminal end buds (TEB), terminal ducts (TD) and alveolar buds (AB) structures. Carcinogenicity correlates with the densities of TEB and TD. The effects of IgA and IgM and carcinogens will be monitored on these structures as well as on L.I. (Labeling Index) and the numbers of tumors. The right glands will be longitudinally sectioned for autoradiography (i.e., L.I. measurements) and stained for tumor quantification. The scoring of tumors will be done by three methods. Palpable tumors will be measured, the number of tumors in whole mounts will be estimated by stereomicroscopy and microtumors will be counted in the sections. The dose and timing of methyl tritium labeled thymidine ($^3$H-TdR) treatment of the animals has been defined. DNA synthesis can be measured at any time prepubertal rats because the estrus cycle has not begun. After puberty, DNA synthesis is measured at estrus. Five rats will be included in each time point. This sample size has yielded significant (P<0.05) differences between prepubertal animals and those at 110 days. The unpaired t test will be used to compare the results from different age groups to determine when a significant difference in DNA synthesis has been identified (i.e. P<0.05). The age groups to be studied will be 30 to 35 days, 35 to 40 days, 40 to 45 days, 45 to 50 days, 60 to 65 days, 80 to 85 days, 100 to 110 days, 120 to 150 days, 200 to 230 days and retired breeders at 270+ days.

First, the age of young female rats will be identified in which DNA synthesis is maximized. DNA synthesis will be monitored by $^3$H-TdR incorporation. This initial study is expected to confirm, under the present test conditions, those data reported by others in the literature. Age groups spanning 20 days to 270+ days will be assessed. When the period of maximum DNA synthesis is identified, IgA and IgM injections will be used to suppress DNA synthesis during this time. After the period of most rapid DNA synthesis has been identified, the females of that group will be treated i.p. with IgA and IgM. To determine dose, RIA of the serum collected from each animal group listed above will be performed to establish the concentrations of IgA and IgM in the circulation of sexually mature adult and multiparous females. After an effective immunoglobulin dose is found, the appropriate age group will be treated with IgA/IgM and the effects on carcinogenesis assessed versus control animals. The doses of the immunoglobulins will be increased until blood levels in the adolescent rat equal or exceed those of mature females. These doses will be administered before the start of DNA synthesis and throughout the period of carcinogen treatment. When DNA synthesis has been suppressed as judged by total label incorporation into DNA, measurement of L.I. and TEB measurements, the three environmental carcinogens will be administered to separate groups of fifteen rats and monitor tumor development as described above. The unpaired t test will be used to compare the results from between the control group (vehicle only) and each carcinogen treated group. The differences between carcinogen groups will be compared as described above. A significant (p<0.05) suppression of carcinogenesis and a significant suppression of TEB development are expected to be identified. The expected result is that carcinogens will be less effective in those rats receiving DNA synthesis inhibiting doses of IgA/IgM.

Next, the conditions for inducing increased B-cell populations in breast tissue will be identified. Initially, the B-cell content of mammary tissue as a function of age will be monitored. This control study will be correlated with the time period of maximum DNA synthesis. The content of B-cells is expected to be low in those age groups showing a maximum DNA synthesis rate. Next, using oral challenges, the most effective "immunogen" to induce an increased population of B-cells in mammary tissue will be determined. The end point of these studies will be to induce sufficient numbers of B-cells to prevent the "window" increase in DNA synthesis. When conditions have been established to prevent this rise, the animal will be treated with carcinogens and monitored for tumor development and survival. The oral "immunization" is expected to reduce the effectiveness of the carcinogen.

All secretory tissues from human adults contain substantial numbers of IgA and IgM producing immunocytes. The immunocytes in lactating human mammary are about 80% IgA secreting and 10% IgM. We will use the animal groups described above to evaluate the effect of age on IgA & IgM immunocytes in rat mammary glands. Immunocytes in histological sections will be detected by fluorescence after incubation with secretory component and the appropriate primary and secondary antisera. Detailed descriptions of the fixation and detection methods have been presented. It is expected that adolescent females will have lower numbers of IgA and IgM immunocytes (p<0.05) than adults or multiparous females. Comparisons between the groups will be based on median values and the Mann-Whitney non-parametric test (one tail).

Next, "oral challenges" will be used to increase the numbers of IgA and IgM immunocytes in the mammary glands of immature/pubertal female rats. In contrast to historical suggestions of oral immunization of mucosal tissues, including applications to neoplasia, the present, non-conventional "oral immunization" project preferably includes the use of immunogens that show promise with regard to breast. The most promising of these are non-pathogenic strains of E. coli. The first of these is E. coli 083 that has been used in humans to increase sIgA secretions in colostrum. Remarkably, high levels of sIgA were induced in colostrum without causing intestinal disturbances. Ingestion by infants or non-pregnant adults was without symptoms. The colostrum contained numerous immunocytes that secreted IgA against the O antigen of the bacteria. Furthermore, eight or more prevalent types of E. coli induced milk antibodies/immunocytes against the lipopolysaccharide (LPS) of the bacteria. Indeed, even the LPS alone induced high levels of colostrum immunocytes secreting IgA. The present study will begin with E. coli 083 and the LPS from it. The methods of analysis of antibodies in the blood and in rat colostrum will be done as described. Dosing of the bacterium and LPS will be developed to block the "window" of DNA synthesis. When effective dosing regiments have been found, we will analyze the effects of the carcinogens to determine if they are effective when DNA synthesis is suppressed. Also, the state of differentiation of the gland will be analyzed by measuring terminal end buds (TEB), terminal ducts (TD) and alveolar buds (AB). Both carcinogenesis and differentiation are expected to be inhibited.

In a third phase of the studies, it will be determined if disruption of the function of the secretory immune system causes adult and multiparous female rats to become more sensitive to carcinogens. Virgin female rats of 114 days or older will be studied as will retired breeders of more than 250 days age. These animals will be treated with antibody against the poly-Ig receptor. The doses of antiserum to disrupt the secretory immune system will be established by monitoring IgA/IgM secretion into bile, uterine fluids and breast milk. Also, mammary DNA synthesis will be monitored. When secretion is blocked effectively, the susceptibility of these animals to carcinogens will be measured. The disruption of the interaction of IgA/IgM with the poly-Ig receptor is expected to increase DNA synthesis in the mammary gland and therefore increase susceptibility to carcinogens.

Because rats do not undergo menopause, a different approach to investigating the possible "window" in mid-life females will be used. For this study, the interaction of IgA and IgM with the poly-Ig receptor will be disrupted using polyclonal antibodies against the receptor. The antibodies will be confirmed effective by blocking $^{125}$I-IgA binding to breast cancer cell receptors using methods. The effect of these antibodies in vivo will be measured by monitoring DNA synthesis in the adults of 110 to 120 days, 200 to 220 days and retired breeders. Also, the secretion of IgA, IgM, secretory component and J chain into bile, uterine fluids and breast milk will be monitored by the methods described. Similar methods with J chain polyclonal antibodies have proven very effective in rats. When the secretions have been diminished satisfactorily, antibody treated animals will be treated simultaneously with carcinogens. It is expected that DNA synthesis will increase in adult and multiparous animals treated with the antibodies and that the carcinogens will become more effective.

Applicability to Humans. Human female breast cancer incidence rates increase dramatically after age 50 and now approach one in eight by age 75. The existing data suggest that the causal mutations most likely occur at earlier ages. However, milk/breast secretions decrease dramatically after menopause. Perimenopausal and postmenopausal women may also have a previously unrecognized "window" of increased vulnerability because the activity of the secretory immune system decreases with the approach of mid-life. Accordingly, the IgA, IgM and IgG1 inhibitor compositions will also be employed to aid in determining whether mutations can arise later in life due to the natural age related reduction in the growth inhibitory function of the secretory immune system.

Example 41

Bacterial Oncogenesis and Prevention by Oral Immunization

The present example addresses the cause of breast and prostate cancer, as well as cancers of other steroid hormone responsive tissues, from the perspective of determining what is causing the normal mucosal epithelial cells of these tissues to become transformed to the malignant state. It is now proposed that certain bacteria are carcinogenic (oncogenic), especially in mucosal epithelial tissues, and a screening procedure for isolating and identifying oncogenic bacteria, or bacterial that are likely to be oncogenic has been devised.

Also presented herein is a two-fold immunization plan to prevent or reduce the risk of occurrence of cancer of the breast, prostate, and other steroid hormone responsive mucosal endothelial tissues. The first kind of immunization involves immunizing an individual in the conventional way to invoke a natural immune response in which antibacterial immunoglobulins target and eliminate specific oncogenic bacteria. The second kind of "immunization," which was previously unknown, is to stimulate the natural secretory immune system to produce steroid hormone reversible cell growth inhibitors (i.e., "immunoglobulin inhibitors"), which the inventor has discovered are active forms of IgA, IgM and IgG1. These inhibitors have activity for regulating steroid hormone reversible cell growth in mucosal epithelial tissues, such as breast and prostate. Alternatively, the individual may be "passively immunized" by local or systemic administration of IgA, IgM and IgG1. By means of their cell growth regulatory function, the active forms of IgA, IgM and IgG1 are believed by the inventor to protect the mucosal epithelial tissues from the deleterious effects of bacterial oncogenesis which lead to cancerous cell growth.

As disclosed hereinabove and in U.S. patent application Ser. No. 09/852,958/PCT/US2001/15183 entitled "Compositions and Methods for Demonstrating Secretory Immune System Regulation of Steroid Hormone Responsive Cancer Cell Growth," hereby incorporated herein by reference, the secretory immune system immunoglobulins IgA, IgM and IgG1 are potent inhibitors of steroid hormone responsive cancer cell growth in chemically defined serum-free medium. This serum-free cell culture system constitutes a preferred in vitro model of in vivo tumor cell growth that is superior to previously available serum-free systems. The inhibitory activity is mediated by poly-Ig receptor or a poly-Ig-like receptor. Among other things, this discovery has strong physiological significance in humans related to the well-known production of IgA, IgM and IgG1 in breast tissue and the secretion of these same immunoglobulins into breast milk. In the past, the IgA, IgM and IgG1 of milk were thought to serve only as an antibacterial protection for the suckling offspring. These same immunoglobulins, particularly in the form of polymeric IgA and pentameric IgM and IgG1, may also protect the mother and provide a new means of preventing or reducing her risk of breast cancer. Similar negative regulation by IgA, IgM and IgG1 has also been demonstrated by the inventor in androgen responsive prostate cancer cells. Analogous results are also indicated in steroid hormone responsive cancers of all other mucosal epithelial tissues that either secrete or are bathed by IgA, IgM and IgG1 in the body. These include not only tissues of the breast, prostate, pituitary and kidney, but also any other tissue that lines a cavity or secretes IgA/IgM/IgG1, such as tissues of the gastrointestinal tract (i.e. oral cavity mucosa, salivary/parotid glands, esophagus, stomach, small intestine and colon), war ducts and nasal passages, liver and bile ducts, bladder, pancreas, adrenals, kidney tubules and glomeruli, lungs, the female reproductive tract (i.e. ovaries, fallopian tubes, uterus, cervix and vagina) and the secretory anterior pituitary gland. All of these glandular/mucosal tissues either secrete or are bathed by polymeric IgA, secretory IgA (sIgA), IgM and IgG1. Cancers arising from these tissues account for 80% of the epithelial malignancies of humans.

In light of the discovery that the secretory immune system immunoglobulins IgA, IgM (and IgG1 in humans) are potent inhibitors of steroid hormone responsive cancer cell growth, in the preceding Example, it has been demonstrated how the steroid hormone responsive tissues in the body may be protected from the cancer causing actions of certain environmental carcinogens by enhancement of the IgA, IgM and IgG1 secreted by or coming in contact with those tissues. In this way, DNA synthesis dependent mutations can be prevented or substantially reduced in those tissues.

Certain bacterial products, either alone or in cooperation with leukocytes, are responsible for production of "reactive oxygen and nitrogen" that lead to malignant transformation of breast and prostate epithelial cells. Immunity to these oncogenic bacteria can confer resistance to this process and thereby reduce the risk of breast and prostate cancer. By employing the bacterial screening procedures that are described below, bacteria that are likely to be inducers of cancer in vivo are identified. These bacteria, or a combination of bacteria, or immunogens derived from the oncogenic bacteria, can then be used to develop specific antimicrobial therapies. One such antimicrobial therapy includes the production of secretory immunity via oral administration of the inactivated or otherwise attenuated bacteria to confer mucosal immunity. Alternatively, nasal or rectal administration routes may be employed to produce mucosal immunity in an individual considered to be at risk of developing cancer in a mucosal tissue. Another means of protecting an individual against the oncogenic action of the bacteria isolated or identified as set forth below is to induce systemic immunity to the bacteria, using conventional techniques for raising systemic antibodies to a microorganism.

Moreover, by employing conventional diagnostic immunology and other immune-based tests of plasma or other bodily secretions, it can be determined if an individual has been or is actively infected by the suspected oncogenic bacteria, which has been isolated or identified according to the screening procedures described below. With this information, predictions can be made as to which individuals may be at higher risk for development of cancer in the affected tissue. Alternatively, or additionally, a variety of conventional metabolic/chemical inhibitor approaches may be employed to destroy the potentially oncogenic bacteria in the affected tissues. For example, administration of an effective dose of an appropriate antibiotic to an individual infected by an oncogenic bacteria.

In light of the discovery regarding the role of the natural secretory immune system in regulating the growth of cancer, and finding indirect support in the literature, it is now concluded that bacterial infections are likely to be an important factor in development of prostate cancer, and that bacteria are also likely to be a primary cause of cancers of breast and other mucosal epithelial tissues. Accordingly, the following screening procedures are provided for isolating and identifying bacteria from breast and prostate sources and assessing their transforming activity.

Screening Procedure for Identifying Carcinogenic Bacteria. Human milk will be collected from pregnant volunteers either directly or via professional organizations working with nursing mothers. Alternatively, nipple aspirate fluid will be obtained from non-cancerous volunteers and breast cancer patients prior to surgery or chemotherapy, preferably as described (Trock B and McLesky S Proceedings of the Era of Hope 2000 Meeting, Department of Defense Breast Cancer Research Program, Atlanta, Ga., June, 2000). Breast tissue samples from non-surgical volunteers will be collected under conditions that exclude skin origin bacteria. Breast cancer samples obtained during surgery will also be directly cultured and evaluated. Those samples will include normal breast tissue (e.g. from reduction mammoplasty) and tumor specimens from breast cancer patients.

Specimens of semen/seminal fluid will be obtained from normal volunteers of different ages. Because cancer causing mutations may be present for several years before the clinical manifestation of disease, samples will be collected from young adult men <35 years of age as well as from men into their seventies (highest rate). In addition, surgical samples will be cultivated and otherwise analyzed to identify the types of bacteria present and their relative frequencies. The samples will be classified as (i) bacterial prostatitis, (ii) nonbacterial prostatitis, and (iii) asymptomatic inflammatory prostatitis (Lipsky B A (1999) *Am J Med* 106, 327-334).

Special care will be given to the analysis of clinical samples for bacterial content. Some considerations have been discussed by others (Sandin R L and Rinaldi M (1996) *Infect Dis Clin North Am* 10, 413-430). Precautions will be taken to avoid inclusion of extraneous bacteria in the samples, and to ensure quality control, including those indicated. Gram stain negative versus gram stain positive bacteria will be classified. Gram stain negative bacilli cause most prostatitis (Lipsky B A (1999) *Am J Med* 106, 327-334). For breast samples, this must still be established. This is the first selection process to be used to reduce the number of possible bacteria.

The next selection process will use colony derive bacteria to conduct the "Ames Test" to identify bacteria producing mutagens (Ames B N (1979) *Science* 204, 587-593). This test is based on the scientifically accepted concept that DNA damage appears to be the major cause of cancer. This assay employs an in vitro mutagenesis test using the bacterium Salmonella. The culture medium from each form of bacteria isolated can be tested directly for mutagenic activity using any of several strains of Salmonella developed for this purpose. The different types of screening methods have been reviewed (Hill D C (1998) *Adv Biochem Eng Biotechnol* 59, 73-121). Addition improvements in the Ames Test have been introduced to provide more quantitative evidence that the assay is providing significant results with respect to cancer bioassays (Bogen K T (1995) *Environ Mol Mutagen* 25, 3749). The results will be analyzed by statistical methods (Kim B S and Margolin B H (1999) *Mutat Res* 436, 113-122). The results of this test will establish which bacterial isolates produce mutagenic metabolites (e.g. reactive oxygen and nitrogen species).

The Ames Test can also be applied to demonstrate that the bacteria cause an "oxidative burst" mediated by neurophils and macrophages. In this case, the leukocytes are incubated with the bacteria to generate the active mutagenic species. This approach resolves the issue of whether the products of the bacteria are the mutagens themselves or if the activation of leukocytes is required. The various kinds of mutagenesis will be considered in light of human oncogenesis criteria (Miller J H (1996) *Cancer Surv* 28, 141-153).

Another type of selection has special application to breast cancer. Milk contains the protein lactoferrin (Masson D and Taylor C (1978) *J Clin Path* 31, 316-327). It is well known to be bactericidal by virtue of its high affinity for iron (FeIII) (Arnold R et al. (1977) *Science* 197, 263-265). Most bacteria have an absolute requirement for FeII to grow. However, some have developed "lactoferrin receptors" that permit them to acquire the necessary iron even through it is in complex with lactoferrin. The inventor predicts that mutagenic types of bacteria in breast secretions/milk will survive and grow in the presence of high concentrations of lactoferrin. This offers a potent means of selecting for the bacteria being sought.

Bacteria that meet the criteria described above will be cultured and the medium tested with non-tumorigenic human breast epithelial cells to determine if the cells are altered to a malignant phenotype. The test of altered growth will first be done in serum-free chemically defined medium, prepared as described the foregoing examples and in U.S. patent application Ser. No. 09/852,958/PCT/US2001/15183 entitled "Compositions and Methods for Demonstrating Secretory Immune System Regulation of Steroid Hormone Responsive Cancer Cell Growth", or in Moreno-Cuevas and Sirbasku et al. (2000b), the disclosures of which are incorporated herein by reference. Transformed cells have reduced growth factor and adhesion requirements. Also, the cells will be tested for colony formation in standard assays. Normal epithelial cells will not form colonies in soft agar. Tumor or transformed cells will form colonies. There is a very strong correlation between colony forming activity in soft agar and tumorigenicity in host animals. These tests are expected to confirm that the mutagenic effects seen with the Ames Test can be translated to transformation of human breast cancer cells. Also, normal human prostate epithelial cells are available and will be used to perform a similar sequence of studies.

In addition to meeting the foregoing applicable selection criteria, some of the bacteria are expected by the inventor to also possess an immunoglobulin protease activity, i.e., its own "immunoprotective" mechanism. Both seminal fluid and breast secretions contain high concentrations of IgA. IgA is secreted by prostate and breast epithelial cells. The secreted IgA acts to kill bacteria in these fluids thereby protecting the tissue. Several types of organisms are known to secrete proteases that cleave the IgA into inactive Fab and Fe components. Examples are *Streptococcus pneumoniae* (Wani J H et al. (1996) *Infect Immun* 64, 3967-3974), *Haemophilus influenza* serotype b (Poulsen K et al. (1989) *Infect Immun* 57, 3097-3105), *Neisseria gonorrhoeae* (Simpson D A et al. (1988) *J Bacteriol* 170, 1866-1873), *Bacteroides melaninogenicus* (Mortensen S B and Kilian M (1984) *Infect Immun* 45, 550-557). These are only a few examples of bacterial protease activities that have been described in the literature and which are consistent with, and provide indirect support for, this oncogenic bacterial selection criterion.

Finally, to define the bacteria identity, the inventor will apply PCR methods (Wagar E A (1996) *J Clin Lab Anal* 10, 331-334). Techniques that may be applied include, for example, (1) use of specific PCR primers for known and new bacteria, (2) PCR amplification of conserved 16S rRNA sequences, and (3) RDA-PCR which is also called "reverse PCR". This technique can be used to identify unique infectious agents in disease tissues. Additional PCR technology is available for most of the microbes that are likely to be encountered.

Although the foregoing protocol has been described with respect to breast and prostate fluids and tissue specimens, it should be understood that similar protocols can be employed with fluids, secretions or tissue specimens from other mucosal epithelial tissues, including those of the gastrointestinal tract (i.e. oral cavity mucosa, salivary/parotid glands, esophagus, stomach, small intestine and colon), tear ducts and nasal passages, liver and bile ducts, bladder, pancreas, adrenals, kidney tubules and glomeruli, lungs, the female reproductive tract (i.e. ovaries, fallopian tubes, uterus, cervix and vagina) and the secretory anterior pituitary gland.

Reduction of Breast Cancer Risk by Immunization. One very important application of the bacteria that are identified as oncogenic, or likely to cause cancer in breast tissue, is to use oral challenges to develop mucosal immunity against the bacteria. For the purposes of this disclosure, the term "oncogenic bacteria" refers to the forms of bacteria that cause cancer. According to a preferred regime for preventing or reducing the risk of breast cancer, oral immunization will be administered to men and women of all ages to stimulate the natural secretory immune system to produce increased local tissue antibacterial immunoglobulins IgA and IgM. Existing techniques will be employed, such as those described (Del Giudice G et al. (1999) *Methods* 19, 148-155). Because of their established natural antimicrobial properties (Heremans J F (1970) In: *Immunoglobulins, Biological Aspects and Clinical Uses*, Merler E, ed. National Academy of Sciences, Washington, D.C., 1970), the inventor expects that the secretory immunoglobulins will prevent or substantially reduce the risk of breast and prostate cancer by targeting and eliminating the bacteria. The first phase of this disclosure (i.e. identification of oncogenic bacteria) is a first step toward achievement of the second phase, i.e., implementing natural immune system prevention methods. Such a prevention method is applicable to reducing the risk of breast cancer in women without regard to age, race, existing risk factors, ethnic background or socio-economic status. Similarly, but preferably using oncogenic bacteria identified in prostate tissue, the natural secretory immune system will be stimulated to protect against prostate cancer in men. In a preferred embodiments, the natural secretory immune system will be stimulated to eliminate the oncogenic bacteria via conventional antigen-antibody recognition chemistry, and/or to protect breast and prostate tissue from the deleterious effects of bacterial oncogenesis via the non-conventional cell growth inhibitory effects of the secretory immune system.

B cells of the lamina propria of breast and prostate tissue secrete IgA and IgM. These cells originate from the Peyer's patches of the small intestine (Owen R L (1999) *Seminar Immunol* 11, 157-163) and migrate to breast and prostate after a maturation process in the circulation. Entry of B cells into the circulation is stimulated by oral agents (Boyaka P N et al. (1999) *Am J Trop Med Hyg* 60 (4 suppl), 3545). This includes bacterial challenge. The IgA and IgM produced in breast tissue is destined for secretion into milk (Nathavitharana K A et al. (1995) *Arch Dis Chil Fetal Neonatal Ed* 72, F102-F106). The IgA and IgM produced in prostate tissue are destined for secretion into seminal fluid (Stern J E et al. (1992) *J Reprod Immunol* 22, 73-85). The immunoglobulins are transported across mucosal epithelium by poly-Ig receptor mediated transcytosis (Mostov K E (1994) *Annu Rev Immunol* 12, 63-84). In all secretions of mucosal tissues, IgA and IgM are primary antimicrobial agents. This process has been described in detail (Mestecky J and McGhee J R (1987) *Adv Immunol* 40, 153-245).

After identifying the types and strains of bacteria most likely to cause breast and prostate cancer, inactivated forms or attenuated forms of the bacteria will be used as oral challenges to develop mucosal immunity using known techniques such as those described (Viret J F et al. (1999) *Infect Immun* 67, 3680-3685). A similar approach was used by Sabin to develop mucosal immunity against the poliovirus (Valtanen S et al. (2000) *J Infect Dis* 182, 1-5; Fiore L et al. (1997) *J Virol* 71, 6905-6912).

Although oral immunization against breast cancer has been described above, it should be understood that protection against cancers of the prostate or other mucosal epithelial tissues, including those of the gastrointestinal tract (i.e. oral cavity mucosa, salivary/parotid glands, esophagus, stomach, small intestine and colon), tear ducts and nasal passages, liver and bile ducts, bladder, pancreas, adrenals, kidney tubules and glomeruli, lungs, the female reproductive tract (i.e. ovaries, fallopian tubes, uterus, cervix and vagina) and the secretory anterior pituitary gland, may be achieved similarly.

In addition to inducing a conventional type of mucosal immunity against the oncogenic bacteria, a second kind of "immunization," will also be employed in which the natural secretory immune system is stimulated to produce active forms of IgA, IgM and IgG1 that have activity for regulating cancer cell growth in mucosal epithelial tissues, especially the steroid hormone responsive tissues of breast and prostate. Alternatively, an individual may be "passively immunized" by local or systemic administration of IgA, IgM and IgG1 to inhibit cancer cell growth. As a result of their cell growth regulatory function, the active forms of IgA, Ig and IgG1 are expected to protect those types of tissues from the deleterious effects of bacterial oncogenesis that lead to cancerous cell growth. For example, by reducing the "imprinting" of cancer related genetic changes in prepubescent females or by preventing growth of early stage tumors in postmenopausal women. Preferably the IgA, IgM and IgG1 are raised against specific oncogenic bacteria, however a broad spectrum of IgA, IgM and IgG1 molecular species appear to exert steroid hormone reversible growth inhibition in these tissues. Continuing studies are directed at pinpointing the most effective species of IgA, IgM and IgG1 for inhibiting cancer cell growth arising from a given tissue and suppressing the effects of transformation.

Conclusions. A bacterial origin for certain cancers is consistent with, and indirectly supported by the work of others relating to the possible involvement of bacteria with Hodgkin's disease. Because many reproductive, child bearing and socioeconomic patterns are shared as risk factors for breast cancer and Bodgkin's disease in young women, there may well be a common etiology. Moreover, in light of the fact that no viral origin of human breast cancer has been established to date, the inventor concludes that other more common infective agents are more likely the cause of breast and prostate cancer. One published study has used Cytomegalovirus (CMV) infection distribution as a surrogate to test the hypothesis that breast cancer may be of infectious origin (Richardson A (1997) *Med Hypotheses* 48, 491-497). Although it is not likely that CMV is causative for breast cancer, it is found in human milk and is transmitted to offspring during the breast-feeding period (Diosi P (1997) *Roum Arch Microbiol Immunol* 56, 165-178). Those reports, viewed in light of the present disclosure, support the inventor's alternate interpretation of that information, i.e., that fortuitous bacterial infection, which spreads like viral infections, is actually the origin of breast cancer.

Human milk contains many microorganisms/bacteria. To date, none have been identified that are primary candidates as causative agents of breast cancer. The published work pertaining to milk microbiology will be of great benefit when reevaluated by the appropriate discriminators of the present screening procedure for identifying oncogenic bacteria. The existing literature contains many candidates that will be examined as primary causative agents for breast cancer, employing the screening process described herein.

The "reactive outbursts" from bacterial-challenged leukocytes may serve as an additional cause of cancers of the male reproductive tract, including those of prostate. Although this proposal has not been presented before regarding a mechanism for the development of prostate cancers, it is consistent with the results of studies reported in the literature that neutrophil and macrophage overproduction of reactive oxygen species damage the tissues and sperm (Ochsendorf F R (1999) *Human Reprod Update* 5, 399-420). Because prostate cancer increases dramatically with age, one focus of the inventor's further investigations will be on microorganisms that are common to men over 35 years of age. A previous study by others has shown that the Enterobacteriaceae are more frequently involved in prostatitis in this age group than in younger men (Joly-Guillou M L and Lasry S (1999) *Drugs* 57, 743-750). The Enterobacteriaceae, as well as other potentially oncogenic bacteria, will be examined in ongoing studies as primary causative agents for breast cancer, employing the new screening process.

The secretory immune system is an integral part of the physiology of all mucosal epithelial tissues. Most mucosal tissues secrete immunoglobulins (IgA and IgM) into the lumen of biological passageways. Although breast, prostate, pituitary and kidney cancer cells were employed in the foregoing examples, it should be understood that any tissue that lines a cavity and/or secretes IgA/IgM is a candidate for the same or similar compositions and methods for the diagnosis, treatment, deterrence or prevention. These include the gastrointestinal tract (i.e. oral cavity mucosa, salivary/parotid glands, esophagus, stomach, small intestine and colon), tear ducts and nasal passages, liver and bile ducts, bladder, pancreas, adrenals, kidney tubules and glomeruli, lungs, the female reproductive tract (i.e. ovaries, fallopian tubes, uterus, cervix and vagina) and the secretory anterior pituitary gland. All of these glandular/mucosal tissues either secrete or are bathed by polymeric IgA, secretory IgA (sIgA) and IgM. Cancers arising from these tissues account for 80% of the epithelial malignancies of humans.

As discussed in Example 37, it is interesting to note that in ataxia telangectasia (A-T) there is an increased incidence of malignancies, with epithelial carcinomas being the predominate kind. Laboratory evaluations of A-T patients also show, among other abnormalities that about 75% of the patients are deficient in IgA and IgM. A number of studies have indicated that female relatives of A-T patients suffer excess risk of breast cancer (Easton D F (1994) *Int. J. Radiat. Biol* 66 (6 Suppl), S177-S182) or gastric cancer (J. O. Bay et al. (1998) *Int. J Oncol.* 12, 1385-1390). The contribution of heterozygous A-T mutations to familial breast cancer is believed not to significant (Chen J et al. (1998) *Cancer Res.* 58, 1376-1379).

Prior to the present invention, the ability to arrest cell proliferation of early, steroid hormone responsive mucosal/epithelial malignancies has never been attributed to IgA/IgM/IgG1. In addition to looking at certain bacteria as potential causes of malignancy, exposure to non-pathogenic bacteria may serve to continuously stimulate the body's production of protective levels of IgA/IgM/IgG1 to protect against, or counteract, the cell proliferation-causing effects of the harmful bacteria.

Example 42

Treatment of Steroid Hormone Responsive Breast or Prostate Cancer by Administration of IgA/IgM/IgG1

In this example it is demonstrated that prolonged inhibition of cancer cell growth by IgA/IgM causes cell death. This effect is exploited in therapeutic methods that have been devised.

In the in vitro assays described in preceding Examples, which are considered to be model systems for predicting in vivo tumor growth effects, IgA and IgM were shown to behave as steroid hormone reversible inhibitors of $ER^+$ breast and $AR^+$ prostate cancer cell growth in the classical sense of the long sought after chalones. During the initial stages, the immunoglobulins arrest cell growth without causing cell death. Steroid hormones can reverse the inhibition during this period. However, as with most cancer cells, prolonged blockage of the cell cycle causes cell death (this is the well known basis for chemotherapy). Accordingly, these in vitro studies are the basis for the in vivo therapeutic use of IgM in rats to block the growth of carcinogen-induced mammary tumors and to treat existing tumors after induction, or those arising from implantation of MTW9/PL2 cells. In contrast to classical chemotherapy that attacks cells of many different types, the effects of IgA and IgM are specific for mucous epithelial cells and are non-toxic to normal organs.

Preferably the most active forms and/or subtypes of IgA/IgM/IgG1 will be employed, i.e., those forms of immunoglobulins that act as negative growth regulators for human breast and prostate cancer cells. The subclasses and pertinent allotypes of IgA will be investigated for growth regulating activity with human breast and prostate cancer cells in serum-free defined culture and for specific binding of $^{125}$I-labeled immunoglobulin to cell membrane receptors. The presently disclosed results strongly imply that polymeric forms are the primary or only biologically active immunoglobulins. To establish this conclusively, the effects of monomeric, dimeric and polymeric IgA on the growth of the ER$^+$ human breast cancer cell lines T47D, MCF-7 and ZR-75-1 will be assessed, employing the above-described growth assay procedures and materials. Cell numbers will be determined with triplicate dishes and the results converted to cell population doublings (CPD) to allow a direct comparison of the specific activities of each IgA form. Each form of IgA or fragment will be $^{125}$I-labeled by the chloramine T method. The labeled forms will be used to assess specific binding as total binding minus binding in the presence of a 100-fold excess of the same unlabeled preparation. For each fragment or protein (i.e. those that mediate estrogen effects), the time, concentration and temperature dependence of binding will be assessed. Scatchard analysis will be used to estimate the numbers of sites per cell and association constants (Ka). Reciprocal competitions with unlabeled and labeled dimeric IgA will be used to confirm that the purified types or fragments associate with the same receptors.

The IgA1 and IgA2 will be purified from serum and human colostrum as described. The monomeric, dimeric and polymeric forms of each will be purified by size exclusion and ion exchange FPLC. If IgA2 only possess activity, it will be further separated into the A2(m)1 and A2(m)2 allotypes. The purifications will be monitored exactly as described I the literature. If the most active form is dimeric (and polymeric), it will be additional strong evidence that the poly-Ig receptor is mediating the growth response. Were the monomers found to have significant activity, that will imply that the poly-Ig receptor may not be the (only) active mediating site. Next, the active IgA will be fragmented beginning with IgA protease that cleaves at the classical hinges. The methods will yield separable Fab fragments from IgA1 as well as a larger fragment containing the J chain, the secretory component and the Fc fragments, using standard techniques that are known to those of skill in the art and which can be readily implemented. Each specified fragment will be purified and assayed for growth mediating effects and receptor binding.

Following the confirmatory studies, preferably the most active immunoglobulin species (e.g., dimeric IgA, polymeric IgM, and/or IgG1) will be administered to other animal subjects or human patients suffering from a hormone responsive breast or prostate cancer, or other glandular/mucosal epithelial cancer. Preferably an effective dosage of the immunoglobulin composition will be introduced directly as one or more intravenous treatments using known methodologies for optimizing dosage and delivering it to the subject. Administration can be done intraperitoneally or subcutaneously as well. It should not be overlooked that this treatment protocol is quite different from conventional immunotherapies that rely entirely on effecting passive immunity to disease organisms and/or their antigenic determinants. In the present case, the treatment is designed to primarily provide the necessary level and/or forms or subtypes of polymeric/dimeric IgAs, pentameric IgM and/or IgG1s for binding with the respective poly-Ig and Fcγ receptors on the target cells sufficient to produce the desired inhibition or arrest of cell proliferation.

Formulations and Processes. For introduction into the body, pharmaceutical compositions containing the immunoglobulin inhibitors are manufactured in a manner that is well known in the art, e.g., by means of conventional mixing, dissolving, granulating, dragee-making, levigating, emulsifying, encapsulating, entrapping, and lyophilizing processes. The physiologically acceptable carriers are non-toxic to recipients at the dosages and concentrations employed. The formulation used varies according to the route of administration selected (e.g., solution, emulsion, capsule). For solutions or emulsions, suitable carriers include, for example, aqueous or alcoholic/aqueous solutions, emulsions or suspensions, including saline and buffered media. Pharmaceutical formulations suitable for parenteral administration may be formulated in aqueous solutions, preferably in physiologically compatible buffers such as Hanks's solution, Ringer's solution, or physiologically buffered saline. See, generally, "Remington's Pharmaceutical Science," 16th Edition, Mack, Ed. (1980). For inhalation, the immunoglobulin inhibitors can be solubilized and loaded into a suitable dispenser for administration (e.g., an atomizer, nebulizer or pressurized aerosol dispenser).

An "effective amount," as used herein, is defined as that quantity which alleviates, to any degree, or eliminates the condition for which the mammal is being treated. The determination of an effective dose is well within the capability of those skilled in the art. For any composition, the therapeutically effective dose can be estimated initially either in cell culture assays (e.g., one of the model assay systems described herein), or in animal models, usually mice, rabbits, dogs, or pigs. The animal model may also be used to determine the appropriate concentration range and route of administration. Such information can then be used to determine useful doses and routes for administration in humans.

The immunoglobulin inhibitors can be administered individually, together or in combination with other drugs or agents. For example, an anti-cancer composition is prepared by conjugating a cytotoxic agent or a chemotherapeutic agent to an immunoglobulin inhibitor of steroid hormone responsive cancer cell growth, the inhibitor comprising IgA, IgM or IgG1, or any combination of those.

Example 43

Monoclonal Antibodies that Mimic or Block IgA or IgM Binding to the Poly-Ig Receptor In this Example, the use of new monoclonal antibodies that act like IgA and IgM to inhibit breast and prostate cancer growth by binding to the poly Ig receptor, or that act to block the binding of IgA/IgM to the poly-Ig receptor is described. Also described is a method of developing hybridoma cells that secrete both mimicking and blocking antibodies. The monoclonal antibodies will be raised as described (Kohler G and Milstein C (1975) *Nature* (Lond) 256, 495).

Mimicking Antibodies. IgA and IgM mimicking monoclonal antibodies will be used in treatment protocols either alone or with conventional anti-hormone therapy. They also will be used in diagnostic methods to analyze patient specimens for poly-Ig receptor content by immunohistochemistry and other standard immunological techniques that are well known in the art.

Blocking Antibodies. A second class of monoclonal antibody secreting hybridoma cells will be obtained from the same protocols used to generate the hybridoma cells that secrete mimicking antibodies. This second type of blocking monoclonal antibodies prevents the binding of IgA to the poly-Ig receptor. The hybridoma cells that secrete this type of antibody and the antibodies themselves are useful reagents. Blocking antibodies will have a variety of therapeutic and/or diagnostic uses.

Features. One advantage of using monoclonal antibodies that mimic the IgA/IgM binding to the poly-Ig receptor is that the poly-Ig receptor can be targeted as a new site for anticancer intervention. While commercially prepared polyclonal antibodies against the receptor are available (Accurate Chemicals), there are no reports of their applicability to human therapy. It is not likely that rabbit polyclonal antibodies against the receptor will be useful in humans due to the strong antigenic response they will elicit. Also, there are two reports of panels of monoclonal antibodies directed against epitopes of IgA (Reimer C B et al. (1989) *Immunol Lett* 21, 209-216) and IgA plus the receptor (Mestecky J et al. (1996) *J Immunol Methods* 193, 103-148). None of these monoclonal antibodies has been tested for activity as an anticancer agent, nor is there any evidence that any act on the poly-Ig receptor to either mimic or block the action of IgA on breast or prostate cancer cells or on cancer cells of any of the other IgA or IgM secreting tissues of the body. One monoclonal antibody, MAB 6G11, has been described that binds to domain 1 of the poly-Ig receptor (Bakos M A et al. (1994) *Molecular Immunology* 31, 165-168). This same domain also binds IgA and IgM, implying that MAB 6G11 may be a blocking or possibly a mimicking antibody. However, direct studies of this aspect were not reported, and the monoclonal antibody was not used for anti-cancer purposes.

Examples of Other Types of Monoclonal Antibodies to Receptors. There have been similar projects based on the receptors for other hormones and growth factors. The use of blocking monoclonal antibodies as therapy for cancer is known (Baselga J and Mendelsohn J (1994) *Pharmacology Therapeutics* 64, 127-154). The best example is the monoclonal antibodies raised against the epidermal growth factor (EGF) receptor Baselga J and Mendelsohn J (1994) *Breast Cancer Res Treat* 29, 127-138). Another example is the monoclonal antibody rhuMab against the HER2/Neu proto-oncogene receptor which is over expressed by breast cancer cells Baselga J et al. (1996) *J Clin Oncol* 14, 737-744). These immunoglobulins are designed to block the growth stimulating effects of EGF/transforming growth factor (TGFα). Both EGF and TGFα cause cancer cell growth including breast and prostate. Anti-EGF and anti-HER2/neu receptor monoclonal antibodies are now commercial anticancer products.

The Target is a Negative Acting Receptor. In the case of growth factor receptor directed antibodies, the growth factor competes for (and often neutralizes) the inhibiting action of the immunoglobulin, which can be a significant problem. In contrast, the presently described mimicking antibodies target a negative acting receptor. The presence of endogenous IgA or IgM has no effect because the monoclonal antibody and the natural ligand have the same function, i.e., they both inhibit growth. There is no need to be concerned about the presence of IgA or IgM, as they will not interfere with this treatment. The mouse monoclonal antibodies against the poly-Ig receptor will be converted to human immunoglobulins by genetic engineering. This will prevent an immunological response against the mouse epitopes that will reduce antibody effectiveness. Monoclonal antibody therapy is non-invasive and can be administered frequently over a long duration. Both mimicking and blocking monoclonal antibodies are important because both are expected to have therapeutic value. The poly-Ig receptor is localized in mucosal tissues (e.g. GI tract, lungs, breast ducts, prostate gland, uterine lining, ovary, kidney tubules and urinary tract, and salivary gland) (Brandtzaeg P (1995) *Acta Path Microbiol Immunol Scand* 103, 1-19). An important advantage of this disclosure is that monoclonal antibodies against the breast/prostate poly-Ig receptor can also be expected to have therapeutic effects with cancers of at least some of these other tissues.

Development Protocols. Various strategies may be used to raise monoclonal antibodies to the human poly-Ig receptor. One approach is to use standard solid-phase chemical synthesis to prepare peptides corresponding to the known amino acid sequence of the extracellular domain of the poly-Ig receptor. The extracellular ligand-binding domain, which is approximately 80% of the whole receptor, was first named the "secretory component" because it was found in association with secreted IgA and IgM. Monoclonal antibodies against secretory component can be assayed to determine if they act as mimicking or blocking agents, employing a cell growth assay described herein. An alternative approach will be to use a combination of immunoprecipitation, affinity chromatography and immunoaffinity chromatography to purify the intact (complete) poly-Ig receptor. The purified receptor will then be used to raise monoclonal antibodies, which can then be screened for mimicking and blocking activity in a suitable cell growth assay described above.

Example 44

Delivery of Chemotherapeutic Agents and Cytotoxins to Cancer Cells via IgA/IgM/IgG1 or Monoclonal Antibodies to Poly-Ig Receptor In this Example, polymeric IgA/IgM and monoclonal antibodies to the poly-Ig receptor are used to deliver chemotherapeutic agents and cytotoxins to breast cancer and prostate cancer cells, and thereby cause the cancer cells to die. The specific delivery of cytotoxic agents to cancer cells has a long history (Shimizu N (1987) *Methods Enzymol* 147, 382-387). The conceptual basis of this approach is to chemically conjugate a cytotoxic protein or compound to an antibody or hormone that delivers the toxin-conjugate to cancer cells specifically, thereby causing their death. Very commonly, these agents are linked to monoclonal antibodies with (relative) specificity for the type of cancer targeted. The monoclonal antibodies usually are directed against cell surface receptors for hormones or growth factors or other over expressed cell membrane proteins.

Toxin-IgA/IgM/poly Ig Receptor Conjugates are New. Of the identifiable literature related to toxin conjugates, approximately 50% appears to pertain to cancer related applications of this technology, none of which refer to IgA or IgM as vehicles or to the poly-Ig receptor as a target for toxin conjugates. Although several extensive reviews of the topic have been published, and many reports have been published on the status and problems associated with the use of monoclonal antibodies for diagnosis and treatment of cancer, none of those references describe the use of IgA, IgM or poly-Ig receptor/toxin conjugates in breast or prostate cancer. Certain toxin conjugates have been previously described for breast cancer treatment, including several bifunctional reagents, and fusion proteins between ligands and antibodies and toxins. A range of protein and compound toxins are available, and it is envisioned that one or more of those will be suitable for conjugating to IgA, IgM or the poly-Ig receptor. A preferred toxic substance for conjugating to IgA, IgM or the poly-Ig receptor topic is an iron-containing compound, suitable for effecting the delivery of Fe (III) to cells, according to the present method. As demonstrated in previous Examples, Fe (III) is a potent cytotoxin for $ER^+$ breast cancer cells and $AR^+$ prostate cancer cells.

Advantages. Although many different monoclonal antibodies have been developed and used to target both chemical and protein toxins to cancer cells, the present approach employs IgA/IgM as the preferred vehicle(s) for delivery of the toxins and is directed toward a specific target (e.g., the poly-Ig receptor). The use of the poly-Ig receptor is advantageous because that receptor is more localized to secretory/mucosal epithelial tissues that are the primary origins of the major cancers of the body than are the other targets that are typically used for targeting of toxins to cancer cells. The discovery that polymeric IgA and IgM regulate estrogen responsive ($ER^+$) breast cancer cells and androgen responsive ($AR^+$) prostate cancer cells has opened new possibilities with regard to targeting the receptor that mediates their function. Since non-mucosal cells do not express the poly-Ig receptor, therapeutic methods that target poly-Ig receptor bearing cancer cells via the secretory immune system also have certain advantages. One benefit of such a method is that many important organs (e.g., heart and brain) will not be affected by the treatment.

While the preferred embodiments of the invention have been shown and described, modifications thereof can be made by one skilled in the art without departing from the spirit and teachings of the invention. For example, one of skill in the art can readily appreciate that for many applications, such as estimating risk of cancer, establishing a prognosis, diagnosing, treating, or preventing cancer, a number of the methods, strategies, techniques and compositions described in the Examples may in some cases be advantageously combined, or used in conjunction, to provide a desirable test, treatment or composition. Likewise, in some embodiments, it may be desirable to combine one of the new methods or compositions with a conventional anti-cancer therapy or test procedure. The embodiments described herein are exemplary only, and are not intended to be limiting. Many variations and modifications of the invention disclosed herein are possible and are within the scope of the invention. Accordingly, the scope of protection is not limited by the description set out above, but is only limited by the claims which follow, that scope including all equivalents of the subject matter of the claims. Each and every claim is incorporated into the specification as an embodiment of the present invention. Thus the claims are a further description and are an addition to the preferred embodiments of the present invention. The disclosures of U.S. Provisional Patent Application No. 60/203,314 filed May 10, 2000; 60/208,348 filed May 31, 2000; 60/208,111 filed May 31, 2000; 60/229,071 filed Aug. 30, 2000 and 60/231,273 filed Sep. 8, 2000, are hereby incorporated herein by reference. All patents, patent applications and publications cited herein are hereby incorporated herein by reference.

What is claimed is:

1. A method to quantitate immunoglobulin steroid hormone response inhibitor in a sample comprising:
    treating a sample to effectively remove steroid hormones from said sample;
    conducting an immunoglobulin steroid hormone inhibition assay by adding the treated sample to a first group of steroid-hormone responsive tumor cells which have been transferred to serum-free media or steroid hormone depleted serum, said cells being from a cultured cell line selected from the group consisting of: T47D; MCF-7A; ZR-75-1; GH3; GH1; GH4C1; or H-301;
    conducting an immunoglobulin steroid hormone inhibition positive control assay by adding a known amount of plasma immunoglobulin selected from the group consisting of plasma IgA or plasma IgM to a second group of said selected steroid-hormone responsive tumor cells which have been transferred to serum-free media or steroid hormone depleted serum;
    determining an amount of said added treated sample at which said treated sample inhibits steroid-hormone mediated cell growth in said inhibition assay; and
    comparing said amount of said added treated sample to said amount of plasma immunoglobulin added to said positive control assay to quantitate an amount of immunoglobulin steroid hormone response inhibitor in said treated sample.

2. A method of detecting inhibition of steroid hormone responsive cell growth wherein the inhibition can be reversed by the steroid hormone, the method comprising:
    obtaining at least two samples of identical mucosal epithelial cultured cells;
    treating one of said cell samples with purified polymeric IgM;
    leaving one of said cell samples untreated with no addition of polymeric IgM;
    incubating said cell samples under cell growth promoting conditions;
    measuring post-incubation, cell population doublings in the cell samples; and
    detecting inhibition of steroid hormone responsive cell growth from a decreased cell population doublings in the cell sample treated with purified IgM compared with the cell sample left untreated.

3. A method of detecting inhibition of steroid hormone responsive cell growth wherein the inhibition can be reversed by the steroid hormone, the method comprising:
    obtaining at least two samples of identical mucosal epithelial cultured cells;
    treating one of said cell samples with purified plasma IgA;
    leaving one of said cell samples untreated with no addition of plasma IgA;
    incubating said cell samples under cell growth promoting conditions;
    measuring post-incubation, cell population doublings in the cell samples; and
    detecting inhibition of steroid hormone responsive cell growth from a decreased cell population doublings in the cell sample treated with purified plasma IgA compared with the cell sample left untreated.

4. A method to detect estrogenic activity of a substance of interest, the method comprising:
    adding an inhibitory amount of purified IgM to at least two samples of a maintained steroid hormone-responsive cancer cell population in a nutrient medium;
    adding an amount of the substance of interest to one of the cell samples to yield a test mixture;
    designating the cell sample without any added substance of interest as a control mixture;
    incubating the cell samples for a period of time under cell growth promoting conditions;

measuring the cell population in the cell samples after the period of time; and detecting estrogenic activity of the substance of interest from increased cell population doublings in the cell sample treated with the substance of interest compared with the cell sample without any added substance of interest.

5. A method to detect estrogenic activity of a substance of interest, the method comprising:
adding an inhibitory amount of purified IgA to at least two samples of a maintained steroid hormone-responsive cancer cell population in a nutrient medium;
adding an amount of the substance of interest to one of the cell samples to yield a test mixture;
designating the cell sample without any added substance of interest as a control mixture;
incubating the cell samples for a period of time under cell growth promoting conditions;
measuring the cell population in the cell samples after the period of time; and
detecting estrogenic activity of the substance of interest from increased cell population doublings in the cell sample treated with the substance of interest compared with the cell sample without any added substance of interest.

6. A method to detect estrogenic activity of a substance of interest, the method comprising:
adding an inhibitory amount of purified IgM to at least three samples of a maintained steroid hormone-responsive cancer cell population in a nutrient medium;
adding an amount of the substance of interest to one of the cell samples to yield a test mixture;
adding an amount of estrogen to one of the cell samples to yield a standard mixture;
designating the cell sample without any added substance of interest as a control mixture;
incubating the cell samples for a period of time under cell growth promoting conditions;
measuring the cell population in the cell samples after the period of time; and
detecting estrogenic activity of the substance of interest from a significant increase in cell population doublings in the test mixture and the standard mixture compared with the control mixture.

7. A method to detect estrogenic activity of a substance of interest, the method comprising:
adding an inhibitory amount of purified IgA to at least three samples of a maintained steroid hormone-responsive cancer cell population in a nutrient medium;
adding an amount of the substance of interest to one of the cell samples to yield a test mixture;
adding an amount of estrogen to one of the cell samples to yield a positive control mixture;
designating the cell sample without said substance of interest or estrogen as a negative control mixture;
incubating the cell samples for a period of time under cell growth promoting conditions;
measuring the cell population in the cell samples after the period of time; and
detecting estrogenic activity of the substance of interest from a significant increase in cell population doublings in the test mixture and the standard mixture compared with the control mixture.

8. The method of claim 1 wherein said cells are further selected from the group of cell lines consisting of T47D, MCF-7A, or ZR-75-1.

9. The method of claim 8 wherein said cells are from the T47D cell line.

10. The method of claim 8 wherein said cells are from the ZR-75-1 cell line.

11. The method of claim 8 wherein said cells are from the MCF-7A cell line.

12. The method of claim 1 wherein said cells are further selected from the group of cell lines consisting of GH1, GH3 and GH4C1.

13. The method of claim 12 wherein said cells are from the GH4C1 cell line.

14. The method of claim 1 wherein said cells are from the H-301 cell line.

* * * * *